US012806246B2

(12) United States Patent
Stirner et al.

(10) Patent No.: US 12,806,246 B2
(45) Date of Patent: Nov. 24, 2026

(54) METHODS OF REDUCING THE SEVERITY OF TOXICITY IN BCMA CAR-T TREATMENTS

(71) Applicant: Juno Therapeutics, Inc., Seattle, WA (US)

(72) Inventors: Mariana Cota Stirner, Seattle, WA (US); Mirna Mujacic, Seattle, WA (US); Todd Devries, Bainbridge Island, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 900 days.

(21) Appl. No.: 17/917,923

(22) PCT Filed: Apr. 9, 2021

(86) PCT No.: PCT/US2021/026702
§ 371 (c)(1),
(2) Date: Oct. 7, 2022

(87) PCT Pub. No.: WO2021/207689
PCT Pub. Date: Oct. 14, 2021

(65) Prior Publication Data

US 2023/0149462 A1 May 18, 2023

Related U.S. Application Data

(60) Provisional application No. 63/008,564, filed on Apr. 10, 2020.

(51) Int. Cl.

| | |
|---|---|
| ***A61K 38/17*** | (2006.01) |
| ***A61K 35/12*** | (2015.01) |
| ***A61K 38/20*** | (2006.01) |
| ***A61K 39/395*** | (2006.01) |
| ***A61K 40/11*** | (2025.01) |
| ***A61K 40/31*** | (2025.01) |
| ***A61K 40/42*** | (2025.01) |
| ***A61P 7/00*** | (2006.01) |
| ***A61P 35/00*** | (2006.01) |
| ***A61P 37/06*** | (2006.01) |

(52) U.S. Cl.
CPC ...... *A61K 38/1774* (2013.01); *A61K 38/2006* (2013.01); *A61K 39/3955* (2013.01); *A61K 40/11* (2025.01); *A61K 40/31* (2025.01); *A61K 40/4215* (2025.01); *A61P 7/00* (2018.01); *A61P 35/00* (2018.01); *A61P 37/06* (2018.01); *A61K 2035/124* (2013.01); *A61K 2239/31* (2023.05); *A61K 2239/38* (2023.05); *A61K 2239/48* (2023.05)

(58) Field of Classification Search
CPC ........... A61K 38/1774; A61K 38/2006; A61K 39/3955; A61K 40/11; A61K 40/31; A61K 40/4215; A61K 2035/124; A61P 7/00; A61P 35/00; A61P 37/06
See application file for complete search history.

(56) References Cited

U.S. PATENT DOCUMENTS

| | | | |
|---|---|---|---|
| 4,452,773 | A | 6/1984 | Molday |
| 4,690,915 | A | 9/1987 | Rosenberg |
| 4,795,698 | A | 1/1989 | Owen |
| 5,087,616 | A | 2/1992 | Myers et al. |
| 5,168,062 | A | 12/1992 | Stinski |
| 5,200,084 | A | 4/1993 | Liberti |
| 5,219,740 | A | 6/1993 | Miller |
| 5,283,173 | A | 2/1994 | Fields et al. |
| 5,385,839 | A | 1/1995 | Stinski |
| 5,424,297 | A | 6/1995 | Rubio et al. |
| 5,468,614 | A | 11/1995 | Fields et al. |
| 5,504,090 | A | 4/1996 | Neely |
| 5,545,627 | A | 8/1996 | Jacobson et al. |
| 5,565,566 | A | 10/1996 | Olsson |
| 5,670,501 | A | 9/1997 | Peck et al. |
| 5,786,360 | A | 7/1998 | Neely |
| 5,861,405 | A | 1/1999 | Jacobson et al. |
| 5,981,524 | A | 11/1999 | Peck et al. |
| 5,994,136 | A | 11/1999 | Naldini et al. |
| 6,013,516 | A | 1/2000 | Verma et al. |
| 6,040,177 | A | 3/2000 | Riddell |
| 6,060,273 | A | 5/2000 | Dirks et al. |
| 6,066,642 | A | 5/2000 | Jacobson et al. |
| 6,111,090 | A | 8/2000 | Gorman et al. |
| 6,117,998 | A | 9/2000 | Neely |
| 6,123,655 | A | 9/2000 | Fell |

(Continued)

FOREIGN PATENT DOCUMENTS

| | | |
|---|---|---|
| EP | 0090505 | 8/1990 |
| EP | 0452342 | 10/1991 |

(Continued)

OTHER PUBLICATIONS

US 8,252,592 B2, 08/2012, Sadelain (withdrawn)
US 8,450,329 B2, 05/2013, Pingda et al. (withdrawn)
Oliai et al. (Interleukin-1 blockade to prevent severe immune effector cell associated neurotoxicity syndrome; Trial in progress. Journal for Immuno Therapy of Cancer 2019, 7(Suppl 1):P406. (Year: 2019).*
Gavriatopoulou et al., "Anti-BCMA antibodies in the future management of multiple myeloma," Expert Rev Anticancer Ther. (Apr. 2019, e-pub. Mar. 18, 2019) 19(4):319-326.

(Continued)

*Primary Examiner* — Elly-Gerald Stoica

(57) ABSTRACT

Provided are methods and uses related to adoptive cell therapy involving the administration of doses of cells, such as T cells, for treating disease and conditions, including certain plasma cell malignancies. The cells express recombinant receptors such as chimeric antigen receptors (CARs) specific to B-cell maturation antigen (BCMA). In some embodiments, the methods are for treating subjects with multiple myeloma (MM).

30 Claims, 6 Drawing Sheets

Specification includes a Sequence Listing.

(56) References Cited

U.S. PATENT DOCUMENTS

| | | | |
|---|---|---|---|
| 6,207,453 | B1 | 3/2001 | Maass et al. |
| 6,232,297 | B1 | 5/2001 | Linden et al. |
| 6,313,131 | B1 | 11/2001 | Lawyer |
| 6,322,771 | B1 | 11/2001 | Linden et al. |
| 6,326,390 | B1 | 12/2001 | Leung et al. |
| 6,410,319 | B1 | 6/2002 | Raubitschek et al. |
| 6,451,995 | B1 | 9/2002 | Cheung et al. |
| 6,733,433 | B1 | 5/2004 | Fell |
| 7,025,962 | B1 | 4/2006 | Gorman et al. |
| 7,070,995 | B2 | 7/2006 | Jensen |
| 7,132,255 | B2 | 11/2006 | Blumberg |
| 7,141,575 | B2 | 11/2006 | Gillespie et al. |
| 7,265,209 | B2 | 9/2007 | Jensen |
| 7,354,762 | B2 | 4/2008 | Jensen |
| 7,405,219 | B2 | 7/2008 | Gillespie et al. |
| 7,446,179 | B2 | 11/2008 | Jensen |
| 7,446,190 | B2 | 11/2008 | Sadelain |
| 7,446,191 | B2 | 11/2008 | Jensen |
| 7,618,632 | B2 | 11/2009 | Collins et al. |
| 7,812,135 | B2 | 10/2010 | Smith et al. |
| 7,943,743 | B2 | 5/2011 | Korman et al. |
| 8,008,449 | B2 | 8/2011 | Korman et al. |
| 8,008,450 | B2 | 8/2011 | Williams et al. |
| 8,080,554 | B2 | 12/2011 | Sitkovsky et al. |
| 8,124,084 | B2 | 2/2012 | Lefrancois et al. |
| 8,153,765 | B2 | 4/2012 | Park et al. |
| 8,324,353 | B2 | 12/2012 | Jensen |
| 8,339,645 | B2 | 12/2012 | Nakawaki et al. |
| 8,354,509 | B2 | 1/2013 | Carven et al. |
| 8,388,967 | B2 | 3/2013 | Smith et al. |
| 8,389,282 | B2 | 3/2013 | Sadelain |
| 8,497,118 | B2 | 7/2013 | Jensen |
| 8,586,023 | B2 | 11/2013 | Shiku et al. |
| 8,591,886 | B2 | 11/2013 | Ponath et al. |
| 8,603,477 | B2 | 12/2013 | Afar et al. |
| 8,609,089 | B2 | 12/2013 | Langermann et al. |
| 8,716,301 | B2 | 5/2014 | Sitkovsky et al. |
| 8,802,374 | B2 | 8/2014 | Jensen |
| 8,883,500 | B2 | 11/2014 | Sitkovsky et al. |
| 8,987,279 | B2 | 3/2015 | Bamford et al. |
| 2002/0131960 | A1 | 9/2002 | Sadelain |
| 2003/0170238 | A1 | 9/2003 | Gruenberg et al. |
| 2004/0047858 | A1 | 3/2004 | Blumberg et al. |
| 2006/0270045 | A1 | 11/2006 | Cregg et al. |
| 2008/0171951 | A1 | 7/2008 | Fell |
| 2009/0082299 | A1 | 3/2009 | Felber et al. |
| 2010/0028330 | A1 | 2/2010 | Collins et al. |
| 2010/0247521 | A1 | 9/2010 | Jones et al. |
| 2010/0260748 | A1 | 10/2010 | Elkins et al. |
| 2011/0003380 | A1 | 1/2011 | Miltenyi |
| 2011/0081311 | A1 | 4/2011 | Pavlakis et al. |
| 2012/0039906 | A1 | 2/2012 | Olive |
| 2012/0114649 | A1 | 5/2012 | Langermann et al. |
| 2012/0141413 | A1 | 6/2012 | Pavlakis et al. |
| 2012/0177598 | A1 | 7/2012 | Lefrancois et al. |
| 2012/0189622 | A1 | 7/2012 | Tesar et al. |
| 2013/0149337 | A1 | 6/2013 | Cooper |
| 2013/0156774 | A1 | 6/2013 | Kuchroo et al. |
| 2013/0287748 | A1 | 10/2013 | June |
| 2014/0056922 | A1 | 2/2014 | Sitkovsky et al. |
| 2014/0161828 | A1 | 6/2014 | Armitage et al. |
| 2014/0271618 | A1 | 9/2014 | Markel et al. |
| 2014/0377240 | A1 | 12/2014 | Sitkovsky et al. |
| 2015/0210769 | A1 | 7/2015 | Freeman et al. |
| 2015/0218274 | A1 | 8/2015 | Sabatos-Peyton et al. |
| 2015/0259420 | A1 | 9/2015 | Triebel et al. |
| 2016/0046724 | A1 | 2/2016 | Brogdon et al. |
| 2017/0183418 | A1 | 6/2017 | Galletto |

FOREIGN PATENT DOCUMENTS

| | | | |
|---|---|---|---|
| EP | 1866339 | 12/2007 | |
| EP | 1947183 | 7/2008 | |
| EP | 2537416 | 12/2012 | |
| WO | WO 1992/008796 | 5/1992 | |
| WO | WO 1994/028143 | 12/1994 | |
| WO | WO 1999/020758 | 4/1999 | |
| WO | WO 1999/040196 | 8/1999 | |
| WO | WO 1999/052552 | 10/1999 | |
| WO | WO 2000/014257 | 3/2000 | |
| WO | WO 2000/038762 | 7/2000 | |
| WO | WO 2001/003720 | 1/2001 | |
| WO | WO 2002/055083 | 7/2002 | |
| WO | WO 2005/007190 | 1/2005 | |
| WO | WO 2005/055808 | 6/2005 | |
| WO | WO 2005/115451 | 12/2005 | |
| WO | WO 2006/121168 | 5/2006 | |
| WO | WO 2006/083289 | 8/2006 | |
| WO | WO 2006/099875 | 9/2006 | |
| WO | WO 2007/005874 | 1/2007 | |
| WO | WO 2007/133822 | 11/2007 | |
| WO | WO 2008/147482 | 12/2008 | |
| WO | WO 2009/072003 | 6/2009 | |
| WO | WO 2009/076524 | 6/2009 | |
| WO | WO 2009/080829 | 7/2009 | |
| WO | WO 2009/101611 | 8/2009 | |
| WO | WO 2009/114335 | 9/2009 | |
| WO | WO 2010/003118 | 1/2010 | |
| WO | WO 2010/019570 | 2/2010 | |
| WO | WO 2010/027827 | 3/2010 | |
| WO | WO 2010/033140 | 3/2010 | |
| WO | WO 2010/077634 | 7/2010 | |
| WO | WO 2010/104949 | 9/2010 | |
| WO | WO 2010/125571 | 11/2010 | |
| WO | WO 2011/028683 | 3/2011 | |
| WO | WO 2011/051726 | 5/2011 | |
| WO | WO 2011/066342 | 6/2011 | |
| WO | WO 2011/090754 | 7/2011 | |
| WO | WO 2012/092612 | 7/2012 | |
| WO | WO 2012/129514 | 9/2012 | |
| WO | WO 2013/006490 | 1/2013 | |
| WO | WO 2013/039954 | 3/2013 | |
| WO | WO 2013/054331 | 4/2013 | |
| WO | WO 2013/071154 | 5/2013 | |
| WO | WO 2013/082366 | 6/2013 | |
| WO | WO 2013/123061 | 8/2013 | |
| WO | WO 2013/126726 | 8/2013 | |
| WO | WO 2013/166321 | 11/2013 | |
| WO | WO 2014/022332 | 2/2014 | |
| WO | WO 2014/031687 | 2/2014 | |
| WO | WO 2014/055668 | 4/2014 | |
| WO | WO 2014/059251 | 4/2014 | |
| WO | WO 2014/190273 | 11/2014 | |
| WO | WO 2014/210064 | 12/2014 | |
| WO | WO 2015/079417 | 6/2015 | |
| WO | WO 2015/164675 | 10/2015 | |
| WO | WO 2016/014789 | 1/2016 | |
| WO | WO 2016/073602 | 5/2016 | |
| WO | WO 2016/090320 | 6/2016 | |
| WO | WO 2016/090327 | 6/2016 | |
| WO | WO 2017/025038 | 2/2017 | |
| WO | WO 2017/173256 | 10/2017 | |
| WO | WO 2018/014038 | 1/2018 | |
| WO | WO 2018/028647 | 2/2018 | |
| WO | WO 2018/085690 | 5/2018 | |
| WO | WO2018204427 | * 11/2018 | ............. A61K 35/17 |
| WO | WO 2018/223101 | 12/2018 | |
| WO | WO 2019/089969 | 5/2019 | |
| WO | WO 2019/090003 | 5/2019 | |
| WO | WO 2019/090364 | 5/2019 | |
| WO | WO 2019/108900 | 6/2019 | |
| WO | WO 2020/033916 | 8/2019 | |
| WO | WO 2019/173636 | 9/2019 | |
| WO | WO 2019/210153 | 10/2019 | |
| WO | WO 2019/226329 | 11/2019 | |
| WO | WO 2019/232503 | 12/2019 | |
| WO | WO 2020/033927 | 2/2020 | |
| WO | WO 2021/113776 | 6/2023 | |

OTHER PUBLICATIONS

Norelli et al., "Monocyte-derived IL-1 and IL-6 are differentially required for cytokine-release syndrome and neurotoxicity due to

(56) References Cited

OTHER PUBLICATIONS

CAR T cells," Nat Med (Jun. 2018, e-pub. May 28, 2018) 24(6):739-748.
Yamazaki et al., "IL-1 inhibitors," The Journal of the Japanese Society of Internal Medicine (Oct. 10, 2011) 100(10):2985-2990. English machine translation provided.
Abdallah et al., "SGNBCMA-001: A phase 1 study of SEA-BCMA, a non-fucosylated monoclonal antibody, in subjects with relapsed or refractory multiple myeloma," Journal of Clinical Oncology 2019 37:15_suppl, TPS8054-TPS8054.
Ali et al., "T cells expressing an anti-B-cell maturation antigen chimeric antigen receptor cause remissions of multiple myeloma," Blood (2016) 128 (13): 1688-1700.
Al-Lazikani et al., "Standard Conformations for the Canonical Structures of Immunoglobulins," J. Mol. Biol. (1997) 273: 927-948.
Allard et al., "Targeting CD73 Enhances the Antitumor Activity of Anti-PD-1 and Anti-CTLA-4 mAbs," Clin Cancer Res (2013) 19(20):5626-5635.
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.
Beavis et al., "Blockade of A2A receptors potently suppresses the metastasis of CD73+ tumors," PNAS (2013) 110(36):14711-14716.
Benson et al., "CS1-directed monoclonal antibody therapy for multiple myeloma," J Clin Oncol. (2012) 30(16):2013-2015.
Berdeja et al., "Updated Results from an Ongoing Phase 1 Clinical Study of bb21217 Anti-BCMA CAR T Cell Therapy," Blood 2019; Abstract 927.
Berger, R. et al., "Phase I Safety and Pharmacokinetic Study of CT-011, A Humanized Antibody Interacting With PD-1, in Patients With Advanced Hematologic Malignancies," Cancer Therapy: Clinical (2008) 14(10):3044-3051.
Bertilaccio et al., "Low-Dose Lenalidomide Improves CAR-Based Immunotherapy in CLL by Reverting T-Cell Defects In Vivo," Blood (2013) 122:4171.
Blank et al., "Contribution of the PD-L1/PD-1 Pathway to T-cell Exhaustion: An Update on Implications for Chronic Infections and Tumor Evasion," Cancer Immunol Immunother (2007) 56(5): 739-745.
Boris-Lawrie, K.A. et al. "Recent advances in retrovirus vector technology", Curr Opin Genet Dev. (1993) 3(1):102-109.
Borrega et al., "In the Eye of the Storm: Immune-mediated Toxicities Associated With CAR-T Cell Therapy," Hemasphere. (2019) 29;3(2):e191.
Borrello et al., "BCMA CAR T cells: the winding path to success," J Clin Invest. (2019) 129(6):2175-2177.
Brahmer et al., "Safety and Activity of anti-PD-L1 Antibody in Patients With Advanced Cancer," N Engl J Med. (2012) 366(26): 2455-2465.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.
Brentjens et al., "Safety and persistence of adoptively transferred autologous CD19-targeted T cells in patients with relapsed or chemotherapy refractory B-cell leukemias," Blood (2011) 118(18):4817-4828.
Brown et al., "Structure-based mutagenesis of the human immunodeficiency virus type 1 DNA attachment site: effects on integration and cDNA synthesis," J Virol. (1999) 73(11): 9011-20.
Brudno et al., "Toxicities of chimeric antigen receptor T cells: recognition and management," Blood (May 2016) 127(26):3321-3330.
Brummelkamp et al., "A system for stable expression of short interfering RNAs in mammalian cells," Science (2002) 296(5567):550-553.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Carlens et al., "Ex vivo T lymphocyte expansion for retroviral transduction: influence of serum-free media on variations in cell expansion rates and lymphocyte subset distribution," Exp Hematol (2000) 28(10): 1137-46.
Carpenter et al., "B-cell maturation antigen is a promising target for adoptive T-cell therapy of multiple myeloma," Clin Cancer Res (2013) 19(8):2048-2060.
Carroll et al., "Targeting the molecular basis for tumour hypoxia," Expert Rev Mol Med (2005) 7(6):1-16.
Cavaletti et al., "Chemotherapy-induced peripheral neurotoxicity," Nat Rev Neurol (2010) 6(12):657-666.
Cavalieri et al., "Human T lymphocytes transduced by lentiviral vectors in the absence of TCR activation maintain an intact immune competence," Blood (2003) 102(2): 497-505.
Chicaybam et al., "An efficient low cost method for gene transfer to T lymphocytes," PLoS One (2013) 8(3): e60298.
Cho et al., "Human mammalian cell sorting using a highly integrated micro-fabricated fluorescence-activated cell sorter (microFACS)," Lab Chip (2010) 10: 1567-1573.
Cho et al., "Targeting B Cell Maturation Antigen (BCMA) in Multiple Myeloma: Potential Uses of BCMA-Based Immunotherapy," Front Immunol. (2018) 9:1821.
Cho et al., "AMG 701 Potently Induces Anti-Multiple Myeloma (MM) Functions of T Cells and IMiDs Further Enhance Its Efficacy to Prevent MM Relapse In Vivo," Blood (2019) 134 (Supplement_1): 135.
Cho et al., "AMG 701, a half-life extended anti-BCMA BiTE®, potently induces T cell-redirected lysis of human multiple myeloma cells and can be combined with IMiDs to overcome the immunosuppressive bone marrow microenvironment," Clinical Lymphoma, Myeloma and Leukemia. (2019) 19(10):e54.
Chu et al., "CS1-specific chimeric antigen receptor (CAR)-engineered natural killer cells enhance in vitro and in vivo antitumor activity against human multiple myeloma," Leukemia. (2014) 28(4):917-27.
Clackson et al. "Making antibody fragments using phage display libraries," Nature (1991) 352:624-628.
Clinical Trial Study Record No. NCT01822652. "Study Evaluating the Safety and Efficacy of JCARH125 in Subjects With Relapsed and/or Refractory Multiple Myeloma (EVOLVE)," First posted Feb. 12, 2018. Last updated Mar. 1, 2023.
Cohen et al., B-cell maturation antigen-specific CAR T cells are clinically active in multiple myeloma. J Clin Invest Mar. 21, 2019; 129(6):2210-2221.
Cooper et al., "T-cell clones can be rendered specific for CD19: toward the selective augmentation of the graft-versus-B-lineage leukemia effect," Blood (2003) 101:1637-1644.
Cooper et al., "Safety and Preliminary Clinical Activity of REGN5458, an Anti-Bcma x Anti-CD3 Bispecific Antibody, in Patients with Relapsed/Refractory Multiple Myeloma," Blood (2019) 134 (Supplement_1): 3176.
Coquery et al., "Regulatory roles of the tumor necrosis factor receptor BCMA," Crit Rev Immunol (2012) 32(4):287-305.
Costa et al., "First Clinical Study of the B-Cell Maturation Antigen (BCMA) 2+1 T Cell Engager (TCE) CC-93269 in Patients (Pts) with Relapsed/Refractory Multiple Myeloma (RRMM): Interim Results of a Phase 1 Multicenter Trial," Blood (2019) 134 (Supplement_1): 143.
Costa et al., "Anakinra prophylaxis in patients with relapsed/refractory multiple myeloma receiving orvacabtagene autoleucel," ASCO 2021, May 7, 2021, Poster 2537.
Costa et al., "Anakinra (AKR) prophylaxis (ppx) in patients (pts) with relapsed/refractory multiple myeloma (RRMM) receiving orvacabtagene autoleucel (orva-cel)," Journal of Clinical Oncology. (2021) 39(15_suppl):2537-2537.
Costello et al., "Phase 2 Study of the Response and Safety of P-Bcma-101 CAR-T Cells in Patients with Relapsed/Refractory (r/r) Multiple Myeloma (MM) (PRIME)," Blood (2019) 134 (Supplement_1): 3184.

(56) References Cited

OTHER PUBLICATIONS

Cronstein et al., “Adenosine modulates the generation of superoxide anion by stimulated human neutrophils via interaction with a specific cell surface receptor,” Ann N Y Acad Sci (1985) 451:291-301.
Cronstein et al., “Engagement of adenosine receptors inhibits hydrogen peroxide (H2O2-) release by activated human neutrophils,” Clin Immunol Immunopathol (1987) 42(1):76-85.
Davila et al., “CD19 CAR-targeted T cells induce long-term remission and B Cell Aplasia in an immunocompetent mouse model of B cell acute lymphoblastic leukemia,” PLoS One (2013) 8(4): e61338.
Davila et al., “Efficacy and toxicity management of 19-28z CAR T cell therapy in B cell acute lymphoblastic leukemia,” Sci Transl Med (2014) 6:224ra25.
Davila et al., “How do CARs work ?: Early insights from recent clinical studies targeting CD19,” Oncoimmunology (2012) 1(9):1577-1583.
De Felipe, “Skipping the co-expression problem: the new 2A “CHYSEL” technology,” Genet Vaccines Ther Sep. 13, 2004;2(1):13.
De Felipe, “Targeting of proteins derived from self-processing polyproteins containing multiple signal sequences,” Traffic (2004) 5(8):616-626.
Duell et al., “Bispecific Antibodies in the Treatment of Hematologic Malignancies,” Clin Pharmacol Ther. (2019) 106(4):781-791.
Dull et al., “A Third-Generation Lentivirus Vector with a Conditional Packaging System,” J. Viral. (1998) 72:8463-8471.
Engelman et al., “Multiple effects of mutations in human immunodeficiency virus type 1 integrase on viral replication,” J Viral (1995) 69(5):2729-2736.
Fecteau et al., “Lenalidomide inhibits the proliferation of CLL cells via a cereblon/p21WAF1/Cip1-dependent mechanism independent of functional p53,” Blood (2014) 124:1637-1644.
Fedorov et al., “PD-1- and CTLA-4-based inhibitory chimeric antigen receptors (iCARs) divert off-target immunotherapy responses,” Sci. Transl. Medicine (2013) 5(215).
Finger et al., “The Human PD-1 Gene: Complete cDNA, Genomic Organization, and Developmentally Regulated Expression in B Cell Progenitors,” Gene (1997) 197(1-2): 177-187.
Flatman et al., “Process analytics for purification of monoclonal antibodies,” J. Chromatogr. (2007) B 848:79-87.
Fu et al., “Efficacy and Safety of CAR-T Therapy with Safety Switch Targeting Bcma for Patients with Relapsed/Refractory Multiple Myeloma in a Phase 1 Clinical Study,” Blood. (2019) 134 (Supplement_1): 3154.
Garfall et al., “Immunotherapy with chimeric antigen receptors for multiple myeloma,” Discov Med (2014) 17(91):37-46.
Genscript Biotech Corporation Release dated Mar. 13, 2018, Voluntary Announcement Research and Development Update; Clinical Trials granted for LCAR-B38M CAR-T for autologous infusion; 2 pages.
Gerngross et al., “Advances in the Production of Human Therapeutic Proteins in Yeasts and Filamentous Fungi,” Nature Biotechnology. (2004) 22(11):1409-1414.
Ghermezi et al., Serum B-cell maturation antigen: a novel biomarker to predict outcomes for multiple myeloma patients. Haematologica. (2017) 102(4):785-795.
Gildener-Leapman et al., “Promising systemic immunotherapies in head and neck squamous cell carcinoma,” Oral Oncol (2013) 49(12):1089-1096.
Girgis et al., “Exploratory Pharmacokinetic/Pharmacodynamic and Tolerability Study of BCMAxCD3 in Cynomolgus Monkeys,” Blood. (2016) 128 (22): 5668.
Godin et al., “Microfluidics and photonics for Bio-System-on-a-Chip: a review of advancements in technology towards a microfluidic flow cytometry chip,” J Biophoton. (2008) 1(5):355-376.
Goldberg et al., “Engineering a targeted delivery platform using Centyrins,” Protein Eng Des Sel. (2016) 29(12):563-572.
Grupp et al., “Chimeric Antigen Receptor-Modified T Cells for Acute Lymphoid Leukemia,” N Engl J Med (2013) 368:1509-1518.
Gust et al., “Endothelial Activation and Blood-Brain Barrier Disruption in Neurotoxicity after Adoptive Immunotherapy with CD19 CAR-T Cells,” Cancer Discov. (2017) 7(12): 1404-1419.
Hausler et al., “Anti-CD39 and anti-CD73 antibodies A1 and 7G2 improve targeted therapy in ovarian cancer by blocking adenosine-dependent immune evasion,” Am J transl Res (2014) 6(2):129-139.
Hay et al., “Cytokine release syndrome and neurotoxicity after CD19 chimeric antigen receptor-modified (CAR-) T cell therapy,” Br J Haematol. (2018) 183(3):364-374.
Hermans et al., “The VITAL Assay: a Versatile Fluorometric Technique for Assessing CTL- and NKT-Mediated Cytotoxicity Against Multiple Targets in Vitro and in Vivo,” J. Immunological Methods. (2004) 285(1):25-40.
Hershfield, “PEG-ADA: an alternative to haploidentical bone marrow transplantation and an adjunct to gene therapy for adenosine deaminase deficiency,” Hum Mutat (1995) 5(2):107-112.
Hipp et al., “A Novel BCMA/CD3 Bispecific T-Cell Engager for the Treatment of Multiple Myeloma Induces Selective Lysis In Vitro and In Vivo,” Leukemia (2017) 31:1743-1744.
Honegger et al., “Yet another numbering scheme for immunoglobulin variable domains: an automatic modeling and analysis tool,” J Mol Biol, (2001) 8;309(3):657-670.
Huang et al., “DNA transposons for modification of human primary T lymphocytes,” Methods Mol Biol (2009) 506: 115-126.
Hudecek et al., “Receptor affinity and extracellular domain modifications affect tumor recognition by ROR1-specific chimeric antigen receptor T cells,” Clin. Cancer Res. (2013) 19:3153.
Hudecek et al., “The nonsignaling extracellular spacer domain of chimeric antigen receptors is decisive for in vivo antitumor activity,” Cancer Immunol Res (2015) 3(2):125-135.
Jensen al., “Antitransgene Rejection Responses Contribute to Attenuated Pe1 •sistence of Adoptively Transferred CD20/CD 19-Specitic Chimeric Antigen Receptor Redirected T Cells in Humans,” Biol. Blood Marrow Transplant 16: 1245-1256 (2010).
Jie et al., “Phase 1 Trial of the Safety and Efficacy of Fully Human Anti-Bcma CAR T Cells in Relapsed/Refractory Multiple Myeloma,” Blood (2019) 134 (Supplement_1): 4435.
Jin et al., “CD73 on tumor cells impairs antitumor T-cell responses: a novel mechanism of tumor-induced immune suppression,” Cancer Res (2010) 70(6):2245-2255.
Johnston, et al., “Biolistic transformation: microbes to mice,” Nature (1990) 346: 776-777.
Kindt et al. (2007). “Antigens and Antibodies,” Chapter 4 In Kuby Immunology 6th Ed., W.H. Freeman and Co., p. 91.
Kinneer et al., “Preclinical Evaluation of MEDI2228, a BCMA-Targeting Pyrrolobenzodiazepine-Linked Antibody Drug Conjugate for the Treatment of Multiple Myeloma,” Blood (2017) 130 (Supplement 1): 3153.
Klebanoff et al., “Sorting through subsets: which T-cell populations mediate highly effective adoptive immunotherapy?,” J Immunother. (2012) 35(9): 651-660.
Kochenderfer et al., “B-cell depletion and remissions of malignancy along with cytokine-associated toxicity in a clinical trial of anti-CD19 chimeric-antigen-receptor-transduced T cells,” Blood (2012) 119(12):2709-2720.
Kochenderfer et al., “Construction and preclinical evaluation of an anti-CD19 chimeric antigen receptor,” J. Immunotherapy (2009) 32(7): 689-702.
Koste et al., “T-cell receptor transfer into human T cells with ecotropic retroviral vectors,” Gene Therapy (2014) 21: 533-538.
Kumar et al., “International Myeloma Working Group consensus criteria for response and minimal residual disease assessment in multiple myeloma,” Lancet Oncol (2016) 17(8):e328-e346.
Kuramitsu et al., “Lenalidomide enhances the function of chimeric antigen receptor T cells against the epidermal growth factor receptor variant III by enhancing immune synapses,” Cancer Gene Ther. (2015) 22(10):487-95.
Lamers et al., “Immune responses to transgene and retroviral vector in patients treated with ex vivo-engineered T cells,” Blood (2011) 117(1):72-82.
Lee et al.,, “Current concepts in the diagnosis and management of cytokine release syndrome,” Blood. (2014) 124(2):188-95.

(56) References Cited

OTHER PUBLICATIONS

Lee et al., Erratum for current concepts in the diagnosis and management of cytokine release syndrome. Blood. Aug. 20, 2015;126(8):1048.
Lefranc et al., "IMGT unique numbering for immunoglobulin and T cell receptor variable domains and Ig superfamily V-like domains," Dev Comp Immunol (2003) 27(1):55-77.
Legend Biotech Release dated Dec. 3, 2018, "Updated Data from Phase 1/2 Open-Label Study of BCMA-Directed CAR-T Cell Therapy LCAR-B38M Show Tolerable Safety Profile, High Overall Response and MRD Negative Rate in Treatment of Patients with Advanced Relapsed or Refractory Multiple Myeloma," 5 pgs.
Legend Biotech Release dated Apr. 15, 2019, "New Data from LEGEND-2 Study of LCAR-B38M BCMA CAR-T Therapy Show High Overall Response in Patients with Advanced Relapsed or Refractory Multiple Myeloma," 4 pgs.
Lehmberg et al., Consensus recommendations for the diagnosis and management of hemophagocytic lymphohistiocytosis associated with malignancies. Haematologica. Aug. 2015; 100(8): 997-1004.
Leone et al., "A2aR antagonists: Next generation checkpoint blockade for cancer immunotherapy," Comput Struct Biotechnol J. (2015) 13:265-272.
Lesokhin et al., "A Phase I, Open-Label Study to Evaluate the Safety, Pharmacokinetic, Pharmacodynamic, and Clinical Activity of PF-06863135, a B-Cell Maturation Antigen/CD3 Bispecific Antibody, in Patients with Relapsed/Refractory Advanced Multiple Myeloma," Blood (2018) 132 (Supplement 1): 3229.
Li et al., "Efficacy and Safety of Fully Human Bcma Targeting CAR T Cell Therapy in Relapsed/Refractory Multiple Myeloma," Blood (2019) 134 (Supplement_1): 929.
Li et al., "Optimization of humanized IgGs in glycoengineered Pichia pastoris," Nat Biotechnol. (2006) 24(2):210-5.
Lim et al., "Anti-CD20 monoclonal antibodies: historical and future perspectives," Haematologica (2010) 95(1):135-143.
Lin et al., "Recent updates on CAR T clinical trials for multiple myeloma," Mol Cancer. (2019) 18(1):154.
Lipson et al., "Durable Cancer Regression Off-Treatment and Effective Reinduction Therapy With an anti-PD-1 Antibody," Clin Cancer Res (2013) 19(2): 462-468.
Liu et al., "Inclusion of Strep-Tag II in design of antigen receptors for T cell immunotherapy," Nat Biotechnol. (2016) 34(4): 430-434.
Long et al., "4-1BB costimulation ameliorates T cell exhaustion induced by tonic signaling of chimeric antigen receptors," Nat Med. (2015) 21(6):581-90.
Lupton S. D. et al., "Dominant positive and negative selection using a hygromycin phosphotransferase-thymidine kinase fusion gene," Mol. and Cell Biol. (1991) 11(6): 3374-3378.
MacCallum et al., "Antibody-antigen interactions: Contact analysis and binding site topography," J. Mol. Biol. (1996) 262, 732-745.
Madduri et al., "Results from CARTITUDE-1: A Phase 1b/2 Study of JNJ-4528, a CAR-T Cell Therapy Directed Against B-Cell Maturation Antigen (BCMA), in Patients with Relapsed and/or Refractory Multiple Myeloma (R/R MM)," Blood. (2019) 134 (Supplement_1): 577.
Mailankody et al., JCARH125, anti-BCMA CAR T-cell therapy for relapsed/refractory multiple myeloma: initial proof of concept results from a phase 1/2 multicenter study (EVOLVE). Blood. 2018; 132(1); Abstract 957.
Mailankody et al., "Orvacabtagene autoleucel (orva-cel), a B-cell maturation antigen (BCMA)-directed CAR T cell therapy for patients (pts) with relapsed/refractory multiple myeloma (RRMM): update of the phase 1/2 EVOLVE study (NCT03430011)," Journal of Clinical Oncology. (2020) 38(15_suppl):8504-8504.
Manuri et al., "piggyBac transposon/transposase system to generate CD19-specific T cells for the treatment of B-lineage malignancies," Hum Gene Ther (2010) 21(4): 427-437.
Martin et al., "Modeling antibody hypervariable loops: a combined algorithm," Proc Natl Acad Sci U S A. (1989) 86(23): 9268-9272.
McWilliams et al., "Mutations in the 5' end of the human immunodeficiency virus type 1 polypurine tract affect RNase H cleavage specificity and virus titer," J Viral (2003) 77(20):11150-11157.
Menzies et al., "New combinations and immunotherapies for melanoma: latest evidence and clinical utility," Ther Adv Med Oncol (2013) 5(5):278-285.
Methods in Molecular Medicine, vol. 58: Metastasis Research Protocols, vol. 2: Cell Behavior In Vitro and In Vivo, p. 17-25 Edited by: S. A. Brooks and U. Schumacher © Humana Press Inc., Totowa, NJ.
Miller et al., "Improved retroviral vectors for gene transfer and expression," BioTechniques (1989) 7:980-990.
Miller et al., "Retrovirus packaging cells," Human Gene Therapy (1990) 1:5-14.
Miyagishi et al., "U6 promoter-driven siRNAs with four uridine 3' overhangs efficiently suppress targeted gene expression in mammalian cells" Nat Biotechnol (2002) 20(5):497-500.
Miyoshi et al. "Development of a self-inactivating lentivirus vector," J Viral (1998) 72(10):8150-8157.
Monney et al., "Th1-specific cell surface protein Tim-3 regulates macrophage activation and severity of an autoimmune disease," Nature (2002) 415(6871):536-541.
Mullard, A. "The BCMA bonanza," Nat Rev Drug Discov. (2019) 18(7):481-484.
Mullen et al., "Transfer of the bacterial gene for cytosine deaminase to mammalian cells confers lethal sensitivity to 5-fluorocytosine: a negative selection system," Proc Natl Acad Sci USA. (1992) 89(1):33-7.
Naldini et al., Efficient transfer, integration, and sustained long-term expression of the transgene in adult rat brains injected with a lentiviral vector, Proc Natl Acad Sci U S A. (1996) 93(21): 11382-11388.
Naldini et al., "In vivo gene delivery and stable transduction of nondividing cells by a lentiviral vector," Science. (1996) 272(5259): 263-267.
Naldini et al., "Lentiviruses as gene transfer agents for delivery to non-dividing cells", Curr Opin Biotechnol., Oct. 9, (1998); 5:457-63.
Ngiow et al., "Anti-TIM3 Antibody Promotes T Cell IFN-γ-mediated Antitumor Immunity and Suppresses Established Tumors," Cancer Res (2011) 71(10): 3540-3551.
O'Donnell et al., "New monoclonal antibodies on the horizon in multiple myeloma," Ther Adv Hematol. (2017) 8(2):41-53.
Ohta et al., "A2A adenosine receptor protects tumors from antitumor T cells," PNAS (2006) 103(35):13132-13137.
Oken et al., "Toxicity and response criteria of the Eastern Cooperative Oncology Group," Am J Clin Oncol (1982) 5(6):649-655.
Otahal et al., "Lenalidomide enhances antitumor functions of chimeric antigen receptor modified T cells," Oncoimmunology (2015) 5(4):e1115940.
Ott, et al., "CTLA-4 and PD-1/PD-L1 Blockade: New Immunotherapeutic Modalities with Durable Clinical Benefit in Melanoma Patients," Clin Cancer Res (2013) 19(19):5300-5309.
Pardoll, "The blockade of immune checkpoints in cancer immunotherapy," Nature Reviews Cancer (2012) 12:252-264.
Park et al.,, "Adoptive transfer of chimeric antigen receptor re-directed cytolytic T lymphocyte clones in patients with neuroblastoma," Molecular Therapy (2007) 15(4):825-833.
Park et al., "Treating cancer with genetically engineered T cells," Trends Biotechnol. (2011) 29(11): 550-557.
Philpott et al., "Use of Nonintegrating Lentiviral Vectors for Gene Therapy," Human Gene Therapy (2007) 18:483.
Pinna et al., "Novel investigational adenosine A2A receptor antagonists for Parkinson's disease," Expert Opin Investig Drugs (2009) 18:1619-1631.
Portolano et al., "Lack of promiscuity in autoantigen-specific H and L chain combinations as revealed by human H and L chain "roulette"," J. Immunol. (1993) 150:880-887.
Powell et al., "Sequence and structural determinants required for priming of plus-strand DNA synthesis by the human immunodeficiency virus type 1 polypurine tract," J Viral (1996) 70(8):5288-5296.

(56) References Cited

OTHER PUBLICATIONS

Powers et al., "PASylation of IL-1 receptor antagonist (IL-1Ra) retains IL-1 blockade and extends its duration in mouse urate crystal-induced peritonitis," J Biol Chem. (2020) 295(3):868-882.
Radvanyi et al., "Antagonist Antibodies to PD-1 and B7-H1 (PD-L1) in the Treatment of Advanced Human Cancer—Letter," Clin Cancer Res (2013) 19(19): 5541.
Raje et al., Anti-BCMA CAR T-cell therapy bb2121 in relapsed or refractory multiple myeloma. N Engl J Med. May 2, 2019; 380(18):1726-1737.
Raje et al., "Safety, Clinical Activity, Pharmacokinetics, and Pharmacodynamics from a Phase I Study of PF-06863135, a B-Cell Maturation Antigen (BCMA)-CD3 Bispecific Antibody, in Patients with Relapsed/Refractory Multiple Myeloma (RRMM)," Blood. (2019) 134 (Supplement_1): 1869.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3:319-338.
Robert et al., "What is the role of cytotoxic T lymphocyte-associated antigen 4 blockade in patients with metastatic melanoma? ," Oncologist (2009) 14(8):848-861.
Roberts et al., "Inhibition by adenosine of reactive oxygen metabolite production by human polymorphonuclear leucocytes," Biochem J (1985) 227(2):669-674.
Rosenberg, et al., "Cell transfer immunotherapy for metastatic solid cancer—what clinicians need to know," Nat Rev Clin Oncol. (2011) 8(10):577-85.
Sadelain et al., "The basic principles of chimeric antigen receptor design," Cancer Discov. (2013) 3(4): 388-398.
Savoldo et al., "CD28 costimulation improves expansion and persistence of chimeric antigen receptor-modified T cells in lymphoma patients," JCI (2011) 121(5):1822-1826.
Scarpa et al., "Characterization of recombinant helper retroviruses from Moloney-based vectors in ecotropic and amphotropic packaging cell lines," Virology (1991) 180:849-852.
Scatchard, G. (1949). "The Attractions of Proteins for Small Molecules and Ions," Annals of the New York Academy of Sciences, Department of Chemistry, Massachusetts Institute of Technology, MA, 51(4)660-672.
Schrier et al., "The effects of adenosine agonists on human neutrophil function," J Immunol (1986) 137(10):3284-3289.
Sharma et al., "Efficient sleeping beauty DNA transposition from DNA minicircles," Molec Ther Nucl Acids (2013) 2, e74.
Shimabukuro-Vornhagen et al., "Cytokine release syndrome," J Immunother Cancer. (2018) 6(1):56.
Shinohara et al., "Structure and Chromosomal Localization of the Human PD-1 Gene (PDCD1)," Genomics (1994) 23(3): 704-706.
Sitkovsky, M. et al. "Hostile, Hypoxia-A2-Adenosinergic Tumor Biology as the Next Barrier to Overcome for Tumor Immunologists," Cancer Immunol. Res. (2014) 2(7):598-605, 15 pages.
Smith et al., "Ex vivo expansion of human T cells for adoptive immunotherapy using the novel xeno-free CTS immune cell serum replacement," Clin Transl Immunol (2015) 4:e31.
Sorensen et al., "Performance status assessment in cancer patients. An inter-observer variability study," Br J Cancer (1993) 67(4):773-775.
Steiner et al., "CAR-T cells in multiple myeloma: current status," memo—Magazine of European Medical Oncology (2020) 13: 43-49.
Sterner et al., "GM-CSF Blockade during Chimeric Antigen Receptor T Cell Therapy Reduces Cytokine Release Syndrome and Neurotoxicity and May Enhance Their Effector Functions," Blood. (2018) 132 (Supplement 1): 961.
Sterner et al., "GM-CSF inhibition reduces cytokine release syndrome and neuroinflammation but enhances CAR-T cell function in xenografts," Blood. (2019) 133 (7): 697-709.
Tai et al., "Novel anti-B-cell maturation antigen antibody-drug conjugate (GSK2857916) selectively induces killing of multiple myeloma," Blood (2014) 123(20):3128-3138.
Tai et al., "Antibody-based therapies in multiple myeloma," Bone Marrow Res. (2011) 2011:924058.
Tarassishin et al., "LPS and IL-1 differentially activate mouse and human astrocytes: role of CD14," Glia.(2014) 62(6):999-1013.
Teachey et al., "Identification of Predictive Biomarkers for Cytokine Release Syndrome after Chimeric Antigen Receptor T-cell therapy for Acute Lymphoblastic Leukemia." Cancer Discovery (2016) 6(6): 664-679.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Timmerman et al., "Functional reconstruction and synthetic mimicry of a conformational epitope using CLIPS technology," J Mol Recognit (2007) 20(5):283-299.
Topalian, S.L. et al., "Safety, activity, and immune correlates of anti-PD-1 antibody in cancer," New England Journal of Medicine. (2012) 366:2443-2454.
Topp et al., "Evaluation of AMG 420, an anti-BCMA bispecific T-cell engager (BiTE) immunotherapy, in R/R multiple myeloma (MM) patients: Updated results of a first-in-human (FIH) phase I dose escalation study," Journal of Clinical Oncology. 2019. 37(15) 8007.
Tsukahara et al., "CD19 target-engineered T-cells accumulate at tumor lesions in human B-cell lymphoma xenograft mouse models," Biochem Biophys Res Commun (2013) 438(1): 84-9.
Turtle et al., "Engineered T cells for anti-cancer therapy," Curr. Opin. Immunol. (2012) 24(5): 633-39.
Van Epps et al., "SEA-BCMA: A highly active enhanced antibody for multiple myeloma," Cancer Res (2018) 78 (13_Supplement): 3833.
Van Tendeloo et al., "High-level transgene expression in primary human T lymphocytes and adult bone marrow CD34+ cells via electroporation-mediated gene delivery," Gene Therapy (2000) 7(16): 1431-1437.
Verhoeyen et al., "Lentiviral vector gene transfer into human T cells," Methods Mol Biol. (2009) 506: 97-114.
Wada et al., "Sequencing CTLA-4 blockade with cell-based immunotherapy for prostate cancer," J Transl Med (2013) 11:89.
Wadhwa et al., "Receptor mediated glycotargeting," J. Drug Targeting (1995) 3(2):111-127.
Wang et al., "Phenotypic and functional attributes of lentivirus-modified CD19-specific human CD8+ central memory T cells manufactured at clinical scale," J Immunother. (2012) 35(9):689-701.
Wang et al., "Long-Term Follow-up of a Phase 1, First-in-Human Open-Label Study of LCAR-B38M, a Structurally Differentiated Chimeric Antigen Receptor T (CAR-T) Cell Therapy Targeting B-Cell Maturation Antigen (BCMA), in Patients (pts) with Relapsed/Refractory Multiple Myeloma (RRMM)," Blood. 2019. 134 (Supplement_1): 579.
Weber, "Review: Anti-CTLA-4 Antibody Ipilimumab: Case Studies of Clinical Response and Immune-Related Adverse Events," The Oncologist (2007) 12(7):864-872.
Wigler et al., "Transfer of purified herpes virus thymidine kinase gene to cultured mouse cells," Cell (1977) 11(1):223-232.
Wilson, "Tech.Sight. Analyzing biomolecular interactions," Science (2002) 295(5562): 2103-2105.
Wolff et al., "Monoclonal Antibody Homodimers: Enhanced Antitumor Activity in Nude Mice," Can Res. (1993) 53:2560-2565.
Wu et al., "Adoptive T-cell therapy using autologous tumor-infiltrating lymphocytes for metastatic melanoma: current status and future outlook," Cancer (2012) 18(2): 160-75.
Xing et al., "Anti-Bcma PBD MEDI2228 Combats Drug Resistance and Synergizes with Bortezomib and Inhibitors to DNA Damage Response in Multiple Myeloma," Blood. (2019) 134 (Supplement_1): 1817.
Xu et al., "Cytokine release syndrome in cancer immunotherapy with chimeric antigen receptor engineered T cells," Cancer Letters (2014) 343(2):172-178.

(56) References Cited

OTHER PUBLICATIONS

Xu et al., "Exploratory trial of a biepitopic CAR T-targeting B cell maturation antigen in relapsed/refractory multiple myeloma," Proc Natl Acad Sci USA. (2019) 116(19):9543-9551.
Yao et al., "Developing a Novel Anti-Bcma CAR-T for Relapsed or Refractory Multiple Myeloma," Blood. 2019; 134(Supplement_1):50.
Zhang et al., "CD73: a novel target for cancer immunotherapy," Cancer Res (2010) 70(16):6407-6411.
Zhao et al., "A Phase 1, Open-Label Study Oflcar-B38M, A Chimeric Antigen Receptor T Cell Therapy Directed Against B Cell Maturation Antigen, In Patients With Relapsed or Refractory Multiple Myeloma," Journal Of Hematology & Oncology (2018) 11(141):1-8.
Zheng et al., "Protein L: a novel reagent for the detection of chimeric antigen receptor (CAR) expression by flow cytometry," J Transl Med (2012) 10:29, 6 pages.
Zheng et al., "A novel anti-CEACAM5 monoclonal antibody, CC4, suppresses colorectal tumor growth and enhances NK cells-mediated tumor immunity," PLoS One. (2011) 6(6):e21146.
Zufferey et al. "Self-Inactivating Lentivirus Vector for Safe and Efficient In Vivo Gene Delivery," J. Viral (1998) 72(12):9873-9880.
Zufferey et al., "Multiply attenuated lentiviral vector achieves efficient gene delivery in vivo," Nat Biotechnol. Sep. 1997;15(9):871-875.
Giavridis et al., "Car T cell-induced cytokine release syndrome is mediated by macrophages and abated by IL-1 blockade," Nat Med (Jun. 2018, e-pub. May 2, 20188) 24(6):731-738.

* cited by examiner

SEQUENCE LISTING

<160> NUMBER OF SEQ ID NOS: 312

<210> SEQ ID NO 1
<211> LENGTH: 15
<212> TYPE: PRT
<213> ORGANISM: Artificial Sequence
<220> FEATURE:
<223> OTHER INFORMATION: (4GS)3 linker

<400> SEQUENCE: 1

```
Gly Gly Gly Gly Ser Gly Gly Gly Gly Ser Gly Gly Gly Gly Ser
1               5                   10                  15
```

<210> SEQ ID NO 2
<211> LENGTH: 4
<212> TYPE: PRT
<213> ORGANISM: Artificial Sequence
<220> FEATURE:
<223> OTHER INFORMATION: 3GS linker

<400> SEQUENCE: 2

```
Gly Gly Gly Ser
1
```

<210> SEQ ID NO 3
<211> LENGTH: 41
<212> TYPE: DNA
<213> ORGANISM: Artificial Sequence
<220> FEATURE:
<223> OTHER INFORMATION: 4-1BB/CD3 zeta predicted splice acceptor site

<400> SEQUENCE: 3

```
gctgagagtc aagttttcca ggtccgccga cgctccagcc t                        41
```

<210> SEQ ID NO 4
<211> LENGTH: 42
<212> TYPE: PRT
<213> ORGANISM: Artificial Sequence
<220> FEATURE:
<223> OTHER INFORMATION: 4-1BB-derived intracellular co-signaling
      sequence

<400> SEQUENCE: 4

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 5
<211> LENGTH: 126
<212> TYPE: DNA
<213> ORGANISM: Artificial Sequence
<220> FEATURE:
<223> OTHER INFORMATION: 4-1BB-derived intracellular co-signaling
      sequence

<400> SEQUENCE: 5

```
aagcggggga gaaagaaact gctgtatatt ttcaaacagc cctttatgag acctgtgcag     60

actacccagg aggaagacgg atgcagctgt aggtttcccg aggaagagga aggaggctgt    120

gagctg                                                               126
```

<210> SEQ ID NO 6

<211> LENGTH: 126
<212> TYPE: DNA
<213> ORGANISM: Artificial Sequence
<220> FEATURE:
<223> OTHER INFORMATION: 4-1BB-derived intracellular co-signaling sequence

<400> SEQUENCE: 6
aagcggggca gaaagaagct gctctacatc ttcaagcagc ccttcatgcg gcccgtgcag 60
accacacaag aggaagatgg ctgctcctgc agattccccg aggaagaaga aggcggctgc 120
gagctg 126

<210> SEQ ID NO 7
<211> LENGTH: 5
<212> TYPE: PRT
<213> ORGANISM: Artificial Sequence
<220> FEATURE:
<223> OTHER INFORMATION: 4GS linker

<400> SEQUENCE: 7

Gly Gly Gly Gly Ser
1 5

<210> SEQ ID NO 8
<211> LENGTH: 684
<212> TYPE: DNA
<213> ORGANISM: Artificial Sequence
<220> FEATURE:
<223> OTHER INFORMATION: Alternative CO/SSE spacer

<400> SEQUENCE: 8
gaatctaagt acggaccgcc ttgtcctcct tgtcccgctc ctcctgttgc cggaccttcc 60
gtgttcctgt ttcctccaaa gcctaaggac accctgatga tcagcaggac ccctgaagtg 120
acctgcgtgg tggtggatgt gtcccaagag gatcccgagg tgcagttcaa ctggtatgtg 180
gacggcgtgg aagtgcacaa cgccaagacc aagcctagag aggaacagtt ccagagcacc 240
tacagagtgg tgtccgtgct gacagtgctg caccaggatt ggctgaacgg caaagagtac 300
aagtgcaagg tgtccaacaa gggcctgcct agcagcatcg agaaaaccat ctccaaggcc 360
aagggccagc caagagagcc ccaggtttac acactgcctc caagccaaga ggaaatgacc 420
aagaatcagg tgtccctgac atgcctggtc aagggcttct acccctccga tatcgccgtg 480
gaatgggaga gcaatggcca gcctgagaac aactacaaga ccacacctcc tgtgctggac 540
agcgacggca gtttcttcct gtatagtaga ctcaccgtgg ataaatcaag atggcaagag 600
ggcaacgtgt tcagctgcag cgtgatgcac gaggccctgc acaaccacta cacccagaaa 660
agcctgagcc tgtctctggg caag 684

<210> SEQ ID NO 9
<211> LENGTH: 1959
<212> TYPE: DNA
<213> ORGANISM: Artificial Sequence
<220> FEATURE:
<223> OTHER INFORMATION: anti-BMCA CAR

<400> SEQUENCE: 9
gaggtgcagc tggtggagtc cggaggaggc ctggtgaagc caggaggctc cctgaggctg 60
tcttgcgcag ccagcggctt cacctttagc gactactata tgtcctggat cagacaggca 120
cctggcaagg gcctggagtg ggtgagctac atcagctcct ctggctccac aatctactat 180
gccgactctg tgaagggccg gtttaccatc agcagagata acgccaagaa ttccctgtat 240

```
ctgcagatga acagcctgag ggccgaggac acagccgtgt actattgcgc caaggtggac    300

ggcgattaca ccgaggatta ttggggccag ggcacactgg tgaccgtgag ctccggcggc    360

ggcggctctg gaggaggagg cagcggcgga ggaggctccc agtctgccct gacacagcca    420

gccagcgtgt ccggctctcc cggacagtcc atcacaatct cttgtaccgg ctctagctcc    480

gacgtgggca agtacaacct ggtgtcctgg tatcagcagc cccctggcaa ggcccctaag    540

ctgatcatct acgatgtgaa caagaggcca tctggcgtga gcaatcgctt cagcggctcc    600

aagtctggca ataccgccac actgaccatc agcggcctgc agggcgacga tgaggcagat    660

tactattgtt ctagctacgg cggcagcaga tcctacgtgt tcggcacagg caccaaggtg    720

accgtgctgg aatctaagta cggaccgcct tgtcctcctt gtcccgctcc tcctgttgcc    780

ggaccttccg tgttcctgtt tcctccaaag cctaaggaca ccctgatgat cagcaggacc    840

cctgaagtga cctgcgtggt ggtggatgtg tcccaagagg atcccgaggt gcagttcaac    900

tggtatgtgg acggcgtgga agtgcacaac gccaagacca agcctagaga ggaacagttc    960

cagagcacct acagagtggt gtccgtgctg acagtgctgc accaggattg gctgaacggc   1020

aaagagtaca agtgcaaggt gtccaacaag ggcctgccta gcagcatcga gaaaaccatc   1080

tccaaggcca agggccagcc aagagagccc caggtttaca cactgcctcc aagccaagag   1140

gaaatgacca agaatcaggt gtccctgaca tgcctggtca agggcttcta cccctccgat   1200

atcgccgtgg aatgggagag caatggccag cctgagaaca actacaagac cacacctcct   1260

gtgctggaca gcgacggcag tttcttcctg tatagtagac tcaccgtgga taaatcaaga   1320

tggcaagagg gcaacgtgtt cagctgcagc gtgatgcacg aggccctgca caaccactac   1380

acccagaaaa gcctgagcct gtctctgggc aagatgttct gggtgctcgt ggtcgttggc   1440

ggagtgctgg cctgttacag cctgctggtt accgtggcct tcatcatctt ttgggtcaag   1500

cggggcagaa agaagctgct ctacatcttc aagcagccct tcatgcggcc cgtgcagacc   1560

acacaagagg aagatggctg ctcctgcaga ttccccgagg aagaagaagg cggctgcgag   1620

ctgagagtga agttcagcag atccgccgac gctccagcct atcagcaggg ccaaaaccag   1680

ctgtacaacg agctgaacct ggggagaaga gaagagtacg acgtgctgga taagcggaga   1740

ggcagagatc ctgaaatggg cggcaagccc agacggaaga atcctcaaga gggcctgtat   1800

aatgagctgc agaaagacaa gatggccgag gcctacagcg agatcggaat gaagggcgag   1860

cgcagaagag gcaagggaca cgatggactg taccagggcc tgagcaccgc caccaaggat   1920

acctatgacg cactgcacat gcaggccctg ccacctaga                           1959
```

<210> SEQ ID NO 10
<211> LENGTH: 1950
<212> TYPE: DNA
<213> ORGANISM: Artificial Sequence
<220> FEATURE:
<223> OTHER INFORMATION: anti-BMCA CAR

<400> SEQUENCE: 10

```
gaggtgcagc tggtgcagag cggaggaggc ctggtgcagc ctggcaggtc cctgcgcctg     60

tcttgcaccg ccagcggctt cacatttggc gactatgcca tgtcctggtt caagcaggca    120

ccaggcaagg gcctggagtg ggtgggcttt atccgctcta aggcctacgg cggcaccaca    180

gagtatgccg ccagcgtgaa gggccggttc accatcagcc gggacgactc taagagcatc    240

gcctacctgc agatgaactc tctgaagacc gaggacacag ccgtgtacta ttgcgcagca    300
```

tggagcgccc caaccgatta ttggggccag ggcaccctgg tgacagtgag ctccggcggc 360
ggcggctctg gaggaggagg aagcggagga ggaggatccg acatccagat gacacagtcc 420
cctgcctttc tgtccgcctc tgtgggcgat agggtgaccg tgacatgtcg cgcctcccag 480
ggcatctcta actacctggc ctggtatcag cagaagcccg gcaatgcccc tcggctgctg 540
atctacagcg cctccaccct gcagagcgga gtgccctccc ggttcagagg aaccggctat 600
ggcacagagt tttctctgac catcgacagc ctgcagccag aggatttcgc cacatactat 660
tgtcagcagt cttacaccag ccggcagaca tttggccccg gcacaagact ggatatcaag 720
gagtctaaat acggaccgcc ttgtcctcct tgtcccgctc ctcctgttgc cggaccttcc 780
gtgttcctgt ttcctccaaa gcctaaggac accctgatga tcagcaggac ccctgaagtg 840
acctgcgtgg tggtggatgt gtcccaagag gatcccgagg tgcagttcaa ctggtatgtg 900
gacggcgtgg aagtgcacaa cgccaagacc aagcctagag aggaacagtt ccagagcacc 960
tacagagtgg tgtccgtgct gacagtgctg caccaggatt ggctgaacgg caaagagtac 1020
aagtgcaagg tgtccaacaa gggcctgcct agcagcatcg agaaaaccat ctccaaggcc 1080
aagggccagc caagagagcc ccaggtttac acactgcctc caagccaaga ggaaatgacc 1140
aagaatcagg tgtccctgac atgcctggtc aagggcttct acccctccga tatcgccgtg 1200
gaatgggaga gcaatggcca gcctgagaac aactacaaga ccacacctcc tgtgctggac 1260
agcgacggca gtttcttcct gtatagtaga ctcaccgtgg ataaatcaag atggcaagag 1320
ggcaacgtgt tcagctgcag cgtgatgcac gaggccctgc acaaccacta cacccagaaa 1380
agcctgagcc tgtctctggg caagatgttc tgggtgctcg tggtcgttgg cggagtgctg 1440
gcctgttaca gcctgctggt taccgtggcc ttcatcatct tttgggtcaa gcggggcaga 1500
aagaagctgc tctacatctt caagcagccc ttcatgcggc ccgtgcagac cacacaagag 1560
gaagatggct gctcctgcag attccccgag gaagaagaag gcggctgcga gctgagagtg 1620
aagttcagca gatccgccga cgctccagcc tatcagcagg gccaaaacca gctgtacaac 1680
gagctgaacc tggggagaag agaagagtac gacgtgctgg ataagcggag aggcagagat 1740
cctgaaatgg gcggcaagcc cagacggaag aatcctcaag agggcctgta taatgagctg 1800
cagaaagaca agatggccga ggcctacagc gagatcggaa tgaagggcga gcgcagaaga 1860
ggcaagggac acgatggact gtaccagggc ctgagcaccg ccaccaagga tacctatgac 1920
gcactgcaca tgcaggccct gccacctaga 1950

<210> SEQ ID NO 11
<211> LENGTH: 1953
<212> TYPE: DNA
<213> ORGANISM: Artificial Sequence
<220> FEATURE:
<223> OTHER INFORMATION: anti-BMCA CAR

<400> SEQUENCE: 11
gaggtgcagc tggtggagtc cggaggaggc ctggtgaagc caggaggctc tctgaggctg 60
agctgcgcag cctccggctt caccttttct gactactata tgagctggat caggcaggca 120
ccaggcaagg gcctggagtg ggtgtcttac atcagctcct ctggcagcac aatctactat 180
gccgactccg tgaagggcag gttcaccatc tctcgcgata acgccaagaa tagcctgtat 240
ctgcagatga actccctgcg ggccgaggat acagccgtgt actattgcgc caaggtggac 300
ggcccccctt cctttgatat ctggggccag ggcacaatgg tgaccgtgag ctccggagga 360
ggaggatccg gcggaggagg ctctggcggc ggcggctcta gctatgtgct gacccagcca 420
ccatccgtgt ctgtggcacc tggacagaca gcaaggatca cctgtggagc aaacaatatc 480
ggcagcaagt ccgtgcactg gtaccagcag aagcctggcc aggccccaat gctggtggtg 540
tatgacgatg acgatcggcc cagcggcatc cctgagagat ttctggcag caactccggc 600 aataccgcca cactgaccat ctctggagtg gaggcaggcg acgaggcaga ttacttctgt 660
cacctgtggg accggagcag agatcactac gtgttcggca caggcaccaa gctgaccgtg 720
ctggaatcta agtacggacc gccttgtcct ccttgtcccg ctcctcctgt tgccggacct 780
tccgtgttcc tgtttcctcc aaagcctaag gacaccctga tgatcagcag gacccctgaa 840
gtgacctgcg tggtggtgga tgtgtcccaa gaggatcccg aggtgcagtt caactggtat 900
gtggacggcg tggaagtgca caacgccaag accaagccta gagaggaaca gttccagagc 960
acctacagag tggtgtccgt gctgacagtg ctgcaccagg attggctgaa cggcaaagag 1020
tacaagtgca aggtgtccaa caagggcctg cctagcagca tcgagaaaac catctccaag 1080
gccaagggcc agccaagaga gccccaggtt tacacactgc ctccaagcca agaggaaatg 1140
accaagaatc aggtgtccct gacatgcctg gtcaagggct tctacccctc cgatatcgcc 1200
gtggaatggg agagcaatgg ccagcctgag aacaactaca agaccacacc tcctgtgctg 1260
gacagcgacg gcagtttctt cctgtatagt agactcaccg tggataaatc aagatggcaa 1320
gagggcaacg tgttcagctg cagcgtgatg cacgaggccc tgcacaacca ctacacccag 1380
aaaagcctga gcctgtctct gggcaagatg ttctgggtgc tcgtggtcgt tggcggagtg 1440
ctggcctgtt acagcctgct ggttaccgtg gccttcatca tcttttgggt caagcggggc 1500
agaaagaagc tgctctacat cttcaagcag cccttcatgc ggcccgtgca gaccacacaa 1560
gaggaagatg gctgctcctg cagattcccc gaggaagaag aaggcggctg cgagctgaga 1620
gtgaagttca gcagatccgc cgacgctcca gcctatcagc agggccaaaa ccagctgtac 1680
aacgagctga acctggggag aagagaagag tacgacgtgc tggataagcg gagaggcaga 1740
gatcctgaaa tgggcggcaa gcccagacgg aagaatcctc aagagggcct gtataatgag 1800
ctgcagaaag acaagatggc cgaggcctac agcgagatcg gaatgaaggg cgagcgcaga 1860
agaggcaagg gacacgatgg actgtaccag ggcctgagca ccgccaccaa ggatacctat 1920
gacgcactgc acatgcaggc cctgccacct aga 1953

<210> SEQ ID NO 12
<211> LENGTH: 1974
<212> TYPE: DNA
<213> ORGANISM: Artificial Sequence
<220> FEATURE:
<223> OTHER INFORMATION: anti-BMCA CAR

<400> SEQUENCE: 12
agctatgagc tgacacagcc tccaagcgcc tctggcacac ctggacagcg agtgacaatg 60
agctgtagcg gcaccagcag caacatcggc agccacagcg tgaactggta tcagcagctg 120
cctggcacag cccctaaact gctgatctac accaacaacc agcggcctag cggcgtgccc 180
gatagatttt ctggcagcaa gagcggcaca agcgccagcc tggctatttc tggactgcag 240
agcgaggacg aggccgacta ttattgtgcc gcctgggacg gctctctgaa cggccttgtt 300
tttggcggag gcaccaagct gacagtgctg ggatctagag gtggcggagg atctggcggc 360
ggaggaagcg gaggcggcgg atctcttgaa atggctgaag tgcagctggt gcagtctggc 420
gccgaagtga agaagcctgg cgagagcctg aagatcagct gcaaaggcag cggctacagc 480

```
ttcaccagct actggatcgg ctgggtccga cagatgcctg gcaaaggcct tgagtggatg    540
ggcatcatct accccggcga cagcgacacc agatacagcc ctagctttca gggccacgtg    600
accatcagcg ccgacaagtc tatcagcacc gcctacctgc agtggtccag cctgaaggcc    660
tctgacaccg ccatgtacta ctgcgccaga tactctggca gcttcgacaa ttggggccag    720
ggcacactgg tcaccgtgtc cagcgagtct aaatacggac cgccttgtcc tccttgtccc    780
gctcctcctg ttgccggacc ttccgtgttc ctgtttcctc caaagcctaa ggacaccctg    840
atgatcagca ggacccctga agtgacctgc gtggtggtgg atgtgtccca agaggatccc    900
gaggtgcagt tcaactggta tgtggacggc gtggaagtgc acaacgccaa gaccaagcct    960
agagaggaac agttccagag cacctacaga gtggtgtccg tgctgacagt gctgcaccag   1020
gattggctga acggcaaaga gtacaagtgc aaggtgtcca acaagggcct gcctagcagc   1080
atcgagaaaa ccatctccaa ggccaagggc cagccaagag agccccaggt ttacacactg   1140
cctccaagcc aagaggaaat gaccaagaat caggtgtccc tgacatgcct ggtcaagggc   1200
ttctacccct ccgatatcgc cgtggaatgg gagagcaatg gccagcctga gaacaactac   1260
aagaccacac ctcctgtgct ggacagcgac ggcagtttct tcctgtatag tagactcacc   1320
gtggataaat caagatggca agagggcaac gtgttcagct gcagcgtgat gcacgaggcc   1380
ctgcacaacc actacaccca gaaaagcctg agcctgtctc tgggcaagat gttctgggtg   1440
ctcgtggtcg ttggcggagt gctggcctgt tacagcctgc tggttaccgt ggccttcatc   1500
atcttttggg tcaagcgggg cagaaagaag ctgctctaca tcttcaagca gcccttcatg   1560
cggcccgtgc agaccacaca agaggaagat ggctgctcct gcagattccc cgaggaagaa   1620
gaaggcggct gcgagctgag agtgaagttc agcagatccg ccgacgctcc agcctatcag   1680
cagggccaaa accagctgta caacgagctg aacctgggga gaagagaaga gtacgacgtg   1740
ctggataagc ggagaggcag agatcctgaa atgggcggca agcccagacg gaagaatcct   1800
caagagggcc tgtataatga gctgcagaaa gacaagatgg ccgaggccta cagcgagatc   1860
ggaatgaagg gcgagcgcag aagaggcaag ggacacgatg gactgtacca gggcctgagc   1920
accgccacca aggataccta tgacgcactg cacatgcagg ccctgccacc taga         1974
```

<210> SEQ ID NO 13
<211> LENGTH: 1962
<212> TYPE: DNA
<213> ORGANISM: Artificial Sequence
<220> FEATURE:
<223> OTHER INFORMATION: anti-BMCA CAR

<400> SEQUENCE: 13

```
cagtctgccc tgacacagcc tgccagcgtt agtgctagtc ccggacagtc tatcgccatc     60
agctgtaccg gcaccagctc tgacgttggc tggtatcagc agcaccctgg caaggcccct    120
aagctgatga tctacgagga cagcaagagg cccagcggcg tgtccaatag attcagcggc    180
agcaagagcg gcaacaccgc cagcctgaca attagcggac tgcaggccga ggacgaggcc    240
gattactact gcagcagcaa cacccggtcc agcacactgg tttttggcgg aggcaccaag    300
ctgacagtgc tgggatctag aggtggcgga ggatctggcg gcggaggaag cggaggcggc    360
ggatctcttg aaatggctga agtgcagctg gtgcagtctg gcgccgagat gaagaaacct    420
ggcgcctctc tgaagctgag ctgcaaggcc agcggctaca ccttcatcga ctactacgtg    480
tactggatgc ggcaggcccc tggacaggga ctcgaatcta tgggctggat caaccccaat    540
agcggcggca ccaattacgc ccagaaattc cagggcagag tgaccatgac cagagacacc    600
```

```
agcatcagca ccgcctacat ggaactgagc cggctgagat ccgacgacac cgccatgtac     660

tactgcgcca gatctcagcg cgacggctac atggattatt ggggccaggg aaccctggtc     720

accgtgtcca gcgagtctaa atacggaccg ccttgtcctc cttgtcccgc tcctcctgtt     780

gccggacctt ccgtgttcct gtttcctcca aagcctaagg acaccctgat gatcagcagg     840

acccctgaag tgacctgcgt ggtggtggat gtgtcccaag aggatcccga ggtgcagttc     900

aactggtatg tggacggcgt ggaagtgcac aacgccaaga ccaagcctag agaggaacag     960

ttccagagca cctacagagt ggtgtccgtg ctgacagtgc tgcaccagga ttggctgaac    1020

ggcaaagagt acaagtgcaa ggtgtccaac aagggcctgc ctagcagcat cgagaaaacc    1080

atctccaagg ccaagggcca gccaagagag ccccaggttt acacactgcc tccaagccaa    1140

gaggaaatga ccaagaatca ggtgtccctg acatgcctgg tcaagggctt ctacccctcc    1200

gatatcgccg tggaatggga gagcaatggc cagcctgaga acaactacaa gaccacacct    1260

cctgtgctgg acagcgacgg cagtttcttc ctgtatagta gactcaccgt ggataaatca    1320

agatggcaag agggcaacgt gttcagctgc agcgtgatgc acgaggccct gcacaaccac    1380

tacacccaga aaagcctgag cctgtctctg ggcaagatgt tctgggtgct cgtggtcgtt    1440

ggcggagtgc tggcctgtta cagcctgctg gttaccgtgg ccttcatcat cttttgggtc    1500

aagcggggca gaaagaagct gctctacatc ttcaagcagc ccttcatgcg gcccgtgcag    1560

accacacaag aggaagatgg ctgctcctgc agattccccg aggaagaaga aggcggctgc    1620

gagctgagag tgaagttcag cagatccgcc gacgctccag cctatcagca gggccaaaac    1680

cagctgtaca acgagctgaa cctggggaga agagaagagt acgacgtgct ggataagcgg    1740

agaggcagag atcctgaaat gggcggcaag cccagacgga agaatcctca agagggcctg    1800

tataatgagc tgcagaaaga caagatggcc gaggcctaca gcgagatcgg aatgaagggc    1860

gagcgcagaa gaggcaaggg acacgatgga ctgtaccagg gcctgagcac cgccaccaag    1920

gatacctatg acgcactgca catgcaggcc ctgccaccta ga                        1962
```

<210> SEQ ID NO 14
<211> LENGTH: 1959
<212> TYPE: DNA
<213> ORGANISM: Artificial Sequence
<220> FEATURE:
<223> OTHER INFORMATION: anti-BMCA CAR

<400> SEQUENCE: 14

```
cagtctgccc tgacacagcc tgccagcgtt agtgctagtc ccggacagtc tatcgccatc      60

agctgtaccg gcaccagctc tgacgttggc tggtatcagc agcaccctgg caaggcccct     120

aagctgatga tctacgagga cagcaagagg cccagcggcg tgtccaatag attcagcggc     180

agcaagagcg gcaacaccgc cagcctgaca attagcggac tgcaggccga ggacgaggcc     240

gattactact gcagcagcaa cacccggtcc agcacactgg tttttggcgg aggcaccaag     300

ctgacagtgc tgggatctag aggtggcgga ggatctggcg gcggaggaag cggaggcggc     360

ggatctcttg aaatggctga agtgcagctg gtgcagtctg gcgccgagat gaagaaacct     420

ggcgcctctc tgaagctgag ctgcaaggcc agcggctaca ccttcatcga ctactacgtg     480

tactggatgc ggcaggcccc tggacaggga ctcgaatcta tgggctggat caaccccaat     540

agcggcggca ccaattacgc ccagaaattc cagggcagag tgaccatgac cagagacacc     600

agcatcagca ccgcctacat ggaactgagc cggctgagat ccgacgacac cgccatgtac     660
```

```
tactgcgcca gatctcagcg cgacggctac atggattatt ggggccaggg aaccctggtc    720

accgtgtcca gcgagtctaa atacggaccg ccttgtcctc cttgtcccgc tcctcctgtt    780

gccggacctt ccgtgttcct gtttcctcca aagcctaagg acaccctgat gatcagcagg    840

acccctgaag tgacctgcgt ggtggtggat gtgtcccaag aggatcccga ggtgcagttc    900

aactggtatg tggacggcgt ggaagtgcac aacgccaaga ccaagcctag agaggaacag    960

ttccagagca cctacagagt ggtgtccgtg ctgacagtgc tgcaccagga ttggctgaac   1020

ggcaaagagt acaagtgcaa ggtgtccaac aagggcctgc ctagcagcat cgagaaaacc   1080

atctccaagg ccaagggcca gccaagagag ccccaggttt acacactgcc tccaagccaa   1140

gaggaaatga ccaagaatca ggtgtccctg acatgcctgg tcaagggctt ctacccctcc   1200

gatatcgccg tggaatggga gagcaatggc cagcctgaga acaactacaa gaccacacct   1260

cctgtgctgg acagcgacgg cagtttcttc ctgtatagta gactcaccgt ggataaatca   1320

agatggcaag agggcaacgt gttcagctgc agcgtgatgc acgaggccct gcacaaccac   1380

tacacccaga aaagcctgag cctgtctctg ggcaagatgt tctgggtgct cgtggtcgtt   1440

ggcggagtgc tggcctgtta cagcctgctg gttaccgtgg ccttcatcat cttttgggtc   1500

aggagtaaga ggagcaggct cctgcacagt gactacatga acatgactcc ccgccgcccc   1560

gggcccaccc gcaagcatta ccagccctat gccccaccac gcgacttcgc agcctatcgc   1620

tccagagtga agttcagcag atccgccgac gctccagcct atcagcaggg ccaaaaccag   1680

ctgtacaacg agctgaacct ggggagaaga gaagagtacg acgtgctgga taagcggaga   1740

ggcagagatc ctgaaatggg cggcaagccc agacggaaga atcctcaaga gggcctgtat   1800

aatgagctgc agaaagacaa gatggccgag gcctacagcg agatcggaat gaagggcgag   1860

cgcagaagag gcaagggaca cgatggactg taccagggcc tgagcaccgc caccaaggat   1920

acctatgacg cactgcacat gcaggccctg ccacctaga                          1959
```

<210> SEQ ID NO 15
<211> LENGTH: 653
<212> TYPE: PRT
<213> ORGANISM: Artificial Sequence
<220> FEATURE:
<223> OTHER INFORMATION: anti-BMCA CAR

<400> SEQUENCE: 15

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Asp Tyr Thr Glu Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
```

```
    130                 135                 140

Gly Ser Pro Gly Gln Ser Ile Thr Ile Ser Cys Thr Gly Ser Ser Ser
145                 150                 155                 160

Asp Val Gly Lys Tyr Asn Leu Val Ser Trp Tyr Gln Gln Pro Pro Gly
                165                 170                 175

Lys Ala Pro Lys Leu Ile Ile Tyr Asp Val Asn Lys Arg Pro Ser Gly
            180                 185                 190

Val Ser Asn Arg Phe Ser Gly Ser Lys Ser Gly Asn Thr Ala Thr Leu
        195                 200                 205

Thr Ile Ser Gly Leu Gln Gly Asp Asp Glu Ala Asp Tyr Tyr Cys Ser
    210                 215                 220

Ser Tyr Gly Gly Ser Arg Ser Tyr Val Phe Gly Thr Gly Thr Lys Val
225                 230                 235                 240

Thr Val Leu Glu Ser Lys Tyr Gly Pro Pro Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Gln Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
        435                 440                 445

Cys Ser Val Met His Glu Ala Leu His Asn His Tyr Thr Gln Lys Ser
    450                 455                 460

Leu Ser Leu Ser Leu Gly Lys Met Phe Trp Val Leu Val Val Val Gly
465                 470                 475                 480

Gly Val Leu Ala Cys Tyr Ser Leu Leu Val Thr Val Ala Phe Ile Ile
                485                 490                 495

Phe Trp Val Lys Arg Gly Arg Lys Lys Leu Leu Tyr Ile Phe Lys Gln
            500                 505                 510

Pro Phe Met Arg Pro Val Gln Thr Thr Gln Glu Glu Asp Gly Cys Ser
        515                 520                 525

Cys Arg Phe Pro Glu Glu Glu Glu Gly Gly Cys Glu Leu Arg Val Lys
    530                 535                 540

Phe Ser Arg Ser Ala Asp Ala Pro Ala Tyr Gln Gln Gly Gln Asn Gln
545                 550                 555                 560
```

Leu Tyr Asn Glu Leu Asn Leu Gly Arg Arg Glu Glu Tyr Asp Val Leu
565 570 575

Asp Lys Arg Arg Gly Arg Asp Pro Glu Met Gly Gly Lys Pro Arg Arg
580 585 590

Lys Asn Pro Gln Glu Gly Leu Tyr Asn Glu Leu Gln Lys Asp Lys Met
595 600 605

Ala Glu Ala Tyr Ser Glu Ile Gly Met Lys Gly Glu Arg Arg Arg Gly
610 615 620

Lys Gly His Asp Gly Leu Tyr Gln Gly Leu Ser Thr Ala Thr Lys Asp
625 630 635 640

Thr Tyr Asp Ala Leu His Met Gln Ala Leu Pro Pro Arg
645 650

<210> SEQ ID NO 16
<211> LENGTH: 650
<212> TYPE: PRT
<213> ORGANISM: Artificial Sequence
<220> FEATURE:
<223> OTHER INFORMATION: anti-BMCA CAR

<400> SEQUENCE: 16

Glu Val Gln Leu Val Gln Ser Gly Gly Gly Leu Val Gln Pro Gly Arg
1 5 10 15

Ser Leu Arg Leu Ser Cys Thr Ala Ser Gly Phe Thr Phe Gly Asp Tyr
20 25 30

Ala Met Ser Trp Phe Lys Gln Ala Pro Gly Lys Gly Leu Glu Trp Val
35 40 45

Gly Phe Ile Arg Ser Lys Ala Tyr Gly Gly Thr Thr Glu Tyr Ala Ala
50 55 60

Ser Val Lys Gly Arg Phe Thr Ile Ser Arg Asp Asp Ser Lys Ser Ile
65 70 75 80

Ala Tyr Leu Gln Met Asn Ser Leu Lys Thr Glu Asp Thr Ala Val Tyr
85 90 95

Tyr Cys Ala Ala Trp Ser Ala Pro Thr Asp Tyr Trp Gly Gln Gly Thr
100 105 110

Leu Val Thr Val Ser Ser Gly Gly Gly Gly Ser Gly Gly Gly Gly Ser
115 120 125

Gly Gly Gly Gly Ser Asp Ile Gln Met Thr Gln Ser Pro Ala Phe Leu
130 135 140

Ser Ala Ser Val Gly Asp Arg Val Thr Val Thr Cys Arg Ala Ser Gln
145 150 155 160

Gly Ile Ser Asn Tyr Leu Ala Trp Tyr Gln Gln Lys Pro Gly Asn Ala
165 170 175

Pro Arg Leu Leu Ile Tyr Ser Ala Ser Thr Leu Gln Ser Gly Val Pro
180 185 190

Ser Arg Phe Arg Gly Thr Gly Tyr Gly Thr Glu Phe Ser Leu Thr Ile
195 200 205

Asp Ser Leu Gln Pro Glu Asp Phe Ala Thr Tyr Tyr Cys Gln Gln Ser
210 215 220

Tyr Thr Ser Arg Gln Thr Phe Gly Pro Gly Thr Arg Leu Asp Ile Lys
225 230 235 240

Glu Ser Lys Tyr Gly Pro Pro Cys Pro Pro Cys Pro Ala Pro Pro Val
245 250 255

Ala Gly Pro Ser Val Phe Leu Phe Pro Pro Lys Pro Lys Asp Thr Leu
260 265 270

```
Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Gln Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys Met Phe Trp Val Leu Val Val Val Gly Gly Val Leu
465                 470                 475                 480

Ala Cys Tyr Ser Leu Leu Val Thr Val Ala Phe Ile Ile Phe Trp Val
                485                 490                 495

Lys Arg Gly Arg Lys Lys Leu Leu Tyr Ile Phe Lys Gln Pro Phe Met
            500                 505                 510

Arg Pro Val Gln Thr Thr Gln Glu Glu Asp Gly Cys Ser Cys Arg Phe
        515                 520                 525

Pro Glu Glu Glu Glu Gly Gly Cys Glu Leu Arg Val Lys Phe Ser Arg
    530                 535                 540

Ser Ala Asp Ala Pro Ala Tyr Gln Gln Gly Gln Asn Gln Leu Tyr Asn
545                 550                 555                 560

Glu Leu Asn Leu Gly Arg Arg Glu Glu Tyr Asp Val Leu Asp Lys Arg
                565                 570                 575

Arg Gly Arg Asp Pro Glu Met Gly Gly Lys Pro Arg Arg Lys Asn Pro
            580                 585                 590

Gln Glu Gly Leu Tyr Asn Glu Leu Gln Lys Asp Lys Met Ala Glu Ala
        595                 600                 605

Tyr Ser Glu Ile Gly Met Lys Gly Glu Arg Arg Arg Gly Lys Gly His
    610                 615                 620

Asp Gly Leu Tyr Gln Gly Leu Ser Thr Ala Thr Lys Asp Thr Tyr Asp
625                 630                 635                 640

Ala Leu His Met Gln Ala Leu Pro Pro Arg
                645                 650
```

<210> SEQ ID NO 17
<211> LENGTH: 651
<212> TYPE: PRT
<213> ORGANISM: Artificial Sequence
<220> FEATURE:

<223> OTHER INFORMATION: anti-BMCA CAR

<400> SEQUENCE: 17

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Ser Tyr Val Leu Thr Gln Pro Pro Ser Val Ser
    130                 135                 140

Val Ala Pro Gly Gln Thr Ala Arg Ile Thr Cys Gly Ala Asn Asn Ile
145                 150                 155                 160

Gly Ser Lys Ser Val His Trp Tyr Gln Gln Lys Pro Gly Gln Ala Pro
                165                 170                 175

Met Leu Val Val Tyr Asp Asp Asp Asp Arg Pro Ser Gly Ile Pro Glu
            180                 185                 190

Arg Phe Ser Gly Ser Asn Ser Gly Asn Thr Ala Thr Leu Thr Ile Ser
        195                 200                 205

Gly Val Glu Ala Gly Asp Glu Ala Asp Tyr Phe Cys His Leu Trp Asp
    210                 215                 220

Arg Ser Arg Asp His Tyr Val Phe Gly Thr Gly Thr Lys Leu Thr Val
225                 230                 235                 240

Leu Glu Ser Lys Tyr Gly Pro Pro Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Gln Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
        355                 360                 365

Gln Val Tyr Thr Leu Pro Pro Ser Gln Glu Glu Met Thr Lys Asn Gln
    370                 375                 380

Val Ser Leu Thr Cys Leu Val Lys Gly Phe Tyr Pro Ser Asp Ile Ala
385                 390                 395                 400
```

```
Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
    450                 455                 460

Leu Ser Leu Gly Lys Met Phe Trp Val Leu Val Val Val Gly Gly Val
465                 470                 475                 480

Leu Ala Cys Tyr Ser Leu Leu Val Thr Val Ala Phe Ile Ile Phe Trp
                485                 490                 495

Val Lys Arg Gly Arg Lys Lys Leu Leu Tyr Ile Phe Lys Gln Pro Phe
            500                 505                 510

Met Arg Pro Val Gln Thr Thr Gln Glu Glu Asp Gly Cys Ser Cys Arg
        515                 520                 525

Phe Pro Glu Glu Glu Glu Gly Gly Cys Glu Leu Arg Val Lys Phe Ser
    530                 535                 540

Arg Ser Ala Asp Ala Pro Ala Tyr Gln Gln Gly Gln Asn Gln Leu Tyr
545                 550                 555                 560

Asn Glu Leu Asn Leu Gly Arg Arg Glu Glu Tyr Asp Val Leu Asp Lys
                565                 570                 575

Arg Arg Gly Arg Asp Pro Glu Met Gly Gly Lys Pro Arg Arg Lys Asn
            580                 585                 590

Pro Gln Glu Gly Leu Tyr Asn Glu Leu Gln Lys Asp Lys Met Ala Glu
        595                 600                 605

Ala Tyr Ser Glu Ile Gly Met Lys Gly Glu Arg Arg Arg Gly Lys Gly
    610                 615                 620

His Asp Gly Leu Tyr Gln Gly Leu Ser Thr Ala Thr Lys Asp Thr Tyr
625                 630                 635                 640

Asp Ala Leu His Met Gln Ala Leu Pro Pro Arg
                645                 650
```

<210> SEQ ID NO 18
<211> LENGTH: 658
<212> TYPE: PRT
<213> ORGANISM: Artificial Sequence
<220> FEATURE:
<223> OTHER INFORMATION: anti-BMCA CAR

<400> SEQUENCE: 18

```
Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Gly Thr Lys Leu Thr Val Leu Gly Ser
            100                 105                 110
```

```
Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly His Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Tyr Ser Gly Ser Phe Asp Asn Trp Gly Gln
225                 230                 235                 240

Gly Thr Leu Val Thr Val Ser Ser Glu Ser Lys Tyr Gly Pro Pro Cys
                245                 250                 255

Pro Pro Cys Pro Ala Pro Pro Val Ala Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser Gln Glu Asp Pro Glu Val Gln Phe
    290                 295                 300

Asn Trp Tyr Val Asp Gly Val Glu Val His Asn Ala Lys Thr Lys Pro
305                 310                 315                 320

Arg Glu Glu Gln Phe Gln Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Gly Leu Pro Ser Ser Ile Glu Lys Thr Ile Ser Lys Ala
        355                 360                 365

Lys Gly Gln Pro Arg Glu Pro Gln Val Tyr Thr Leu Pro Pro Ser Gln
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Arg Leu Thr Val Asp Lys Ser Arg Trp Gln Glu
        435                 440                 445

Gly Asn Val Phe Ser Cys Ser Val Met His Glu Ala Leu His Asn His
    450                 455                 460

Tyr Thr Gln Lys Ser Leu Ser Leu Ser Leu Gly Lys Met Phe Trp Val
465                 470                 475                 480

Leu Val Val Val Gly Gly Val Leu Ala Cys Tyr Ser Leu Leu Val Thr
                485                 490                 495

Val Ala Phe Ile Ile Phe Trp Val Lys Arg Gly Arg Lys Lys Leu Leu
            500                 505                 510

Tyr Ile Phe Lys Gln Pro Phe Met Arg Pro Val Gln Thr Thr Gln Glu
        515                 520                 525

Glu Asp Gly Cys Ser Cys Arg Phe Pro Glu Glu Glu Glu Gly Gly Cys
```

```
    530                 535                 540

Glu Leu Arg Val Lys Phe Ser Arg Ser Ala Asp Ala Pro Ala Tyr Gln
545                 550                 555                 560

Gln Gly Gln Asn Gln Leu Tyr Asn Glu Leu Asn Leu Gly Arg Arg Glu
                565                 570                 575

Glu Tyr Asp Val Leu Asp Lys Arg Arg Gly Arg Asp Pro Glu Met Gly
            580                 585                 590

Gly Lys Pro Arg Arg Lys Asn Pro Gln Glu Gly Leu Tyr Asn Glu Leu
        595                 600                 605

Gln Lys Asp Lys Met Ala Glu Ala Tyr Ser Glu Ile Gly Met Lys Gly
    610                 615                 620

Glu Arg Arg Arg Gly Lys Gly His Asp Gly Leu Tyr Gln Gly Leu Ser
625                 630                 635                 640

Thr Ala Thr Lys Asp Thr Tyr Asp Ala Leu His Met Gln Ala Leu Pro
                645                 650                 655

Pro Arg


<210> SEQ ID NO 19
<211> LENGTH: 654
<212> TYPE: PRT
<213> ORGANISM: Artificial Sequence
<220> FEATURE:
<223> OTHER INFORMATION: anti-BMCA CAR

<400> SEQUENCE: 19

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Gly Ser Leu Glu Met Ala Glu Val
        115                 120                 125

Gln Leu Val Gln Ser Gly Ala Glu Met Lys Lys Pro Gly Ala Ser Leu
    130                 135                 140

Lys Leu Ser Cys Lys Ala Ser Gly Tyr Thr Phe Ile Asp Tyr Tyr Val
145                 150                 155                 160

Tyr Trp Met Arg Gln Ala Pro Gly Gln Gly Leu Glu Ser Met Gly Trp
                165                 170                 175

Ile Asn Pro Asn Ser Gly Gly Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Met Tyr Tyr Cys Ala Arg
    210                 215                 220

Ser Gln Arg Asp Gly Tyr Met Asp Tyr Trp Gly Gln Gly Thr Leu Val
225                 230                 235                 240
```

```
Thr Val Ser Ser Glu Ser Lys Tyr Gly Pro Pro Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser Gln Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Gln Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
        355                 360                 365

Arg Glu Pro Gln Val Tyr Thr Leu Pro Pro Ser Gln Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Arg Leu Thr Val Asp Lys Ser Arg Trp Gln Glu Gly Asn Val Phe
        435                 440                 445

Ser Cys Ser Val Met His Glu Ala Leu His Asn His Tyr Thr Gln Lys
    450                 455                 460

Ser Leu Ser Leu Ser Leu Gly Lys Met Phe Trp Val Leu Val Val Val
465                 470                 475                 480

Gly Gly Val Leu Ala Cys Tyr Ser Leu Leu Val Thr Val Ala Phe Ile
                485                 490                 495

Ile Phe Trp Val Lys Arg Gly Arg Lys Lys Leu Leu Tyr Ile Phe Lys
            500                 505                 510

Gln Pro Phe Met Arg Pro Val Gln Thr Thr Gln Glu Glu Asp Gly Cys
        515                 520                 525

Ser Cys Arg Phe Pro Glu Glu Glu Glu Gly Gly Cys Glu Leu Arg Val
    530                 535                 540

Lys Phe Ser Arg Ser Ala Asp Ala Pro Ala Tyr Gln Gln Gly Gln Asn
545                 550                 555                 560

Gln Leu Tyr Asn Glu Leu Asn Leu Gly Arg Arg Glu Glu Tyr Asp Val
                565                 570                 575

Leu Asp Lys Arg Arg Gly Arg Asp Pro Glu Met Gly Gly Lys Pro Arg
            580                 585                 590

Arg Lys Asn Pro Gln Glu Gly Leu Tyr Asn Glu Leu Gln Lys Asp Lys
        595                 600                 605

Met Ala Glu Ala Tyr Ser Glu Ile Gly Met Lys Gly Glu Arg Arg Arg
    610                 615                 620

Gly Lys Gly His Asp Gly Leu Tyr Gln Gly Leu Ser Thr Ala Thr Lys
625                 630                 635                 640

Asp Thr Tyr Asp Ala Leu His Met Gln Ala Leu Pro Pro Arg
                645                 650
```

<210> SEQ ID NO 20
<211> LENGTH: 653
<212> TYPE: PRT
<213> ORGANISM: Artificial Sequence
<220> FEATURE:
<223> OTHER INFORMATION: anti-BMCA CAR

<400> SEQUENCE: 20

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Gly Ser Leu Glu Met Ala Glu Val
        115                 120                 125

Gln Leu Val Gln Ser Gly Ala Glu Met Lys Lys Pro Gly Ala Ser Leu
    130                 135                 140

Lys Leu Ser Cys Lys Ala Ser Gly Tyr Thr Phe Ile Asp Tyr Tyr Val
145                 150                 155                 160

Tyr Trp Met Arg Gln Ala Pro Gly Gln Gly Leu Glu Ser Met Gly Trp
                165                 170                 175

Ile Asn Pro Asn Ser Gly Gly Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Met Tyr Tyr Cys Ala Arg
    210                 215                 220

Ser Gln Arg Asp Gly Tyr Met Asp Tyr Trp Gly Gln Gly Thr Leu Val
225                 230                 235                 240

Thr Val Ser Ser Glu Ser Lys Tyr Gly Pro Pro Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser Gln Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Gln Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
        355                 360                 365

```
Arg Glu Pro Gln Val Tyr Thr Leu Pro Pro Ser Gln Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Arg Leu Thr Val Asp Lys Ser Arg Trp Gln Glu Gly Asn Val Phe
        435                 440                 445

Ser Cys Ser Val Met His Glu Ala Leu His Asn His Tyr Thr Gln Lys
    450                 455                 460

Ser Leu Ser Leu Ser Leu Gly Lys Met Phe Trp Val Leu Val Val Val
465                 470                 475                 480

Gly Gly Val Leu Ala Cys Tyr Ser Leu Leu Val Thr Val Ala Phe Ile
                485                 490                 495

Ile Phe Trp Val Arg Ser Lys Arg Ser Arg Leu Leu His Ser Asp Tyr
            500                 505                 510

Met Asn Met Thr Pro Arg Arg Pro Gly Pro Thr Arg Lys His Tyr Gln
        515                 520                 525

Pro Tyr Ala Pro Pro Arg Asp Phe Ala Ala Tyr Arg Ser Arg Val Lys
    530                 535                 540

Phe Ser Arg Ser Ala Asp Ala Pro Ala Tyr Gln Gln Gly Gln Asn Gln
545                 550                 555                 560

Leu Tyr Asn Glu Leu Asn Leu Gly Arg Arg Glu Glu Tyr Asp Val Leu
                565                 570                 575

Asp Lys Arg Arg Gly Arg Asp Pro Glu Met Gly Gly Lys Pro Arg Arg
            580                 585                 590

Lys Asn Pro Gln Glu Gly Leu Tyr Asn Glu Leu Gln Lys Asp Lys Met
        595                 600                 605

Ala Glu Ala Tyr Ser Glu Ile Gly Met Lys Gly Glu Arg Arg Arg Gly
    610                 615                 620

Lys Gly His Asp Gly Leu Tyr Gln Gly Leu Ser Thr Ala Thr Lys Asp
625                 630                 635                 640

Thr Tyr Asp Ala Leu His Met Gln Ala Leu Pro Pro Arg
                645                 650


<210> SEQ ID NO 21
<211> LENGTH: 5
<212> TYPE: PRT
<213> ORGANISM: Artificial Sequence
<220> FEATURE:
<223> OTHER INFORMATION: BCMA epitope

<400> SEQUENCE: 21

Tyr Phe Asp Ser Leu
1               5


<210> SEQ ID NO 22
<211> LENGTH: 14
<212> TYPE: PRT
<213> ORGANISM: Artificial Sequence
<220> FEATURE:
<223> OTHER INFORMATION: BCMA-23 CDR-L1

<400> SEQUENCE: 22

Thr Gly Ser Ser Ser Asp Val Gly Lys Tyr Asn Leu Val Ser
1               5                   10
```

<210> SEQ ID NO 23
<211> LENGTH: 7
<212> TYPE: PRT
<213> ORGANISM: Artificial Sequence
<220> FEATURE:
<223> OTHER INFORMATION: BCMA-23 CDR-L2

<400> SEQUENCE: 23

Asp Val Asn Lys Arg Pro Ser
1               5

<210> SEQ ID NO 24
<211> LENGTH: 10
<212> TYPE: PRT
<213> ORGANISM: Artificial Sequence
<220> FEATURE:
<223> OTHER INFORMATION: BCMA-23 CDR-L3

<400> SEQUENCE: 24

Ser Ser Tyr Gly Gly Ser Arg Ser Tyr Val
1               5                   10

<210> SEQ ID NO 25
<211> LENGTH: 41
<212> TYPE: DNA
<213> ORGANISM: Artificial Sequence
<220> FEATURE:
<223> OTHER INFORMATION: BCMA-23 predicted splice acceptor site

<400> SEQUENCE: 25
ggctgattat tattgtagct catatggagg tagtaggtct t                           41

<210> SEQ ID NO 26
<211> LENGTH: 41
<212> TYPE: DNA
<213> ORGANISM: Artificial Sequence
<220> FEATURE:
<223> OTHER INFORMATION: BCMA-23 predicted splice acceptor site

<400> SEQUENCE: 26
ctactacatg agctggatcc gccaggctcc agggaagggg c                           41

<210> SEQ ID NO 27
<211> LENGTH: 41
<212> TYPE: DNA
<213> ORGANISM: Artificial Sequence
<220> FEATURE:
<223> OTHER INFORMATION: BCMA-23 predicted splice acceptor site (O/SSE)

<400> SEQUENCE: 27
ctactatatg tcctggatca gacaggcacc tggcaagggc c                           41

<210> SEQ ID NO 28
<211> LENGTH: 41
<212> TYPE: DNA
<213> ORGANISM: Artificial Sequence
<220> FEATURE:
<223> OTHER INFORMATION: BCMA-23 predicted splice acceptor site (O/SSE)

<400> SEQUENCE: 28
ggcagattac tattgttcta gctacggcgg cagcagatcc t                           41

<210> SEQ ID NO 29
<211> LENGTH: 243
<212> TYPE: PRT

<213> ORGANISM: Artificial Sequence
<220> FEATURE:
<223> OTHER INFORMATION: BCMA-23 scFv

<400> SEQUENCE: 29

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Lys Val Asp Gly Asp Tyr Thr Glu Asp Tyr Trp Gly Gln Gly Thr
100 105 110

Leu Val Thr Val Ser Ser Gly Gly Gly Gly Ser Gly Gly Gly Gly Ser
115 120 125

Gly Gly Gly Gly Ser Gln Ser Ala Leu Thr Gln Pro Ala Ser Val Ser
130 135 140

Gly Ser Pro Gly Gln Ser Ile Thr Ile Ser Cys Thr Gly Ser Ser Ser
145 150 155 160

Asp Val Gly Lys Tyr Asn Leu Val Ser Trp Tyr Gln Gln Pro Pro Gly
165 170 175

Lys Ala Pro Lys Leu Ile Ile Tyr Asp Val Asn Lys Arg Pro Ser Gly
180 185 190

Val Ser Asn Arg Phe Ser Gly Ser Lys Ser Gly Asn Thr Ala Thr Leu
195 200 205

Thr Ile Ser Gly Leu Gln Gly Asp Asp Glu Ala Asp Tyr Tyr Cys Ser
210 215 220

Ser Tyr Gly Gly Ser Arg Ser Tyr Val Phe Gly Thr Gly Thr Lys Val
225 230 235 240

Thr Val Leu

<210> SEQ ID NO 30
<211> LENGTH: 729
<212> TYPE: DNA
<213> ORGANISM: Artificial Sequence
<220> FEATURE:
<223> OTHER INFORMATION: BCMA-23 scFv

<400> SEQUENCE: 30
gaagtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggccgtgt attactgtgc gaaagtagac 300
ggagactaca cagaggacta ctggggccag ggaaccctgg tcaccgtctc ctcaggtgga 360
ggcggttcag gcggaggtgg ctctggcggt ggcggatcgc agtctgccct gactcagcct 420
gcctccgtgt ctgggtctcc tggacagtcg atcactatct cctgcactgg aagcagcagt 480
gatgttggca aatataatct tgtctcctgg taccaacagc ccccaggcaa agcccccaag 540
ctcataattt atgacgtcaa taagcggccc tcaggggttt ctaatcgctt ctctggctcc 600
aagtctggca acacggccac cctgacaatc tctgggctcc agggtgacga cgaggctgat 660
tattattgta gctcatatgg aggtagtagg tcttatgtct tcggaactgg gaccaaggtg 720
accgtccta 729

<210> SEQ ID NO 31
<211> LENGTH: 729
<212> TYPE: DNA
<213> ORGANISM: Artificial Sequence
<220> FEATURE:
<223> OTHER INFORMATION: BCMA-23 scFv

<400> SEQUENCE: 31
gaggtgcagc tggtggagtc cggaggaggc ctggtgaagc caggaggctc cctgaggctg 60
tcttgcgcag ccagcggctt cacctttagc gactactata tgtcctggat cagacaggca 120
cctggcaagg gcctggagtg ggtgagctac atcagctcct ctggctccac aatctactat 180
gccgactctg tgaagggccg gtttaccatc agcagagata acgccaagaa ttccctgtat 240
ctgcagatga acagcctgag ggccgaggac acagccgtgt actattgcgc caaggtggac 300
ggcgattaca ccgaggatta ttggggccag ggcacactgg tgaccgtgag ctccggcggc 360
ggcggctctg gaggaggagg cagcggcgga ggaggctccc agtctgccct gacacagcca 420
gccagcgtgt ccggctctcc cggacagtcc atcacaatct cttgtaccgg ctctagctcc 480
gacgtgggca agtacaacct ggtgtcctgg tatcagcagc cccctggcaa ggcccctaag 540
ctgatcatct acgatgtgaa caagaggcca tctggcgtga gcaatcgctt cagcggctcc 600
aagtctggca ataccgccac actgaccatc agcggcctgc agggcgacga tgaggcagat 660
tactattgtt ctagctacgg cggcagcaga tcctacgtgt tcggcacagg caccaaggtg 720
accgtgctg 729

<210> SEQ ID NO 32
<211> LENGTH: 118
<212> TYPE: PRT
<213> ORGANISM: Artificial Sequence
<220> FEATURE:
<223> OTHER INFORMATION: BCMA-23 VH Chain

<400> SEQUENCE: 32

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Lys Val Asp Gly Asp Tyr Thr Glu Asp Tyr Trp Gly Gln Gly Thr
100 105 110

Leu Val Thr Val Ser Ser
115

<210> SEQ ID NO 33
<211> LENGTH: 110
<212> TYPE: PRT
<213> ORGANISM: Artificial Sequence
<220> FEATURE:
<223> OTHER INFORMATION: BCMA-23 VL Chain

<400> SEQUENCE: 33

Gln Ser Ala Leu Thr Gln Pro Ala Ser Val Ser Gly Ser Pro Gly Gln
1 5 10 15

Ser Ile Thr Ile Ser Cys Thr Gly Ser Ser Ser Asp Val Gly Lys Tyr
20 25 30

Asn Leu Val Ser Trp Tyr Gln Gln Pro Pro Gly Lys Ala Pro Lys Leu
35 40 45

Ile Ile Tyr Asp Val Asn Lys Arg Pro Ser Gly Val Ser Asn Arg Phe
50 55 60

Ser Gly Ser Lys Ser Gly Asn Thr Ala Thr Leu Thr Ile Ser Gly Leu
65 70 75 80

Gln Gly Asp Asp Glu Ala Asp Tyr Tyr Cys Ser Ser Tyr Gly Gly Ser
85 90 95

Arg Ser Tyr Val Phe Gly Thr Gly Thr Lys Val Thr Val Leu
100 105 110

<210> SEQ ID NO 34
<211> LENGTH: 5
<212> TYPE: PRT
<213> ORGANISM: Artificial Sequence
<220> FEATURE:
<223> OTHER INFORMATION: BCMA-23, -26 CDR-H1

<400> SEQUENCE: 34

Asp Tyr Tyr Met Ser
1 5

<210> SEQ ID NO 35
<211> LENGTH: 17
<212> TYPE: PRT
<213> ORGANISM: Artificial Sequence
<220> FEATURE:
<223> OTHER INFORMATION: BCMA-23, -26 CDR-H2

<400> SEQUENCE: 35

Tyr Ile Ser Ser Ser Gly Ser Thr Ile Tyr Tyr Ala Asp Ser Val Lys
1 5 10 15

Gly

<210> SEQ ID NO 36
<211> LENGTH: 9
<212> TYPE: PRT
<213> ORGANISM: Artificial Sequence
<220> FEATURE:
<223> OTHER INFORMATION: BCMA-23 CDR-H3

<400> SEQUENCE: 36

Val Asp Gly Asp Tyr Thr Glu Asp Tyr
1 5

<210> SEQ ID NO 37
<211> LENGTH: 5
<212> TYPE: PRT
<213> ORGANISM: Artificial Sequence
<220> FEATURE:

<223> OTHER INFORMATION: BCMA-25 CDR-H1

<400> SEQUENCE: 37

Asp Tyr Ala Met Ser
1               5

<210> SEQ ID NO 38
<211> LENGTH: 19
<212> TYPE: PRT
<213> ORGANISM: Artificial Sequence
<220> FEATURE:
<223> OTHER INFORMATION: BCMA-25 CDR-H2

<400> SEQUENCE: 38

Phe Ile Arg Ser Lys Ala Tyr Gly Gly Thr Thr Glu Tyr Ala Ala Ser
1               5                   10                  15

Val Lys Gly

<210> SEQ ID NO 39
<211> LENGTH: 7
<212> TYPE: PRT
<213> ORGANISM: Artificial Sequence
<220> FEATURE:
<223> OTHER INFORMATION: BCMA-25 CDR-H3

<400> SEQUENCE: 39

Trp Ser Ala Pro Thr Asp Tyr
1               5

<210> SEQ ID NO 40
<211> LENGTH: 11
<212> TYPE: PRT
<213> ORGANISM: Artificial Sequence
<220> FEATURE:
<223> OTHER INFORMATION: BCMA-25 CDR-L1

<400> SEQUENCE: 40

Arg Ala Ser Gln Gly Ile Ser Asn Tyr Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: BCMA-25 CDR-L2

<400> SEQUENCE: 41

Ser Ala Ser Thr Leu Gln Ser
1               5

<210> SEQ ID NO 42
<211> LENGTH: 9
<212> TYPE: PRT
<213> ORGANISM: Artificial Sequence
<220> FEATURE:
<223> OTHER INFORMATION: BCMA-25 CDR-L3

<400> SEQUENCE: 42

Gln Gln Ser Tyr Thr Ser Arg Gln Thr
1               5

<210> SEQ ID NO 43
<211> LENGTH: 41
<212> TYPE: DNA
<213> ORGANISM: Artificial Sequence
<220> FEATURE:
<223> OTHER INFORMATION: BCMA-25 predicted splice acceptor site

<400> SEQUENCE: 43
ctatgccatg tcctggttca ggcaggcacc aggcaagggc c 41

<210> SEQ ID NO 44
<211> LENGTH: 41
<212> TYPE: DNA
<213> ORGANISM: Artificial Sequence
<220> FEATURE:
<223> OTHER INFORMATION: BCMA-25 predicted splice acceptor site

<400> SEQUENCE: 44
gtccgcctct gtgggcgata gggtgaccgt gacatgtcgc g 41

<210> SEQ ID NO 45
<211> LENGTH: 41
<212> TYPE: DNA
<213> ORGANISM: Artificial Sequence
<220> FEATURE:
<223> OTHER INFORMATION: BCMA-25 predicted splice acceptor site

<400> SEQUENCE: 45
gtgggcttta tccgctctaa ggcctacggc ggcaccacag a 41

<210> SEQ ID NO 46
<211> LENGTH: 41
<212> TYPE: DNA
<213> ORGANISM: Artificial Sequence
<220> FEATURE:
<223> OTHER INFORMATION: BCMA-25 predicted splice acceptor site

<400> SEQUENCE: 46
gtgacatgtc gcgcctccca gggcatctct aactacctgg c 41

<210> SEQ ID NO 47
<211> LENGTH: 41
<212> TYPE: DNA
<213> ORGANISM: Artificial Sequence
<220> FEATURE:
<223> OTHER INFORMATION: BCMA-25 predicted splice acceptor site

<400> SEQUENCE: 47
tacagcgcct ccaccctgca gagcggagtg ccctcccggt t 41

<210> SEQ ID NO 48
<211> LENGTH: 41
<212> TYPE: DNA
<213> ORGANISM: Artificial Sequence
<220> FEATURE:
<223> OTHER INFORMATION: BCMA-25 predicted splice acceptor site (O/SSE)

<400> SEQUENCE: 48
ctatgccatg tcctggttca agcaggcacc aggcaagggc c 41

<210> SEQ ID NO 49
<211> LENGTH: 240
<212> TYPE: PRT
<213> ORGANISM: Artificial Sequence
<220> FEATURE:
<223> OTHER INFORMATION: BCMA-25 scFv sequence

<400> SEQUENCE: 49

Glu Val Gln Leu Val Gln Ser Gly Gly Gly Leu Val Gln Pro Gly Arg
1 5 10 15

```
Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ala Phe Leu
    130                 135                 140

Ser Ala Ser Val Gly Asp Arg Val Thr Val Thr Cys Arg Ala Ser Gln
145                 150                 155                 160

Gly Ile Ser Asn Tyr Leu Ala Trp Tyr Gln Gln Lys Pro Gly Asn Ala
                165                 170                 175

Pro Arg Leu Leu Ile Tyr Ser Ala Ser Thr Leu Gln Ser Gly Val Pro
            180                 185                 190

Ser Arg Phe Arg Gly Thr Gly Tyr Gly Thr Glu Phe Ser Leu Thr Ile
        195                 200                 205

Asp Ser Leu Gln Pro Glu Asp Phe Ala Thr Tyr Tyr Cys Gln Gln Ser
    210                 215                 220

Tyr Thr Ser Arg Gln Thr Phe Gly Pro Gly Thr Arg Leu Asp Ile Lys
225                 230                 235                 240


<210> SEQ ID NO 50
<211> LENGTH: 720
<212> TYPE: DNA
<213> ORGANISM: Artificial Sequence
<220> FEATURE:
<223> OTHER INFORMATION: BCMA-25 scFV

<400> SEQUENCE: 50

gaggtgcagc tggtgcagag cggaggaggc ctggtgcagc ctggcaggtc cctgcgcctg      60

tcttgcaccg ccagcggctt cacatttggc gactatgcca tgtcctggtt caggcaggca     120

ccaggcaagg gcctggagtg ggtgggcttt atccgctcta aggcctacgg cggcaccaca     180

gagtatgccg ccagcgtgaa gggccggttc accatcagcc gggacgactc taagagcatc     240

gcctacctgc agatgaactc tctgaagacc gaggacacag ccgtgtacta ttgcgcagca     300

tggagcgccc caaccgatta ttggggccag ggcaccctgg tgacagtgag ctccggcggc     360

ggcggctctg gaggaggagg aagcggagga ggaggatccg acatccagat gacacagtcc     420

cctgcctttc tgtccgcctc tgtgggcgat agggtgaccg tgacatgtcg cgcctcccag     480

ggcatctcta actacctggc ctggtatcag cagaagcccg gcaatgcccc tcggctgctg     540

atctacagcg cctccaccct gcagagcgga gtgccctccc ggttcagagg aaccggctat     600

ggcacagagt tttctctgac catcgacagc ctgcagccag aggatttcgc cacatactat     660

tgtcagcagt cttacaccag ccggcagaca tttggccccg gcacaagact ggatatcaag     720


<210> SEQ ID NO 51
```

<211> LENGTH: 720
<212> TYPE: DNA
<213> ORGANISM: Artificial Sequence
<220> FEATURE:
<223> OTHER INFORMATION: BCMA-25 scFV (O/SSE)

<400> SEQUENCE: 51

```
gaggtgcagc tggtgcagag cggaggaggc ctggtgcagc ctggcaggtc cctgcgcctg      60

tcttgcaccg ccagcggctt cacatttggc gactatgcca tgtcctggtt caagcaggca     120

ccaggcaagg gcctggagtg ggtgggcttt atccgctcta aggcctacgg cggcaccaca     180

gagtatgccg ccagcgtgaa gggccggttc accatcagcc gggacgactc taagagcatc     240

gcctacctgc agatgaactc tctgaagacc gaggacacag ccgtgtacta ttgcgcagca     300

tggagcgccc caaccgatta ttggggccag ggcaccctgg tgacagtgag ctccggcggc     360

ggcggctctg gaggaggagg aagcggagga ggaggatccg acatccagat gacacagtcc     420

cctgcctttc tgtccgcctc tgtgggcgat agggtgaccg tgacatgtcg cgcctcccag     480

ggcatctcta actacctggc ctggtatcag cagaagcccg gcaatgcccc tcggctgctg     540

atctacagcg cctccaccct gcagagcgga gtgccctccc ggttcagagg aaccggctat     600

ggcacagagt tttctctgac catcgacagc ctgcagccag aggatttcgc cacatactat     660

tgtcagcagt cttacaccag ccggcagaca tttggccccg gcacaagact ggatatcaag     720
```

<210> SEQ ID NO 52
<211> LENGTH: 118
<212> TYPE: PRT
<213> ORGANISM: Artificial Sequence
<220> FEATURE:
<223> OTHER INFORMATION: BCMA-25 VH chain

<400> SEQUENCE: 52

```
Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser
        115
```

<210> SEQ ID NO 53
<211> LENGTH: 107
<212> TYPE: PRT
<213> ORGANISM: Artificial Sequence
<220> FEATURE:
<223> OTHER INFORMATION: BCMA-25 VL chain

<400> SEQUENCE: 53

```
Asp Ile Gln Met Thr Gln Ser Pro Ala Phe Leu Ser Ala Ser Val Gly
1               5                   10                  15
```

```
Asp Arg Val Thr Val Thr Cys Arg Ala Ser Gln Gly Ile Ser Asn Tyr
            20                  25                  30

Leu Ala Trp Tyr Gln Gln Lys Pro Gly Asn Ala Pro Arg Leu Leu Ile
        35                  40                  45

Tyr Ser Ala Ser Thr Leu Gln Ser Gly Val Pro Ser Arg Phe Arg Gly
    50                  55                  60

Thr Gly Tyr Gly Thr Glu Phe Ser Leu Thr Ile Asp Ser Leu Gln Pro
65                  70                  75                  80

Glu Asp Phe Ala Thr Tyr Tyr Cys Gln Gln Ser Tyr Thr Ser Arg Gln
                85                  90                  95

Thr Phe Gly Pro Gly Thr Arg Leu Asp Ile Lys
            100                 105


<210> SEQ ID NO 54
<211> LENGTH: 9
<212> TYPE: PRT
<213> ORGANISM: Artificial Sequence
<220> FEATURE:
<223> OTHER INFORMATION: BCMA-26 CDR-H3

<400> SEQUENCE: 54

Val Asp Gly Pro Pro Ser Phe Asp Ile
1               5


<210> SEQ ID NO 55
<211> LENGTH: 11
<212> TYPE: PRT
<213> ORGANISM: Artificial Sequence
<220> FEATURE:
<223> OTHER INFORMATION: BCMA-26 CDR-L1

<400> SEQUENCE: 55

Gly Ala Asn Asn Ile Gly Ser Lys Ser Val His
1               5                   10


<210> SEQ ID NO 56
<211> LENGTH: 7
<212> TYPE: PRT
<213> ORGANISM: Artificial Sequence
<220> FEATURE:
<223> OTHER INFORMATION: BCMA-26 CDR-L2

<400> SEQUENCE: 56

Asp Asp Asp Asp Arg Pro Ser
1               5


<210> SEQ ID NO 57
<211> LENGTH: 11
<212> TYPE: PRT
<213> ORGANISM: Artificial Sequence
<220> FEATURE:
<223> OTHER INFORMATION: BCMA-26 CDR-L3

<400> SEQUENCE: 57

His Leu Trp Asp Arg Ser Arg Asp His Tyr Val
1               5                   10


<210> SEQ ID NO 58
<211> LENGTH: 241
<212> TYPE: PRT
<213> ORGANISM: Artificial Sequence
<220> FEATURE:
<223> OTHER INFORMATION: BCMA-26 scFv sequence

<400> SEQUENCE: 58
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Ser Tyr Val Leu Thr Gln Pro Pro Ser Val Ser
    130                 135                 140

Val Ala Pro Gly Gln Thr Ala Arg Ile Thr Cys Gly Ala Asn Asn Ile
145                 150                 155                 160

Gly Ser Lys Ser Val His Trp Tyr Gln Gln Lys Pro Gly Gln Ala Pro
                165                 170                 175

Met Leu Val Val Tyr Asp Asp Asp Asp Arg Pro Ser Gly Ile Pro Glu
            180                 185                 190

Arg Phe Ser Gly Ser Asn Ser Gly Asn Thr Ala Thr Leu Thr Ile Ser
        195                 200                 205

Gly Val Glu Ala Gly Asp Glu Ala Asp Tyr Phe Cys His Leu Trp Asp
    210                 215                 220

Arg Ser Arg Asp His Tyr Val Phe Gly Thr Gly Thr Lys Leu Thr Val
225                 230                 235                 240

Leu
```

<210> SEQ ID NO 59
<211> LENGTH: 723
<212> TYPE: DNA
<213> ORGANISM: Artificial Sequence
<220> FEATURE:
<223> OTHER INFORMATION: BCMA-26 scFV

<400> SEQUENCE: 59

```
gaggtgcagc tggtggagtc cggaggaggc ctggtgaagc caggaggctc tctgaggctg     60

agctgcgcag cctccggctt caccttttct gactactata tgagctggat caggcaggca    120

ccaggcaagg gcctggagtg ggtgtcttac atcagctcct ctggcagcac aatctactat    180

gccgactccg tgaagggcag gttcaccatc tctcgcgata acgccaagaa tagcctgtat    240

ctgcagatga actccctgcg ggccgaggat acagccgtgt actattgcgc caaggtggac    300

ggcccccctt cctttgatat ctggggccag ggcacaatgg tgaccgtgag ctccggagga    360

ggaggatccg gcggaggagg ctctggcggc ggcggctcta gctatgtgct gacccagcca    420

ccatccgtgt ctgtggcacc tggacagaca gcaaggatca cctgtggagc aaacaatatc    480

ggcagcaagt ccgtgcactg gtaccagcag aagcctggcc aggccccaat gctggtggtg    540

tatgacgatg acgatcggcc cagcggcatc cctgagagat tttctggcag caactccggc    600

aataccgcca cactgaccat ctctggagtg gaggcaggcg acgaggcaga ttacttctgt    660
```

cacctgtggg accggagcag agatcactac gtgttcggca caggcaccaa gctgaccgtg 720
ctg 723

<210> SEQ ID NO 60
<211> LENGTH: 723
<212> TYPE: DNA
<213> ORGANISM: Artificial Sequence
<220> FEATURE:
<223> OTHER INFORMATION: BCMA-26 scFV (O/SSE)

<400> SEQUENCE: 60
gaggtgcagc tggtggagtc cggaggaggc ctggtgaagc caggaggctc tctgaggctg 60
agctgcgcag cctccggctt cacctttttct gactactata tgagctggat caggcaggca 120
ccaggcaagg gcctggagtg ggtgtcttac atcagctcct ctggcagcac aatctactat 180
gccgactccg tgaagggcag gttcaccatc tctcgcgata acgccaagaa tagcctgtat 240
ctgcagatga actccctgcg ggccgaggat acagccgtgt actattgcgc caaggtggac 300
ggcccccctt cctttgatat ctggggccag ggcacaatgg tgaccgtgag ctccggagga 360
ggaggatccg gcggaggagg ctctggcggc ggcggctcta gctatgtgct gacccagcca 420
ccatccgtgt ctgtggcacc tggacagaca gcaaggatca cctgtggagc aaacaatatc 480
ggcagcaagt ccgtgcactg gtaccagcag aagcctggcc aggccccaat gctggtggtg 540
tatgacgatg acgatcggcc cagcggcatc cctgagagat tttctggcag caactccggc 600
aataccgcca cactgaccat ctctggagtg gaggcaggcg acgaggcaga ttacttctgt 660
cacctgtggg accggagcag agatcactac gtgttcggca caggcaccaa gctgaccgtg 720
ctg 723

<210> SEQ ID NO 61
<211> LENGTH: 118
<212> TYPE: PRT
<213> ORGANISM: Artificial Sequence
<220> FEATURE:
<223> OTHER INFORMATION: BCMA-26 VH Chain

<400> SEQUENCE: 61

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser
        115

<210> SEQ ID NO 62
<211> LENGTH: 108
<212> TYPE: PRT

<213> ORGANISM: Artificial Sequence
<220> FEATURE:
<223> OTHER INFORMATION: BCMA-26 VL chain

<400> SEQUENCE: 62

```
Ser Tyr Val Leu Thr Gln Pro Pro Ser Val Ser Val Ala Pro Gly Gln
1               5                   10                  15

Thr Ala Arg Ile Thr Cys Gly Ala Asn Asn Ile Gly Ser Lys Ser Val
            20                  25                  30

His Trp Tyr Gln Gln Lys Pro Gly Gln Ala Pro Met Leu Val Val Tyr
        35                  40                  45

Asp Asp Asp Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Phe Cys His Leu Trp Asp Arg Ser Arg Asp His
                85                  90                  95

Tyr Val Phe Gly Thr Gly Thr Lys Leu Thr Val Leu
            100                 105
```

<210> SEQ ID NO 63
<211> LENGTH: 8
<212> TYPE: PRT
<213> ORGANISM: Artificial Sequence
<220> FEATURE:
<223> OTHER INFORMATION: BCMA-52 CDR-H1

<400> SEQUENCE: 63

```
Gly Tyr Ser Phe Thr Ser Tyr Trp
1               5
```

<210> SEQ ID NO 64
<211> LENGTH: 10
<212> TYPE: PRT
<213> ORGANISM: Artificial Sequence
<220> FEATURE:
<223> OTHER INFORMATION: BCMA-52 CDR-H1

<400> SEQUENCE: 64

```
Gly Tyr Ser Phe Thr Ser Tyr Trp Ile Gly
1               5                   10
```

<210> SEQ ID NO 65
<211> LENGTH: 7
<212> TYPE: PRT
<213> ORGANISM: Artificial Sequence
<220> FEATURE:
<223> OTHER INFORMATION: BCMA-52 CDR-H1

<400> SEQUENCE: 65

```
Gly Tyr Ser Phe Thr Ser Tyr
1               5
```

<210> SEQ ID NO 66
<211> LENGTH: 5
<212> TYPE: PRT
<213> ORGANISM: Artificial Sequence
<220> FEATURE:
<223> OTHER INFORMATION: BCMA-52 CDR-H1

<400> SEQUENCE: 66

```
Ser Tyr Trp Ile Gly
1               5
```

<210> SEQ ID NO 67
<211> LENGTH: 8
<212> TYPE: PRT
<213> ORGANISM: Artificial Sequence
<220> FEATURE:
<223> OTHER INFORMATION: BCMA-52 CDR-H2

<400> SEQUENCE: 67

Ile Tyr Pro Gly Asp Ser Asp Thr
1               5

<210> SEQ ID NO 68
<211> LENGTH: 10
<212> TYPE: PRT
<213> ORGANISM: Artificial Sequence
<220> FEATURE:
<223> OTHER INFORMATION: BCMA-52 CDR-H2

<400> SEQUENCE: 68

Ile Ile Tyr Pro Gly Asp Ser Asp Thr Arg
1               5                   10

<210> SEQ ID NO 69
<211> LENGTH: 6
<212> TYPE: PRT
<213> ORGANISM: Artificial Sequence
<220> FEATURE:
<223> OTHER INFORMATION: BCMA-52 CDR-H2

<400> SEQUENCE: 69

Tyr Pro Gly Asp Ser Asp
1               5

<210> SEQ ID NO 70
<211> LENGTH: 17
<212> TYPE: PRT
<213> ORGANISM: Artificial Sequence
<220> FEATURE:
<223> OTHER INFORMATION: BCMA-52 CDR-H2

<400> SEQUENCE: 70

Ile Ile Tyr Pro Gly Asp Ser Asp Thr Arg Tyr Ser Pro Ser Phe Gln
1               5                   10                  15

Gly

<210> SEQ ID NO 71
<211> LENGTH: 9
<212> TYPE: PRT
<213> ORGANISM: Artificial Sequence
<220> FEATURE:
<223> OTHER INFORMATION: BCMA-52 CDR-H3

<400> SEQUENCE: 71

Ala Arg Tyr Ser Gly Ser Phe Asp Asn
1               5

<210> SEQ ID NO 72
<211> LENGTH: 7
<212> TYPE: PRT
<213> ORGANISM: Artificial Sequence
<220> FEATURE:
<223> OTHER INFORMATION: BCMA-52 CDR-H3

<400> SEQUENCE: 72

Tyr Ser Gly Ser Phe Asp Asn
1               5

<210> SEQ ID NO 73
<211> LENGTH: 8
<212> TYPE: PRT
<213> ORGANISM: Artificial Sequence
<220> FEATURE:
<223> OTHER INFORMATION: BCMA-52 CDR-L1

<400> SEQUENCE: 73

Ser Ser Asn Ile Gly Ser His Ser
1               5

<210> SEQ ID NO 74
<211> LENGTH: 13
<212> TYPE: PRT
<213> ORGANISM: Artificial Sequence
<220> FEATURE:
<223> OTHER INFORMATION: BCMA-52 CDR-L1

<400> SEQUENCE: 74

Ser Gly Thr Ser Ser Asn Ile Gly Ser His Ser Val Asn
1               5                   10

<210> SEQ ID NO 75
<211> LENGTH: 3
<212> TYPE: PRT
<213> ORGANISM: Artificial Sequence
<220> FEATURE:
<223> OTHER INFORMATION: BCMA-52 CDR-L2

<400> SEQUENCE: 75

Thr Asn Asn
1

<210> SEQ ID NO 76
<211> LENGTH: 7
<212> TYPE: PRT
<213> ORGANISM: Artificial Sequence
<220> FEATURE:
<223> OTHER INFORMATION: BCMA-52 CDR-L2

<400> SEQUENCE: 76

Thr Asn Asn Gln Arg Pro Ser
1               5

<210> SEQ ID NO 77
<211> LENGTH: 11
<212> TYPE: PRT
<213> ORGANISM: Artificial Sequence
<220> FEATURE:
<223> OTHER INFORMATION: BCMA-52 CDR-L3

<400> SEQUENCE: 77

Ala Ala Trp Asp Gly Ser Leu Asn Gly Leu Val
1               5                   10

<210> SEQ ID NO 78
<211> LENGTH: 41
<212> TYPE: DNA
<213> ORGANISM: Artificial Sequence
<220> FEATURE:
<223> OTHER INFORMATION: BCMA-52 predicted splice acceptor site

<400> SEQUENCE: 78
ctggccatca gtggcctcca gtctgaggat gaggctgatt a                          41

<210> SEQ ID NO 79
<211> LENGTH: 41
<212> TYPE: DNA
<213> ORGANISM: Artificial Sequence
<220> FEATURE:
<223> OTHER INFORMATION: BCMA-52 predicted splice acceptor site

<400> SEQUENCE: 79
agatacagcc cgtccttcca aggccacgtc accatctcag c 41

<210> SEQ ID NO 80
<211> LENGTH: 41
<212> TYPE: DNA
<213> ORGANISM: Artificial Sequence
<220> FEATURE:
<223> OTHER INFORMATION: BCMA-52 predicted splice acceptor site (O/SSE)

<400> SEQUENCE: 80
ctggctattt ctggactgca gagcgaggac gaggccgact a 41

<210> SEQ ID NO 81
<211> LENGTH: 41
<212> TYPE: DNA
<213> ORGANISM: Artificial Sequence
<220> FEATURE:
<223> OTHER INFORMATION: BCMA-52 predicted splice acceptor site (O/SSE)

<400> SEQUENCE: 81
agatacagcc ctagctttca gggccacgtg accatcagcg c 41

<210> SEQ ID NO 82
<211> LENGTH: 744
<212> TYPE: DNA
<213> ORGANISM: Artificial Sequence
<220> FEATURE:
<223> OTHER INFORMATION: BCMA-52 scFv

<400> SEQUENCE: 82
tcctatgagc tgactcagcc accctcagcg tctgggaccc ccgggcagag ggtcaccatg 60
tcttgttctg gaaccagctc caacatcgga agtcactctg taaactggta ccagcagctc 120
ccaggaacgg cccccaaact cctcatctat actaataatc agcggccctc aggggtccct 180
gaccgattct ctggctccaa gtctggcacc tcagcctccc tggccatcag tggcctccag 240
tctgaggatg aggctgatta ttactgtgca gcatgggatg gcagcctgaa tggtctggta 300
ttcggcggag ggaccaagct gaccgtccta ggttctagag gtggtggtgg tagcggcggc 360
ggcggctctg gtggtggtgg atccctcgag atggccgagg tgcagctggt gcagtctgga 420
gcagaggtga aaaagcccgg ggagtctctg aagatctcct gtaagggttc tggatacagc 480
tttaccagct actggatcgg ctgggtgcgc cagatgcccg ggaaaggcct ggagtggatg 540
gggatcatct atcctggtga ctctgatacc agatacagcc cgtccttcca aggccacgtc 600
accatctcag ctgacaagtc catcagcact gcctacctgc agtggagcag cctgaaggcc 660
tcggacaccg ccatgtatta ctgtgcgcgc tactctggtt ctttcgataa ctggggtcaa 720
ggtactctgg tgaccgtctc ctca 744

<210> SEQ ID NO 83
<211> LENGTH: 248
<212> TYPE: PRT
<213> ORGANISM: Artificial Sequence
<220> FEATURE:
<223> OTHER INFORMATION: BCMA-52 scFv

<400> SEQUENCE: 83

Ser Tyr Glu Leu Thr Gln Pro Pro Ser Ala Ser Gly Thr Pro Gly Gln
1 5 10 15

Arg Val Thr Met Ser Cys Ser Gly Thr Ser Ser Asn Ile Gly Ser His
20 25 30

Ser Val Asn Trp Tyr Gln Gln Leu Pro Gly Thr Ala Pro Lys Leu Leu
35 40 45

Ile Tyr Thr Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Gly Ser Leu
85 90 95

Asn Gly Leu Val Phe Gly Gly Gly Thr Lys Leu Thr Val Leu Gly Ser
100 105 110

Arg Gly Gly Gly Gly Ser Gly Gly Gly Gly Ser Gly Gly Gly Gly Ser
115 120 125

Leu Glu Met Ala Glu Val Gln Leu Val Gln Ser Gly Ala Glu Val Lys
130 135 140

Lys Pro Gly Glu Ser Leu Lys Ile Ser Cys Lys Gly Ser Gly Tyr Ser
145 150 155 160

Phe Thr Ser Tyr Trp Ile Gly Trp Val Arg Gln Met Pro Gly Lys Gly
165 170 175

Leu Glu Trp Met Gly Ile Ile Tyr Pro Gly Asp Ser Asp Thr Arg Tyr
180 185 190

Ser Pro Ser Phe Gln Gly His Val Thr Ile Ser Ala Asp Lys Ser Ile
195 200 205

Ser Thr Ala Tyr Leu Gln Trp Ser Ser Leu Lys Ala Ser Asp Thr Ala
210 215 220

Met Tyr Tyr Cys Ala Arg Tyr Ser Gly Ser Phe Asp Asn Trp Gly Gln
225 230 235 240

Gly Thr Leu Val Thr Val Ser Ser
245

<210> SEQ ID NO 84
<211> LENGTH: 744
<212> TYPE: DNA
<213> ORGANISM: Artificial Sequence
<220> FEATURE:
<223> OTHER INFORMATION: BCMA-52 scFv (O/SSE)

<400> SEQUENCE: 84
agctatgagc tgacacagcc tccaagcgcc tctggcacac ctggacagcg agtgacaatg 60
agctgtagcg gcaccagcag caacatcggc agccacagcg tgaactggta tcagcagctg 120
cctggcacag cccctaaact gctgatctac accaacaacc agcggcctag cggcgtgccc 180
gatagatttt ctggcagcaa gagcggcaca agcgccagcc tggctatttc tggactgcag 240
agcgaggacg aggccgacta ttattgtgcc gcctgggacg gctctctgaa cggccttgtt 300
tttggcggag gcaccaagct gacagtgctg ggatctagag gtggcggagg atctggcggc 360
ggaggaagcg gaggcggcgg atctcttgaa atggctgaag tgcagctggt gcagtctggc 420
gccgaagtga agaagcctgg cgagagcctg aagatcagct gcaaaggcag cggctacagc 480
ttcaccagct actggatcgg ctgggtccga cagatgcctg gcaaaggcct tgagtggatg 540
ggcatcatct accccggcga cagcgacacc agatacagcc ctagctttca gggccacgtg 600
accatcagcg ccgacaagtc tatcagcacc gcctacctgc agtggtccag cctgaaggcc 660
tctgacaccg ccatgtacta ctgcgccaga tactctggca gcttcgacaa ttggggccag 720
ggcacactgg tcaccgtgtc cagc 744

<210> SEQ ID NO 85
<211> LENGTH: 116
<212> TYPE: PRT
<213> ORGANISM: Artificial Sequence
<220> FEATURE:
<223> OTHER INFORMATION: BCMA-52 VH chain

<400> SEQUENCE: 85

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Gly Trp Val Arg Gln Met Pro Gly Lys Gly Leu Glu Trp Met
35 40 45

Gly Ile Ile Tyr Pro Gly Asp Ser Asp Thr Arg Tyr Ser Pro Ser Phe
50 55 60

Gln Gly His Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Tyr Ser Gly Ser Phe Asp Asn Trp Gly Gln Gly Thr Leu Val
100 105 110

Thr Val Ser Ser
115

<210> SEQ ID NO 86
<211> LENGTH: 350
<212> TYPE: DNA
<213> ORGANISM: Artificial Sequence
<220> FEATURE:
<223> OTHER INFORMATION: BCMA-52 VH chain

<400> SEQUENCE: 86
gaggtgcagc tggtgcagtc tggagcagag gtgaaaaagc ccggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatac 180
agcccgtcct tccaaggcca cgtcaccatc tcagctgaca agtccatcag cactgcctac 240
ctgcagtgga gcagcctgaa ggcctcggac accgccatgt attactgtgc gcgctactct 300
ggttctttcg ataactgggg tcaaggtact ctggtgaccg tctcctcagc 350

<210> SEQ ID NO 87
<211> LENGTH: 348
<212> TYPE: DNA
<213> ORGANISM: Artificial Sequence
<220> FEATURE:
<223> OTHER INFORMATION: BCMA-52 VH chain (O/SSE)

<400> SEQUENCE: 87
gaagtgcagc tggtgcagtc tggcgccgaa gtgaagaagc ctggcgagag cctgaagatc 60
agctgcaaag gcagcggcta cagcttcacc agctactgga tcggctgggt ccgacagatg 120
cctggcaaag gccttgagtg gatgggcatc atctaccccg gcgacagcga caccagatac 180
agccctagct ttcagggcca cgtgaccatc agcgccgaca agtctatcag caccgcctac 240
ctgcagtggt ccagcctgaa ggcctctgac accgccatgt actactgcgc cagatactct 300
ggcagcttcg acaattgggg ccagggcaca ctggtcaccg tgtccagc 348

<210> SEQ ID NO 88
<211> LENGTH: 111
<212> TYPE: PRT
<213> ORGANISM: Artificial Sequence
<220> FEATURE:
<223> OTHER INFORMATION: BCMA-52 VL chain

<400> SEQUENCE: 88

Ser Tyr Glu Leu Thr Gln Pro Pro Ser Ala Ser Gly Thr Pro Gly Gln
1 5 10 15

Arg Val Thr Met Ser Cys Ser Gly Thr Ser Ser Asn Ile Gly Ser His
20 25 30

Ser Val Asn Trp Tyr Gln Gln Leu Pro Gly Thr Ala Pro Lys Leu Leu
35 40 45

Ile Tyr Thr Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Gly Ser Leu
85 90 95

Asn Gly Leu Val Phe Gly Gly Gly Thr Lys Leu Thr Val Leu Gly
100 105 110

<210> SEQ ID NO 89
<211> LENGTH: 333
<212> TYPE: DNA
<213> ORGANISM: Artificial Sequence
<220> FEATURE:
<223> OTHER INFORMATION: BCMA-52 VL chain

<400> SEQUENCE: 89
tcctatgagc tgactcagcc accctcagcg tctgggaccc ccgggcagag ggtcaccatg 60
tcttgttctg gaaccagctc caacatcgga agtcactctg taaactggta ccagcagctc 120
ccaggaacgg cccccaaact cctcatctat actaataatc agcggccctc aggggtccct 180
gaccgattct ctggctccaa gtctggcacc tcagcctccc tggccatcag tggcctccag 240
tctgaggatg aggctgatta ttactgtgca gcatgggatg gcagcctgaa tggtctggta 300
ttcggcggag ggaccaagct gaccgtccta ggt 333

<210> SEQ ID NO 90
<211> LENGTH: 333
<212> TYPE: DNA
<213> ORGANISM: Artificial Sequence
<220> FEATURE:
<223> OTHER INFORMATION: BCMA-52 VL chain (O/SSE)

<400> SEQUENCE: 90
agctatgagc tgacacagcc tccaagcgcc tctggcacac ctggacagcg agtgacaatg 60
agctgtagcg gcaccagcag caacatcggc agccacagcg tgaactggta tcagcagctg 120
cctggcacag cccctaaact gctgatctac accaacaacc agcggcctag cggcgtgccc 180
gatagatttt ctggcagcaa gagcggcaca agcgccagcc tggctatttc tggactgcag 240
agcgaggacg aggccgacta ttattgtgcc gcctgggacg gctctctgaa cggccttgtt 300
tttggcggag gcaccaagct gacagtgctg gga 333

<210> SEQ ID NO 91
<211> LENGTH: 5
<212> TYPE: PRT
<213> ORGANISM: Artificial Sequence
<220> FEATURE:
<223> OTHER INFORMATION: BCMA-52-scFV-mFc BCMA binding epitope 1

<400> SEQUENCE: 91

Gln Asn Glu Tyr Phe
1 5

<210> SEQ ID NO 92
<211> LENGTH: 6
<212> TYPE: PRT
<213> ORGANISM: Artificial Sequence
<220> FEATURE:
<223> OTHER INFORMATION: BCMA-52-scFV-mFc BCMA binding epitope 2

<400> SEQUENCE: 92

Cys Ile Pro Cys Gln Leu
1 5

<210> SEQ ID NO 93
<211> LENGTH: 5
<212> TYPE: PRT
<213> ORGANISM: Artificial Sequence
<220> FEATURE:
<223> OTHER INFORMATION: BCMA-52-scFV-mFc BCMA binding epitope 3

<400> SEQUENCE: 93

Cys Gln Arg Tyr Cys
1 5

<210> SEQ ID NO 94
<211> LENGTH: 8
<212> TYPE: PRT
<213> ORGANISM: Artificial Sequence
<220> FEATURE:
<223> OTHER INFORMATION: BCMA-55 CDR-H1

<400> SEQUENCE: 94

Gly Tyr Thr Phe Ile Asp Tyr Tyr
1 5

<210> SEQ ID NO 95
<211> LENGTH: 10
<212> TYPE: PRT
<213> ORGANISM: Artificial Sequence
<220> FEATURE:
<223> OTHER INFORMATION: BCMA-55 CDR-H1

<400> SEQUENCE: 95

Gly Tyr Thr Phe Ile Asp Tyr Tyr Val Tyr
1 5 10

<210> SEQ ID NO 96
<211> LENGTH: 7
<212> TYPE: PRT
<213> ORGANISM: Artificial Sequence
<220> FEATURE:
<223> OTHER INFORMATION: BCMA-55 CDR-H1

<400> SEQUENCE: 96

Gly Tyr Thr Phe Ile Asp Tyr
1 5

<210> SEQ ID NO 97
<211> LENGTH: 5
<212> TYPE: PRT
<213> ORGANISM: Artificial Sequence
<220> FEATURE:
<223> OTHER INFORMATION: BCMA-55 CDR-H1

<400> SEQUENCE: 97

Asp Tyr Tyr Val Tyr
1               5

<210> SEQ ID NO 98
<211> LENGTH: 8
<212> TYPE: PRT
<213> ORGANISM: Artificial Sequence
<220> FEATURE:
<223> OTHER INFORMATION: BCMA-55 CDR-H2

<400> SEQUENCE: 98

Ile Asn Pro Asn Ser Gly Gly Thr
1               5

<210> SEQ ID NO 99
<211> LENGTH: 10
<212> TYPE: PRT
<213> ORGANISM: Artificial Sequence
<220> FEATURE:
<223> OTHER INFORMATION: BCMA-55 CDR-H2

<400> SEQUENCE: 99

Trp Ile Asn Pro Asn Ser Gly Gly Thr Asn
1               5                   10

<210> SEQ ID NO 100
<211> LENGTH: 6
<212> TYPE: PRT
<213> ORGANISM: Artificial Sequence
<220> FEATURE:
<223> OTHER INFORMATION: BCMA-55 CDR-H2

<400> SEQUENCE: 100

Asn Pro Asn Ser Gly Gly
1               5

<210> SEQ ID NO 101
<211> LENGTH: 17
<212> TYPE: PRT
<213> ORGANISM: Artificial Sequence
<220> FEATURE:
<223> OTHER INFORMATION: BCMA-55 CDR-H2

<400> SEQUENCE: 101

Trp Ile Asn Pro Asn Ser Gly Gly Thr Asn Tyr Ala Gln Lys Phe Gln
1               5                   10                  15

Gly

<210> SEQ ID NO 102
<211> LENGTH: 11
<212> TYPE: PRT
<213> ORGANISM: Artificial Sequence
<220> FEATURE:
<223> OTHER INFORMATION: BCMA-55 CDR-H3

<400> SEQUENCE: 102

Ala Arg Ser Gln Arg Asp Gly Tyr Met Asp Tyr 1 5 10

<210> SEQ ID NO 103
<211> LENGTH: 9
<212> TYPE: PRT
<213> ORGANISM: Artificial Sequence
<220> FEATURE:
<223> OTHER INFORMATION: BCMA-55 CDR-H3

<400> SEQUENCE: 103

Ser Gln Arg Asp Gly Tyr Met Asp Tyr
1 5

<210> SEQ ID NO 104
<211> LENGTH: 9
<212> TYPE: PRT
<213> ORGANISM: Artificial Sequence
<220> FEATURE:
<223> OTHER INFORMATION: BCMA-55 CDR-L1

<400> SEQUENCE: 104

Ile Ser Cys Thr Gly Thr Ser Ser Asp
1 5

<210> SEQ ID NO 105
<211> LENGTH: 8
<212> TYPE: PRT
<213> ORGANISM: Artificial Sequence
<220> FEATURE:
<223> OTHER INFORMATION: BCMA-55 CDR-L1

<400> SEQUENCE: 105

Thr Gly Thr Ser Ser Asp Val Gly
1 5

<210> SEQ ID NO 106
<211> LENGTH: 3
<212> TYPE: PRT
<213> ORGANISM: Artificial Sequence
<220> FEATURE:
<223> OTHER INFORMATION: BCMA-55 CDR-L2

<400> SEQUENCE: 106

Glu Asp Ser
1

<210> SEQ ID NO 107
<211> LENGTH: 7
<212> TYPE: PRT
<213> ORGANISM: Artificial Sequence
<220> FEATURE:
<223> OTHER INFORMATION: BCMA-55 CDR-L2

<400> SEQUENCE: 107

Glu Asp Ser Lys Arg Pro Ser
1 5

<210> SEQ ID NO 108
<211> LENGTH: 10
<212> TYPE: PRT
<213> ORGANISM: Artificial Sequence
<220> FEATURE:
<223> OTHER INFORMATION: BCMA-55 CDR-L3

<400> SEQUENCE: 108

Ser Ser Asn Thr Arg Ser Ser Thr Leu Val
1 5 10

<210> SEQ ID NO 109
<211> LENGTH: 41
<212> TYPE: DNA
<213> ORGANISM: Artificial Sequence
<220> FEATURE:
<223> OTHER INFORMATION: BCMA-55 predicted splice acceptor site

<400> SEQUENCE: 109
gccctcaggg gtttctaatc gcttctctgg ctccaagtct g 41

<210> SEQ ID NO 110
<211> LENGTH: 41
<212> TYPE: DNA
<213> ORGANISM: Artificial Sequence
<220> FEATURE:
<223> OTHER INFORMATION: BCMA-55 predicted splice acceptor site

<400> SEQUENCE: 110
cgaggctgat tattactgca gctcaaatac aagaagcagc a 41

<210> SEQ ID NO 111
<211> LENGTH: 41
<212> TYPE: DNA
<213> ORGANISM: Artificial Sequence
<220> FEATURE:
<223> OTHER INFORMATION: BCMA-55 predicted splice acceptor site (O/SSE)

<400> SEQUENCE: 111
cgaggccgat tactactgca gcagcaacac ccggtccagc a 41

<210> SEQ ID NO 112
<211> LENGTH: 41
<212> TYPE: DNA
<213> ORGANISM: Artificial Sequence
<220> FEATURE:
<223> OTHER INFORMATION: BCMA-55 predicted splice acceptor site (O/SSE)

<400> SEQUENCE: 112
gcccagcggc gtgtccaata gattcagcgg cagcaagagc g 41

<210> SEQ ID NO 113
<211> LENGTH: 732
<212> TYPE: DNA
<213> ORGANISM: Artificial Sequence
<220> FEATURE:
<223> OTHER INFORMATION: BCMA-55 scFv

<400> SEQUENCE: 113
caatctgccc tgactcagcc tgcctccgtg tctgcgtctc ctggacagtc gatcgccatc 60
tcctgcactg gaaccagcag tgacgttggt tggtatcaac agcacccagg caaagccccc 120
aaactcatga tttatgagga cagtaagcgg ccctcagggg tttctaatcg cttctctggc 180
tccaagtctg gcaacacggc ctccctgacc atctctgggc tccaggctga ggacgaggct 240
gattattact gcagctcaaa tacaagaagc agcactttgg tgttcggcgg agggaccaag 300
ctgaccgtcc taggttctag aggtggtggt ggtagcggcg gcggcggctc tggtggtggt 360
ggatccctcg agatggccga agtgcagctg gtgcagtctg gggctgagat gaagaagcct 420
ggggcctcac tgaagctctc ctgcaaggct tctggataca ccttcatcga ctactatgta 480
tactggatgc gacaggcccc tggacaaggg cttgagtcca tgggatggat caaccctaac 540
agtggtggca caaactatgc acagaagttt cagggcaggg tcaccatgac cagggacacg 600
tccatcagca cagcctacat ggagctgagc aggctgagat ctgacgacac cgccatgtat 660
tactgtgcgc gctcccagcg tgacggttac atggattact ggggtcaagg tactctggtg 720
accgtctcct ca 732

<210> SEQ ID NO 114
<211> LENGTH: 244
<212> TYPE: PRT
<213> ORGANISM: Artificial Sequence
<220> FEATURE:
<223> OTHER INFORMATION: BCMA-55 scFv

<400> SEQUENCE: 114

Gln Ser Ala Leu Thr Gln Pro Ala Ser Val Ser Ala Ser Pro Gly Gln
1 5 10 15

Ser Ile Ala Ile Ser Cys Thr Gly Thr Ser Ser Asp Val Gly Trp Tyr
20 25 30

Gln Gln His Pro Gly Lys Ala Pro Lys Leu Met Ile Tyr Glu Asp Ser
35 40 45

Lys Arg Pro Ser Gly Val Ser Asn Arg Phe Ser Gly Ser Lys Ser Gly
50 55 60

Asn Thr Ala Ser Leu Thr Ile Ser Gly Leu Gln Ala Glu Asp Glu Ala
65 70 75 80

Asp Tyr Tyr Cys Ser Ser Asn Thr Arg Ser Ser Thr Leu Val Phe Gly
85 90 95

Gly Gly Thr Lys Leu Thr Val Leu Gly Ser Arg Gly Gly Gly Gly Ser
100 105 110

Gly Gly Gly Gly Ser Gly Gly Gly Gly Ser Leu Glu Met Ala Glu Val
115 120 125

Gln Leu Val Gln Ser Gly Ala Glu Met Lys Lys Pro Gly Ala Ser Leu
130 135 140

Lys Leu Ser Cys Lys Ala Ser Gly Tyr Thr Phe Ile Asp Tyr Tyr Val
145 150 155 160

Tyr Trp Met Arg Gln Ala Pro Gly Gln Gly Leu Glu Ser Met Gly Trp
165 170 175

Ile Asn Pro Asn Ser Gly Gly Thr Asn Tyr Ala Gln Lys Phe Gln Gly
180 185 190

Arg Val Thr Met Thr Arg Asp Thr Ser Ile Ser Thr Ala Tyr Met Glu
195 200 205

Leu Ser Arg Leu Arg Ser Asp Asp Thr Ala Met Tyr Tyr Cys Ala Arg
210 215 220

Ser Gln Arg Asp Gly Tyr Met Asp Tyr Trp Gly Gln Gly Thr Leu Val
225 230 235 240

Thr Val Ser Ser

<210> SEQ ID NO 115
<211> LENGTH: 732
<212> TYPE: DNA
<213> ORGANISM: Artificial Sequence
<220> FEATURE:
<223> OTHER INFORMATION: BCMA-55 scFv (O/SSE)

<400> SEQUENCE: 115
cagtctgccc tgacacagcc tgccagcgtt agtgctagtc ccggacagtc tatcgccatc 60
agctgtaccg gcaccagctc tgacgttggc tggtatcagc agcaccctgg caaggcccct 120
aagctgatga tctacgagga cagcaagagg cccagcggcg tgtccaatag attcagcggc 180

```
agcaagagcg gcaacaccgc cagcctgaca attagcggac tgcaggccga ggacgaggcc    240

gattactact gcagcagcaa caccccggtcc agcacactgg tttttggcgg aggcaccaag    300

ctgacagtgc tgggatctag aggtggcgga ggatctggcg gcggaggaag cggaggcggc    360

ggatctcttg aaatggctga agtgcagctg gtgcagtctg gcgccgagat gaagaaacct    420

ggcgcctctc tgaagctgag ctgcaaggcc agcggctaca ccttcatcga ctactacgtg    480

tactggatgc ggcaggcccc tggacaggga ctcgaatcta tgggctggat caaccccaat    540

agcggcggca ccaattacgc ccagaaattc cagggcagag tgaccatgac cagagacacc    600

agcatcagca ccgcctacat ggaactgagc cggctgagat ccgacgacac cgccatgtac    660

tactgcgcca gatctcagcg cgacggctac atggattatt ggggccaggg aaccctggtc    720

accgtgtcca gc                                                        732
```

```
<210> SEQ ID NO 116
<211> LENGTH: 118
<212> TYPE: PRT
<213> ORGANISM: Artificial Sequence
<220> FEATURE:
<223> OTHER INFORMATION: BCMA-55 VH chain

<400> SEQUENCE: 116

Glu Val Gln Leu Val Gln Ser Gly Ala Glu Met Lys Lys Pro Gly Ala
1               5                   10                  15

Ser Leu Lys Leu Ser Cys Lys Ala Ser Gly Tyr Thr Phe Ile Asp Tyr
            20                  25                  30

Tyr Val Tyr Trp Met Arg Gln Ala Pro Gly Gln Gly Leu Glu Ser Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
                85                  90                  95

Ala Arg Ser Gln Arg Asp Gly Tyr Met Asp Tyr Trp Gly Gln Gly Thr
            100                 105                 110

Leu Val Thr Val Ser Ser
        115
```

```
<210> SEQ ID NO 117
<211> LENGTH: 354
<212> TYPE: DNA
<213> ORGANISM: Artificial Sequence
<220> FEATURE:
<223> OTHER INFORMATION: BCMA-55 VH chain

<400> SEQUENCE: 117

gaagtgcagc tggtgcagtc tggggctgag atgaagaagc ctggggcctc actgaagctc     60

tcctgcaagg cttctggata caccttcatc gactactatg tatactggat gcgacaggcc    120

cctggacaag ggcttgagtc catgggatgg atcaacccta acagtggtgg cacaaactat    180

gcacagaagt ttcagggcag ggtcaccatg accagggaca cgtccatcag cacagcctac    240

atggagctga gcaggctgag atctgacgac accgccatgt attactgtgc gcgctcccag    300

cgtgacggtt acatggatta ctggggtcaa ggtactctgg tgaccgtctc ctca          354
```

```
<210> SEQ ID NO 118
<211> LENGTH: 354
```

<212> TYPE: DNA
<213> ORGANISM: Artificial Sequence
<220> FEATURE:
<223> OTHER INFORMATION: BCMA-55 VH chain (O/SSE)

<400> SEQUENCE: 118
gaagtgcagc tggtgcagtc tggcgccgag atgaagaaac ctggcgcctc tctgaagctg 60
agctgcaagg ccagcggcta caccttcatc gactactacg tgtactggat gcggcaggcc 120
cctggacagg gactcgaatc tatgggctgg atcaacccca atagcggcgg caccaattac 180
gcccagaaat tccagggcag agtgaccatg accagagaca ccagcatcag caccgcctac 240
atggaactga gccggctgag atccgacgac accgccatgt actactgcgc cagatctcag 300
cgcgacggct acatggatta ttggggccag ggaaccctgg tcaccgtgtc cagc 354

<210> SEQ ID NO 119
<211> LENGTH: 105
<212> TYPE: PRT
<213> ORGANISM: Artificial Sequence
<220> FEATURE:
<223> OTHER INFORMATION: BCMA-55 VL chain

<400> SEQUENCE: 119

Gln Ser Ala Leu Thr Gln Pro Ala Ser Val Ser Ala Ser Pro Gly Gln
1 5 10 15

Ser Ile Ala Ile Ser Cys Thr Gly Thr Ser Ser Asp Val Gly Trp Tyr
20 25 30

Gln Gln His Pro Gly Lys Ala Pro Lys Leu Met Ile Tyr Glu Asp Ser
35 40 45

Lys Arg Pro Ser Gly Val Ser Asn Arg Phe Ser Gly Ser Lys Ser Gly
50 55 60

Asn Thr Ala Ser Leu Thr Ile Ser Gly Leu Gln Ala Glu Asp Glu Ala
65 70 75 80

Asp Tyr Tyr Cys Ser Ser Asn Thr Arg Ser Ser Thr Leu Val Phe Gly
85 90 95

Gly Gly Thr Lys Leu Thr Val Leu Gly
100 105

<210> SEQ ID NO 120
<211> LENGTH: 312
<212> TYPE: DNA
<213> ORGANISM: Artificial Sequence
<220> FEATURE:
<223> OTHER INFORMATION: BCMA-55 VL chain

<400> SEQUENCE: 120
caatctgccc tgactcagcc tgcctccgtg tctgcgtctc ctggacagtc gatcgccatc 60
tcctgcactg gaaccagcag tgacgttggt tggtatcaac agcacccagg caaagccccc 120
aaactcatga tttatgagga cagtaagcgg ccctcagggg tttctaatcg cttctctggc 180
tccaagtctg gcaacacggc ctccctgacc atctctgggc tccaggctga ggacgaggct 240
gattattact gcagctcaaa tacaagaagc agcactttgg tgttcggcgg agggaccaag 300
ctgaccgtcc ta 312

<210> SEQ ID NO 121
<211> LENGTH: 312
<212> TYPE: DNA
<213> ORGANISM: Artificial Sequence
<220> FEATURE:
<223> OTHER INFORMATION: BCMA-55 VL chain (O/SSE)

<400> SEQUENCE: 121
cagtctgccc tgacacagcc tgccagcgtt agtgctagtc ccggacagtc tatcgccatc 60
agctgtaccg gcaccagctc tgacgttggc tggtatcagc agcaccctgg caaggcccct 120
aagctgatga tctacgagga cagcaagagg cccagcggcg tgtccaatag attcagcggc 180
agcaagagcg gcaacaccgc cagcctgaca attagcggac tgcaggccga ggacgaggcc 240
gattactact gcagcagcaa cacccggtcc agcacactgg tttttggcgg aggcaccaag 300
ctgacagtgc tg 312

<210> SEQ ID NO 122
<211> LENGTH: 5
<212> TYPE: PRT
<213> ORGANISM: Artificial Sequence
<220> FEATURE:
<223> OTHER INFORMATION: BCMA-55-scFV-mFc BCMA binding epitope 1

<400> SEQUENCE: 122

Met Leu Met Ala Gly
1               5

<210> SEQ ID NO 123
<211> LENGTH: 6
<212> TYPE: PRT
<213> ORGANISM: Artificial Sequence
<220> FEATURE:
<223> OTHER INFORMATION: BCMA-55-scFV-mFc BCMA binding epitope 2

<400> SEQUENCE: 123

Tyr Phe Asp Ser Leu Leu
1               5

<210> SEQ ID NO 124
<211> LENGTH: 11
<212> TYPE: PRT
<213> ORGANISM: Artificial Sequence
<220> FEATURE:
<223> OTHER INFORMATION: BCMA-55-scFV-mFc BCMA binding epitope 3

<400> SEQUENCE: 124

Gln Leu Arg Cys Ser Ser Asn Thr Pro Pro Leu
1               5                   10

<210> SEQ ID NO 125
<211> LENGTH: 117
<212> TYPE: PRT
<213> ORGANISM: Artificial Sequence
<220> FEATURE:
<223> OTHER INFORMATION: BCMA-C1 VH Chain

<400> SEQUENCE: 125

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

```
Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser
        115


<210> SEQ ID NO 126
<211> LENGTH: 243
<212> TYPE: PRT
<213> ORGANISM: Artificial Sequence
<220> FEATURE:
<223> OTHER INFORMATION: BCMA-C1 VH-VL scFv

<400> SEQUENCE: 126

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Gly Ser Asp Ile Val Leu Thr Gln Ser Pro Pro Ser Leu Ala
    130                 135                 140

Met Ser Leu Gly Lys Arg Ala Thr Ile Ser Cys Arg Ala Ser Glu Ser
145                 150                 155                 160

Val Thr Ile Leu Gly Ser His Leu Ile His Trp Tyr Gln Gln Lys Pro
                165                 170                 175

Gly Gln Pro Pro Thr Leu Leu Ile Gln Leu Ala Ser Asn Val Gln Thr
            180                 185                 190

Gly Val Pro Ala Arg Phe Ser Gly Ser Gly Ser Arg Thr Asp Phe Thr
        195                 200                 205

Leu Thr Ile Asp Pro Val Glu Glu Asp Asp Val Ala Val Tyr Tyr Cys
    210                 215                 220

Leu Gln Ser Arg Thr Ile Pro Arg Thr Phe Gly Gly Gly Thr Lys Leu
225                 230                 235                 240

Glu Ile Lys


<210> SEQ ID NO 127
<211> LENGTH: 111
<212> TYPE: PRT
<213> ORGANISM: Artificial Sequence
<220> FEATURE:
<223> OTHER INFORMATION: BCMA-C1 VL Chain

<400> SEQUENCE: 127

Asp Ile Val Leu Thr Gln Ser Pro Pro Ser Leu Ala Met Ser Leu Gly
1               5                   10                  15
```

```
Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110


<210> SEQ ID NO 128
<211> LENGTH: 243
<212> TYPE: PRT
<213> ORGANISM: Artificial Sequence
<220> FEATURE:
<223> OTHER INFORMATION: BCMA-C1 VL-VH scFv

<400> SEQUENCE: 128

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Ile
        115                 120                 125

Gln Leu Val Gln Ser Gly Pro Glu Leu Lys Lys Pro Gly Glu Thr Val
    130                 135                 140

Lys Ile Ser Cys Lys Ala Ser Gly Tyr Thr Phe Thr Asp Tyr Ser Ile
145                 150                 155                 160

Asn Trp Val Lys Arg Ala Pro Gly Lys Gly Leu Lys Trp Met Gly Trp
                165                 170                 175

Ile Asn Thr Glu Thr Arg Glu Pro Ala Tyr Ala Tyr Asp Phe Arg Gly
            180                 185                 190

Arg Phe Ala Phe Ser Leu Glu Thr Ser Ala Ser Thr Ala Tyr Leu Gln
        195                 200                 205

Ile Asn Asn Leu Lys Tyr Glu Asp Thr Ala Thr Tyr Phe Cys Ala Leu
    210                 215                 220

Asp Tyr Ser Tyr Ala Met Asp Tyr Trp Gly Gln Gly Thr Ser Val Thr
225                 230                 235                 240

Val Ser Ser


<210> SEQ ID NO 129
<211> LENGTH: 244
<212> TYPE: PRT
```

<213> ORGANISM: Artificial Sequence
<220> FEATURE:
<223> OTHER INFORMATION: BCMA-C2 VH-VL scFv

<400> SEQUENCE: 129

Gln Ile Gln Leu Val Gln Ser Gly Pro Asp Leu Lys Lys Pro Gly Glu
1 5 10 15

Thr Val Lys Leu Ser Cys Lys Ala Ser Gly Tyr Thr Phe Thr Asn Phe
20 25 30

Gly Met Asn Trp Val Lys Gln Ala Pro Gly Lys Gly Phe Lys Trp Met
35 40 45

Ala Trp Ile Asn Thr Tyr Thr Gly Glu Ser Tyr Phe Ala Asp Asp Phe
50 55 60

Lys Gly Arg Phe Ala Phe Ser Val Glu Thr Ser Ala Thr Thr Ala Tyr
65 70 75 80

Leu Gln Ile Asn Asn Leu Lys Thr Glu Asp Thr Ala Thr Tyr Phe Cys
85 90 95

Ala Arg Gly Glu Ile Tyr Tyr Gly Tyr Asp Gly Gly Phe Ala Tyr Trp
100 105 110

Gly Gln Gly Thr Leu Val Thr Val Ser Ala Gly Gly Gly Gly Ser Gly
115 120 125

Gly Gly Gly Ser Gly Gly Gly Gly Ser Asp Val Val Met Thr Gln Ser
130 135 140

His Arg Phe Met Ser Thr Ser Val Gly Asp Arg Val Ser Ile Thr Cys
145 150 155 160

Arg Ala Ser Gln Asp Val Asn Thr Ala Val Ser Trp Tyr Gln Gln Lys
165 170 175

Pro Gly Gln Ser Pro Lys Leu Leu Ile Phe Ser Ala Ser Tyr Arg Tyr
180 185 190

Thr Gly Val Pro Asp Arg Phe Thr Gly Ser Gly Ser Gly Ala Asp Phe
195 200 205

Thr Leu Thr Ile Ser Ser Val Gln Ala Glu Asp Leu Ala Val Tyr Tyr
210 215 220

Cys Gln Gln His Tyr Ser Thr Pro Trp Thr Phe Gly Gly Gly Thr Lys
225 230 235 240

Leu Asp Ile Lys

<210> SEQ ID NO 130
<211> LENGTH: 244
<212> TYPE: PRT
<213> ORGANISM: Artificial Sequence
<220> FEATURE:
<223> OTHER INFORMATION: BCMA-C2 VL-VH scFv

<400> SEQUENCE: 130

Asp Val Val Met Thr Gln Ser His Arg Phe Met Ser Thr Ser Val Gly
1 5 10 15

Asp Arg Val Ser Ile Thr Cys Arg Ala Ser Gln Asp Val Asn Thr Ala
20 25 30

Val Ser Trp Tyr Gln Gln Lys Pro Gly Gln Ser Pro Lys Leu Leu Ile
35 40 45

Phe Ser Ala Ser Tyr Arg Tyr Thr Gly Val Pro Asp Arg Phe Thr Gly
50 55 60

Ser Gly Ser Gly Ala Asp Phe Thr Leu Thr Ile Ser Ser Val Gln Ala
65 70 75 80

Glu Asp Leu Ala Val Tyr Tyr Cys Gln Gln His Tyr Ser Thr Pro Trp

```
                85                  90                  95

Thr Phe Gly Gly Gly Thr Lys Leu Asp Ile Lys Gly Gly Gly Gly Ser
            100                 105                 110

Gly Gly Gly Gly Ser Gly Gly Gly Gly Ser Gln Ile Gln Leu Val Gln
        115                 120                 125

Ser Gly Pro Asp Leu Lys Lys Pro Gly Glu Thr Val Lys Leu Ser Cys
    130                 135                 140

Lys Ala Ser Gly Tyr Thr Phe Thr Asn Phe Gly Met Asn Trp Val Lys
145                 150                 155                 160

Gln Ala Pro Gly Lys Gly Phe Lys Trp Met Ala Trp Ile Asn Thr Tyr
                165                 170                 175

Thr Gly Glu Ser Tyr Phe Ala Asp Asp Phe Lys Gly Arg Phe Ala Phe
            180                 185                 190

Ser Val Glu Thr Ser Ala Thr Thr Ala Tyr Leu Gln Ile Asn Asn Leu
        195                 200                 205

Lys Thr Glu Asp Thr Ala Thr Tyr Phe Cys Ala Arg Gly Glu Ile Tyr
    210                 215                 220

Tyr Gly Tyr Asp Gly Gly Phe Ala Tyr Trp Gly Gln Gly Thr Leu Val
225                 230                 235                 240

Thr Val Ser Ala


<210> SEQ ID NO 131
<211> LENGTH: 122
<212> TYPE: PRT
<213> ORGANISM: Artificial Sequence
<220> FEATURE:
<223> OTHER INFORMATION: BCMA-C2 VH Chain

<400> SEQUENCE: 131

Gln Ile Gln Leu Val Gln Ser Gly Pro Asp Leu Lys Lys Pro Gly Glu
1               5                   10                  15

Thr Val Lys Leu Ser Cys Lys Ala Ser Gly Tyr Thr Phe Thr Asn Phe
            20                  25                  30

Gly Met Asn Trp Val Lys Gln Ala Pro Gly Lys Gly Phe Lys Trp Met
        35                  40                  45

Ala Trp Ile Asn Thr Tyr Thr Gly Glu Ser Tyr Phe Ala Asp Asp Phe
    50                  55                  60

Lys Gly Arg Phe Ala Phe Ser Val Glu Thr Ser Ala Thr Thr Ala Tyr
65                  70                  75                  80

Leu Gln Ile Asn Asn Leu Lys Thr Glu Asp Thr Ala Thr Tyr Phe Cys
                85                  90                  95

Ala Arg Gly Glu Ile Tyr Tyr Gly Tyr Asp Gly Gly Phe Ala Tyr Trp
            100                 105                 110

Gly Gln Gly Thr Leu Val Thr Val Ser Ala
        115                 120


<210> SEQ ID NO 132
<211> LENGTH: 107
<212> TYPE: PRT
<213> ORGANISM: Artificial Sequence
<220> FEATURE:
<223> OTHER INFORMATION: BCMA-C2 VL Chain

<400> SEQUENCE: 132

Asp Val Val Met Thr Gln Ser His Arg Phe Met Ser Thr Ser Val Gly
1               5                   10                  15

Asp Arg Val Ser Ile Thr Cys Arg Ala Ser Gln Asp Val Asn Thr Ala
```

```
            20                  25                  30

Val Ser Trp Tyr Gln Gln Lys Pro Gly Gln Ser Pro Lys Leu Leu Ile
        35                  40                  45

Phe Ser Ala Ser Tyr Arg Tyr Thr Gly Val Pro Asp Arg Phe Thr Gly
    50                  55                  60

Ser Gly Ser Gly Ala Asp Phe Thr Leu Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Asp Ile Lys
            100                 105


<210> SEQ ID NO 133
<211> LENGTH: 9
<212> TYPE: PRT
<213> ORGANISM: Artificial Sequence
<220> FEATURE:
<223> OTHER INFORMATION: BMCA epitope

<400> SEQUENCE: 133

Gln Asn Glu Tyr Phe Asp Ser Leu Leu
1               5


<210> SEQ ID NO 134
<211> LENGTH: 39
<212> TYPE: PRT
<213> ORGANISM: Artificial Sequence
<220> FEATURE:
<223> OTHER INFORMATION: CD28 ectodomain spacer

<400> SEQUENCE: 134

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35


<210> SEQ ID NO 135
<211> LENGTH: 117
<212> TYPE: DNA
<213> ORGANISM: Artificial Sequence
<220> FEATURE:
<223> OTHER INFORMATION: CD28 ectodomain spacer

<400> SEQUENCE: 135

attgaagtta tgtatcctcc tccttaccta gacaatgaga agagcaatgg aaccattatc      60

catgtgaaag ggaaacacct ttgtccaagt cccctatttc ccggaccttc taagccc        117


<210> SEQ ID NO 136
<211> LENGTH: 41
<212> TYPE: PRT
<213> ORGANISM: Artificial Sequence
<220> FEATURE:
<223> OTHER INFORMATION: CD28 endo

<400> SEQUENCE: 136

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30
```

```
Pro Arg Asp Phe Ala Ala Tyr Arg Ser
        35                  40


<210> SEQ ID NO 137
<211> LENGTH: 123
<212> TYPE: DNA
<213> ORGANISM: Artificial Sequence
<220> FEATURE:
<223> OTHER INFORMATION: CD28 endo

<400> SEQUENCE: 137

aggagtaaga ggagcaggct cctgcacagt gactacatga acatgactcc ccgccgcccc     60

gggcccaccc gcaagcatta ccagccctat gccccaccac gcgacttcgc agcctatcgc    120

tcc                                                                  123


<210> SEQ ID NO 138
<211> LENGTH: 28
<212> TYPE: PRT
<213> ORGANISM: Artificial Sequence
<220> FEATURE:
<223> OTHER INFORMATION: CD28 transmembrane domain

<400> SEQUENCE: 138

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25


<210> SEQ ID NO 139
<211> LENGTH: 84
<212> TYPE: DNA
<213> ORGANISM: Artificial Sequence
<220> FEATURE:
<223> OTHER INFORMATION: CD28 transmembrane domain

<400> SEQUENCE: 139

atgttttggg tgctggtcgt ggtcggaggg gtgctggcct gttacagcct gctggtgaca     60

gtcgctttca tcatcttctg ggtg                                            84


<210> SEQ ID NO 140
<211> LENGTH: 84
<212> TYPE: DNA
<213> ORGANISM: Artificial Sequence
<220> FEATURE:
<223> OTHER INFORMATION: CD28 transmembrane domain

<400> SEQUENCE: 140

atgttctggg tgctcgtggt cgttggcgga gtgctggcct gttacagcct gctggttacc     60

gtggccttca tcatcttttg ggtc                                            84


<210> SEQ ID NO 141
<211> LENGTH: 41
<212> TYPE: DNA
<213> ORGANISM: Artificial Sequence
<220> FEATURE:
<223> OTHER INFORMATION: CD28TM predicted splice acceptor site

<400> SEQUENCE: 141

aggggtgctg gcctgttaca gcctgctggt gacagtcgct t                         41


<210> SEQ ID NO 142
<211> LENGTH: 16
<212> TYPE: PRT
```

<213> ORGANISM: Artificial Sequence
<220> FEATURE:
<223> OTHER INFORMATION: CD33 signal peptide

<400> SEQUENCE: 142

Met Pro Leu Leu Leu Leu Leu Pro Leu Leu Trp Ala Gly Ala Leu Ala
1               5                   10                  15

<210> SEQ ID NO 143
<211> LENGTH: 112
<212> TYPE: PRT
<213> ORGANISM: Artificial Sequence
<220> FEATURE:
<223> OTHER INFORMATION: CD3-zeta derived intracellular signaling domain

<400> SEQUENCE: 143

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 144
<211> LENGTH: 336
<212> TYPE: DNA
<213> ORGANISM: Artificial Sequence
<220> FEATURE:
<223> OTHER INFORMATION: CD3-zeta derived intracellular signaling domain

<400> SEQUENCE: 144
agagtcaagt tttccaggtc cgccgacgct ccagcctacc agcaggggca gaaccagctg     60
tacaacgagc tgaacctggg cagaagggaa gagtacgacg tcctggataa gcggagaggc    120
cgggaccctg agatgggcgg caagcctcgg cggaagaacc cccaggaagg cctgtataac    180
gaactgcaga aagacaagat ggccgaggcc tacagcgaga tcggcatgaa gggcgagcgg    240
aggcggggca agggccacga cggcctgtat cagggcctgt ccaccgccac caaggatacc    300
tacgacgccc tgcacatgca ggccctgccc ccaagg                              336

<210> SEQ ID NO 145
<211> LENGTH: 336
<212> TYPE: DNA
<213> ORGANISM: Artificial Sequence
<220> FEATURE:
<223> OTHER INFORMATION: CD3-zeta derived intracellular signaling domain

<400> SEQUENCE: 145
agagtgaagt tcagcagatc cgccgacgct ccagcctatc agcagggcca aaaccagctg     60
tacaacgagc tgaacctggg gagaagagaa gagtacgacg tgctggataa gcggagaggc    120
agagatcctg aaatgggcgg caagcccaga cggaagaatc ctcaagaggg cctgtataat    180
gagctgcaga aagacaagat ggccgaggcc tacagcgaga tcggaatgaa gggcgagcgc    240
agaagaggca agggacacga tggactgtac cagggcctga gcaccgccac caaggatacc 300
tatgacgcac tgcacatgca ggccctgcca cctaga 336

<210> SEQ ID NO 146
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 146

Met Ala Leu Pro Val Thr Ala Leu Leu Leu Pro Leu Ala Leu Leu Leu
1 5 10 15

His Ala

<210> SEQ ID NO 147
<211> LENGTH: 183
<212> TYPE: PRT
<213> ORGANISM: Macaca fascicularis
<220> FEATURE:
<223> OTHER INFORMATION: Cynomolgus BCMA; GenBank No. EHH60172.1

<400> SEQUENCE: 147

Met Leu Gln Met Ala Arg Gln Cys Ser Gln Asn Glu Tyr Phe Asp Ser
1 5 10 15

Leu Leu His Asp Cys Lys Pro Cys Gln Leu Arg Cys Ser Ser Thr Pro
20 25 30

Pro Leu Thr Cys Gln Arg Tyr Cys Asn Ala Ser Met Thr Asn Ser Val
35 40 45

Lys Gly Met Asn Ala Ile Leu Trp Thr Cys Leu Gly Leu Ser Leu Ile
50 55 60

Ile Ser Leu Ala Val Phe Val Leu Thr Phe Leu Leu Arg Lys Met Ser
65 70 75 80

Ser Glu Pro Leu Lys Asp Glu Phe Lys Asn Thr Gly Ser Gly Leu Leu
85 90 95

Gly Met Ala Asn Ile Asp Leu Glu Lys Gly Arg Thr Gly Asp Glu Ile
100 105 110

Val Leu Pro Arg Gly Leu Glu Tyr Thr Val Glu Glu Cys Thr Cys Glu
115 120 125

Asp Cys Ile Lys Asn Lys Pro Lys Val Asp Ser Asp His Cys Phe Pro
130 135 140

Leu Pro Ala Met Glu Glu Gly Ala Thr Ile Leu Val Thr Thr Lys Thr
145 150 155 160

Asn Asp Tyr Cys Asn Ser Leu Ser Ala Ala Leu Ser Val Thr Glu Ile
165 170 175

Glu Lys Ser Ile Ser Ala Arg
180

<210> SEQ ID NO 148
<211> LENGTH: 20
<212> TYPE: PRT
<213> ORGANISM: Artificial Sequence
<220> FEATURE:
<223> OTHER INFORMATION: E2A peptide

<400> SEQUENCE: 148

Gln Cys Thr Asn Tyr Ala Leu Leu Lys Leu Ala Gly Asp Val Glu Ser
1 5 10 15

Asn Pro Gly Pro
20

<210> SEQ ID NO 149
<211> LENGTH: 23
<212> TYPE: PRT
<213> ORGANISM: Artificial Sequence
<220> FEATURE:
<223> OTHER INFORMATION: E2A peptide

<400> SEQUENCE: 149

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 150
<211> LENGTH: 20
<212> TYPE: DNA
<213> ORGANISM: Artificial Sequence
<220> FEATURE:
<223> OTHER INFORMATION: EF1a/HTLV promoter forward primer

<400> SEQUENCE: 150 cttttcgca acgggtttgc 20

<210> SEQ ID NO 151
<211> LENGTH: 544
<212> TYPE: DNA
<213> ORGANISM: Artificial Sequence
<220> FEATURE:
<223> OTHER INFORMATION: EF1alpha promoter with HTLV1 enhancer

<400> SEQUENCE: 151
ggatctgcga tcgctccggt gcccgtcagt gggcagagcg cacatcgccc acagtccccg 60
agaagttggg gggaggggtc ggcaattgaa ccggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctac 544

<210> SEQ ID NO 152
<211> LENGTH: 22
<212> TYPE: PRT
<213> ORGANISM: Artificial Sequence
<220> FEATURE:
<223> OTHER INFORMATION: F2A peptide

<400> SEQUENCE: 152

Val Lys Gln Thr Leu Asn Phe Asp Leu Leu Lys Leu Ala Gly Asp Val
1 5 10 15

Glu Ser Asn Pro Gly Pro
20

<210> SEQ ID NO 153

<211> LENGTH: 25
<212> TYPE: PRT
<213> ORGANISM: Artificial Sequence
<220> FEATURE:
<223> OTHER INFORMATION: F2A peptide

<400> SEQUENCE: 153

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 154
<211> LENGTH: 22
<212> TYPE: PRT
<213> ORGANISM: Artificial Sequence
<220> FEATURE:
<223> OTHER INFORMATION: GMCSFR alpha chain signal peptide

<400> SEQUENCE: 154

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 155
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 155
atgcttctcc tggtgacaag ccttctgctc tgtgagttac cacacccagc attcctcctg     60
atccca                                                                66

<210> SEQ ID NO 156
<211> LENGTH: 229
<212> TYPE: PRT
<213> ORGANISM: Artificial Sequence
<220> FEATURE:
<223> OTHER INFORMATION: Hinge-CH2-CH3 spacer

<400> SEQUENCE: 156

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln

```
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 157
<211> LENGTH: 119
<212> TYPE: PRT
<213> ORGANISM: Artificial Sequence
<220> FEATURE:
<223> OTHER INFORMATION: Hinge-CH3 spacer

<400> SEQUENCE: 157

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115


<210> SEQ ID NO 158
<211> LENGTH: 11
<212> TYPE: PRT
<213> ORGANISM: Homo sapiens
<220> FEATURE:
<223> OTHER INFORMATION: Human BCMA epitope (residues 17-27)

<400> SEQUENCE: 158

Leu Leu His Ala Cys Ile Pro Cys Gln Leu Arg
1               5                   10


<210> SEQ ID NO 159
<211> LENGTH: 7
<212> TYPE: PRT
<213> ORGANISM: Homo sapiens
<220> FEATURE:
<223> OTHER INFORMATION: Human BCMA epitope (residues 21-27)

<400> SEQUENCE: 159

Cys Ile Pro Cys Gln Leu Arg
1               5
```

<210> SEQ ID NO 160
<211> LENGTH: 10
<212> TYPE: PRT
<213> ORGANISM: Homo sapiens
<220> FEATURE:
<223> OTHER INFORMATION: Human BCMA epitope (residues 30-39)

<400> SEQUENCE: 160

Ser Asn Thr Pro Pro Leu Thr Cys Gln Arg
1 5 10

<210> SEQ ID NO 161
<211> LENGTH: 7
<212> TYPE: PRT
<213> ORGANISM: Homo sapiens
<220> FEATURE:
<223> OTHER INFORMATION: Human BCMA epitope (residues 44-50)

<400> SEQUENCE: 161

Ser Val Thr Asn Ser Val Lys
1 5

<210> SEQ ID NO 162
<211> LENGTH: 7
<212> TYPE: PRT
<213> ORGANISM: Homo sapiens
<220> FEATURE:
<223> OTHER INFORMATION: Human BCMA epitope (residues 8-15)

<400> SEQUENCE: 162

Cys Ser Gln Asn Glu Tyr Phe
1 5

<210> SEQ ID NO 163
<211> LENGTH: 135
<212> TYPE: PRT
<213> ORGANISM: Homo sapiens
<220> FEATURE:
<223> OTHER INFORMATION: Human BCMA Variant; GenBank No. ABN42510.1

<400> SEQUENCE: 163

Met Leu Gln Met Ala Gly Gln Cys Ser Gln Asn Glu Tyr Phe Asp Ser
1 5 10 15

Leu Leu His Ala Cys Ile Pro Cys Gln Leu Arg Cys Ser Ser Asn Thr
20 25 30

Pro Pro Leu Thr Cys Gln Arg Tyr Cys Asn Ala Arg Ser Gly Leu Leu
35 40 45

Gly Met Ala Asn Ile Asp Leu Glu Lys Ser Arg Thr Gly Asp Glu Ile
50 55 60

Ile Leu Pro Arg Gly Leu Glu Tyr Thr Val Glu Glu Cys Thr Cys Glu
65 70 75 80

Asp Cys Ile Lys Ser Lys Pro Lys Val Asp Ser Asp His Cys Phe Pro
85 90 95

Leu Pro Ala Met Glu Glu Gly Ala Thr Ile Leu Val Thr Thr Lys Thr
100 105 110

Asn Asp Tyr Cys Lys Ser Leu Pro Ala Ala Leu Ser Ala Thr Glu Ile
115 120 125

Glu Lys Ser Ile Ser Ala Arg
130 135

<210> SEQ ID NO 164

<211> LENGTH: 184
<212> TYPE: PRT
<213> ORGANISM: Homo sapiens
<220> FEATURE:
<223> OTHER INFORMATION: Human BCMA; GenBank No. BAB60895.1

<400> SEQUENCE: 164

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 165
<211> LENGTH: 184
<212> TYPE: PRT
<213> ORGANISM: Homo sapiens
<220> FEATURE:
<223> OTHER INFORMATION: Human BCMA; NCBI No. NP_001183.2

<400> SEQUENCE: 165

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
```

```
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180


<210> SEQ ID NO 166
<211> LENGTH: 20
<212> TYPE: PRT
<213> ORGANISM: Artificial Sequence
<220> FEATURE:
<223> OTHER INFORMATION: human IgG -kappa signal peptide

<400> SEQUENCE: 166

Met Val Leu Gln Thr Gln Val Phe Ile Ser Leu Leu Leu Trp Ile Ser
1               5                   10                  15

Gly Ala Tyr Gly
            20


<210> SEQ ID NO 167
<211> LENGTH: 60
<212> TYPE: DNA
<213> ORGANISM: Artificial Sequence
<220> FEATURE:
<223> OTHER INFORMATION: human IgG -kappa signal sequence

<400> SEQUENCE: 167

atggtgctgc agacccaggt gttcatcagc ctgctgctgt ggatctccgg agcatacgga     60


<210> SEQ ID NO 168
<211> LENGTH: 60
<212> TYPE: DNA
<213> ORGANISM: Artificial Sequence
<220> FEATURE:
<223> OTHER INFORMATION: human IgG -kappa signal sequence

<400> SEQUENCE: 168

atggtgctgc agacacaggt gttcatcagc ctgctgctgt ggatctccgg agcatacgga     60


<210> SEQ ID NO 169
<211> LENGTH: 60
<212> TYPE: DNA
<213> ORGANISM: Artificial Sequence
<220> FEATURE:
<223> OTHER INFORMATION: human IgG -kappa signal sequence

<400> SEQUENCE: 169

atggtgctgc agacccaggt gttcatcagc ctgctgctgt ggatctctgg cgcctacggc     60


<210> SEQ ID NO 170
<211> LENGTH: 60
<212> TYPE: DNA
<213> ORGANISM: Artificial Sequence
<220> FEATURE:
<223> OTHER INFORMATION: human IgG -kappa signal sequence

<400> SEQUENCE: 170

atggtgctgc agacccaggt gttcatcagc ctgctgctgt ggatctctgg cgcctatgga     60


<210> SEQ ID NO 171
<211> LENGTH: 60
<212> TYPE: DNA
```

<213> ORGANISM: Artificial Sequence
<220> FEATURE:
<223> OTHER INFORMATION: human IgG -kappa signal sequence

<400> SEQUENCE: 171
atggtgctgc agacacaggt gttcatctcc ctgctgctgt ggatctctgg agcatacgga 60

<210> SEQ ID NO 172
<211> LENGTH: 326
<212> TYPE: PRT
<213> ORGANISM: Homo sapiens
<220> FEATURE:
<223> OTHER INFORMATION: Human IgG2 Fc (Uniprot P01859)

<400> SEQUENCE: 172

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
```

325

<210> SEQ ID NO 173
<211> LENGTH: 327
<212> TYPE: PRT
<213> ORGANISM: Homo sapiens
<220> FEATURE:
<223> OTHER INFORMATION: Human IgG4 Fc (Uniprot P01861)

<400> SEQUENCE: 173

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 174
<211> LENGTH: 228
<212> TYPE: PRT

<213> ORGANISM: Artificial Sequence
<220> FEATURE:
<223> OTHER INFORMATION: IgG4/IgG2 hinge- IgG2/IgG4 CH2- IgG4 CH3 spacer

<400> SEQUENCE: 174

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225

<210> SEQ ID NO 175
<211> LENGTH: 684
<212> TYPE: DNA
<213> ORGANISM: Artificial Sequence
<220> FEATURE:
<223> OTHER INFORMATION: IgG4/IgG2 hinge- IgG2/IgG4 CH2- IgG4 CH3 spacer

<400> SEQUENCE: 175
gaatctaagt acggaccgcc ctgccctccc tgccctgctc ctcctgtggc tggaccaagc 60
gtgttcctgt ttccacctaa gcctaaagat accctgatga tttcccgcac acctgaagtg 120
acttgcgtgg tcgtggacgt gagccaggag gatccagaag tgcagttcaa ctggtacgtg 180
gacggcgtgg aagtccacaa tgctaagact aaaccccgag aggaacagtt tcagtcaact 240
taccgggtcg tgagcgtgct gaccgtcctg catcaggatt ggctgaacgg gaaggagtat 300
aagtgcaaag tgtctaataa gggactgcct agctccatcg agaaaacaat tagtaaggca 360
aaagggcagc ctcgagaacc acaggtgtat accctgcccc ctagccagga ggaaatgacc 420
aagaaccagg tgtccctgac atgtctggtc aaaggcttct atccaagtga catcgccgtg 480
gagtgggaat caaatgggca gcccgagaac aattacaaga ccacaccacc cgtgctggac 540
tctgatggaa gtttctttct gtattccagg ctgaccgtgg ataaatctcg ctggcaggag 600
ggcaacgtgt tctcttgcag tgtcatgcac gaagccctgc acaatcatta tacacagaag 660
tcactgagcc tgtccctggg caaa 684

<210> SEQ ID NO 176
<211> LENGTH: 18
<212> TYPE: PRT
<213> ORGANISM: Artificial Sequence
<220> FEATURE:
<223> OTHER INFORMATION: Linker

<400> SEQUENCE: 176

Gly Ser Thr Ser Gly Ser Gly Lys Pro Gly Ser Gly Glu Gly Ser Thr
1 5 10 15

Lys Gly

<210> SEQ ID NO 177
<211> LENGTH: 399
<212> TYPE: DNA
<213> ORGANISM: Artificial Sequence
<220> FEATURE:
<223> OTHER INFORMATION: MND promoter

<400> SEQUENCE: 177
tttatttagt ctccagaaaa aggggggaat gaaagacccc acctgtaggt ttggcaagct 60
aggatcaagg ttaggaacag agagacagca gaatatgggc caaacaggat atctgtggta 120
agcagttcct gccccggctc agggccaaga acagttggaa cagcagaata tgggccaaac 180
aggatatctg tggtaagcag ttcctgcccc ggctcagggc caagaacaga tggtccccag 240
atgcggtccc gccctcagca gtttctagag aaccatcaga tgtttccagg gtgccccaag 300
gacctgaaat gaccctgtgc cttatttgaa ctaaccaatc agttcgcttc tcgcttctgt 360
tcgcgcgctt ctgctccccg agctcaataa aagagcccca 399

<210> SEQ ID NO 178
<211> LENGTH: 554
<212> TYPE: DNA
<213> ORGANISM: Artificial Sequence
<220> FEATURE:
<223> OTHER INFORMATION: modified EF1 alpha promoter

<400> SEQUENCE: 178
ggatctgcga tcgctccggt gcccgtcagt gggcagagcg cacatcgccc acagtccccg 60
agaagttggg gggaggggtc ggcaattgaa ccggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacggctag cgcc 554

<210> SEQ ID NO 179
<211> LENGTH: 185
<212> TYPE: PRT

<213> ORGANISM: Mus musculus
<220> FEATURE:
<223> OTHER INFORMATION: Mouse BCMA; NCBI No. NP_035738.1

<400> SEQUENCE: 179

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
            20                  25                  30

Gln Pro Tyr Cys Asp Pro Ser Val Thr Ser Ser Val Lys Gly Thr Tyr
        35                  40                  45

Thr Val Leu Trp Ile Phe Leu Gly Leu Thr Leu Val Leu Ser Leu Ala
    50                  55                  60

Leu Phe Thr Ile Ser Phe Leu Leu Arg Lys Met Asn Pro Glu Ala Leu
65                  70                  75                  80

Lys Asp Glu Pro Gln Ser Pro Gly Gln Leu Asp Gly Ser Ala Gln Leu
                85                  90                  95

Asp Lys Ala Asp Thr Glu Leu Thr Arg Ile Arg Ala Gly Asp Asp Arg
            100                 105                 110

Ile Phe Pro Arg Ser Leu Glu Tyr Thr Val Glu Glu Cys Thr Cys Glu
        115                 120                 125

Asp Cys Val Lys Ser Lys Pro Lys Gly Asp Ser Asp His Phe Phe Pro
    130                 135                 140

Leu Pro Ala Met Glu Glu Gly Ala Thr Ile Leu Val Thr Thr Lys Thr
145                 150                 155                 160

Gly Asp Tyr Gly Lys Ser Ser Val Pro Thr Ala Leu Gln Ser Val Met
                165                 170                 175

Gly Met Glu Lys Pro Thr His Thr Arg
            180                 185

<210> SEQ ID NO 180
<211> LENGTH: 41
<212> TYPE: DNA
<213> ORGANISM: Artificial Sequence
<220> FEATURE:
<223> OTHER INFORMATION: Optimized splice acceptor site

<400> SEQUENCE: 180
cagtttcttc ctgtatagta gactcaccgt ggataaatca a                         41

<210> SEQ ID NO 181
<211> LENGTH: 41
<212> TYPE: DNA
<213> ORGANISM: Artificial Sequence
<220> FEATURE:
<223> OTHER INFORMATION: Optimized splice acceptor site

<400> SEQUENCE: 181
gggcaacgtg ttcagctgca gcgtgatgca cgaggccctg c                         41

<210> SEQ ID NO 182
<211> LENGTH: 41
<212> TYPE: DNA
<213> ORGANISM: Artificial Sequence
<220> FEATURE:
<223> OTHER INFORMATION: Optimized splice acceptor site

<400> SEQUENCE: 182
cggagtgctg gcctgttaca gcctgctggt taccgtggcc t                         41

<210> SEQ ID NO 183
<211> LENGTH: 41
<212> TYPE: DNA
<213> ORGANISM: Artificial Sequence
<220> FEATURE:
<223> OTHER INFORMATION: Optimized splice acceptor site

<400> SEQUENCE: 183
gctgagagtg aagttcagca gatccgccga cgctccagcc t 41

<210> SEQ ID NO 184
<211> LENGTH: 41
<212> TYPE: DNA
<213> ORGANISM: Artificial Sequence
<220> FEATURE:
<223> OTHER INFORMATION: Optimized splice acceptor site

<400> SEQUENCE: 184
acacctccac tggatcccca agagctggat atcctgaaaa c 41

<210> SEQ ID NO 185
<211> LENGTH: 41
<212> TYPE: DNA
<213> ORGANISM: Artificial Sequence
<220> FEATURE:
<223> OTHER INFORMATION: Optimized splice acceptor site

<400> SEQUENCE: 185
accggattcc tcctgatcca agcctggcca gagaacagaa c 41

<210> SEQ ID NO 186
<211> LENGTH: 41
<212> TYPE: DNA
<213> ORGANISM: Artificial Sequence
<220> FEATURE:
<223> OTHER INFORMATION: Optimized splice acceptor site

<400> SEQUENCE: 186
acggccagtt tagcctggct gtggtgtctc tgaacatcac c 41

<210> SEQ ID NO 187
<211> LENGTH: 41
<212> TYPE: DNA
<213> ORGANISM: Artificial Sequence
<220> FEATURE:
<223> OTHER INFORMATION: Optimized splice acceptor site

<400> SEQUENCE: 187
aagtttcttt ctgtattcca gactgaccgt ggataaatct c 41

<210> SEQ ID NO 188
<211> LENGTH: 41
<212> TYPE: DNA
<213> ORGANISM: Artificial Sequence
<220> FEATURE:
<223> OTHER INFORMATION: Optimized splice acceptor site

<400> SEQUENCE: 188
cgccttgtcc tccttgtccc gctcctcctg ttgccggacc t 41

<210> SEQ ID NO 189
<211> LENGTH: 15
<212> TYPE: DNA
<213> ORGANISM: Artificial Sequence
<220> FEATURE:
<223> OTHER INFORMATION: Optimized splice donor site

<400> SEQUENCE: 189
agtctaaata cggac 15

<210> SEQ ID NO 190
<211> LENGTH: 15
<212> TYPE: DNA
<213> ORGANISM: Artificial Sequence
<220> FEATURE:
<223> OTHER INFORMATION: Optimized splice donor site

<400> SEQUENCE: 190
tcaactggta tgtgg 15

<210> SEQ ID NO 191
<211> LENGTH: 15
<212> TYPE: DNA
<213> ORGANISM: Artificial Sequence
<220> FEATURE:
<223> OTHER INFORMATION: Optimized splice donor site

<400> SEQUENCE: 191
accatctcca aggcc 15

<210> SEQ ID NO 192
<211> LENGTH: 15
<212> TYPE: DNA
<213> ORGANISM: Artificial Sequence
<220> FEATURE:
<223> OTHER INFORMATION: Optimized splice donor site

<400> SEQUENCE: 192
gccccaggtt tacac 15

<210> SEQ ID NO 193
<211> LENGTH: 15
<212> TYPE: DNA
<213> ORGANISM: Artificial Sequence
<220> FEATURE:
<223> OTHER INFORMATION: Optimized splice donor site

<400> SEQUENCE: 193
tcagcagatc cgccg 15

<210> SEQ ID NO 194
<211> LENGTH: 15
<212> TYPE: DNA
<213> ORGANISM: Artificial Sequence
<220> FEATURE:
<223> OTHER INFORMATION: Optimized splice donor site

<400> SEQUENCE: 194
ctcctgtgtg aactc 15

<210> SEQ ID NO 195
<211> LENGTH: 15
<212> TYPE: DNA
<213> ORGANISM: Artificial Sequence
<220> FEATURE:
<223> OTHER INFORMATION: Optimized splice donor site

<400> SEQUENCE: 195
tcggaaagtg tgcaa 15

<210> SEQ ID NO 196
<211> LENGTH: 15

<212> TYPE: DNA
<213> ORGANISM: Artificial Sequence
<220> FEATURE:
<223> OTHER INFORMATION: Optimized splice donor site

<400> SEQUENCE: 196
cagcacggcc agttt 15

<210> SEQ ID NO 197
<211> LENGTH: 15
<212> TYPE: DNA
<213> ORGANISM: Artificial Sequence
<220> FEATURE:
<223> OTHER INFORMATION: Optimized splice donor site

<400> SEQUENCE: 197
aaccggggcg agaac 15

<210> SEQ ID NO 198
<211> LENGTH: 15
<212> TYPE: DNA
<213> ORGANISM: Artificial Sequence
<220> FEATURE:
<223> OTHER INFORMATION: Optimized splice donor site

<400> SEQUENCE: 198
ctggaaggcg agccc 15

<210> SEQ ID NO 199
<211> LENGTH: 15
<212> TYPE: DNA
<213> ORGANISM: Artificial Sequence
<220> FEATURE:
<223> OTHER INFORMATION: Optimized splice donor site

<400> SEQUENCE: 199
tgttcatgtg agcgg 15

<210> SEQ ID NO 200
<211> LENGTH: 684
<212> TYPE: DNA
<213> ORGANISM: Artificial Sequence
<220> FEATURE:
<223> OTHER INFORMATION: optimized SSE IgG4/IgG2 hinge- IgG2/IgG4 CH2-
IgG4 CH3 spacer

<400> SEQUENCE: 200
gagtctaaat acggaccgcc ttgtcctcct tgtcccgctc ctcctgttgc cggaccttcc 60
gtgttcctgt ttcctccaaa gcctaaggac accctgatga tcagcaggac ccctgaagtg 120
acctgcgtgg tggtggatgt gtcccaagag gatcccgagg tgcagttcaa ctggtatgtg 180
gacggcgtgg aagtgcacaa cgccaagacc aagcctagag aggaacagtt ccagagcacc 240
tacagagtgg tgtccgtgct gacagtgctg caccaggatt ggctgaacgg caaagagtac 300
aagtgcaagg tgtccaacaa gggcctgcct agcagcatcg agaaaaccat ctccaaggcc 360
aagggccagc caagagagcc ccaggtttac acactgcctc caagccaaga ggaaatgacc 420
aagaatcagg tgtccctgac atgcctggtc aagggcttct acccctccga tatcgccgtg 480
gaatgggaga gcaatggcca gcctgagaac aactacaaga ccacacctcc tgtgctggac 540
agcgacggca gtttcttcct gtatagtaga ctcaccgtgg ataaatcaag atggcaagag 600
ggcaacgtgt tcagctgcag cgtgatgcac gaggccctgc acaaccacta cacccagaaa 660
agcctgagcc tgtctctggg caag 684

<210> SEQ ID NO 201
<211> LENGTH: 19
<212> TYPE: PRT
<213> ORGANISM: Artificial Sequence
<220> FEATURE:
<223> OTHER INFORMATION: P2A peptide

<400> SEQUENCE: 201

Ala Thr Asn Phe Ser Leu Leu Lys Gln Ala Gly Asp Val Glu Glu Asn
1 5 10 15

Pro Gly Pro

<210> SEQ ID NO 202
<211> LENGTH: 22
<212> TYPE: PRT
<213> ORGANISM: Artificial Sequence
<220> FEATURE:
<223> OTHER INFORMATION: P2A peptide

<400> SEQUENCE: 202

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 203
<211> LENGTH: 41
<212> TYPE: DNA
<213> ORGANISM: Artificial Sequence
<220> FEATURE:
<223> OTHER INFORMATION: predicted splice acceptor site

<400> SEQUENCE: 203
cgccttgtcc tccttgtcca gctcctcctg ttgccggacc t 41

<210> SEQ ID NO 204
<211> LENGTH: 41
<212> TYPE: DNA
<213> ORGANISM: Artificial Sequence
<220> FEATURE:
<223> OTHER INFORMATION: predicted splice acceptor site

<400> SEQUENCE: 204
cagtttcttc ctgtatagta gactcaccgt ggataaatca a 41

<210> SEQ ID NO 205
<211> LENGTH: 41
<212> TYPE: DNA
<213> ORGANISM: Artificial Sequence
<220> FEATURE:
<223> OTHER INFORMATION: predicted splice acceptor site

<400> SEQUENCE: 205
accggattcc tcctgattca ggcctggcca gagaacagaa c 41

<210> SEQ ID NO 206
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 206
cgtctaggta agttt 15

<210> SEQ ID NO 207
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 207
gaccaaggtg accgt 15

<210> SEQ ID NO 208
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 208
tgcactggta ccagc 15

<210> SEQ ID NO 209
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 209
taaactggta ccagc 15

<210> SEQ ID NO 210
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 210
atctcctgta agggt 15

<210> SEQ ID NO 211
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 211
ggtcaaggta ctctg 15

<210> SEQ ID NO 212
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 212
gaggacagta agcgg 15

<210> SEQ ID NO 213
<211> LENGTH: 15
<212> TYPE: DNA
<213> ORGANISM: Artificial Sequence
<220> FEATURE:

<223> OTHER INFORMATION: Predicted splice donor site

<400> SEQUENCE: 213
ggtcaaggta ctctg 15

<210> SEQ ID NO 214
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 214
tgcctccgtg tctgc 15

<210> SEQ ID NO 215
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 215
caccaaggtg accgt 15

<210> SEQ ID NO 216
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 216
tgaactggta tcagc 15

<210> SEQ ID NO 217
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 217
atctcttgaa atggt 15

<210> SEQ ID NO 218
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 218
ggccagggca cactg 15

<210> SEQ ID NO 219
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 219
gaggacagca agagg 15

<210> SEQ ID NO 220
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 220
ggccagggaa ccctg 15

<210> SEQ ID NO 221
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 221
tgccagcgtt agtgc 15

<210> SEQ ID NO 222
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 222
aatctaagta cggac 15

<210> SEQ ID NO 223
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 223
tcaactggta cgtgg 15

<210> SEQ ID NO 224
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 224
acaattagta aggca 15

<210> SEQ ID NO 225
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 225
accacaggtg tatac 15

<210> SEQ ID NO 226
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 226
tttccaggtc cgccg 15

<210> SEQ ID NO 227
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 227
ctgctctgtg agtta 15

<210> SEQ ID NO 228
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 228
acgcaaagtg tgtaa 15

<210> SEQ ID NO 229
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 229
caacatggtc agttt 15

<210> SEQ ID NO 230
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 230
aacagaggtg aaaac 15

<210> SEQ ID NO 231
<211> LENGTH: 15
<212> TYPE: DNA
<213> ORGANISM: Artificial Sequence
<220> FEATURE:
<223> OTHER INFORMATION: Predicted splice donor site

<400> SEQUENCE: 231
ctggagggtg agcca 15

<210> SEQ ID NO 232
<211> LENGTH: 41
<212> TYPE: DNA
<213> ORGANISM: Artificial Sequence
<220> FEATURE:
<223> OTHER INFORMATION: promoter predicted splice acceptor site

<400> SEQUENCE: 232
tggctccgcc tttttcccga gggtggggga gaaccgtata t 41

<210> SEQ ID NO 233
<211> LENGTH: 41

<212> TYPE: DNA
<213> ORGANISM: Artificial Sequence
<220> FEATURE:
<223> OTHER INFORMATION: promoter predicted splice acceptor site

<400> SEQUENCE: 233
tgaactgcgt ccgccgtcta ggtaagttta aagctcaggt c 41

<210> SEQ ID NO 234
<211> LENGTH: 41
<212> TYPE: DNA
<213> ORGANISM: Artificial Sequence
<220> FEATURE:
<223> OTHER INFORMATION: promoter predicted splice acceptor site

<400> SEQUENCE: 234
ttctgttctg cgccgttaca gatccaagct gtgaccggcg c 41

<210> SEQ ID NO 235
<211> LENGTH: 20
<212> TYPE: DNA
<213> ORGANISM: Artificial Sequence
<220> FEATURE:
<223> OTHER INFORMATION: Reverse primer 5' of WPRE

<400> SEQUENCE: 235
gatatcgaat tcctgcagcc 20

<210> SEQ ID NO 236
<211> LENGTH: 684
<212> TYPE: DNA
<213> ORGANISM: Artificial Sequence
<220> FEATURE:
<223> OTHER INFORMATION: Spacer - codon optimized

<400> SEQUENCE: 236
gagtctaaat acggaccgcc ttgtcctcct tgtccagctc ctcctgttgc cggaccttcc 60
gtgttcctgt ttcctccaaa gcctaaggac accctgatga tcagcaggac ccctgaagtg 120
acctgcgtgg tggtggatgt gtcccaagag gatcccgagg tgcagttcaa ttggtacgtg 180
gacggcgtgg aagtgcacaa cgccaagacc aagcctagag aggaacagtt ccagagcacc 240
tacagagtgg tgtccgtgct gacagtgctg caccaggatt ggctgaacgg caaagagtac 300
aagtgcaagg tgtccaacaa gggcctgcct agcagcatcg agaaaaccat ctccaaggcc 360
aagggccagc caagagagcc ccaggtttac acactgcctc caagccaaga ggaaatgacc 420
aagaatcagg tgtccctgac atgcctggtc aagggcttct acccctccga tatcgccgtg 480
gaatgggaga gcaatggcca gcctgagaac aactacaaga ccacacctcc tgtgctggac 540
agcgacggca gtttcttcct gtatagtaga ctcaccgtgg ataaatcaag atggcaagag 600
ggcaacgtgt tcagctgcag cgtgatgcac gaggccctgc acaaccacta cacccagaaa 660
agcctgagcc tgtctctggg caaa 684

<210> SEQ ID NO 237
<211> LENGTH: 12
<212> TYPE: PRT
<213> ORGANISM: Artificial Sequence
<220> FEATURE:
<223> OTHER INFORMATION: Spacer (IgG4hinge)

<400> SEQUENCE: 237

Glu Ser Lys Tyr Gly Pro Pro Cys Pro Pro Cys Pro
1 5 10

<210> SEQ ID NO 238
<211> LENGTH: 36
<212> TYPE: DNA
<213> ORGANISM: Artificial Sequence
<220> FEATURE:
<223> OTHER INFORMATION: Spacer (IgG4hinge)

<400> SEQUENCE: 238
gaatctaagt acggaccgcc ctgcccccct tgccct 36

<210> SEQ ID NO 239
<211> LENGTH: 41
<212> TYPE: DNA
<213> ORGANISM: Artificial Sequence
<220> FEATURE:
<223> OTHER INFORMATION: spacer predicted splice acceptor site

<400> SEQUENCE: 239
aagtttcttt ctgtattcca ggctgaccgt ggataaatct c 41

<210> SEQ ID NO 240
<211> LENGTH: 41
<212> TYPE: DNA
<213> ORGANISM: Artificial Sequence
<220> FEATURE:
<223> OTHER INFORMATION: spacer predicted splice acceptor site

<400> SEQUENCE: 240
gggcaacgtg ttctcttgca gtgtcatgca cgaagccctg c 41

<210> SEQ ID NO 241
<211> LENGTH: 18
<212> TYPE: PRT
<213> ORGANISM: Artificial Sequence
<220> FEATURE:
<223> OTHER INFORMATION: T2A peptide

<400> SEQUENCE: 241

Glu Gly Arg Gly Ser Leu Leu Thr Cys Gly Asp Val Glu Glu Asn Pro
1               5                   10                  15

Gly Pro

<210> SEQ ID NO 242
<211> LENGTH: 21
<212> TYPE: PRT
<213> ORGANISM: Artificial Sequence
<220> FEATURE:
<223> OTHER INFORMATION: T2A peptide

<400> SEQUENCE: 242

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 243
<211> LENGTH: 24
<212> TYPE: PRT
<213> ORGANISM: Artificial Sequence
<220> FEATURE:
<223> OTHER INFORMATION: T2A peptide

<400> SEQUENCE: 243

Leu Glu Gly Gly Gly Glu Gly Arg Gly Ser Leu Leu Thr Cys Gly Asp 1 5 10 15

Val Glu Glu Asn Pro Gly Pro Arg
20

<210> SEQ ID NO 244
<211> LENGTH: 72
<212> TYPE: DNA
<213> ORGANISM: Artificial Sequence
<220> FEATURE:
<223> OTHER INFORMATION: T2A peptide

<400> SEQUENCE: 244
ctcgagggcg gcggagaggg cagaggaagt cttctaacat gcggtgacgt ggaggagaat 60
cccggcccta gg 72

<210> SEQ ID NO 245
<211> LENGTH: 72
<212> TYPE: DNA
<213> ORGANISM: Artificial Sequence
<220> FEATURE:
<223> OTHER INFORMATION: T2A peptide

<400> SEQUENCE: 245
cttgaaggtg gtggcgaagg cagaggcagc ctgcttacat gcggagatgt ggaagagaac 60
cccggaccta ga 72

<210> SEQ ID NO 246
<211> LENGTH: 357
<212> TYPE: PRT
<213> ORGANISM: Artificial Sequence
<220> FEATURE:
<223> OTHER INFORMATION: truncated EGFR (tEGFR) sequence

<400> SEQUENCE: 246

Met Leu Leu Leu Val Thr Ser Leu Leu Leu Cys Glu Leu Pro His Pro
1 5 10 15

Ala Phe Leu Leu Ile Pro Arg Lys Val Cys Asn Gly Ile Gly Ile Gly
20 25 30

Glu Phe Lys Asp Ser Leu Ser Ile Asn Ala Thr Asn Ile Lys His Phe
35 40 45

Lys Asn Cys Thr Ser Ile Ser Gly Asp Leu His Ile Leu Pro Val Ala
50 55 60

Phe Arg Gly Asp Ser Phe Thr His Thr Pro Pro Leu Asp Pro Gln Glu
65 70 75 80

Leu Asp Ile Leu Lys Thr Val Lys Glu Ile Thr Gly Phe Leu Leu Ile
85 90 95

Gln Ala Trp Pro Glu Asn Arg Thr Asp Leu His Ala Phe Glu Asn Leu
100 105 110

Glu Ile Ile Arg Gly Arg Thr Lys Gln His Gly Gln Phe Ser Leu Ala
115 120 125

Val Val Ser Leu Asn Ile Thr Ser Leu Gly Leu Arg Ser Leu Lys Glu
130 135 140

Ile Ser Asp Gly Asp Val Ile Ile Ser Gly Asn Lys Asn Leu Cys Tyr
145 150 155 160

Ala Asn Thr Ile Asn Trp Lys Lys Leu Phe Gly Thr Ser Gly Gln Lys
165 170 175

Thr Lys Ile Ile Ser Asn Arg Gly Glu Asn Ser Cys Lys Ala Thr Gly
180 185 190

```
Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355


<210> SEQ ID NO 247
<211> LENGTH: 1074
<212> TYPE: DNA
<213> ORGANISM: Artificial Sequence
<220> FEATURE:
<223> OTHER INFORMATION: truncated EGFR (tEGFR) sequence

<400> SEQUENCE: 247

atgcttctcc tggtgacaag ccttctgctc tgtgagttac cacacccagc attcctcctg     60

atcccacgca aagtgtgtaa cggaataggt attggtgaat ttaaagactc actctccata    120

aatgctacga atattaaaca cttcaaaaac tgcacctcca tcagtggcga tctccacatc    180

ctgccggtgg catttagggg tgactccttc acacatactc ctcctctgga tccacaggaa    240

ctggatattc tgaaaaccgt aaaggaaatc acagggtttt tgctgattca ggcttggcct    300

gaaaacagga cggacctcca tgcctttgag aacctagaaa tcatacgcgg caggaccaag    360

caacatggtc agttttctct tgcagtcgtc agcctgaaca taacatcctt gggattacgc    420

tccctcaagg agataagtga tggagatgtg ataatttcag gaaacaaaaa tttgtgctat    480

gcaaatacaa taaactggaa aaaactgttt gggacctccg gtcagaaaac caaaattata    540

agcaacagag gtgaaaacag ctgcaaggcc acaggccagg tctgccatgc cttgtgctcc    600

cccgagggct gctggggccc ggagcccagg gactgcgtct cttgccggaa tgtcagccga    660

ggcagggaat gcgtggacaa gtgcaacctt ctggagggtg agccaaggga gtttgtggag    720

aactctgagt gcatacagtg ccacccagag tgcctgcctc aggccatgaa catcacctgc    780

acaggacggg gaccagacaa ctgtatccag tgtgcccact acattgacgg cccccactgc    840

gtcaagacct gcccggcagg agtcatggga gaaaacaaca ccctggtctg gaagtacgca    900

gacgccggcc atgtgtgcca cctgtgccat ccaaactgca cctacggatg cactgggcca    960

ggtcttgaag gctgtccaac gaatgggcct aagatcccgt ccatcgccac tgggatggtg   1020

ggggccctcc tcttgctgct ggtggtggcc ctggggatcg gcctcttcat gtga         1074
```

<210> SEQ ID NO 248
<211> LENGTH: 1074
<212> TYPE: DNA
<213> ORGANISM: Artificial Sequence
<220> FEATURE:
<223> OTHER INFORMATION: truncated EGFR (tEGFR) sequence (O/SSE)

<400> SEQUENCE: 248
atgctgctcc tcgtgacaag cctgctcctg tgtgaactcc ctcatccagc ttttctgctc 60
attcctcgga aagtgtgcaa cggcatcggc atcggagagt tcaaggacag cctgagcatc 120
aatgccacca acatcaagca cttcaagaat tgcaccagca tcagcggcga cctgcacatt 180
ctgcctgtgg cctttagagg cgacagcttc acccacacac ctccactgga tccccaagag 240
ctggatatcc tgaaaaccgt gaaagagatt accggattcc tcctgatcca agcctggcca 300
gagaacagaa ccgatctgca cgccttcgag aacctcgaga tcatcagagg ccggaccaaa 360
cagcacggcc agtttagcct ggctgtggtg tctctgaaca tcaccagtct gggcctgaga 420
agcctgaaag aaatctccga cggcgacgtg atcatctccg gaaacaagaa cctgtgctac 480
gccaacacca tcaactggaa gaagctgttc ggcacctccg gccagaaaac aaagatcatc 540
tctaaccggg gcgagaacag ctgcaaggcc accggacaag tttgtcacgc cctgtgtagc 600
cctgaaggct gttggggacc cgaacctaga gactgtgtgt cctgccggaa tgtgtcccgg 660
ggcagagaat gtgtggataa gtgcaacctg ctggaaggcg agccccgcga gtttgtggaa 720
aacagcgagt gcatccagtg tcaccccgag tgtctgcccc aggccatgaa cattacatgc 780
accggcagag gccccgacaa ctgtattcag tgcgcccact acatcgacgg ccctcactgc 840
gtgaaaacat gtccagctgg cgtgatggga gagaacaaca ccctcgtgtg gaagtatgcc 900
gacgccggac atgtgtgcca cctgtgtcac cctaattgca cctacggctg taccggacct 960
ggcctggaag gatgccctac aaacggccct aagatcccca gcattgccac cggaatggtt 1020
ggagccctgc tgcttctgtt ggtggtggcc ctcggaatcg gcctgttcat gtga 1074

<210> SEQ ID NO 249
<211> LENGTH: 41
<212> TYPE: DNA
<213> ORGANISM: Artificial Sequence
<220> FEATURE:
<223> OTHER INFORMATION: truncated marker predicted splice acceptor site

<400> SEQUENCE: 249
actcctcctc tggatccaca ggaactggat attctgaaaa c 41

<210> SEQ ID NO 250
<211> LENGTH: 41
<212> TYPE: DNA
<213> ORGANISM: Artificial Sequence
<220> FEATURE:
<223> OTHER INFORMATION: truncated marker predicted splice acceptor site

<400> SEQUENCE: 250
acagggtttt tgctgattca ggcttggcct gaaaacagga c 41

<210> SEQ ID NO 251
<211> LENGTH: 41
<212> TYPE: DNA
<213> ORGANISM: Artificial Sequence
<220> FEATURE:
<223> OTHER INFORMATION: truncated marker predicted splice acceptor site

<400> SEQUENCE: 251
atggtcagtt ttctcttgca gtcgtcagcc tgaacataac a 41

<210> SEQ ID NO 252
<211> LENGTH: 15
<212> TYPE: DNA
<213> ORGANISM: Artificial Sequence
<220> FEATURE:
<223> OTHER INFORMATION: truncated marker predicted splice donor site

<400> SEQUENCE: 252
tcttcatgtg agcgg 15

<210> SEQ ID NO 253
<211> LENGTH: 589
<212> TYPE: DNA
<213> ORGANISM: Artificial Sequence
<220> FEATURE:
<223> OTHER INFORMATION: Woodchuck Hepatitis Virus (WHP)
Posttranscriptional Regulatory Element (WPRE)

<400> SEQUENCE: 253
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgc 589

<210> SEQ ID NO 254
<211> LENGTH: 15
<212> TYPE: DNA
<213> ORGANISM: Artificial Sequence
<220> FEATURE:
<223> OTHER INFORMATION: predicted splice site

<400> SEQUENCE: 254
tcaattggta cgtgg 15

<210> SEQ ID NO 255
<211> LENGTH: 21
<212> TYPE: PRT
<213> ORGANISM: Artificial Sequence
<220> FEATURE:
<223> OTHER INFORMATION: Linker

<400> SEQUENCE: 255

Ser Arg Gly Gly Gly Gly Ser Gly Gly Gly Gly Ser Gly Gly Gly Gly
1 5 10 15

Ser Leu Glu Met Ala
20

<210> SEQ ID NO 256
<211> LENGTH: 153
<212> TYPE: PRT
<213> ORGANISM: Artificial Sequence
<220> FEATURE:
<223> OTHER INFORMATION: Anakinra

<400> SEQUENCE: 256

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150

<210> SEQ ID NO 257
<211> LENGTH: 15
<212> TYPE: PRT
<213> ORGANISM: Artificial Sequence
<220> FEATURE:
<223> OTHER INFORMATION: CDR-L1

<400> SEQUENCE: 257

Arg Ala Ser Glu Ser Val Thr Ile Leu Gly Ser His Leu Ile His
1               5                   10                  15

<210> SEQ ID NO 258
<211> LENGTH: 7
<212> TYPE: PRT
<213> ORGANISM: Artificial Sequence
<220> FEATURE:
<223> OTHER INFORMATION: CDR-L2

<400> SEQUENCE: 258

Leu Ala Ser Asn Val Gln Thr
1               5

<210> SEQ ID NO 259
<211> LENGTH: 9
<212> TYPE: PRT
<213> ORGANISM: Artificial Sequence
<220> FEATURE:
<223> OTHER INFORMATION: CDR-L3

<400> SEQUENCE: 259

Leu Gln Ser Arg Thr Ile Pro Arg Thr
1               5

<210> SEQ ID NO 260
<211> LENGTH: 5
<212> TYPE: PRT
<213> ORGANISM: Artificial Sequence

<220> FEATURE:
<223> OTHER INFORMATION: CDR-H1

<400> SEQUENCE: 260

Asp Tyr Ser Ile Asn
1 5

<210> SEQ ID NO 261
<211> LENGTH: 17
<212> TYPE: PRT
<213> ORGANISM: Artificial Sequence
<220> FEATURE:
<223> OTHER INFORMATION: CDR-H2

<400> SEQUENCE: 261

Trp Ile Asn Thr Glu Thr Arg Glu Pro Ala Tyr Ala Tyr Asp Phe Arg
1 5 10 15

Gly

<210> SEQ ID NO 262
<211> LENGTH: 8
<212> TYPE: PRT
<213> ORGANISM: Artificial Sequence
<220> FEATURE:
<223> OTHER INFORMATION: CDR-H3

<400> SEQUENCE: 262

Asp Tyr Ser Tyr Ala Met Asp Tyr
1 5

<210> SEQ ID NO 263
<211> LENGTH: 493
<212> TYPE: PRT
<213> ORGANISM: Artificial Sequence
<220> FEATURE:
<223> OTHER INFORMATION: Anti-BCMA CAR

<400> SEQUENCE: 263

Met Ala Leu Pro Val Thr Ala Leu Leu Leu Pro Leu Ala Leu Leu Leu
1 5 10 15

His Ala Ala Arg Pro Asp Ile Val Leu Thr Gln Ser Pro Pro Ser Leu
20 25 30

Ala Met Ser Leu Gly Lys Arg Ala Thr Ile Ser Cys Arg Ala Ser Glu
35 40 45

Ser Val Thr Ile Leu Gly Ser His Leu Ile His Trp Tyr Gln Gln Lys
50 55 60

Pro Gly Gln Pro Pro Thr Leu Leu Ile Gln Leu Ala Ser Asn Val Gln
65 70 75 80

Thr Gly Val Pro Ala Arg Phe Ser Gly Ser Gly Ser Arg Thr Asp Phe
85 90 95

Thr Leu Thr Ile Asp Pro Val Glu Glu Asp Asp Val Ala Val Tyr Tyr
100 105 110

Cys Leu Gln Ser Arg Thr Ile Pro Arg Thr Phe Gly Gly Gly Thr Lys
115 120 125

Leu Glu Ile Lys Gly Ser Thr Ser Gly Ser Gly Lys Pro Gly Ser Gly
130 135 140

Glu Gly Ser Thr Lys Gly Gln Ile Gln Leu Val Gln Ser Gly Pro Glu
145 150 155 160

Leu Lys Lys Pro Gly Glu Thr Val Lys Ile Ser Cys Lys Ala Ser Gly
165 170 175

```
Tyr Thr Phe Thr Asp Tyr Ser Ile Asn Trp Val Lys Arg Ala Pro Gly
            180                 185                 190

Lys Gly Leu Lys Trp Met Gly Trp Ile Asn Thr Glu Thr Arg Glu Pro
        195                 200                 205

Ala Tyr Ala Tyr Asp Phe Arg Gly Arg Phe Ala Phe Ser Leu Glu Thr
    210                 215                 220

Ser Ala Ser Thr Ala Tyr Leu Gln Ile Asn Asn Leu Lys Tyr Glu Asp
225                 230                 235                 240

Thr Ala Thr Tyr Phe Cys Ala Leu Asp Tyr Ser Tyr Ala Met Asp Tyr
                245                 250                 255

Trp Gly Gln Gly Thr Ser Val Thr Val Ser Ser Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 264
<211> LENGTH: 1485
<212> TYPE: DNA
<213> ORGANISM: Artificial Sequence
<220> FEATURE:
<223> OTHER INFORMATION: Anti-BCMA CAR

<400> SEQUENCE: 264

```
atggcactcc ccgtcaccgc ccttctcttg cccctcgccc tgctgctgca tgctgccagg      60

cccgacattg tgctcactca gtcacctccc agcctggcca tgagcctggg aaaaagggcc     120

accatctcct gtagagccag tgagtccgtc acaatcttgg ggagccatct tattcactgg     180

tatcagcaga agcccgggca gcctccaacc cttcttattc agctcgcgtc aaacgtccag     240

acgggtgtac ctgccagatt ttctggtagc gggtcccgca ctgattttac actgaccata     300
```

```
gatccagtgg aagaagacga tgtggccgtg tattattgtc tgcagagcag aacgattcct    360
cgcacatttg gtgggggtac taagctggag attaagggaa gcacgtccgg ctcagggaag    420
ccgggctccg gcgagggaag cacgaagggg caaattcagc tggtccagag cggacctgag    480
ctgaaaaaac ccggcgagac tgttaagatc agttgtaaag catctggcta taccttcacc    540
gactacagca taaattgggt gaaacgggcc cctggaaagg gcctcaaatg gatgggttgg    600
atcaataccg aaactaggga gcctgcttat gcatatgact tccgcgggag attcgccttt    660
tcactcgaga catctgcctc tactgcttac ctccaaataa acaacctcaa gtatgaagat    720
acagccactt acttttgcgc cctcgactat agttacgcca tggactactg gggacaggga    780
acctccgtta ccgtcagttc cgcggccgca accacaacac ctgctccaag gccccccaca    840
cccgctccaa ctatagccag ccaaccattg agcctcagac ctgaagcttg caggcccgca    900
gcaggaggcg ccgtccatac gcgaggcctg gacttcgcgt gtgatattta tatttgggcc    960
cctttggccg gaacatgtgg ggtgttgctt ctctcccttg tgatcactct gtattgtaag   1020
cgcgggagaa agaagctcct gtacatcttc aagcagcctt ttatgcgacc tgtgcaaacc   1080
actcaggaag aagatgggtg ttcatgccgc ttccccgagg aggaagaagg agggtgtgaa   1140
ctgagggtga aattttctag aagcgccgat gctcccgcat atcagcaggg tcagaatcag   1200
ctctacaatg aattgaatct cggcaggcga gaagagtacg atgttctgga caagagacgg   1260
ggcagggatc ccgagatggg gggaaagccc cggagaaaaa atcctcagga ggggttgtac   1320
aatgagctgc agaaggacaa gatggctgaa gcctatagcg agatcggaat gaaaggcgaa   1380
agacgcagag gcaaggggca tgacggtctg taccagggtc tctctacagc caccaaggac   1440
acttatgatg cgttgcatat gcaagccttg ccaccccgct aatga                   1485
```

<210> SEQ ID NO 265
<211> LENGTH: 495
<212> TYPE: PRT
<213> ORGANISM: Artificial Sequence
<220> FEATURE:
<223> OTHER INFORMATION: Multivalent anti-BCMA CAR

<400> SEQUENCE: 265

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Glu Ala Ser Gly Phe
        35                  40                  45

Thr Leu Asp Tyr Tyr Ala Ile Gly Trp Phe Arg Gln Ala Pro Gly Lys
    50                  55                  60

Glu Arg Glu Gly Val Ile Cys Ile Ser Arg Ser Asp Gly Ser Thr Tyr
65                  70                  75                  80

Tyr Ala Asp Ser Val Lys Gly Arg Phe Thr Ile Ser Arg Asp Asn Ala
                85                  90                  95

Lys Lys Thr Val Tyr Leu Gln Met Ile Ser Leu Lys Pro Glu Asp Thr
            100                 105                 110

Ala Ala Tyr Tyr Cys Ala Ala Gly Ala Asp Cys Ser Gly Tyr Leu Arg
        115                 120                 125

Asp Tyr Glu Phe Arg Gly Gln Gly Thr Gln Val Thr Val Ser Ser Gly
    130                 135                 140

Gly Gly Gly Ser Gln Val Gln Leu Val Glu Ser Gly Gly Gly Leu Val
```

```
145                 150                 155                 160

Gln Pro Gly Gly Ser Leu Arg Leu Ser Cys Glu Ala Ser Gly Phe Thr
                165                 170                 175

Leu Asp Tyr Tyr Ala Ile Gly Trp Phe Arg Gln Ala Pro Gly Lys Glu
            180                 185                 190

Arg Glu Gly Val Ile Cys Ile Ser Arg Ser Asp Gly Ser Thr Tyr Tyr
        195                 200                 205

Ala Asp Ser Val Lys Gly Arg Phe Thr Ile Ser Arg Asp Asn Ala Lys
    210                 215                 220

Lys Thr Val Tyr Leu Gln Met Ile Ser Leu Lys Pro Glu Asp Thr Ala
225                 230                 235                 240

Ala Tyr Tyr Cys Ala Ala Gly Ala Asp Cys Ser Gly Tyr Leu Arg Asp
                245                 250                 255

Tyr Glu Phe Arg Gly Gln Gly Thr Gln Val Thr Val Ser Ser Thr Ser
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495


<210> SEQ ID NO 266
<211> LENGTH: 622
<212> TYPE: PRT
<213> ORGANISM: Artificial Sequence
<220> FEATURE:
<223> OTHER INFORMATION: Multivalent anti-BCMA CAR

<400> SEQUENCE: 266

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
```

```
            20                  25                  30

Val Gln Pro Gly Gly Ser Leu Arg Leu Ser Cys Glu Ala Ser Gly Phe
        35                  40                  45

Thr Leu Asp Tyr Tyr Ala Ile Gly Trp Phe Arg Gln Ala Pro Gly Lys
    50                  55                  60

Glu Arg Glu Gly Val Ile Cys Ile Ser Arg Ser Asp Gly Ser Thr Tyr
65                  70                  75                  80

Tyr Ala Asp Ser Val Lys Gly Arg Phe Thr Ile Ser Arg Asp Asn Ala
                85                  90                  95

Lys Lys Thr Val Tyr Leu Gln Met Ile Ser Leu Lys Pro Glu Asp Thr
            100                 105                 110

Ala Ala Tyr Tyr Cys Ala Ala Gly Ala Asp Cys Ser Gly Tyr Leu Arg
        115                 120                 125

Asp Tyr Glu Phe Arg Gly Gln Gly Thr Gln Val Thr Val Ser Ser Gly
    130                 135                 140

Gly Gly Gly Ser Gln Val Gln Leu Val Glu Ser Gly Gly Gly Leu Val
145                 150                 155                 160

Gln Pro Gly Gly Ser Leu Arg Leu Ser Cys Glu Ala Ser Gly Phe Thr
                165                 170                 175

Leu Asp Tyr Tyr Ala Ile Gly Trp Phe Arg Gln Ala Pro Gly Lys Glu
            180                 185                 190

Arg Glu Gly Val Ile Cys Ile Ser Arg Ser Asp Gly Ser Thr Tyr Tyr
        195                 200                 205

Ala Asp Ser Val Lys Gly Arg Phe Thr Ile Ser Arg Asp Asn Ala Lys
    210                 215                 220

Lys Thr Val Tyr Leu Gln Met Ile Ser Leu Lys Pro Glu Asp Thr Ala
225                 230                 235                 240

Ala Tyr Tyr Cys Ala Ala Gly Ala Asp Cys Ser Gly Tyr Leu Arg Asp
                245                 250                 255

Tyr Glu Phe Arg Gly Gln Gly Thr Gln Val Thr Val Ser Ser Gly Gly
            260                 265                 270

Gly Gly Ser Gln Val Gln Leu Val Glu Ser Gly Gly Gly Leu Val Gln
        275                 280                 285

Pro Gly Gly Ser Leu Arg Leu Ser Cys Glu Ala Ser Gly Phe Thr Leu
    290                 295                 300

Asp Tyr Tyr Ala Ile Gly Trp Phe Arg Gln Ala Pro Gly Lys Glu Arg
305                 310                 315                 320

Glu Gly Val Ile Cys Ile Ser Arg Ser Asp Gly Ser Thr Tyr Tyr Ala
                325                 330                 335

Asp Ser Val Lys Gly Arg Phe Thr Ile Ser Arg Asp Asn Ala Lys Lys
            340                 345                 350

Thr Val Tyr Leu Gln Met Ile Ser Leu Lys Pro Glu Asp Thr Ala Ala
        355                 360                 365

Tyr Tyr Cys Ala Ala Gly Ala Asp Cys Ser Gly Tyr Leu Arg Asp Tyr
    370                 375                 380

Glu Phe Arg Gly Gln Gly Thr Gln Val Thr Val Ser Ser Thr Ser Thr
385                 390                 395                 400

Thr Thr Pro Ala Pro Arg Pro Pro Thr Pro Ala Pro Thr Ile Ala Ser
                405                 410                 415

Gln Pro Leu Ser Leu Arg Pro Glu Ala Cys Arg Pro Ala Ala Gly Gly
            420                 425                 430

Ala Val His Thr Arg Gly Leu Asp Phe Ala Cys Asp Ile Tyr Ile Trp
        435                 440                 445
```

```
Ala Pro Leu Ala Gly Thr Cys Gly Val Leu Leu Leu Ser Leu Val Ile
    450                 455                 460

Thr Leu Tyr Cys Lys Arg Gly Arg Lys Lys Leu Leu Tyr Ile Phe Lys
465                 470                 475                 480

Gln Pro Phe Met Arg Pro Val Gln Thr Thr Gln Glu Glu Asp Gly Cys
                485                 490                 495

Ser Cys Arg Phe Pro Glu Glu Glu Glu Gly Gly Cys Glu Leu Arg Val
            500                 505                 510

Lys Phe Ser Arg Ser Ala Asp Ala Pro Ala Tyr Gln Gln Gly Gln Asn
        515                 520                 525

Gln Leu Tyr Asn Glu Leu Asn Leu Gly Arg Arg Glu Glu Tyr Asp Val
    530                 535                 540

Leu Asp Lys Arg Arg Gly Arg Asp Pro Glu Met Gly Gly Lys Pro Arg
545                 550                 555                 560

Arg Lys Asn Pro Gln Glu Gly Leu Tyr Asn Glu Leu Gln Lys Asp Lys
                565                 570                 575

Met Ala Glu Ala Tyr Ser Glu Ile Gly Met Lys Gly Glu Arg Arg Arg
            580                 585                 590

Gly Lys Gly His Asp Gly Leu Tyr Gln Gly Leu Ser Thr Ala Thr Lys
        595                 600                 605

Asp Thr Tyr Asp Ala Leu His Met Gln Ala Leu Pro Pro Arg
    610                 615                 620


<210> SEQ ID NO 267
<211> LENGTH: 488
<212> TYPE: PRT
<213> ORGANISM: Artificial Sequence
<220> FEATURE:
<223> OTHER INFORMATION: Multivalent anti-BCMA CAR

<400> SEQUENCE: 267

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Glu Val Gln Leu Val Glu Ser Gly Gly Gly Leu Val Gln Ala Gly
145                 150                 155                 160

Gly Ser Leu Arg Leu Ser Cys Ala Ala Ser Gly Arg Thr Phe Thr Met
                165                 170                 175

Gly Trp Phe Arg Gln Ala Pro Gly Lys Glu Arg Glu Phe Val Ala Ala
            180                 185                 190
```

Ile Ser Leu Ser Pro Thr Leu Ala Tyr Tyr Ala Glu Ser Val Lys Gly
195 200 205

Arg Phe Thr Ile Ser Arg Asp Asn Ala Lys Asn Thr Val Val Leu Gln
210 215 220

Met Asn Ser Leu Lys Pro Glu Asp Thr Ala Leu Tyr Tyr Cys Ala Ala
225 230 235 240

Asp Arg Lys Ser Val Met Ser Ile Arg Pro Asp Tyr Trp Gly Gln Gly
245 250 255

Thr Gln Val Thr Val Ser Ser Thr Ser Thr Thr Thr Pro Ala Pro Arg
260 265 270

Pro Pro Thr Pro Ala Pro Thr Ile Ala Ser Gln Pro Leu Ser Leu Arg
275 280 285

Pro Glu Ala Cys Arg Pro Ala Ala Gly Gly Ala Val His Thr Arg Gly
290 295 300

Leu Asp Phe Ala Cys Asp Ile Tyr Ile Trp Ala Pro Leu Ala Gly Thr
305 310 315 320

Cys Gly Val Leu Leu Leu Ser Leu Val Ile Thr Leu Tyr Cys Lys Arg
325 330 335

Gly Arg Lys Lys Leu Leu Tyr Ile Phe Lys Gln Pro Phe Met Arg Pro
340 345 350

Val Gln Thr Thr Gln Glu Glu Asp Gly Cys Ser Cys Arg Phe Pro Glu
355 360 365

Glu Glu Glu Gly Gly Cys Glu Leu Arg Val Lys Phe Ser Arg Ser Ala
370 375 380

Asp Ala Pro Ala Tyr Gln Gln Gly Gln Asn Gln Leu Tyr Asn Glu Leu
385 390 395 400

Asn Leu Gly Arg Arg Glu Glu Tyr Asp Val Leu Asp Lys Arg Arg Gly
405 410 415

Arg Asp Pro Glu Met Gly Gly Lys Pro Arg Arg Lys Asn Pro Gln Glu
420 425 430

Gly Leu Tyr Asn Glu Leu Gln Lys Asp Lys Met Ala Glu Ala Tyr Ser
435 440 445

Glu Ile Gly Met Lys Gly Glu Arg Arg Arg Gly Lys Gly His Asp Gly
450 455 460

Leu Tyr Gln Gly Leu Ser Thr Ala Thr Lys Asp Thr Tyr Asp Ala Leu
465 470 475 480

His Met Gln Ala Leu Pro Pro Arg
485

<210> SEQ ID NO 268
<211> LENGTH: 498
<212> TYPE: PRT
<213> ORGANISM: Artificial Sequence
<220> FEATURE:
<223> OTHER INFORMATION: Multivalent anti-BCMA CAR

<400> SEQUENCE: 268

Met Ala Leu Pro Val Thr Ala Leu Leu Leu Pro Leu Ala Leu Leu Leu
1 5 10 15

His Ala Ala Arg Pro Gln Val Lys Leu Glu Glu Ser Gly Gly Gly Leu
20 25 30

Val Gln Ala Gly Arg Ser Leu Arg Leu Ser Cys Ala Ala Ser Glu His
35 40 45

Thr Phe Ser Ser His Val Met Gly Trp Phe Arg Gln Ala Pro Gly Lys
50 55 60

```
Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Ala Gly Gly Ser Leu Arg Leu Ser
                165                 170                 175

Cys Ala Ala Ser Gly Arg Thr Phe Thr Met Gly Trp Phe Arg Gln Ala
            180                 185                 190

Pro Gly Lys Glu Arg Glu Phe Val Ala Ala Ile Ser Leu Ser Pro Thr
        195                 200                 205

Leu Ala Tyr Tyr Ala Glu Ser Val Lys Gly Arg Phe Thr Ile Ser Arg
    210                 215                 220

Asp Asn Ala Lys Asn Thr Val Val Leu Gln Met Asn Ser Leu Lys Pro
225                 230                 235                 240

Glu Asp Thr Ala Leu Tyr Tyr Cys Ala Ala Asp Arg Lys Ser Val Met
                245                 250                 255

Ser Ile Arg Pro Asp Tyr Trp Gly Gln Gly Thr Gln Val Thr Val Ser
            260                 265                 270

Ser Thr Ser Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Glu Gly Gly Cys
    370                 375                 380

Glu Leu Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480
```

```
Thr Ala Thr Lys Asp Thr Tyr Asp Ala Leu His Met Gln Ala Leu Pro
                485                 490                 495

Pro Arg


<210> SEQ ID NO 269
<211> LENGTH: 508
<212> TYPE: PRT
<213> ORGANISM: Artificial Sequence
<220> FEATURE:
<223> OTHER INFORMATION: Multivalent anti-BCMA CAR

<400> SEQUENCE: 269

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175

Val Gln Ala Gly Gly Ser Leu Arg Leu Ser Cys Ala Ala Ser Gly Arg
            180                 185                 190

Thr Phe Thr Met Gly Trp Phe Arg Gln Ala Pro Gly Lys Glu Arg Glu
        195                 200                 205

Phe Val Ala Ala Ile Ser Leu Ser Pro Thr Leu Ala Tyr Tyr Ala Glu
    210                 215                 220

Ser Val Lys Gly Arg Phe Thr Ile Ser Arg Asp Asn Ala Lys Asn Thr
225                 230                 235                 240

Val Val Leu Gln Met Asn Ser Leu Lys Pro Glu Asp Thr Ala Leu Tyr
                245                 250                 255

Tyr Cys Ala Ala Asp Arg Lys Ser Val Met Ser Ile Arg Pro Asp Tyr
            260                 265                 270

Trp Gly Gln Gly Thr Gln Val Thr Val Ser Ser Thr Ser Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
```

```
            340                 345                 350

Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505


<210> SEQ ID NO 270
<211> LENGTH: 493
<212> TYPE: PRT
<213> ORGANISM: Artificial Sequence
<220> FEATURE:
<223> OTHER INFORMATION: Multivalent anti-BCMA CAR

<400> SEQUENCE: 270

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Gly Gly Gly Gly Ser
    130                 135                 140

Gly Gly Gly Gly Ser Gln Val Lys Leu Glu Glu Ser Gly Gly Gly Leu
145                 150                 155                 160

Val Gln Ala Gly Arg Ser Leu Arg Leu Ser Cys Ala Ala Ser Glu His
                165                 170                 175

Thr Phe Ser Ser His Val Met Gly Trp Phe Arg Gln Ala Pro Gly Lys
            180                 185                 190

Glu Arg Glu Ser Val Ala Val Ile Gly Trp Arg Asp Ile Ser Thr Ser
```

```
        195                 200                 205

Tyr Ala Asp Ser Val Lys Gly Arg Phe Thr Ile Ser Arg Asp Asn Ala
    210                 215                 220

Lys Lys Thr Leu Tyr Leu Gln Met Asn Ser Leu Lys Pro Glu Asp Thr
225                 230                 235                 240

Ala Val Tyr Tyr Cys Ala Ala Arg Arg Ile Asp Ala Ala Asp Phe Asp
                245                 250                 255

Ser Trp Gly Gln Gly Thr Gln Val Thr Val Ser Ser Thr Ser Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 271
<211> LENGTH: 498
<212> TYPE: PRT
<213> ORGANISM: Artificial Sequence
<220> FEATURE:
<223> OTHER INFORMATION: Multivalent anti-BCMA CAR

<400> SEQUENCE: 271

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
```

```
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Gly Gly Gly Gly Ser
    130                 135                 140

Gly Gly Gly Gly Ser Gly Gly Gly Gly Ser Gln Val Lys Leu Glu Glu
145                 150                 155                 160

Ser Gly Gly Gly Leu Val Gln Ala Gly Arg Ser Leu Arg Leu Ser Cys
                165                 170                 175

Ala Ala Ser Glu His Thr Phe Ser Ser His Val Met Gly Trp Phe Arg
            180                 185                 190

Gln Ala Pro Gly Lys Glu Arg Glu Ser Val Ala Val Ile Gly Trp Arg
        195                 200                 205

Asp Ile Ser Thr Ser Tyr Ala Asp Ser Val Lys Gly Arg Phe Thr Ile
    210                 215                 220

Ser Arg Asp Asn Ala Lys Lys Thr Leu Tyr Leu Gln Met Asn Ser Leu
225                 230                 235                 240

Lys Pro Glu Asp Thr Ala Val Tyr Tyr Cys Ala Ala Arg Arg Ile Asp
                245                 250                 255

Ala Ala Asp Phe Asp Ser Trp Gly Gln Gly Thr Gln Val Thr Val Ser
            260                 265                 270

Ser Thr Ser Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Glu Gly Gly Cys
    370                 375                 380

Glu Leu Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495
```

Pro Arg

<210> SEQ ID NO 272
<211> LENGTH: 503
<212> TYPE: PRT
<213> ORGANISM: Artificial Sequence
<220> FEATURE:
<223> OTHER INFORMATION: Multivalent anti-BCMA CAR

<400> SEQUENCE: 272

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Gly Gly Gly Gly Ser
    130                 135                 140

Gly Gly Gly Gly Ser Gly Gly Gly Gly Ser Gly Gly Gly Gly Ser Gln
145                 150                 155                 160

Val Lys Leu Glu Glu Ser Gly Gly Gly Leu Val Gln Ala Gly Arg Ser
                165                 170                 175

Leu Arg Leu Ser Cys Ala Ala Ser Glu His Thr Phe Ser Ser His Val
            180                 185                 190

Met Gly Trp Phe Arg Gln Ala Pro Gly Lys Glu Arg Glu Ser Val Ala
        195                 200                 205

Val Ile Gly Trp Arg Asp Ile Ser Thr Ser Tyr Ala Asp Ser Val Lys
    210                 215                 220

Gly Arg Phe Thr Ile Ser Arg Asp Asn Ala Lys Lys Thr Leu Tyr Leu
225                 230                 235                 240

Gln Met Asn Ser Leu Lys Pro Glu Asp Thr Ala Val Tyr Tyr Cys Ala
                245                 250                 255

Ala Arg Arg Ile Asp Ala Ala Asp Phe Asp Ser Trp Gly Gln Gly Thr
            260                 265                 270

Gln Val Thr Val Ser Ser Thr Ser Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Lys Arg Gly
            340                 345                 350

```
Arg Lys Lys Leu Leu Tyr Ile Phe Lys Gln Pro Phe Met Arg Pro Val
        355                 360                 365

Gln Thr Thr Gln Glu Glu Asp Gly Cys Ser Cys Arg Phe Pro Glu Glu
    370                 375                 380

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
        435                 440                 445

Leu Tyr Asn Glu Leu Gln Lys Asp Lys Met Ala Glu Ala Tyr Ser Glu
    450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
            500


<210> SEQ ID NO 273
<211> LENGTH: 489
<212> TYPE: PRT
<213> ORGANISM: Artificial Sequence
<220> FEATURE:
<223> OTHER INFORMATION: Multivalent anti-BCMA CAR

<400> SEQUENCE: 273

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Ala Val Gln Leu Val Glu Ser Gly Gly Gly Leu Val Gln Ala Gly
145                 150                 155                 160

Asp Ser Leu Arg Leu Thr Cys Thr Ala Ser Gly Arg Ala Phe Ser Thr
                165                 170                 175

Tyr Phe Met Ala Trp Phe Arg Gln Ala Pro Gly Lys Glu Arg Glu Phe
            180                 185                 190

Val Ala Gly Ile Ala Trp Ser Gly Gly Ser Thr Ala Tyr Ala Asp Ser
        195                 200                 205
```

Val Lys Gly Arg Phe Thr Ile Ser Arg Asp Asn Ala Lys Asn Thr Val
    210                 215                 220

Tyr Leu Gln Met Asn Ser Leu Lys Ser Glu Asp Thr Ala Val Tyr Tyr
225                 230                 235                 240

Cys Ala Ser Arg Gly Ile Glu Val Glu Glu Phe Gly Ala Trp Gly Gln
                245                 250                 255

Gly Thr Gln Val Thr Val Ser Ser Thr Ser Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 274
<211> LENGTH: 499
<212> TYPE: PRT
<213> ORGANISM: Artificial Sequence
<220> FEATURE:
<223> OTHER INFORMATION: Multivalent anti-BCMA CAR

<400> SEQUENCE: 274

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

```
Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Gly Gly Gly Gly Ser Gly Gly Gly Gly Ser Ala Val Gln Leu Val
145                 150                 155                 160

Glu Ser Gly Gly Gly Leu Val Gln Ala Gly Asp Ser Leu Arg Leu Thr
                165                 170                 175

Cys Thr Ala Ser Gly Arg Ala Phe Ser Thr Tyr Phe Met Ala Trp Phe
            180                 185                 190

Arg Gln Ala Pro Gly Lys Glu Arg Glu Phe Val Ala Gly Ile Ala Trp
        195                 200                 205

Ser Gly Gly Ser Thr Ala Tyr Ala Asp Ser Val Lys Gly Arg Phe Thr
    210                 215                 220

Ile Ser Arg Asp Asn Ala Lys Asn Thr Val Tyr Leu Gln Met Asn Ser
225                 230                 235                 240

Leu Lys Ser Glu Asp Thr Ala Val Tyr Tyr Cys Ala Ser Arg Gly Ile
                245                 250                 255

Glu Val Glu Glu Phe Gly Ala Trp Gly Gln Gly Thr Gln Val Thr Val
            260                 265                 270

Ser Ser Thr Ser Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
            340                 345                 350

Leu Tyr Ile Phe Lys Gln Pro Phe Met Arg Pro Val Gln Thr Thr Gln
        355                 360                 365

Glu Glu Asp Gly Cys Ser Cys Arg Phe Pro Glu Glu Glu Glu Gly Gly
    370                 375                 380

Cys Glu Leu Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg
```

<210> SEQ ID NO 275
<211> LENGTH: 509
<212> TYPE: PRT
<213> ORGANISM: Artificial Sequence
<220> FEATURE:
<223> OTHER INFORMATION: Multivalent anti-BCMA CAR

<400> SEQUENCE: 275

Met Ala Leu Pro Val Thr Ala Leu Leu Leu Pro Leu Ala Leu Leu Leu
1 5 10 15

His Ala Ala Arg Pro Gln Val Lys Leu Glu Glu Ser Gly Gly Gly Leu
20 25 30

Val Gln Ala Gly Arg Ser Leu Arg Leu Ser Cys Ala Ala Ser Glu His
35 40 45

Thr Phe Ser Ser His Val Met Gly Trp Phe Arg Gln Ala Pro Gly Lys
50 55 60

Glu Arg Glu Ser Val Ala Val Ile Gly Trp Arg Asp Ile Ser Thr Ser
65 70 75 80

Tyr Ala Asp Ser Val Lys Gly Arg Phe Thr Ile Ser Arg Asp Asn Ala
85 90 95

Lys Lys Thr Leu Tyr Leu Gln Met Asn Ser Leu Lys Pro Glu Asp Thr
100 105 110

Ala Val Tyr Tyr Cys Ala Ala Arg Arg Ile Asp Ala Ala Asp Phe Asp
115 120 125

Ser Trp Gly Gln Gly Thr Gln Val Thr Val Ser Ser Gly Gly Gly Gly
130 135 140

Ser Gly Gly Gly Gly Ser Gly Gly Gly Gly Ser Gly Gly Gly Gly Ser
145 150 155 160

Gly Gly Gly Gly Ser Ala Val Gln Leu Val Glu Ser Gly Gly Gly Leu
165 170 175

Val Gln Ala Gly Asp Ser Leu Arg Leu Thr Cys Thr Ala Ser Gly Arg
180 185 190

Ala Phe Ser Thr Tyr Phe Met Ala Trp Phe Arg Gln Ala Pro Gly Lys
195 200 205

Glu Arg Glu Phe Val Ala Gly Ile Ala Trp Ser Gly Gly Ser Thr Ala
210 215 220

Tyr Ala Asp Ser Val Lys Gly Arg Phe Thr Ile Ser Arg Asp Asn Ala
225 230 235 240

Lys Asn Thr Val Tyr Leu Gln Met Asn Ser Leu Lys Ser Glu Asp Thr
245 250 255

Ala Val Tyr Tyr Cys Ala Ser Arg Gly Ile Glu Val Glu Glu Phe Gly
260 265 270

Ala Trp Gly Gln Gly Thr Gln Val Thr Val Ser Ser Thr Ser Thr Thr
275 280 285

Thr Pro Ala Pro Arg Pro Pro Thr Pro Ala Pro Thr Ile Ala Ser Gln
290 295 300

Pro Leu Ser Leu Arg Pro Glu Ala Cys Arg Pro Ala Ala Gly Gly Ala
305 310 315 320

Val His Thr Arg Gly Leu Asp Phe Ala Cys Asp Ile Tyr Ile Trp Ala
325 330 335

Pro Leu Ala Gly Thr Cys Gly Val Leu Leu Leu Ser Leu Val Ile Thr
340 345 350

Leu Tyr Cys Lys Arg Gly Arg Lys Lys Leu Leu Tyr Ile Phe Lys Gln
355 360 365

```
Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505


<210> SEQ ID NO 276
<211> LENGTH: 494
<212> TYPE: PRT
<213> ORGANISM: Artificial Sequence
<220> FEATURE:
<223> OTHER INFORMATION: Multivalent anti-BCMA CAR

<400> SEQUENCE: 276

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
            20                  25                  30

Val Gln Ala Gly Asp Ser Leu Arg Leu Thr Cys Thr Ala Ser Gly Arg
        35                  40                  45

Ala Phe Ser Thr Tyr Phe Met Ala Trp Phe Arg Gln Ala Pro Gly Lys
    50                  55                  60

Glu Arg Glu Phe Val Ala Gly Ile Ala Trp Ser Gly Gly Ser Thr Ala
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Ser Glu Asp Thr
            100                 105                 110

Ala Val Tyr Tyr Cys Ala Ser Arg Gly Ile Glu Val Glu Glu Phe Gly
        115                 120                 125

Ala Trp Gly Gln Gly Thr Gln Val Thr Val Ser Ser Gly Gly Gly Gly
    130                 135                 140

Ser Gly Gly Gly Gly Ser Gln Val Lys Leu Glu Glu Ser Gly Gly Gly
145                 150                 155                 160

Leu Val Gln Ala Gly Arg Ser Leu Arg Leu Ser Cys Ala Ala Ser Glu
                165                 170                 175

His Thr Phe Ser Ser His Val Met Gly Trp Phe Arg Gln Ala Pro Gly
            180                 185                 190

Lys Glu Arg Glu Ser Val Ala Val Ile Gly Trp Arg Asp Ile Ser Thr
        195                 200                 205

Ser Tyr Ala Asp Ser Val Lys Gly Arg Phe Thr Ile Ser Arg Asp Asn
    210                 215                 220
```

Ala Lys Lys Thr Leu Tyr Leu Gln Met Asn Ser Leu Lys Pro Glu Asp
225 230 235 240

Thr Ala Val Tyr Tyr Cys Ala Ala Arg Arg Ile Asp Ala Ala Asp Phe
245 250 255

Asp Ser Trp Gly Gln Gly Thr Gln Val Thr Val Ser Ser Thr Ser Thr
260 265 270

Thr Thr Pro Ala Pro Arg Pro Pro Thr Pro Ala Pro Thr Ile Ala Ser
275 280 285

Gln Pro Leu Ser Leu Arg Pro Glu Ala Cys Arg Pro Ala Ala Gly Gly
290 295 300

Ala Val His Thr Arg Gly Leu Asp Phe Ala Cys Asp Ile Tyr Ile Trp
305 310 315 320

Ala Pro Leu Ala Gly Thr Cys Gly Val Leu Leu Leu Ser Leu Val Ile
325 330 335

Thr Leu Tyr Cys Lys Arg Gly Arg Lys Lys Leu Leu Tyr Ile Phe Lys
340 345 350

Gln Pro Phe Met Arg Pro Val Gln Thr Thr Gln Glu Glu Asp Gly Cys
355 360 365

Ser Cys Arg Phe Pro Glu Glu Glu Glu Gly Gly Cys Glu Leu Arg Val
370 375 380

Lys Phe Ser Arg Ser Ala Asp Ala Pro Ala Tyr Gln Gln Gly Gln Asn
385 390 395 400

Gln Leu Tyr Asn Glu Leu Asn Leu Gly Arg Arg Glu Glu Tyr Asp Val
405 410 415

Leu Asp Lys Arg Arg Gly Arg Asp Pro Glu Met Gly Gly Lys Pro Arg
420 425 430

Arg Lys Asn Pro Gln Glu Gly Leu Tyr Asn Glu Leu Gln Lys Asp Lys
435 440 445

Met Ala Glu Ala Tyr Ser Glu Ile Gly Met Lys Gly Glu Arg Arg Arg
450 455 460

Gly Lys Gly His Asp Gly Leu Tyr Gln Gly Leu Ser Thr Ala Thr Lys
465 470 475 480

Asp Thr Tyr Asp Ala Leu His Met Gln Ala Leu Pro Pro Arg
485 490

<210> SEQ ID NO 277
<211> LENGTH: 499
<212> TYPE: PRT
<213> ORGANISM: Artificial Sequence
<220> FEATURE:
<223> OTHER INFORMATION: Multivalent anti-BCMA CAR

<400> SEQUENCE: 277

Met Ala Leu Pro Val Thr Ala Leu Leu Leu Pro Leu Ala Leu Leu Leu
1 5 10 15

His Ala Ala Arg Pro Ala Val Gln Leu Val Glu Ser Gly Gly Gly Leu
20 25 30

Val Gln Ala Gly Asp Ser Leu Arg Leu Thr Cys Thr Ala Ser Gly Arg
35 40 45

Ala Phe Ser Thr Tyr Phe Met Ala Trp Phe Arg Gln Ala Pro Gly Lys
50 55 60

Glu Arg Glu Phe Val Ala Gly Ile Ala Trp Ser Gly Gly Ser Thr Ala
65 70 75 80

Tyr Ala Asp Ser Val Lys Gly Arg Phe Thr Ile Ser Arg Asp Asn Ala
85 90 95

```
Lys Asn Thr Val Tyr Leu Gln Met Asn Ser Leu Lys Ser Glu Asp Thr
            100                 105                 110

Ala Val Tyr Tyr Cys Ala Ser Arg Gly Ile Glu Val Glu Glu Phe Gly
        115                 120                 125

Ala Trp Gly Gln Gly Thr Gln Val Thr Val Ser Ser Gly Gly Gly Gly
    130                 135                 140

Ser Gly Gly Gly Gly Ser Gly Gly Gly Gly Ser Gln Val Lys Leu Glu
145                 150                 155                 160

Glu Ser Gly Gly Gly Leu Val Gln Ala Gly Arg Ser Leu Arg Leu Ser
                165                 170                 175

Cys Ala Ala Ser Glu His Thr Phe Ser Ser His Val Met Gly Trp Phe
            180                 185                 190

Arg Gln Ala Pro Gly Lys Glu Arg Glu Ser Val Ala Val Ile Gly Trp
        195                 200                 205

Arg Asp Ile Ser Thr Ser Tyr Ala Asp Ser Val Lys Gly Arg Phe Thr
    210                 215                 220

Ile Ser Arg Asp Asn Ala Lys Lys Thr Leu Tyr Leu Gln Met Asn Ser
225                 230                 235                 240

Leu Lys Pro Glu Asp Thr Ala Val Tyr Tyr Cys Ala Ala Arg Arg Ile
                245                 250                 255

Asp Ala Ala Asp Phe Asp Ser Trp Gly Gln Gly Thr Gln Val Thr Val
            260                 265                 270

Ser Ser Thr Ser Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
            340                 345                 350

Leu Tyr Ile Phe Lys Gln Pro Phe Met Arg Pro Val Gln Thr Thr Gln
        355                 360                 365

Glu Glu Asp Gly Cys Ser Cys Arg Phe Pro Glu Glu Glu Glu Gly Gly
    370                 375                 380

Cys Glu Leu Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg
```

<210> SEQ ID NO 278
<211> LENGTH: 504
<212> TYPE: PRT
<213> ORGANISM: Artificial Sequence
<220> FEATURE:
<223> OTHER INFORMATION: Multivalent anti-BCMA CAR

<400> SEQUENCE: 278

Met Ala Leu Pro Val Thr Ala Leu Leu Leu Pro Leu Ala Leu Leu Leu
1 5 10 15

His Ala Ala Arg Pro Ala Val Gln Leu Val Glu Ser Gly Gly Gly Leu
20 25 30

Val Gln Ala Gly Asp Ser Leu Arg Leu Thr Cys Thr Ala Ser Gly Arg
35 40 45

Ala Phe Ser Thr Tyr Phe Met Ala Trp Phe Arg Gln Ala Pro Gly Lys
50 55 60

Glu Arg Glu Phe Val Ala Gly Ile Ala Trp Ser Gly Gly Ser Thr Ala
65 70 75 80

Tyr Ala Asp Ser Val Lys Gly Arg Phe Thr Ile Ser Arg Asp Asn Ala
85 90 95

Lys Asn Thr Val Tyr Leu Gln Met Asn Ser Leu Lys Ser Glu Asp Thr
100 105 110

Ala Val Tyr Tyr Cys Ala Ser Arg Gly Ile Glu Val Glu Glu Phe Gly
115 120 125

Ala Trp Gly Gln Gly Thr Gln Val Thr Val Ser Ser Gly Gly Gly Gly
130 135 140

Ser Gly Gly Gly Gly Ser Gly Gly Gly Gly Ser Gly Gly Gly Gly Ser
145 150 155 160

Gln Val Lys Leu Glu Glu Ser Gly Gly Gly Leu Val Gln Ala Gly Arg
165 170 175

Ser Leu Arg Leu Ser Cys Ala Ala Ser Glu His Thr Phe Ser Ser His
180 185 190

Val Met Gly Trp Phe Arg Gln Ala Pro Gly Lys Glu Arg Glu Ser Val
195 200 205

Ala Val Ile Gly Trp Arg Asp Ile Ser Thr Ser Tyr Ala Asp Ser Val
210 215 220

Lys Gly Arg Phe Thr Ile Ser Arg Asp Asn Ala Lys Lys Thr Leu Tyr
225 230 235 240

Leu Gln Met Asn Ser Leu Lys Pro Glu Asp Thr Ala Val Tyr Tyr Cys
245 250 255

Ala Ala Arg Arg Ile Asp Ala Ala Asp Phe Asp Ser Trp Gly Gln Gly
260 265 270

Thr Gln Val Thr Val Ser Ser Thr Ser Thr Thr Thr Pro Ala Pro Arg
275 280 285

Pro Pro Thr Pro Ala Pro Thr Ile Ala Ser Gln Pro Leu Ser Leu Arg
290 295 300

Pro Glu Ala Cys Arg Pro Ala Ala Gly Gly Ala Val His Thr Arg Gly
305 310 315 320

Leu Asp Phe Ala Cys Asp Ile Tyr Ile Trp Ala Pro Leu Ala Gly Thr
325 330 335

Cys Gly Val Leu Leu Leu Ser Leu Val Ile Thr Leu Tyr Cys Lys Arg
340 345 350

Gly Arg Lys Lys Leu Leu Tyr Ile Phe Lys Gln Pro Phe Met Arg Pro
355 360 365

Val Gln Thr Thr Gln Glu Glu Asp Gly Cys Ser Cys Arg Phe Pro Glu

```
    370                 375                 380

Glu Glu Glu Gly Gly Cys Glu Leu Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
        435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500


<210> SEQ ID NO 279
<211> LENGTH: 498
<212> TYPE: PRT
<213> ORGANISM: Artificial Sequence
<220> FEATURE:
<223> OTHER INFORMATION: Multivalent anti-BCMA CAR

<400> SEQUENCE: 279

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gln Val Lys Leu Glu Glu Ser Gly Gly Arg Leu Val Gln Pro Arg
145                 150                 155                 160

Gly Ser Leu Arg Leu Ser Cys Ala Gly Ser Gly Arg Thr Phe Ser Thr
                165                 170                 175

Tyr Gly Met Ala Trp Phe Arg Gln Ala Pro Gly Lys Glu Arg Glu Phe
            180                 185                 190

Val Ala Ser Lys Ala Ser Met Asn Tyr Ser Gly Arg Thr Tyr Tyr Ala
        195                 200                 205

Asp Ser Val Lys Gly Arg Phe Thr Ile Ala Arg Asp Asn Ala Lys Asn
    210                 215                 220

Met Val Phe Leu Gln Met Asn Asn Leu Lys Pro Glu Asp Thr Ala Val
```

225 230 235 240

Tyr Tyr Cys Ala Ala Gly Thr Gly Cys Ser Thr Tyr Gly Cys Phe Asp
245 250 255

Ala Gln Ile Ile Asp Tyr Trp Gly Lys Gly Thr Leu Val Thr Val Ser
260 265 270

Ser Thr Ser Thr Thr Thr Pro Ala Pro Arg Pro Pro Thr Pro Ala Pro
275 280 285

Thr Ile Ala Ser Gln Pro Leu Ser Leu Arg Pro Glu Ala Cys Arg Pro
290 295 300

Ala Ala Gly Gly Ala Val His Thr Arg Gly Leu Asp Phe Ala Cys Asp
305 310 315 320

Ile Tyr Ile Trp Ala Pro Leu Ala Gly Thr Cys Gly Val Leu Leu Leu
325 330 335

Ser Leu Val Ile Thr Leu Tyr Cys Lys Arg Gly Arg Lys Lys Leu Leu
340 345 350

Tyr Ile Phe Lys Gln Pro Phe Met Arg Pro Val Gln Thr Thr Gln Glu
355 360 365

Glu Asp Gly Cys Ser Cys Arg Phe Pro Glu Glu Glu Glu Gly Gly Cys
370 375 380

Glu Leu Arg Val Lys Phe Ser Arg Ser Ala Asp Ala Pro Ala Tyr Gln
385 390 395 400

Gln Gly Gln Asn Gln Leu Tyr Asn Glu Leu Asn Leu Gly Arg Arg Glu
405 410 415

Glu Tyr Asp Val Leu Asp Lys Arg Arg Gly Arg Asp Pro Glu Met Gly
420 425 430

Gly Lys Pro Arg Arg Lys Asn Pro Gln Glu Gly Leu Tyr Asn Glu Leu
435 440 445

Gln Lys Asp Lys Met Ala Glu Ala Tyr Ser Glu Ile Gly Met Lys Gly
450 455 460

Glu Arg Arg Arg Gly Lys Gly His Asp Gly Leu Tyr Gln Gly Leu Ser
465 470 475 480

Thr Ala Thr Lys Asp Thr Tyr Asp Ala Leu His Met Gln Ala Leu Pro
485 490 495

Pro Arg

<210> SEQ ID NO 280
<211> LENGTH: 508
<212> TYPE: PRT
<213> ORGANISM: Artificial Sequence
<220> FEATURE:
<223> OTHER INFORMATION: Multivalent anti-BCMA CAR

<400> SEQUENCE: 280

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Met
20 25 30

Val Gln Ala Gly Asp Ser Leu Arg Leu Ser Cys Val Gln Ser Thr Tyr
35 40 45

Thr Val Asn Ser Asp Val Met Gly Trp Phe Arg Gln Ala Pro Gly Lys
50 55 60

Glu Arg Glu Phe Val Gly Ala Ile Met Trp Asn Asp Gly Ile Thr Tyr
65 70 75 80

Leu Gln Asp Ser Val Lys Gly Arg Phe Thr Ile Phe Arg Asp Asn Ala
85 90 95

```
Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gly Gly Gly Gly Ser Gly Gly Gly Gly Ser Gln Val Lys Leu Glu
145                 150                 155                 160

Glu Ser Gly Gly Arg Leu Val Gln Pro Arg Gly Ser Leu Arg Leu Ser
                165                 170                 175

Cys Ala Gly Ser Gly Arg Thr Phe Ser Thr Tyr Gly Met Ala Trp Phe
            180                 185                 190

Arg Gln Ala Pro Gly Lys Glu Arg Glu Phe Val Ala Ser Lys Ala Ser
        195                 200                 205

Met Asn Tyr Ser Gly Arg Thr Tyr Tyr Ala Asp Ser Val Lys Gly Arg
    210                 215                 220

Phe Thr Ile Ala Arg Asp Asn Ala Lys Asn Met Val Phe Leu Gln Met
225                 230                 235                 240

Asn Asn Leu Lys Pro Glu Asp Thr Ala Val Tyr Tyr Cys Ala Ala Gly
                245                 250                 255

Thr Gly Cys Ser Thr Tyr Gly Cys Phe Asp Ala Gln Ile Ile Asp Tyr
            260                 265                 270

Trp Gly Lys Gly Thr Leu Val Thr Val Ser Ser Thr Ser Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505
```

<210> SEQ ID NO 281
<211> LENGTH: 518
<212> TYPE: PRT
<213> ORGANISM: Artificial Sequence
<220> FEATURE:
<223> OTHER INFORMATION: Multivalent anti-BCMA CAR

<400> SEQUENCE: 281

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Gln Val Lys Leu Glu Glu Ser Gly Gly Arg Leu
                165                 170                 175

Val Gln Pro Arg Gly Ser Leu Arg Leu Ser Cys Ala Gly Ser Gly Arg
            180                 185                 190

Thr Phe Ser Thr Tyr Gly Met Ala Trp Phe Arg Gln Ala Pro Gly Lys
        195                 200                 205

Glu Arg Glu Phe Val Ala Ser Lys Ala Ser Met Asn Tyr Ser Gly Arg
    210                 215                 220

Thr Tyr Tyr Ala Asp Ser Val Lys Gly Arg Phe Thr Ile Ala Arg Asp
225                 230                 235                 240

Asn Ala Lys Asn Met Val Phe Leu Gln Met Asn Asn Leu Lys Pro Glu
                245                 250                 255

Asp Thr Ala Val Tyr Tyr Cys Ala Ala Gly Thr Gly Cys Ser Thr Tyr
            260                 265                 270

Gly Cys Phe Asp Ala Gln Ile Ile Asp Tyr Trp Gly Lys Gly Thr Leu
        275                 280                 285

Val Thr Val Ser Ser Thr Ser Thr Thr Thr Pro Ala Pro Arg Pro Pro
    290                 295                 300

Thr Pro Ala Pro Thr Ile Ala Ser Gln Pro Leu Ser Leu Arg Pro Glu
305                 310                 315                 320

Ala Cys Arg Pro Ala Ala Gly Gly Ala Val His Thr Arg Gly Leu Asp
                325                 330                 335

Phe Ala Cys Asp Ile Tyr Ile Trp Ala Pro Leu Ala Gly Thr Cys Gly
            340                 345                 350

Val Leu Leu Leu Ser Leu Val Ile Thr Leu Tyr Cys Lys Arg Gly Arg
        355                 360                 365

```
Lys Lys Leu Leu Tyr Ile Phe Lys Gln Pro Phe Met Arg Pro Val Gln
    370                 375                 380

Thr Thr Gln Glu Glu Asp Gly Cys Ser Cys Arg Phe Pro Glu Glu Glu
385                 390                 395                 400

Glu Gly Gly Cys Glu Leu Arg Val Lys Phe Ser Arg Ser Ala Asp Ala
                405                 410                 415

Pro Ala Tyr Gln Gln Gly Gln Asn Gln Leu Tyr Asn Glu Leu Asn Leu
            420                 425                 430

Gly Arg Arg Glu Glu Tyr Asp Val Leu Asp Lys Arg Arg Gly Arg Asp
        435                 440                 445

Pro Glu Met Gly Gly Lys Pro Arg Arg Lys Asn Pro Gln Glu Gly Leu
    450                 455                 460

Tyr Asn Glu Leu Gln Lys Asp Lys Met Ala Glu Ala Tyr Ser Glu Ile
465                 470                 475                 480

Gly Met Lys Gly Glu Arg Arg Arg Gly Lys Gly His Asp Gly Leu Tyr
                485                 490                 495

Gln Gly Leu Ser Thr Ala Thr Lys Asp Thr Tyr Asp Ala Leu His Met
            500                 505                 510

Gln Ala Leu Pro Pro Arg
        515


<210> SEQ ID NO 282
<211> LENGTH: 503
<212> TYPE: PRT
<213> ORGANISM: Artificial Sequence
<220> FEATURE:
<223> OTHER INFORMATION: Multivalent anti-BCMA CAR

<400> SEQUENCE: 282

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gly Gly Gly Gly Ser Gln Val Lys Leu Glu Glu Ser Gly Gly Arg
145                 150                 155                 160

Leu Val Gln Pro Arg Gly Ser Leu Arg Leu Ser Cys Ala Gly Ser Gly
                165                 170                 175

Arg Thr Phe Ser Thr Tyr Gly Met Ala Trp Phe Arg Gln Ala Pro Gly
            180                 185                 190

Lys Glu Arg Glu Phe Val Ala Ser Lys Ala Ser Met Asn Tyr Ser Gly
        195                 200                 205
```

```
Arg Thr Tyr Tyr Ala Asp Ser Val Lys Gly Arg Phe Thr Ile Ala Arg
    210                 215                 220

Asp Asn Ala Lys Asn Met Val Phe Leu Gln Met Asn Asn Leu Lys Pro
225                 230                 235                 240

Glu Asp Thr Ala Val Tyr Tyr Cys Ala Ala Gly Thr Gly Cys Ser Thr
                245                 250                 255

Tyr Gly Cys Phe Asp Ala Gln Ile Ile Asp Tyr Trp Gly Lys Gly Thr
            260                 265                 270

Leu Val Thr Val Ser Ser Thr Ser Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Lys Arg Gly
            340                 345                 350

Arg Lys Lys Leu Leu Tyr Ile Phe Lys Gln Pro Phe Met Arg Pro Val
        355                 360                 365

Gln Thr Thr Gln Glu Glu Asp Gly Cys Ser Cys Arg Phe Pro Glu Glu
    370                 375                 380

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
        435                 440                 445

Leu Tyr Asn Glu Leu Gln Lys Asp Lys Met Ala Glu Ala Tyr Ser Glu
    450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
            500


<210> SEQ ID NO 283
<211> LENGTH: 508
<212> TYPE: PRT
<213> ORGANISM: Artificial Sequence
<220> FEATURE:
<223> OTHER INFORMATION: Multivalent anti-BCMA CAR

<400> SEQUENCE: 283

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60
```

```
Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gly Gly Gly Gly Ser Gly Gly Gly Gly Ser Gln Val Lys Leu Glu
145                 150                 155                 160

Glu Ser Gly Gly Arg Leu Val Gln Pro Arg Gly Ser Leu Arg Leu Ser
                165                 170                 175

Cys Ala Gly Ser Gly Arg Thr Phe Ser Thr Tyr Gly Met Ala Trp Phe
            180                 185                 190

Arg Gln Ala Pro Gly Lys Glu Arg Glu Phe Val Ala Ser Lys Ala Ser
        195                 200                 205

Met Asn Tyr Ser Gly Arg Thr Tyr Tyr Ala Asp Ser Val Lys Gly Arg
    210                 215                 220

Phe Thr Ile Ala Arg Asp Asn Ala Lys Asn Met Val Phe Leu Gln Met
225                 230                 235                 240

Asn Asn Leu Lys Pro Glu Asp Thr Ala Val Tyr Tyr Cys Ala Ala Gly
                245                 250                 255

Thr Gly Cys Ser Thr Tyr Gly Cys Phe Asp Ala Gln Ile Ile Asp Tyr
            260                 265                 270

Trp Gly Lys Gly Thr Leu Val Thr Val Ser Ser Thr Ser Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
```

```
                485                 490                 495

Tyr Asp Ala Leu His Met Gln Ala Leu Pro Pro Arg
            500                 505


<210> SEQ ID NO 284
<211> LENGTH: 513
<212> TYPE: PRT
<213> ORGANISM: Artificial Sequence
<220> FEATURE:
<223> OTHER INFORMATION: Multivalent anti-BCMA CAR

<400> SEQUENCE: 284

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Gln Val Lys Leu Glu Glu Ser Gly Gly Arg Leu Val Gln Pro Arg Gly
                165                 170                 175

Ser Leu Arg Leu Ser Cys Ala Gly Ser Gly Arg Thr Phe Ser Thr Tyr
            180                 185                 190

Gly Met Ala Trp Phe Arg Gln Ala Pro Gly Lys Glu Arg Glu Phe Val
        195                 200                 205

Ala Ser Lys Ala Ser Met Asn Tyr Ser Gly Arg Thr Tyr Tyr Ala Asp
    210                 215                 220

Ser Val Lys Gly Arg Phe Thr Ile Ala Arg Asp Asn Ala Lys Asn Met
225                 230                 235                 240

Val Phe Leu Gln Met Asn Asn Leu Lys Pro Glu Asp Thr Ala Val Tyr
                245                 250                 255

Tyr Cys Ala Ala Gly Thr Gly Cys Ser Thr Tyr Gly Cys Phe Asp Ala
            260                 265                 270

Gln Ile Ile Asp Tyr Trp Gly Lys Gly Thr Leu Val Thr Val Ser Ser
        275                 280                 285

Thr Ser Thr Thr Thr Pro Ala Pro Arg Pro Pro Thr Pro Ala Pro Thr
    290                 295                 300

Ile Ala Ser Gln Pro Leu Ser Leu Arg Pro Glu Ala Cys Arg Pro Ala
305                 310                 315                 320

Ala Gly Gly Ala Val His Thr Arg Gly Leu Asp Phe Ala Cys Asp Ile
                325                 330                 335

Tyr Ile Trp Ala Pro Leu Ala Gly Thr Cys Gly Val Leu Leu Leu Ser
```

```
            340                 345                 350

Leu Val Ile Thr Leu Tyr Cys Lys Arg Gly Arg Lys Lys Leu Leu Tyr
        355                 360                 365

Ile Phe Lys Gln Pro Phe Met Arg Pro Val Gln Thr Thr Gln Glu Glu
    370                 375                 380

Asp Gly Cys Ser Cys Arg Phe Pro Glu Glu Glu Glu Gly Gly Cys Glu
385                 390                 395                 400

Leu Arg Val Lys Phe Ser Arg Ser Ala Asp Ala Pro Ala Tyr Gln Gln
                405                 410                 415

Gly Gln Asn Gln Leu Tyr Asn Glu Leu Asn Leu Gly Arg Arg Glu Glu
            420                 425                 430

Tyr Asp Val Leu Asp Lys Arg Arg Gly Arg Asp Pro Glu Met Gly Gly
        435                 440                 445

Lys Pro Arg Arg Lys Asn Pro Gln Glu Gly Leu Tyr Asn Glu Leu Gln
    450                 455                 460

Lys Asp Lys Met Ala Glu Ala Tyr Ser Glu Ile Gly Met Lys Gly Glu
465                 470                 475                 480

Arg Arg Arg Gly Lys Gly His Asp Gly Leu Tyr Gln Gly Leu Ser Thr
                485                 490                 495

Ala Thr Lys Asp Thr Tyr Asp Ala Leu His Met Gln Ala Leu Pro Pro
            500                 505                 510

Arg


<210> SEQ ID NO 285
<211> LENGTH: 500
<212> TYPE: PRT
<213> ORGANISM: Artificial Sequence
<220> FEATURE:
<223> OTHER INFORMATION: Multivalent anti-BCMA CAR

<400> SEQUENCE: 285

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
        35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125

Gly Cys Phe Asp Ala Gln Ile Ile Asp Tyr Trp Gly Lys Gly Thr Leu
    130                 135                 140

Val Thr Val Ser Ser Gly Gly Gly Gly Ser Gln Val Lys Leu Glu Glu
145                 150                 155                 160

Ser Gly Gly Gly Leu Val Gln Ala Gly Gly Ser Leu Arg Leu Ser Cys
                165                 170                 175

Ala Ala Ser Gly Gly Thr Leu Ser Lys Asn Thr Val Ala Trp Val Arg
            180                 185                 190
```

```
Gln Ala Pro Gly Lys Glu Arg Gly Phe Val Thr Ser Ile Thr Cys Asp
        195                 200                 205

Gly Arg Thr Thr Tyr Tyr Ala Asn Ser Val Asn Gly Arg Phe Pro Ile
    210                 215                 220

Asn Arg Asn Asn Ala Glu Asn Leu Val Val Leu Gln Met Asn Ser Leu
225                 230                 235                 240

Lys Pro Asp Asp Thr Ala Leu Tyr Tyr Cys Ala Ala Tyr Arg Lys Ser
                245                 250                 255

Ile Met Ser Ile Gln Pro Asp Tyr Trp Gly Gln Gly Thr Gln Val Thr
            260                 265                 270

Val Ser Ser Thr Ser Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Lys Arg Gly Arg Lys Lys
            340                 345                 350

Leu Leu Tyr Ile Phe Lys Gln Pro Phe Met Arg Pro Val Gln Thr Thr
        355                 360                 365

Gln Glu Glu Asp Gly Cys Ser Cys Arg Phe Pro Glu Glu Glu Glu Gly
    370                 375                 380

Gly Cys Glu Leu Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
                405                 410                 415

Arg Glu Glu Tyr Asp Val Leu Asp Lys Arg Arg Gly Arg Asp Pro Glu
            420                 425                 430

Met Gly Gly Lys Pro Arg Arg Lys Asn Pro Gln Glu Gly Leu Tyr Asn
        435                 440                 445

Glu Leu Gln Lys Asp Lys Met Ala Glu Ala Tyr Ser Glu Ile Gly Met
    450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
                485                 490                 495

Leu Pro Pro Arg
            500
```

<210> SEQ ID NO 286
<211> LENGTH: 510
<212> TYPE: PRT
<213> ORGANISM: Artificial Sequence
<220> FEATURE:
<223> OTHER INFORMATION: Multivalent anti-BCMA CAR

<400> SEQUENCE: 286

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
        35                  40                  45
```

```
Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125

Gly Cys Phe Asp Ala Gln Ile Ile Asp Tyr Trp Gly Lys Gly Thr Leu
    130                 135                 140

Val Thr Val Ser Ser Gly Gly Gly Gly Ser Gly Gly Gly Gly Ser Gly
145                 150                 155                 160

Gly Gly Gly Ser Gln Val Lys Leu Glu Glu Ser Gly Gly Gly Leu Val
                165                 170                 175

Gln Ala Gly Gly Ser Leu Arg Leu Ser Cys Ala Ala Ser Gly Gly Thr
            180                 185                 190

Leu Ser Lys Asn Thr Val Ala Trp Val Arg Gln Ala Pro Gly Lys Glu
        195                 200                 205

Arg Gly Phe Val Thr Ser Ile Thr Cys Asp Gly Arg Thr Thr Tyr Tyr
    210                 215                 220

Ala Asn Ser Val Asn Gly Arg Phe Pro Ile Asn Arg Asn Asn Ala Glu
225                 230                 235                 240

Asn Leu Val Val Leu Gln Met Asn Ser Leu Lys Pro Asp Asp Thr Ala
                245                 250                 255

Leu Tyr Tyr Cys Ala Ala Tyr Arg Lys Ser Ile Met Ser Ile Gln Pro
            260                 265                 270

Asp Tyr Trp Gly Gln Gly Thr Gln Val Thr Val Ser Ser Thr Ser Thr
        275                 280                 285

Thr Thr Pro Ala Pro Arg Pro Pro Thr Pro Ala Pro Thr Ile Ala Ser
    290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
                325                 330                 335

Ala Pro Leu Ala Gly Thr Cys Gly Val Leu Leu Leu Ser Leu Val Ile
            340                 345                 350

Thr Leu Tyr Cys Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460
```

Met Ala Glu Ala Tyr Ser Glu Ile Gly Met Lys Gly Glu Arg Arg Arg
465 470 475 480

Gly Lys Gly His Asp Gly Leu Tyr Gln Gly Leu Ser Thr Ala Thr Lys
485 490 495

Asp Thr Tyr Asp Ala Leu His Met Gln Ala Leu Pro Pro Arg
500 505 510

<210> SEQ ID NO 287
<211> LENGTH: 520
<212> TYPE: PRT
<213> ORGANISM: Artificial Sequence
<220> FEATURE:
<223> OTHER INFORMATION: Multivalent anti-BCMA CAR

<400> SEQUENCE: 287

Met Ala Leu Pro Val Thr Ala Leu Leu Leu Pro Leu Ala Leu Leu Leu
1 5 10 15

His Ala Ala Arg Pro Gln Val Lys Leu Glu Glu Ser Gly Gly Arg Leu
20 25 30

Val Gln Pro Arg Gly Ser Leu Arg Leu Ser Cys Ala Gly Ser Gly Arg
35 40 45

Thr Phe Ser Thr Tyr Gly Met Ala Trp Phe Arg Gln Ala Pro Gly Lys
50 55 60

Glu Arg Glu Phe Val Ala Ser Lys Ala Ser Met Asn Tyr Ser Gly Arg
65 70 75 80

Thr Tyr Tyr Ala Asp Ser Val Lys Gly Arg Phe Thr Ile Ala Arg Asp
85 90 95

Asn Ala Lys Asn Met Val Phe Leu Gln Met Asn Asn Leu Lys Pro Glu
100 105 110

Asp Thr Ala Val Tyr Tyr Cys Ala Ala Gly Thr Gly Cys Ser Thr Tyr
115 120 125

Gly Cys Phe Asp Ala Gln Ile Ile Asp Tyr Trp Gly Lys Gly Thr Leu
130 135 140

Val Thr Val Ser Ser Gly Gly Gly Gly Ser Gly Gly Gly Gly Ser Gly
145 150 155 160

Gly Gly Gly Ser Gly Gly Gly Gly Ser Gly Gly Gly Gly Ser Gln Val
165 170 175

Lys Leu Glu Glu Ser Gly Gly Gly Leu Val Gln Ala Gly Gly Ser Leu
180 185 190

Arg Leu Ser Cys Ala Ala Ser Gly Gly Thr Leu Ser Lys Asn Thr Val
195 200 205

Ala Trp Val Arg Gln Ala Pro Gly Lys Glu Arg Gly Phe Val Thr Ser
210 215 220

Ile Thr Cys Asp Gly Arg Thr Thr Tyr Tyr Ala Asn Ser Val Asn Gly
225 230 235 240

Arg Phe Pro Ile Asn Arg Asn Asn Ala Glu Asn Leu Val Val Leu Gln
245 250 255

Met Asn Ser Leu Lys Pro Asp Asp Thr Ala Leu Tyr Tyr Cys Ala Ala
260 265 270

Tyr Arg Lys Ser Ile Met Ser Ile Gln Pro Asp Tyr Trp Gly Gln Gly
275 280 285

Thr Gln Val Thr Val Ser Ser Thr Ser Thr Thr Thr Pro Ala Pro Arg
290 295 300

Pro Pro Thr Pro Ala Pro Thr Ile Ala Ser Gln Pro Leu Ser Leu Arg
305 310 315 320

Pro Glu Ala Cys Arg Pro Ala Ala Gly Gly Ala Val His Thr Arg Gly
325 330 335

Leu Asp Phe Ala Cys Asp Ile Tyr Ile Trp Ala Pro Leu Ala Gly Thr
340 345 350

Cys Gly Val Leu Leu Leu Ser Leu Val Ile Thr Leu Tyr Cys Lys Arg
355 360 365

Gly Arg Lys Lys Leu Leu Tyr Ile Phe Lys Gln Pro Phe Met Arg Pro
370 375 380

Val Gln Thr Thr Gln Glu Glu Asp Gly Cys Ser Cys Arg Phe Pro Glu
385 390 395 400

Glu Glu Glu Gly Gly Cys Glu Leu Arg Val Lys Phe Ser Arg Ser Ala
405 410 415

Asp Ala Pro Ala Tyr Gln Gln Gly Gln Asn Gln Leu Tyr Asn Glu Leu
420 425 430

Asn Leu Gly Arg Arg Glu Glu Tyr Asp Val Leu Asp Lys Arg Arg Gly
435 440 445

Arg Asp Pro Glu Met Gly Gly Lys Pro Arg Arg Lys Asn Pro Gln Glu
450 455 460

Gly Leu Tyr Asn Glu Leu Gln Lys Asp Lys Met Ala Glu Ala Tyr Ser
465 470 475 480

Glu Ile Gly Met Lys Gly Glu Arg Arg Arg Gly Lys Gly His Asp Gly
485 490 495

Leu Tyr Gln Gly Leu Ser Thr Ala Thr Lys Asp Thr Tyr Asp Ala Leu
500 505 510

His Met Gln Ala Leu Pro Pro Arg
515 520

<210> SEQ ID NO 288
<211> LENGTH: 505
<212> TYPE: PRT
<213> ORGANISM: Artificial Sequence
<220> FEATURE:
<223> OTHER INFORMATION: Multivalent anti-BCMA CAR

<400> SEQUENCE: 288

Met Ala Leu Pro Val Thr Ala Leu Leu Leu Pro Leu Ala Leu Leu Leu
1 5 10 15

His Ala Ala Arg Pro Gln Val Lys Leu Glu Glu Ser Gly Gly Arg Leu
20 25 30

Val Gln Pro Arg Gly Ser Leu Arg Leu Ser Cys Ala Gly Ser Gly Arg
35 40 45

Thr Phe Ser Thr Tyr Gly Met Ala Trp Phe Arg Gln Ala Pro Gly Lys
50 55 60

Glu Arg Glu Phe Val Ala Ser Lys Ala Ser Met Asn Tyr Ser Gly Arg
65 70 75 80

Thr Tyr Tyr Ala Asp Ser Val Lys Gly Arg Phe Thr Ile Ala Arg Asp
85 90 95

Asn Ala Lys Asn Met Val Phe Leu Gln Met Asn Asn Leu Lys Pro Glu
100 105 110

Asp Thr Ala Val Tyr Tyr Cys Ala Ala Gly Thr Gly Cys Ser Thr Tyr
115 120 125

Gly Cys Phe Asp Ala Gln Ile Ile Asp Tyr Trp Gly Lys Gly Thr Leu
130 135 140

Val Thr Val Ser Ser Gly Gly Gly Gly Ser Gly Gly Gly Gly Ser Gln
145 150 155 160

Val Lys Leu Glu Glu Ser Gly Gly Gly Leu Val Gln Ala Gly Gly Ser
165 170 175

Leu Arg Leu Ser Cys Ala Ala Ser Gly Gly Thr Leu Ser Lys Asn Thr
180 185 190

Val Ala Trp Val Arg Gln Ala Pro Gly Lys Glu Arg Gly Phe Val Thr
195 200 205

Ser Ile Thr Cys Asp Gly Arg Thr Thr Tyr Tyr Ala Asn Ser Val Asn
210 215 220

Gly Arg Phe Pro Ile Asn Arg Asn Asn Ala Glu Asn Leu Val Val Leu
225 230 235 240

Gln Met Asn Ser Leu Lys Pro Asp Asp Thr Ala Leu Tyr Tyr Cys Ala
245 250 255

Ala Tyr Arg Lys Ser Ile Met Ser Ile Gln Pro Asp Tyr Trp Gly Gln
260 265 270

Gly Thr Gln Val Thr Val Ser Ser Thr Ser Thr Thr Thr Pro Ala Pro
275 280 285

Arg Pro Pro Thr Pro Ala Pro Thr Ile Ala Ser Gln Pro Leu Ser Leu
290 295 300

Arg Pro Glu Ala Cys Arg Pro Ala Ala Gly Gly Ala Val His Thr Arg
305 310 315 320

Gly Leu Asp Phe Ala Cys Asp Ile Tyr Ile Trp Ala Pro Leu Ala Gly
325 330 335

Thr Cys Gly Val Leu Leu Leu Ser Leu Val Ile Thr Leu Tyr Cys Lys
340 345 350

Arg Gly Arg Lys Lys Leu Leu Tyr Ile Phe Lys Gln Pro Phe Met Arg
355 360 365

Pro Val Gln Thr Thr Gln Glu Glu Asp Gly Cys Ser Cys Arg Phe Pro
370 375 380

Glu Glu Glu Glu Gly Gly Cys Glu Leu Arg Val Lys Phe Ser Arg Ser
385 390 395 400

Ala Asp Ala Pro Ala Tyr Gln Gln Gly Gln Asn Gln Leu Tyr Asn Glu
405 410 415

Leu Asn Leu Gly Arg Arg Glu Glu Tyr Asp Val Leu Asp Lys Arg Arg
420 425 430

Gly Arg Asp Pro Glu Met Gly Gly Lys Pro Arg Arg Lys Asn Pro Gln
435 440 445

Glu Gly Leu Tyr Asn Glu Leu Gln Lys Asp Lys Met Ala Glu Ala Tyr
450 455 460

Ser Glu Ile Gly Met Lys Gly Glu Arg Arg Arg Gly Lys Gly His Asp
465 470 475 480

Gly Leu Tyr Gln Gly Leu Ser Thr Ala Thr Lys Asp Thr Tyr Asp Ala
485 490 495

Leu His Met Gln Ala Leu Pro Pro Arg
500 505

<210> SEQ ID NO 289
<211> LENGTH: 510
<212> TYPE: PRT
<213> ORGANISM: Artificial Sequence
<220> FEATURE:
<223> OTHER INFORMATION: Multivalent anti-BCMA CAR

<400> SEQUENCE: 289

Met Ala Leu Pro Val Thr Ala Leu Leu Leu Pro Leu Ala Leu Leu Leu
1 5 10 15

```
His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
        35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125

Gly Cys Phe Asp Ala Gln Ile Ile Asp Tyr Trp Gly Lys Gly Thr Leu
    130                 135                 140

Val Thr Val Ser Ser Gly Gly Gly Gly Ser Gly Gly Gly Gly Ser Gly
145                 150                 155                 160

Gly Gly Gly Ser Gln Val Lys Leu Glu Glu Ser Gly Gly Gly Leu Val
                165                 170                 175

Gln Ala Gly Gly Ser Leu Arg Leu Ser Cys Ala Ala Ser Gly Gly Thr
            180                 185                 190

Leu Ser Lys Asn Thr Val Ala Trp Val Arg Gln Ala Pro Gly Lys Glu
        195                 200                 205

Arg Gly Phe Val Thr Ser Ile Thr Cys Asp Gly Arg Thr Thr Tyr Tyr
    210                 215                 220

Ala Asn Ser Val Asn Gly Arg Phe Pro Ile Asn Arg Asn Asn Ala Glu
225                 230                 235                 240

Asn Leu Val Val Leu Gln Met Asn Ser Leu Lys Pro Asp Asp Thr Ala
                245                 250                 255

Leu Tyr Tyr Cys Ala Ala Tyr Arg Lys Ser Ile Met Ser Ile Gln Pro
            260                 265                 270

Asp Tyr Trp Gly Gln Gly Thr Gln Val Thr Val Ser Ser Thr Ser Thr
        275                 280                 285

Thr Thr Pro Ala Pro Arg Pro Pro Thr Pro Ala Pro Thr Ile Ala Ser
    290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
                325                 330                 335

Ala Pro Leu Ala Gly Thr Cys Gly Val Leu Leu Leu Ser Leu Val Ile
            340                 345                 350

Thr Leu Tyr Cys Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
```

```
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510


<210> SEQ ID NO 290
<211> LENGTH: 515
<212> TYPE: PRT
<213> ORGANISM: Artificial Sequence
<220> FEATURE:
<223> OTHER INFORMATION: Multivalent anti-BCMA CAR

<400> SEQUENCE: 290

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
        35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125

Gly Cys Phe Asp Ala Gln Ile Ile Asp Tyr Trp Gly Lys Gly Thr Leu
    130                 135                 140

Val Thr Val Ser Ser Gly Gly Gly Gly Ser Gly Gly Gly Gly Ser Gly
145                 150                 155                 160

Gly Gly Gly Ser Gly Gly Gly Gly Ser Gln Val Lys Leu Glu Glu Ser
                165                 170                 175

Gly Gly Gly Leu Val Gln Ala Gly Gly Ser Leu Arg Leu Ser Cys Ala
            180                 185                 190

Ala Ser Gly Gly Thr Leu Ser Lys Asn Thr Val Ala Trp Val Arg Gln
        195                 200                 205

Ala Pro Gly Lys Glu Arg Gly Phe Val Thr Ser Ile Thr Cys Asp Gly
    210                 215                 220

Arg Thr Thr Tyr Tyr Ala Asn Ser Val Asn Gly Arg Phe Pro Ile Asn
225                 230                 235                 240

Arg Asn Asn Ala Glu Asn Leu Val Val Leu Gln Met Asn Ser Leu Lys
                245                 250                 255

Pro Asp Asp Thr Ala Leu Tyr Tyr Cys Ala Ala Tyr Arg Lys Ser Ile
            260                 265                 270

Met Ser Ile Gln Pro Asp Tyr Trp Gly Gln Gly Thr Gln Val Thr Val
        275                 280                 285

Ser Ser Thr Ser Thr Thr Thr Pro Ala Pro Arg Pro Pro Thr Pro Ala
```

```
    290                 295                 300

Pro Thr Ile Ala Ser Gln Pro Leu Ser Leu Arg Pro Glu Ala Cys Arg
305                 310                 315                 320

Pro Ala Ala Gly Gly Ala Val His Thr Arg Gly Leu Asp Phe Ala Cys
                325                 330                 335

Asp Ile Tyr Ile Trp Ala Pro Leu Ala Gly Thr Cys Gly Val Leu Leu
            340                 345                 350

Leu Ser Leu Val Ile Thr Leu Tyr Cys Lys Arg Gly Arg Lys Lys Leu
        355                 360                 365

Leu Tyr Ile Phe Lys Gln Pro Phe Met Arg Pro Val Gln Thr Thr Gln
    370                 375                 380

Glu Glu Asp Gly Cys Ser Cys Arg Phe Pro Glu Glu Glu Glu Gly Gly
385                 390                 395                 400

Cys Glu Leu Arg Val Lys Phe Ser Arg Ser Ala Asp Ala Pro Ala Tyr
                405                 410                 415

Gln Gln Gly Gln Asn Gln Leu Tyr Asn Glu Leu Asn Leu Gly Arg Arg
            420                 425                 430

Glu Glu Tyr Asp Val Leu Asp Lys Arg Arg Gly Arg Asp Pro Glu Met
        435                 440                 445

Gly Gly Lys Pro Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515
```

<210> SEQ ID NO 291
<211> LENGTH: 492
<212> TYPE: PRT
<213> ORGANISM: Artificial Sequence
<220> FEATURE:
<223> OTHER INFORMATION: Multivalent anti-BCMA CAR

<400> SEQUENCE: 291

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

Pro Asp Tyr Trp Gly Gln Gly Thr Gln Val Thr Val Ser Ser Gly Gly
```

```
    130                 135                 140

Gly Gly Ser Gln Val Gln Leu Val Glu Ser Gly Gly Gly Leu Val Gln
145                 150                 155                 160

Ala Gly Gly Ser Leu Arg Leu Ser Cys Ala Ala Ser Gly Gly Thr Leu
                165                 170                 175

Ser Lys Asn Thr Val Ala Trp Phe Arg Gln Ala Pro Gly Lys Glu Arg
            180                 185                 190

Gly Phe Val Ala Ser Ile Thr Trp Asp Gly Arg Thr Thr Tyr Tyr Ala
        195                 200                 205

Asp Ser Val Lys Gly Arg Phe Thr Ile Ser Arg Asp Asn Ala Lys Asn
    210                 215                 220

Thr Val Tyr Leu Gln Met Asn Ser Leu Lys Pro Glu Asp Thr Ala Val
225                 230                 235                 240

Tyr Val Cys Ala Asp Leu Gly Lys Trp Pro Ala Gly Pro Ala Asp Tyr
                245                 250                 255

Trp Gly Gln Gly Thr Gln Val Thr Val Ser Ser Thr Ser Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 292
<211> LENGTH: 502
<212> TYPE: PRT
<213> ORGANISM: Artificial Sequence
<220> FEATURE:
<223> OTHER INFORMATION: Multivalent anti-BCMA CAR

<400> SEQUENCE: 292

```
Met Ala Leu Pro Val Thr Ala Leu Leu Leu Pro Leu Ala Leu Leu Leu
```

```
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

Pro Asp Tyr Trp Gly Gln Gly Thr Gln Val Thr Val Ser Ser Gly Gly
    130                 135                 140

Gly Gly Ser Gly Gly Gly Gly Ser Gly Gly Gly Gly Ser Gln Val Gln
145                 150                 155                 160

Leu Val Glu Ser Gly Gly Gly Leu Val Gln Ala Gly Gly Ser Leu Arg
                165                 170                 175

Leu Ser Cys Ala Ala Ser Gly Gly Thr Leu Ser Lys Asn Thr Val Ala
            180                 185                 190

Trp Phe Arg Gln Ala Pro Gly Lys Glu Arg Gly Phe Val Ala Ser Ile
        195                 200                 205

Thr Trp Asp Gly Arg Thr Thr Tyr Tyr Ala Asp Ser Val Lys Gly Arg
    210                 215                 220

Phe Thr Ile Ser Arg Asp Asn Ala Lys Asn Thr Val Tyr Leu Gln Met
225                 230                 235                 240

Asn Ser Leu Lys Pro Glu Asp Thr Ala Val Tyr Val Cys Ala Asp Leu
                245                 250                 255

Gly Lys Trp Pro Ala Gly Pro Ala Asp Tyr Trp Gly Gln Gly Thr Gln
            260                 265                 270

Val Thr Val Ser Ser Thr Ser Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
            420                 425                 430
```

Pro Glu Met Gly Gly Lys Pro Arg Arg Lys Asn Pro Gln Glu Gly Leu
435 440 445

Tyr Asn Glu Leu Gln Lys Asp Lys Met Ala Glu Ala Tyr Ser Glu Ile
450 455 460

Gly Met Lys Gly Glu Arg Arg Arg Gly Lys Gly His Asp Gly Leu Tyr
465 470 475 480

Gln Gly Leu Ser Thr Ala Thr Lys Asp Thr Tyr Asp Ala Leu His Met
485 490 495

Gln Ala Leu Pro Pro Arg
500

<210> SEQ ID NO 293
<211> LENGTH: 512
<212> TYPE: PRT
<213> ORGANISM: Artificial Sequence
<220> FEATURE:
<223> OTHER INFORMATION: Multivalent anti-BCMA CAR

<400> SEQUENCE: 293

Met Ala Leu Pro Val Thr Ala Leu Leu Leu Pro Leu Ala Leu Leu Leu
1 5 10 15

His Ala Ala Arg Pro Gln Val Lys Leu Glu Glu Ser Gly Gly Gly Leu
20 25 30

Val Gln Ala Gly Gly Ser Leu Arg Leu Ser Cys Ala Ala Ser Gly Gly
35 40 45

Thr Leu Ser Lys Asn Thr Val Ala Trp Val Arg Gln Ala Pro Gly Lys
50 55 60

Glu Arg Gly Phe Val Thr Ser Ile Thr Cys Asp Gly Arg Thr Thr Tyr
65 70 75 80

Tyr Ala Asn Ser Val Asn Gly Arg Phe Pro Ile Asn Arg Asn Asn Ala
85 90 95

Glu Asn Leu Val Val Leu Gln Met Asn Ser Leu Lys Pro Asp Asp Thr
100 105 110

Ala Leu Tyr Tyr Cys Ala Ala Tyr Arg Lys Ser Ile Met Ser Ile Gln
115 120 125

Pro Asp Tyr Trp Gly Gln Gly Thr Gln Val Thr Val Ser Ser Gly Gly
130 135 140

Gly Gly Ser Gly Gly Gly Gly Ser Gly Gly Gly Gly Ser Gly Gly Gly
145 150 155 160

Gly Ser Gly Gly Gly Gly Ser Gln Val Gln Leu Val Glu Ser Gly Gly
165 170 175

Gly Leu Val Gln Ala Gly Gly Ser Leu Arg Leu Ser Cys Ala Ala Ser
180 185 190

Gly Gly Thr Leu Ser Lys Asn Thr Val Ala Trp Phe Arg Gln Ala Pro
195 200 205

Gly Lys Glu Arg Gly Phe Val Ala Ser Ile Thr Trp Asp Gly Arg Thr
210 215 220

Thr Tyr Tyr Ala Asp Ser Val Lys Gly Arg Phe Thr Ile Ser Arg Asp
225 230 235 240

Asn Ala Lys Asn Thr Val Tyr Leu Gln Met Asn Ser Leu Lys Pro Glu
245 250 255

Asp Thr Ala Val Tyr Val Cys Ala Asp Leu Gly Lys Trp Pro Ala Gly
260 265 270

Pro Ala Asp Tyr Trp Gly Gln Gly Thr Gln Val Thr Val Ser Ser Thr
275 280 285

```
Ser Thr Thr Thr Pro Ala Pro Arg Pro Pro Thr Pro Ala Pro Thr Ile
    290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Phe Ala Cys Asp Ile Tyr
                325                 330                 335

Ile Trp Ala Pro Leu Ala Gly Thr Cys Gly Val Leu Leu Leu Ser Leu
            340                 345                 350

Val Ile Thr Leu Tyr Cys Lys Arg Gly Arg Lys Lys Leu Leu Tyr Ile
        355                 360                 365

Phe Lys Gln Pro Phe Met Arg Pro Val Gln Thr Thr Gln Glu Glu Asp
    370                 375                 380

Gly Cys Ser Cys Arg Phe Pro Glu Glu Glu Glu Gly Gly Cys Glu Leu
385                 390                 395                 400

Arg Val Lys Phe Ser Arg Ser Ala Asp Ala Pro Ala Tyr Gln Gln Gly
                405                 410                 415

Gln Asn Gln Leu Tyr Asn Glu Leu Asn Leu Gly Arg Arg Glu Glu Tyr
            420                 425                 430

Asp Val Leu Asp Lys Arg Arg Gly Arg Asp Pro Glu Met Gly Gly Lys
        435                 440                 445

Pro Arg Arg Lys Asn Pro Gln Glu Gly Leu Tyr Asn Glu Leu Gln Lys
    450                 455                 460

Asp Lys Met Ala Glu Ala Tyr Ser Glu Ile Gly Met Lys Gly Glu Arg
465                 470                 475                 480

Arg Arg Gly Lys Gly His Asp Gly Leu Tyr Gln Gly Leu Ser Thr Ala
                485                 490                 495

Thr Lys Asp Thr Tyr Asp Ala Leu His Met Gln Ala Leu Pro Pro Arg
            500                 505                 510


<210> SEQ ID NO 294
<211> LENGTH: 497
<212> TYPE: PRT
<213> ORGANISM: Artificial Sequence
<220> FEATURE:
<223> OTHER INFORMATION: Multivalent anti-BCMA CAR

<400> SEQUENCE: 294

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

Pro Asp Tyr Trp Gly Gln Gly Thr Gln Val Thr Val Ser Ser Gly Gly
    130                 135                 140
```

Gly Gly Ser Gly Gly Gly Gly Ser Gln Val Gln Leu Val Glu Ser Gly
145 150 155 160

Gly Gly Leu Val Gln Ala Gly Gly Ser Leu Arg Leu Ser Cys Ala Ala
165 170 175

Ser Gly Gly Thr Leu Ser Lys Asn Thr Val Ala Trp Phe Arg Gln Ala
180 185 190

Pro Gly Lys Glu Arg Gly Phe Val Ala Ser Ile Thr Trp Asp Gly Arg
195 200 205

Thr Thr Tyr Tyr Ala Asp Ser Val Lys Gly Arg Phe Thr Ile Ser Arg
210 215 220

Asp Asn Ala Lys Asn Thr Val Tyr Leu Gln Met Asn Ser Leu Lys Pro
225 230 235 240

Glu Asp Thr Ala Val Tyr Val Cys Ala Asp Leu Gly Lys Trp Pro Ala
245 250 255

Gly Pro Ala Asp Tyr Trp Gly Gln Gly Thr Gln Val Thr Val Ser Ser
260 265 270

Thr Ser Thr Thr Thr Pro Ala Pro Arg Pro Pro Thr Pro Ala Pro Thr
275 280 285

Ile Ala Ser Gln Pro Leu Ser Leu Arg Pro Glu Ala Cys Arg Pro Ala
290 295 300

Ala Gly Gly Ala Val His Thr Arg Gly Leu Asp Phe Ala Cys Asp Ile
305 310 315 320

Tyr Ile Trp Ala Pro Leu Ala Gly Thr Cys Gly Val Leu Leu Leu Ser
325 330 335

Leu Val Ile Thr Leu Tyr Cys Lys Arg Gly Arg Lys Lys Leu Leu Tyr
340 345 350

Ile Phe Lys Gln Pro Phe Met Arg Pro Val Gln Thr Thr Gln Glu Glu
355 360 365

Asp Gly Cys Ser Cys Arg Phe Pro Glu Glu Glu Glu Gly Gly Cys Glu
370 375 380

Leu Arg Val Lys Phe Ser Arg Ser Ala Asp Ala Pro Ala Tyr Gln Gln
385 390 395 400

Gly Gln Asn Gln Leu Tyr Asn Glu Leu Asn Leu Gly Arg Arg Glu Glu
405 410 415

Tyr Asp Val Leu Asp Lys Arg Arg Gly Arg Asp Pro Glu Met Gly Gly
420 425 430

Lys Pro Arg Arg Lys Asn Pro Gln Glu Gly Leu Tyr Asn Glu Leu Gln
435 440 445

Lys Asp Lys Met Ala Glu Ala Tyr Ser Glu Ile Gly Met Lys Gly Glu
450 455 460

Arg Arg Arg Gly Lys Gly His Asp Gly Leu Tyr Gln Gly Leu Ser Thr
465 470 475 480

Ala Thr Lys Asp Thr Tyr Asp Ala Leu His Met Gln Ala Leu Pro Pro
485 490 495

Arg

<210> SEQ ID NO 295
<211> LENGTH: 502
<212> TYPE: PRT
<213> ORGANISM: Artificial Sequence
<220> FEATURE:
<223> OTHER INFORMATION: Multivalent anti-BCMA CAR

<400> SEQUENCE: 295

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

Pro Asp Tyr Trp Gly Gln Gly Thr Gln Val Thr Val Ser Ser Gly Gly
    130                 135                 140

Gly Gly Ser Gly Gly Gly Gly Ser Gly Gly Gly Gly Ser Gln Val Gln
145                 150                 155                 160

Leu Val Glu Ser Gly Gly Gly Leu Val Gln Ala Gly Gly Ser Leu Arg
                165                 170                 175

Leu Ser Cys Ala Ala Ser Gly Gly Thr Leu Ser Lys Asn Thr Val Ala
            180                 185                 190

Trp Phe Arg Gln Ala Pro Gly Lys Glu Arg Gly Phe Val Ala Ser Ile
        195                 200                 205

Thr Trp Asp Gly Arg Thr Thr Tyr Tyr Ala Asp Ser Val Lys Gly Arg
    210                 215                 220

Phe Thr Ile Ser Arg Asp Asn Ala Lys Asn Thr Val Tyr Leu Gln Met
225                 230                 235                 240

Asn Ser Leu Lys Pro Glu Asp Thr Ala Val Tyr Val Cys Ala Asp Leu
                245                 250                 255

Gly Lys Trp Pro Ala Gly Pro Ala Asp Tyr Trp Gly Gln Gly Thr Gln
            260                 265                 270

Val Thr Val Ser Ser Thr Ser Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
```

```
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
            500


<210> SEQ ID NO 296
<211> LENGTH: 507
<212> TYPE: PRT
<213> ORGANISM: Artificial Sequence
<220> FEATURE:
<223> OTHER INFORMATION: Multivalent anti-BCMA CAR

<400> SEQUENCE: 296

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

Pro Asp Tyr Trp Gly Gln Gly Thr Gln Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Val Glu Ser Gly Gly Gly Leu Val Gln Ala
                165                 170                 175

Gly Gly Ser Leu Arg Leu Ser Cys Ala Ala Ser Gly Gly Thr Leu Ser
            180                 185                 190

Lys Asn Thr Val Ala Trp Phe Arg Gln Ala Pro Gly Lys Glu Arg Gly
        195                 200                 205

Phe Val Ala Ser Ile Thr Trp Asp Gly Arg Thr Thr Tyr Tyr Ala Asp
    210                 215                 220

Ser Val Lys Gly Arg Phe Thr Ile Ser Arg Asp Asn Ala Lys Asn Thr
225                 230                 235                 240

Val Tyr Leu Gln Met Asn Ser Leu Lys Pro Glu Asp Thr Ala Val Tyr
                245                 250                 255

Val Cys Ala Asp Leu Gly Lys Trp Pro Ala Gly Pro Ala Asp Tyr Trp
            260                 265                 270

Gly Gln Gly Thr Gln Val Thr Val Ser Ser Thr Ser Thr Thr Thr Pro
```

```
        275                 280                 285

Ala Pro Arg Pro Pro Thr Pro Ala Pro Thr Ile Ala Ser Gln Pro Leu
    290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Leu Ser Leu Val Ile Thr Leu Tyr
            340                 345                 350

Cys Lys Arg Gly Arg Lys Lys Leu Leu Tyr Ile Phe Lys Gln Pro Phe
        355                 360                 365

Met Arg Pro Val Gln Thr Thr Gln Glu Glu Asp Gly Cys Ser Cys Arg
    370                 375                 380

Phe Pro Glu Glu Glu Glu Gly Gly Cys Glu Leu Arg Val Lys Phe Ser
385                 390                 395                 400

Arg Ser Ala Asp Ala Pro Ala Tyr Gln Gln Gly Gln Asn Gln Leu Tyr
                405                 410                 415

Asn Glu Leu Asn Leu Gly Arg Arg Glu Glu Tyr Asp Val Leu Asp Lys
            420                 425                 430

Arg Arg Gly Arg Asp Pro Glu Met Gly Gly Lys Pro Arg Arg Lys Asn
        435                 440                 445

Pro Gln Glu Gly Leu Tyr Asn Glu Leu Gln Lys Asp Lys Met Ala Glu
    450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
                485                 490                 495

Asp Ala Leu His Met Gln Ala Leu Pro Pro Arg
            500                 505


<210> SEQ ID NO 297
<211> LENGTH: 491
<212> TYPE: PRT
<213> ORGANISM: Artificial Sequence
<220> FEATURE:
<223> OTHER INFORMATION: Multivalent anti-BCMA CAR

<400> SEQUENCE: 297

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
        115                 120                 125

Asp Tyr Trp Gly Gln Gly Thr Gln Val Thr Val Ser Ser Gly Gly Gly
```

```
    130                 135                 140

Gly Ser Asp Val Gln Leu Val Glu Ser Gly Gly Gly Leu Val Gln Ala
145                 150                 155                 160

Gly Gly Ser Leu Arg Leu Ser Cys Ala Ala Ser Gly Gly Thr Leu Ser
                165                 170                 175

Lys Asn Thr Val Ala Trp Val Arg Gln Ala Pro Gly Lys Glu Arg Gly
            180                 185                 190

Phe Val Thr Ser Ile Thr Cys Asp Gly Arg Thr Thr Tyr Tyr Ala Asn
        195                 200                 205

Ser Val Lys Gly Arg Phe Pro Ile Ser Arg Asp Asn Ala Glu Asn Thr
    210                 215                 220

Val Tyr Leu Gln Met Asn Ser Leu Lys Pro Glu Asp Thr Ala Gly Tyr
225                 230                 235                 240

Val Cys Ala Asp Leu Gly Lys Trp Pro Ala Gly Ser Ala Asp Tyr Trp
                245                 250                 255

Gly Gln Gly Thr His Val Thr Val Ser Ser Thr Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 298
<211> LENGTH: 501
<212> TYPE: PRT
<213> ORGANISM: Artificial Sequence
<220> FEATURE:
<223> OTHER INFORMATION: Multivalent anti-BCMA CAR

<400> SEQUENCE: 298

Met Ala Leu Pro Val Thr Ala Leu Leu Leu Pro Leu Ala Leu Leu Leu
```

-continued

```
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
        115                 120                 125

Asp Tyr Trp Gly Gln Gly Thr Gln Val Thr Val Ser Ser Gly Gly Gly
    130                 135                 140

Gly Ser Gly Gly Gly Gly Ser Gly Gly Gly Gly Ser Asp Val Gln Leu
145                 150                 155                 160

Val Glu Ser Gly Gly Gly Leu Val Gln Ala Gly Gly Ser Leu Arg Leu
                165                 170                 175

Ser Cys Ala Ala Ser Gly Gly Thr Leu Ser Lys Asn Thr Val Ala Trp
            180                 185                 190

Val Arg Gln Ala Pro Gly Lys Glu Arg Gly Phe Val Thr Ser Ile Thr
        195                 200                 205

Cys Asp Gly Arg Thr Thr Tyr Tyr Ala Asn Ser Val Lys Gly Arg Phe
    210                 215                 220

Pro Ile Ser Arg Asp Asn Ala Glu Asn Thr Val Tyr Leu Gln Met Asn
225                 230                 235                 240

Ser Leu Lys Pro Glu Asp Thr Ala Gly Tyr Val Cys Ala Asp Leu Gly
                245                 250                 255

Lys Trp Pro Ala Gly Ser Ala Asp Tyr Trp Gly Gln Gly Thr His Val
            260                 265                 270

Thr Val Ser Ser Thr Ser Thr Thr Thr Pro Ala Pro Arg Pro Pro Thr
        275                 280                 285

Pro Ala Pro Thr Ile Ala Ser Gln Pro Leu Ser Leu Arg Pro Glu Ala
    290                 295                 300

Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
                325                 330                 335

Leu Leu Leu Ser Leu Val Ile Thr Leu Tyr Cys Lys Arg Gly Arg Lys
            340                 345                 350

Lys Leu Leu Tyr Ile Phe Lys Gln Pro Phe Met Arg Pro Val Gln Thr
        355                 360                 365

Thr Gln Glu Glu Asp Gly Cys Ser Cys Arg Phe Pro Glu Glu Glu Glu
    370                 375                 380

Gly Gly Cys Glu Leu Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
                405                 410                 415

Arg Arg Glu Glu Tyr Asp Val Leu Asp Lys Arg Arg Gly Arg Asp Pro
            420                 425                 430
```

Glu Met Gly Gly Lys Pro Arg Arg Lys Asn Pro Gln Glu Gly Leu Tyr
435 440 445

Asn Glu Leu Gln Lys Asp Lys Met Ala Glu Ala Tyr Ser Glu Ile Gly
450 455 460

Met Lys Gly Glu Arg Arg Arg Gly Lys Gly His Asp Gly Leu Tyr Gln
465 470 475 480

Gly Leu Ser Thr Ala Thr Lys Asp Thr Tyr Asp Ala Leu His Met Gln
485 490 495

Ala Leu Pro Pro Arg
500

<210> SEQ ID NO 299
<211> LENGTH: 511
<212> TYPE: PRT
<213> ORGANISM: Artificial Sequence
<220> FEATURE:
<223> OTHER INFORMATION: Multivalent anti-BCMA CAR

<400> SEQUENCE: 299

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Gly Leu
20 25 30

Val Gln Ala Gly Gly Ser Leu Arg Leu Ser Cys Ala Ala Ser Gly Gly
35 40 45

Thr Leu Ser Lys Asn Thr Val Ala Trp Phe Arg Gln Ala Pro Gly Lys
50 55 60

Glu Arg Gly Phe Val Ala Ser Ile Thr Trp Asp Gly Arg Thr Thr Tyr
65 70 75 80

Tyr Ala Asp Ser Val Lys Gly Arg Phe Thr Ile Ser Arg Asp Asn Ala
85 90 95

Lys Asn Thr Val Tyr Leu Gln Met Asn Ser Leu Lys Pro Glu Asp Thr
100 105 110

Ala Val Tyr Val Cys Ala Asp Leu Gly Lys Trp Pro Ala Gly Pro Ala
115 120 125

Asp Tyr Trp Gly Gln Gly Thr Gln Val Thr Val Ser Ser Gly Gly Gly
130 135 140

Gly Ser Gly Gly Gly Gly Ser Gly Gly Gly Gly Ser Gly Gly Gly Gly
145 150 155 160

Ser Gly Gly Gly Gly Ser Asp Val Gln Leu Val Glu Ser Gly Gly Gly
165 170 175

Leu Val Gln Ala Gly Gly Ser Leu Arg Leu Ser Cys Ala Ala Ser Gly
180 185 190

Gly Thr Leu Ser Lys Asn Thr Val Ala Trp Val Arg Gln Ala Pro Gly
195 200 205

Lys Glu Arg Gly Phe Val Thr Ser Ile Thr Cys Asp Gly Arg Thr Thr
210 215 220

Tyr Tyr Ala Asn Ser Val Lys Gly Arg Phe Pro Ile Ser Arg Asp Asn
225 230 235 240

Ala Glu Asn Thr Val Tyr Leu Gln Met Asn Ser Leu Lys Pro Glu Asp
245 250 255

Thr Ala Gly Tyr Val Cys Ala Asp Leu Gly Lys Trp Pro Ala Gly Ser
260 265 270

Ala Asp Tyr Trp Gly Gln Gly Thr His Val Thr Val Ser Ser Thr Ser
275 280 285

Thr Thr Thr Pro Ala Pro Arg Pro Pro Thr Pro Ala Pro Thr Ile Ala
290 295 300

Ser Gln Pro Leu Ser Leu Arg Pro Glu Ala Cys Arg Pro Ala Ala Gly
305 310 315 320

Gly Ala Val His Thr Arg Gly Leu Asp Phe Ala Cys Asp Ile Tyr Ile
325 330 335

Trp Ala Pro Leu Ala Gly Thr Cys Gly Val Leu Leu Leu Ser Leu Val
340 345 350

Ile Thr Leu Tyr Cys Lys Arg Gly Arg Lys Lys Leu Leu Tyr Ile Phe
355 360 365

Lys Gln Pro Phe Met Arg Pro Val Gln Thr Thr Gln Glu Glu Asp Gly
370 375 380

Cys Ser Cys Arg Phe Pro Glu Glu Glu Glu Gly Gly Cys Glu Leu Arg
385 390 395 400

Val Lys Phe Ser Arg Ser Ala Asp Ala Pro Ala Tyr Gln Gln Gly Gln
405 410 415

Asn Gln Leu Tyr Asn Glu Leu Asn Leu Gly Arg Arg Glu Glu Tyr Asp
420 425 430

Val Leu Asp Lys Arg Arg Gly Arg Asp Pro Glu Met Gly Gly Lys Pro
435 440 445

Arg Arg Lys Asn Pro Gln Glu Gly Leu Tyr Asn Glu Leu Gln Lys Asp
450 455 460

Lys Met Ala Glu Ala Tyr Ser Glu Ile Gly Met Lys Gly Glu Arg Arg
465 470 475 480

Arg Gly Lys Gly His Asp Gly Leu Tyr Gln Gly Leu Ser Thr Ala Thr
485 490 495

Lys Asp Thr Tyr Asp Ala Leu His Met Gln Ala Leu Pro Pro Arg
500 505 510

<210> SEQ ID NO 300
<211> LENGTH: 496
<212> TYPE: PRT
<213> ORGANISM: Artificial Sequence
<220> FEATURE:
<223> OTHER INFORMATION: Multivalent anti-BCMA CAR

<400> SEQUENCE: 300

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Gly Leu
20 25 30

Val Gln Ala Gly Gly Ser Leu Arg Leu Ser Cys Ala Ala Ser Gly Gly
35 40 45

Thr Leu Ser Lys Asn Thr Val Ala Trp Phe Arg Gln Ala Pro Gly Lys
50 55 60

Glu Arg Gly Phe Val Ala Ser Ile Thr Trp Asp Gly Arg Thr Thr Tyr
65 70 75 80

Tyr Ala Asp Ser Val Lys Gly Arg Phe Thr Ile Ser Arg Asp Asn Ala
85 90 95

Lys Asn Thr Val Tyr Leu Gln Met Asn Ser Leu Lys Pro Glu Asp Thr
100 105 110

Ala Val Tyr Val Cys Ala Asp Leu Gly Lys Trp Pro Ala Gly Pro Ala
115 120 125

Asp Tyr Trp Gly Gln Gly Thr Gln Val Thr Val Ser Ser Gly Gly Gly
130 135 140

Gly Ser Gly Gly Gly Gly Ser Asp Val Gln Leu Val Glu Ser Gly Gly
145 150 155 160

Gly Leu Val Gln Ala Gly Gly Ser Leu Arg Leu Ser Cys Ala Ala Ser
165 170 175

Gly Gly Thr Leu Ser Lys Asn Thr Val Ala Trp Val Arg Gln Ala Pro
180 185 190

Gly Lys Glu Arg Gly Phe Val Thr Ser Ile Thr Cys Asp Gly Arg Thr
195 200 205

Thr Tyr Tyr Ala Asn Ser Val Lys Gly Arg Phe Pro Ile Ser Arg Asp
210 215 220

Asn Ala Glu Asn Thr Val Tyr Leu Gln Met Asn Ser Leu Lys Pro Glu
225 230 235 240

Asp Thr Ala Gly Tyr Val Cys Ala Asp Leu Gly Lys Trp Pro Ala Gly
245 250 255

Ser Ala Asp Tyr Trp Gly Gln Gly Thr His Val Thr Val Ser Ser Thr
260 265 270

Ser Thr Thr Thr Pro Ala Pro Arg Pro Pro Thr Pro Ala Pro Thr Ile
275 280 285

Ala Ser Gln Pro Leu Ser Leu Arg Pro Glu Ala Cys Arg Pro Ala Ala
290 295 300

Gly Gly Ala Val His Thr Arg Gly Leu Asp Phe Ala Cys Asp Ile Tyr
305 310 315 320

Ile Trp Ala Pro Leu Ala Gly Thr Cys Gly Val Leu Leu Leu Ser Leu
325 330 335

Val Ile Thr Leu Tyr Cys Lys Arg Gly Arg Lys Lys Leu Leu Tyr Ile
340 345 350

Phe Lys Gln Pro Phe Met Arg Pro Val Gln Thr Thr Gln Glu Glu Asp
355 360 365

Gly Cys Ser Cys Arg Phe Pro Glu Glu Glu Glu Gly Gly Cys Glu Leu
370 375 380

Arg Val Lys Phe Ser Arg Ser Ala Asp Ala Pro Ala Tyr Gln Gln Gly
385 390 395 400

Gln Asn Gln Leu Tyr Asn Glu Leu Asn Leu Gly Arg Arg Glu Glu Tyr
405 410 415

Asp Val Leu Asp Lys Arg Arg Gly Arg Asp Pro Glu Met Gly Gly Lys
420 425 430

Pro Arg Arg Lys Asn Pro Gln Glu Gly Leu Tyr Asn Glu Leu Gln Lys
435 440 445

Asp Lys Met Ala Glu Ala Tyr Ser Glu Ile Gly Met Lys Gly Glu Arg
450 455 460

Arg Arg Gly Lys Gly His Asp Gly Leu Tyr Gln Gly Leu Ser Thr Ala
465 470 475 480

Thr Lys Asp Thr Tyr Asp Ala Leu His Met Gln Ala Leu Pro Pro Arg
485 490 495

<210> SEQ ID NO 301
<211> LENGTH: 501
<212> TYPE: PRT
<213> ORGANISM: Artificial Sequence
<220> FEATURE:
<223> OTHER INFORMATION: Multivalent anti-BCMA CAR

<400> SEQUENCE: 301

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Gly Leu
20 25 30

Val Gln Ala Gly Gly Ser Leu Arg Leu Ser Cys Ala Ala Ser Gly Gly
35 40 45

Thr Leu Ser Lys Asn Thr Val Ala Trp Phe Arg Gln Ala Pro Gly Lys
50 55 60

Glu Arg Gly Phe Val Ala Ser Ile Thr Trp Asp Gly Arg Thr Thr Tyr
65 70 75 80

Tyr Ala Asp Ser Val Lys Gly Arg Phe Thr Ile Ser Arg Asp Asn Ala
85 90 95

Lys Asn Thr Val Tyr Leu Gln Met Asn Ser Leu Lys Pro Glu Asp Thr
100 105 110

Ala Val Tyr Val Cys Ala Asp Leu Gly Lys Trp Pro Ala Gly Pro Ala
115 120 125

Asp Tyr Trp Gly Gln Gly Thr Gln Val Thr Val Ser Ser Gly Gly Gly
130 135 140

Gly Ser Gly Gly Gly Gly Ser Gly Gly Gly Gly Ser Asp Val Gln Leu
145 150 155 160

Val Glu Ser Gly Gly Gly Leu Val Gln Ala Gly Gly Ser Leu Arg Leu
165 170 175

Ser Cys Ala Ala Ser Gly Gly Thr Leu Ser Lys Asn Thr Val Ala Trp
180 185 190

Val Arg Gln Ala Pro Gly Lys Glu Arg Gly Phe Val Thr Ser Ile Thr
195 200 205

Cys Asp Gly Arg Thr Thr Tyr Tyr Ala Asn Ser Val Lys Gly Arg Phe
210 215 220

Pro Ile Ser Arg Asp Asn Ala Glu Asn Thr Val Tyr Leu Gln Met Asn
225 230 235 240

Ser Leu Lys Pro Glu Asp Thr Ala Gly Tyr Val Cys Ala Asp Leu Gly
245 250 255

Lys Trp Pro Ala Gly Ser Ala Asp Tyr Trp Gly Gln Gly Thr His Val
260 265 270

Thr Val Ser Ser Thr Ser Thr Thr Thr Pro Ala Pro Arg Pro Pro Thr
275 280 285

Pro Ala Pro Thr Ile Ala Ser Gln Pro Leu Ser Leu Arg Pro Glu Ala
290 295 300

Cys Arg Pro Ala Ala Gly Gly Ala Val His Thr Arg Gly Leu Asp Phe
305 310 315 320

Ala Cys Asp Ile Tyr Ile Trp Ala Pro Leu Ala Gly Thr Cys Gly Val
325 330 335

Leu Leu Leu Ser Leu Val Ile Thr Leu Tyr Cys Lys Arg Gly Arg Lys
340 345 350

Lys Leu Leu Tyr Ile Phe Lys Gln Pro Phe Met Arg Pro Val Gln Thr
355 360 365

Thr Gln Glu Glu Asp Gly Cys Ser Cys Arg Phe Pro Glu Glu Glu Glu
370 375 380

Gly Gly Cys Glu Leu Arg Val Lys Phe Ser Arg Ser Ala Asp Ala Pro
385 390 395 400

Ala Tyr Gln Gln Gly Gln Asn Gln Leu Tyr Asn Glu Leu Asn Leu Gly
405 410 415

Arg Arg Glu Glu Tyr Asp Val Leu Asp Lys Arg Arg Gly Arg Asp Pro
420 425 430

Glu Met Gly Gly Lys Pro Arg Arg Lys Asn Pro Gln Glu Gly Leu Tyr
        435                 440                 445

Asn Glu Leu Gln Lys Asp Lys Met Ala Glu Ala Tyr Ser Glu Ile Gly
    450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
            500

<210> SEQ ID NO 302
<211> LENGTH: 506
<212> TYPE: PRT
<213> ORGANISM: Artificial Sequence
<220> FEATURE:
<223> OTHER INFORMATION: Multivalent anti-BCMA CAR

<400> SEQUENCE: 302

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
        115                 120                 125

Asp Tyr Trp Gly Gln Gly Thr Gln Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Val Gln Leu Val Glu Ser Gly Gly Gly Leu Val Gln Ala Gly
                165                 170                 175

Gly Ser Leu Arg Leu Ser Cys Ala Ala Ser Gly Gly Thr Leu Ser Lys
            180                 185                 190

Asn Thr Val Ala Trp Val Arg Gln Ala Pro Gly Lys Glu Arg Gly Phe
        195                 200                 205

Val Thr Ser Ile Thr Cys Asp Gly Arg Thr Thr Tyr Tyr Ala Asn Ser
    210                 215                 220

Val Lys Gly Arg Phe Pro Ile Ser Arg Asp Asn Ala Glu Asn Thr Val
225                 230                 235                 240

Tyr Leu Gln Met Asn Ser Leu Lys Pro Glu Asp Thr Ala Gly Tyr Val
                245                 250                 255

Cys Ala Asp Leu Gly Lys Trp Pro Ala Gly Ser Ala Asp Tyr Trp Gly
            260                 265                 270

Gln Gly Thr His Val Thr Val Ser Ser Thr Ser Thr Thr Pro Ala
        275                 280                 285

Pro Arg Pro Pro Thr Pro Ala Pro Thr Ile Ala Ser Gln Pro Leu Ser
290 295 300

Leu Arg Pro Glu Ala Cys Arg Pro Ala Ala Gly Gly Ala Val His Thr
305 310 315 320

Arg Gly Leu Asp Phe Ala Cys Asp Ile Tyr Ile Trp Ala Pro Leu Ala
325 330 335

Gly Thr Cys Gly Val Leu Leu Leu Ser Leu Val Ile Thr Leu Tyr Cys
340 345 350

Lys Arg Gly Arg Lys Lys Leu Leu Tyr Ile Phe Lys Gln Pro Phe Met
355 360 365

Arg Pro Val Gln Thr Thr Gln Glu Glu Asp Gly Cys Ser Cys Arg Phe
370 375 380

Pro Glu Glu Glu Glu Gly Gly Cys Glu Leu Arg Val Lys Phe Ser Arg
385 390 395 400

Ser Ala Asp Ala Pro Ala Tyr Gln Gln Gly Gln Asn Gln Leu Tyr Asn
405 410 415

Glu Leu Asn Leu Gly Arg Arg Glu Glu Tyr Asp Val Leu Asp Lys Arg
420 425 430

Arg Gly Arg Asp Pro Glu Met Gly Gly Lys Pro Arg Arg Lys Asn Pro
435 440 445

Gln Glu Gly Leu Tyr Asn Glu Leu Gln Lys Asp Lys Met Ala Glu Ala
450 455 460

Tyr Ser Glu Ile Gly Met Lys Gly Glu Arg Arg Arg Gly Lys Gly His
465 470 475 480

Asp Gly Leu Tyr Gln Gly Leu Ser Thr Ala Thr Lys Asp Thr Tyr Asp
485 490 495

Ala Leu His Met Gln Ala Leu Pro Pro Arg
500 505

<210> SEQ ID NO 303
<211> LENGTH: 10
<212> TYPE: PRT
<213> ORGANISM: Artificial Sequence
<220> FEATURE:
<223> OTHER INFORMATION: BCMA epitope

<400> SEQUENCE: 303

Met Leu Gln Met Ala Gly Gln Cys Ser Gln
1 5 10

<210> SEQ ID NO 304
<211> LENGTH: 14
<212> TYPE: PRT
<213> ORGANISM: Artificial Sequence
<220> FEATURE:
<223> OTHER INFORMATION: BCMA epitope

<400> SEQUENCE: 304

Cys Ser Gln Asn Glu Tyr Phe Asp Ser Leu Leu His Ala Cys
1 5 10

<210> SEQ ID NO 305
<211> LENGTH: 13
<212> TYPE: PRT
<213> ORGANISM: Artificial Sequence
<220> FEATURE:
<223> OTHER INFORMATION: BCMA epitope

<400> SEQUENCE: 305

Asn Glu Tyr Phe Asp Ser Leu Leu His Ala Cys Ile Pro 1 5 10

<210> SEQ ID NO 306
<211> LENGTH: 11
<212> TYPE: PRT
<213> ORGANISM: Artificial Sequence
<220> FEATURE:
<223> OTHER INFORMATION: BCMA epitope

<400> SEQUENCE: 306

Ala Cys Ile Pro Cys Gln Leu Arg Cys Ser Ser
1 5 10

<210> SEQ ID NO 307
<211> LENGTH: 19
<212> TYPE: PRT
<213> ORGANISM: Artificial Sequence
<220> FEATURE:
<223> OTHER INFORMATION: BCMA epitope

<400> SEQUENCE: 307

Cys Gln Leu Arg Cys Ser Ser Asn Thr Pro Pro Leu Thr Cys Gln Arg
1 5 10 15

Tyr Cys Asn

<210> SEQ ID NO 308
<211> LENGTH: 10
<212> TYPE: PRT
<213> ORGANISM: Artificial Sequence
<220> FEATURE:
<223> OTHER INFORMATION: BCMA epitope

<400> SEQUENCE: 308

Leu Thr Cys Gln Arg Tyr Cys Asn Ala Ser
1 5 10

<210> SEQ ID NO 309
<211> LENGTH: 12
<212> TYPE: PRT
<213> ORGANISM: Artificial Sequence
<220> FEATURE:
<223> OTHER INFORMATION: BCMA epitope

<400> SEQUENCE: 309

Ala Ser Val Thr Asn Ser Val Lys Gly Thr Asn Ala
1 5 10

<210> SEQ ID NO 310
<211> LENGTH: 334
<212> TYPE: PRT
<213> ORGANISM: Artificial Sequence
<220> FEATURE:
<223> OTHER INFORMATION: Anti-BCMA Centyrin CAR

<400> SEQUENCE: 310

Met Ala Leu Pro Val Thr Ala Leu Leu Leu Pro Leu Ala Leu Leu Leu
1 5 10 15

His Ala Ala Arg Pro Met Leu Pro Ala Pro Lys Asn Leu Val Val Ser
20 25 30

Arg Ile Thr Glu Asp Ser Ala Arg Leu Ser Trp Thr Ala Pro Asp Ala
35 40 45

Ala Phe Asp Ser Phe Pro Ile Arg Tyr Ile Glu Thr Leu Ile Trp Gly
50 55 60

Glu Ala Ile Trp Leu Asp Val Pro Gly Ser Glu Arg Ser Tyr Asp Leu

```
65                  70                  75                  80

Thr Gly Leu Lys Pro Gly Thr Glu Tyr Ala Val Val Ile Thr Gly Val
                85                  90                  95

Lys Gly Gly Arg Phe Ser Ser Pro Leu Val Ala Ser Phe Thr Thr Thr
            100                 105                 110

Thr Thr Pro Ala Pro Arg Pro Pro Thr Pro Ala Pro Thr Ile Ala Ser
        115                 120                 125

Gln Pro Leu Ser Leu Arg Pro Glu Ala Cys Arg Pro Ala Ala Gly Gly
    130                 135                 140

Ala Val His Thr Arg Gly Leu Asp Phe Ala Cys Asp Ile Tyr Ile Trp
145                 150                 155                 160

Ala Pro Leu Ala Gly Thr Cys Gly Val Leu Leu Leu Ser Leu Val Ile
                165                 170                 175

Thr Leu Tyr Cys Lys Arg Gly Arg Lys Lys Leu Leu Tyr Ile Phe Lys
            180                 185                 190

Gln Pro Phe Met Arg Pro Val Gln Thr Thr Gln Glu Glu Asp Gly Cys
        195                 200                 205

Ser Cys Arg Phe Pro Glu Glu Glu Glu Gly Gly Cys Glu Leu Arg Val
    210                 215                 220

Lys Phe Ser Arg Ser Ala Asp Ala Pro Ala Tyr Lys Gln Gly Gln Asn
225                 230                 235                 240

Gln Leu Tyr Asn Glu Leu Asn Leu Gly Arg Arg Glu Glu Tyr Asp Val
                245                 250                 255

Leu Asp Lys Arg Arg Gly Arg Asp Pro Glu Met Gly Gly Lys Pro Arg
            260                 265                 270

Arg Lys Asn Pro Gln Glu Gly Leu Tyr Asn Glu Leu Gln Lys Asp Lys
        275                 280                 285

Met Ala Glu Ala Tyr Ser Glu Ile Gly Met Lys Gly Glu Arg Arg Arg
    290                 295                 300

Gly Lys Gly His Asp Gly Leu Tyr Gln Gly Leu Ser Thr Ala Thr Lys
305                 310                 315                 320

Asp Thr Tyr Asp Ala Leu His Met Gln Ala Leu Pro Pro Arg
                325                 330


<210> SEQ ID NO 311
<211> LENGTH: 21
<212> TYPE: PRT
<213> ORGANISM: Artificial Sequence
<220> FEATURE:
<223> OTHER INFORMATION: Signal sequence

<400> SEQUENCE: 311

Met Ala Leu Pro Val Thr Ala Leu Leu Leu Pro Leu Ala Leu Leu Leu
1               5                   10                  15

His Ala Ala Arg Pro
            20


<210> SEQ ID NO 312
<211> LENGTH: 472
<212> TYPE: PRT
<213> ORGANISM: Artificial Sequence
<220> FEATURE:
<223> OTHER INFORMATION: Anti-BCMA CAR

<400> SEQUENCE: 312

Asp Ile Val Leu Thr Gln Ser Pro Pro Ser Leu Ala Met Ser Leu Gly
1               5                   10                  15
```

```
Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Glu Thr Val Lys Ile Ser Cys Lys Ala Ser Gly Tyr Thr Phe Thr Asp
145                 150                 155                 160

Tyr Ser Ile Asn Trp Val Lys Arg Ala Pro Gly Lys Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Glu Thr Ser Ala Ser Thr Ala
        195                 200                 205

Tyr Leu Gln Ile Asn Asn Leu Lys Tyr Glu Asp Thr Ala Thr Tyr Phe
    210                 215                 220

Cys Ala Leu Asp Tyr Ser Tyr Ala Met Asp Tyr Trp Gly Gln Gly Thr
225                 230                 235                 240

Ser Val Thr Val Ser Ser Ala Ala Ala Thr Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Ile Tyr Ile Trp Ala Pro Leu Ala Gly Thr
    290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
```

-continued

```
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470
```

METHODS OF REDUCING THE SEVERITY OF TOXICITY IN BCMA CAR-T TREATMENTS

CROSS REFERENCE TO RELATED APPLICATIONS

This application is a national stage application under 35 U.S.C. § 371 of International Application No. PCT/US2021/026702, filed internationally on Apr. 9, 2021 which claims priority to U.S. provisional application No. 63/008,564, filed Apr. 10, 2020, entitled "METHODS AND USES RELATED TO CELL THERAPY ENGINEERED WITH A CHIMERIC ANTIGEN RECEPTOR TARGETING B-CELL MATURATION ANTIGEN," the contents of which are incorporated by reference in their entirety for all purposes.

INCORPORATION BY REFERENCE OF SEQUENCE LISTING

The present application is being filed along with a Sequence Listing in electronic format. The Sequence Listing is provided as a file entitled 735042023640SeqList.Txt, created Apr. 8, 2021, which is 345,310 bytes in size. The information in the electronic format of the Sequence Listing is incorporated by reference in its entirety.

FIELD

The present disclosure relates in some aspects to methods and uses related to adoptive cell therapy involving the administration of doses of cells, such as T cells, for treating disease and conditions, including certain plasma cell malignancies. The cells express recombinant receptors such as chimeric antigen receptors (CARs) specific to B-cell maturation antigen (BCMA). In some embodiments, the methods are for treating subjects with multiple myeloma (MM).

BACKGROUND

B-cell maturation antigen (BCMA) is a transmembrane type III protein expressed on mature B lymphocytes. Following the binding of BCMA to one of its ligands, B cell activator of the TNF family (BAFF) or a proliferation inducing ligand (APRIL), a pro-survival cell signal is delivered to the B cell, which has been found to be required for plasma cell survival. The expression of BCMA has been linked to several diseases including cancer, autoimmune disorders and infectious diseases. Various BCMA-directed therapies, including BCMA-binding chimeric antigen receptors (CARs), and cells expressing such CARs, are available. However, there remains a need for improved methods for treating diseases and conditions associated with BCMA, including adoptive cell therapy methods involving engineered anti-BCMA CAR expressing cells. Provided herein are embodiments that meet such needs.

SUMMARY

Provided herein are methods and uses for treating a subject having or suspected of having a disease or disorder associated with B-cell maturation antigen (BCMA) expression. Also provided are methods and uses for reducing the severity of, attenuating, and/or preventing the onset of a toxicity in a subject having or suspected of having a disease or disorder associated with B-cell maturation antigen (BCMA) expression to be treated with a cell therapy.

Provided herein are methods and uses for treating a subject having or suspected of having a disease or disorder associated with B-cell maturation antigen (BCMA) expression that involves administering to the subject a dose of an interleukin-1 receptor antagonist (IL-1Ra) and a cell therapy that includes a dose of engineered T cells that express a first chimeric antigen receptor (CAR) specific for BCMA, wherein at least one dose of the IL-1Ra is administered prior to the dose of engineered T cells.

Provided herein are methods and uses for treating a subject having or suspected of having a disease or disorder associated with B-cell maturation antigen (BCMA) expression that involves administering a cell therapy that includes a dose of engineered T cells that express a first chimeric antigen receptor (CAR) specific for BCMA to a subject that has been administered at least one dose of an interleukin-1 receptor antagonist (IL-1Ra).

Provided herein are methods and uses for treating a subject having or suspected of having a disease or disorder associated with B-cell maturation antigen (BCMA) expression, involving administering at least one dose of an interleukin-1 receptor antagonist (IL-1Ra) to a subject who is a candidate for a cell therapy that includes a dose of engineered T cells that express a first chimeric antigen receptor (CAR) specific for BCMA.

Provided herein are methods and uses for reducing the severity of, attenuating, and/or preventing the onset of a toxicity in a subject having or suspected of having a disease or disorder associated with B-cell maturation antigen (BCMA) expression to be treated with a cell therapy that involves administering to the subject a dose of an interleukin-1 receptor antagonist (IL-1Ra) and a cell therapy that includes a dose of engineered T cells that express a first chimeric antigen receptor (CAR) specific for BCMA, wherein at least one dose of the IL-1Ra is administered prior to the dose of engineered T cells.

Provided herein are methods and uses for reducing the severity of, attenuating, and/or preventing the onset of a toxicity in a subject having or suspected of having a disease or disorder associated with B-cell maturation antigen (BCMA) expression to be treated with a cell therapy that involves administering a cell therapy that includes a dose of engineered T cells that express a first chimeric antigen receptor (CAR) specific for BCMA to a subject that has been administered at least one dose of an interleukin-1 receptor antagonist (IL-1Ra).

Provided herein are methods and uses for reducing the severity of, attenuating, and/or preventing the onset of a toxicity in a subject having or suspected of having a disease or disorder associated with B-cell maturation antigen (BCMA) expression to be treated with a cell therapy, including administering at least one dose of an interleukin-1 receptor antagonist (IL-1Ra) to a subject who is a candidate for a cell therapy including a dose of engineered T cells that express a first chimeric antigen receptor (CAR) specific for BCMA.

In some of any of the provided embodiments, the subject has been administered the at least one dose of the IL-1Ra within at or about 24 hours prior to the dose of engineered T cells.

In some of any of the provided embodiments, the at least one dose of the IL-1Ra includes at least two dose of the IL-1Ra.

Provided herein are methods and uses for treating a subject having or suspected of having a disease or disorder associated with B-cell maturation antigen (BCMA) expression that involves administering to the subject at least two doses of an interleukin-1 receptor antagonist (IL-1Ra) and a cell therapy that includes a dose of engineered T cells that express a first chimeric antigen receptor (CAR) specific for BCMA, wherein at least one dose of the IL-1Ra is administered within at or about 24 hours prior to the administration of the dose of engineered T cells; and at least one dose of the IL-1Ra is administered after the administration of the dose of engineered T cells.

Provided herein are methods and uses for treating a subject having or suspected of having a disease or disorder associated with B-cell maturation antigen (BCMA) expression, including administering to the subject at least two doses of an interleukin-1 receptor antagonist (IL-1Ra), wherein at least one dose of the IL-1Ra is administered within about or about 24 hours prior to administration of a cell therapy including a dose of engineered T cells that express a first chimeric antigen receptor (CAR) specific for BCMA to the subject; and at least one dose of the IL-1Ra is administered after the administration of the dose of engineered T cells.

Provided herein are methods and uses for treating a subject having or suspected of having a disease or disorder associated with B-cell maturation antigen (BCMA) expression, including administering to the subject a cell therapy including a dose of engineered T cells that express a first chimeric antigen receptor (CAR) specific for BCMA, wherein the subject has been administered at least one dose of an interleukin-1 receptor antagonist (IL-1Ra) within about or about 24 hours prior to administration of the dose of engineered T cells; and the subject is to be administered at least one dose of the IL-1Ra after the administration of the dose of engineered T cells.

Provided herein are methods and uses for treating a subject having or suspected of having a disease or disorder associated with B-cell maturation antigen (BCMA) expression that involves administering a cell therapy that includes a dose of engineered T cells that express a first chimeric antigen receptor (CAR) specific for BCMA to a subject that has been administered at least one dose of an interleukin-1 receptor antagonist (IL-1Ra) within at or about 24 hour prior to the administration of the dose of engineered T cells; and administering at least one dose of the IL-1Ra after the administration of the dose of engineered T cells.

Provided herein are methods and uses for reducing the severity of, attenuating, and/or preventing the onset of a toxicity in a subject having or suspected of having a disease or disorder associated with B-cell maturation antigen (BCMA) expression to be treated with a cell therapy that involves administering to the subject at least two doses of an interleukin-1 receptor antagonist (IL-1Ra) and a cell therapy that includes a dose of engineered T cells that express a first chimeric antigen receptor (CAR) specific for BCMA, wherein at least one dose of the IL-1Ra is administered within at or about 24 hours prior to the administration of the dose of engineered T cells; and at least one dose of the IL-1Ra is administered after the administration of the dose of engineered T cells.

Provided herein are methods and uses for reducing the severity of, attenuating, and/or preventing the onset of a toxicity in a subject having or suspected of having a disease or disorder associated with B-cell maturation antigen (BCMA) expression to be treated with a cell therapy that involves administering a cell therapy that includes a dose of engineered T cells that express a first chimeric antigen receptor (CAR) specific for BCMA to a subject that has been administered at least one dose of an interleukin-1 receptor antagonist (IL-1Ra) within at or about 24 hour prior to the administration of the dose of engineered T cells; and administering at least one dose of the IL-1Ra is administered after the administration of the dose of engineered T cells.

In some of any of the provided embodiments, the at least one dose of IL-1Ra administered prior to the dose of engineered T cells is administered within at or about 21, 18, 15 or 12 hours prior to administration of the dose of engineered T cells. In some of any of the provided embodiments, the at least one dose of IL-1Ra administered prior to the dose of engineered T cells is administered within at or about 21 hours prior to administration of the dose of engineered T cells. In some of any of the provided embodiments, the at least one dose of IL-1Ra administered prior to the dose of engineered T cells is administered within at or about 18 hours prior to administration of the dose of engineered T cells. In some of any of the provided embodiments, the at least one dose of IL-1Ra administered prior to the dose of engineered T cells is administered within at or about 15 hours prior to administration of the dose of engineered T cells. In some of any of the provided embodiments, the at least one dose of IL-1Ra administered prior to the dose of engineered T cells is administered within at or about 12 hours prior to administration of the dose of engineered T cells.

In some of any of the provided embodiments, the at least one dose of the IL-Ra administered prior to the dose of engineered cells includes at least two doses of the IL-1Ra administered prior to the administration of the dose of engineered T cells.

In some of any of the provided embodiments, one dose of the at least two doses of IL-1Ra is administered prior to the dose of engineered T cells. In some of any of the provided embodiments, one dose of the at least two doses of IL-1Ra is administered is administered within at or about 6, 5, 4, 3 or 2 hours prior to administration of the dose of engineered T cells. In some embodiments, one dose of the at least two doses of IL-1RA2 is administered at or about 6 hours prior to administration of the dose of engineered T cells. In some embodiments, one dose of the at least two doses of IL-1RA2 is administered at or about 5 hours prior to administration of the dose of engineered T cells. In some embodiments, one dose of the at least two doses of IL-1RA2 is administered at or about 4 hours prior to administration of the dose of engineered T cells. In some of any of the provided embodiments, one dose of the at least two doses of IL-1Ra is administered within at or about 3 hours prior to administration of the dose of engineered T cells. In some embodiments, one dose of the at least two doses of IL-1RA2 is administered at or about 2 hours prior to administration of the dose of engineered T cells. In some of any of the provided embodiments, one dose of the at least two doses of IL-1Ra is administered within at or about 24 hours prior to, and one dose of the at least two doses of IL-1Ra is administered within at or about 3 hours prior to, administration of the dose of engineered T cells.

In some of any of the provided embodiments, the methods and uses also involve administering at least one dose of the IL-1Ra after administering the dose of engineered T cells. In some of any of the provided embodiments, the at least one dose of the IL-1Ra administered after the dose of engineered cells includes at least 2, 3, 4, 5, 6, 7 or 8 doses of the IL-1Ra administered after administering the dose of engineered T cells. In some of any of the provided embodiments, the at least one dose of the IL-1Ra administered after the dose of engineered cells includes at least 2 doses of the IL-1Ra administered after administering the dose of engineered T cells. In some of any of the provided embodiments, the at least one dose of the IL-1Ra administered after the dose of engineered cells includes 3, 4, 5, 6 or 7 doses of IL-1Ra administered after the administration of the dose of engineered T cells. In some of any of the provided embodiments, the at least one dose of the IL-1Ra administered after the dose of engineered cells includes at least 3 doses of the IL-1Ra administered after administering the dose of engineered T cells. In some of any of the provided embodiments, the at least one dose of the IL-1Ra administered after the dose of engineered cells includes at least 4 doses of the IL-1Ra administered after administering the dose of engineered T cells. In some of any of the provided embodiments, the at least one dose of the IL-1Ra administered after the dose of engineered cells includes 5 doses of IL-1Ra administered after the administration of the dose of engineered T cells. In some of any of the provided embodiments, the at least one dose of the IL-1Ra administered after the dose of engineered cells includes at least 6 doses of the IL-1Ra administered after administering the dose of engineered T cells. In some of any of the provided embodiments, the at least one dose of the IL-1Ra administered after the dose of engineered cells includes at least 7 doses of the IL-1Ra administered after administering the dose of engineered T cells. In some of any of the provided embodiments, the at least one dose of the IL-1Ra administered after the dose of engineered cells includes at least 8 doses of the IL-1Ra administered after administering the dose of engineered T cells.

In some of any of the provided embodiments, the at least one dose of the IL-1Ra administered after the dose of engineered cells is administered daily for consecutive days. In some of any of the provided embodiments, the at least one dose of IL-1Ra administered after the administration of the dose of engineered T cells is 4 doses, wherein one of the four doses is administered each day for 4 consecutive days after the administration of the dose of engineered T cells. In some of any of the provided embodiments, the at least one dose of IL-1Ra administered after the administration of the dose of engineered T cells is 5 doses administered daily for 5 consecutive days after the administration of the dose of engineered T cells. In some embodiments, a dose of the IL-1Ra is administered every 24 hours (q24 h) on Days 2-5.

Provided herein are methods and uses for reducing the severity of, attenuating, and/or preventing the onset of a toxicity in a subject having or suspected of having a disease or disorder associated with B-cell maturation antigen (BCMA) expression to be treated with a cell therapy, involving administering to the subject at least 6 doses of an interleukin-1 receptor antagonist (IL-1Ra) and a cell therapy including a dose of engineered T cells that express a first chimeric antigen receptor (CAR) specific for BCMA, wherein the cell therapy is administered on Day 1 and: (a) one dose of the IL-1Ra is administered within about or about 24 hours prior to the administration of the dose of engineered T cells, optionally the night before the administration of the dose of the engineered T cells; (b) one dose of the IL-1Ra is administered within about or about 3 hours prior to the administration of the dose of engineered T cells on Day 1; (c) four doses of the IL-1Ra are administered after the administration of the dose of engineered T cells, wherein one dose of the four doses is administered each day on Days 2, 3, 4, and 5.

In some of any of the provided embodiments, methods and uses also involve administering at least one additional dose of the IL-1Ra after the administration of the dose of engineered cells if the subject exhibits symptoms or signs of a cytokine release syndrome (CRS). In some of any of the provided embodiments, the at least one additional dose of the IL-1Ra includes administration of a plurality of doses. In some of any of the provided embodiments, the plurality of doses is administered daily for consecutive days, until the symptoms or signs of CRS is resolved. In some of any of the provided embodiments, the plurality of doses is administered twice daily for consecutive days, until the symptoms or signs of CRS is resolved. In some embodiments, a dose of the IL-1Ra is administered every 12 hours (q12 h). In some embodiments, if the subject exhibits symptoms or signs of a cytokine release syndrome (CRS), a dose of IL-1Ra is administered every 12 hours (q12 h) until the symptoms or signs of CRS resolve.

In some of any of the provided embodiments, the daily administration of the IL-1Ra is administered at or at about the same time each day.

In some of any of the provided embodiments, the IL-1Ra is a recombinant IL-1Ra. In some of any of the provided embodiments, the IL-1Ra includes the sequence set forth in SEQ ID NO:256 or a sequence having at least 90%, 91%, 92%, 93%, 94%, 95%, 96%, 97%, 98% or 99% or higher sequence identity to SEQ ID NO:256 that retains function as an IL-1R antagonist. In some of any of the provided embodiments, the IL-1Ra includes the sequence set forth in SEQ ID NO:256. In some of any of the provided embodiments, the IL-1Ra includes a sequence having at least 90%, 91%, 92%, 93%, 94%, 95%, 96%, 97%, 98% or 99% or higher sequence identity to SEQ ID NO:256 that retains function as an IL-1R antagonist. In some of any of the provided embodiments, the IL-1Ra is anakinra. In some embodiments, anakinra is recombinant anakinra.

In some of any of the provided embodiments, each dose of the recombinant IL-1Ra is at or about 500 mg, at or about 400, at or about 300, at or about 200 mg, at or about 100 or at or about 50 mg, or a range defined by any of the foregoing. In some of any of the provided embodiments, each dose of the IL-1Ra is at or about 500 mg, at or about 400, at or about 300, at or about 200 mg, at or about 100 or at or about 50 mg, or a range defined by any of the foregoing. In some of any of the provided embodiments, each dose of the IL-1Ra is at or about 500 mg. In some of any of the provided embodiments, each dose of the IL-1Ra is at or about 400 mg. In some of any of the provided embodiments, each dose of the IL-1Ra is at or about 300 mg. In some of any of the provided embodiments, each dose of the IL-1Ra is at or about 200 mg. In some of any of the provided embodiments, each dose of the recombinant IL-1Ra is from at or about 50 mg to at or about 200 mg. In some of any of the provided embodiments, each dose of the recombinant IL-1Ra is at or about 100 mg. In some of any of the provided embodiments, each dose of the IL-1Ra is at or about 50 mg. In some of any of the provided embodiments, the IL-1Ra is administered subcutaneously.

In some of any of the provided embodiments, the methods and uses reduce the severity of, attenuates, and/or prevents the onset of a toxicity associated with administration of the cell therapy. In some of any of the provided embodiments, the methods and uses reduce the severity of the onset of a toxicity associated with administration of the cell therapy. In some of any of the provided embodiments, the methods and uses attenuates the onset of a toxicity associated with administration of the cell therapy. In some of any of the provided embodiments, the methods and uses prevents the onset of a toxicity associated with administration of the cell therapy.

In some of any of the provided embodiments, the toxicity is a cytokine release syndrome (CRS). In some of any of the provided embodiments, the CRS is a severe CRS or a grade 3 or higher CRS. In some of any of the provided embodiments, the CRS is a severe. In some of any of the provided embodiments, the CRS is a 3 or higher CRS. In some of any of the provided embodiments, the toxicity is a neurotoxicity (NT). In some of any of the provided embodiments, the NT is a severe NT or a grade 2 or higher NT or a grade 3 or higher NT. In some of any of the provided embodiments, the NT is a severe NT. In some of any of the provided embodiments, the NT is a grade 2 or higher NT. In some of any of the provided embodiments, the NT is a grade 3 or higher NT. In some of any of the provided embodiments, the toxicity is a macrophage activation syndrome (MAS) or a hemophagocytic lympho-histiocytosis (HLH). In some of any of the provided embodiments, the toxicity is a macrophage activation syndrome (MAS). In some of any of the provided embodiments, the toxicity is a hemophagocytic lympho-histiocytosis (HLH).

In some of any of the provided embodiments, at or prior to the administration of the dose of engineered T cells, the subject has been administered one or more prior BCMA-directed therapy selected from among: a prior dose of engineered T cells that express a second CAR specific for BCMA; a prior administration of a BCMA-directed T cell engager (TCE); and a prior administration of a BCMA-directed antibody-drug conjugate (ADC).

Provided herein are methods and uses for treating a subject having or suspected of having a disease or disorder associated with B-cell maturation antigen (BCMA) expression that involves administering to the subject a cell therapy that includes a dose of engineered T cells that express a first chimeric antigen receptor (CAR) specific for BCMA, wherein at or prior to the administration of the dose of engineered T cells, the subject has been administered one or more prior BCMA-directed therapy selected from among: a prior dose of engineered T cells that express a second CAR specific for BCMA; a prior administration of a BCMA-directed T cell engager (TCE); and a prior administration of a BCMA-directed antibody-drug conjugate (ADC).

Provided herein are methods and uses for treating a subject having or suspected of having a disease or disorder associated with B-cell maturation antigen (BCMA) expression that involves administering to the subject a cell therapy that includes a dose of engineered T cells that express a first chimeric antigen receptor (CAR) specific for BCMA, to a subject that has previously received one or more prior BCMA-directed therapy selected from among: a prior dose of engineered T cells that express a second CAR specific for BCMA; a prior administration of a BCMA-directed T cell engager (TCE); and a prior administration of a BCMA-directed antibody-drug conjugate (ADC).

In some of any of the provided embodiments, the subject has relapsed following or has been refractory to the one or more prior BCMA-directed therapy. In some of any of the provided embodiments, the subject has relapsed following the one or more prior BCMA-directed therapy. In some of any of the provided embodiments, the subject has been refractory to the one or more prior BCMA-directed therapy. In some of any of the provided embodiments, the subject has relapsed following or has been refractory to the one or more prior BCMA-directed therapy within at or about 1 year prior to the administration of the dose of engineered T cells that express the first CAR. In some of any of the provided embodiments, the subject has relapsed following the one or more prior BCMA-directed therapy within at or about 1 year prior to the administration of the dose of engineered T cells that express the first CAR. In some of any of the provided embodiments, the subject has been refractory to the one or more prior BCMA-directed therapy within at or about 1 year prior to the administration of the dose of engineered T cells that express the first CAR. In some of any of the provided embodiments, the subject has relapsed following or has been refractory to the one or more prior BCMA-directed therapy within at or about 6 months prior to the administration of the dose of engineered T cells that express the first CAR. In some of any of the provided embodiments, the subject has relapsed following the one or more prior BCMA-directed therapy within at or about 6 months prior to the administration of the dose of engineered T cells that express the first CAR. In some of any of the provided embodiments, the subject has been refractory to the one or more prior BCMA-directed therapy within at or about 6 months prior to the administration of the dose of engineered T cells that express the first CAR. In some of any of the provided embodiments, the subject has relapsed following or has been refractory to the one or more prior BCMA-directed therapy within at or about 3 months prior to the administration of the dose of engineered T cells that express the first CAR. In some of any of the provided embodiments, the subject has relapsed following the one or more prior BCMA-directed therapy within at or about 3 months prior to the administration of the dose of engineered T cells that express the first CAR. In some of any of the provided embodiments, the subject has been refractory to the one or more prior BCMA-directed therapy within at or about 3 months prior to the administration of the dose of engineered T cells that express the first CAR.

In some of any of the provided embodiments, the BCMA-directed TCE is or includes a bispecific antibody or a bispecific T cell engager (BiTE). In some of any of the provided embodiments, the BCMA-directed TCE is a bispecific antibody. In some of any of the provided embodiments, the BCMA-directed TCE includes a bispecific antibody. In some of any of the provided embodiments, the BCMA-directed TCE is a bispecific T cell engager (BiTE). In some of any of the provided embodiments, the BCMA-directed TCE includes a bispecific T cell engager (BiTE). In some of any of the provided embodiments, the BCMA-directed TCE is selected from among one or more of AMG 420/BI 836909, AMG 701, CC-93269, JNJ-64007957, PF-06863135 and REGN5458. In some of any of the provided embodiments, the BCMA-directed TCE is AMG 420/BI 836909. In some of any of the provided embodiments, the BCMA-directed TCE is AMG 701. In some of any of the provided embodiments, the BCMA-directed TCE is CC-93269. In some of any of the provided embodiments, the BCMA-directed TCE is JNJ-64007957. In some of any of the provided embodiments, the BCMA-directed TCE is PF-06863135. In some of any of the provided embodiments, the BCMA-directed TCE is REGN5458.

In some of any of the provided embodiments, the BCMA-directed ADC is selected from among one or more of Belantamab mafodotin (GSK2857916), MEDI2228, CC-99712 and AMG 224. In some of any of the provided embodiments, the BCMA-directed ADC is Belantamab mafodotin (GSK2857916). In some of any of the provided embodiments, the BCMA-directed ADC is MEDI2228. In some of any of the provided embodiments, the BCMA-directed ADC is CC-99712. In some of any of the provided embodiments, the BCMA-directed ADC is AMG 224.

In some of any of the provided embodiments, the first CAR contains: (a) an extracellular antigen-binding domain, comprising: a variable heavy chain ($V_H$) comprising a heavy chain complementarity determining region 1 (CDR-H1), a heavy chain complementarity determining region 2 (CDR-H2) and a heavy chain complementarity determining region 3 (CDR-H3) contained within the sequence set forth in SEQ ID NO: 116 and a variable light chain ($V_L$) comprising a light chain complementarity determining region 1 (CDR-L1), a light chain complementarity determining region 2 (CDR-L2) and a light chain complementarity determining region 3 (CDR-L3) contained within the sequence set forth in SEQ ID NO: 119; a $V_H$ comprising a CDR-H1, a CDR-H2 and a CDR-H3 sequences set forth in SEQ ID NOS: 97, 101 and 103, respectively, and a $V_L$ comprising a CDR-L1, a CDR-L2 and a CDR-L3 sequences set forth in SEQ ID NOS: 105, 107 and 108, respectively; a $V_H$ comprising a CDR-H1, a CDR-H2 and a CDR-H3 sequences set forth in SEQ ID NOS: 96, 100 and 103, respectively, and a $V_L$ comprising a CDR-L1, a CDR-L2 and a CDR-L3 sequences set forth in SEQ ID NOS: 105, 107 and 108, respectively; a $V_H$ comprising a CDR-H1, a CDR-H2 and a CDR-H3 sequences set forth in SEQ ID NOS: 95, 99 and 103, respectively, and a $V_L$ comprising a CDR-L1, a CDR-L2 and a CDR-L3 sequences set forth in SEQ ID NOS: 105, 107 and 108, respectively; a $V_H$ comprising a CDR-H1, a CDR-H2 and a CDR-H3 sequences set forth in SEQ ID NOS: 94, 98 and 102, respectively, and a $V_L$ comprising a CDR-L1, a CDR-L2 and a CDR-L3 sequences set forth in SEQ ID NOS: 104, 106 and 108, respectively; or a $V_H$ comprising the amino acid sequence of SEQ ID NO: 116 and a $V_L$ comprising the amino acid sequence of SEQ ID NO: 119; (b) a spacer comprising an IgG4/2 chimeric hinge or a modified IgG4 hinge; an IgG2/4 chimeric $C_H2$ region; and an IgG4 $C_H3$ region, such as a spacer that is about 228 amino acids in length; or a spacer set forth in SEQ ID NO: 174; (c) a transmembrane domain; and (d) an intracellular signaling region comprising a cytoplasmic signaling domain of a CD3-zeta (CD3ζ) chain and a costimulatory signaling region comprising an intracellular signaling domain of a T cell costimulatory molecule or a signaling portion thereof.

In some of any of the provided embodiments, the $V_H$ is or includes the amino acid sequence of SEQ ID NO: 116; and the $V_L$ is or includes the amino acid sequence of SEQ ID NO: 119. In some of any of the provided embodiments, the $V_H$ is the amino acid sequence of SEQ ID NO: 116; and the $V_L$ is the amino acid sequence of SEQ ID NO: 119. In some of any of the provided embodiments, the $V_H$ includes the amino acid sequence of SEQ ID NO: 116; and the $V_L$ includes the amino acid sequence of SEQ ID NO: 119.

In some of any of the provided embodiments, the extracellular antigen-binding domain includes an scFv. In some of any of the provided embodiments, the extracellular antigen-binding domain is an scFv. In some of any of the provided embodiments, the $V_H$ and the $V_L$ are joined by a flexible linker. In some of any of the provided embodiments, the flexible linker includes the amino acid sequence GGGGSGGGGSGGGGS (SEQ ID NO:1). In some of any of the provided embodiments, the flexible linker is the amino acid sequence GGGGSGGGGSGGGGS (SEQ ID NO:1). In some of any of the provided embodiments, the $V_H$ is carboxy-terminal to the $V_L$.

In some of any of the provided embodiments, the extracellular antigen-binding domain includes the amino acid sequence of SEQ ID NO: 114 or an amino acid sequence having at least 90%, 91%, 92%, 93%, 94%, 95%, 96%, 97%, 98%, or 99% sequence identity to the amino acid sequence of SEQ ID NO: 114. In some of any of the provided embodiments, the extracellular antigen-binding domain includes the amino acid sequence of SEQ ID NO: 114. In some of any of the provided embodiments, the extracellular antigen-binding domain includes an amino acid sequence having at least 90%, 91%, 92%, 93%, 94%, 95%, 96%, 97%, 98%, or 99% sequence identity to the amino acid sequence of SEQ ID NO: 114.

In some of any of the provided embodiments, a nucleic acid encoding the extracellular antigen-binding domain includes (a) the sequence of nucleotides of SEQ ID NO:113; (b) a sequence of nucleotides that has at least 90% sequence identity thereto; or (c) a degenerate sequence of (a) or (b). In some of any of the provided embodiments, a nucleic acid encoding the extracellular antigen-binding domain includes the sequence of nucleotides of SEQ ID NO:113. In some of any of the provided embodiments, a nucleic acid encoding the extracellular antigen-binding domain includes a sequence of nucleotides that has at least 90% sequence identity to SEQ ID NO:113. In some of any of the provided embodiments, the nucleic acid encoding the extracellular antigen-binding domain includes the sequence of nucleotides of SEQ ID NO:115.

In some of any of the provided embodiments, the transmembrane domain is or includes a transmembrane domain from human CD28. In some of any of the provided embodiments, the transmembrane domain is a transmembrane domain from human CD28. In some of any of the provided embodiments, the transmembrane domain includes a transmembrane domain from human CD28. In some of any of the provided embodiments, the transmembrane domain is or includes the sequence set forth in SEQ ID NO:138 or a sequence of amino acids that has at least 90% sequence identity to SEQ ID NO:138. In some of any of the provided embodiments, the transmembrane domain is or includes the sequence set forth in SEQ ID NO:138. In some of any of the provided embodiments, the transmembrane domain the sequence set forth in SEQ ID NO:138. In some of any of the provided embodiments, the transmembrane domain includes the sequence set forth in SEQ ID NO:138. In some of any of the provided embodiments, the transmembrane domain is or includes a sequence of amino acids that has at least 90% sequence identity to SEQ ID NO:138. In some of any of the provided embodiments, the transmembrane domain is a sequence of amino acids that has at least 90% sequence identity to SEQ ID NO:138. In some of any of the provided embodiments, the transmembrane domain includes a sequence of amino acids that has at least 90% sequence identity to SEQ ID NO:138.

In some embodiments, the first CAR contains an extracellular antigen-binding domain having: a variable heavy chain ($V_H$) comprising a heavy chain complementarity determining region 1 (CDR-H1), a heavy chain complementarity determining region 2 (CDR-H2) and a heavy chain complementarity determining region 3 (CDR-H3) contained within the sequence set forth in SEQ ID NO: 125 and a variable light chain ($V_L$) comprising a light chain complementarity determining region 1 (CDR-L1), a light chain complementarity determining region 2 (CDR-L2) and a light chain complementarity determining region 3 (CDR-L3) contained within the sequence set forth in SEQ ID NO: 127; and/or a $V_H$ comprising a CDR-H1, a CDR-H2 and a CDR-H3 sequences set forth in SEQ ID NOS: 260, 261, and 262, respectively, and a $V_L$ comprising a CDR-L1, a CDR-L2 and a CDR-L3 sequences set forth in SEQ ID NOS: 257, 258, and 259, respectively. In some embodiments, the $V_H$ is or includes the amino acid sequence of SEQ ID NO: 125; and the $V_L$ is or includes the amino acid sequence of SEQ ID NO: 127. In some embodiments, the extracellular antigen-binding domain includes the amino acid sequence of SEQ ID NO: 128 or an amino acid sequence having at least 90%, 91%, 92%, 93%, 94%, 95%, 96%, 97%, 98%, or 99% sequence identity to the amino acid sequence of SEQ ID NO: 128.

In some of any of the provided embodiments, the cytoplasmic signaling domain is or includes the sequence set forth in SEQ ID NO:143 or a sequence of amino acids that has at least 90% sequence identity to SEQ ID NO:143. In some of any of the provided embodiments, the cytoplasmic signaling domain is or includes the sequence set forth in SEQ ID NO:143. In some of any of the provided embodiments, the cytoplasmic signaling domain is the sequence set forth in SEQ ID NO:143. In some of any of the provided embodiments, the cytoplasmic signaling domain includes the sequence set forth in SEQ ID NO:143. In some of any of the provided embodiments, the cytoplasmic signaling domain is or includes a sequence of amino acids that has at least 90% sequence identity to SEQ ID NO:143. In some of any of the provided embodiments, the cytoplasmic signaling domain is a sequence of amino acids that has at least 90% sequence identity to SEQ ID NO:143. In some of any of the provided embodiments, the cytoplasmic signaling domain includes a sequence of amino acids that has at least 90% sequence identity to SEQ ID NO:143.

In some of any of the provided embodiments, the costimulatory signaling region includes an intracellular signaling domain of CD28, 4-1BB, or ICOS, or a signaling portion thereof. In some of any of the provided embodiments, the costimulatory signaling region includes an intracellular signaling domain of CD28. In some of any of the provided embodiments, the costimulatory signaling region includes an intracellular signaling domain of ICOS. In some of any of the provided embodiments, the costimulatory signaling region includes an intracellular signaling domain of 4-1BB. In some of any of the provided embodiments, the 4-1BB is human 4-1BB. In some of any of the provided embodiments, the costimulatory signaling region is or includes the sequence set forth in SEQ ID NO:4 or a sequence of amino acids that has at least 90% sequence identity to the sequence set forth in SEQ ID NO: 4. In some of any of the provided embodiments, the costimulatory signaling region is or includes the sequence set forth in SEQ ID NO: 4. In some of any of the provided embodiments, the costimulatory signaling region is the sequence set forth in SEQ ID NO: 4. In some of any of the provided embodiments, the costimulatory signaling region includes the sequence set forth in SEQ ID NO: 4. In some of any of the provided embodiments, the costimulatory signaling region is a sequence of amino acids that has at least 90% sequence identity to the sequence set forth in SEQ ID NO: 4. In some of any of the provided embodiments, the costimulatory signaling region includes a sequence of amino acids that has at least 90% sequence identity to the sequence set forth in SEQ ID NO: 4.

In some of any of the provided embodiments, the costimulatory signaling region is between the transmembrane domain and the cytoplasmic signaling domain of a CD3-zeta (CD3ζ) chain.

In some of any of the provided embodiments, the first CAR contains from its N to C terminus, in order: the extracellular antigen-binding domain, the spacer, the transmembrane domain and the intracellular signaling region.

In some of any of the provided embodiments, the first CAR contains (a) an extracellular antigen-binding domain, comprising: a variable heavy chain ($V_H$) comprising a heavy chain complementarity determining region 1 (CDR-H1), a heavy chain complementarity determining region 2 (CDR-H2) and a heavy chain complementarity determining region 3 (CDR-H3) contained within the sequence set forth in SEQ ID NO: 116 and a variable light chain ($V_L$) comprising a light chain complementarity determining region 1 (CDR-L1), a light chain complementarity determining region 2 (CDR-L2) and a light chain complementarity determining region 3 (CDR-L3) contained within the sequence set forth in SEQ ID NO: 119; (b) a spacer comprising a modified IgG4 hinge; an IgG2/4 chimeric $C_H2$ region; and an IgG4 $C_H3$ region, that is about 228 amino acids in length; (c) a transmembrane domain from a human CD28; and (d) an intracellular signaling region comprising a cytoplasmic signaling domain of a CD3-zeta (CD3ζ) chain and a costimulatory signaling region comprising an intracellular signaling domain of a 4-1BB.

In some of any of the provided embodiments, the first CAR contains (a) an extracellular antigen-binding domain, comprising the sequence set forth in SEQ ID NO: 114 or a sequence of amino acids having at least 90% sequence identity to the amino acid sequence of SEQ ID NO: 114; (b) a spacer comprising the sequence set forth in SEQ ID NO: 174 or a sequence of amino acids that has at least 90% sequence identity to SEQ ID NO:174; (c) a transmembrane domain comprising the sequence set forth in SEQ ID NO:138 or a sequence of amino acids that has at least 90% sequence identity to SEQ ID NO:138; and (d) an intracellular signaling region comprising a cytoplasmic signaling comprising the sequence set forth in SEQ ID NO:143 or a sequence of amino acids that has at least 90% sequence identity to SEQ ID NO:143 and a costimulatory signaling region comprising the sequence set forth in SEQ ID NO:4 or a sequence of amino acids that has at least 90% sequence identity to the sequence set forth in SEQ ID NO: 4.

In some of any of the provided embodiments, the first CAR contains (a) an extracellular antigen-binding domain, comprising the sequence set forth in SEQ ID NO: 114; (b) a spacer comprising the sequence set forth in SEQ ID NO: 174; (c) a transmembrane domain comprising the sequence set forth in SEQ ID NO:138; and (d) an intracellular signaling region comprising a cytoplasmic signaling comprising the sequence set forth in SEQ ID NO:143 and a costimulatory signaling region comprising the sequence set forth in SEQ ID NO:4.

In some of any of the provided embodiments, the first CAR contains the sequence set forth in SEQ ID NO:19. In some of any of the provided embodiments, the first CAR is encoded by a polynucleotide sequence comprising the sequence set forth in SEQ ID NO: 13 or a sequence that exhibits at least 85%, 86%, 87%, 88%, 89%, 90%, 91%, 92%, 93%, 94%, 95%, 96%, 97%, 98%, or 99% sequence identity thereto. In some of any of the provided embodiments, the first CAR is encoded by a polynucleotide sequence comprising the sequence set forth in SEQ ID NO: 13. In some of any of the provided embodiments, the first CAR is encoded by a polynucleotide sequence that exhibits at least 85%, 86%, 87%, 88%, 89%, 90%, 91%, 92%, 93%, 94%, 95%, 96%, 97%, 98%, or 99% sequence identity to SEQ ID NO: 13.

In some embodiments, wherein the first CAR contains the sequence set forth in SEQ ID NO: 312.

In some of any of the provided embodiments, the first CAR and the second CAR bind to the same epitope of BCMA.

In some of any of the provided embodiments, the first CAR and the second CAR bind to different epitopes of BCMA.

In some of any of the provided embodiments, the first CAR and the second CAR are different.

In some of any of the provided embodiments, the second CAR includes: a $V_H$ region comprising a CDR-H1, a CDR-H2, and a CDR-H3 comprising the amino acid sequence of SEQ ID NOs:257, 258. and 259, respectively; and a $V_L$ region comprising a CDR-L1, CDR-L2, and CDR-L3 comprising the amino acid sequence of SEQ ID NOs:260, 261, and 262, respectively; a $V_H$ region comprising the sequence set forth in SEQ ID NO:125 and a $V_L$ region comprising the sequence set forth in SEQ ID NO:127; the amino acid residues 22-493 of the sequence set forth in SEQ ID NO:265; and/or the sequence encoded by SEQ ID NO:266. In some of any of the provided embodiments, the second CAR includes a $V_H$ region comprising a CDR-H1, a CDR-H2, and a CDR-H3 comprising the amino acid sequence of SEQ ID NOs: 260, 261, and 262, respectively; and a $V_L$ region comprising a CDR-L1, CDR-L2, and CDR-L3 comprising the amino acid sequence of SEQ ID NOs: 257, 258, and 259, respectively. In some of any of the provided embodiments, the second CAR includes a $V_H$ region comprising the sequence set forth in SEQ ID NO:125 and a $V_L$ region comprising the sequence set forth in SEQ ID NO:127. In some of any of the provided embodiments, the second CAR includes the amino acid residues 22-493 of the sequence set forth in SEQ ID NO:263. In some of any of the provided embodiments, the second CAR includes the sequence encoded by SEQ ID NO:264. In some of any of the provided embodiments, the second CAR includes the amino acid residues 22-493 of the sequence set forth in SEQ ID NO:263 and the sequence encoded by SEQ ID NO:264. In some of any of the provided embodiments, the second CAR includes the amino acid residues 22-493 of the sequence set forth in SEQ ID NO:263 and/or the sequence encoded by SEQ ID NO:264. In some embodiments, the second CAR includes the sequence encoded by SEQ ID NO:312.

In some of any of the provided embodiments, the second CAR is a multivalent CAR. In some of any of the provided embodiments, the second CAR includes the amino acid residues beginning at residue 22 to the end of the sequence set forth in any one of SEQ ID NOS: 267-304. In some of any of the provided embodiments, the second CAR is a multivalent CAR. In some of any of the provided embodiments, the second CAR includes the amino acid residues beginning at residue 22 to the end of the sequence set forth in any one of SEQ ID NOS: 265-302.

In some of any of the provided embodiments, the second CAR includes a Centyrin-containing CAR. In some of any of the provided embodiments, the second CAR includes the amino acid residues 22-334 of the sequence set forth in SEQ ID NO: 310.

In some of any of the provided embodiments, the first CAR and the second CAR are the same.

In some of any of the provided embodiments, the dose of engineered T cells that express the first CAR is generated from a sample comprising T cells obtained from the same subject that has previously been administered the prior dose of engineered T cells comprising the second CAR. In some of any of the provided embodiments, the dose of engineered T cells that express the first CAR is generated from a sample comprising T cells obtained from the subject after the subject has been administered the prior dose of engineered T cells comprising the second CAR.

In some of any of the provided embodiments, prior to the administration of the dose of engineered T cells that express the first CAR, the method further includes assessing, in a test sample obtained from the subject, the presence or amount of (i) cells expressing the second CAR or (ii) a nucleotide sequence present in the construct encoding the second CAR. In some of any of the provided embodiments, prior to the administration of the dose of engineered T cells that express the first CAR, the method further includes assessing, in a test sample obtained from the subject, the presence or amount of cells expressing the second CAR. In some of any of the provided embodiments, prior to the administration of the dose of engineered T cells that express the first CAR, the method further includes assessing, in a test sample obtained from the subject, the presence or amount of a nucleotide sequence present in the construct encoding the second CAR. In some of any of the provided embodiments, the test sample is obtained from the subject at the same time as obtaining the sample comprising T cells for generating the dose of engineered T cells that express the first CAR from the same subject.

In some of any of the provided embodiments, prior to administering the dose of engineered T cells that express the first CAR, the method further includes assessing the presence or amount of (i) cells expressing the second CAR or a (ii) nucleotide sequence present in the construct encoding the second CAR in a composition comprising the dose of engineered T cells that express the first CAR. In some of any of the provided embodiments, prior to administering the dose of engineered T cells that express the first CAR, the method further includes assessing the presence or amount of cells expressing the second CAR. In some of any of the provided embodiments, prior to administering the dose of engineered T cells that express the first CAR, the method further includes assessing the presence or amount of a nucleotide sequence present in the construct encoding the second CAR in a composition comprising the dose of engineered T cells that express the first CAR. In some of any of the provided embodiments, the assessing the presence or amount of cells expressing the second CAR is carried out by contacting the sample or the dose of composition comprising the engineered T cells with a purified or recombinant BCMA. In some of any of the provided embodiments, the assessing the presence or amount of cells expressing the second CAR is carried out by contacting the sample or the dose of engineered T cells with a BCMA-Fc.

In some of any of the provided embodiments, the assessing the presence or amount of the nucleotide sequence present in a construct encoding the second CAR is carried out by quantitative polymerase chain reaction (qPCR).

In some of any of the provided embodiments, the binding of the extracellular antigen-binding domain and/or the first CAR, or a measure indicative of function or activity of the first CAR following exposure to cells expressing surface BCMA, is not reduced or blocked or is not substantially reduced or blocked in the presence of a soluble or shed form of BCMA. In some of any of the provided embodiments, the binding of the extracellular antigen-binding domain to cells expressing surface BCMA, is not reduced or blocked or is not substantially reduced or blocked in the presence of a soluble or shed form of BCMA. In some of any of the provided embodiments, the binding of the first CAR to cells expressing surface BCMA, is not reduced or blocked or is not substantially reduced or blocked in the presence of a soluble or shed form of BCMA. In some of any of the provided embodiments, a measure indicative of function or activity of the first CAR following exposure to cells expressing surface BCMA is not reduced or blocked or is not substantially reduced or blocked in the presence of a soluble or shed form of BCMA. In some of any of the provided embodiments, the concentration or amount of the soluble or shed form of the BCMA corresponds to a concentration or amount present in serum or blood or plasma of the subject or of a multiple myeloma patient, or on average in a multiple myeloma patient population, or at a concentration or amount of the soluble or shed BCMA at which the binding or measure is reduced or blocked, or is substantially reduced or blocked, for cells expressing a reference anti-BCMA recombinant receptor, such as a reference anti-BCMA CAR, in the same assay.

In some of any of the provided embodiments, the dose of engineered T cells that express the first CAR contains between at or about $1\times10^7$ CAR+ T cells and at or about $2\times10^9$ CAR+ T cells. In some of any of the provided embodiments, the dose of engineered T cells that express the first CAR contains between at or about $1\times10^7$ CAR+ T cells and at or about $1\times10^9$ CAR+ T cells. In some of any of the provided embodiments, the dose of engineered T cells that express the first CAR contains between at or about $1\times10^8$ CAR+ T cells and at or about $1\times10^8$ CAR+ T cells. In some of any of the provided embodiments, the dose of engineered T cells includes at or about $5\times10^7$ cells or CAR+ T cells. In some of any of the provided embodiments, the dose of engineered T cells that express the first CAR contains at or about $1\times10^8$ cells or CAR+ T cells. In some of any of the provided embodiments, the dose of engineered T cells that express the first CAR contains at or about $1.5\times10^8$ cells or CAR+ T cells. In some of any of the provided embodiments, the dose of engineered T cells that express the first CAR contains at or about $2\times10^8$ cells or CAR+ T cells. In some of any of the provided embodiments, the dose of engineered T cells that express the first CAR contains at or about $2.5\times10^8$ cells or CAR+ T cells. In some of any of the provided embodiments, the dose of engineered T cells that express the first CAR contains at or about $3\times10^8$ cells or CAR+ T cells. In some of any of the provided embodiments, the dose of engineered T cells that express the first CAR contains at or about $3.5\times10^8$ cells or CAR+ T cells. In some of any of the provided embodiments, the dose of engineered T cells that express the first CAR contains at or about $4\times10^8$ cells or CAR+ T cells. In some of any of the provided embodiments, the dose of engineered T cells that express the first CAR contains at or about $4.5\times10^8$ cells or CAR+ T cells. In some of any of the provided embodiments, the dose of engineered T cells that express the first CAR contains at or about $5\times10^8$ cells or CAR+ T cells. In some of any of the provided embodiments, the dose of engineered T cells that express the first CAR contains at or about $5.5\times10^8$ cells or CAR+ T cells. In some of any of the provided embodiments, the dose of engineered T cells that express the first CAR contains at or about $6\times10^8$ cells or CAR+ T cells. In some of any of the provided embodiments, the dose of engineered T cells that express the first CAR contains at or about $8\times10^8$ cells or CAR+ T cells. In some of any of the provided embodiments, the dose of engineered T cells that express the first CAR contains at or about $1\times10^9$ cells or CAR+ T cells. In some of any of the provided embodiments, the dose of engineered T cells that express the first CAR contains at or about $1.5\times10^9$ cells or CAR+ T cells. In some of any of the provided embodiments, the dose of engineered T cells that express the first CAR contains at or about $2\times10^9$ cells or CAR+ T cells.

In some of any of the provided embodiments, the dose of engineered T cells that express the first CAR contains a combination of $CD4^+$ T cells and $CD8^+$ T cells. In some of any of the provided embodiments, the dose of engineered T cells that express the first CAR includes a combination of $CD4^+$ CAR+ T cells and $CD8^+$ CAR+ T cells. In some of any of the provided embodiments, the ratio of $CD4^+$ CAR+ T cells to $CD8^+$ CAR+ T cells and/or of $CD4^+$ T cells to $CD8^+$ T cells is or is approximately 1:1 or is between at or approximately 1:3 and at or approximately 3:1. In some of any of the provided embodiments, the ratio of $CD4^+$ CAR+ T cells to $CD8^+$ CAR+ T cells is or is approximately 1:1. In some of any of the provided embodiments, the ratio of $CD4^+$ CAR+ T cells to $CD8^+$ CAR+ T cells is or is between at or approximately 1:3 and at or approximately 3:1. In some of any of the provided embodiments, the dose of engineered T cells that express the first CAR includes a combination of $CD4^+$ CAR+ T cells and $CD8^+$ CAR+ T cells. In some of any of the provided embodiments, the ratio of $CD4^+$ T cells to $CD8^+$ T cells is or is approximately 1:1 or is between at or approximately 1:3 and at or approximately 3:1. In some of any of the provided embodiments, the ratio of $CD4^+$ T cells to $CD8^+$ T cells is or is approximately 1:1. In some of any of the provided embodiments, the ratio of $CD4^+$ T cells to $CD8^+$ T cells is or is between at or approximately 1:3 and at or approximately 3:1.

In some of any of the provided embodiments, the dose of engineered T cells that express the first CAR contains $CD3^+$ CAR+ T cells.

In some of any of the provided embodiments, less than at or about 25%, 20%, 15%, 10%, 9%, 8%, 7%, 6%, 5%, 4%, 3%, 2% or 1% of the CAR+ T cells in the dose of engineered T cells that express the first CAR express a marker of apoptosis, such as Annexin V or active Caspase 3. In some of any of the provided embodiments, less than at or about 25%, 20%, 15%, 10%, 9%, 8%, 7%, 6%, 5%, 4%, 3%, 2% or 1% of the CAR+ T cells in the dose of engineered T cells that express the first CAR express a marker of apoptosis. In some embodiments, the marker of apoptosis is Annexin V. In some embodiments, the marker of apoptosis is active Caspase 3.

In some of any of the provided embodiments, prior to the administration of the dose of engineered T cells that express the first CAR, the subject has been administered a lymphodepleting therapy that includes the administration of fludarabine at or about 20-40 $mg/m^2$ body surface area of the subject. In some of any of the provided embodiments, prior to the administration of the dose of engineered T cells that express the first CAR, the subject has been administered a lymphodepleting therapy that includes the administration of fludarabine at or about 30 $mg/m^2$, daily, for 2-4 days. In some of any of the provided embodiments, prior to the administration of the dose of engineered T cells that express the first CAR, the subject has been administered a lymphodepleting therapy that includes the administration of cyclophosphamide at or about 200-400 $mg/m^2$ body surface area of the subject. In some of any of the provided embodiments, prior to the administration of the dose of engineered T cells that express the first CAR, the subject has been administered a lymphodepleting therapy that includes the administration of cyclophosphamide at or about 300 $mg/m^2$, daily, for 2-4 days. In some of any of the provided embodiments, the lymphodepleting therapy includes the administration of fludarabine at or about 30 $mg/m^2$ body surface area of the subject, daily, and cyclophosphamide at or about 300 $mg/m^2$ body surface area of the subject, daily, for 3 days.

In some of any of the provided embodiments, the disease or disorder associated with BCMA expression is an autoimmune disease or disorder. In some of any of the provided embodiments, the disease or disorder associated with BCMA expression is a cancer. In some of any of the provided embodiments, a BCMA-expressing cancer.

In some of any of the provided embodiments, the cancer is a B cell malignancy. In some of any of the provided embodiments, the cancer is a lymphoma, a leukemia, or a plasma cell malignancy. In some of any of the provided embodiments, the cancer is a lymphoma and the lymphoma is Burkitt lymphoma, non-Hodgkin's lymphoma (NHL), Hodgkin's lymphoma, Waldenstrom macroglobulinemia, follicular lymphoma, small non-cleaved cell lymphoma, mucosa-associated lymphatic tissue lymphoma (MALT), marginal zone lymphoma, splenic lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), or mantle cell lymphoma (MCL). In some of any of the provided embodiments, the cancer is a leukemia and the leukemia is chronic lymphocytic leukemia (CLL), plasma cell leukemia or acute lymphocytic leukemia (ALL). In some of any of the provided embodiments, the cancer is a plasma cell malignancy and the plasma cell malignancy is multiple myeloma (MM) or plasmacytoma. In some of any of the provided embodiments, the cancer is multiple myeloma (MM). In some of any of the provided embodiments, the cancer is a relapsed and/or refractory multiple myeloma (R/R MM). In some of any of the provided embodiments, the cancer is a relapsed or refractory multiple myeloma (R/R MM). In some of any of the provided embodiments, the cancer is a relapsed multiple myeloma (MM). In some of any of the provided embodiments, the cancer is a refractory multiple myeloma (MM).

In some of any of the provided embodiments, the subject has been administered three or more prior therapies for the disease or disorder, such as four or more prior therapies. In some of any of the provided embodiments, the three or more prior therapies for the disease or disorder, or the four or more prior therapies are selected from among: autologous stem cell transplant (ASCT); an immunomodulatory agent; a proteasome inhibitor; and an anti-CD38 antibody. In some of any of the provided embodiments, the immunomodulatory agent is selected from among thalidomide, lenalidomide and pomalidomide. In some of any of the provided embodiments, the proteasome inhibitor is selected from among bortezomib, carfilzomib and ixazomib. In some of any of the provided embodiments, the anti-CD38 antibody is or includes daratumumab.

In some of any of the provided embodiments, the subject has been administered between 3 and 15 or between 4 and 15 prior therapies or about 10 prior therapies. In some of any of the provided embodiments, the subject has relapsed following or has been refractory to the one or more of the three or more prior therapies. In some of any of the provided embodiments, the subject has relapsed following or has been refractory to the one or more prior therapies. In some of any of the provided embodiments, the subject has relapsed following or has been refractory to at least 3 or at least 4 prior therapies. In some of any of the provided embodiments, the subject has relapsed following or has been refractory to at least 3 prior therapies. In some of any of the provided embodiments, the subject has relapsed following or has been refractory to at least 4 prior therapies. In some of any of the provided embodiments, the subject has been refractory to or has not responded to bortezomib, carfilzomib, lenalidomide, pomalidomide and/or an anti-CD38 monoclonal antibody.

In some of any of the provided embodiments, the subject has had prior autologous stem cell transplant. In some of any of the provided embodiments, the subject has not had prior autologous stem cell transplant.

In some of any of the provided embodiments, the subject does not have an active or a history of plasma cell leukemia (PCL). In some of any of the provided embodiments, the subject has developed secondary plasma cell leukemia (PCL).

In some of any of the provided embodiments, the subject is an adult subject or is 25 or 35 years of age or older. In some of any of the provided embodiments, the subject is an adult subject. In some of any of the provided embodiments, the subject is 25 years of age or older. In some of any of the provided embodiments, the subject is 35 years of age or older.

In some of any of the provided embodiments, the subject has a time from diagnosis of the disease or disorder of approximately 4 years or between 2 and 15 years or between 2 and 12 years.

In some of any of the provided embodiments, the subject has IMWG high risk cytogenetics.

DETAILED DESCRIPTION

Figure 1:
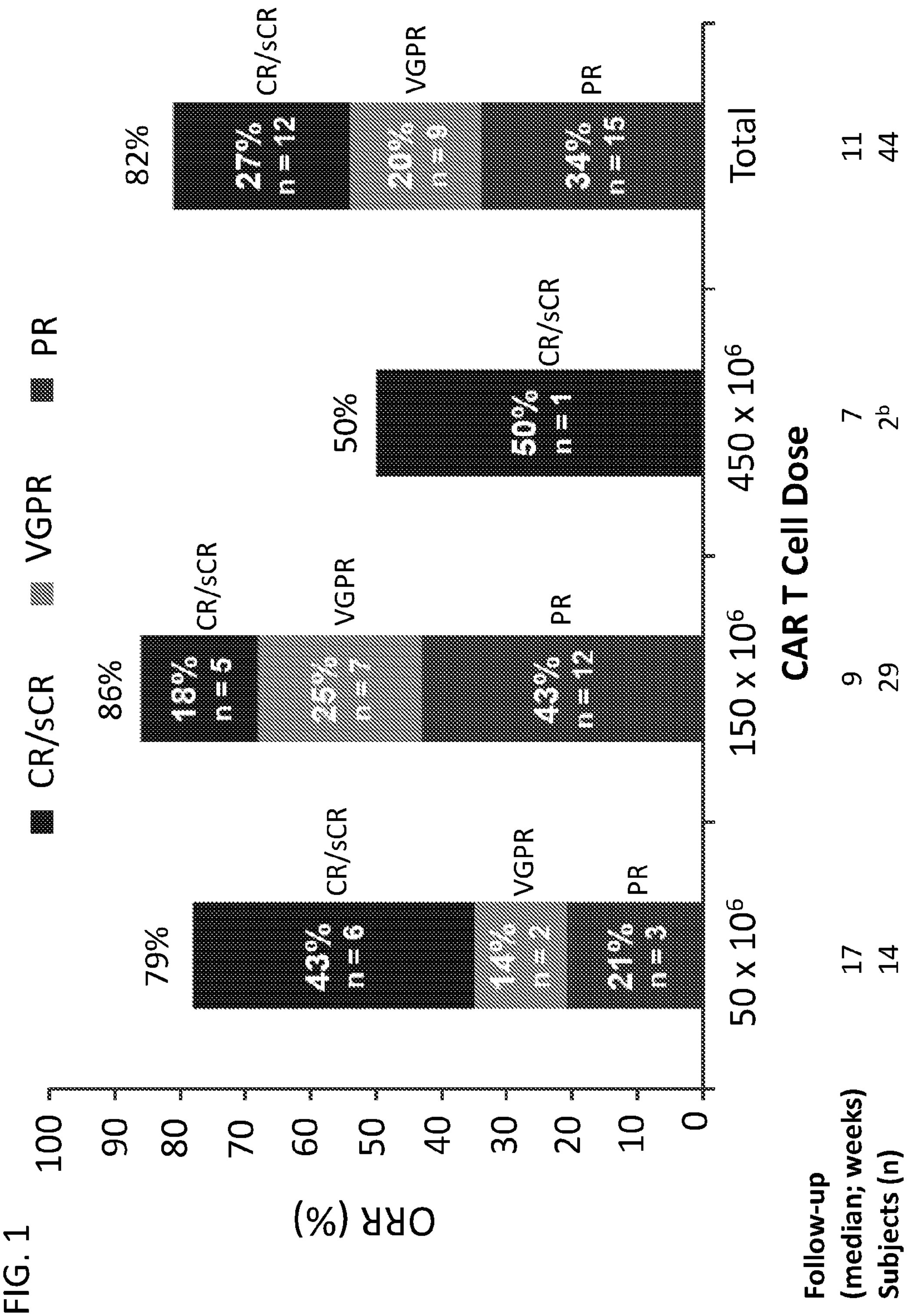
FIG. 1 shows the objective response rate (ORR), including rates of complete response (CR) and stringent complete response (sCR), very good partial response (VGPR), and partial response (PR) in human subjects with relapsed and/or refractory multiple myeloma (MM) that have been administered compositions containing autologous T cells expressing a CAR specific for B-cell maturation antigen (BCMA), at a single dose of dose level 1 (DL1) containing $5\times10^7$ total CAR+ T cells, a single dose of dose level 2 (DL2) containing $1.5\times10^8$ total CAR+ T cells, or a single dose of dose level 3 (DL3) containing $4.5\times10^8$ total CAR+ T cells. [b]One subject in the DL3 cohort was not evaluable for efficacy due to the lack of post-baseline response evaluation at Day 29.

Provided herein are methods and uses, engineered cells, compositions, combinations, articles of manufacture and compounds, including those binding, targeting or directed to B cell maturation antigen (BCMA) and BCMA-expressing cells and diseases. The provided methods can be used for treating diseases or conditions associated with BCMA. It is observed that BCMA is expressed on certain diseases and conditions such as malignancies or tissues or cells thereof, e.g., on malignant plasma cells, particularly in subjects with multiple myeloma (MM), including relapsed/refractory multiple myeloma (R/R MM), for example, with little expression on normal tissues. Among the provided embodiments are approaches useful in the treatment of such diseases and conditions and/or for targeting such cell types, including cells comprising BCMA-binding recombinant receptors, including chimeric antigen receptors (CARs), and compositions and articles of manufacture comprising the same.

In some aspects, provided are method of treatment that involve administering an interleukin-1 receptor antagonist (IL-1Ra), such as a recombinant IL-1Ra, in combination with the BCMA-targeted cell therapy. In embodiments of the provided methods, the IL-1Ra is administered just prior to, concurrently with, and/or just subsequent to administering the BCMA-targeted cell therapy (e.g. anti-BCMA CAR-T cells). In particular embodiments, at least one dose of the IL-1Ra is administered just prior to administration of the BCMA-targeted cell therapy (e.g. anti-BCMA CAR-T cells), and may be continued for a short time (e.g. up to one week or 5 days) after administration of the BCMA-targeted therapy, to reduce, prevent and/or attenuate possible toxicities associated with cell therapy. Thus, in some aspects, the provided methods provide for prophylactic treatment of toxicity that may or that could result in the subject upon administration of the BCMA-targeted cell therapy (e.g. anti-BCMA CAR-T cells) In some aspects, the provided approaches are also useful in reducing the severity of, attenuating, and/or preventing the onset of a toxicity, such as cytokine release syndrome (CRS), neurotoxicity (NT)/neurological events (NE) and/or macrophage activating syndrome (MAS), that, in some cases, may be associated with such treatments, including cell therapy, for example a cell therapy with cells comprising BCMA-binding recombinant receptors, including chimeric antigen receptors (CARs), and compositions comprising the same. In some aspects, the methods and uses delay the onset of a toxicity associated with administration of the cell therapy, optionally cytokine release syndrome (CRS), by one day or more. In some embodiments, the methods and uses delay the onset of CRS associated with administration of the cell therapy by one day or more.

In some aspects, also provided are methods of treatment that involve administering a cell therapy, for example comprising engineered cells expressing a recombinant receptor that binds, targets or is directed to BCMA, to subjects that have previously received one or more prior therapies directed to BCMA. In some aspects, subjects may have received prior therapies that are directed to BCMA, including prior treatments or therapy with BCMA-binding or BCMA-targeting agents, such as a BCMA-targeting antibody-drug conjugate (ADC), a BCMA-targeting T cell engager (TCE) or cells expressing a BCMA-targeting chimeric antigen receptor (CAR). In some aspects, the subject may not respond to, relapse following or is refractory to the prior therapies, such as prior BCMA-directed therapies. In some aspects, the provided methods and uses can be employed in subjects that did not respond to, relapsed following or became refractory to prior BCMA-directed therapies. In some aspects, the provided embodiments can lead to advantageous effects of a high response rate, low incidences of adverse events (e.g., toxicity), prolonged response, and in some cases, improvement in the response over time, for example, in subjects that did not respond to, relapsed following or became refractory to prior therapies, such as prior BCMA-directed therapies.

The methods provided herein involve administration of a dose of cells, such as containing or enriched in T cells, expressing a recombinant receptor, such as a CAR, that is directed against or binds BCMA. The BCMA-binding recombinant receptors generally can contain antigen-binding domains that include antibodies (including antigen-binding antibody fragments, such as single chain fragments, including single chain variable fragments (scFv), single domain antibody fragments, heavy chain variable ($V_H$) regions) specific for BCMA. The engineered or recombinant cells, e.g., engineered T cells, expressing such BCMA-binding recombinant receptors, e.g., anti-BCMA CARs and/or containing nucleic acids encoding such receptors, can be provided as compositions for use in the provided methods and for administering therapeutic doses containing such cells.

Adoptive cell therapies (including those involving the administration of cells expressing recombinant receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. In certain contexts, available approaches to adoptive cell therapy may not always be entirely satisfactory. In some aspects, the ability of the administered cells to recognize and bind to a target, e.g., target antigen such as BCMA, to traffic, localize to and successfully enter appropriate sites within the subject, tumors, and environments thereof, to become activated, expand, to exert various effector functions, including cytotoxic killing and secretion of various factors such as cytokines, to persist, including long-term, to differentiate, transition or engage in reprogramming into certain phenotypic states to provide effective and robust recall responses following clearance and re-exposure to target ligand or antigen, and avoid or reduce exhaustion, anergy, terminal differentiation, and/or differentiation into a suppressive state.

In some aspects, available approaches for treatment of diseases or disorders such as multiple myeloma is complex and may not always be entirely satisfactory. In some aspects, choosing a treatment regimen can depend on numerous factors including drug availability, response to prior therapy, aggressiveness of the relapse, eligibility for autologous stem cell transplantation (ASCT), and whether the relapse occurred on or off therapy. In some aspects, MM results in relapses and remissions, and existing regimen in some cases can result in relapse and/or toxicity from the treatment. In some cases, subjects with particularly aggressive disease, such as subjects that have persistent or relapsed disease after various therapies, subjects with a high disease burden, such as a high tumor burden, and/or subjects with particularly aggressive types of disease, such as plasmacytoma, can be particularly difficult to treat, and responses to certain therapies in these subjects can be poor or have a short duration. In some cases, subjects who have been heavily pre-treated, e.g., subjects who have relapsed after several different prior therapies, can exhibit a low response rate and/or high incidence of adverse events.

In some aspects, the therapeutic effect of adoptive cell therapy may be limited by the development of a toxicity (e.g., CRS, NT or MAS) in the subject to whom such cells are administered, which toxicity in some cases can be severe, at certain doses or exposure of administered cells. In some cases, while a higher dose of such cells can increase the therapeutic effect, for example, by increasing exposure to the cells such as by promoting expansion and/or persistence, they may also result in a greater risk of developing a toxicity or a more severe toxicity. In some aspects, some of the administered cells can contain cells that expand or proliferate rapidly, which also may contribute to a risk of developing a toxicity or a more severe toxicity. Also, in some cases, subjects with a higher disease burden also may be at a greater risk for developing a toxicity or a more severe toxicity. Certain available methods for dosing subjects cell therapy may not always be entirely satisfactory. Increasing a dose of cells or promoting expansion or proliferation of administered cells in the subject can be related to higher response rates, but also an increase in development of toxicity.

The provided methods involving administration of IL-1Ra (e.g., recombinant IL-1Ra) prior to and/or in combination with the BCMA-targeted cell therapy, such as for prophylactic treatment, and permits systematic management of toxicities that may be associated with immunotherapies and/or adoptive cell therapies. The provided methods offer advantages over available approaches in preventing, reducing the severity of, attenuating, ameliorating, treating, and/or preventing the onset of a toxicity, such as a CRS, NT and/or MAS that may be associated with cell therapy. In some aspects, the provided methods for reducing the severity of, attenuating, and/or preventing the onset of a toxicity involve prophylactic administration of a therapeutic agent, such as a recombinant IL-1Ra, prior to administration of a dose of cells for cell therapy. In some aspects, prophylactic administration of the additional therapeutic agent, such as a recombinant IL-1Ra, can provide an advantage of reducing the severity of, attenuating, and/or preventing the onset of a toxicity starting at the time of administration of the cell therapy, without reducing the potency or therapeutic effect of the cell therapy. In some aspects, the provided methods and uses permit dosing of cells that can achieve or can be associated with a high or specified desired degree of likelihood of a treatment outcome (e.g., a favorable outcome or response, such as a complete response, stringent complete response or very good partial response and/or a durable response or outcome), and also associated with a relatively low or minimized or desired degree of likelihood of risk of developing a toxic outcome or toxicity following administration to the subject of the cell therapy.

In some aspects, the provided methods and uses result in a cell therapy that exhibits prolonged persistence of the cells after administration of the cells, along with a high response rate and a low rate of toxicity (e.g., CRS or NE, such as grade 3 or higher CRS or grade 3 or higher neurotoxicity). In some aspects, it has been observed herein that a relatively high dose of BCMA-binding CAR-expressing cells can be administered, and such doses are observed to result in a high rate of objective response with low rate of toxicity, including very low incidence of severe toxicities (e.g., grade 3 or higher CRS or grade 3 or higher neurotoxicity). In some aspects, the provided methods can be used to further reduce the severity of, attenuate, delay or prevent the onset of toxicities, such as severe toxicities, by prophylactically administering a therapeutic agent for ameliorating toxicities. In some cases, the provided embodiments also permit improved expansion and/or persistence of the administered engineered cells, and in some cases result in prolonged response and/or response that is improved over time. In some aspects, treatment of subjects with aggressive or refractory disease (e.g., heavily pre-treated subjects, subjects with a high tumor burden and/or subjects with aggressive disease types) according to the provided embodiments, was observed to provide a safe, effective and durable treatment.

In various aspects, the BCMA-binding recombinant receptors for use in the provided methods and uses, including polynucleotides encoding such receptors, engineered cells and cell compositions, exhibit certain desired properties that can overcome or counteract certain limitations that can reduce optimal responses to cell therapy. In some aspects, cell therapy with engineered cells expressing a BCMA-binding recombinant receptor is administered to subjects that have previously received but did not respond to, relapsed after and/or became refractory to a prior BCMA-directed therapy.

In some aspects, compositions containing engineered cells expressing an exemplary BCMA-binding recombinant receptor herein was observed to exhibit consistency of cell health of the engineered cells, and was associated with improved clinical response. In some contexts, the engineered cells and cell compositions for use in the provided methods and uses, can provide various advantages over available therapies targeting BCMA, for example in preventing, reducing the severity of, attenuating, ameliorating, treating, and/or preventing the onset of a toxicity, and to improve the activity of the recombinant receptors and response to BCMA-targeting cell therapies. In addition, the provided methods and uses of the engineered cells or compositions comprising the engineered cells, has been observed to provide an advantage in treating subjects, that results in a high response rate, a durable response, and low rate of adverse events, at various different dose levels tested, including relatively high doses. Further, the provided methods and uses of the engineered cells or compositions comprising the engineered cells, has been observed to provide an advantage in treating subjects with particularly aggressive and/or refractory disease, or subjects who have relapsed and/or are refractory to numerous different prior treatments, including prior BCMA-directed treatments for the disease.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. METHODS AND USES FOR ENGINEERED CELLS EXPRESSING CHIMERIC ANTIGEN RECEPTORS SPECIFIC FOR B-CELL MATURATION ANTIGEN

Provided herein are methods of administering and uses, such as therapeutic and prophylactic uses, of engineered cells expressing B cell maturation antigen (BCMA)-binding recombinant receptors (e.g., CARs), engineered cells expressing the recombinant receptors (e.g., CARs), plurality of engineered cells expressing the receptors, and/or compositions comprising the same, such as in the treatment of diseases, conditions, and disorders. In some aspects, the disease, condition or disorder includes those in which BCMA is expressed, such as a cancer or a tumor. In some aspects, the provided methods involve administration of engineered cells or compositions thereof to subjects that have received prior treatments or therapy that is directed to BCMA, such as prior treatments or therapy with BCMA-binding or BCMA-targeting agents, such as a BCMA-targeting antibody-drug conjugate (ADC), a BCMA-targeting T cell engager (TCE) or cells expressing a BCMA-targeting chimeric antigen receptor (CAR). Among such methods, such as methods of treatment, and uses are those that involve administering to a subject engineered cells, such as a plurality of engineered cells, expressing an anti-BCMA recombinant receptor (e.g. CAR). Also provided are methods of combination therapy and/or treatment. In some aspects, also provided are prophylactic and therapeutic methods and uses that involve administration of the engineered cells or compositions thereof and an additional agent.

In some aspects, also provided are combination therapy methods that involve administration of an additional therapeutic agent, for example, a therapeutic agent for prophylactic uses for reducing the severity of, attenuating, and/or preventing the onset of a toxicity (for example, cytokine release syndrome (CRS), neurotoxicity (NT)/neurological events (NE) and/or macrophage activating syndrome (MAS) that, in some cases, may be associated with a cell therapy. In some aspects, the additional therapeutic agent is an interleukin-1 receptor antagonist (IL-1Ra), e.g., anakinra. In some aspects, the provided methods and uses include the treatment of particular subjects, such as subjects that have been previously administered a BCMA-directed therapy, such as a prior therapy that involved a BCMA-binding molecule (e.g., chimeric antigen receptors (CARs), T cell engagers, antibodies, antibody-drug conjugates). In some aspects, the provided methods allow the treatment of subjects that have previously received a prior BCMA-directed therapy, and did not respond to, relapsed after and/or become refractory to the prior BCMA-directed therapy.

Such provided methods and uses include therapeutic methods and uses, for example, involving administration of the engineered cells (e.g., expressing a recombinant receptor specific for BCMA), or compositions containing the same and/or in combination with an additional therapeutic agent (e.g., recombinant IL-1Ra), to a subject having a disease, condition, or disorder associated with BCMA such as a disease, condition, or disorder associated with BCMA expression (e.g., multiple myeloma), and/or in which cells or tissues express, e.g., specifically express, BCMA. In some embodiments, the cell and/or composition is/are administered in an effective amount to effect treatment of the disease or disorder. In some embodiments, the cell and/or the additional therapeutic agent (e.g., recombinant IL-1Ra) is/are administered in an effective amount to effect reducing the severity of, attenuating, and/or preventing the onset of a toxicity that, in some cases, may be associated with a cell therapy.

Provided herein are uses of cells (e.g., engineered cells expressing recombinant receptors such as CARs), compositions and/or an additional therapeutic agent (e.g., recombinant IL-1Ra) in such methods and treatments, and in the manufacture or preparation of a medicament in order to carry out such therapeutic and/or prophylactic methods. In some aspects, provided are engineered cells and/or compositions containing the same, for use in the manufacture of a medicament for the treatment of a disease or disorder, such as a disease or disorder associated with BCMA, for example, a multiple myeloma. In some aspects, provided are one or more additional therapeutic agents (e.g., recombinant IL-1Ra), for use in the manufacture of a medicament for reducing the severity of, attenuating, and/or preventing the onset of a toxicity that may be associated with a cell therapy, such as any cell therapy described herein. In some aspects, provided are combinations, such as combinations comprising engineered cells and/or compositions containing the same, and an additional therapeutic agent (e.g., recombinant IL-1Ra) for use in the manufacture of one or more medicament(s) for the treatment of a disease or disorder.

In some embodiments, the methods are carried out by administering the engineered cells expressing the recombinant receptor, or compositions comprising the same and/or the additional therapeutic agent (e.g., recombinant IL-1Ra), to the subject having, having had, or suspected of having the disease or condition. In some embodiments, the methods thereby treat the disease or condition or disorder in the subject. Also provided herein are use of any of the compositions, such as pharmaceutical compositions provided herein, for the treatment of a disease or disorder associated with BCMA, such as use in a treatment regimen. In some embodiments, the methods thereby reduces the severity of, attenuates, and/or prevents the onset of a toxicity that, in some cases, may be associated with a cell therapy, in a subject having a disease or disorder to be treated with engineered cells (e.g., expressing a recombinant receptor specific for BCMA) and/or compositions comprising engineered cells. Also provided herein are use of any of the compositions, such as pharmaceutical compositions provided herein, and/or combinations, such as a combination of pharmaceutical compositions provided herein, for the treatment of a disease or disorder associated with BCMA, such as use in a treatment regimen; and/or for a prophylactic treatment regiment, for example, to reduce the severity of, attenuate, and/or prevent the onset of a toxicity that, in some cases, may be associated with a cell therapy.

The provided embodiments, in some contexts, are also based on an observation from a clinical study that administration of engineered cells expressing a particular BCMA-binding recombinant receptor, such as those described herein, results in a high response rate and a low rate of adverse events such as cytokine release syndrome (CRS) or neurological events (NE; or neurotoxicity; NT). In some aspects, the provided methods and uses permit administration of a relatively high dose of the engineered cells for cell therapy, which can result in a high response rate with low adverse events.

A. Therapeutic Methods and Uses

Provided herein are methods of administering and uses, such as therapeutic uses, of engineered cells expressing BCMA-binding recombinant receptors (e.g., CARs), engineered cells expressing the recombinant receptors (e.g., CARs), plurality of engineered cells expressing the receptors, and/or compositions comprising the same.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or subject being treated. A sufficient or significant delay can, in effect, encompass prevention, in that the subject does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the engineered cells and compositions as described herein are used to delay development of a disease or to slow the progression of a disease and/or to reducing the severity of, attenuating, and/or preventing the onset of an adverse event or a side effect, e.g., a toxicity.

As used herein, to "suppress" a function or activity is to reduce the function or activity when compared to otherwise same conditions except for a condition or parameter of interest, or alternatively, as compared to another condition. For example, an antibody or composition or cell which suppresses tumor growth reduces the rate of growth of the tumor compared to the rate of growth of the tumor in the absence of the antibody or composition or cell.

An "effective amount" of an agent, e.g., a pharmaceutical formulation, antibody, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation, antibody, cells, or composition refers to an amount effective, at dosages and for periods of time necessary, to achieve a desired therapeutic result, such as for treatment of a disease, condition, or disorder, and/or pharmacokinetic or pharmacodynamics effect of the treatment. The therapeutically effective amount may vary according to factors such as the disease state, age, sex, and weight of the subject, and the populations of cells administered. In some embodiments, the provided methods involve administering the molecules, antibodies, cells, and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

As used herein, a "subject" or an "individual" is a mammal. In some embodiments, a "mammal" includes humans, non-human primates, domestic and farm animals, and zoo, sports, or pet animals, such as dogs, horses, rabbits, cattle, pigs, hamsters, gerbils, mice, ferrets, rats, cats, monkeys, etc. In some embodiments, the subject is human.

Methods for administration of cells for adoptive cell therapy are known and may be used in connection with the provided methods and compositions. For example, adoptive T cell therapy methods are described, e.g., in US Pat. App. Pub. No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

1. Subjects and Indications to be Treated

Among the diseases to be treated is any disease or disorder associated with BCMA or any disease or disorder in which BCMA is specifically expressed and/or in which BCMA has been targeted for treatment (also referred to herein interchangeably as a "BCMA-associated disease or disorder"). Cancers associated with BCMA expression include hematologic malignancies such as multiple myeloma, Waldenstrom macroglobulinemia, as well as both Hodgkin's and non-Hodgkin's lymphomas. See Coquery et al., *Crit Rev Immunol.,* 2012, 32(4):287-305 for a review of BCMA. Since BCMA has been implicated in mediating tumor cell survival, it is a potential target for cancer therapy. Chimeric antigen receptors containing mouse anti-human BCMA antibodies and cells expressing such chimeric receptors have been previously described. See Carpenter et al., *Clin Cancer Res.,* 2013, 19(8):2048-2060.

In some embodiments, the disease or disorder associated with BCMA is a B cell-related disorder. In some embodiments, the disease or disorder associated with BCMA is one or more diseases or conditions from among glioblastoma, lymphomatoid granulomatosis, post-transplant lymphoproliferative disorder, an immunoregulatory disorder, heavy-chain disease, primary or immunocyte-associated amyloidosis, or monoclonal gammopathy of undetermined significance.

In some embodiments, the disease or disorder associated with BCMA is an autoimmune disease or disorder. Such autoimmune diseases or disorder include, but are not limited to, systemic lupus erythematosus (SLE), lupus nephritis, inflammatory bowel disease, rheumatoid arthritis (e.g., juvenile rheumatoid arthritis), ANCA associated vasculitis, idiopathic thrombocytopenia purpura (ITP), thrombotic thrombocytopenia purpura (TTP), autoimmune thrombocytopenia, Chagas' disease, Grave's disease, Wegener's granulomatosis, polyarteritis nodosa, Sjogren's syndrome, pemphigus vulgaris, scleroderma, multiple sclerosis, psoriasis, IgA nephropathy, IgM polyneuropathies, vasculitis, diabetes mellitus, Reynaud's syndrome, anti-phospholipid syndrome, Goodpasture's disease, Kawasaki disease, autoimmune hemolytic anemia, myasthenia gravis, or progressive glomerulonephritis.

In certain diseases and conditions, BCMA is expressed on malignant cells and cancers. In some embodiments, the cancer (e.g., a BCMA-expressing cancer) is a B cell malignancy. In some embodiments, the cancer (e.g., a BCMA-expressing cancer) is a lymphoma, a leukemia, or a plasma cell malignancy. Lymphomas contemplated herein include, but are not limited to, Burkitt lymphoma (e.g., endemic Burkitt lymphoma or sporadic Burkitt lymphoma), non-Hodgkin's lymphoma (NHL), Hodgkin's lymphoma, Waldenstrom macroglobulinemia, follicular lymphoma, small non-cleaved cell lymphoma, mucosa-associated lymphatic tissue lymphoma (MALT), marginal zone lymphoma, splenic lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), or mantle cell lymphoma (MCL). Leukemias contemplated here, include, but are not limited to, chronic lymphocytic leukemia (CLL), plasma cell leukemia or acute lymphocytic leukemia (ALL). Also contemplated herein are plasma cell malignancies including, but not limited to, multiple myeloma (e.g., non-secretory multiple myeloma, smoldering multiple myeloma) or plasmacytoma. In some embodiments the disease or condition is multiple myeloma (MM), such as relapsed and/or refractory multiple myeloma (R/R MM). In some embodiments, the disease or condition is a plasmacytoma, such as extramedullary plasmacytoma. In some embodiments, the subject does not have a plasmacytoma, such as extramedullary plasmacytoma. Among the diseases, disorders or conditions associated with BCMA (e.g., a BCMA-expressing cancer) that can be treated include, but are not limited to, neuroblastoma, renal cell carcinoma, colon cancer, colorectal cancer, breast cancer, epithelial squamous cell cancer, melanoma, myeloma (e.g., multiple myeloma), stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer.

In some embodiments, the methods may identify a subject who has, is suspected to have, or is at risk for developing a BCMA-associated disease or disorder. Hence, provided are methods for identifying subjects with diseases or disorders associated with elevated BCMA expression and selecting them for treatment with an engineered cell expressing BCMA-binding recombinant receptors (e.g., CARs).

In some aspects, for example, a subject may be screened for the presence of a disease or disorder associated with elevated BCMA expression, such as a BCMA-expressing cancer. In some embodiments, the methods include screening for or detecting the presence of a BCMA-associated disease, e.g. a tumor or a cancer, such as multiple myeloma. Thus, in some aspects, a sample may be obtained from a patient suspected of having a disease or disorder associated with elevated BCMA expression and assayed for the expression level of BCMA. In some aspects, a subject who tests positive for a BCMA-associated disease or disorder may be selected for treatment by the present methods, and may be administered a therapeutically effective amount of engineered cells comprising the recombinant receptor (e.g., CAR) that binds to BCMA or a pharmaceutical composition thereof as described herein.

2. Prior Therapies

In some embodiments, prior to the initiation of administration of the engineered cells, the subject has received one or more prior therapies. In some aspects, the subject to be treated in accordance with the provided methods and uses include subjects that have received one or more prior therapies. In some aspects, the subject to be treated in accordance with the provided methods and uses include subjects that have received one or more prior therapies and have relapsed following and/or have become refractory to the one or more prior therapies. In some embodiments, the subject has received at least 1, 2, 3, 4, 5, 6, 7, 8, 9, 10, 11, 12, 13, 14, 15, 16, 17, 18, 19 or 20 or more prior therapies. In some embodiments, the subject has received at least 3, 4, 5, 6, 7, 8, 9, 10 or more prior therapies. In some embodiments, any one or more of the prior therapies is a BCMA-directed therapy, such as a BCMA-directed anti-myeloma therapy.

In some embodiments, the subject has received a BCMA-directed therapy prior to administration of the engineered cells. In some embodiments, prior to the initiation of administration of the engineered cells, the subject has received 1, 2 or 3 prior BCMA-directed therapies. In some embodiments, the subject has received one or more prior BCMA-directed therapy selected from among: a T-cell engager (TCE) therapy, an antibody-drug conjugate (ADC) therapy, and a chimeric antigen receptor-expressing T cell (CAR T cell) therapy. In some embodiments, the subject has received one or more prior BCMA-directed therapy selected from among: a BCMA-directed T-cell engager (TCE) therapy, a BCMA-directed antibody-drug conjugate (ADC) therapy, and a BCMA-directed CAR T-cell therapy. In some embodiments, the prior BCMA-directed therapy comprises a monoclonal antibody. In some aspects, exemplary prior BCMA-directed therapies include, but are not limited to, those described in Mullard et al., Nat Rev Drug Discov. 2019 July; 18(7):481-484; Duell et al., (2019) Clin. Pharmacol. Ther., 106: 781-791; O'Donnell et al., Ther Adv Hematol. 2017 February; 8(2): 41-53; Borrello et al., J Clin Invest. 2019; 129(6):2175-2177; Lin et al. Molecular Cancer (2019) 18:154; and Steiner et al., (2020) memo—Magazine of European Medical Oncology 13:43-49 or any BCMA-directed therapies described herein.

In some embodiments, the prior BCMA-directed therapy is an anti-BCMA monoclonal antibody. Exemplary anti-BCMA monoclonal antibody includes SEA-BCMA, an afucosylated monoclonal antibody (see, e.g., Van Epps et al., Cancer Res Jul. 1, 2018 (78) (13 Supplement) 3833; Abdallah et al., Journal of Clinical Oncology 2019 37:15_suppl, TPS8054-TPS8054).

In some of any embodiments, the subject has not responded to, has persistent or relapsed disease following, or has been or has become refractory to, one or more prior therapies. In some aspects, the subject has relapsed or has been refractory to the one or more prior therapies, for example, at the time of or prior to the administration of the cell therapy with cells expressing the BCMA-binding recombinant receptors described herein (e.g., BCMA-binding CAR). In some aspects, the subject has not responded to, has relapsed following or has been refractory to one or more prior BCMA-directed therapies. In some embodiments, the subjects to be treated in accordance with the provided methods or uses include subjects that did not respond to, have relapsed after and/or have been refractory to one or more prior BCMA-directed therapies. In some aspects, the BCMA-directed therapies include one or more of: a T-cell engager (TCE) therapy, an antibody-drug conjugate (ADC) therapy and a CAR T-cell therapy, such as any described herein. In some aspects, the subject to be treated in accordance with the provided embodiments include subjects that have relapsed following or have been refractory to one or more prior BCMA-directed therapies described herein.

In some of any of the embodiments, the subject has relapsed following or has been refractory to the prior BCMA-directed therapy within at or about 18 months, 1 year, 9 months, 6 months or 3 months prior to the administration of the dose of engineered T cells comprising the BCMA-binding CAR described herein. In some of any of the embodiments, the subject has relapsed following or has been refractory to the prior BCMA-directed therapy within at or about 1 year prior to the administration of the dose of engineered T cells comprising the BCMA-binding CAR described herein. In some of any of the embodiments, the subject has relapsed following or has been refractory to the prior BCMA-directed therapy within at or about 6 months prior to the administration of the dose of engineered T cells comprising the BCMA-binding CAR described herein. In some of any of the embodiments, the subject has relapsed following or has been refractory to the prior BCMA-directed therapy within at or about 3 months prior to the administration of the dose of engineered T cells comprising the BCMA-binding CAR described herein.

a. T Cell Engager (TCE)

In some embodiments, the prior BCMA-directed therapy is a T-cell engager (TCE) therapy. In some aspects, TCEs are antibodies which bind simultaneously to the surface of a tumor cell antigen and a component of the T-cell receptor (TCR) complex to induce T cell-mediated killing of tumor cells harboring the target surface antigen. In some aspects, after formation of a cytolytic synapse, the T cells release perforin and granzyme B, finally resulting in apoptosis of the tumor cells. Activation of T cells can lead to transient release of cytokines, which engages other immune cells and broadens the immune response against the tumor tissue and can result in proliferation of T cells and serial killing of tumor cells. Exemplary TCE therapies include bispecific T-cell engager (BiTE) therapy and bispecific antibodies (see, e.g., Mullard et al., Nat Rev Drug Discov. 2019 July; 18(7):481-484; Duell et al., (2019) Clin. Pharmacol. Ther., 106: 781-791; O'Donnell et al., Ther Adv Hematol. 2017 February; 8(2): 41-53). In some embodiments, the BCMA-directed TCE targets BCMA and CD3, for example a BiTE that includes two single-chain variable fragments (scFv), one directed against BCMA, fused to one that is directed against the CD3 antigen found on T lymphocytes.

Exemplary prior BCMA-directed TCE include, but are not limited to, AMG 420/BI 836909 (anti-BCMA/anti-CD3 BiTE; Hipp et al., Leukemia (2017) 31:1743-1751; Topp et al. Journal of Clinical Oncology. 2019. 37(15) suppl, 8007-8007), AMG 701 (a half-life extended anti-BCMA/anti-CD3 BiTE; Cho et al. Blood. 2019. 134 (Supplement_1):135; Cho et al., Clinical Lymphoma, Myeloma and Leukemia, 19(10):e54), CC-93269 (anti-BCMA/anti-CD3 bispecific antibody; Costa et al. ASH Annual Meeting. 2019. Abstract #143), JNJ-64007957 (anti-CD3/anti-BCMA bispecific monoclonal antibody; Girgis et al. Blood. 2016. 128(22): 5668), PF-06863135 (anti-CD3/anti-BCMA bispecific monoclonal antibody; Lesokhin et al., Blood (2018) 132 (Supplement 1): 3229; Raje et al., Blood (2019) 134 (Supplement_1): 1869) and REGN5458 (anti-BCMA/anti-CD3 BiTE; Cooper et al. Blood. 2019. 134 (Supplement_1): 3176).

b. Antibody-Drug Conjugate (ADC)

In some embodiments, the prior BCMA-directed therapy is an antibody-drug conjugate (ADC) therapy. ADCs include recombinant monoclonal antibodies (mAbs) covalently bound to biologically active drugs (also referred to as a "payload," e.g., cytotoxic chemicals) by chemical linkers with labile bonds, e.g., synthetic chemical linkers. In some aspects, the ADC, by virtue of the antibody moiety, identifies and binds to the antigen on the surface of target cells, such as tumor cells, and then is absorbed or internalized. After the ADC is internalized, the biologically active drug, e.g., cytotoxic chemicals, are released in the lysosomes and transported to cytosol to kill the target cells. In some aspects, ADCs can also trigger antibody-dependent cell-mediated cytotoxicity (ADCC) and antibody-dependent cellular-mediated phagocytosis of target cells, e.g., tumor cells. In some embodiments, the prior BCMA-directed therapy includes an ADC that comprises an antibody or an antigen-binding fragment thereof that is specific for, binds to and/or targets BCMA.

Exemplary prior BCMA-directed ADCs include, but are not limited to Belantamab mafodotin (GSK2857916), MEDI2228, CC-99712 and AMG 224. In some embodiments, the prior BCMA-directed ADC is Belantamab mafodotin (GSK2857916), containing a humanized, afucosylated IgG1 mAb with high affinity to BCMA ($K_D$ of ~0.5 nM) conjugated to an anti-mitotic agent, monomethyl auristatin F, via a non-cleavable linker, maleimidocaproyl (see, e.g.; Tai et al. Blood. 2014. 123(20):3128-3138). In some embodiments, the prior BCMA-directed ADC is MEDI2228, containing an anti-BCMA antibody conjugated via a protease-cleavable pyrrolobenzodiazepine linker (see, e.g.; Kinneer et al. Blood. 2017. 130 (Supplement_1): 3153; Xing et al., Blood (2019) 134 (Supplement_1): 1817). In some embodiments, the prior BCMA-directed ADC is CC-99712. In some embodiments, the prior BCMA-directed ADC is AMG 224, (anti-BCMA-MCC-DM1; anti-BCMA is an anti-human BCMA IgG1 antibody; MCC is the non-cleavable linker 4-(N-maleimidomethyl) cyclohexane-1-carboxylate conjugated to lysine residues in the antibody; and DM1 is a semi-synthetic derivative of the ansamycin antibiotic maytansine conjugated to MCC; see, e.g., O'Donnell et al., Ther Adv Hematol. 2017 February; 8(2): 41-53).

c. Chimeric Antigen Receptor (CAR)-Expressing T Cells

In some embodiments, the prior BCMA-directed therapy is a chimeric antigen receptor-expressing T cell (CAR T cell) therapy. In some embodiments, the prior BCMA-directed CAR T cell therapy comprises engineered cells, e.g., engineered T cells expressing any of the anti-BCMA recombinant receptors.

Exemplary prior BCMA-directed CAR T cell therapy include, but are not limited to Idecabtagene vicleucel (Idecel, bb2121; Raje et al. N Engl J Med. 2019. 380:1726-1737), JNJ-4528 (Madduri et al. Blood. 2019. 134 (Supplement_1): 577)/LCAR-B38M (Wang et al. Blood. 2019. 134 (Supplement_1): 579), P-BCMA-101 (Costello et al. Blood. 2019. 134 (Supplement_1): 3184), bb21217 (Berdeja et al. Blood. 2019. 134 (Supplement_1): 927), CT103A (Li et al. Blood. 2019; 134(Supplement_1):929), CT053 (Ji et al., Blood. 2019; 134(Supplement_1):4435), MTV273, CART-BCMA, C-CAR088 (Yao et al. Blood. 2019; 134(Supplement_1):50) or any BCMA-directed CAR T therapy described in, for example, WO 2018/085690; WO 2016/094304; WO 2018/085690; WO 2016/014789; WO 2019/108900; WO/2018/014038; WO 2017/173256; WO 2016/090320, WO 2016/090327, WO 2019/090003; WO 2017/025038; US 2016/0046724; US 2017/0183418; Fu et al., Blood. 2019; 134:3154; Cohen et al. J. Clin. Invest. 2019. 129(6): 2210-2221; Ali et al., Blood 2016; 128(13):1688 1700; Borrello et al., J Clin Invest. 2019; 129(6):2175-2177; Lin et al. Molecular Cancer (2019) 18:154; and Steiner et al., (2020) memo—Magazine of European Medical Oncology 13:43-49).

In some embodiments, the prior BCMA-directed CAR T cell therapy comprises engineered cells expressing any BCMA-binding recombinant receptors described herein, for example any anti-BCMA CARs described in Section III. In some aspects, the prior BCMA-directed CAR T therapy comprises engineered cells expressing an anti-BCMA CAR described in WO 2019/090003. In some aspects, the prior BCMA-directed CAR T therapy comprises engineered cells expressing an anti-BCMA CAR that contains an antigen-binding domain that is an scFv containing a variable heavy ($V_H$) region and/or a variable light ($V_L$) region derived from an antibody or an antigen-binding fragment thereof described in WO 2016/090320, WO 2016/090327, WO 2010/104949, WO 2017/173256 or Carpenter et al., *Clin Cancer Res.*, 2013, 19(8):2048-2060, each of which are hereby incorporated by reference in their entirety.

In some embodiments, the prior BCMA-directed CAR T cell therapy comprises an anti-BCMA CAR comprising a $V_H$ region comprising a CDR-H1, a CDR-H2, and a CDR-H3 comprising the amino acid sequence of SEQ ID NOs:

257, 258, and 259, respectively; and a $V_L$ region comprising a CDR-L1, CDR-L2, and CDR-L3 comprising the amino acid sequence of SEQ ID NOs:260, 261, and 262, respectively; and/or a $V_H$ region comprising the sequence set forth in SEQ ID NO:125 and a $V_L$ region comprising the sequence set forth in SEQ ID NO:127; and/or the amino acid residues 22-493 of the sequence set forth in SEQ ID NO:265, and/or the sequence encoded by SEQ ID NO:266. In some embodiments, the prior BCMA-directed CAR T cell therapy comprises an anti-BCMA CAR comprising a $V_H$ region comprising a CDR-H1, a CDR-H2, and a CDR-H3 comprising the amino acid sequence of SEQ ID NOs:260, 261, and 262, respectively; and a $V_L$ region comprising a CDR-L1, CDR-L2, and CDR-L3 comprising the amino acid sequence of SEQ ID NOs: 257, 258, and 259, respectively; and/or a $V_H$ region comprising the sequence set forth in SEQ ID NO:125 and a $V_L$ region comprising the sequence set forth in SEQ ID NO:127; and/or the amino acid residues 22-493 of the sequence set forth in SEQ ID NO:263, and/or the sequence encoded by SEQ ID NO:264. In some embodiments, the prior BCMA-directed CAR T cell therapy comprises an anti-BCMA CAR comprising the mature polypeptide sequence of the sequence set forth in SEQ ID NO:265. In some embodiments, the prior BCMA-directed CAR T cell therapy comprises an anti-BCMA CAR comprising the mature polypeptide sequence of the sequence set forth in SEQ ID NO:263. In some embodiments, the prior BCMA-directed CAR T cell therapy comprises an anti-BCMA CAR comprising the sequence set forth in SEQ ID NO:312. In some embodiments, the prior BCMA-directed CAR T cell therapy is or comprises Idecabtagene vicleucel (Ide-cel, bb2121) (see, e.g., Raje et al. N Engl J Med. 2019. 380: 1726-1737; WO 2018/085690; WO 2016/094304; WO 2018/085690 or WO 2016/014789, each of which are hereby incorporated by reference in their entirety). In some embodiments, the prior BCMA-directed CAR T cell therapy is or comprises an anti-BCMA CAR whose sequence is set forth in WO 2018/085690; WO 2016/094304; WO 2018/085690 or WO 2016/014789, each of which are hereby incorporated by reference in their entirety.

In some embodiments, the prior BCMA-directed CAR T cell therapy comprises an anti-BCMA CAR that is a multivalent CAR, such as a dual epitope-binding CAR, for example, a CAR comprising two different single-domain antibodies, e.g., VHH, directed to different epitopes on BCMA. In some aspects, the prior BCMA-directed CAR T cell therapy comprises an anti-BCMA CAR that binds to one or more epitopes of BCMA selected from among the sequences set forth in SEQ ID NOS:303-309. In some embodiments, the prior BCMA-directed CAR T cell therapy is or comprises JNJ-4528 (also called LCAR-B38M) (see, e.g., Madduri et al. Blood. 2019. 134 (Supplement_1): 577; Wang et al. Blood. 2019. 134 (Supplement_1): 579; Xu et al. PNAS 2019. 116(19) 9543-9551; Zhao et al., Journal of Hematology & Oncology 11:141 (2018); WO 2018/028647; WO 2017/025038, each of which are hereby incorporated by reference in their entirety). In some embodiments, the prior BCMA-directed CAR T cell therapy comprises a CAR comprising the amino acid residues beginning at residue 22 to the end of the sequence set forth in any one of SEQ ID NOS: 265-302, and/or the mature polypeptide sequence of the sequence set forth in any one of SEQ ID NOS: 2675-302, and/or the CAR encoded by a sequence of nucleotides that encodes the CAR set forth in any one of SEQ ID NOS: 265-302; and/or any described in WO 2018/028647 or WO 2017/025038, which are each hereby incorporated by reference in their entirety. In some embodiments, the prior BCMA-directed CAR T cell therapy comprises a CAR comprising the amino acid residues beginning at residue 22 to the end of the sequence set forth in any one of SEQ ID NOS: 265-302.

In some aspects, the prior BCMA-directed CAR T cell therapy comprises a Centyrin as an extracellular binding domain, instead of a single chain variable fragment (scFv). In some aspects, Centyrins are modified fibronectin type III (FN3) domain proteins with high specificity and a large range of binding affinities, but are smaller than an scFv (see, e.g., Goldberg et al., Protein Eng Des Sel. 2016 December; 29(12):563-572). In some embodiments, the prior BCMA-directed CAR T cell therapy is or comprises P-BCMA-101 (Costello et al. Blood. 2019. 134 (Supplement_1): 3184; Fu et al., Blood. 2019; 134:3154; WO 2018/014038 and WO 2019/173636, which are each hereby incorporated by reference in their entirety). In some embodiments, the prior BCMA-directed CAR T cell therapy comprises a CAR comprising the amino acid residues 22-334 of the sequence set forth in SEQ ID NO: 310, and/or the mature polypeptide sequence of the sequence set forth in SEQ ID NO:310, and/or the CAR encoded by a sequence of nucleotides that encodes the CAR set forth in any one of SEQ ID NO:310 and/or any described in WO 2018/014038 or WO 2019/173636, which are each hereby incorporated by reference in their entirety. In some embodiments, the prior BCMA-directed CAR T cell therapy comprises a CAR comprising the amino acid residues 22-334 of the sequence set forth in SEQ ID NO: 310.

For subjects that have received a prior adoptive cell therapy, such as a prior BCMA-directed recombinant receptor (e.g., CAR) expressing T cell therapy (CAR T cell therapy), the provided methods and uses also include assessing a sample obtained from the subject to be treated, for the presence, amount and/or level of the prior BCMA-directed recombinant receptor (e.g., CAR). In some aspects, the assessment for the presence, amount and/or level of the prior BCMA-directed recombinant receptor (e.g., CAR) can be used to detect existing cells in the subject that express the prior administered recombinant receptor-expressing cells, and if necessary, select cells that have not been previously engineered with a prior recombinant receptor or cells that do not express the prior recombinant receptor. In some aspects, such methods can be used to reduce or prevent re-engineering of cells that have already been engineered with a prior recombinant receptor (e.g., CAR).

In some of any embodiments, if cells expressing the prior BCMA-directed CAR are not present in the sample obtained from the subject, or a nucleotide sequence present in the construct encoding the prior BCMA-directed CAR is not present in the sample obtained from the subject, for example, in a sample obtained for generating the cells for engineering to express the BCMA-binding recombinant receptors provided herein, the subject is selected for administration of the cells engineered to express the BCMA-binding recombinant receptors provided herein. In some aspects, the subject is still selected for administration of the cells engineered to express the BCMA-binding recombinant receptors provided herein even though the cells expressing the prior BCMA-directed CAR are present in the sample obtained from the subject or a nucleotide sequence present in the construct encoding the prior BCMA-directed CAR is present in the sample obtained from the subject. In some aspects, the methods and uses can involve selecting T cells that do not comprise the prior BCMA-directed CAR for generating the dose of engineered T cells comprising the BCMA-binding recombinant receptors provided herein, if cells expressing the prior BCMA-directed CAR are present in the sample obtained from the subject, or a nucleotide sequence present in the construct encoding the prior BCMA-directed CAR is present in the sample obtained from the subject. In some of any embodiments, if cells expressing the prior BCMA-directed CAR are present in the sample obtained from the subject, or a nucleotide sequence present in the construct encoding the prior BCMA-directed CAR is present in the sample obtained from the subject, such cells expressing the prior BCMA-directed CAR or comprising the nucleotide encoding the prior BCMA-directed CAR, are excluded from engineering, e.g., engineering to express the BCMA-binding recombinant receptors provided herein and/or from administration, for example, excluded from the composition for administration to the subject.

In some aspects, for subjects that have received a prior BCMA-directed recombinant receptor expressing cell (e.g., CAR T cell) therapy, a sample containing primary cells obtained from the subject, for example, for engineering the cells to express the BCMA specific CAR as described herein, such as in Section III below, is assessed for the presence of the prior recombinant receptor.

In some aspects, the sample from the subject to be treated can be assessed by detecting the expression of the prior recombinant receptor or the presence of nucleic acid sequences encoding the prior recombinant receptor. In some aspects, the presence of the prior recombinant receptor can be assessed using any methods that can detect the presence, absence, level and/or amount of a protein or a nucleic acid from a biological sample. In some embodiments, the presence of the prior recombinant receptor can be assessed using any methods that can be used to assess or determine the pharmacokinetic parameters, bioavailability, persistence, expansion and/or number of engineered cells after administration of the engineered cell or cell composition to a subject, such as a subject having a disease or condition for therapy that has been administered a prior recombinant receptor expressing cell therapy, e.g., a prior BCMA-directed CAR T cell therapy.

In some aspects, a sample from the subject to be treated in accordance with the provided embodiments is assessed for the presence and/or amount of cells that have been previously engineered with a prior recombinant receptor based on the expression of the prior recombinant receptor. The presence and/or amount of cells that have been previously engineered with a prior recombinant receptor in the sample from the subject can be assessed using, for example, nucleic acid-based methods, such as quantitative PCR (qPCR); or cell-based methods, such as flow cytometry, or other assays, such as an immunoassay, ELISA, or chromatography/mass spectrometry-based assays. Prior recombinant receptors or cells expressing the prior recombinant receptors may be detected by flow cytometry-based or quantitative PCR-based methods and extrapolation to total cell numbers using known methods. See, e.g., Brentjens et al., *Sci Transl Med.* 2013 5(177), Park et al, *Molecular Therapy* 15(4):825-833 (2007), Savoldo et al., *JCI* 121(5): 1822-1826 (2011), Davila et al., (2013) *PLoS ONE* 8(4): e61338, Davila et al., *Oncoimmunology* 1(9):1577-1583 (2012), Lamers, *Blood* 2011 117:72-82, Jensen et al., *Biol Blood Marrow Transplant* 2010 September; 16(9): 1245-1256, Brentjens et al., *Blood* 2011 118(18):4817-4828.

Exemplary nucleic acid based methods to assess the presence of prior recombinant receptor include polymerase chain reaction-based methods, such as quantitative PCR (qPCR), digital PCR (dPCR) or droplet digital PCR (ddPCR). In some aspects, the presence, absence and/or amount of a particular sequence can be detected using a probe or a primer, that can specifically bind, detect, recognize and/or amplify all or a portion of the nucleic acid sequence encoding the prior recombinant receptor. In some embodiments, the primers or probe used for qPCR or other nucleic acid-based methods are specific for binding, recognizing and/or amplifying nucleic acids encoding the recombinant protein (e.g., the prior recombinant receptor), and/or other components or elements of the plasmid and/or vector, including regulatory elements, e.g., promoters, transcriptional and/or post-transcriptional regulatory elements or response elements, or markers, e.g., surrogate markers. In some aspects, exemplary nucleic acid based methods to assess the presence of prior recombinant receptors include high-throughput RNA sequencing (RNA-seq) or other high-throughput methods to assess expression of nucleic acids in a sample.

In some embodiments, for subjects that have received a prior BCMA-directed recombinant receptor expressing cell (e.g., CAR T cell) therapy, a sample containing primary cells obtained from the subject is assessed by qPCR using probes or primers that can detect and/or amplify sequences that are specific to the prior BCMA-directed recombinant receptor or other components of the nucleic acids used for engineering (e.g., regulatory elements, viral sequences, etc.). In some aspects, the primary cells from the subject are used for engineering with the BCMA-specific CAR in accordance with the methods and uses provided herein, if the sample from the subject contains low levels, for example, lower than the lower limit of detection (LLOD) of the prior recombinant receptor as detected by qPCR.

Exemplary cell- or protein-based methods to assess the presence of prior recombinant receptor include flow cytometry, an enzyme-linked immunosorbent assay (ELISA), enzyme immunoassay (EIA), radioimmunoassay (RIA), surface plasmon resonance (SPR), Western Blot, Lateral flow assay, immunohistochemistry, protein array or immuno-PCR (iPCR).

In some embodiments, for subjects that have received a prior BCMA-directed recombinant receptor expressing cell (e.g., CAR T cell) therapy, a sample containing primary cells obtained from the subject is assessed by flow cytometry using reagents such as an isolated or purified antigen, e.g., a recombinantly expressed antigen, for example, recombinant BCMA-Fc (soluble human BCMA fused at its C-terminus to an Fc region of IgG). In some aspects, the primary cells from the subject are used for engineering with the BCMA-specific CAR in accordance with the methods and uses provided herein, if the sample from the subject contains low levels, for example, lower than the lower limit of detection (LLOD) of the prior recombinant receptor as detected by flow cytometry using BCMA-Fc.

d. Other Prior Therapies and Histories

In some aspects, the subject to be treated in accordance with the provided methods and uses is a subject that has relapsed following or has been refractory to the one or more prior therapies. In some aspects, the prior therapies include treatment with autologous stem cell transplant (ASCT); an immunomodulatory agent; a proteasome inhibitor; and an anti-CD38 antibody; unless the subject was not a candidate for or was contraindicated for one or more of the therapies. In some aspects, the subject has relapsed or has been refractory to the three or more prior therapies, including treatment with three or more therapies selected from (1) an autologous stem cell transplantation, (2) a proteasome inhibitor and an immunomodulatory agent, either alone or in combination, and (3) an anti-CD38 monoclonal antibody, as a part of a combination therapy or a monotherapy; unless the subject was not a candidate for or was contraindicated for one or more of the therapies. In some embodiments, the immunomodulatory agent is selected from among thalidomide, lenalidomide or pomalidomide. In some embodiments, the proteasome inhibitor is selected from among bortezomib, carfilzomib or ixazomib. In some embodiments, the anti-CD38 antibody is or comprises daratumumab. In some embodiments, the subject must have undergone at least 2 consecutive cycles of treatment for each regimen unless progressive disease was the best response to the regimen.

In some aspects, a subject may be screened for the level of soluble BCMA (sBCMA), e.g., from a biological sample from the subject, such as the blood or serum. In some aspects, a subject may be screened for the level of sBCMA prior to treatment with the cell therapy. In some aspects, the methods include screening for or detecting the level or amount of sBCMA in a subject that has a disease or disorder associated with BCMA expression, e.g., a tumor or a cancer, such as multiple myeloma. In some aspects, a sample may be obtained from a patient suspected of having a disease or disorder associated with BCMA and assayed for the level or amount of sBCMA, for example, using an assay to detect soluble protein levels, such as an enzyme-linked immunosorbent assay (ELISA). In some aspects, in subjects having a multiple myeloma (MM), sBCMA levels can correlate with the proportion of plasma cells in bone marrow biopsies. In some aspects, in subjects having a multiple myeloma (MM), sBCMA levels can correlate with reduced response to treatment or shorter overall survival or progression free survival (see, e.g., Ghermezi et al., Haematologica 2017, 102(4): 785-795). In some aspects, a subject who exhibits low sBCMA levels may be selected for treatment by the present methods, and may be administered a therapeutically effective amount of engineered cells comprising the recombinant receptor (e.g., CAR) that binds to BCMA or a pharmaceutical composition thereof as described herein. In some aspects, a subject who exhibits high sBCMA levels may be selected for treatment by the present methods, and may be administered a therapeutically effective amount of engineered cells comprising the recombinant receptor (e.g., CAR) that binds to BCMA or a pharmaceutical composition thereof as described herein, wherein the antigen-binding domain of the CAR has a low affinity for binding soluble BCMA. In some embodiments, ability of the antigen-binding domain of the CAR to bind cell surface BCMA is not reduced or is not substantially reduced in the presence of sBCMA.

In some embodiments, the subject has persistent or relapsed disease, e.g., following treatment with another BCMA-specific antibody and/or cells expressing a BCMA-targeting chimeric receptor and/or other therapy, including chemotherapy, radiation, and/or hematopoietic stem cell transplantation (HSCT), e.g., allogeneic HSCT or autologous HSCT. In some embodiments, the administration effectively treats the subject despite the subject having become resistant to another BCMA-targeted therapy. In some embodiments, the subject has not relapsed but is determined to be at risk for relapse, such as at a high risk of relapse, and thus the compound or composition is administered prophylactically, e.g., to reduce the likelihood of or prevent relapse.

In some embodiments, the subject is one that is eligible for a transplant, such as is eligible for a hematopoietic stem cell transplantation (HSCT), e.g., allogeneic HSCT or autologous HSCT. In some such embodiments, the subject has not previously received a transplant, despite being eligible, prior to administration of the engineered cells expressing an BCMA-binding recombinant receptor (e.g., CAR), plurality of engineered cells expressing the receptors, and/or compositions comprising the same, as provided herein.

In some embodiments, the subject is one that is not eligible for a transplant, such as is not eligible for a hematopoietic stem cell transplantation (HSCT), e.g., allogenic HSCT or autologous HSCT. In some such embodiments, such a subject is administered the engineered cells expressing an BCMA-binding recombinant receptor (e.g., CAR), plurality of engineered cells expressing the receptors, and/or compositions comprising the same, according to the provided embodiments herein.

In some embodiments, the method can involve including or excluding particular subjects for therapy with the provided anti-BCMA antibodies, recombinant receptors and/or cells comprising such receptors, based on particular criteria, diagnosis or indication. In some embodiments, at the time of administration of the dose of cells or pre-treatment lymphodepleting chemotherapy, the subject has not had active, or a history of, plasma cell leukemia (PCL). In some embodiments, if the subject had active, or a history of, PCL at the time of administration, the subject can be excluded from being treated according to the provided methods. In some embodiments, if the subject develops a PCL, such as secondary PCL, at the time of administration, the subject can be excluded from being treated according to the provided methods. In some embodiments, the assessment for the criteria, diagnosis or indication can be performed at the time of screening the subjects for eligibility or suitability of treatment according to the provided methods, at various steps of the treatment regimen, at the time of receiving lymphodepleting therapy, and/or at or immediately prior to the initiation of administration of the engineered cells or composition thereof.

3. Administration of Engineered Cells

In some embodiments, the methods involve adoptive cell therapy, whereby genetically engineered cells expressing the recombinant receptors (e.g., CARs) that bind BCMA are administered to subjects. Such administration can promote activation of the cells (e.g., T cell activation) in a BCMA-targeted manner, such that the cells of the disease or disorder are targeted for destruction.

Thus, the provided methods and uses include methods and uses for adoptive cell therapy. In some embodiments, the methods include administration of the cells or a composition containing the cells to a subject, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of the disease or condition, such as by lessening tumor burden in a BCMA-expressing cancer.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al.

(2013) Biochem Biophys Res Commun 438(1): 84-9; Davila et al. (2013) PLoS ONE 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, to whom the cells, cell populations, or compositions are administered, is a primate, such as a human. In some embodiments, the subject, to whom the cells, cell populations, or compositions are administered, is a non-human primate (NHP). In some embodiments, the non-human primate is a monkey (e.g., cynomolgus monkey) or an ape. The subject can be male or female and can be any suitable age, including infant, juvenile, adolescent, adult, and geriatric subjects. In some embodiments, the subject is a non-primate mammal, such as a rodent (e.g., mouse, rat, etc.). In some examples, the patient or subject is a validated animal model for disease, adoptive cell therapy, and/or for assessing toxic outcomes such as cytokine release syndrome (CRS).

The engineered cells expressing a BCMA-binding recombinant receptor (e.g., CAR), plurality of engineered cells expressing the receptors, and/or compositions comprising the same, can be administered by any suitable means, for example, by injection, e.g., intravenous or subcutaneous injections, intraocular injection, periocular injection, subretinal injection, intravitreal injection, trans-septal injection, subscleral injection, intrachoroidal injection, intracameral injection, subconjunctival injection, subconjunctival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, intracranial, intrathoracic, or subcutaneous administration. Dosing and administration may depend in part on whether the administration is brief or chronic. Various dosing schedules include but are not limited to single or multiple administrations over various time-points, bolus administration, and pulse infusion.

For the prevention or treatment of disease, the appropriate dosage of the engineered cells or compositions comprising the same may depend on the type of disease to be treated, the type of engineered cells or compositions comprising the same, the severity and course of the disease, whether the engineered cells or compositions comprising the same is administered for preventive or therapeutic purposes, previous therapy, the patient's clinical history and response to the recombinant receptor or cell, and the discretion of the attending physician. The compositions and molecules and cells are in some embodiments suitably administered to the patient at one time or over a series of treatments.

In some embodiments, the treatment does not induce an immune response by the subject to the therapy, and/or does not induce such a response to a degree that prevents effective treatment of the disease or condition. In some aspects, the degree of immunogenicity and/or graft versus host response is less than that observed with a different but comparable treatment. For example, in the case of adoptive cell therapy using cells expressing CARs including the provided anti-BCMA antibodies, the degree of immunogenicity in some embodiments is reduced compared to CARs including a different antibody that binds to a similar, e.g., overlapping epitope and/or that competes for binding to BCMA with the antibody, such as a mouse or monkey or rabbit or humanized antibody.

In certain embodiments, in the context of genetically engineered cells containing the recombinant receptors, a subject is administered the range of at or about 0.1 million to at or about 100 billion cells and/or that amount of cells per kilogram of body weight of the subject, such as, e.g., 0.1 million to at or about 50 billion cells (e.g., at or about 5 million cells, at or about 25 million cells, at or about 500 million cells, at or about 1 billion cells, at or about 5 billion cells, at or about 20 billion cells, at or about 30 billion cells, at or about 40 billion cells, or a range defined by any two of the foregoing values), 1 million to at or about 50 billion cells (e.g., at or about 5 million cells, at or about 25 million cells, at or about 500 million cells, at or about 1 billion cells, at or about 5 billion cells, at or about 20 billion cells, at or about 30 billion cells, at or about 40 billion cells, or a range defined by any two of the foregoing values), such as at or about 10 million to at or about 100 billion cells (e.g., at or about 20 million cells, at or about 25 million cells, at or about 30 million cells, at or about 40 million cells, at or about 50 million cells, at or about 60 million cells, at or about 70 million cells, at or about 80 million cells, at or about 90 million cells, at or about 10 billion cells, at or about 25 billion cells, at or about 50 billion cells, at or about 75 billion cells, at or about 90 billion cells, or a range defined by any two of the foregoing values), and in some cases at or about 100 million cells to at or about 50 billion cells (e.g., at or about 120 million cells, at or about 150 million cells, at or about 250 million cells, at or about 300 million cells, at or about 350 million cells, at or about 450 million cells, at or about 600 million cells, at or about 650 million cells, at or about 800 million cells, at or about 900 million cells, at or about 1.2 billion cells, at or about 3 billion cells, at or about 30 billion cells, at or about 45 billion cells) or any value in between these ranges and/or per kilogram of body weight of the subject. Again, dosages may vary depending on attributes particular to the disease or disorder and/or patient and/or other treatments.

In some embodiments, the methods comprises administering a dose of the engineered cells or a composition comprising a dose of the engineered cells. In some embodiments, the engineered cells or compositions containing engineered cells can be used in a treatment regimen, wherein the treatment regimen comprises administering a dose of the engineered cells or a composition comprising a dose of the engineered cells. In some embodiments, the dose can contain, for example, a particular number or range of recombinant receptor-expressing T cells, total T cells, or total peripheral blood mononuclear cells (PBMCs), such as any number of such cells described herein. In some embodiments, a composition containing a dose of the cells can be administered. In some aspects, the number, amount or proportion of CAR-expressing (CAR+) cells in a cell population or a cell composition can be assessed by detection of a surrogate marker, e.g., by flow cytometry or other means, or by detecting binding of a labelled molecule, such as a labelled antigen, that can specifically bind to the receptors provided herein.

In connection with the provided methods, the cells administered are immune cells engineered to express the BCMA-binding (anti-BCMA) recombinant receptor, e.g., CAR. In some embodiments the immune cells are T cells. In some embodiments, the administered cells are CD4+ T cells. In some embodiments the administered cells are CD8+ T cells. In some embodiments, the administered cells are a combination of CD4+ T cells and CD8+ T cells, such as a combination of CD4+ CAR T cells and CD8+ CAR T cells, which in some aspects are within the same vessel or cell composition or suspension. In some examples the ratio of CD4+ cells to CD8+ cells (CD4:CD8) administered, such as ratio within the suspension or composition or vessel, is 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1. In some embodiments, the ratio is between 1:3 and 3:1 or is between at or about 1:4 to at or about 4:1, or between at or about 1:3 to at or about 3:1, or between at or about 1:2 to at or about 2:1, or any of such ratios, within a tolerated error rate. In some embodiments, the ratio is between at or about 1:3 to at or about 3:1. In some embodiments, the ratio is between at or about 1:2 to at or about 2:1. In some aspects, among subjects receiving the therapy and/or among subjects from whom samples are taken and processed to produce the cell compositions, the ratio of CD4+ CAR-T cells to CD8+ CAR-T cells or ratio of CD4+ to CD8+ cells is within a desired range, such as between at or about 1:4 to at or about 4:1, or between at or about 1:3 to at or about 3:1, or between at or about 1:2 to at or about 2:1, or is within such desired ratio for a given percentage of such subjects, such as for at least 65%, at least 70%, at least 75% or at least 80% or at least 85% or at least 90% or at least 95%, of such subjects.

In some embodiments, for example, where the subject is a human, the dose includes more than at or about $1\times10^6$ total recombinant receptor (e.g., CAR)-expressing (CAR+) cells, T cells, or peripheral blood mononuclear cells (PBMCs) and fewer than at or about $2\times10^9$ total recombinant receptor (e.g., CAR)-expressing cells, T cells, or peripheral blood mononuclear cells (PBMCs), e.g., in the range of at or about $1.0\times10^7$ to at or about $1.2\times10^9$ such cells, such as at or about $1.0\times10^7$, $1.5\times10^7$, $2.0\times10^7$, $2.5\times10^7$, $5\times10^7$, $1.5\times10^8$, $3\times10^8$, $4.5\times10^8$, $6\times10^8$, $8\times10^8$ or $1.2\times10^9$ total such cells, or the range between any two of the foregoing values. In some embodiments, for example, where the subject is a human, the dose includes more than at or about $1\times10^6$ total recombinant receptor (e.g., CAR)-expressing (CAR+) cells, T cells, or peripheral blood mononuclear cells (PBMCs) and fewer than at or about $2\times10^9$ total recombinant receptor (e.g., CAR)-expressing cells, T cells, or peripheral blood mononuclear cells (PBMCs), e.g., in the range of at or about $2.5\times10^7$ to at or about $1.2\times10^9$ such cells, such as at or about $2.5\times10^7$, $5\times10^7$, $1.5\times10^8$, $3\times10^8$, $4.5\times10^8$, $6\times10^8$, $8\times10^8$ or $1.2\times10^9$ total such cells, or the range between any two of the foregoing values. In some embodiments, for example, where the subject is a human, the dose includes at or about $5\times10^7$ total recombinant receptor (e.g., CAR)-expressing cells, T cells, or peripheral blood mononuclear cells (PBMCs). In some embodiments, for example, where the subject is a human, the dose includes at or about $1.5\times10^8$ total recombinant receptor (e.g., CAR)-expressing cells, T cells, or peripheral blood mononuclear cells (PBMCs). In some embodiments, for example, where the subject is a human, the dose includes at or about $3\times10^8$ total recombinant receptor (e.g., CAR)-expressing cells, T cells, or peripheral blood mononuclear cells (PBMCs). In some embodiments, for example, where the subject is a human, the dose includes at or about $4.5\times10^8$ total recombinant receptor (e.g., CAR)-expressing cells, T cells, or peripheral blood mononuclear cells (PBMCs). In some embodiments, for example, where the subject is a human, the dose includes at or about $6\times10^8$ total recombinant receptor (e.g., CAR)-expressing cells, T cells, or peripheral blood mononuclear cells (PBMCs). In some embodiments, for example, where the subject is a human, the dose includes at or about $8\times10^8$ total recombinant receptor (e.g., CAR)-expressing cells, T cells, or peripheral blood mononuclear cells (PBMCs). In some embodiments, for example, where the subject is a human, the dose includes at or about $1.2\times10^9$ total recombinant receptor (e.g., CAR)-expressing cells, T cells, or peripheral blood mononuclear cells (PBMCs).

In some embodiments, the dose of genetically engineered cells comprises from at or about $1\times10^5$ to at or about $2\times10^9$ total CAR-expressing (CAR+) T cells, from at or about $1\times10^5$ to at or about $5\times10^8$ total CAR+ T cells, from at or about $1\times10^5$ to at or about $2.5\times10^8$ total CAR+ T cells, from at or about $1\times10^5$ to at or about $1\times10^8$ total CAR+ T cells, from at or about $1\times10^5$ to at or about $5\times10^7$ total CAR+ T cells, from at or about $1\times10^5$ to at or about $2.5\times10^7$ total CAR+ T cells, from at or about $1\times10^5$ to at or about $1\times10^7$ total CAR+ T cells, from at or about $1\times10^5$ to at or about $5\times10^6$ total CAR+ T cells, from at or about $1\times10^5$ to at or about $2.5\times10^6$ total CAR+ T cells, from at or about $1\times10^5$ to at or about $1\times10^6$ total CAR+ T cells, from at or about $1\times10^6$ to at or about $5\times10^8$ total CAR+ T cells, from at or about $1\times10^6$ to at or about $2.5\times10^8$ total CAR+ T cells, from at or about $1\times10^6$ to at or about $1\times10^8$ total CAR+ T cells, from at or about $1\times10^6$ to at or about $5\times10^7$ total CAR+ T cells, from at or about $1\times10^6$ to at or about $2.5\times10^7$ total CAR+ T cells, from at or about $1\times10^6$ to at or about $1\times10^7$ total CAR+ T cells, from at or about $1\times10^6$ to at or about $5\times10^6$ total CAR+ T cells, from at or about $1\times10^6$ to at or about $2.5\times10^6$ total CAR+ T cells, from at or about $2.5\times10^6$ to at or about $5\times10^8$ total CAR+ T cells, from at or about $2.5\times10^6$ to at or about $2.5\times10^8$ total CAR+ T cells, from at or about $2.5\times10^6$ to at or about $1\times10^8$ total CAR+ T cells, from at or about $2.5\times10^6$ to at or about $5\times10^7$ total CAR+ T cells, from at or about $2.5\times10^6$ to at or about $2.5\times10^7$ total CAR+ T cells, from at or about $2.5\times10^6$ to at or about $1\times10^7$ total CAR+ T cells, from at or about $2.5\times10^6$ to at or about $5\times10^6$ total CAR+ T cells, from at or about $5\times10^6$ to at or about $5\times10^8$ total CAR+ T cells, from at or about $5\times10^6$ to at or about $2.5\times10^8$ total CAR+ T cells, from at or about $5\times10^6$ to at or about $1\times10^8$ total CAR+ T cells, from at or about $5\times10^6$ to at or about $5\times10^7$ total CAR+ T cells, from at or about $5\times10^6$ to at or about $2.5\times10^7$ total CAR+ T cells, from at or about $5\times10^6$ to at or about $1\times10^7$ total CAR+ T cells, from at or about $1\times10^7$ to at or about $5\times10^8$ total CAR+ T cells, from at or about $1\times10^7$ to at or about $2.5\times10^8$ total CAR+ T cells, from at or about $1\times10^7$ to at or about $1\times10^8$ total CAR+ T cells, from at or about $1\times10^7$ to at or about $5\times10^7$ total CAR+ T cells, from at or about $1\times10^7$ to at or about $2.5\times10^7$ total CAR+ T cells, from at or about $2.5\times10^7$ to at or about $5\times10^8$ total CAR+ T cells, from at or about $2.5\times10^7$ to at or about $2.5\times10^8$ total CAR+ T cells, from at or about $2.5\times10^7$ to at or about $1\times10^8$ total CAR+ T cells, from at or about $2.5\times10^7$ to at or about $5\times10^7$ total CAR+ T cells, from at or about $5\times10^7$ to at or about $5\times10^8$ total CAR+ T cells, from at or about $5\times10^7$ to at or about $2.5\times10^8$ total CAR+ T cells, from at or about $5\times10^7$ to at or about $1\times10^8$ total CAR+ T cells, from at or about $1\times10^8$ to at or about $5\times10^8$ total CAR+ T cells, from at or about $1\times10^8$ to at or about $2.5\times10^8$ total CAR+ T cells, from at or about or $2.5\times10^8$ to at or about $5\times10^8$ total CAR+ T cells. In some embodiments, the dose of genetically engineered cells comprises from at or about $1.0\times10^7$ to at or about $8\times10^8$ total CAR+ (CAR+) T cells, from at or about $1.0\times10^7$ to at or about $6.5\times10^8$ total CAR+ T cells, from at or about $1.5\times10^7$ to at or about $6.5\times10^8$ total CAR+ T cells, from at or about $1.5\times10^7$ to at or about $6.0\times10^8$ total CAR+ T cells, from at or about $2.5\times10^7$ to at or about $6.0\times10^8$ total CAR+ T cells, or from at or about $5.0\times10^7$ to at or about $6.0\times10^8$ total CAR+ T cells. In some embodiments, the dose of genetically engineered cells comprises from at or about $0.5\times10^8$ to at or about $8\times10^8$ total CAR+ (CAR+) T cells. In some embodiments, the dose of genetically engineered cells comprises from at or about $1.5\times10^8$ to at or about $4.5\times10^8$ total CAR+ (CAR+) T cells. In some embodiments, the dose of genetically engineered cells comprises from at or about $1.5\times10^8$ to at or about $5.4\times10^8$ total CAR+ (CAR+) T cells. In some embodiments, the dose is at or about $5\times10^7$ total CAR+ cells. In some embodiments, the dose is at or about $1.0\times10^7$ total CAR+ cells. In some embodiments, the dose is at or about $1.5\times10^8$ total CAR+ cells. In some embodiments, the dose is at or about $3\times10^8$ total CAR+ cells. In some embodiments, the dose is at or about $3.5\times10^8$ total CAR+ cells. In some embodiments, the dose is at or about $4.0\times10^8$ total CAR+ cells. In some embodiments, the dose is at or about $4.5\times10^8$ total CAR+ cells. In some embodiments, the dose is at or about $5.0\times10^8$ total CAR+ cells. In some embodiments, the dose is at or about $5.4\times10^8$ total CAR+ cells. In some embodiments, the dose is at or about $5.5\times10^8$ total CAR+ cells. In some embodiments, the dose is at or about $6\times10^8$ total CAR+ cells. In some embodiments, the dose is at or about $6.5\times10^8$ total CAR+ cells. In some embodiments, the dose is at or about $7.0\times10^8$ total CAR+ cells. In some embodiments, the dose is at or about $7.5\times10^8$ total CAR+ cells. In some embodiments, the dose is at or about $8\times10^8$ total CAR+ cells. In some embodiments, the dose is at or about $1.2\times10^9$ total CAR+ cells.

In some embodiments, the dose of genetically engineered cells comprises between at or about $2.5\times10^7$ CAR+ (CAR+) T cells, total T cells, or total peripheral blood mononuclear cells (PBMCs) and at or about $1.2\times10^9$ CAR+ T cells, total T cells, or total PBMCs, between at or about $5.0\times10^7$ CAR+ T cells, total T cells, or total peripheral blood mononuclear cells (PBMCs) and at or about $6.0\times10^8$ CAR+ T cells, total T cells, or total PBMCs, between at or about $5.0\times10^7$ CAR+ T cells and at or about $4.5\times10^8$ CAR+ T cells, total T cells, or total peripheral blood mononuclear cells (PBMCs), between at or about $1.5\times10^8$ CAR+ T cells and at or about $3.0\times10^8$ CAR+ T cells, total T cells, or total PBMCs, each inclusive. In some embodiments, the number is with reference to the total number of CD3+ or CD8+, in some cases also CAR+ (e.g. CAR+) cells. In some embodiments, the dose comprises a number of cell from or from about $2.5\times10^7$ to or to about $1.2\times10^9$ CD3+ or CD8+ total T cells or CD3+ or CD8+ CAR+ cells, from or from about $5.0\times10^7$ to or to about $6.0\times10^8$ CD3+ or CD8+ total T cells or CD3+ or CD8+ CAR+ cells, from or from about $5.0\times10^7$ to or to about $4.5\times10^8$ CD3+ or CD8+ total T cells or CD3+ or CD8+ CAR+ cells, or from or from about $1.5\times10^8$ to or to about $3.0\times10^8$ CD3+ or CD8+ total T cells or CD3+ or CD8+ CAR+ cells, each inclusive.

In some embodiments, the dose of genetically engineered cells is with reference to the total number of CD3+ CAR+ (CAR+) or CD4+/CD8+ CAR+ (CAR+) cells. In some embodiments, the dose comprises a number of genetically engineered cells from or from about $1.0\times10^7$ to or to about $1.2\times10^9$ CD3+ or CD4+/CD8+ total T cells or CD3+ CAR+ or CD4+/CD8+ CAR+ cells, from or from about $1.5\times10^7$ to or to about $1.2\times10^9$ CD3+ or CD4+/CD8+ total T cells or CD3+ CAR+ or CD4+/CD8+ CAR+ cells, from or from about $2.0\times10^7$ to or to about $1.2\times10^9$ CD3+ or CD4+/CD8+ total T cells or CD3+ CAR+ or CD4+/CD8+ CAR+ cells, from or from about $2.5\times10^7$ to or to about $1.2\times10^9$ CD3+ or CD4+/CD8+ total T cells or CD3+ CAR+ or CD4+/CD8+ CAR+ cells, from or from about $5.0\times10^7$ to or to about $6.0\times10^8$ CD3+ or CD4+/CD8+ total T cells or CD3+ CAR+ or CD4+/CD8+ CAR+ cells, from or from about $5.0\times10^7$ to or to about $4.5\times10^8$ CD3+ or CD4+/CD8+ total T cells or CD3+ CAR+ or CD4+/CD8+ CAR+ cells, or from or from about $1.5\times10^8$ to or to about $3.0\times10^8$ CD3+ or CD4+/CD8+ total T cells or CD3+ CAR+ or CD4+/CD8+ CAR+ cells, each inclusive. In some embodiments, the dose comprises at or about $1.0\times10^7$, $1.5\times10^7$, $2.0\times10^7$, $2.5\times10^7$, $5\times10^7$, $1.5\times10^8$, $3\times10^8$, $4.5\times10^8$, $6\times10^8$, $8\times10^8$ or $1.2\times10^9$ CD3+ or CD4+/CD8+ total T cells or CD3+ CAR+ or CD4+/CD8+ CAR+ cells. In some embodiments, the dose comprises at or about $2.5\times10^7$, $5\times10^7$, $1.5\times10^8$, $3\times10^8$, $4.5\times10^8$, $6\times10^8$, $8\times10^8$ or $1.2\times10^9$ CD3+ CAR+ cells. In some embodiments, the dose comprises at or about $1.0\times10^7$, $1.5\times10^7$, $2.0\times10^7$, $2.5\times10^7$, $5\times10^7$, $1.5\times10^8$, $3\times10^8$, $4.5\times10^8$, $6\times10^8$, $8\times10^8$ or $1.2\times10^9$ CD4+/CD8+ CAR+ cells. In some embodiments, the dose is at or about $5\times10^7$CD3+ CAR+ cells. In some embodiments, the dose is at or about $1.5\times10^8$ CD3+ CAR+ cells. In some embodiments, the dose is at or about $3\times10^8$ CD3+ CAR+ cells. In some embodiments, the dose is at or about $4.5\times10^8$ CD3+ CAR+ cells. In some embodiments, the dose is at or about $6\times10^8$ CD3+ CAR+ cells. In some embodiments, the dose is at or about $6.5\times10^8$ CD3+ CAR+ cells. In some embodiments, the dose is at or about $8\times10^8$ CD3+ CAR+ cells. In some embodiments, the dose is at or about $1.2\times10^9$ CD3+ CAR+ cells.

In some embodiments, the dose is at or about $1.0\times10^7$ CD4+/CD8+ CAR+ cells. In some embodiments, the dose is at or about $1.5\times10^7$ CD4+/CD8+ CAR+ cells. In some embodiments, the dose is at or about $2.0\times10^7$ CD4+/CD8+ CAR+ cells. In some embodiments, the dose is at or about $2.5\times10^7$ CD4+/CD8+ CAR+ cells. In some embodiments, the dose is at or about $5\times10^7$CD4+/CD8+ CAR+ cells. In some embodiments, the dose is at or about $1.5\times10^8$ CD4+/CD8+ CAR+ cells. In some embodiments, the dose is at or about $3\times10^8$ CD4+/CD8+ CAR+ cells. In some embodiments, the dose is at or about $4.5\times10^8$ CD4+/CD8+ CAR+ cells. In some embodiments, the dose is at or about $6\times10^8$ CD4+/CD8+ CAR+ cells. In some embodiments, the dose is at or about $8\times10^8$ CD4+/CD8+ CAR+ cells. In some embodiments, the dose is at or about $1.2\times10^9$ CD4+/CD8+ CAR+ cells. In some embodiments, the dose is at or about $2.5\times10^7$ CD4+ or CD8+ CAR+ cells. In some embodiments, the dose is at or about $5\times10^7$CD4+ or CD8+ CAR+ cells. In some embodiments, the dose is at or about $1.5\times10^8$ CD4+ or CD8+ CAR+ cells. In some embodiments, the dose is at or about $3\times10^8$ CD4+ or CD8+ CAR+ cells. In some embodiments, the dose is at or about $4.5\times10^8$ CD4+ or CD8+ CAR+ cells. In some embodiments, the dose is at or about $6\times10^8$ CD4+ or CD8+ CAR+ cells. In some embodiments, the dose is at or about $6.5\times10^8$ CD4+ or CD8+ CAR+ cells. In some embodiments, the dose is at or about $8\times10^8$ CD4+ or CD8+

CAR+ cells. In some embodiments, the dose is at or about $1.2\times10^9$ CD4+ or CD8+ CAR+ cells.

In some embodiments, the T cells of the dose include CD4+ T cells, CD8+ T cells or CD4+ T cells and CD8+ T cells.

In some embodiments, for example, where the subject is human, the total of CD4+ T cells and CD8+ T cells of the dose includes between at or about $1\times10^6$ and at or about $2\times10^9$ total CAR-expressing CD4+ cells and CAR-expressing CD8+ cells, e.g., in the range of at or about $2.5\times10^7$ to at or about $1.2\times10^9$ such cells, for example, in the range of at or about $5\times10^7$ to at or about $4.5\times10^8$ such cells; such as at or about $1.0\times10^7$, at or about $2.5\times10^7$, at or about $2.0\times10^7$, at or about $2.5\times10^7$, at or about $5\times10^7$, at or about $1.5\times10^8$, at or about $3\times10^8$, at or about $4.5\times10^8$, at or about $6\times10^8$, at or about $6.5\times10^8$, at or about $8\times10^8$, or at or about $1.2\times10^9$ total such cells, or the range between any two of the foregoing values. In some embodiments, for example, where the subject is human, the CD8+ T cells of the dose, including in a dose including CD4+ T cells and CD8+ T cells, includes between at or about $1\times10^6$ and at or about $2\times10^9$ total recombinant receptor (e.g., CAR)-expressing CD8+ cells, e.g., in the range of at or about $2.5\times10^7$ to at or about $1.2\times10^9$ such cells, for example, in the range of at or about $5\times10^7$ to at or about $4.5\times10^8$ such cells; such as at or about $2.5\times10^7$, at or about $5\times10^7$, at or about $1.5\times10^8$, at or about $3\times10^8$, at or about $4.5\times10^8$, at or about $6\times10^8$, at or about $8\times10^8$, or at or about $1.2\times10^9$ total such cells, or the range between any two of the foregoing values.

In some embodiments, the dose of cells, e.g., recombinant receptor-expressing T cells, is administered to the subject as a single dose or is administered only one time within a period of two weeks, one month, three months, six months, 1 year or more. In some embodiments, the patient is administered multiple doses, and each of the doses or the total dose can be within any of the foregoing values. In some embodiments, the engineered cells for administration or composition of engineered cells for administration, exhibits properties indicative of or consistent with cell health. In some embodiments, at or about or at least at or about 70%, 75%, 80%, 85%, or 90% CAR+ cells of such dose exhibit one or more properties or phenotypes indicative of cell health or biologically active CAR cell, such as absence expression of an apoptotic marker.

In particular embodiments, the phenotype is or includes an absence of apoptosis and/or an indication the cell is undergoing the apoptotic process. Apoptosis is a process of programmed cell death that includes a series of stereotyped morphological and biochemical events that lead to characteristic cell changes and death, including blebbing, cell shrinkage, nuclear fragmentation, chromatin condensation, chromosomal DNA fragmentation, and global mRNA decay. In some aspects, early stages of apoptosis can be indicated by activation of certain caspases, e.g., 2, 8, 9, and 10. In some aspects, middle to late stages of apoptosis are characterized by further loss of membrane integrity, chromatin condensation and DNA fragmentation, include biochemical events such as activation of caspases 3, 6, and 7.

In particular embodiments, the phenotype is negative expression of one or more factors associated with programmed cell death, for example pro-apoptotic factors known to initiate apoptosis, e.g., members of the death receptor pathway, activated members of the mitochondrial (intrinsic) pathway, such as Bcl-2 family members, e.g., Bax, Bad, and Bid, and caspases. In certain embodiments, the phenotype is the absence of an indicator, e.g., an Annexin V molecule or by TUNEL staining, that will preferentially bind to cells undergoing apoptosis when incubated with or contacted to a cell composition. In some embodiments, the phenotype is or includes the expression of one or more markers that are indicative of an apoptotic state in the cell. In some embodiments, the phenotype is lack of expression and/or activation of a caspase, such as caspase 3. In some aspects, activation of caspase-3 is indicative of an increase or revival of apoptosis. In certain embodiments, caspase activation can be detected by known methods. In some embodiments, an antibody that binds specifically to an activated caspase (i.e., binds specifically to the cleaved polypeptide) can be used to detect caspase activation. In particular embodiments, the phenotype is or includes active caspase 3−. In some embodiments, the marker of apoptosis is a reagent that detects a feature in a cell that is associated with apoptosis. In certain embodiments, the reagent is an annexin V molecule.

In some embodiments, the compositions containing the engineered cells for administration contain a certain number or amount of cells that exhibit phenotypes indicative of or consistent with cell health. In some of any embodiments, less than about 25%, 20%, 15%, 10%, 9%, 8%, 7%, 6%, 5%, 4%, 3%, 2% or 1% of the CAR+ T cells in the dose of engineered T cells express a marker of apoptosis, optionally Annexin V or active Caspase 3. In some of any embodiments, less than 5%, 4%, 3%, 2% or 1% of the CAR+ T cells in the dose of engineered T cells express Annexin V or active Caspase 3.

In some embodiments, the engineered cells or compositions comprising the same are administered as part of a combination treatment, such as simultaneously with or sequentially with, in any order, another therapeutic intervention, such as another antibody or engineered cell or receptor or agent, such as a cytotoxic or therapeutic agent.

The engineered cells or compositions comprising the same in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the engineered cells or compositions comprising the same are administered prior to the one or more additional therapeutic agents. In some embodiments, the engineered cells or compositions comprising the same are administered after to the one or more additional therapeutic agents.

In some embodiments, the subject may receive a bridging therapy after leukapheresis and before lymphodepleting chemotherapy. A treating physician can determine if bridging therapy is necessary, for example for disease control, during manufacturing of the provided composition or cells. In some embodiments, bridging therapies do not include biological agents, such as antibodies (e.g., Daratumumab). In some embodiments, bridging therapies are discontinued prior to initiation of lymphodepletion. In some embodiments, bridging therapies are discontinued 1 day, 2 days 3 days, 4 days, 5 days, 7 days, 10 days, 14 days, 21 days, 28 days, 45 days, or 60 days before lymphodepletion.

Once the cells are administered to a mammal (e.g., a human), the biological activity of the engineered cell populations and/or antibodies in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., *J. Immunotherapy,* 32(7): 689-702 (2009), and Herman et al. *J. Immunological Methods,* 285 (1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load.

In certain embodiments, engineered cells are modified in any number of ways, such that their therapeutic or prophylactic efficacy is increased. For example, the engineered CAR or TCR expressed by the population in some embodiments are conjugated either directly or indirectly through a linker to a targeting moiety. The practice of conjugating compounds, e.g., the CAR or TCR, to targeting moieties is known in the art. See, for instance, Wadwa et al., *J. Drug Targeting,* 3(2):111 (1995), and U.S. Pat. No. 5,087,616, incorporated by reference in its entirety.

4. Treatment Outcomes

In some embodiments, the dose and/or frequency of administration is determined based on the outcome of the therapy, such as efficacy, response and/or safety, such as the lack or reduction of an adverse event, such as a toxicity, including CRS, NT and/or MAS.

a. Response

In some embodiments, efficacy is determined by evaluating disease status. Exemplary methods for assessing disease status include: measurement of M protein in biological fluids, such as blood and/or urine, by electrophoresis and immunofixation; quantification of sFLC (κ and λ) in blood; skeletal survey; and imaging by positron emission tomography (PET)/computed tomography (CT) in subjects with extramedullary disease. In some embodiments, disease status can be evaluated by bone marrow examination. In some examples, dose and/or frequency of administration is determined by the expansion and persistence of the recombinant receptor or cell in the blood and/or bone marrow. In some embodiments, dose and/or frequency of administration is determined based on the antitumor activity of the recombinant receptor or engineered cell. In some embodiments antitumor activity is determined by the overall response rate (ORR) and/or International Myeloma Working Group (IMWG) Uniform Response Criteria (see Kumar et al. (2016) Lancet Oncol 17(8):e328-346). In some embodiments, response is evaluated using minimal residual disease (MRD) assessment. In some embodiments, MRD can be assessed by methods such as flow cytometry and high-throughput sequencing, e.g., deep sequencing. In some aspects, subjects that have a MRD-negative disease include those exhibiting an absence of aberrant clonal plasma cells on bone marrow aspirate, ruled out by an assay with a minimum sensitivity of 1 in $10^5$ nucleated cells or higher (i.e., $10^{-5}$ sensitivity), such as flow cytometry (next-generation flow cytometry; NGF) or high-throughput sequencing, e.g., deep sequencing or next-generation sequencing (NGS).

In some aspects, sustained MRD-negative includes subjects that exhibit MRD negativity in the marrow (NGF or NGS, or both) and by imaging as defined below, confirmed a minimum of 1 year apart. Subsequent evaluations can be used to further specify the duration of negativity (e.g., MRD-negative at 5 years). In some aspects, flow MRD-negative includes subjects that exhibit an absence of phenotypically aberrant clonal plasma cells by NGF on bone marrow aspirates using the EuroFlow standard operation procedure for MRD detection in multiple myeloma (or validated equivalent method) with a minimum sensitivity of 1 in $10^5$ nucleated cells or higher. In some aspects, sequencing MRD-negative includes subjects that exhibit an absence of clonal plasma cells by NGS on bone marrow aspirate in which presence of a clone is defined as less than two identical sequencing reads obtained after DNA sequencing of bone marrow aspirates using the LymphoSIGHT platform (or validated equivalent method) with a minimum sensitivity of 1 in $10^5$ nucleated cells or higher. In some aspects, imaging plus MRD-negative includes subjects that exhibit MRD negativity as assessed by NGF or NGS plus disappearance of every area of increased tracer uptake found at baseline or a preceding PET/CT or decrease to less mediastinal blood pool SUV or decrease to less than that of surrounding normal tissue (see Kumar et al. (2016) Lancet Oncol 17(8):e328-346).

In some embodiments, response is evaluated based on the duration of response following administration of the recombinant receptor or cells. In some examples, dose and/or frequency of administration can be based on toxicity. In some embodiments, dose and/or frequency can be determined based on health-related quality of life (HRQoL) of the subject to which the recombinant receptor and/or cells is/are administered. In some embodiments, dose and/or frequency of administration can be changed, i.e., increased or decreased, based on any of the above criteria.

In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of tumor burden is specified. In some embodiments, exemplary parameters for determination include particular clinical outcomes indicative of amelioration or improvement in the tumor. Such parameters include: duration of disease control, including objective response (OR), complete response (CR), stringent complete response (sCR), very good partial response (VGPR), partial response (PR), minimal response (MR), Stable disease (SD), Progressive disease (PD) or relapse (see, e.g., International Myeloma Working Group (IMWG) Uniform Response Criteria; see Kumar et al. (2016) Lancet Oncol 17(8):e328-346), objective response rate (ORR), progression-free survival (PFS) and overall survival (OS). In some embodiments, response is evaluated using minimal residual disease (MRD) assessment. Specific thresholds for the parameters can be set to determine the efficacy of the methods provided herein. In some embodiments, the disease or disorder to be treated is multiple myeloma. In some embodiments, measurable disease criteria for multiple myeloma can include (1) serum M-protein 1 g/dL or greater; (2) Urine M-protein 200 mg or greater/24 hour; (3) involved serum free light chain (sFLC) level 10 mg/dL or greater, with abnormal κ to λ ratio. In some cases, light chain disease is acceptable only for subjects without measurable disease in the serum or urine.

In some aspects, the response to the therapy, e.g., according to the provided embodiments, can be measured at a designated time point after the initiation of administration of the cell therapy. In some embodiments, the designated time point is at or about 1, 2, 3, 6, 9, 12, 18, 24, 30 or 36 months following initiation of the administration, or within a range defined by any of the foregoing. In some embodiments, the designated time point is 4, 8, 12, 16, 20, 24, 28, 32, 36, 48 or 52 weeks following initiation of the administration, or within a range defined by any of the foregoing. In some embodiments, the designated time point is at or about 1 month following initiation of the administration. In some embodiments, the designated time point is at or about 3 months following initiation of the administration. In some embodiments, the designated time point is at or about 6 months following initiation of the administration. In some embodiments, the designated time point is at or about 9 months following initiation of the administration. In some embodiments, the designated time point is at or about 12 months following initiation of the administration.

In some embodiments, the response or outcome determined at or about 3, 6, 9 or 12 months after the designated time point is equal to or improved compared to the response or outcome determined at the initial designated time point. For example, in some aspects, if the response or outcome determined at the initial designated time point is stable disease (SD), progressive disease (PD) or relapse, the subject treated according to the provided embodiments can show an equal or improved response or outcome (e.g., exhibiting a better response outcome according to the International Myeloma Working Group (IMWG) Uniform Response Criteria; see Kumar et al. (2016) Lancet Oncol 17(8):e328-346) at a subsequent time point, after at or about 3, 6, 9 or 12 months after the initial designated time point, that is equal to the response or outcome at the initial designated time point, or a response or outcome that is objective response (OR), complete response (CR), stringent complete response (sCR), very good partial response (VGPR) or partial response (PR). In some aspects, subjects treated according to the provided embodiments can show a response or outcome that is improved between two time point of determination. In some aspects, the subject can exhibit a PR or VGPR in the initial designated time point for assessment, e.g., at 4 weeks after the initiation of administration, then exhibit an improved response, such as a CR or an sCR, at a later time point, e.g., at 12 weeks after the initiation of administration. In some respects, progression-free survival (PFS) is described as the length of time during and after the treatment of a disease, such as cancer, that a subject lives with the disease but it does not get worse. In some aspects, objective response (OR) is described as a measurable response. In some aspects, objective response rate (ORR; also known in some cases as overall response rate) is described as the proportion of patients who achieved CR or PR. In some aspects, overall survival (OS) is described as the length of time from either the date of diagnosis or the start of treatment for a disease, such as cancer, that subjects diagnosed with the disease are still alive. In some aspects, event-free survival (EFS) is described as the length of time after treatment for a cancer ends that the subject remains free of certain complications or events that the treatment was intended to prevent or delay. These events may include the return of the cancer or the onset of certain symptoms, such as bone pain from cancer that has spread to the bone, or death.

In some embodiments, the measure of duration of response (DOR) includes the time from documentation of tumor response to disease progression. In some embodiments, the parameter for assessing response can include durable response, e.g., response that persists after a period of time from initiation of therapy. In some embodiments, durable response is indicated by the response rate at approximately 1, 2, 3, 4, 5, 6, 7, 8, 9, 10, 11, 12, 18 or 24 months after initiation of therapy. In some embodiments, the response or outcome is durable for greater than at or about 3, 6, 9 or 12 months.

In some embodiments, the Eastern Cooperative Oncology Group (ECOG) performance status indicator can be used to assess or select subjects for treatment, e.g., subjects who have had poor performance from prior therapies (see, e.g., Oken et al. (1982) Am J Clin Oncol. 5:649-655). The ECOG Scale of Performance Status describes a patient's level of functioning in terms of their ability to care for themselves, daily activity, and physical ability (e.g., walking, working, etc.). In some embodiments, an ECOG performance status of 0 indicates that a subject can perform normal activity. In some aspects, subjects with an ECOG performance status of 1 exhibit some restriction in physical activity but the subject is fully ambulatory. In some aspects, patients with an ECOG performance status of 2 is more than 50% ambulatory. In some cases, the subject with an ECOG performance status of 2 may also be capable of self-care; see e.g., Sorensen et al., (1993) Br J Cancer 67(4) 773-775. In some embodiments, the subject that are to be administered according to the methods or treatment regimen provided herein include those with an ECOG performance status of 0 or 1.

In some embodiments, the administration can treat the subject despite the subject having become resistant to another therapy. In some embodiments, when administered to subjects according to the embodiments described herein, the dose or the composition is capable of achieving objective response (OR), in at least 50%, at least 60%, at least 70%, at least 80%, at least 90%, or at least 95% of subjects that were administered. In some embodiments, OR includes subjects who achieve stringent complete response (sCR), complete response (CR), very good partial response (VGPR), partial response (PR) and minimal response (MR). In some embodiments, when administered to subjects according to the embodiments described herein, the dose or the composition is capable of achieving stringent complete response (sCR), complete response (CR), very good partial response (VGPR) or partial response (PR), in at least 50%, 60%, 70%, 80%, or 85% of subjects that were administered. In some embodiments, when administered to subjects according to the embodiments described herein, the dose or the composition is capable of achieving stringent complete response (sCR) or complete response (CR) at least 20%, 30%, 40% 50%, 60% or 70% of subjects that were administered. In some embodiments, exemplary doses include about $1.0\times10^7$, $1.5\times10^7$, $2.0\times10^7$, $2.5\times10^7$, $5.0\times10^7$, $1.5\times10^8$, $3.0\times10^8$, $4.5\times10^8$, $6.0\times10^8$ or $8.0\times10^8$ CAR-expressing (CAR+) T cells. In some embodiments, exemplary doses include about $5.0\times10^7$, $1.5\times10^8$, $3.0\times10^8$, $4.5\times10^8$, $6.0\times10^8$ or $8.0\times10^8$ CAR-expressing (CAR+) T cells. In some embodiments, exemplary doses include about $5.0\times10^7$, $1.5\times10^8$, $3.0\times10^8$, $4.5\times10^8$, $6.0\times10^8$ or $8.0\times10^8$ CAR-expressing (CAR+) T cells. In some aspects, particular response to the treatment, e.g., according to the methods provided herein, can be assessed based on the International Myeloma Working Group (IMWG) Uniform Response Criteria (see Kumar et al. (2016) Lancet Oncol 17(8):e328-346).

In some embodiments, exemplary doses to achieve particular outcomes, such as OR and/or an absence of toxicity or severe toxicity, includes about $5.0\times10^7$ CAR-expressing (CAR+) T cells. In some embodiments, exemplary doses to achieve particular outcomes, such as OR and/or an absence of toxicity or severe toxicity, includes about $1.5\times10^8$ CAR+ T cells. In some embodiments, exemplary doses to achieve particular outcomes, such as OR and/or an absence of toxicity or severe toxicity, includes about $3.0\times10^8$ CAR+ T cells. In some embodiments, exemplary doses to achieve particular outcomes, such as OR and/or an absence of toxicity or severe toxicity, includes about $4.5\times10^8$ CAR+ T cells. In some embodiments, exemplary doses to achieve particular outcomes, such as OR and/or an absence of toxicity or severe toxicity, includes about $6.0\times10^8$ CAR+ T cells. In some aspects, exemplary doses to achieve particular outcomes, such as OR and/or an absence of toxicity or severe toxicity, includes about $8.0\times10^8$ CAR+ T cells b. Safety In some embodiments, toxicity, adverse events and/or side effects of treatment can be monitored and used to assess the administration of one or more additional therapeutic agents (e.g., recombinant IL-1Ra) and/or to adjust the dose and/or frequency of the additional therapeutic agent; and/or to adjust dose and/or frequency of administration of the recombinant receptor, e.g., CAR, cells, and or compositions. For example, adverse events and laboratory abnormalities can be monitored and used to adjust dose and/or frequency of administration. Adverse events include infusion reactions, cytokine release syndrome (CRS), neurotoxicity (NT), macrophage activation syndrome (MAS)/hemophagocytic lympho-histiocytosis (HLH) and tumor lysis syndrome (TLS). Any of such events can establish dose-limiting toxicities and warrant decrease in dose and/or a termination of treatment. Other side effects or adverse events which can be used as a guideline for establishing dose and/or frequency of administration include non-hematologic adverse events, which include but are not limited to fatigue, fever or febrile neutropenia, increase in transaminases for a set duration (e.g., less than or equal to 2 weeks or less than or equal to 7 days), headache, bone pain, hypotension, hypoxia, chills, diarrhea, nausea/vomiting, neurotoxicity (e.g., confusion, aphasia, seizures, convulsions, lethargy, and/or altered mental status), disseminated intravascular coagulation, other asymptomatic non-hematological clinical laboratory abnormalities, such as electrolyte abnormalities. Other side effects or adverse events which can be used as a guideline for establishing dose and/or frequency of administration include hematologic adverse events, which include but are not limited to neutropenia, leukopenia, thrombocytopenia, animal, and/or B-cell aplasia and hypogammaglobinemia.

In some embodiments, a toxic outcome in a subject to administration of a therapeutic agent (e.g. CAR T-cells) can be assessed or monitored. In some embodiments, the toxic outcome is or is associated with the presence of a toxic event, such as cytokine release syndrome (CRS), severe CRS (sCRS), macrophage activation syndrome (MAS), tumor lysis syndrome, fever of at least at or about 38 degrees Celsius for three or more days and a plasma level of C-reactive protein (CRP) of at least at or about 20 mg/dL, neurotoxicity (NT) and/or severe neurotoxicity (sNT). In some embodiments, the toxic outcome is a sign, or symptom, particular signs, and symptoms and/or quantities or degrees thereof which presence or absence may specify a particular extent, severity or level of toxicity in a subject. It is within the level of a skilled artisan to specify or determine a particular sign, symptom and/or quantities or degrees thereof that are related to an undesired toxic outcome of a therapeutic agent (e.g. CAR− T cells).

In some aspects, the toxic outcome is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure. In some aspects, fever, especially high fever (≥38.5° C. or ≥101.3° F.), is associated with CRS. In some cases, features or symptoms of CRS mimic infection. In some embodiments, infection is also considered in subjects presenting with CRS symptoms, and monitoring by cultures and empiric antibiotic therapy can be administered. Other symptoms associated with CRS can include cardiac dysfunction, adult respiratory distress syndrome, renal and/or hepatic failure, coagulopathies, disseminated intravascular coagulation, and capillary leak syndrome.

In the context of administering CAR-expressing cells, CRS typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-113, IL-6, IL-8, and IL-10. CRS has been described to be more severe in subjects with multiple myeloma with higher disease burden and is associated with increased serum cytokines including IL-6, IFN-γ, and other cytokines together with elevation of inflammatory markers, C reactive protein (CRP) and ferritin (Cohen et al., J Clin Invest. 2019:1-12; Brudno et al., Blood 2016; 127(26):3321 3330; Lee et al., Blood 2015; 126(8):104; Davila et al., Sci Transl Med 2014; 6(224):224ra225).

Exemplary signs or symptoms associated with CRS include fever, rigors, chills, hypotension, dyspnea, acute respiratory distress syndrome (ARDS), encephalopathy, aspartate transaminase (AST)/alanine transaminase (ALT) elevation, renal failure, cardiac disorders, hypoxia, neurologic disturbances, and death. Neurological complications include delirium, seizure-like activity, confusion, word-finding difficulty, aphasia, and/or becoming obtunded. Other CRS-related signs or outcomes include fatigue, nausea, headache, seizure, tachycardia, myalgias, rash, acute vascular leak syndrome, liver function impairment, and renal failure. In some aspects, CRS is associated with an increase in one or more factors such as serum-ferritin, d-dimer, aminotransferases, lactate dehydrogenase and triglycerides, or with hypofibrinogenemia or hepatosplenomegaly. Other exemplary signs or symptoms associated with CRS include hemodynamic instability, febrile neutropenia, increase in serum C-reactive protein (CRP), changes in coagulation parameters (for example, international normalized ratio (INR), prothrombin time (PTI) and/or fibrinogen), changes in cardiac and other organ function, and/or absolute neutrophil count (ANC).

In some embodiments, signs or symptoms associated with CRS include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines (e.g. IFNγ or IL-6); and/or at least one clinical sign of toxicity, such as hypotension (e.g., as measured by at least one intravenous vasoactive pressor); hypoxia (e.g., plasma oxygen ($PO_2$) levels of less than at or about 90%); and/or one or more neurologic disorders (including mental status changes, obtundation, and seizures). In some embodiments, neurotoxicity (NT) can be observed concurrently with CRS.

Exemplary CRS-related outcomes include increased or high serum levels of one or more factors, including cytokines and chemokines and other factors associated with CRS. Exemplary outcomes further include increases in synthesis or secretion of one or more of such factors. Such synthesis or secretion can be by the T cell or a cell that interacts with the T cell, such as an innate immune cell or B cell.

CRS criteria that appear to correlate with the onset of CRS to predict which patients are more likely to be at risk for developing sCRS have been developed (see Davila et al. Sci Transl Med 2014; 6(224):224ra225). Factors include fevers, hypoxia, hypotension, neurologic changes, elevated serum levels of inflammatory cytokines whose treatment-induced elevation can correlate well with both pretreatment tumor burden and sCRS symptoms. Other guidelines on the diagnosis and management of CRS are known (see e.g., Lee et al, Blood. 2014; 124(2):188-95). In some embodiments, the criteria reflective of CRS grade are those detailed in Table 1 below.

TABLE 1

Exemplary Grading Criteria for CRS

| Grade | Description of Symptoms |
|---|---|
| 1 Mild | Not life-threatening, require only symptomatic treatment such as antipyretics and anti-emetics (e.g., fever, nausea, fatigue, headache, myalgias, malaise) |
| 2 Moderate | Require and respond to moderate intervention:<br>Oxygen requirement <40%, or<br>Hypotension responsive to fluids or low dose of a single vasopressor, or<br>Grade 2 organ toxicity (by CTCAE v4.0) |
| 3 Severe | Require and respond to aggressive intervention:<br>Oxygen requirement ≥40%, or<br>Hypotension requiring high dose of a single vasopressor (e.g., norepinephrine ≥ 20 μg/kg/min, dopamine ≥ 10 μg/kg/min, phenylephrine ≥ 200 μg/kg/min, or epinephrine ≥ 10 μg/kg/min), or<br>Hypotension requiring multiple vasopressors (e.g., vasopressin + one of the above agents, or combination vasopressors equivalent to ≥20 μg/kg/min norepinephrine), or<br>Grade 3 organ toxicity or Grade 4 transaminitis (by CTCAE v4.0) |
| 4 Life-threatening | Life-threatening:<br>Requirement for ventilator support, or<br>Grade 4 organ toxicity (excluding transaminitis) |
| 5 Fatal | Death |

In some embodiments, a criteria reflective of CRS grade are those detailed in Table 2 below.

TABLE 2

Exemplary Grading Criteria for CRS

| | Symptoms/Signs | CRS Grade 1 (mild) | CRS Grade 2 (moderate) | CRS Grade 3 (severe) | CRS Grade 4 (life-threatening) |
|---|---|---|---|---|---|
| | | | CRS grade is defined by the most severe symptom (excluding fever) | | |
| Vital Signs | Temperature ≥ 38.5° C./101.3° F. | Yes | Yes | Yes | Yes |
| | SBP ≤ 90 mm Hg | N/A | Responds to IV fluid or single low-dose vasopressor[a] | Needs high-dose[a] or multiple vasopressors | Life-threatening |
| | Need for oxygen to reach $SaO_2$ > 90% | N/A | FiO2 < 40% | $FiO_2$ ≥ 40% | Needs ventilator support |
| Organ Toxicity | | N/A | Grade 2 | Grade 3 or transaminitis Grade 4 | Grade 4 (excluding transaminitis) |

In some embodiments, high-dose vasopressor therapy include those described in Table 3 below.

TABLE 3

| High dose vasopressors (all doses required for ≥3 hours) | |
|---|---|
| Vasopressor | Dose |
| Norepinephrine monotherapy | ≥20 μg/min |
| Dopamine monotherapy | ≥10 μg/kg/min |
| Phenylephrine monotherapy | ≥200 μg/min |
| Epinephrine monotherapy | ≥10 μg/min |
| If on vasopressin | Vasopressin + norepinephrine equivalent (NE) of ≥10 μg/min[a] |
| If on combination vasopressors (not vasopressin) | Norepinephrine equivalent of ≥20 μg/min[a] |

[a]VASST Trial Vasopressor Equivalent Equation: Norepinephrine equivalent dose = [norepinephrine (μg/min)] + [dopamine (μg/kg/min) ÷ 2] + [epinephrine (μg/min)] + [phenylephrine (μg/min) ÷ 10]

In some embodiments, the toxic outcome is severe CRS. In some embodiments, the toxic outcome is the absence of severe CRS (e.g. moderate or mild CRS). In some embodiments, severe CRS includes CRS with a grade of 3 or greater, such as set forth in Table 1 and Table 2. In some embodiments, severe CRS includes CRS with a grade of 2 or higher, such as grades 2, 3, 4 or 5 CRS.

In some aspects, the toxic outcome is or is associated with neurotoxicity. In some embodiments, signs or symptoms associated with a clinical risk of neurotoxicity include confusion, delirium, aphasia, expressive aphasia, obtundation, myoclonus, lethargy, altered mental status, convulsions, seizure-like activity, seizures (optionally as confirmed by electroencephalogram (EEG)), elevated levels of beta amyloid (Aβ), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli *Nature Reviews Neurology* 6, 657-666 (December 2010); National Cancer Institute—Common Toxicity Criteria version 4.03 (NCI-CTCAE v4.03). In some embodiments, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 4. In some embodiments, severe neurotoxicity includes neurotoxicity with a grade of 2 or higher, such as grades 2, 3, 4 or 5 neurotoxicity.

TABLE 4

| Exemplary Grading Criteria for neurotoxicity | |
|---|---|
| Grade | Description of Symptoms |
| 1 Asymptomatic or Mild | Mild or asymptomatic symptoms |
| 2 Moderate | Presence of symptoms that limit instrumental activities of daily living (ADL), such as preparing meals, shopping for groceries or clothes, using the telephone, managing money |
| 3 Severe | Presence of symptoms that limit self-care ADL, such as bathing, dressing and undressing, feeding self, using the toilet, taking medications |
| 4 Life-threatening | Symptoms that are life-threatening, requiring urgent intervention |
| 5 Fatal | Death |

In some aspects, neurotoxicity is may be associated with CRS or may be independent from or separate from CRS. In some aspects, neurotoxicity can be associated with early onset of CRS and rapid elevation of inflammatory cytokines both within the serum and central nervous system (CNS), possibly resulting in the disruption of the blood-brain barrier (BBB) (Gus et al., Cancer Discov 2017; 7(12):1404 1419). In some aspects, increases in peak serum IL-6, IFN-γ, and MIP-1α can be associated with neurotoxicity. In some cases, neurotoxicity is also associated with an increase in peak endogenous IL-1Ra, an endogenous inhibitor of the pro-inflammatory effects of IL-1 alpha (IL-1α) and IL-1 beta (IL-1β), which in some cases are involved in neurotoxicity. In some aspects, levels of cytokines usually associated with a systemic inflammation (e.g., IL-6, IL-10, and interferon-gamma (IFNγ)) are observed to be higher in cases of severe neurotoxicity.

In some embodiments, the toxic outcome is a dose-limiting toxicity. In some embodiments, the toxic outcome is the absence of a dose-limiting toxicity. In some embodiments, a dose-limiting toxicity (DLT) is defined as any grade 3 or higher toxicity as assessed by any known or published guidelines for assessing the particular toxicity, such as any described above and including the National Cancer Institute (NCI) Common Terminology Criteria for Adverse Events (CTCAE) version 4.0.

In some aspects, the toxicity is a macrophage activation syndrome (MAS) (also called hemophagocytic lymphohistiocytosis (HLH)). In some aspects, MAS/HLH is associated with impaired NK and cytotoxic T cell function, and has a wide range of causes, symptoms, and outcomes. In some aspects, MAS/HLH results in a hyperinflammatory response with some characteristics that overlap with CRS. In some aspects, MAS can be associated with uncontrolled activation and proliferation of administered cells and subsequent activation of macrophages. In some aspects, MAS can be characterized by high-grade, non-remitting fever, cytopenias, and hepatosplenomegaly. Exemplary observations found in MAS include elevated inflammatory cytokine levels, serum ferritin, soluble IL-2 receptor (sCD25), triglycerides, decreased circulating natural killer (NK) cells, elevated levels of transaminases, signs of acute liver failure, coagulopathy, and disseminated intravascular coagulopathy. In some aspects, there are overlap in clinical manifestations and observations between MAS and CRS, but there are also distinguishing features such as hepatosplenomegaly and lymphadenopathy. In some aspects, subjects with hematological malignancies have a higher risk of developing MAS/HLH. In some cases, subjects with MAS/HLH or CRS-related MAS/HLH-like syndrome (MALS), show elevated levels of cytokines such as IL-18, IL-8, IP-10, MCP-1, MIG, and/or MIP-1β (see, e.g., Teachy et al., Cancer Discov. 2016; 6:664-679; Shimabukuro-Vornhagen, Journal for ImmunoTherapy of Cancer. 2018; 6:56).

Exemplary signs or symptoms associated with a clinical risk of MAS/HLH include continuous high fever (≥38.5° C.) and enlarged lymphohematopoietic organs (spleno/hepatomegaly), occasionally accompanied by adenopathy, in some cases, pulmonary, neurologic, cutaneous, and gastrointestinal involvement may also be present; laboratory observations such as pancytopenia, hyperferritinemia, hypofibrinogenemia and raised D-dimer levels, hypertriglyceridemia, and abnormalities in liver function. In some aspects, ongoing infections can be a trigger for MAS/HLH, and ongoing infections are monitored using standard tests for infections caused by the most common viruses such as herpes, cytomegalovirus (CMV), and Epstein-Barr virus (EBV), and other infectious agents (e.g., mycobacteria, parasites, and fungi, particularly *Candida* and *Mucor*) is be ruled out according to specific clinical or epidemiological features. In some aspects, bone marrow aspirates are tested for signs associated with MAS/HLH.

In some aspects, exemplary diagnostic criteria for MAS/HLH can be based on the HLH-2004 consensus criteria, further revised in 2014 for HLH associated with malignancies (Lehmberg et al., Haematologica. 2015; 100(8):997-1004); in some cases, if either of the two following criteria below are met:

1. A molecular diagnosis consistent with MAS/HLH
2. Diagnostic criteria for MAS/HLH fulfilled (5 out of the 8 criteria below):
   a. high persistent fever (≥38.5° C.)
   b. splenomegaly
   c. cytopenias (affecting 2 of 3 lineages in the peripheral blood): Hemoglobin <90 g/L, platelets $<100\times10^9$/L, and neutrophils $<1.0\times10^9$/L
   d. triglycerides ≥3.0 mmol/L (i.e., 265 mg/dL) or fibrinogen ≤1.5 g/L
   e. hemophagocytosis in bone marrow, spleen, and/or lymph nodes
   f. low or absent NK-cell activity (according to local laboratory reference range)
   g. ferritin ≥500 ng/mL
   h. soluble CD25 (i.e., soluble IL-2 receptor)≥2,400 U/mL.

In some embodiments, treatment according to the provided methods can result in a lower rate and/or lower degree of toxicity, toxic outcome or symptom, toxicity-promoting profile, factor, or property, such as a symptom or outcome associated with or indicative of cytokine release syndrome (CRS) or neurotoxicity, such as severe CRS or severe neurotoxicity, or MAS/HLH, for example, compared to administration of other therapies. In some embodiments, treatment according to the provided methods can result in both a higher response rate, e.g., higher rate of OR, CR, sCR, VGPR or PR, and/or a more durable response, together with a lower rate and/or lower degree of toxicity, toxic outcome or symptom, toxicity-promoting profile, factor, or property, such as a symptom or outcome associated with or indicative of cytokine release syndrome (CRS) or neurotoxicity, such as severe CRS or severe neurotoxicity, or MAS/HLH, for example, compared to administration of other therapies. In some embodiments, treatment according to the provided methods can result in both a higher response rate and a lower rate or degree of toxicity. In some aspects, such results can also be accompanied by higher expansion or prolonged persistence of the administered cells, compared to administration of other therapies.

B. Combination Therapy

Also provided are methods of combination therapy that includes administering and uses, such as therapeutic and prophylactic uses, of the BCMA-binding recombinant receptors (e.g., CARs), engineered cells expressing the recombinant receptors (e.g., CARs), plurality of engineered cells expressing the receptors, and/or compositions comprising the same, and one or more additional therapeutic agent.

In some embodiments, the BCMA-binding recombinant receptor (e.g., chimeric antigen receptor) and/or engineered cells expressing said molecules (e.g., recombinant receptor) described herein are administered as part of a combination treatment or combination therapy, such as simultaneously with, sequentially with or intermittently with, in any order, one or more additional therapeutic intervention. In some embodiments, the one or more additional therapeutic intervention includes, for example, an antibody, an engineered cell, a receptor and/or an agent, such as a cell expressing a recombinant receptor, and/or cytotoxic or therapeutic agent, e.g., a chemotherapeutic agent. In some embodiments, the combination therapy includes administration of one or more additional agents, therapies and/or treatments, e.g., any of the additional agents, therapy and/or treatments described herein. In some embodiments, the combination therapy includes administration of one or more additional agents for treatment or therapy, such as agents for ameliorating a toxicity that may be associated with a cell therapy, such as an interleukin-1 receptor antagonist (IL-1Ra), e.g., recombinant IL-1Ra, an IL-6 targeting agent, a steroid; a lymphodepleting therapy, or other agents, such as an immunomodulatory agent, an immune checkpoint inhibitor, an adenosine pathway or adenosine receptor antagonist or agonist and/or a kinase inhibitor. In some embodiments, the combination treatment or combination therapy includes an additional treatment, such as a surgical treatment, transplant, and/or radiation therapy. Also provided are methods of combination treatment or combination therapy that includes BCMA-binding recombinant receptors (e.g., CARs), cells and/or compositions described herein and one or more additional therapeutic interventions.

In some embodiments, the additional agent enhances safety, by virtue of reducing or ameliorating adverse effects of the administered the engineered cells or compositions comprising the same. In some embodiments, the additional agent can treat the same disease, condition or a comorbidity. In some embodiments, the additional agent can ameliorate, reduce or eliminate one or more toxicities, adverse effects or side effects that are associated with administration of the cells and/or compositions, e.g., CAR-expressing cells, and in some aspects can be used in any prophylactic method provided herein. In some embodiments, the additional agent for combination treatment or combination therapy enhances, boosts and/or promotes the efficacy and/or safety of the therapeutic effect of the engineered cells or compositions comprising the same. In some embodiments, the additional agent enhances or improves the efficacy, survival or persistence of the administered cells, e.g., cells expressing the recombinant receptor. In some embodiments, the additional agent is selected from among a protein phosphatase inhibitor, a kinase inhibitor, a cytokine, an immunomodulator, or an agent that decreases the level or activity of a regulatory T (Treg) cell.

Any of the additional agents described herein can be prepared and administered as combination therapy with the engineered cells expressing any BCMA-binding recombinant receptor (e.g., CAR) described herein or compositions comprising the cells, such as in pharmaceutical compositions comprising one or more agents of the combination therapy and a pharmaceutically acceptable carrier, such as any described herein. In some embodiments, the engineered cells expressing any BCMA-binding recombinant receptor (e.g., CAR) described herein or compositions comprising the cells can be administered simultaneously, concurrently or sequentially, in any order with the additional agents, therapy or treatment, wherein such administration provides therapeutically effective levels each of the agents in the body of the subject. In some embodiments, the additional agent can be co-administered with the engineered cells expressing any BCMA-binding recombinant receptor (e.g., CAR) described herein or compositions comprising the cells, for example, as part of the same pharmaceutical composition or using the same method of delivery. In some embodiments, the additional agent is administered simultaneously with the engineered cells expressing the BCMA-binding recombinant receptors and/or compositions described herein, but in separate compositions. In some embodiments, the additional agent is an additional engineered cell, e.g., cell engineered to express a different recombinant receptor, and is administered in the same composition or in a separate composition. In some embodiments, the additional agent is incubated with the engineered cell, e.g., CAR-expressing cells, prior to administration of the cells.

In some examples, the one or more additional agents are administered subsequent to or prior to the administration of the engineered cells expressing the BCMA-binding recombinant receptors and/or compositions described herein, separated by a selected time period. In some examples, the time period is 1 day, 2 days, 3 days, 4 days, 5 days, 6 days, 1 week, 2 weeks, 3 weeks, 1 month, 2 months, or 3 months. In some examples, the one or more additional agents are administered multiple times and/or the engineered cells expressing the BCMA-binding recombinant receptors and/or compositions described herein, is administered multiple times. For example, in some embodiments, the additional agent is administered prior to the engineered cells expressing the BCMA-binding recombinant receptors and/or compositions described herein, e.g., two weeks, 12 days, 10 days, 8 days, one week, 6 days, 5 days, 4 days, 3 days, 2 days or 1 day before the administration. For example, in some embodiments, the additional agent is administered after the engineered cells expressing the BCMA-binding recombinant receptors and/or compositions described herein, e.g., two weeks, 12 days, 10 days, 8 days, one week, 6 days, 5 days, 4 days, 3 days, 2 days or 1 day after the administration.

The dose of the additional agent can be any therapeutically effective amount, e.g., any dose amount described herein, and the appropriate dosage of the additional agent may depend on the type of disease to be treated, the type, dose and/or frequency of the recombinant receptor, cell and/or composition administered, the severity and course of the disease, whether the recombinant receptor, cell and/or composition is administered for preventive or therapeutic purposes, previous therapy, the patient's clinical history and response to the recombinant receptor, cell and/or composition, and the discretion of the attending physician. The recombinant receptor, cell and/or composition and/or the additional agent and/or therapy can be administered to the patient at one time, repeated or administered over a series of treatments.

In some aspects, administration of a dose of engineered cells and/or a composition containing the engineered cells, is repeated. In some aspects, the subject receives one or more additional doses of the engineered cells and/or a composition containing the engineered cells, that is the same as the initial dose of the engineered cells and/or composition containing the engineered cells. In some aspects, the subject receives one or more additional doses of the engineered cells and/or a composition containing the engineered cells, that is different from the initial dose of the engineered cells and/or composition containing the engineered cells. In some aspects, the additional dose is higher than the initial dose. In some aspects the additional dose is lower than the initial dose. In some embodiments, the subject is only administered one dose of engineered cells and/or composition containing the engineered cells. In some embodiments, administration of a dose of engineered cells and/or a composition containing the engineered cells, is not repeated.

1. Prophylactic Therapy

In some aspects, the provided methods and uses involve administration of an additional therapy as a prophylactic therapy. In some embodiments, for prophylactic therapy, the additional agent and/or combination therapy, is administered prior to a certain event or at an earlier stage of the disease. In some aspects, the prophylactic therapy begins prior to administration of the cell therapy and/or prior to the development of an outcome of cell therapy, e.g., such as development of adverse events such as a toxicity from a cell therapy. In some embodiments, the prophylactic therapy includes preventative measures, such as a therapy for prevention of adverse events such as a toxicity after administration of the cell therapy. In some aspects, provided are methods for reducing the severity of, attenuating, and/or preventing the onset of a toxicity in a subject to be treated with a cell therapy. In some aspects, the toxicity includes a toxicity that may be associated with a cell therapy.

In some embodiments, the prophylactic therapy can enhance, boost and/or promote the safety of the therapeutic effect of the engineered cells expressing the recombinant receptor binding to BCMA as described herein and/or compositions comprising such cells. In some embodiments, the additional agent, e.g., for prophylactic therapy, enhances safety, by virtue of reducing or ameliorating adverse effects of the engineered cells or compositions. In some embodiments, the additional agent can ameliorate, reduce or eliminate one or more toxicities, adverse effects or side effects that are associated with administration of the engineered cells or compositions, e.g., CAR-expressing cells. As described above, adverse events, such as toxicities, that can be associated with cell therapy, such as adoptive cell therapy, can include cytokine release syndrome (CRS), neurotoxicity (also called neurological events; NE), and macrophage activating syndrome (MAS). In some aspects, macrophage-produced IL-1 plays a role in triggering CRS. In some aspects, CRS can also be associated with disseminated intravascular coagulation and can exhibit clinical and pathological pictures that are similar to MAS (see, e.g., Hay et al. British Journal of Haematology 2018; 183 (3): 364-374).

In some aspects, the additional agent for combination therapy is an interleukin-1 receptor antagonists (IL-1Ra). In some embodiments, the IL-1Ra is administered as a prophylactic treatment. In some aspects, the IL-1Ra is administered prior to administration of a dose of the engineered cells, e.g., T cells expressing the recombinant receptor. In some embodiments, at least one dose of the IL-1Ra is administered prior to the administration of the dose of engineered cells. In some aspects, the administration of the IL-1Ra is continued after administration of a dose of engineered cells. In some aspects, at least one dose of the IL-1Ra is administered after the administration of a dose of cells.

In some aspects, the IL-1Ra for combination therapy and/or prophylactic therapy is anakinra (Kineret) or a modified form thereof, such as an anakinra modified with an N-terminal Pro-Ala-Ser (PAS) moiety (see, e.g., Powers et al., J Biol Chem. 2020 Jan. 17; 295(3):868-882). In some aspects, the IL-1Ra is anakinra. An exemplary sequence of anakinra is set forth in SEQ ID NO:256. In some aspects, anakinra is a recombinant IL-1Ra approved for administration for subjects with moderate to severe active rheumatoid arthritis (RA) that is 18 years of age or older. IL-1 blockade through IL-1Ra can prevent severe CRS while maintaining intact antitumor efficacy of administered cell therapy. IL-1Ra can cross the blood-brain barrier, and thus can reduce the severity of neurological events, and can be used to reduce MAS/HLH. Human microglia activated by IL-1 may produce inducible nitric oxide synthase and pro-inflammatory cytokines (Tarassishin et al., Glia 62, 999-1013 (2014)), accordingly, blocking IL-1 can result in reduction or prevention of severe CRS and severe neurological events. In some aspects, administration of an IL-1Ra as a prophylactic therapy can result improvements in the onset, incidence and severity of adverse events, such as CRS, neurological events or MAS.

In some aspects, the subject receives the IL-1Ra, e.g., anakinra, as a prophylactic therapy, such as to reduce the severity of, attenuate, and/or prevent the onset of a toxicity that can be associated with an adoptive cell therapy, such as a cell therapy comprising a dose of engineered cells, for example engineered T cells comprising a chimeric antigen receptor (CAR) specific for B-cell maturation antigen (BCMA) as provided herein. In some aspects, the one or more dose of IL-1Ra administered prior to the dose of engineered T cells is a prophylactic administration.

In some of any of the embodiments, the subject receives at least one dose of the IL-1Ra prior to the dose of engineered cells. In some aspects, the cell therapy comprising a dose of engineered cells comprising a CAR specific for BCMA is administered to a subject that has already been administered at least one dose of an IL-1Ra. In some embodiments, the provided methods and uses involve administering to the subject at least one dose of an IL-1Ra prior to administering a cell therapy comprising a dose of engineered T cells comprising a CAR specific for BCMA. In some aspects, the at least one dose of IL-1Ra administered prior to the dose of engineered T cells is a prophylactic administration of the IL-1Ra.

In some of any of the provided embodiments, at least one dose of the IL-1Ra is administered to the subject within at or about 24 hours prior to the dose of engineered T cells.

In some of any embodiments, the methods and uses involve administering at least two doses of an IL-1Ra and a cell therapy comprising a dose of engineered T cells comprising a CAR specific for BCMA. In some aspects, at least one dose of the IL-1Ra is administered within at or about 24 hours prior to the dose of engineered T cells; and at least one dose of the IL-1Ra is administered after the dose of engineered T cells. In some aspects, the dose of engineered T cells comprising a CAR specific for BCMA is administered to a subject that has been administered at least one dose of an IL-1Ra within at or about 24 hour prior to the dose of engineered T cells; and administering at least one dose of the IL-1Ra is administered after the dose of engineered T cells.

In some of any of the provided embodiments, at least one dose of the IL-1Ra is administered to the subject within at or about 24 hours prior to the dose of engineered T cells. In some aspects, at least one dose of the IL-1Ra is administered to the subject within at or about 21, 18, 15, 12, 9, 6 or 3 hours, or a range defined by any of the foregoing, prior to the dose of engineered T cells. In some aspects, at least one dose of the IL-1Ra is administered to the subject within at or about 24, 21, 18, 15 or 12 hours, or a range defined by any of the foregoing, prior to the dose of engineered T cells. In some aspects, at least one dose of the IL-1Ra is administered to the subject within at or about 21 hours prior to the dose of engineered T cells. In some aspects, at least one dose of the IL-1Ra is administered to the subject within at or about 18 hours prior to the dose of engineered T cells. In some aspects, at least one dose of the IL-1Ra is administered to the subject within at or about 15 hours prior to the dose of engineered T cells. In some aspects, at least one dose of the IL-1Ra is administered to the subject within at or about 12 hours prior to the dose of engineered T cells. In some aspects, at least one dose of the IL-1Ra is administered to the subject the evening or night prior to administration of the dose of engineered T cells. In some aspects, the methods and uses involve administering at least one dose of the IL-1Ra within at or about 6, 5, 4, 3 or 2 hours prior to administration of the dose of engineered T cells. In some aspects, at least one dose of the IL-1Ra is administered within at or about 3 hours prior to administration of the dose of engineered T cells. In some of any embodiments, at least two doses of the IL-1Ra are administered prior to the administration of the dose of engineered T cells. In some aspects, one dose of IL-1Ra is administered within at or about 24 hours and one dose of IL-1Ra is administered within at or about 3 hours prior to administration of the dose of engineered T cells. In some aspects, one dose of IL-1Ra is administered within at or about 18 hours and one dose of IL-1Ra is administered within at or about 3 hours prior to administration of the dose of engineered T cells. In some aspects, one dose of IL-1Ra is administered within at or about 12 hours and one dose of IL-1Ra is administered within at or about 3 hours prior to administration of the dose of engineered T cells. In some aspects, one dose of the IL-1Ra is administered to the subject the evening or night prior to administration of the dose of engineered T cells and one dose of IL-1Ra is administered within at or about 3 hours prior to administration of the dose of engineered T cells.

In some aspects, at least two doses of the IL-1Ra are administered to the subject. In some aspects, the subject is administered at least 2, 3, 4, 5, 6, 7, 8, 9 or 10 doses of the IL-1Ra.

In some of any of the embodiments, at least one dose of the IL-1Ra is administered to the subject after administering the dose of engineered T cells. In some aspects, at least 2, 3, 4, 5, 6, 7, 8, 9 or 10 doses of the IL-1Ra is administered to the subject after administering the dose of the engineered T cells. In some aspects, at least 2, 3, 4, 5, 6, 7 or 8 doses of the IL-1Ra is administered after administering the dose of engineered T cells. In some aspects, 3, 4, 5, 6 or 7 doses of IL-1Ra is administered after the administration of the dose of engineered T cells. In some embodiments, 5 doses of IL-1Ra is administered after the administration of the dose of engineered T cells. In some embodiments, 4 doses of IL-1Ra is administered after the administration of the dose of engineered T cells.

In some of any of the embodiments, the dose of the IL-1Ra is administered daily for consecutive days. In some aspects, such doses are administered daily for consecutive days after administration of the dose of engineered T cells. In some aspects, each of the 5 doses of IL-1Ra administered after the administration of the dose of engineered T cells is administered daily for 5 consecutive days after the administration of the dose of engineered T cells. In some aspects, each of the 4 doses of IL-1Ra administered after the administration of the dose of engineered T cells is administered daily for 4 consecutive days after the administration of the dose of engineered T cells. In some aspects, the dose of engineered T cells is administered on Day 1 and one of the 4 doses of IL-1Ra administered after the administration of the dose of engineered T cells is administered on each of Day 2, Day 3, Day 4, and Day 5.

In some aspects, the subject is administered a total of 2, 3, 4, 5, 6, 7, 8, 9 or 10 doses of the IL-1Ra. In some aspects, the subject is administered a total of 5, 6, 7, 8 or 9 doses of the IL-1Ra. In some aspects, the subject is administered a total of 7 doses of the IL-1Ra. In some aspects, the subject is administered a total of 8 doses of the IL-1Ra. In some aspects, the subject is administered a total of 9 doses of the IL-1Ra.

In some of any of the provided embodiments, the daily administration of the IL-1Ra is administered at or about the same time each day. In some of any of the provided embodiments, the doses of the daily administration of the IL-1Ra are administered about 24 hours apart (q24 h).

In some aspects, the methods and uses also include administering at least one additional dose of the IL-1Ra if the subject exhibits signs or symptoms of a toxicity, or upon onset of a toxicity, such as a cytokine release syndrome (CRS), a neurotoxicity (NT) or a macrophage activation syndrome (MAS)/hemophagocytic lympho-histiocytosis (HLH). In some aspects, at least one additional dose of the IL-1Ra is administered to the subject after the administration of the engineered T cells if the subject exhibits signs or symptoms of or upon onset of a CRS. In some aspects, the at least one additional dose of the IL-1Ra is administered every two days, once daily, twice a day, three times a day or four times a day. In some aspects, the at least one additional dose of the IL-1Ra is administered twice daily. In some aspects, the at least one additional dose of the IL-1Ra is administered once daily. In some aspects, the at least one additional dose of the IL-1Ra is administered until the signs or symptoms of CRS is resolved. In some aspects, the at least one additional dose of the IL-1Ra is one additional dose. Thus, in some aspects, if the subject exhibits signs or symptoms of or upon onset of a CRS, a dose of the IL-1RA is administered twice daily. In some aspects, if the subject exhibits signs or symptoms of or upon onset of a CRS, a dose of the IL-1RA is administered about every 12 hours (q12 h).

In some of any of the embodiments, the IL-1Ra, administered in combination with the cell therapy, e.g., a cell therapy comprising a dose of engineered T cells expressing an anti-BCMA chimeric antigen receptor (CAR), is a recombinant IL-1Ra. In some aspects, the recombinant IL-1Ra is non-glycosylated. In some aspects, the recombinant IL-1Ra is anakinra. In some of any of the embodiments, the IL-1Ra comprises the sequence set forth in SEQ ID NO:256 or a sequence comprising at least 90%, 91%, 92%, 93%, 94%, 95%, 96%, 97%, 98% or 99% or higher sequence identity to SEQ ID NO:256 that retains function as an IL-1R antagonist. In some of any of the embodiments, the IL-1Ra comprises the sequence set forth in SEQ ID NO:256. In some aspects, the IL-1Ra is anakinra and each dose of anakinra is at or about 500, 400, 300, 200, 100 or 50 mg, or a range defined by any of the foregoing. In some embodiments, each of the dose of anakinra is at or about 200 mg. In some embodiments, each of the dose of anakinra is at or about 100 mg.

In some embodiments, the IL-1Ra is administered by subcutaneous administration. In some aspects, the anakinra is administered at a dose of at or about 100 mg, daily, by subcutaneous administration. In some aspects, if the subject exhibits signs or symptoms of or upon onset of a CRS, the anakinra is administered at a dose of at or about 100 mg, twice daily, by subcutaneous administration.

In some of any of the embodiments, the methods and uses involve a prophylactic administration of a recombinant IL-1Ra, such as anakinra, in combination with a cell therapy comprising engineered T cells expressing a chimeric antigen receptor (CAR) specific for BCMA as described herein (for example, comprising a $V_H$ region comprising the sequence set forth in SEQ ID NO:125 and a $V_L$ region comprising the sequence set forth in SEQ ID NO:127), to a subject that has a disease or disorder, such as a multiple myeloma (MM), e.g., a relapsed or refractory multiple myeloma (R/R MM). In some of any of the embodiments, the methods and uses involve administration of two doses of the IL-Ra, such as each dose comprising 100 mg anakinra administered subcutaneously, prior to the administration of the cell therapy, wherein one dose of the recombinant IL-1Ra is administered the night or evening before administration of the cell therapy, and one dose of the recombinant IL-1Ra is administered at or about 3 hours before the administration of the cell therapy. In some of any of the embodiments, the methods and uses also involve continuing to administer IL-1Ra after administration of the cell therapy, daily for 5 consecutive days, each dose comprising 100 mg anakinra administered subcutaneously. In some of any of the embodiments, the methods and uses also involve continuing to administer IL-1Ra after administration of the cell therapy, daily for 4 consecutive days, each dose comprising 100 mg anakinra administered subcutaneously. In some of any of the embodiments, if the subject exhibits signs or symptoms of CRS or upon onset of CRS, one or more doses of the recombinant IL-1Ra is administered, twice daily, until the resolution of the CRS. In some of any of the embodiments, the recombinant IL-1Ra is administered at or approximately the same time every day. In some of any of the embodiments, one dose of the IL-1Ra is administered about every 24 hours. In some of any of the embodiments, one dose of the IL-1Ra is administered about every 12 hours.

In some of any of the embodiments, the methods and uses involve administration of two doses of the IL-1Ra, such as each dose comprising 100 mg anakinra administered subcutaneously, prior to the administration of the cell therapy, wherein one dose of the IL-1Ra is administered the night or evening before administration of the cell therapy, and one dose of the IL-1Ra is administered at or about 3 hours before the administration of the cell therapy (Day 1), and daily administration of one dose of the IL-1Ra (e.g. q24 h), such as a dose comprising about 100 mg anakinra administered subcutaneously, on Days 2-5.

In some of any of the embodiments, the methods and uses involve administration of two doses of the IL-1Ra, such as each dose comprising 100 mg anakinra administered subcutaneously, prior to the administration of the cell therapy, wherein one dose of the recombinant IL-1Ra is administered the night or evening before administration of the cell therapy, and one dose of the IL-1Ra is administered at or about 3 hours before the administration of the cell therapy (Day 1), and if the subject exhibits signs or symptoms, or onset, of a CRS, daily administration of two doses of the IL-1Ra (e.g. q12 h), such as a dose comprising about 100 mg anakinra administered subcutaneously, on Days 2-5.

In some of any embodiments, the provided methods and uses, for example the prophylactic methods and uses, reduces the severity of, attenuates, and/or prevents the onset of a toxicity. In some of any embodiments, the toxicity is a cytokine release syndrome (CRS). In some of any embodiments, the CRS is a severe CRS or a grade 3 or higher CRS. In some of any embodiments, the toxicity is a neurotoxicity (NT). In some of any embodiments, the NT is a severe NT or a grade 2 or higher NT or a grade 3 or higher NT. In some of any embodiments, the toxicity is a macrophage activation syndrome (MAS) or a hemophagocytic lympho-histiocytosis (HLH).

In some embodiments, the methods are used for prophylactic treatment of a subject who is identified as a subject who is at risk of developing a toxicity after administration of the engineered T cells (e.g. CAR T cells). For instance, certain subjects may exhibit risk factors that render them more susceptible or likely to develop toxicity, such as severe CRS, once they are administered an adoptive T cell therapy (e.g. CAR T cells). Hence, provided are methods for identifying a subject at risk of developing a toxicity following the administration of engineered T cells (e.g CAR T cells) and selecting the subject for treatment with any of the prophylactic methods described herein prior to the subject receiving the administration of the engineered T cells (e.g. CAR T cells).

In some embodiments, the toxicity is cytokine release syndrome (CRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78. CRS criteria that appear to correlate with the onset of CRS to predict which patients are more likely to be at risk for developing sCRS have been developed (see Davilla et al. Science translational medicine. 2014; 6(224):224ra25). Exemplary features of CRS are described in Section I.4.b.

In some embodiments, the subject is selected for treatment with any of the methods described herein if the subject is identified as at risk of developing a toxicity following administration of engineered T cells (e.g. CAR T cells). In some embodiments, a subject is identified as at risk of developing a toxicity (e.g. CRS) if the subject exhibits one or more factors. In some embodiments, factors include fevers, hypoxia, hypotension, neurologic changes, and/or elevated levels of inflammatory markers. In some embodiments, an inflammatory marker is C-reactive protein (CRP), erythrocyte sedimentation rate (ESR), albumin, ferritin, β2 microglobulin (β2-M), lactate dehydrogenase (LDH), a cytokine or a chemokine. In some cases, the inflammatory marker is LDH. In some examples, the inflammatory marker is a cytokine or a chemokine that is IL-7, IL15, MIP-1alpha or TNF-alpha. In some embodiments, factors include a volumetric measure of tumor burden. In some embodiments, the volumetric measure of tumor burden is a sum of the products of diameters (SPD), longest tumor diameters (LD), sum of longest tumor diameters (SLD), tumor volume, necrosis volume, necrosis-tumor ratio (NTR), peritumoral edema (PTE), and edema-tumor ratio (ETR).

In some embodiments, a subject is identified as at risk of developing a toxicity following administration of the engineered T cells if the level of an inflammatory marker in a sample from the subject is above a threshold value. In some embodiments, the inflammatory marker is LDH. In some embodiments, the threshold value is or is about 300 units per liter, is or is about 400 units per liter, is or is about 500 units per liter or is or is about 600 units per liter. In some embodiments, the inflammatory marker is LDH, and the threshold value is or is about 300 units per liter, is or is about 400 units per liter, is or is about 500 units per liter or is or is about 600 units per liter.

In some embodiments, a subject is identified as at risk of developing a toxicity following the administration of the engineered T cells if a volumetric measure of tumor burden in the subject is above a threshold value. In some embodiments, the volumetric measure of tumor burden is SPD. In some embodiments, the threshold value is or is about 30 $cm^2$, is or is about 40 $cm^2$, is or is about 50 $cm^2$, is or is about 60 $cm^2$, or is or is about 70 $cm^2$. In some embodiments, the volumetric measure is SPD and the threshold value is or is about 30 $cm^2$,is or is about 40 $cm^2$, is or is about 50 $cm^2$, is or is about 60 $cm^2$, or is or is about 70 $cm^2$.

2. Lymphodepleting Therapy

In some embodiments, the additional therapy is a lymphodepleting therapy. Lymphodepleting chemotherapy is thought to improve engraftment and activity of recombinant receptor-expressing cells, such as CAR T cells. In some embodiments, lymphodepleting chemotherapy may enhance adoptively transferred tumor-specific T cells to proliferate in vivo through homeostatic proliferation. In some embodiments, chemotherapy may reduce or eliminate CD4+CD25+ regulatory T cells, which can suppress the function of tumor-targeted adoptively transferred T cells. In some embodiments, lymphodepleting chemotherapy prior to adoptive T-cell therapy may enhance the expression of stromal cell-derived factor 1 (SDF-1) in the bone marrow, enhancing the homing of modified T cells to the primary tumor site through binding of SDF-1 with CXCR-4 expressed on the T-cell surface. In some embodiments, lymphodepleting chemotherapy may further reduce the subject's tumor burden and potentially lower the risk and severity of CRS.

In some embodiments, lymphodepletion is performed on a subject, e.g., prior to administering engineered cells, e.g., CAR-expressing cells. In some embodiments, the lymphodepletion comprises administering one or more of melphalan, Cytoxan, cyclophosphamide, and/or fludarabine. In some embodiments, a lymphodepleting chemotherapy is administered to the subject prior to, concurrently with, or after administration (e.g., infusion) of engineered cells, e.g., CAR-expressing cells. In an example, the lymphodepleting chemotherapy is administered to the subject prior to administration of engineered cells, e.g., CAR-expressing cells. In some embodiments the lymphodepleting chemotherapy is administered 1 to 10 days prior to administration of engineered cells, such as 1, 2, 3, 4, 5, 6, 7, 8, 9, or 10 days prior to the initiation of administration of engineered cells, or at least 2 days prior, such as at least 3, 4, 5, 6, or 7 days prior, to the initiation of administration of engineered cell. In some embodiments, the subject is administered a preconditioning agent no more than 7 days prior, such as no more than 6, 5, 4, 3, or 2 days prior, to the initiation of administration of engineered cell. The number of days after lymphodepleting chemotherapy that the engineered ells are administered can be determined based on clinical or logistical circumstances. In some examples, dose adjustments or other changes to the lymphodepleting chemotherapy regimen can implemented due to a subject's health, such as the subject's underlying organ function, as determined by the treating physician.

In some embodiments, lymphodepleting chemotherapy comprises administration of a lymphodepleting agent, such as cyclophosphamide, fludarabine, or combinations thereof. In some embodiments, the subject is administered cyclophosphamide at a dose between or between about 20 mg/kg and 100 mg/kg body weight of the subject, such as between or between about 40 mg/kg and 80 mg/kg. In some aspects, the subject is administered about 60 mg/kg of cyclophosphamide. In some embodiments, the cyclophosphamide is administered once daily for one or two days. In some embodiments, where the lymphodepleting agent comprises cyclophosphamide, the subject is administered cyclophosphamide at a dose between or between about 100 mg/m$^2$ and 500 mg/m$^2$ body surface area of the subject, such as between or between about 200 mg/m$^2$ and 400 mg/m$^2$, or 250 mg/m$^2$ and 350 mg/m$^2$, inclusive. In some instances, the subject is administered about 100 mg/m$^2$ of cyclophosphamide. In some instances, the subject is administered about 150 mg/m$^2$ of cyclophosphamide. In some instances, the subject is administered about 200 mg/m$^2$ of cyclophosphamide. In some instances, the subject is administered about 250 mg/m$^2$ of cyclophosphamide. In some instances, the subject is administered about 300 mg/m$^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 2 to 4 days. In some instances, the subject is administered about 300 mg/m$^2$ body surface area of the subject, of cyclophosphamide, daily for 3 days, prior to initiation of the cell therapy. In some embodiments, the subject is administered a total of at or about 300 mg/m$^2$, 400 mg/m$^2$, 500 mg/m$^2$, 600 mg/m$^2$, 700 mg/m$^2$, 800 mg/m$^2$, 900 mg/m$^2$, 1000 mg/m$^2$, 1200 mg/m$^2$, 1500 mg/m$^2$, 1800 mg/m$^2$, 2000 mg/m$^2$, 2500 mg/m$^2$, 2700 mg/m$^2$, 3000 mg/m$^2$, 3300 mg/m$^2$, 3600 mg/m$^2$, 4000 mg/m$^2$ or 5000 mg/m$^2$ cyclophosphamide, or a range defined by any of the foregoing, prior to initiation of the cell therapy.

In some embodiments, where the lymphodepleting agent comprises fludarabine, the subject is administered fludarabine at a dose between or between about 1 mg/m$^2$ and 100 mg/m$^2$ body surface area of the subject, such as between or between about 10 mg/m$^2$ and 75 mg/m$^2$, 15 mg/m$^2$ and 50 mg/m$^2$, 20 mg/m$^2$ and 40 mg/m$^2$, or 24 mg/m$^2$ and 35 mg/m$^2$, inclusive. In some instances, the subject is administered about 10 mg/m$^2$ of fludarabine. In some instances, the subject is administered about 15 mg/m$^2$ of fludarabine. In some instances, the subject is administered about 20 mg/m$^2$ of fludarabine. In some instances, the subject is administered about 25 mg/m$^2$ of fludarabine. In some instances, the subject is administered about 30 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 2 to 4 days. In some instances, the subject is administered about 30 mg/m$^2$ body surface area of the subject, of fludarabine, daily for 3 days, prior to initiation of the cell therapy. In some embodiments, the subject is administered a total of at or about 10 mg/m$^2$, 20 mg/m$^2$, 25 mg/m$^2$, 30 mg/m$^2$, 40 mg/m$^2$, 50 mg/m$^2$, 60 mg/m$^2$, 70 mg/m$^2$, 80 mg/m$^2$, 90 mg/m$^2$, 100 mg/m$^2$, 120 mg/m$^2$, 150 mg/m$^2$, 180 mg/m$^2$, 200 mg/m$^2$, 250 mg/m$^2$, 270 mg/m$^2$, 300 mg/m$^2$, 330 mg/m$^2$, 360 mg/m$^2$, 400 mg/m$^2$ or 500 mg/m$^2$ cyclophosphamide, or a range defined by any of the foregoing, prior to initiation of the cell therapy.

In some embodiments, the lymphodepleting agent comprises a single agent, such as cyclophosphamide or fludarabine. In some embodiments, the subject is administered cyclophosphamide only, without fludarabine or other lymphodepleting agents. In some embodiments, prior to the administration, the subject has received a lymphodepleting therapy comprising the administration of cyclophosphamide at or about 200-400 mg/m$^2$ body surface area of the subject, optionally at or about 300 mg/m$^2$, daily, for 2-4 days. In some embodiments, the subject is administered fludarabine only, for example, without cyclophosphamide or other lymphodepleting agents. In some embodiments, prior to the administration, the subject has received a lymphodepleting therapy comprising the administration of fludarabine at or about 20-40 mg/m$^2$ body surface area of the subject, optionally at or about 30 mg/m$^2$, daily, for 2-4 days.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered fludarabine at or about 30 mg/m$^2$ body surface area of the subject, daily, and cyclophosphamide at or about 300 mg/m$^2$ body surface area of the subject, daily, for 3 days.

In some embodiments, antiemetic therapy, except dexamethasone or other steroids, may be given prior to lymphodepleting chemotherapy. In some embodiments, Mesna may be used for subjects with a history of hemorrhagic cystitis.

3. Other Additional Therapies

In some embodiments, pain management medication such as acetaminophen, or antihistamine, such as diphenhydramine can be administered prior to, during or after administration of the recombinant receptor, engineered T cell or a composition or dose of engineered T cells provided herein, to ameliorate or reduce or eliminate minor side effects associated with treatment. In some examples, red blood cell and platelet transfusions, and/or colony-stimulating factors can be administered reduce or eliminate one or more toxicities, adverse effects or side effects that are associated with administration of the cells and/or compositions, e.g., CAR-expressing cells. In some embodiments, prophylactic or empiric anti-infective agents (e.g., trimethoprim/sulfamethoxazole for pneumocystis pneumonia (PCP) prophylaxis, broad spectrum antibiotics, antifungals, or antiviral agents for febrile neutropenia) can be administered to treat side-effects resulting from treatment. In some examples, when necessary, prophylaxis may be provided to treat lymphopenia and/or neutropenia occurring as a result of treatment.

In some embodiments, the additional therapy, treatment or agent includes chemotherapy, radiation therapy, surgery, transplantation, adoptive cell therapy, antibodies, cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, immune checkpoint inhibitors, antibiotics, angiogenesis inhibitors, metabolic modulators or other therapeutic agents or any combination thereof. In some embodiments, the additional agent is a protein, a peptide, a nucleic acid, a small molecule agent, a cell, a toxin, a lipid, a carbohydrate or combinations thereof, or any other type of therapeutic agent, e.g. radiation. In some embodiments, the additional therapy, agent or treatment includes surgery, chemotherapy, radiation therapy, transplantation, administration of cells expressing a recombinant receptor, e.g., CAR, kinase inhibitor, immune checkpoint inhibitor, mTOR pathway inhibitor, immunosuppressive agents, immunomodulators, antibodies, immunoablative agents, antibodies and/or antigen binding fragments thereof, antibody conjugates, other antibody therapies, cytotoxins, steroids, cytokines, peptide vaccines, hormone therapy, antimetabolites, metabolic modulators, drugs that inhibit either the calcium dependent phosphatase calcineurin or the p70S6 kinase FK506) or inhibit the p70S6 kinase, alkylating agents, anthracyclines, vinca alkaloids, proteasome inhibitors, GITR agonists, protein tyrosine phosphatase inhibitors, protein kinase inhibitors, an oncolytic virus, and/or other types of immunotherapy. In some embodiments, the additional agent or treatment is bone marrow transplantation, T cell ablative therapy using chemotherapy agents such as, fludarabine, external-beam radiation therapy (XRT), cyclophosphamide, and/or antibody therapy.

In some embodiments, the cells, BCMA-binding recombinant receptors and/or compositions, e.g., CAR-expressing cells, are administered in combination with other engineered cells, e.g., other CAR-expressing cells. In some embodiments, the additional agent is a kinase inhibitor, e.g., an inhibitor of Bruton's tyrosine kinase (Btk), e.g., ibrutinib. In some embodiments, the additional agent is an adenosine pathway or adenosine receptor antagonist or agonist. In some embodiments, the additional agent is an immunomodulator such as thalidomide or a thalidomide derivative (e.g., lenalidomide). In some embodiments, the additional agent is a gamma secretase inhibitor, such as a gamma secretase inhibitor that inhibits or reduces intramembrane cleavage of a target of a gamma secretase, e.g. BCMA, on a cell (such as a tumor/cancer cell). In some embodiments, the additional therapy, agent or treatment is a cytotoxic or chemotherapy agent, a biologic therapy (e.g., antibody, e.g., monoclonal antibody, or cellular therapy), or an inhibitor (e.g., kinase inhibitor).

In some embodiments, the additional agent is a chemotherapeutic agent. Exemplary chemotherapeutic agents include an anthracycline (e.g., doxorubicin, such as liposomal doxorubicin); a vinca alkaloid (e.g., vinblastine, vincristine, vindesine, vinorelbine); an alkylating agent (e.g., cyclophosphamide, decarbazine, melphalan, ifosfamide, temozolomide); an immune cell antibody (e.g., alemtuzumab, gemtuzumab, rituximab, tositumomab); an antimetabolite (including, e.g., folic acid antagonists, pyrimidine analogs, purine analogs and adenosine deaminase inhibitors such as fludarabine); a TNFR glucocorticoid induced TNFR related protein (GITR) agonist; a proteasome inhibitor (e.g., aclacinomycin A, gliotoxin or bortezomib); an immunomodulatory such as thalidomide or a thalidomide derivative (e.g., lenalidomide).

In some embodiments, the additional therapy or treatment is cell therapy, e.g., adoptive cell therapy. In some embodiments, the additional therapy includes administration of engineered cells, e.g., additional CAR-expressing cell. In some embodiments, the additional engineered cell is a CAR-expressing cell that expresses the same or different recombinant receptor as the engineered cells provided herein, e.g., anti-BCMA CAR-expressing cells. In some embodiments, the recombinant receptor, e.g., CAR, expressed on the additional engineered cell, recognizes a different antigen and/or epitope. In some embodiments, the recombinant receptor, e.g., CAR, expressed on the additional engineered cell, recognizes a different epitope of the same antigen as the recombinant receptors described herein, e.g., BCMA. In some embodiments, the recombinant receptor, e.g., CAR, expressed on the additional engineered cell, recognizes a different antigen, e.g., a different tumor antigen or combination of antigens. For example, in some embodiments, the recombinant receptor, e.g., CAR, expressed on the additional engineered cell, targets cancer cells that express early lineage markers, e.g., cancer stem cells, while other CAR-expressing cells target cancer cells that express later lineage markers. In such embodiments, the additional engineered cell is administered prior to, concurrently with, or after administration (e.g., infusion) of the CAR-expressing cells described herein. In some embodiments, the additional engineered cell expresses an allogeneic CAR.

In some embodiments, the configurations of one or more of the CAR molecules comprise a primary intracellular signaling domain and two or more, e.g., 2, 3, 4, or 5 or more, costimulatory signaling domains. In some embodiments, the one or more of the CAR molecules may have the same or a different primary intracellular signaling domain, the same or different costimulatory signaling domains, or the same number or a different number of costimulatory signaling domains. In some embodiments, the one or more of the CAR molecules can be configured as a split CAR, in which one of the CAR molecules comprises an antigen binding domain and a costimulatory domain (e.g., 4-1BB), while the other CAR molecule comprises an antigen binding domain and a primary intracellular signaling domain (e.g., CD3 zeta).

In some embodiments, the additional agent is any of the cells engineered to express one or more of the anti-BCMA recombinant receptor and/or cells engineered to express additional molecules, e.g., recombinant receptors, e.g., CARs, that target a different antigen. In some embodiments, the additional agent includes any of the cells or plurality of cells described herein, e.g., in Section III. In some embodiments, the additional agent is a cell engineered to express a recombinant receptor, e.g., CAR, targeting a different epitope and/or antigen, e.g., a different antigen associated with a disease or condition. In some embodiments, the additional agent is a cell engineered to express a recombinant receptor, e.g., CAR, targeting a second or additional antigen expressed in multiple myeloma, e.g., GPRC5D, CD38, CD138, CS-1, BAFF-R, TACI and/or FcRH5.

In some embodiments, the additional agent is an immunomodulatory agent. In some embodiments, the combination therapy includes an immunomodulatory agent that can stimulate, amplify and/or otherwise enhance an anti-tumor immune response, e.g. anti-tumor immune response from the administered engineered cells, such as by inhibiting immunosuppressive signaling or enhancing immunostimulant signaling. In some embodiments, the immunomodulatory agent is a peptide, protein or is a small molecule. In some embodiments, the protein can be a fusion protein or a recombinant protein. In some embodiments, the immunomodulatory agent binds to an immunologic target, such as a cell surface receptor expressed on immune cells, such a T cells, B cells or antigen-presenting cells. For example, in some embodiments, the immunomodulatory agent is an antibody or antigen-binding antibody fragment, a fusion protein, a small molecule or a polypeptide. In some embodiments, the recombinant receptors, cells and/or compositions are administered in combination with an additional agent that is an antibody or an antigen-binding fragment thereof, such as a monoclonal antibody.

In some embodiments, the immunomodulatory agent blocks, inhibits or counteracts a component of the immune checkpoint pathway. The immune system has multiple inhibitory pathways that are involved in maintaining self-tolerance and for modulating immune responses. Tumors can use certain immune-checkpoint pathways as a major mechanism of immune resistance, particularly against T cells that are specific for tumor antigens (Pardoll (2012) Nature Reviews Cancer 12:252-264), e.g., engineered cells such as CAR-expressing cells. Because many such immune checkpoints are initiated by ligand-receptor interactions, they can be readily blocked by antibodies against the ligands and/or their receptors.

Therefore, therapy with antagonistic molecules blocking an immune checkpoint pathway, such as small molecules, nucleic acid inhibitors (e.g., RNAi) or antibody molecules, are becoming promising avenues of immunotherapy for cancer and other diseases. In contrast to the majority of anti-cancer agents, checkpoint inhibitors do not necessarily target tumor cells directly, but rather target lymphocyte receptors or their ligands in order to enhance the endogenous antitumor activity of the immune system.

As used herein, the term "immune checkpoint inhibitor" refers to molecules that totally or partially reduce, inhibit, interfere with or modulate one or more checkpoint proteins. Checkpoint proteins regulate T-cell activation or function. These proteins are responsible for co-stimulatory or inhibitory interactions of T-cell responses. Immune checkpoint proteins regulate and maintain self-tolerance and the duration and amplitude of physiological immune responses. In some embodiments, the subject can be administered an additional agent that can enhance or boost the immune response, e.g., immune response effected by the engineered cells expressing the BCMA-binding recombinant receptors and/or compositions provided herein, against a disease or condition, e.g., a cancer, such as any described herein.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors, ligands and/or receptor-ligand interaction. In some embodiments, modulation, enhancement and/or stimulation of particular receptors can overcome immune checkpoint pathway components. Illustrative immune checkpoint molecules that may be targeted for blocking, inhibition, modulation, enhancement and/or stimulation include, but are not limited to, PD-1 (CD279), PD-L1 (CD274, B7-H1), PDL2 (CD273, B7-DC), CTLA-4, LAG-3 (CD223), TIM-3, 4-1BB (CD137), 4-1BBL (CD137L), GITR (TNFRSF18, AITR), CD40, OX40 (CD134, TNFRSF4), CXCR2, tumor associated antigens (TAA), B7-H3, B7-H4, BTLA, HVEM, GAL9, B7H3, B7H4, VISTA, KIR, 2B4 (belongs to the CD2 family of molecules and is expressed on all NK, γδ, and memory CD8+ (αβ) T cells), CD160 (also referred to as BY55), CGEN-15049, CEACAM (e.g., CEACAM-1, CEACAM-3 and/or CEACAM-5), TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and a transforming growth factor receptor (TGFR; e.g., TGFR beta) Immune checkpoint inhibitors include antibodies, or antigen binding fragments thereof, or other binding proteins, that bind to and block or inhibit and/or enhance or stimulate the activity of one or more of any of the said molecules.

Exemplary immune checkpoint inhibitors include Tremelimumab (CTLA-4 blocking antibody, also known as ticilimumab, CP-675,206), anti-OX40, PD-L1 monoclonal antibody (Anti-B7-H1; MEDI4736), MK-3475 (PD-1 blocker), nivolumab (anti-PD-1 antibody), CT-011 (anti-PD-1 antibody), BY55 monoclonal antibody, AMP224 (anti-PD-L1 antibody), BMS-936559 (anti-PD-L1 antibody), MPLDL3280A (anti-PD-L1 antibody), MSB0010718C (anti-PD-L1 antibody) and ipilimumab (anti-CTLA-4 antibody, also known as Yervoy®, MDX-010 and MDX-101). Exemplary immunomodulatory antibodies include, but are not limited to, Daclizumab (Zenapax), Bevacizumab (Avastin @), Basiliximab, Ipilimumab, Nivolumab, pembrolizumab, MPDL3280A, Pidilizumab (CT-011), MK-3475, BMS-936559, MPDL3280A (Atezolizumab), tremelimumab, IMP321, BMS-986016, LAG525, urelumab, PF-05082566, TRX518, MK-4166, dacetuzumab (SGN-40), lucatumumab (HCD122), SEA-CD40, CP-870, CP-893, MEDI6469, MEDI6383, MOXR0916, AMP-224, MSB0010718C (Avelumab), MEDI4736, PDR001, rHIgM12B7, Ulocuplumab, BKT140, Varlilumab (CDX-1127), ARGX-110, MGA271, lirilumab (BMS-986015, IPH2101), 1PH2201, ARGX-115, Emactuzumab, CC-90002 and MNRP1685A or an antibody-binding fragment thereof. Other exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon gamma, CAS 951209-71-5, available from IRX Therapeutics).

Programmed cell death 1 (PD-1) is an immune checkpoint protein that is expressed in B cells, NK cells, and T cells (Shinohara et al., 1995, Genomics 23:704-6; Blank et al., 2007, Cancer Immunol Immunother 56:739-45; Finger et al., 1997, Gene 197:177-87; Pardoll (2012) Nature Reviews Cancer 12:252-264). The major role of PD-1 is to limit the activity of T cells in peripheral tissues during inflammation in response to infection, as well as to limit autoimmunity. PD-1 expression is induced in activated T cells and binding of PD-1 to one of its endogenous ligands acts to inhibit T-cell activation by inhibiting stimulatory kinases. PD-1 also acts to inhibit the TCR "stop signal". PD-1 is highly expressed on Treg cells and may increase their proliferation in the presence of ligand (Pardoll (2012) Nature Reviews Cancer 12:252-264). Anti-PD 1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85). Exemplary anti-PD-1 antibodies include nivolumab (Opdivo by BMS), pembrolizumab (Keytruda by Merck), pidilizumab (CT-011 by Cure Tech), lambrolizumab (MK-3475 by Merck), and AMP-224 (Merck), nivolumab (also referred to as Opdivo, BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are described in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are described in WO2009/101611. Pembrolizumab (formerly known as lambrolizumab, and also referred to as Keytruda, MK03475; Merck) is a humanized IgG4 monoclonal antibody that binds to PD-1. Pembrolizumab and other humanized anti-PD-1 antibodies are described in U.S. Pat. No. 8,354,509 and WO2009/114335. Other anti-PD-1 antibodies include AMP 514 (Amplimmune), among others, e.g., anti-PD-1 antibodies described in U.S. Pat. No. 8,609,089, US 2010028330, US 20120114649 and/or US 20150210769. AMP-224 (B7-DCIg; Amplimmune; e.g., described in WO2010/027827 and WO2011/066342), is a PD-L2 Fc fusion soluble receptor that blocks the interaction between PD-1 and B7-H1.

PD-L1 (also known as CD274 and B7-H1) and PD-L2 (also known as CD273 and B7-DC) are ligands for PD-1, found on activated T cells, B cells, myeloid cells, macrophages, and some types of tumor cells. Anti-tumor therapies have focused on anti-PD-L1 antibodies. The complex of PD-1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., 2012, N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51). Exemplary anti-PD-L1 antibodies include MDX-1105 (Medarex), MEDI4736 (Medimmune) MPDL3280A (Genentech), BMS-935559 (Bristol-Myers Squibb) and MSB0010718C. MEDI4736 (Medimmune) is a human monoclonal antibody that binds to PD-L1, and inhibits interaction of the ligand with PD-1. MDPL3280A (Genentech/Roche) is a human Fc optimized IgG1 monoclonal antibody that binds to PD-L1. MDPL3280A and other human monoclonal antibodies to PD-L1 are described in U.S. Pat. No. 7,943,743 and U.S Publication No. 20120039906. Other anti-PD-L1 binding agents include YW243.55.S70 (see WO2010/077634) and MDX-1105 (also referred to as BMS-936559, and, e.g., anti-PD-L1 binding agents described in WO2007/005874).

Cytotoxic T-lymphocyte-associated antigen (CTLA-4), also known as CD152, is a co-inhibitory molecule that functions to regulate T-cell activation. CTLA-4 is a member of the immunoglobulin superfamily that is expressed exclusively on T-cells. CTLA-4 acts to inhibit T-cell activation and is reported to inhibit helper T-cell activity and enhance regulatory T-cell immunosuppressive activity. Although the precise mechanism of action of CTLA-4 remains under investigation, it has been suggested that it inhibits T cell activation by outcompeting CD28 in binding to CD80 and CD86, as well as actively delivering inhibitor signals to the T cell (Pardoll (2012) Nature Reviews Cancer 12:252-264). Anti-CTLA-4 antibodies have been used in clinical trials for the treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89). A significant feature of anti-CTLA-4 is the kinetics of anti-tumor effect, with a lag period of up to 6 months after initial treatment required for physiologic response. In some cases, tumors may actually increase in size after treatment initiation, before a reduction is seen (Pardoll (2012) Nature Reviews Cancer 12:252-264). Exemplary anti-CTLA-4 antibodies include ipilimumab (Bristol-Myers Squibb) and tremelimumab (Pfizer). Ipilimumab has recently received FDA approval for treatment of metastatic melanoma (Wada et al., 2013, J Transl Med 11:89).

Lymphocyte activation gene-3 (LAG-3), also known as CD223, is another immune checkpoint protein. LAG-3 has been associated with the inhibition of lymphocyte activity and in some cases the induction of lymphocyte anergy. LAG-3 is expressed on various cells in the immune system including B cells, NK cells, and dendritic cells. LAG-3 is a natural ligand for the MHC class II receptor, which is substantially expressed on melanoma-infiltrating T cells including those endowed with potent immune-suppressive activity. Exemplary anti-LAG-3 antibodies include BMS-986016 (Bristol-Myers Squib), which is a monoclonal antibody that targets LAG-3. IMP701 (Immutep) is an antagonist LAG-3 antibody and IMP731 (Immutep and GlaxoSmithKline) is a depleting LAG-3 antibody. Other LAG-3 inhibitors include IMP321 (Immutep), which is a recombinant fusion protein of a soluble portion of LAG-3 and Ig that binds to MHC class II molecules and activates antigen presenting cells (APC). Other antibodies are described, e.g., in WO2010/019570 and US 2015/0259420

T-cell immunoglobulin domain and mucin domain-3 (TIM-3), initially identified on activated Th1 cells, has been shown to be a negative regulator of the immune response. Blockade of TIM-3 promotes T-cell mediated anti-tumor immunity and has anti-tumor activity in a range of mouse tumor models. Combinations of TIM-3 blockade with other immunotherapeutic agents such as TSR-042, anti-CD137 antibodies and others, can be additive or synergistic in increasing anti-tumor effects. TIM-3 expression has been associated with a number of different tumor types including melanoma, NSCLC and renal cancer, and additionally, expression of intratumoral TIM-3 has been shown to correlate with poor prognosis across a range of tumor types including NSCLC, cervical, and gastric cancers. Blockade of TIM-3 is also of interest in promoting increased immunity to a number of chronic viral diseases. TIM-3 has also been shown to interact with a number of ligands including galectin-9, phosphatidylserine and HMGB1, although which of these, if any, are relevant in regulation of anti-tumor responses is not clear at present. In some embodiments, antibodies, antibody fragments, small molecules, or peptide inhibitors that target TIM-3 can bind to the IgV domain of TIM-3 to inhibit interaction with its ligands. Exemplary antibodies and peptides that inhibit TIM-3 are described in US 2015/0218274, WO2013/006490 and US 2010/0247521. Other anti-TIM-3 antibodies include humanized versions of RMT3-23 (Ngiow et al., 2011, Cancer Res, 71:3540-3551), and clone 8B.2C12 (Monney et al., 2002, Nature, 415:536-541). Bi-specific antibodies that inhibit TIM-3 and PD-1 are described in US 2013/0156774.

In some embodiments, the additional agent is a CEACAM inhibitor (e.g., CEACAM-1, CEACAM-3, and/or CEACAM-5 inhibitor). In some embodiments, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In some embodiments, the anti-CEACAM antibody binds to CEACAM-5 as described in, e.g., Zheng et al. PLoS One. (2011) 6(6): e21146), or cross reacts with CEACAM-1 and CEACAM-5 as described in, e.g., WO 2013/054331 and US 2014/0271618.

4-1BB, also known as CD137, is transmembrane glycoprotein belonging to the TNFR superfamily. 4-1BB receptors are present on activated T cells and B cells and monocytes. An exemplary anti-4-1BB antibody is urelumab (BMS-663513), which has potential immunostimulatory and antineoplastic activities.

Tumor necrosis factor receptor superfamily, member 4 (TNFRSF4), also known as OX40 and CD134, is another member of the TNFR superfamily. OX40 is not constitutively expressed on resting naïve T cells and acts as a secondary co-stimulatory immune checkpoint molecule. Exemplary anti-OX40 antibodies are MEDI6469 and MOXR0916 (RG7888, Genentech).

In some embodiments, the additional agent includes a molecule that decreases the regulatory T cell (Treg) population. Methods that decrease the number of (e.g., deplete) Treg cells are known in the art and include, e.g., CD25 depletion, cyclophosphamide administration, and modulating Glucocorticoid-induced TNFR family related gene (GITR) function. GITR is a member of the TNFR superfamily that is upregulated on activated T cells, which enhances the immune system. Reducing the number of Treg cells in a subject prior to apheresis or prior to administration of engineered cells, e.g., CAR-expressing cells, can reduce the number of unwanted immune cells (e.g., Tregs) in the tumor microenvironment and reduces the subject's risk of relapse. In some embodiments, the additional agent includes a molecule targeting GITR and/or modulating GITR functions, such as a GITR agonist and/or a GITR antibody that depletes regulatory T cells (Tregs). In some embodiments, the additional agent includes cyclophosphamide. In some embodiments, the GITR targeting molecule and/or molecule modulating GITR function (e.g., GITR agonist and/or Treg depleting GITR antibodies) is administered prior to the engineered cells, e.g., CAR-expressing cells. For example, in some embodiments, the GITR agonist can be administered prior to apheresis of the cells. In some embodiments, cyclophosphamide is administered to the subject prior to administration (e.g., infusion or re-infusion) of the engineered cells, e.g., CAR-expressing cells or prior to apheresis of the cells. In some embodiments, cyclophosphamide and an anti-GITR antibody are administered to the subject prior to administration (e.g., infusion or re-infusion) of the engineered cells, e.g., CAR-expressing cells or prior to apheresis of the cells.

In some embodiments, the additional agent is a GITR agonist. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No. 090505B 1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B 1, U.S. Pat. Nos. 7,812,135, 8,388,967, 8,591,886, European Patent No. EP 1866339, PCT Publication No. WO 2011/028683, PCT Publication No. WO 2013/039954, PCT Publication No. WO2005/007190, PCT Publication No. WO 2007/133822, PCT Publication No. WO2005/055808, PCT Publication No. WO 99/40196, PCT Publication No. WO 2001/03720, PCT Publication No. WO99/20758, PCT Publication No. WO2006/083289, PCT Publication No. WO 2005/115451, U.S. Pat. No. 7,618,632, and PCT Publication No. WO 2011/051726, each incorporated by reference in its entireties. An exemplary anti-GITR antibody is TRX518.

In some embodiments, the additional agent enhances tumor infiltration or transmigration of the administered cells, e.g., CAR-expressing cells. For example, in some embodiments, the additional agent stimulates CD40, such as CD40L, e.g., recombinant human CD40L. Cluster of differentiation 40 (CD40) is also a member of the TNFR superfamily. CD40 is a costimulatory protein found on antigen-presenting cells and mediates a broad variety of immune and inflammatory responses. CD40 is also expressed on some malignancies, where it promotes proliferation. Exemplary anti-CD40 antibodies are dacetuzumab (SGN-40), lucatumumab (Novartis, antagonist), SEA-CD40 (Seattle Genetics), and CP-870,893. In some embodiments, the additional agent that enhances tumor infiltration includes tyrosine kinase inhibitor sunitinib, heparanase, and/or chemokine receptors such as CCR2, CCR4, and CCR7.

In some embodiments, the additional agent includes thalidomide drugs or analogs thereof and/or derivatives thereof, such as lenalidomide, pomalidomide or apremilast. See, e.g., Bertilaccio et al., Blood (2013) 122:4171, Otahal et al., Oncoimmunology (2016) 5(4):e1115940; Fecteau et al., Blood (2014) 124(10):1637-1644 and Kuramitsu et al., Cancer Gene Therapy (2015) 22:487-495). Lenalidomide ((RS)-3-(4-Amino-1-oxo-1,3-dihydro-2H-isoindol-2-yl)piperidine-2,6-dione; also known as Revlimid) is a synthetic derivative of thalidomide, and has multiple immunomodulatory effects, including enforcement of immune synapse formation between T cell and antigen presenting cells (APCs). For example, in some cases, lenalidomide modulates T cell responses and results in increased interleukin (IL)-2 production in CD4+ and CD8+ T cells, induces the shift of T helper (Th) responses from Th2 to Th1, inhibits expansion of regulatory subset of T cells (Tregs), and improves functioning of immunological synapses in follicular lymphoma and chronic lymphocytic leukemia (CLL) (Otahal et al., Oncoimmunology (2016) 5(4):e1115940). Lenalidomide also has direct tumoricidal activity in patients with multiple myeloma (MM) and directly and indirectly modulates survival of CLL tumor cells by affecting supportive cells, such as nurse-like cells found in the microenvironment of lymphoid tissues. Lenalidomide also can enhance T-cell proliferation and interferon-γ production in response to activation of T cells via CD3 ligation or dendritic cell-mediated activation. Lenalidomide can also induce malignant B cells to express higher levels of immunostimulatory molecules such as CD80, CD86, HLA-DR, CD95, and CD40 (Fecteau et al., Blood (2014) 124(10):1637-1644). In some embodiments, lenalidomide is administered at a dosage of from about 1 mg to about 20 mg daily, e.g., from about 1 mg to about 10 mg, from about 2.5 mg to about 7.5 mg, from about 5 mg to about 15 mg, such as about 5 mg, 10 mg, 15 mg or 20 mg daily. In some embodiments, lenalidomide is administered at a dose of from about 10 μg/kg to 5 mg/kg, e.g., about 100 μg/kg to about 2 mg/kg, about 200 μg/kg to about 1 mg/kg, about 400 μg/kg to about 600 μg/kg, such as about 500 μg/kg. In some embodiments, rituximab is administered at a dosage of about 350-550 $mg/m^2$ (e.g., 350-375, 375-400, 400-425, 425-450, 450-475, or 475-500 $mg/m^2$), e.g., intravenously. In some embodiments, lenalidomide is administered at a low dose.

In some embodiments, the additional agent is a B-cell inhibitor. In some embodiments, the additional agent is one or more B-cell inhibitors selected from among inhibitors of CD10, CD19, CD20, CD22, CD34, CD123, CD79a, CD79b, CD179b, FLT-3, or ROR1, or a combination thereof. In some embodiments, the B-cell inhibitor is an antibody (e.g., a mono- or bispecific antibody) or an antigen binding fragment thereof. In some embodiments, the additional agent is an engineered cell expressing recombinant receptors that target B-cell targets, e.g., CD10, CD19, CD20, CD22, CD34, CD123, CD79a, CD79b, CD179b, FLT-3, or ROR1.

In some embodiments, the additional agent is a CD20 inhibitor, e.g., an anti-CD20 antibody (e.g., an anti-CD20 mono- or bi-specific antibody) or a fragment thereof. Exemplary anti-CD20 antibodies include but are not limited to rituximab, ofatumumab, ocrelizumab (also known as GA101 or RO5072759), veltuzumab, obinutuzumab, TRU-015 (Trubion Pharmaceuticals), ocaratuzumab (also known as AME-133v or ocaratuzumab), and Pro131921 (Genentech). See, e.g., Lim et al. Haematologica. (2010) 95(1):135-43. In some embodiments, the anti-CD20 antibody comprises rituximab. Rituximab is a chimeric mouse/human monoclonal antibody IgG1 kappa that binds to CD20 and causes cytolysis of a CD20 expressing cell. In some embodiments, the additional agent includes rituximab. In some embodiments, the CD20 inhibitor is a small molecule.

In some embodiments, the additional agent is a CD22 inhibitor, e.g., an anti-CD22 antibody (e.g., an anti-CD22 mono- or bi-specific antibody) or a fragment thereof. Exemplary anti-CD22 antibodies include epratuzumab and RFB4. In some embodiments, the CD22 inhibitor is a small molecule. In some embodiments, the antibody is a monospecific antibody, optionally conjugated to a second agent such as a chemotherapeutic agent. For instance, in some embodiments, the antibody is an anti-CD22 monoclonal antibody-MMAE conjugate (e.g., DCDT2980S). In some embodiments, the antibody is an scFv of an anti-CD22 antibody, e.g., an scFv of antibody RFB4. In some embodiments, the scFv is fused to all of or a fragment of *Pseudomonas* exotoxin-A (e.g., BL22). In some embodiments, the scFv is fused to all of or a fragment of (e.g., a 38 kDa fragment of) *Pseudomonas* exotoxin-A (e.g., moxetumomab pasudotox). In some embodiments, the anti-CD22 antibody is an anti-CD19/CD22 bispecific antibody, optionally conjugated to a toxin. For instance, in some embodiments, the anti-CD22 antibody comprises an anti-CD19/CD22 bispecific portion, (e.g., two scFv ligands, recognizing human CD19 and CD22) optionally linked to all of or a portion of diphtheria toxin (DT), e.g., first 389 amino acids of diphtheria toxin (DT), DT 390, e.g., a ligand-directed toxin such as DT2219ARL). In some embodiments, the bispecific portion (e.g., anti-CD 19/anti-CD22) is linked to a toxin such as deglycosylated ricin A chain (e.g., Combotox).

In some embodiments, the immunomodulatory agent is a cytokine. In some embodiments, the immunomodulatory agent is a cytokine or is an agent that induces increased expression of a cytokine in the tumor microenvironment. Cytokines have important functions related to T cell expansion, differentiation, survival, and homeostasis. Cytokines that can be administered to the subject receiving the engineered cells expressing the BCMA-binding recombinant receptors and/or compositions provided herein include one or more of IL-2, IL-4, IL-7, IL-9, IL-15, IL-18, and IL-21. In some embodiments, the cytokine administered is IL-7, IL-15, or IL-21, or a combination thereof. In some embodiments, administration of the cytokine to the subject that has sub-optimal response to the administration of the engineered cells, e.g., CAR-expressing cells improves efficacy and/or anti-tumor activity of the administered cells, e.g., CAR-expressing cells.

By "cytokine" is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. For example, the immunomodulatory agent is a cytokine and the cytokine is IL-4, TNF-α, GM-CSF or IL-2.

In some embodiments, the additional agent includes an interleukin-15 (IL-15) polypeptide, an interleukin-15 receptor alpha (IL-15Ra) polypeptide, or combination thereof, e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311. In some embodiments, the immunomodulatory agent can contain one or more cytokines. For example, the interleukin can include leukocyte interleukin injection (Multikine), which is a combination of natural cytokines. In some embodiments, the immunomodulatory agent is a Toll-like receptor (TLR) agonist, an adjuvant or a cytokine.

In some embodiments, the additional agent is an agent that ameliorates or neutralizes one or more toxicities or side effects associated with the cell therapy. In some embodiments, the additional agent is selected from among a steroid (e.g., corticosteroid), an inhibitor of TNFα, and an inhibitor of IL-6 or IL-6 signaling. An example of a TNFα inhibitor is an anti-TNFα antibody molecule such as, infliximab, adalimumab, certolizumab pegol, and golimumab. Another example of a TNFα inhibitor is a fusion protein such as etanercept. Small molecule inhibitors of TNFα include, but are not limited to, xanthine derivatives (e.g. pentoxifylline) and bupropion. An example of an IL-6 inhibitor is an anti-IL-6 receptor (anti-IL-6R) antibody molecule such as tocilizumab, sarilumab, elsilimomab, CNTO 328, ALD518/BMS-945429, CNTO 136, CPSI-2364, CDP6038, VX30, ARGX-109, FE301, and FM101. In some embodiments, the anti-IL-6R antibody molecule is tocilizumab. In some aspects, tocilizumab blocks the interaction between interleukin-6 (IL-6), an inflammatory cytokine, and its receptor IL-6 receptor (IL-6R). In some aspects, the inhibitor of IL-6 is an anti-IL-6 antibody. In some aspects, an exemplary anti-IL-6 antibody is siltuximab. In some aspects, siltuximab blocks IL-6 signaling by binding IL-6 itself and preventing IL-6 from activating immune effector cells.

In some aspects, an additional agent that ameliorates or neutralizes one or more toxicities or side effects associated with the cell therapy includes an anti-GM-CSF agent, such as lenzilumab, which is a humanized monoclonal antibody that neutralizes GM-CSF (Sterner et al., Blood (2018) 132 (Supplement 1): 961; Sterner et al., Blood. 2019; 133(7): 697-709); the T cell depleting antibody alemtuzumab, anti-thymocyte globulin (ATG), cyclophosphamide, ruxolitinib, or ibrutinib (Borrega et al., HemaSphere. April 2019; 3(2): 191).

In some embodiments, the additional agent is an IL-1R antagonist, such as anakinra. In some embodiments, the additional agent is anakinra. In some aspects, anakinra is administered to a subject that has a severe CRS that does not respond to treatment with tocilizumab and corticosteroids. In some embodiments, the additional agent is anakinra, and exemplary dosage for anakinra is at or about 25 mg, 50 mg, 60 mg, 70 mg, 80 mg, 90 mg, 100 mg, 110 mg, 120 mg, 125 mg, 150 mg, 200 mg, 250 mg, 300 mg, 400 mg or 500 mg, daily, or any range defined by any of the foregoing, daily, such as 100 mg daily. In some aspects, an exemplary daily dose of anakinra is at or about 100 mg. In some aspects, exemplary daily dose of anakinra is at or about 200 mg. In some aspects, anakinra is administered subcutaneously. In some aspects, anakinra is administered until the resolution of CRS, for example with a daily dose of 100 mg administered SC. In some aspects, anakinra is administered until the resolution of CRS, for example with a daily dose of 200 mg administered SC, such as divided between two 100 mg doses. In some aspects, if the subject exhibits severe CRS, and in some cases, in combination with neurological events or MAS/HLH, anakinra is administered 100 mg, twice daily (e.g., every 12 hours) SC, until the resolution of the adverse events such as CRS, neurological events and/or MAS/HLH.

In some embodiments, the additional agent is a modulator of adenosine levels and/or an adenosine pathway component. Adenosine can function as an immunomodulatory agent in the body. For example, adenosine and some adenosine analogs that non-selectively activate adenosine receptor subtypes decrease neutrophil production of inflammatory oxidative products (Cronstein et al., Ann. N.Y. Acad. Sci. 451:291, 1985; Roberts et al., Biochem. J., 227:669, 1985; Schrier et al., J. Immunol. 137:3284, 1986; Cronstein et al., Clinical Immunol. Immunopath. 42:76, 1987). In some cases, concentration of extracellular adenosine or adenosine analogs can increase in specific environments, e.g., tumor microenvironment (TME). In some cases, adenosine or adenosine analog signaling depends on hypoxia or factors involved in hypoxia or its regulation, e.g., hypoxia inducible factor (HIF). In some embodiments, increase in adenosine signaling can increase in intracellular cAMP and cAMP-dependent protein kinase that results in inhibition of pro-inflammatory cytokine production, and can lead to the synthesis of immunosuppressive molecules and development of Tregs (Sitkovsky et al., Cancer Immunol Res (2014) 2(7):598-605). In some embodiments, the additional agent can reduce or reverse immunosuppressive effects of adenosine, adenosine analogs and/or adenosine signaling. In some embodiments, the additional agent can reduce or reverse hypoxia-driven A2-adenosinergic T cell immunosuppression. In some embodiments, the additional agent is selected from among antagonists of adenosine receptors, extracellular adenosine-degrading agents, inhibitors of adenosine generation by CD39/CD73 ectoenzymes, and inhibitors of hypoxia-HIF-1α signaling. In some embodiments, the additional agent is an adenosine receptor antagonist or agonist.

Inhibition or reduction of extracellular adenosine or the adenosine receptor by virtue of an inhibitor of extracellular adenosine (such as an agent that prevents the formation of, degrades, renders inactive, and/or decreases extracellular adenosine), and/or an adenosine receptor inhibitor (such as an adenosine receptor antagonist) can enhance immune response, such as a macrophage, neutrophil, granulocyte, dendritic cell, T- and/or B cell-mediated response. In addition, inhibitors of the Gs protein mediated cAMP dependent intracellular pathway and inhibitors of the adenosine receptor-triggered Gi protein mediated intracellular pathways, can also increase acute and chronic inflammation.

In some embodiments, the additional agent is an adenosine receptor antagonist or agonist, e.g., an antagonist or agonist of one or more of the adenosine receptors A2a, A2b, A1, and A3. A1 and A3 inhibit, and A2a and A2b stimulate, respectively, adenylate cyclase activity. Certain adenosine receptors, such as A2a, A2b, and A3, can suppress or reduce the immune response during inflammation. Thus, antagonizing immunosuppressive adenosine receptors can augment, boost or enhance immune response, e.g., immune response from administered cells, e.g., CAR-expressing T cells. In some embodiments, the additional agent inhibits the production of extracellular adenosine and adenosine-triggered signaling through adenosine receptors. For example, enhancement of an immune response, local tissue inflammation, and targeted tissue destruction can be enhanced by inhibiting or reducing the adenosine-producing local tissue hypoxia; by degrading (or rendering inactive) accumulated extracellular adenosine; by preventing or decreasing expression of adenosine receptors on immune cells; and/or by inhibiting/antagonizing signaling by adenosine ligands through adenosine receptors.

An antagonist is any substance that tends to nullify the action of another, as an agent that binds to a cell receptor without eliciting a biological response. In some embodiments, the antagonist is a chemical compound that is an antagonist for an adenosine receptor, such as the A2a, A2b, or A3 receptor. In some embodiments, the antagonist is a peptide, or a peptidomimetic, that binds the adenosine receptor but does not trigger a Gi protein dependent intracellular pathway. Exemplary antagonists are described in U.S. Pat. Nos. 5,565,566; 5,545, 627, 5,981,524; 5,861,405; 6,066,642; 6,326,390; 5,670,501; 6,117,998; 6,232,297; 5,786,360; 5,424,297; 6,313,131, 5,504,090; and 6,322,771.

In some embodiments, the additional agent is an A2 receptor (A2R) antagonist, such as an A2a antagonist. Exemplary A2R antagonists include KW6002 (istradefyline), SCH58261, caffeine, paraxanthine, 3,7-dimethyl-1-propargylxanthine (DMPX), 8-(m-chlorostyryl) caffeine (CSC), MSX-2, MSX-3, MSX-4, CGS-15943, ZM-241385, SCH-442416, preladenant, vipadenant (BII014), V2006, ST-1535, SYN-115, PSB-1115, ZM241365, FSPTP, and an inhibitory nucleic acid targeting A2R expression, e.g., siRNA or shRNA, or any antibodies or antigen-binding fragment thereof that targets an A2R. In some embodiments, the additional agent is an A2R antagonist described in, e.g., Ohta et al., Proc Natl Acad Sci USA (2006) 103:13132-13137; Jin et al., Cancer Res. (2010) 70(6):2245-2255; Leone et al., Computational and Structural Biotechnology Journal (2015) 13:265-272; Beavis et al., Proc Natl Acad Sci USA (2013) 110:14711-14716; and Pinna, A., Expert Opin Investig Drugs (2009) 18:1619-1631; Sitkovsky et al., Cancer Immunol Res (2014) 2(7):598-605; U.S. Pat. Nos. 8,080, 554; 8,716,301; US 20140056922; WO2008/147482; U.S. Pat. No. 8,883,500; US 20140377240; WO02/055083; U.S. Pat. Nos. 7,141,575; 7,405,219; 8,883,500; 8,450,329 and 8,987,279).

In some embodiments, the antagonist is an antisense molecule, inhibitory nucleic acid molecule (e.g., small inhibitory RNA (siRNA)) or catalytic nucleic acid molecule (e.g. a ribozyme) that specifically binds mRNA encoding an adenosine receptor. In some embodiments, the antisense molecule, inhibitory nucleic acid molecule or catalytic nucleic acid molecule binds nucleic acids encoding A2a, A2b, or A3. In some embodiments, an antisense molecule, inhibitory nucleic acid molecule or catalytic nucleic acid targets biochemical pathways downstream of the adenosine receptor. For example, the antisense molecule or catalytic nucleic acid can inhibit an enzyme involved in the Gs protein- or Gi protein-dependent intracellular pathway. In some embodiments, the additional agent includes dominant negative mutant form of an adenosine receptor, such as A2a, A2b, or A3.

In some embodiments, the additional agent that inhibits extracellular adenosine includes agents that render extracellular adenosine non-functional (or decrease such function), such as a substance that modifies the structure of adenosine to inhibit the ability of adenosine to signal through adenosine receptors. In some embodiments, the additional agent is an extracellular adenosine-generating or adenosine-degrading enzyme, a modified form thereof or a modulator thereof. For example, in some embodiments, the additional agent is an enzyme (e.g. adenosine deaminase) or another catalytic molecule that selectively binds and destroys the adenosine, thereby abolishing or significantly decreasing the ability of endogenously formed adenosine to signal through adenosine receptors and terminate inflammation.

In some embodiments, the additional agent is an adenosine deaminase (ADA) or a modified form thereof, e.g., recombinant ADA and/or polyethylene glycol-modified ADA (ADA-PEG), which can inhibit local tissue accumulation of extracellular adenosine. ADA-PEG has been used in treatment of patients with ADA SCID (Hershfield (1995) Hum Mutat. 5:107). In some embodiments, an agent that inhibits extracellular adenosine includes agents that prevent or decrease formation of extracellular adenosine, and/or prevent or decrease the accumulation of extracellular adenosine, thereby abolishing, or substantially decreasing, the immunosuppressive effects of adenosine. In some embodiments, the additional agent specifically inhibits enzymes and proteins that are involved in regulation of synthesis and/or secretion of pro-inflammatory molecules, including modulators of nuclear transcription factors. Suppression of adenosine receptor expression or expression of the Gs protein- or Gi protein-dependent intracellular pathway, or the cAMP dependent intracellular pathway, can result in an increase/enhancement of immune response.

In some embodiments, the additional agent can target ectoenzymes that generate or produce extracellular adenosine. In some embodiments, the additional agent targets CD39 and CD73 ectoenzymes, which function in tandem to generate extracellular adenosine. CD39 (also called ectonucleoside triphosphate diphosphohydrolase) converts extracellular ATP (or ADP) to 5'AMP. Subsequently, CD73 (also called 5'nucleotidase) converts 5'AMP to adenosine. The activity of CD39 is reversible by the actions of NDP kinase and adenylate kinase, whereas the activity of CD73 is irreversible. CD39 and CD73 are expressed on tumor stromal cells, including endothelial cells and Tregs, and also on many cancer cells. For example, the expression of CD39 and CD73 on endothelial cells is increased under the hypoxic conditions of the tumor microenvironment. Tumor hypoxia can result from inadequate blood supply and disorganized tumor vasculature, impairing delivery of oxygen (Carroll and Ashcroft (2005), Expert. Rev. Mol. Med. 7(6): 1-16). Hypoxia also inhibits adenylate kinase (AK), which converts adenosine to AMP, leading to very high extracellular adenosine concentration. Thus, adenosine is released at high concentrations in response to hypoxia, which is a condition that frequently occurs the tumor microenvironment (TME), in or around solid tumors. In some embodiments, the additional agent is one or more of anti-CD39 antibody or antigen binding fragment thereof, anti-CD73 antibody or antigen binding fragment thereof, e.g., MEDI9447 or TY/23, α-β-methylene-adenosine diphosphate (ADP), ARL 67156, POM-3, IPH52 (see, e.g., Allard et al. Clin Cancer Res (2013) 19(20):5626-5635; Hausler et al., Am J Transl Res (2014) 6(2):129-139; Zhang, B., Cancer Res. (2010) 70(16):6407-6411).

In some embodiments, the additional agent is an inhibitor of hypoxia inducible factor 1 alpha (HIF-1α) signaling. Exemplary inhibitors of HIF-1α include digoxin, acriflavine, sirtuin-7 and ganetespib.

In some embodiments, the additional agent includes a protein tyrosine phosphatase inhibitor, e.g., a protein tyrosine phosphatase inhibitor described herein. In some embodiments, the protein tyrosine phosphatase inhibitor is an SHP-1 inhibitor, e.g., an SHP-1 inhibitor described herein, such as, e.g., sodium stibogluconate. In some embodiments, the protein tyrosine phosphatase inhibitor is an SHP-2 inhibitor, e.g., an SHP-2 inhibitor described herein.

In some embodiments, the additional agent is a kinase inhibitor. Kinase inhibitors, such as a CDK4 kinase inhibitor, a BTK kinase inhibitor, a MNK kinase inhibitor, or a DGK kinase inhibitor, can regulate the constitutively active survival pathways that exist in tumor cells and/or modulate the function of immune cells. In some embodiments, the kinase inhibitor is a Bruton's tyrosine kinase (BTK) inhibitor, e.g., ibrutinib. In some embodiments, the kinase inhibitor is a phosphatidylinositol-4,5-bisphosphate 3-kinase (PI3K) inhibitor. In some embodiments, the kinase inhibitor is a CDK4 inhibitor, e.g., a CDK4/6 inhibitor. In some embodiments, the kinase inhibitor is an mTOR inhibitor, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor. In some embodiments, the kinase inhibitor is an MNK inhibitor, or a dual PI3K/mTOR inhibitor. In some embodiments, other exemplary kinase inhibitors include the AKT inhibitor perifosine, the mTOR inhibitor temsirolimus, the Src kinase inhibitors dasatinib and fostamatinib, the JAK2 inhibitors pacritinib and ruxolitinib, the PKCβ inhibitors enzastaurin and bryostatin, and the AAK inhibitor alisertib.

In some embodiments, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In some embodiments, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In some embodiments, the kinase inhibitor is a BTK inhibitor, e.g., ibrutinib (1-[(3R)-3-[4-Amino-3-(4-phenoxyphenyl)-1H-pyrazolo[3,4-d]pyrimidin-1-yl]piperidin-1-yl] prop-2-en-1-one; also known as PCI-32765). In some embodiments, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In some embodiments, 1, 2, 3, 4, 5, 6, 7, 8, 9, 10, 11, 12 or more cycles of ibrutinib are administered. In some embodiments, the BTK inhibitor is a BTK inhibitor described in International Application WO 2015/079417.

In some embodiments, the kinase inhibitor is a PI3K inhibitor. PI3K is central to the PI3K/Akt/mTOR pathway involved in cell cycle regulation and lymphoma survival.

Exemplary PI3K inhibitor includes idelalisib (PI3Kδ inhibitor). In some embodiments, the additional agent is idelalisib and rituximab.

In some embodiments, the additional agent is an inhibitor of mammalian target of rapamycin (mTOR). In some embodiments, the kinase inhibitor is an mTOR inhibitor selected from temsirolimus; ridaforolimus (also known as AP23573 and MK8669); everolimus (RAD001); rapamycin (AY22989); simapimod; AZD8055; PF04691502; SF1126; and XL765. In some embodiments, the additional agent is an inhibitor of mitogen-activated protein kinase (MAPK), such as vemurafenib, dabrafenib, and trametinib.

In some embodiments, the additional agent is an agent that regulates pro- or anti-apoptotic proteins. In some embodiments, the additional agent includes a B-cell lymphoma 2 (BCL-2) inhibitor (e.g., venetoclax, also called ABT-199 or GDC-0199; or ABT-737). Venetoclax is a small molecule (4-(4-{[2-(4-Chlorophenyl)-4,4-dimethyl-1-cyclohexen-1-yl]methyl}-1-piperazinyl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) that inhibits the anti-apoptotic protein, BCL-2. Other agents that modulate pro- or anti-apoptotic protein include BCL-2 inhibitor ABT-737, navitoclax (ABT-263); Mcl-1 siRNA or Mcl-1 inhibitor retinoid N-(4-hydroxyphenyl) retinamide (4-HPR) for maximal efficacy. In some embodiments, the additional agent provides a pro-apoptotic stimuli, such as recombinant tumor necrosis factor-related apoptosis-inducing ligand (TRAIL), which can activate the apoptosis pathway by binding to TRAIL death receptors DR-4 and DR-5 on tumor cell surface, or TRAIL-R2 agonistic antibodies.

In some embodiments, the additional agent includes an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. Plasmacytoid dendritic cells (pDCs), macrophages, and dendritic cells (DCs) can express IDO. In some aspects, a decrease in L-tryptophan (e.g., catalyzed by IDO) results in an immunosuppressive milieu by inducing T-cell anergy and apoptosis. Thus, in some aspects, an IDO inhibitor can enhance the efficacy of the engineered cells expressing the BCMA-binding recombinant receptors and/or compositions described herein, e.g., by decreasing the suppression or death of the administered CAR-expressing cell. Exemplary inhibitors of IDO include but are not limited to 1-methyl-tryptophan, indoximod (New Link Genetics) (see, e.g., Clinical Trial Identifier Nos. NCT01191216; NCT01792050), and INCB024360 (Incyte Corp.) (see, e.g., Clinical Trial Identifier Nos. NCT01604889; NCT01685255).

In some embodiments, the additional agent includes a cytotoxic agent, e.g., CPX-351 (Celator Pharmaceuticals), cytarabine, daunorubicin, vosaroxin (Sunesis Pharmaceuticals), sapacitabine (Cyclacel Pharmaceuticals), idarubicin, or mitoxantrone. In some embodiments, the additional agent includes a hypomethylating agent, e.g., a DNA methyltransferase inhibitor, e.g., azacitidine or decitabine.

In another embodiment, the additional therapy is transplantation, e.g., an allogeneic stem cell transplant.

In some embodiments, the additional agent is an oncolytic virus. In some embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

Other exemplary combination therapy, treatment and/or agents include anti-allergenic agents, anti-emetics, analgesics and adjunct therapies. In some embodiments, the additional agent includes cytoprotective agents, such as neuroprotectants, free-radical scavengers, cardioprotectors, anthracycline extravasation neutralizers and nutrients.

In some embodiments, an antibody used as an additional agent is conjugated or otherwise bound to a therapeutic agent, e.g., a chemotherapeutic agent (e.g., Cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein. In some embodiments, the additional agent is an antibody-drug conjugate.

In some embodiments, the additional agent can modulate, inhibit or stimulate particular factors at the DNA, RNA or protein levels, to enhance or boost the efficacy of the engineered cells expressing the BCMA-binding recombinant receptors and/or compositions provided herein. In some embodiments, the additional agent can modulate the factors at the nucleic acid level, e.g., DNA or RNA, within the administered cells, e.g., cells engineered to express recombinant receptors, e.g., CAR. In some embodiments, an inhibitory nucleic acid, e.g., an inhibitory nucleic acid, e.g., a dsRNA, e.g., an siRNA or shRNA, or a clustered regularly interspaced short palindromic repeats (CRISPR), a transcription-activator like effector nuclease (TALEN), or a zinc finger endonuclease (ZFN), can be used to inhibit expression of an inhibitory molecule in the engineered cell, e.g., CAR-expressing cell. In some embodiments the inhibitor is an shRNA. In some embodiments, the inhibitory molecule is inhibited within the engineered cell, e.g., CAR-expressing cell. In some embodiments, a nucleic acid molecule that encodes a dsRNA molecule that inhibits expression of the molecule that modulates or regulates, e.g., inhibits, T-cell function is operably linked to a promoter, e.g., a HI- or a U6-derived promoter such that the dsRNA molecule that inhibits expression of the inhibitory molecule is expressed within the engineered cell, e.g., CAR-expressing cell. See, e.g., Brummelkamp T R, et al. (2002) Science 296: 550-553; Miyagishi M, et al. (2002) Nat. Biotechnol. 19: 497-500.

In some embodiments, the additional agent is capable of disrupting the gene encoding an inhibitory molecule, such as any immune checkpoint inhibitors described herein. In some embodiments, disruption is by deletion, e.g., deletion of an entire gene, exon, or region, and/or replacement with an exogenous sequence, and/or by mutation, e.g., frameshift or missense mutation, within the gene, typically within an exon of the gene. In some embodiments, the disruption results in a premature stop codon being incorporated into the gene, such that the inhibitory molecule is not expressed or is not expressed in a form that is capable of being expressed on the cells surface and/or capable of mediating cell signaling. The disruption is generally carried out at the DNA level. The disruption generally is permanent, irreversible, or not transient.

In some aspects, the disruption is carried out by gene editing, such as using a DNA binding protein or DNA-binding nucleic acid, which specifically binds to or hybridizes to the gene at a region targeted for disruption. In some aspects, the protein or nucleic acid is coupled to or complexed with a nuclease, such as in a chimeric or fusion protein. For example, in some embodiments, the disruption is effected using a fusion comprising a DNA-targeting protein and a nuclease, such as a Zinc Finger Nuclease (ZFN) or TAL-effector nuclease (TALEN), or an RNA-guided nuclease such as a clustered regularly interspersed short palindromic nucleic acid (CRISPR)-Cas system, such as CRISPR-Cas9 system, specific for the gene being disrupted. In some embodiments, methods of producing or generating genetically engineered cells, e.g., CAR-expressing cells, include introducing into a population of cells nucleic acid molecules encoding a genetically engineered antigen receptor (e.g. CAR) and nucleic acid molecules encoding an agent targeting an inhibitory molecule that is a gene editing nuclease, such as a fusion of a DNA-targeting protein and a nuclease such as a ZFN or a TALEN, or an RNA-guided nuclease such as of the CRISPR-Cas9 system, specific for an inhibitory molecule.

II. BCMA-BINDING RECOMBINANT RECEPTORS AND ENCODING POLYNUCLEOTIDES

Provided in some aspects are BCMA-binding recombinant receptors or chimeric antigen receptors that bind or recognize BCMA molecules, polynucleotides encoding BCMA-binding recombinant receptors (e.g., chimeric antigen receptors; CARs), and cells expressing such receptors. In some aspects, the cells expressing the BCMA-binding recombinant receptors and compositions comprising such cells, are employed in accordance with the methods or uses provided herein. The BCMA-binding recombinant receptors generally contain antibodies (e.g., antigen-binding antibody fragments), and/or other binding peptides that specifically recognize, such as specifically bind to BCMA, such as to BCMA proteins, such as human BCMA protein. In some aspects, the agents bind to an extracellular portion of BCMA. Also provided are cells, e.g., engineered cells, comprising such polynucleotides or expressing such receptors, and compositions comprising such engineered cells. In some aspects, also provided are methods employing such cells and compositions, and uses thereof, such as in therapeutic methods.

In some embodiments, the polynucleotides encoding the BCMA-binding recombinant receptors, e.g., CARs, are optimized, or contain certain features designed for optimization, such as for codon usage, to reduce RNA heterogeneity and/or to modify, e.g., increase or render more consistent among cell product lots, expression, such as surface expression, of the encoded receptor. In some embodiments, polynucleotides, encoding BCMA-binding recombinant receptors, are modified as compared to a reference polynucleotide, such as to remove cryptic or hidden splice sites, to reduce RNA heterogeneity. In some embodiments, polynucleotides, encoding BCMA-binding recombinant receptors, are codon optimized, such as for expression in a mammalian, e.g., human, cell, such as in a human T cell. In some aspects, the modified polynucleotides result in in improved, e.g., increased or more uniform or more consistent level of, expression, e.g., surface expression, when expressed in a cell. Such polynucleotides can be utilized in constructs for generation of engineered cells that express the encoded BCMA-binding cell surface protein. Thus, also provided are cells expressing the recombinant receptors encoded by the polynucleotides provided herein and uses thereof in adoptive cell therapy, such as treatment of diseases and disorders associated with BCMA expression, such as multiple myeloma.

Among the polynucleotides are those that encode recombinant receptors, such as antigen receptors, that specifically recognize, such as specifically bind, BCMA, such as a human BCMA. In some aspects, the encoded receptors, such as those containing BCMA-binding polypeptides, and compositions and articles of manufacture and uses of the same, also are provided. In some aspects, such polynucleotides can be used to engineer immune cells, e.g., T cells, to express the BCMA-binding recombinant receptor, for example using methods described herein, e.g., in Section III, to generate engineered cells or cell compositions for use in methods, such as therapeutic and/or prophylactic methods as provided herein.

Among the BCMA-binding polypeptides are antibodies, such as single-chain antibodies (e.g., antigen binding antibody fragments), or portions thereof. In some examples, the recombinant receptors are chimeric antigen receptors, such as those containing anti-BCMA antibodies or antigen-binding fragments thereof. In any of the embodiments, an antibody or antigen binding fragment, in the CARs, that specifically recognizes an antigen, e.g. BCMA, specifically binds to the antigen. The provided polynucleotides can be incorporated into constructs, such as deoxyribonucleic acid (DNA) or ribonucleic acid (RNA) constructs, such as those that can be introduced into cells for expression of the encoded BCMA-binding recombinant receptors.

In some cases, the polynucleotide encoding the BCMA-binding recombinant receptor contains a signal sequence that encodes a signal peptide, in some cases encoded upstream of the nucleic acid sequences encoding the BCMA-binding recombinant receptor, or joined at the 5' terminus of the nucleic acid sequences encoding the antigen-binding domain. In some cases, the polynucleotide containing nucleic acid sequences encoding the BCMA-binding recombinant receptor, e.g., chimeric antigen receptor (CAR), contains a signal sequence that encodes a signal peptide. In some aspects, the signal sequence may encode a signal peptide derived from a native polypeptide. In other aspects, the signal sequence may encode a heterologous or non-native signal peptide. In some aspects, non-limiting exemplary signal peptide include a signal peptide of the IgG kappa chain set forth in SEQ ID NO: 166, encoded by the nucleotide sequence set forth in SEQ ID NO: 167 or 168-171; a GMCSFR alpha chain set forth in SEQ ID NO:154, encoded by the nucleotide sequence set forth in SEQ ID NO:155; a CD8 alpha signal peptide set forth in SEQ ID NO:146; or a CD33 signal peptide set forth in SEQ ID NO:142. In some cases, the polynucleotide encoding the BCMA-binding recombinant receptor can contain nucleic acid sequences encoding additional molecules, such as a surrogate marker or other markers, or can contain additional components, such as promoters, regulatory elements and/or multicistronic elements. In some embodiments, the nucleic acid sequence encoding the BCMA-binding recombinant receptor can be operably linked to any of the additional components.

Further, in some contexts, optimal response to therapy can depend on the ability of the engineered recombinant receptors such as CARs, to be consistently and reliably expressed on the surface of the cells and/or bind the target antigen. For example, in some cases, heterogeneity of the transcribed RNA from an introduced transgene (e.g., encoding the recombinant receptor) can affect the expression and/or activity of the recombinant receptor, in some cases when expressed in a cell, such as a human T cell, used in cell therapy. In some contexts, the length and type of spacer in the recombinant receptor, such as a CAR, can affect the expression, activity and/or function of the receptor.

The provided embodiments, in some contexts, are based on the observation that particular spacers and optimization of the nucleic acid sequences can lead to consistent and robust expression of the recombinant receptor. In some embodiments, the BCMA-binding recombinant receptors employed in the provided methods offer advantages over available approaches for cell therapies, in particular, BCMA-targeting cell therapy. In some embodiments, the BCMA-binding recombinant receptors contain fully human antigen-binding domains, with low affinity for binding soluble BCMA. In some embodiments, the BCMA-binding recombinant receptors contain a modified spacer that result in enhanced binding to BCMA expressed on the surface of target cells. In some embodiments, the BCMA-binding recombinant receptors are observed to exhibit reduced antigen-independent, tonic signaling, which in some cases can result in reduced exhaustion of the cells from antigen-independent signaling, and lack of inhibition by soluble BCMA. In some embodiments, the BCMA-binding recombinant receptors exhibit activity or potency against target cells that express a low density or low level of BCMA. In some aspects, the advantages of the described BCMA-binding recombinant receptors include that they can be used in subjects that have previously received, and/or did not respond to, relapsed following or have become refractory to prior therapies that are directed to BCMA, including prior treatments or therapy with BCMA-binding or BCMA-targeting agents, such as a BCMA-targeting antibody-drug conjugate (ADC), a BCMA-targeting T cell engager (TCE) or cells expressing a BCMA-targeting chimeric antigen receptor (CAR). As provided herein, advantages of the BCMA-binding recombinant receptors, such as the stability, high expression, reduced antigen-independent (e.g., tonic) signaling, low binding by soluble BCMA, a high response rate, low incidences of adverse events (e.g., toxicity), prolonged response, and in some cases, improvement in the response over time, and thus can be employed in subjects that did not respond to, relapsed following or became refractory to prior BCMA-directed therapies.

Also, in some contexts, certain recombinant receptors can exhibit antigen-independent activity or signaling (also known as "tonic signaling"), which could lead to undesirable effects, such as due to increased differentiation and/or exhaustion of T cells that express the recombinant receptor. In some aspects, such activities may limit the T cell's activity, effect or potency. In some cases, during engineering and ex vivo expansion of the cells for recombinant receptor expression, the cells may exhibit phenotypes indicative of exhaustion, due to tonic signaling through the recombinant receptor.

In some contexts, properties of particular target antigens that the recombinant receptors specifically bind, recognize or target, can affect the activity of the receptor. In some contexts, B-cell maturation antigen (BCMA), is typically expressed on malignant plasma cells and is an attractive therapeutic target for cell therapy. In some cases, BCMA is can be cleaved by gamma secretase, generating a soluble BCMA (sBCMA), or "shed" form of BCMA, reducing the BCMA expressed on the surface of target cells. In some cases, the activity of the BCMA-binding recombinant receptors, such as anti-BCMA chimeric antigen receptors (CARs), can be blocked or inhibited by the presence of soluble BCMA. Improved strategies are needed for optimal responses to cell therapies, in particular, for recombinant receptors that specifically bind, recognize or target BCMA, such as BCMA expressed on the surface of the target cells.

The BCMA-binding recombinant receptors, e.g., expressed in the cells employed in the methods and uses provided herein, generally contain an extracellular binding domain and an intracellular signaling domain. Among the BCMA-binding recombinant receptors are polypeptides containing antibodies, including single chain cell surface proteins, e.g., recombinant receptors such as chimeric antigen receptors, containing such antibodies.

Among the BCMA-binding recombinant receptors are single chain cell surface proteins, such as recombinant receptors (e.g., antigen receptors), that include one of the provided antibodies or fragment thereof (e.g., BCMA-binding fragment). The recombinant receptors include antigen receptors that specifically bind to or specifically recognize BCMA, such as antigen receptors containing the provided anti-BCMA antibodies, e.g., antigen-binding fragments. Among the antigen receptors are functional non-TCR antigen receptors, such as chimeric antigen receptors (CARs). Also provided are cells expressing the recombinant receptors and uses thereof in adoptive cell therapy, such as treatment of diseases and disorders associated with BCMA expression.

Exemplary antigen receptors, including CARs, and methods for engineering and introducing such antigen receptors into cells, include those described, for example, in international patent application publication Nos. WO200014257, WO2013126726, WO2012/129514, WO2014031687, WO2013166321, WO2013071154, WO2013123061 U.S. patent application publication Nos. US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application No. EP2537416, each incorporated herein in its entirety; and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 March 18(2): 160-75. In some aspects, the antigen receptors include a CAR as described in U.S. Pat. No. 7,446,190, and those described in International Patent Application Publication No. WO2014055668. Exemplary CARs include CARs as disclosed in any of the aforementioned publications, such as WO2014031687, U.S. Pat. Nos. 8,339,645, 7,446,179, US 2013/0149337, U.S. Pat. Nos. 7,446,190, and 8,389,282, and in which the antigen-binding portion, e.g., scFv, is replaced by an antibody or an antigen-binding fragment thereof, as provided herein.

In some aspects, the BCMA-specific CAR employed in the provided embodiments comprises those described, for example, in WO 2019/090003.

In some aspects, the BCMA-specific CAR employed in the provided embodiments has an amino acid sequence selected from among SEQ ID NOs: 15-20, or an amino acid sequence that exhibits at least or about at least 90%, 91%, 92%, 93%, 94%, 95%, 96%, 97%, 98% or 99% sequence identity to the amino acid sequence set forth in any of SEQ ID NOs 15-20. In some embodiments, the CAR has an amino acid sequence set forth in SEQ ID NO: 19, or an amino acid sequence that exhibits at least or about at least 90%, 91%, 92%, 93%, 94%, 95%, 96%, 97%, 98% or 99% sequence identity to the amino acid sequence set forth in SEQ ID NO:19.

In some embodiments, the CAR is encoded by a polynucleotide, such as an polynucleotide with the nucleic acid sequence set forth in any of SEQ ID NOs 9-14, or a sequences that exhibits at least or at least about 90%, 91%, 92%, 93%, 94%, 95%, 96%, 97%, 98% or 99% sequence identity to the nucleic acid sequence set forth in any of SEQ ID NOs: 9-14. In some embodiments, the CAR is encoded by a polynucleotide, such as an polynucleotide with the nucleic acid sequence set forth in SEQ ID NO:13 or SEQ ID NO: 14, or a sequences that exhibits at least or at least about 90%, 91%, 92%, 93%, 94%, 95%, 96%, 97%, 98% or 99% sequence identity to the nucleic acid sequence set forth in SEQ ID NO: 13 or SEQ ID NO: 14. In some embodiments, the CAR is encoded by a polynucleotide, such as an polynucleotide with the nucleic acid sequence set forth in SEQ ID NO:13 or a sequences that exhibits at least or at least about 90%, 91%, 92%, 93%, 94%, 95%, 96%, 97%, 98% or 99% sequence identity to SEQ ID NO: 13. In some embodiments, the CAR is encoded by a polynucleotide, such as an polynucleotide with the nucleic acid sequence set forth in SEQ ID NO:13. In some embodiments, the CAR is encoded by a polynucleotide, such as an polynucleotide with the nucleic acid sequence set forth in SEQ ID NO:14 or a sequences that exhibits at least or at least about 90%, 91%, 92%, 93%, 94%, 95%, 96%, 97%, 98% or 99% sequence identity to SEQ ID NO: 14. In some embodiments, the CAR is encoded by a polynucleotide, such as an polynucleotide with the nucleic acid sequence set forth in SEQ ID NO:14.

In some embodiments, the nucleic acid encoding the antigen-binding domain comprises (a) the sequence of nucleotides set forth in any of SEQ ID NOS: 30, 31, 50, 51, 59, 60, 82, 84, 113, and 115; (b) a sequence of nucleotides that has at least 90% sequence identity to any of SEQ ID NOS: 30, 31, 50, 51, 59, 60, 82, 84, 113, and 115; or (c) a degenerate sequence of (a) or (b). In some embodiments, the nucleic acid encoding the antigen-binding domain comprises (a) a sequence of nucleotides encoding the amino acid sequence set forth in any of SEQ ID NOS: 29, 49, 58, 83, 114, 126, 128, 129, 130; (b) a sequence of nucleotides that has at least 90% sequence identity to a sequence of nucleotides encoding the amino acid sequence set forth in any of SEQ ID NOS: 29, 49, 58, 83, 114, 126, 128, 129, 130; or (c) a degenerate sequence of (a) or (b).

A. Antigen-Binding Domain

Among the chimeric receptors are chimeric antigen receptors (CARs). The chimeric receptors, such as CARs, generally include an extracellular antigen binding domain that includes, is, or is comprised within or comprises, one of the provided anti-BCMA antibodies. Thus, the chimeric receptors, e.g., CARs, typically include in their extracellular portions one or more BCMA-binding domain, such as one or more antigen-binding fragment, domain, or portion, or one or more antibody variable regions, and/or antibody molecules, such as those described herein.

The term "antibody" herein is used in the broadest sense and includes polyclonal and monoclonal antibodies, including intact antibodies and functional (antigen-binding) antibody fragments, including fragment antigen binding (Fab) fragments, $F(ab')_2$ fragments, Fab' fragments, Fv fragments, recombinant IgG (rIgG) fragments, heavy chain variable ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific or trispecific, antibodies, diabodies, triabodies, and tetrabodies, tandem di-scFv, tandem tri-scFv. Unless otherwise stated, the term "antibody" should be understood to encompass functional antibody fragments thereof also referred to herein as "antigen-binding fragments." The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262: 732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

Table 5, below, lists exemplary position boundaries of CDR-L1, CDR-L2, CDR-L3 and CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-L1 located before CDR-L1, FR-L2 located between CDR-L1 and CDR-L2, FR-L3 located between CDR-L2 and CDR-L3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 5

Boundaries of CDRs according to various numbering schemes.

| CDR | Kabat | Chothia | AbM | Contact |
|---|---|---|---|---|
| CDR-L1 | L24--L34 | L24--L34 | L24--L34 | L30--L36 |
| CDR-L2 | L50--L56 | L50--L56 | L50--L56 | L46--L55 |
| CDR-L3 | L89--L97 | L89--L97 | L89--L97 | L89--L96 |
| CDR-H1 (Kabat Numbering[1]) | H31--H35B | H26--H32.34 | H26--H35B | H30--H35B |
| CDR-H1 (Chothia Numbering[2]) | H31--H35 | H26--H32 | H26--H35 | H30--H35 |
| CDR-H2 | H50--H65 | H52--H56 | H50--H58 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes, or other known schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes, or other known schemes. In some embodiments, specific CDR sequences are specified. Exemplary CDR sequences of provided antibodies are described using various numbering schemes, although it is understood that a provided antibody can include CDRs as described according to any of the other aforementioned numbering schemes or other numbering schemes known to a skilled artisan.

Likewise, unless otherwise specified, a FR or individual specified FR(s) (e.g., FR-H1, FR-H2, FR-H3, FR-H4), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, AbM, IMGT or Contact method, or other known schemes. In other cases, the particular amino acid sequence of a CDR or FR is given.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the antibodies included in the CARs are antibody fragments. An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; heavy chain variable ($V_H$) regions, single-chain antibody molecules such as scFvs and single-domain antibodies comprising only the $V_H$ region; and multispecific antibodies formed from antibody fragments. In some embodiments, the antigen-binding domain in the CARs is or comprises an antibody fragment comprising a variable heavy chain ($V_H$) and a variable light chain ($V_L$) region. In particular embodiments, the antibodies are single-chain antibody fragments comprising a heavy chain variable ($V_H$) region and/or a light chain variable ($V_L$) region, such as scFvs.

Single-domain antibodies (sdAbs) are antibody fragments comprising all or a portion of the heavy chain variable region or all or a portion of the light chain variable region of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the anti-BCMA antibodies included in the CARs are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human. The term includes antigen-binding fragments of human antibodies.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the antibodies included in the CARs are those that are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

In some embodiments, the CAR includes a BCMA-binding portion or portions of the antibody molecule, such as a heavy chain variable ($V_H$) region and/or light chain variable ($V_L$) region of the antibody, e.g., an scFv antibody fragment. In some embodiments, the BCMA-binding CARs described herein, for example, for use in the provided methods, contain an antibody, such as an anti-BCMA antibody, or an antigen-binding fragment thereof that confers the BCMA-binding properties of the CAR. In some embodiments, the antibody or antigen-binding domain can be any anti-BCMA antibody described or derived from any anti-BCMA antibody described. See, e.g., Carpenter et al., *Clin Cancer Res.,* 2013, 19(8):2048-2060, WO 2016090320, WO2016090327, WO2010104949 and WO2017173256. Any of such anti-BCMA antibodies or antigen-binding fragments can be used in the CARs. In some embodiments, the anti-BCMA CAR contains an antigen-binding domain that is an scFv containing a variable heavy ($V_H$) and/or a variable light ($V_L$) region derived from an antibody described in WO 2016090320 or WO2016090327.

In some embodiments, the antibody, e.g., the anti-BCMA antibody or antigen-binding fragment, contains a heavy and/or light chain variable ($V_H$ or $V_L$) region sequence as described, or a sufficient antigen-binding portion thereof. In some embodiments, the anti-BCMA antibody, e.g., antigen-binding fragment, contains a $V_H$ region sequence or sufficient antigen-binding portion thereof that contains a CDR-H1, CDR-H2 and/or CDR-H3 as described. In some embodiments, the anti-BCMA antibody, e.g., antigen-binding fragment, contains a $V_L$ region sequence or sufficient antigen-binding portion that contains a CDR-L1, CDR-L2 and/or CDR-L3 as described. In some embodiments, the anti-BCMA antibody, e.g., antigen-binding fragment, contains a $V_H$ region sequence that contains a CDR-H1, CDR-H2 and/or CDR-H3 as described and contains a $V_L$ region sequence that contains a CDR-L1, CDR-L2 and/or CDR-L3 as described. Also among the antibodies are those having sequences at least at or about 90%, about 91%, about 92%, about 93%, about 94%, about 95%, about 96%, about 97%, about 98%, or about 99% identical to such a sequence.

In some embodiments, the antibody is a single domain antibody (sdAb) comprising only a $V_H$ region sequence or a sufficient antigen-binding portion thereof, such as any of the above described $V_H$ sequences (e.g., a CDR-H1, a CDR-H2, a CDR-H3 and/or a CDR-H4).

In some embodiments, an antibody provided herein (e.g., an anti-BCMA antibody) or antigen-binding fragment thereof comprising a $V_H$ region further comprises a light chain or a sufficient antigen binding portion thereof. For example, in some embodiments, the antibody or antigen-binding fragment thereof contains a $V_H$ region and a $V_L$ region, or a sufficient antigen-binding portion of a $V_H$ and $V_L$ region. In such embodiments, a $V_H$ region sequence can be any of the above described $V_H$ sequence. In some such embodiments, the antibody is an antigen-binding fragment, such as a Fab or an scFv. In some such embodiments, the antibody is a full-length antibody that also contains a constant region.

In some embodiments, the antibody, e.g., antigen-binding fragment thereof, in the CAR, has a heavy chain variable ($V_H$) region having the amino acid sequence selected from any one of SEQ ID NOs: 32, 52, 61, 85, 116, 125, 131, or an amino acid sequence that has at least 90%, 91%, 92%, 93%, 94%, 95%, 96%, 97%, 98%, or 99% sequence identity to the $V_H$ region amino acid selected from any one of SEQ ID NOs: 32, 52, 61, 85, 116, 125, 131, or contains a CDR-H1, CDR-H2, and/or CDR-H3 present in such a $V_H$ sequence. In some embodiments, the antibody or antibody fragment, in the CAR, has a $V_H$ region of any of the antibodies or antibody binding fragments described in WO 2016/090327, WO 2016/090320, or WO 2017/173256.

In some embodiments, the antibody, e.g., antigen-binding fragment thereof, in the CAR, has a light chain variable ($V_L$) region having the amino acid sequence selected from any one of SEQ ID NOs: 33, 53, 62, 88, 119, 127, and 132, or an amino acid sequence that has at least 90%, 91%, 92%, 93%, 94%, 95%, 96%, 97%, 98%, or 99% sequence identity to the $V_L$ region amino acid selected from any one of SEQ ID NOs: 33, 53, 62, 88, 119, 127, and 132, or contains a CDR-L1, CDR-L2, and/or CDR-L3 present in such a $V_L$ sequence. In some embodiments, the antibody or antibody fragment, in the CAR, has a $V_L$ region of any of the antibodies or antibody binding fragments described in WO 2016/090327, WO 2016/090320, or WO 2017/173256.

In some embodiments, the $V_H$ and $V_L$ regions of the antibody, e.g., antigen-binding fragment thereof, in the CAR, comprises: the amino acid sequence of SEQ ID NOS:32 and 33, respectively, or a sequence of amino acids having at least 90% identity to SEQ ID NOS:32 and 33, respectively; the amino acid sequence of SEQ ID NOS:52 and 53, respectively, or a sequence of amino acids having at least 90% identity to SEQ ID NOS:52 and 53, respectively; the amino acid sequence of SEQ ID NOS:61 and 62, respectively, or a sequence of amino acids having at least 90% identity to SEQ ID NOS:61 and 62, respectively; the amino acid sequence of SEQ ID NOS:85 and 88, respectively, or a sequence of amino acids having at least 90% identity to SEQ ID NOS:85 and 88, respectively; the amino acid sequence of SEQ ID NOS:116 and 119, respectively, or a sequence of amino acids having at least 90% identity to SEQ ID NOS:116 and 119, respectively; the amino acid sequence of SEQ ID NOS:125 and 127, respectively, or a sequence of amino acids having at least 90% identity to SEQ ID NOS:125 and 127, respectively; the amino acid sequence of SEQ ID NOS:131 and 132, respectively, or a sequence of amino acids having at least 90% identity to SEQ ID NOS: 131 and 132, respectively.

In some embodiments, the $V_H$ and $V_L$ regions of the antibody or antigen-binding fragment thereof, in the CAR, comprises: the amino acid sequence of SEQ ID NOS:32 and 33, respectively, or a sequence of amino acids having at least 90% identity to SEQ ID NOS:32 and 33, respectively. In some embodiments, the $V_H$ and $V_L$ regions of the antibody or antigen-binding fragment thereof comprises the amino acid sequence of SEQ ID NOS:52 and 53, respectively, or a sequence of amino acids having at least 90% identity to SEQ ID NOS:52 and 53, respectively. In some embodiments, the $V_H$ and $V_L$ regions of the antibody or antigen-binding fragment thereof comprises the amino acid sequence of SEQ ID NOS:61 and 62, respectively, or a sequence of amino acids having at least 90% identity to SEQ ID NOS:61 and 62, respectively. In some embodiments, the $V_H$ and $V_L$ regions of the antibody or antigen-binding fragment thereof comprises the amino acid sequence of SEQ ID NOS:85 and 88, respectively, or a sequence of amino acids having at least 90% identity to SEQ ID NOS:85 and 88, respectively. In some embodiments, the $V_H$ and $V_L$ regions of the antibody or antigen-binding fragment thereof comprises the amino acid sequence of SEQ ID NOS:116 and 119, respectively, or a sequence of amino acids having at least 90% identity to SEQ ID NOS:116 and 119, respectively. In some embodiments, the $V_H$ and $V_L$ regions of the antibody or antigen-binding fragment thereof comprises the amino acid sequence of SEQ ID NOS:125 and 127, respectively, or a sequence of amino acids having at least 90% identity to SEQ ID NOS: 125 and 127, respectively. In some embodiments, the $V_H$ and $V_L$ regions of the antibody or antigen-binding fragment thereof comprises the amino acid sequence of SEQ ID NOS:131 and 132, respectively, or a sequence of amino acids having at least 90% identity to SEQ ID NOS:131 and 132, respectively.

In some embodiments, the $V_H$ and $V_L$ regions of the antibody or antigen-binding fragment thereof, in the CAR, comprises: the amino acid sequence of SEQ ID NOS:32 and 33. In some embodiments, the $V_H$ and $V_L$ regions of the antibody or antigen-binding fragment thereof comprises the amino acid sequence of SEQ ID NOS:52 and 53. In some embodiments, the $V_H$ and $V_L$ regions of the antibody or antigen-binding fragment thereof comprises the amino acid sequence of SEQ ID NOS:61 and 62. In some embodiments, the $V_H$ and $V_L$ regions of the antibody or antigen-binding fragment thereof comprises the amino acid sequence of SEQ ID NOS:85 and 88. In some embodiments, the $V_H$ and $V_L$ regions of the antibody or antigen-binding fragment thereof comprises the amino acid sequence of SEQ ID NOS:116 and 119, respectively. In some embodiments, the $V_H$ and $V_L$ regions of the antibody or antigen-binding fragment thereof comprises the amino acid sequence of SEQ ID NOS:125 and 127, respectively. In some embodiments, the $V_H$ and $V_L$ regions of the antibody or antigen-binding fragment thereof comprises the amino acid sequence of SEQ ID NOS:131 and 132, respectively.

In some embodiments, in the CAR, the antibody or antigen-binding fragment thereof comprises a $V_H$ and a $V_L$ region, and the $V_H$ region comprises a heavy chain complementarity determining region 1 (CDR-H1), a heavy chain complementarity determining region 2 (CDR-H2) and a heavy chain complementarity determining region 3 (CDR-H3) contained within the $V_H$ region amino acid sequence selected from any one of SEQ ID NOs: 32, 52, 61, 85, 116, 125, 131; and the $V_L$ region comprises a light chain complementarity determining region 1 (CDR-L1), a light chain complementarity determining region 2 (CDR-L2) and a light chain complementarity determining region 3 (CDR-L3) contained within the $V_L$ region amino acid sequence selected from any one of SEQ ID NOs: 33, 53, 62, 88, 119, 127, 132.

In some embodiments, in the CAR, the antibody or antigen-binding fragment thereof comprises a $V_H$ and a $V_L$ region, and the $V_H$ region comprises a CDR-H1, a CDR-H2 and a CDR-H3 contained within the amino acid sequence of SEQ ID NO:32, and the $V_L$ region comprises a CDR-L1, a CDR-L2 and a CDR-L3 contained within the amino acid sequence of SEQ ID NO:33; the $V_H$ region comprises a CDR-H1, a CDR-H2 and a CDR-H3 contained within the amino acid sequence of SEQ ID NO:52, and the $V_L$ region comprises a CDR-L1, a CDR-L2 and a CDR-L3 contained within the amino acid sequence of SEQ ID NO:53; the $V_H$ region comprises a CDR-H1, a CDR-H2 and a CDR-H3 contained within the amino acid sequence of SEQ ID NO:61, and the $V_L$ region comprises a CDR-L1, a CDR-L2 and a CDR-L3 contained within the amino acid sequence of SEQ ID NO:62; the $V_H$ region comprises a CDR-H1, a CDR-H2 and a CDR-H3 contained within the amino acid sequence of SEQ ID NO:85, and the $V_L$ region comprises a CDR-L1, a CDR-L2 and a CDR-L3 contained within the amino acid sequence of SEQ ID NO:88; the $V_H$ region comprises a CDR-H1, a CDR-H2 and a CDR-H3 contained within the amino acid sequence of SEQ ID NO:116, and the $V_L$ region comprises a CDR-L1, a CDR-L2 and a CDR-L3 contained within the amino acid sequence of SEQ ID NO:119; the $V_H$ region comprises a CDR-H1, a CDR-H2 and a CDR-H3 contained within the amino acid sequence of SEQ ID NO:125, and the $V_L$ region comprises a CDR-L1, a CDR-L2 and a CDR-L3 contained within the amino acid sequence of SEQ ID NO:127; the $V_H$ region comprises a CDR-H1, a CDR-H2 and a CDR-H3 contained within the amino acid sequence of SEQ ID NO:131, and the $V_L$ region comprises a CDR-L1, a CDR-L2 and a CDR-L3 contained within the amino acid sequence of SEQ ID NO:132.

In some embodiments, in the CAR, the antibody or antigen-binding fragment thereof comprises a $V_H$ and a $V_L$ region, and the $V_H$ region comprises a CDR-H1, a CDR-H2 and a CDR-H3 contained within the amino acid sequence of SEQ ID NO:32, and the $V_L$ region comprises a CDR-L1, a CDR-L2 and a CDR-L3 contained within the amino acid sequence of SEQ ID NO:33. In some embodiments, the $V_H$ region comprises a CDR-H1, a CDR-H2 and a CDR-H3 contained within the amino acid sequence of SEQ ID NO:52, and the $V_L$ region comprises a CDR-L1, a CDR-L2 and a CDR-L3 contained within the amino acid sequence of SEQ ID NO:53. In some embodiments, the $V_H$ region comprises a CDR-H1, a CDR-H2 and a CDR-H3 contained within the amino acid sequence of SEQ ID NO:61, and the $V_L$ region comprises a CDR-L1, a CDR-L2 and a CDR-L3 contained within the amino acid sequence of SEQ ID NO:62. In some embodiments, the $V_H$ region comprises a CDR-H1, a CDR-H2 and a CDR-H3 contained within the amino acid sequence of SEQ ID NO:85, and the $V_L$ region comprises a CDR-L1, a CDR-L2 and a CDR-L3 contained within the amino acid sequence of SEQ ID NO:88. In some embodiments, the $V_H$ region comprises a CDR-H1, a CDR-H2 and a CDR-H3 contained within the amino acid sequence of SEQ ID NO:116, and the $V_L$ region comprises a CDR-L1, a CDR-L2 and a CDR-L3 contained within the amino acid sequence of SEQ ID NO:119. In some embodiments, the $V_H$ region comprises a CDR-H1, a CDR-H2 and a CDR-H3 contained within the amino acid sequence of SEQ ID NO:125, and the $V_L$ region comprises a CDR-L1, a CDR-L2 and a CDR-L3 contained within the amino acid sequence of SEQ ID NO:127. In some embodiments, the $V_H$ region comprises a CDR-H1, a CDR-H2 and a CDR-H3 contained within the amino acid sequence of SEQ ID NO:131, and the $V_L$ region comprises a CDR-L1, a CDR-L2 and a CDR-L3 contained within the amino acid sequence of SEQ ID NO:132.

In some embodiments, the $V_H$ and $V_L$ regions of the antibody or antigen-binding fragment thereof, in the CAR, comprises: the amino acid sequence of SEQ ID NOS:32 and 33, respectively. In some embodiments, the $V_H$ and $V_L$ regions of the antibody or antigen-binding fragment thereof comprises the amino acid sequence of SEQ ID NOS:52 and 53, respectively. In some embodiments, the $V_H$ and $V_L$ regions of the antibody or antigen-binding fragment thereof comprises the amino acid sequence of SEQ ID NOS:61 and 62, respectively. In some embodiments, the $V_H$ and $V_L$ regions of the antibody or antigen-binding fragment thereof comprises the amino acid sequence of SEQ ID NOS:85 and 88, respectively. In some embodiments, the $V_H$ and $V_L$ regions of the antibody or antigen-binding fragment thereof comprises the amino acid sequence of SEQ ID NOS:116 and 119, respectively. In some embodiments, the $V_H$ and $V_L$ regions of the antibody or antigen-binding fragment thereof comprises the amino acid sequence of SEQ ID NOS:125 and 127, respectively. In some embodiments, the $V_H$ and $V_L$ regions of the antibody or antigen-binding fragment thereof comprises the amino acid sequence of SEQ ID NOS:131 and 132, respectively.

In some embodiments, the $V_H$ and $V_L$ regions of the antibody or antigen-binding fragment thereof provided therein comprise the amino acid sequences selected from: SEQ ID NOS:116 and 119, or any antibody or antigen-binding fragment thereof that has at least 90% sequence identity to any of the above $V_H$ and $V_L$, such as at least 90%, 91%, 92%, 93%, 94%, 95%, 96%, 97%, 98%, or 99% sequence identity thereto, or any antibody or antigen-binding fragment thereof that comprises a CDR-H1, CDR-H2 and CDR-H3 contained within the $V_H$ region and a CDR-L1, CDR-L2 and CDR-L3 contained within the $V_L$ region of any of the above $V_H$ and $V_L$. In some embodiments, the $V_H$ and $V_L$ regions of the antibody or antigen-binding fragment thereof provided therein comprise the amino acid sequences selected from: SEQ ID NOS:116 and 119. In some embodiments, an anti-idiotypic antibody, as described in PCT/US2020/063492, is used to detect expression of an antigen-binding domain comprises these sequences.

In some embodiments, the antibody or antigen-binding fragment thereof is a single-chain antibody fragment, such as a single chain variable fragment (scFv) or a diabody or a single domain antibody (sdAb). In some embodiments, the antibody or antigen-binding fragment is a single domain antibody comprising only the $V_H$ region. In some embodiments, the antibody or antigen binding fragment is an scFv comprising a heavy chain variable ($V_H$) region and a light chain variable ($V_L$) region. In some embodiments, the single-chain antibody fragment (e.g. scFv) includes one or more linkers joining two antibody domains or regions, such as a heavy chain variable ($V_H$) region and a light chain variable ($V_L$) region. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline.

Accordingly, the provided anti-BCMA antibodies include single-chain antibody fragments, such as scFvs and diabodies, particularly human single-chain antibody fragments, typically comprising linker(s) joining two antibody domains or regions, such $V_H$ and $V_L$ regions. The linker typically is a peptide linker, e.g., a flexible and/or soluble peptide linker, such as one rich in glycine and serine.

In some aspects, the linkers rich in glycine and serine (and/or threonine) include at least 80%, 85%, 90%, 91%, 92%, 93%, 94%, 95%, 96%, 97%, 98%, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length. Exemplary linkers include linkers having various numbers of repeats of the sequence GGGGS (4GS; SEQ ID NO:7) or GGGS (3GS; SEQ ID NO:2), such as between 2, 3, 4, and 5 repeats of such a sequence. Exemplary linkers include those having or consisting of an sequence set forth in SEQ ID NO:1 (GGGGSGGGGSGGGGS). Exemplary linkers further include those having or consisting of the sequence set forth in SEQ ID NO:176 (GSTSGSGKPGSGEGSTKG). Exemplary linkers further include those having or consisting of the sequence set forth in SEQ ID NO:255 (SRGGGGSGGGGSGGGGSLEMA).

Accordingly, in some embodiments, the provided embodiments include single-chain antibody fragments, e.g., scFvs, comprising one or more of the aforementioned linkers, such as glycine/serine rich linkers, including linkers having repeats of GGGS (SEQ ID NO: 2) or GGGGS (SEQ ID NO: 7), such as the linker set forth in SEQ ID NO:1.

In some embodiments, the linker has an amino acid sequence containing the sequence set forth in SEQ ID NO:1. The fragment, e.g., scFv, may include a $V_H$ region or portion thereof, followed by the linker, followed by a $V_L$ region or portion thereof. The fragment, e.g., the scFv, may include the $V_L$ region or portion thereof, followed by the linker, followed by the $V_H$ region or portion thereof.

Table 6 provides the SEQ ID NOS of exemplary antigen-binding domains, such as antibodies or antigen-binding fragments, that can be comprised in the BCMA-binding recombinant receptors, such as anti-BCMA chimeric antigen receptors (CARs), to be employed in the provided methods and uses. In some embodiments, the BCMA-binding recombinant receptor contains a BCMA-binding antibody or fragment thereof, comprising a $V_H$ region that comprises the CDR-H1, CDR-H2, and CDR-H3 sequence and a $V_L$ region that comprises the CDR-L1, CDR-L2 and CDR-L3 sequence set forth in the SEQ ID NOS listed in each row of Table 6 below (by Kabat numbering). In some embodiments, the BCMA-binding recombinant receptor contains a BCMA-binding antibody or fragment thereof, comprising a $V_H$ region sequence and a $V_L$ region sequence set forth in the SEQ ID NOS listed in each row of Table 6 below, or an antibody comprising a $V_H$ and $V_L$ region amino acid sequence that has at least 90%, 91%, 92%, 93%, 94%, 95%, 96%, 97%, 98%, or 99% sequence identity to the $V_H$ region sequence and the $V_L$ region sequence set forth in the SEQ ID NOS listed in each row of Table 6 below. In some embodiments, the BCMA-binding recombinant receptor contains a BCMA-binding antibody or fragment thereof, comprising a $V_H$ region sequence and a $V_L$ region sequence set forth in the SEQ ID NOS listed in each row of Table 6 below. In some embodiments, the BCMA-binding recombinant receptor contains a BCMA-binding antibody or fragment thereof, comprising an scFv sequence set forth in the SEQ ID NOS listed in each row of Table 6 below, or an antibody comprising an scFv amino acid sequence that has at least 90%, 91%, 92%, 93%, 94%, 95%, 96%, 97%, 98%, or 99% sequence identity to the scFv sequence set forth in the SEQ ID NOS listed in each row of Table 6 below. In some embodiments, the BCMA-binding recombinant receptor contains a BCMA-binding antibody or fragment thereof, comprising an scFv sequence set forth in SEQ ID NO:114 or an antibody comprising an scFv amino acid sequence that has at least 90%, 91%, 92%, 93%, 94%, 95%, 96%, 97%, 98%, or 99% sequence identity thereto. In some embodiments, the BCMA-binding recombinant receptor contains a BCMA-binding antibody or fragment thereof, comprising an scFv sequence set forth in the SEQ ID NOS listed in each row of Table 6 below. In some embodiments, the BCMA-binding recombinant receptor contains a BCMA-binding antibody or fragment thereof, comprising an scFv sequence set forth in SEQ ID NO: 114.

TABLE 6

Sequence identifier (SEQ ID NO) for Exemplary Antigen-binding Domains

| Antigen-binding domain | CDR-H1 | CDR-H2 | CDR-H3 | CDR-L1 | CDR-L2 | CDR-L3 | $V_H$ | $V_L$ | scFv |
|---|---|---|---|---|---|---|---|---|---|
| BCMA-23 | 34 | 35 | 36 | 22 | 23 | 24 | 32 | 33 | 29 |
| BCMA-25 | 37 | 38 | 39 | 40 | 41 | 42 | 52 | 53 | 49 |
| BCMA-26 | 34 | 35 | 54 | 55 | 56 | 57 | 61 | 62 | 58 |
| BCMA-52 | 66 | 70 | 72 | 74 | 76 | 77 | 85 | 88 | 83 |
| BCMA-55 | 97 | 101 | 103 | 105 | 107 | 108 | 116 | 119 | 114 |
| BCMA-C1, $V_H$-$V_L$ | | | | | | | 125 | 127 | 126 |
| BCMA-C1, $V_L$-$V_H$ | | | | | | | 125 | 127 | 128 |
| BCMA-C2, $V_H$-$V_L$ | | | | | | | 131 | 132 | 129 |
| BCMA-C2, $V_L$-$V_H$ | | | | | | | 131 | 132 | 130 |

Among the antibodies, e.g. antigen-binding fragments, in the CARs, are human antibodies. In some embodiments of a provided human anti-BCMA antibody, e.g., antigen-binding fragments, the human antibody contains a $V_H$ region that comprises a portion having at least 95%, 96%, 97%, 98%, 99%, or 100% sequence identity to an amino acid sequence encoded by a germline nucleotide human heavy chain V segment, a portion having at least 95%, 96%, 97%, 98%, 99%, or 100% sequence identity to an amino acid sequence encoded by a germline nucleotide human heavy chain D segment, and/or a portion having at least 95%, 96%, 97%, 98%, 99%, or 100% sequence identity to an amino acid sequence encoded by a germline nucleotide human heavy chain J segment; and/or contains a $V_L$ region that comprises a portion having at least 95%, 96%, 97%, 98%, 99%, or 100% sequence identity to an amino acid sequence encoded by a germline nucleotide human kappa or lambda chain V segment, and/or a portion having at least 95%, 96%, 97%, 98%, 99%, or 100% sequence identity to an amino acid sequence encoded by a germline nucleotide human kappa or lambda chain J segment. In some embodiments, the portion of the $V_H$ region corresponds to the CDR-H1, CDR-H2 and/or CDR-H3. In some embodiments, the portion of the $V_H$ region corresponds to the framework region 1 (FR1), FR2, FR2 and/or FR4. In some embodiments, the portion of the $V_L$ region corresponds to the CDR-L1, CDR-L2 and/or CDR-L3. In some embodiments, the portion of the $V_L$ region corresponds to the FR1, FR2, FR2 and/or FR4.

In some embodiments, the human antibody, e.g., antigen-binding fragment, contains a CDR-H1 having at least 95%, 96%, 97%, 98%, 99%, or 100% sequence identity to an amino acid sequence of the corresponding CDR-H1 region within a sequence encoded by a germline nucleotide human heavy chain V segment. For example, the human antibody in some embodiments contains a CDR-H1 having a sequence that is 100% identical or with no more than one, two or three amino acid differences as compared to the corresponding CDR-H1 region within a sequence encoded by a germline nucleotide human heavy chain V segment.

In some embodiments, the human antibody, e.g., antigen-binding fragment, contains a CDR-H2 having at least 95%, 96%, 97%, 98%, 99%, or 100% sequence identity to an amino acid sequence of the corresponding CDR-H2 region within a sequence encoded by a germline nucleotide human heavy chain V segment. For example, the human antibody in some embodiments contains a CDR-H2 having a sequence that is 100% identical or with no more than one, two or three amino acid difference as compared to the corresponding CDR-H2 region within a sequence encoded by a germline nucleotide human heavy chain V segment.

In some embodiments, the human antibody, e.g., antigen-binding fragment, contains a CDR-H3 having at least 95%, 96%, 97%, 98%, 99%, or 100% sequence identity to an amino acid sequence of the corresponding CDR-H3 region within a sequence encoded by a germline nucleotide human heavy chain V segment, D segment and J segment. For example, the human antibody in some embodiments contains a CDR-H3 having a sequence that is 100% identical or with no more than one, two or three amino acid differences as compared to the corresponding CDR-H3 region within a sequence encoded by a germline nucleotide human heavy chain V segment, D segment and J segment.

In some embodiments, the human antibody, e.g., antigen-binding fragment, contains a CDR-L1 having at least 95%, 96%, 97%, 98%, 99%, or 100% sequence identity to an amino acid sequence of the corresponding CDR-L1 region within a sequence encoded by a germline nucleotide human light chain V segment. For example, the human antibody in some embodiments contains a CDR-L1 having a sequence that is 100% identical or with no more than one, two or three amino acid differences as compared to the corresponding CDR-L1 region within a sequence encoded by a germline nucleotide human light chain V segment.

In some embodiments, the human antibody, e.g., antigen-binding fragment, contains a CDR-L2 having at least 95%, 96%, 97%, 98%, 99%, or 100% sequence identity to an amino acid sequence of the corresponding CDR-L2 region within a sequence encoded by a germline nucleotide human light chain V segment. For example, the human antibody in some embodiments contains a CDR-L2 having a sequence that is 100% identical or with no more than one, two or three amino acid difference as compared to the corresponding CDR-L2 region within a sequence encoded by a germline nucleotide human light chain V segment.

In some embodiments, the human antibody, e.g., antigen-binding fragment, contains a CDR-L3 having at least 95%, 96%, 97%, 98%, 99%, or 100% sequence identity to an amino acid sequence of the corresponding CDR-L3 region within a sequence encoded by a germline nucleotide human light chain V segment and J segment. For example, the human antibody in some embodiments contains a CDR-L3 having a sequence that is 100% identical or with no more than one, two or three amino acid differences as compared to the corresponding CDR-L3 region within a sequence encoded by a germline nucleotide human light chain V segment and J segment.

In some embodiments, the human antibody, e.g., antigen-binding fragment, contains a framework region that contains human germline gene segment sequences. For example, in some embodiments, the human antibody contains a $V_H$ region in which the framework region, e.g. FR1, FR2, FR3 and FR4, has at least 95%, 96%, 97%, 98%, 99%, or 100% sequence identity to a framework region encoded by a human germline antibody segment, such as a V segment and/or J segment. In some embodiments, the human antibody contains a $V_L$ region in which the framework region e.g. FR1, FR2, FR3 and FR4, has at least 95%, 96%, 97%, 98%, 99%, or 100% sequence identity to a framework region encoded by a human germline antibody segment, such as a V segment and/or J segment. For example, in some such embodiments, the framework region sequence contained within the $V_H$ region and/or $V_L$ region differs by no more than 10 amino acids, such as no more than 9, 8, 7, 6, 5, 4, 3, 2 or 1 amino acid, compared to the framework region sequence encoded by a human germline antibody segment.

In some embodiments, the reference antibody can be a mouse anti-BCMA scFv described in International Patent App. Pub. No. WO 2010/104949.

The antibody, e.g., antigen-binding fragment, may contain at least a portion of an immunoglobulin constant region, such as one or more constant region domain. In some embodiments, the constant regions include a light chain constant region and/or a heavy chain constant region 1 ($C_H1$). In some embodiments, the antibody includes a $C_H2$ and/or $C_H3$ domain, such as an Fc region. In some embodiments, the Fc region is an Fc region of a human IgG, such as an IgG1 or IgG4.

B. Spacer

In some embodiments, the recombinant receptor such as a CAR comprising an antibody (e.g., antigen-binding fragment) provided herein, such as those expressed by engineered cells employed in the methods and uses provided herein, further includes a spacer or spacer region. The spacer typically is a polypeptide spacer and in general is located within the CAR between the antigen binding domain and the transmembrane domain of the CAR. In some aspects, the spacer may be or include at least a portion of an immunoglobulin constant region or variant or modified version thereof, such as a hinge region of an immunoglobulin, such as an IgG hinge region, e.g., an IgG4 or IgG4-derived hinge region, and/or a $C_H1/C_L$ and/or Fc region. In some embodiments, the spacer comprises a hinge region that comprises or is CD8alpha. In some embodiments, the CD8alpha is a human CD8alpha. In some embodiments, the constant region or one or more of the portion(s) thereof is of a human IgG, such as of a human IgG4 or IgG1 or IgG2. In general, the spacer, such as the portion of the constant region, serves as a spacer region between the antigen-recognition component (e.g., scFv) and transmembrane domain. In some embodiments, the length and/or composition of the spacer is designed to optimize or promote certain features of the interaction between the CAR and its target; in some aspects, it is designed to optimize the biophysical synapse distance between the CAR-expressing cell and the cell expressing the target of the CAR during or upon or following binding of the CAR to its target on the target-expressing cell; in some aspects, the target expressing cell is a BCMA-expressing tumor cell. In some embodiments, The CAR is expressed by a T-cell, and the length of the spacer is of a length that is compatible for T-cell activation or to optimize CAR T-cell performance. In some embodiments, the spacer is a spacer region, located between the ligand-binding domain and the transmembrane domain, of the recombinant receptor, e.g., CAR. In some embodiments, the spacer region is a region located between the ligand-binding domain and the transmembrane domain, of the recombinant receptor, e.g., CAR.

In some embodiments, the spacer can be of a length that provides for increased responsiveness of the cell following antigen binding, as compared to in the absence of the spacer and/or in the presence of a different spacer, such as one different only in length. In some embodiments, the spacer is at least 100 amino acids in length, such as at least 110, 125, 130, 135, 140, 145, 150, 160, 170, 180, 190, 200, 210, 220, 230, 240, or 250 amino acids in length. In some examples, the spacer is at or about 12 amino acids in length or is no more than 12 amino acids in length. Exemplary spacers include those having at least about 10 to 300 amino acids, about 10 to 200 amino acids, about 50 to 175 amino acids, about 50 to 150 amino acids, about 10 to 125 amino acids, about 50 to 100 amino acids, about 100 to 300 amino acids, about 100 to 250 amino acids, about 125 to 250 amino acids, or about 200 to 250 amino acids, and including any integer between the endpoints of any of the listed ranges. In some embodiments, a spacer or a spacer region is at least about 12 amino acids, at least about 119 amino acids or less, at least about 125 amino acids, at least about 200 amino acids, or at least about 220 amino acids, or at least about 225 amino acids in length.

In some embodiments, the spacer has a length of 125 to 300 amino acids in length, 125 to 250 amino acids in length, 125 to 230 amino acids in length, 125 to 200 amino acids in length, 125 to 180 amino acids in length, 125 to 150 amino acids in length, 150 to 300 amino acids in length, 150 to 250 amino acids in length, 150 to 230 amino acids in length, 150 to 200 amino acids in length, 150 to 180 amino acids in length, 180 to 300 amino acids in length, 180 to 250 amino acids in length, 180 to 230 amino acids in length, 180 to 200 amino acids in length, 200 to 300 amino acids in length, 200 to 250 amino acids in length, 200 to 230 amino acids in length, 230 to 300 amino acids in length, 230 to 250 amino acids in length or 250 to 300 amino acids in length. In some embodiments, the spacer is at least or at least about or is or is about 130, 140, 150, 160, 170, 180, 190, 200, 210, 220, 221, 222, 223, 224, 225, 226, 227, 228 or 229 amino acids in length, or a length between any of the foregoing.

Exemplary spacers include those containing portion(s) of an immunoglobulin constant region such as those containing an Ig hinge, such as an IgG hinge domain. In some aspects, the spacer includes an IgG hinge alone, an IgG hinge linked to one or more of a $C_H2$ and $C_H3$ domain, or IgG hinge linked to the $C_H3$ domain. In some embodiments, the IgG hinge, $C_H2$ and/or $C_H3$ can be derived all or in part from IgG4 or IgG2. In some embodiments, the spacer can be a chimeric polypeptide containing one or more of a hinge, $C_H2$ and/or $C_H3$ sequence(s) derived from IgG4, IgG2, and/or IgG2 and IgG4. In some embodiments, the hinge region comprises all or a portion of an IgG4 hinge region and/or of an IgG2 hinge region, wherein the IgG4 hinge region is optionally a human IgG4 hinge region and the IgG2 hinge region is optionally a human IgG2 hinge region; the $C_H2$ region comprises all or a portion of an IgG4 $C_H2$ region and/or of an IgG2 $C_H2$ region, wherein the IgG4 $C_H2$ region is optionally a human IgG4 $C_H2$ region and the IgG2 $C_H2$ region is optionally a human IgG2 $C_H2$ region; and/or the $C_H3$ region comprises all or a portion of an IgG4 $C_H3$ region and/or of an IgG2 $C_H3$ region, wherein the IgG4 $C_H3$ region is optionally a human IgG4 $C_H3$ region and the IgG2 $C_H3$ region is optionally a human IgG2 $C_H3$ region. In some embodiments, the hinge, $C_H2$ and $C_H3$ comprises all or a portion of each of a hinge region, $C_H2$ and $C_H3$ from IgG4. In some embodiments, the hinge region is chimeric and comprises a hinge region from human IgG4 and human IgG2; the $C_H2$ region is chimeric and comprises a $C_H2$ region from human IgG4 and human IgG2; and/or the $C_H3$ region is chimeric and comprises a $C_H3$ region from human IgG4 and human IgG2. In some embodiments, the spacer comprises an IgG4/2 chimeric hinge or a modified IgG4 hinge comprising at least one amino acid replacement compared to human IgG4 hinge region; an human IgG2/4 chimeric $C_H2$ region; and a human IgG4 $C_H3$ region.

In some embodiments, the spacer can be derived all or in part from IgG4 and/or IgG2 and can contain mutations, such as one or more single amino acid mutations in one or more domains. In some examples, the amino acid modification is a substitution of a proline (P) for a serine (S) in the hinge region of an IgG4. In some embodiments, the amino acid modification is a substitution of a glutamine (Q) for an asparagine (N) to reduce glycosylation heterogeneity, such as an N177Q mutation at position 177, in the $C_H2$ region, of the full-length IgG4 Fc sequence set forth in SEQ ID NO: 173 or an N176Q. at position 176, in the $C_H2$ region, of the full-length IgG2 Fc sequence set forth in SEQ ID NO: 172. In some embodiments, the spacer is or comprises an IgG4/2 chimeric hinge or a modified IgG4 hinge; an IgG2/4 chimeric $C_H2$ region; and an IgG4 $C_H3$ region and optionally is about 228 amino acids in length; or a spacer set forth in SEQ ID NO: 174. In some embodiments, the spacer comprises the amino acid sequence (SEQ ID NO: 174)

ESKYGPPCPPCPAPPVAGPSVFLFPPKPKDTLMISRTPEVTCVVV

DVSQEDPEVQFNWYVDGVEVHNAKTKPREEQFQSTYRVVSVLTVL

HQDWLNGKEYKCKVSNKGLPSSIEKTISKAKGQPREPQVYTLPPS

QEEMTKNQVSLTCLVKGFYPSDIAVEWESNGQPENNYKTTPPVLD

SDGSFFLYSRLTVDKSRWQEGNVFSCSVMHEALHNHYTQKSLSLS

LGK.

In some embodiments, the spacer is encoded by a polynucleotide that has been optimized for codon expression and/or to eliminate splice sites such as cryptic splice sites. In some embodiments, the coding sequence for the spacer comprises the nucleic acid sequence set forth in SEQ ID NO: 200. In some embodiments, the coding sequence for the spacer comprises the nucleic acid sequence set forth in SEQ ID NO: 236 or 8.

Additional exemplary spacers include, but are not limited to, those described in Hudecek et al. (2013) *Clin. Cancer Res.,* 19:3153, Hudecek et al. (2015) *Cancer Immunol. Res.,* 3(2):125-135, or international patent application publication number WO2014031687. In some embodiments, the nucleotide sequence of the spacer is optimized to reduce RNA heterogeneity following expression. In some embodiments, the nucleotide sequence of the spacer is optimized to reduce cryptic splice sites or reduce the likelihood of a splice event at a splice site.

In some embodiments, the spacer has the amino acid sequence set forth in SEQ ID NO:237, and is encoded by the polynucleotide sequence set forth in SEQ ID NO:238. In some embodiments, the spacer has the amino acid sequence set forth in SEQ ID NO:157. In some embodiments, the spacer has the amino acid sequence set forth in SEQ ID NO:156. In some embodiments, the spacer has the amino acid sequence set forth in SEQ ID NO: 134, and is encoded by the polynucleotide sequence set forth in SEQ ID NO: 135. In some embodiments, the spacer has an amino acid sequence set forth in SEQ ID NO: 174, encoded by the polynucleotide sequence set forth in SEQ ID NO: 175, 200, 236 or 8 or a polynucleotide that exhibits at least 85%, 86%, 87%, 88%, 89%, 90%, 91%, 92%, 93%, 94%, 95%, 96%, 97%, 98%, 99% or more sequence identity to SEQ ID NO: 175, 200, 236 or 8. In some embodiments, the spacer has an amino acid sequence that exhibits at least 85%, 86%, 87%, 88%, 89%, 90%, 91%, 92%, 93%, 94%, 95%, 96%, 97%, 98%, 99% or more sequence identity to SEQ ID NO: 174, encoded by a polynucleotide that has been optionally optimized for codon usage and/or to reduce RNA heterogeneity.

In some embodiments, the spacer is or comprises an amino acid sequence encoded by the nucleotide sequence set forth in SEQ ID NO:200.

C. Transmembrane Domain and Intracellular Signaling Components

The antigen-recognition component (e.g., antigen-binding domain) generally is linked to one or more intracellular signaling regions containing signaling components, such as signaling components that mimic stimulation and/or activation through an antigen receptor complex, such as a TCR complex, in the case of a CAR, and/or signal via another cell surface receptor. Thus, in some embodiments, the BCMA-binding domain (e.g., antibody or antigen binding fragment thereof) is linked to one or more transmembrane domains such as those described herein and intracellular signaling regions or domains comprising one or more intracellular components such as those described herein. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane domains include those derived from (i.e. comprise at least the transmembrane domain(s) of) the alpha, beta or zeta chain of the T-cell receptor, CD3 epsilon, CD4, CD5, CD8, CD9, CD16, CD22, CD28, CD33, CD37, CD45, CD64, CD80, CD86, CD134, CD137, and/or CD154. For example, the transmembrane domain can be a CD28 transmembrane domain that comprises the sequence of amino acids set forth in SEQ ID NO: 138, encoded by the nucleic acid sequence set forth in SEQ ID NO: 139 or SEQ ID NO:140. In some embodiments, the transmembrane domain is or comprises a transmembrane domain derived from a CD8alpha. In some embodiments, the CD8alpha is human CD8alpha. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling regions or domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the intracellular signaling domain of the CAR.

The receptor, e.g., the CAR, generally includes an intracellular signaling region comprising at least one intracellular signaling component or components. In some embodiments, the receptor includes an intracellular component or signaling domain of a TCR complex, such as a TCR CD3 chain that mediates T-cell activation and cytotoxicity, e.g., CD3 zeta chain. Thus, in some aspects, the BCMA-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon or following ligation of the CAR, the cytoplasmic domain or intracellular signaling domain of the CAR stimulates and/or activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such classes of cytoplasmic signaling sequences.

In some aspects, the CAR includes a primary cytoplasmic signaling sequence that regulates primary stimulation and/or activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma, CD3 gamma, CD3 delta and CD3 epsilon. In some embodiments, the intracellular signaling region or domain in the CAR contain(s) a cytoplasmic signaling domain, portion thereof, or sequence derived from CD3 zeta. In some embodiments the CD3 zeta comprises the sequence of amino acids set forth in SEQ ID NO: 143, encoded by the nucleic acid sequence set forth in SEQ ID NO: 144 or SEQ ID NO: 145.

In some embodiments, the CAR includes a signaling domain (e.g., an intracellular or cytoplasmic signaling domain) and/or transmembrane portion of a costimulatory molecule, such as a T cell costimulatory molecule. Exemplary costimulatory molecules include CD28, 4-1BB, OX40, DAP10, and ICOS. For example, a costimulatory molecule can be derived from 4-1BB and can comprise the amino acid sequence set forth in SEQ ID NO: 4, encoded by the nucleotide sequence set forth in SEQ ID NO: 5 or SEQ ID NO: 6. In some aspects, the same CAR includes both the stimulatory or activating components (e.g., cytoplasmic signaling sequence) and costimulatory components.

In some embodiments, the stimulatory or activating components are included within one CAR, whereas the costimulatory component is provided by another CAR recognizing another antigen. In some embodiments, the CARs include activating or stimulatory CARs, and costimulatory CARs, both expressed on the same cell (see WO2014/055668). In some aspects, the BCMA-targeting CAR is the stimulatory or activating CAR; in other aspects, it is the costimulatory CAR. In some embodiments, the cells further include inhibitory CARs (iCARs, see Fedorov et al., Sci. Transl. Medicine, 5(215) (December, 2013), such as a CAR recognizing an antigen other than BCMA, whereby a stimulatory or an activating signal delivered through the BCMA-targeting CAR is diminished or inhibited by binding of the inhibitory CAR to its ligand, e.g., to reduce off-target effects.

In certain embodiments, the intracellular signaling region comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and a stimulatory or activation domain, e.g., primary activation domain, in the cytoplasmic portion. Exemplary CARs include intracellular components of CD3-zeta, CD28, and 4-1BB.

In some embodiments, the provided chimeric antigen receptor comprises: (a) an extracellular antigen-binding domain that specifically recognizes B cell maturation antigen (BCMA), such as any antigen-binding domain described herein; (b) a spacer of at least 125 amino acids in length; (c) a transmembrane domain; and (d) an intracellular signaling region. In some embodiments, the antigen-binding domain of such receptor, comprising a $V_H$ region and a $V_L$ region comprising the amino acid sequence of SEQ ID NOs:116 and 119, respectively, or a sequence of amino acids having at least 90% identity to SEQ ID NOS:116 and 119, respectively. In some embodiments, the antigen-binding domain of such receptor, comprising a $V_H$ region that is or comprises a CDR-H1, CDR-H2 and CDR-H3 contained within the $V_H$ region amino acid sequence of SEQ ID NO: 116 and a $V_L$ region that is or comprises a CDR-L1, CDR-L2 and CDR-L3 contained within the $V_L$ region amino acid sequence of SEQ ID NO: 119. In some embodiments, the antigen-binding domain of such receptor, comprising a $V_H$ region comprising a CDR-H1, CDR-H2, and CDR-H3 comprising SEQ ID NOS:97, 101 and 103, respectively, and a $V_L$ region comprising a CDR-L1, CDR-L2, and CDR-L3 comprising SEQ ID NOS:105, 107 and 108, respectively. In some embodiments, the antigen-binding domain of such receptor, comprising a $V_H$ region comprising a CDR-H1, CDR-H2, and CDR-H3 comprising SEQ ID NOS:96, 100 and 103, respectively, and a $V_L$ region comprising a CDR-L1, CDR-L2, and CDR-L3 comprising SEQ ID NOS:105, 107 and 108, respectively. In some embodiments, the antigen-binding domain of such receptor, comprising a $V_H$ region comprising a CDR-H1, CDR-H2, and CDR-H3 comprising SEQ ID NOS: 95, 99 and 103, respectively, and a $V_L$ region comprising a CDR-L1, CDR-L2, and CDR-L3 comprising SEQ ID NOS:105, 107 and 108, respectively. In some embodiments, the antigen-binding domain of such receptor, comprising a $V_H$ region comprising a CDR-H1, CDR-H2, and CDR-H3 comprising SEQ ID NOS: 94, 98 and 102, respectively, and a $V_L$ region comprising a CDR-L1, CDR-L2, and CDR-L3 comprising SEQ ID NOS: 104, 106 and 108, respectively. In some embodiments, the antigen-binding domain of such receptor, comprises a $V_H$ region that is or comprises the amino acid sequence of SEQ ID NO: 116 and a $V_L$ region that is or comprises the amino acid sequence of SEQ ID NO: 119. In some embodiments, the antigen-binding domain of such receptor, comprises the amino acid sequence of SEQ ID NO: 114.

In some embodiments, the intracellular signaling region includes an stimulating cytoplasmic signaling domain. In some embodiments, the stimulating cytoplasmic signaling domain is capable of inducing a primary activation signal in a T cell, is a T cell receptor (TCR) component and/or includes an immunoreceptor tyrosine-based activation motif (ITAM). In some embodiments, the stimulating cytoplasmic signaling domain is or includes a cytoplasmic signaling domain of a CD3-zeta (CD3ζ) chain or a functional variant or signaling portion thereof. In some embodiments, the stimulating cytoplasmic domain is human or is derived from a human protein. In some embodiments, the stimulating cytoplasmic domain is or includes the sequence set forth in SEQ ID NO:143 or a sequence of amino acids that has at least 90% sequence identity to SEQ ID NO:143. In some embodiments, the nucleic acid encoding the stimulating cytoplasmic domain is or includes the sequence set forth in SEQ ID NO:144 or is a codon-optimized sequence and/or degenerate sequence thereof. In other embodiments, the nucleic acid encoding the stimulating cytoplasmic signaling domain is or includes the sequence set forth in SEQ ID NO:145. In some embodiments, the intracellular signaling region further includes a costimulatory signaling region. In some embodiments, the costimulatory signaling region includes an intracellular signaling domain of a T cell costimulatory molecule or a signaling portion thereof. In some embodiments, the costimulatory signaling region includes an intracellular signaling domain of a CD28, a 4-1BB or an ICOS or a signaling portion thereof. In some embodiments, the costimulatory signaling region includes an intracellular signaling domain of 4-1BB. In some embodiments, the costimulatory signaling region is human or is derived from a human protein. In other embodiments, the costimulatory signaling region is or includes the sequence set forth in SEQ ID NO:4 or a sequence of amino acids that exhibits at least 90% sequence identity to the sequence set forth in SEQ ID NO: 4. In some embodiments, the nucleic acid encoding the costimulatory region is or includes the sequence set forth in SEQ ID NO:5 or is a codon-optimized sequence and/or degenerate sequence thereof. In some embodiments, the nucleic acid encoding the costimulatory signaling region includes the sequence set forth in SEQ ID NO:6. In some embodiments, the costimulatory signaling region is between the transmembrane domain and the intracellular signaling region. In some embodiments, the transmembrane domain is or includes a transmembrane domain derived from CD4, CD28, or CD8. In some embodiments, the transmembrane domain is or includes a transmembrane domain derived from a CD28. In some embodiments, the transmembrane domain is human or is derived from a human protein. In other embodiments, the transmembrane domain is or includes the sequence set forth in SEQ ID NO:138 or a sequence of amino acids that exhibits at least 90% sequence identity to SEQ ID NO:138.

Provided are chimeric antigen receptors, comprising: (1) an extracellular antigen-binding domain that specifically binds human B cell maturation antigen (BCMA), wherein the extracellular antigen-binding domain comprises: (i) a variable heavy chain ($V_H$) comprising an amino acid sequence having at least 90%, 91%, 92%, 93%, 94%, 95%, 96%, 97%, 98%, or 99% sequence identity to the $V_H$ region sequence of SEQ ID NO: 116; and (ii) a variable light chain ($V_L$) region comprising an amino acid sequence having at least 90%, 91%, 92%, 93%, 94%, 95%, 96%, 97%, 98%, or 99% sequence identity to the $V_L$ region sequence of any of SEQ ID NO: 119; (2) a spacer set forth in SEQ ID NO: 174 or wherein the nucleic acid encoding the spacer is or comprises the sequence set forth in SEQ ID NO:200; (3) a transmembrane domain, optionally a transmembrane domain from a human CD28; and (4) an intracellular signaling region comprising a cytoplasmic signaling domain of a CD3-zeta (CD3ζ) chain and an intracellular signaling domain of a T cell costimulatory molecule. Also provided are polynucleotides encoding such a chimeric antigen receptor.

In some embodiments, the $V_H$ region comprises a CDR-H1, CDR-H2 and CDR-H3 contained within the $V_H$ region sequence of SEQ ID NO: 116; and the $V_L$ region comprises a CDR-L1, CDR-L2 and CDR-L3 contained within the $V_L$ region sequence of SEQ ID NO: 119; or the $V_H$ region comprises a CDR-H1, CDR-H2, and CDR-H3 comprising the sequence of SEQ ID NOS:97, 101 and 103, respectively, and the $V_L$ region comprises a CDR-L1, CDR-L2, and CDR-L3 comprising the sequence of SEQ ID NOS:105, 107 and 108, respectively; the $V_H$ region comprises a CDR-H1, CDR-H2, and CDR-H3 comprising the sequence of SEQ ID NOS:96, 100 and 103, respectively, and the $V_L$ region comprises a CDR-L1, CDR-L2, and CDR-L3 comprising the sequence of SEQ ID NOS:105, 107 and 108, respectively; the $V_H$ region comprises a CDR-H1, CDR-H2, and CDR-H3 comprising the sequence of SEQ ID NOS:95, 99 and 103, respectively, and the $V_L$ region comprises a CDR-L1, CDR-L2, and CDR-L3 comprising the sequence of SEQ ID NOS:105, 107 and 108, respectively; or the $V_H$ region comprises a CDR-H1, CDR-H2, and CDR-H3 comprising the sequence of SEQ ID NOS:94, 98 and 102, respectively, and the $V_L$ region comprises a CDR-L1, CDR-L2, and CDR-L3 comprising the sequence of SEQ ID NOS:104, 106 and 108, respectively.

Provided are chimeric antigen receptors, comprising: (1) an extracellular antigen-binding domain that specifically binds human B cell maturation antigen (BCMA), wherein the extracellular antigen-binding domain comprises: a variable heavy ($V_H$) region comprising a CDR-H1, CDR-H2 and CDR-H3 contained within the $V_H$ region sequence of SEQ ID NO: 116 and a variable light ($V_L$) region comprising a CDR-L1, CDR-L2 and CDR-L3 contained within the $V_L$ region sequence of SEQ ID NO: 119; or the $V_H$ region comprises a CDR-H1, CDR-H2 and CDR-H3 contained within the $V_H$ region sequence of SEQ ID NO: 116; and the $V_L$ region comprises a CDR-L1, CDR-L2 and CDR-L3 contained within the $V_L$ region sequence of SEQ ID NO: 119; or the $V_H$ region comprises a CDR-H1, CDR-H2, and CDR-H3 comprising the sequence of SEQ ID NOS:97, 101 and 103, respectively, and the $V_L$ region comprises a CDR-L1, CDR-L2, and CDR-L3 comprising the sequence of SEQ ID NOS:105, 107 and 108, respectively; the $V_H$ region comprises a CDR-H1, CDR-H2, and CDR-H3 comprising the sequence of SEQ ID NOS:96, 100 and 103, respectively, and the $V_L$ region comprises a CDR-L1, CDR-L2, and CDR-L3 comprising the sequence of SEQ ID NOS:105, 107 and 108, respectively; the $V_H$ region comprises a CDR-H1, CDR-H2, and CDR-H3 comprising the sequence of SEQ ID NOS:95, 99 and 103, respectively, and the $V_L$ region comprises a CDR-L1, CDR-L2, and CDR-L3 comprising the sequence of SEQ ID NOS:105, 107 and 108, respectively; or the $V_H$ region comprises a CDR-H1, CDR-H2, and CDR-H3 comprising the sequence of SEQ ID NOS:94, 98 and 102, respectively, and the $V_L$ region comprises a CDR-L1, CDR-L2, and CDR-L3 comprising the sequence of SEQ ID NOS:104, 106 and 108, respectively; (2) a spacer set forth in SEQ ID NO: 174 or wherein the nucleic acid encoding the spacer is or comprises the sequence set forth in SEQ ID NO:200; (3) a transmembrane domain, optionally a transmembrane domain from a human CD28; and (4) an intracellular signaling region comprising a cytoplasmic signaling domain of a human CD3-zeta (CD3ζ) chain and an intracellular signaling domain of a T cell costimulatory molecule, optionally from a human 4-1BB or a human CD28. Also provided are polynucleotides encoding such a chimeric antigen receptor. In some embodiments, the extracellular antigen-binding domain comprises the $V_H$ region sequence of SEQ ID NO:116 and the $V_L$ region sequence of SEQ ID NO:119. In some embodiments, the antigen-binding domain of such receptor, comprises the amino acid sequence of SEQ ID NO: 114. In some embodiments, other domains, regions, or components of the chimeric antigen receptor includes any domains, regions, or components described herein.

D. Surrogate Marker

In some embodiments, the CAR, or the polynucleotide that encodes the CAR, further includes a surrogate marker, such as a cell surface marker (e.g., a truncated cell surface marker), which may be used to confirm transduction or engineering of the cell to express the receptor. For example, in some aspects, extrinsic marker genes are utilized in connection with engineered cell therapies to permit detection or selection of cells and, in some cases, also to promote cell suicide by ADCC. Exemplary marker genes include truncated epidermal growth factor receptor (EGFRt), which can be co-expressed with a transgene of interest (e.g., a CAR or TCR) in transduced cells (see, e.g., U.S. Pat. No. 8,802,374). EGFRt contains an epitope recognized by the antibody cetuximab (Erbitux®). For this reason, Erbitux® can be used to identify or select cells that have been engineered with the EGFRt construct, including in cells also co-engineered with another recombinant receptor, such as a chimeric antigen receptor (CAR). Additionally, EGFRt is commonly used as a suicide mechanism in connection with cell therapies. In some aspects, when EGFRt is co-expressed in cells with a transgene of interest (e.g. CAR or TCR), it can be targeted by the cetuximab monoclonal antibody to reduce or deplete the transferred gene-modified cells via ADCC (see U.S. Pat. No. 8,802,374 and Liu et al., Nature Biotech. 2016 April; 34(4): 430-434). Importantly, the suicide killing approach using tEGFR requires availability of the antibody epitope. Another example of such a marker gene is prostate-specific membrane antigen (PSMA) or a modified form thereof. PSMA or modified forms thereof may comprise a sequence of amino acids bound by or recognized by a PSMA-targeting molecule, such as an antibody or an antigen-binding fragment thereof. PSMA-targeting molecules can be used to identify or select cells that have been engineered with a PSMA or modified construct, including in cells also co-engineered with another recombinant receptor, such as a chimeric antigen receptor (CAR) provided herein. In some aspects, the marker includes all or part (e.g., truncated form) of CD34, a nerve growth factor receptor (NGFR), epidermal growth factor receptor (e.g., EGFR), or PSMA.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO:246) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In some embodiments, the marker is or comprises a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, the nucleic acid encoding the marker is operably linked to a polynucleotide encoding for a linker sequence, such as a cleavable linker sequence, e.g., T2A. See WO2014031687. In some embodiments, introduction of a construct encoding the CAR and surrogate marker, separated by a T2A ribosome switch, can express two proteins from the same construct, such that the surrogate marker can be used as a marker to detect cells expressing such construct. In some embodiments, the surrogate marker, and optionally a linker sequence, can be any as disclosed in international publication no. WO2014031687. For example, the marker can be a truncated EGFR (tEGFR) or PSMA that is, optionally, linked to a linker sequence, such as a 2A cleavable linker sequence (e.g., a T2A, P2A, E2A or F2A cleavable linker, described elsewhere herein). An exemplary polypeptide for a truncated EGFR surrogate marker comprises the sequence of amino acids set forth in SEQ ID NO:246 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:246. In some embodiments, the spacer is or comprises a glycine-serine rich sequence or other flexible linker such as known flexible linkers.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells following adoptive transfer and encounter with ligand.

In some cases, CARs are referred to as first, second, and/or third generation CARs. In some aspects, a first generation CAR is one that solely provides a CD3-chain induced signal upon or in response to antigen binding; in some aspects, a second-generation CARs is one that provides such a signal and costimulatory signal, such as one including an intracellular signaling domain from a costimulatory receptor such as CD28 or CD137 (i.e. 4-1BB); in some aspects, a third generation CAR in some aspects is one that includes multiple costimulatory domains of different costimulatory receptors.

In some embodiments, the chimeric antigen receptor includes an extracellular portion containing the antibody or fragment described herein. In some aspects, the chimeric antigen receptor includes an extracellular portion containing the antibody or fragment described herein and an intracellular signaling domain. In some embodiments, the antibody or fragment includes an scFv or a single-domain antibody comprising only the $V_H$ region and the intracellular signaling domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a co-stimulatory molecule (e.g., T cell costimulatory molecule), such as between the transmembrane domain and intracellular signaling domain. In some aspects, the T cell costimulatory molecule is CD28 or 4-1BB.

In some embodiments, the transmembrane domain of the receptor (e.g., CAR) is a transmembrane domain of human CD28 or variant thereof, e.g., a 27-amino acid transmembrane domain of a human CD28 (Accession No.: P10747.1). In some embodiments, the intracellular signaling domain comprises an intracellular costimulatory signaling domain of human CD28 or functional variant thereof, such as a 41 amino acid domain thereof and/or such a domain with an LL to GG substitution at positions 186-187 of a native CD28 protein. In some embodiments, the intracellular domain comprises an intracellular costimulatory signaling domain of 4-1BB or functional variant thereof, such as a 42-amino acid cytoplasmic domain of a human 4-1BB (Accession No. Q07011.1). In some embodiments, the intracellular signaling domain comprises a human CD3 zeta stimulatory signaling domain or functional variant thereof, such as an 112 AA cytoplasmic domain of isoform 3 of human CD31 (Accession No.: P20963.2) or a CD3 zeta signaling domain as described in U.S. Pat. No. 7,446,190.

For example, in some embodiments, the CAR includes a BCMA antibody or fragment, such as any of the human BCMA antibodies, including sdAbs and scFvs, described herein, a spacer such as any of the Ig-hinge containing spacers, a CD28 transmembrane domain, a CD28 intracellular signaling domain, and a CD3 zeta signaling domain. In some embodiments, the CAR includes the BCMA antibody or fragment, such as any of the human BCMA antibodies, including sdAbs and scFvs described herein, a spacer such as any of the Ig-hinge containing spacers, a CD28 transmembrane domain, a 4-1BB intracellular signaling domain, and a CD3 zeta signaling domain. In some embodiments, such CAR constructs further includes a T2A ribosomal skip element and/or a tEGFR sequence, e.g., downstream of the CAR.

In certain embodiments, multispecific recombinant receptors, such as multispecific CARs, can contain any multispecific antibodies, including, e.g. bispecific antibodies, multispecific single-chain antibodies, e.g., diabodies, triabodies, and tetrabodies, tandem di-scFvs, and tandem tri-scFvs, such as any described above in Section I.A.

Other exemplary BCMA-specific CAR employed in the embodiments provided herein include Idecabtagene vicleucel (Ide-cel, bb2121; Raje et al. N Engl J Med. 2019. 380:1726-1737), JNJ-4528 (Madduri et al. Blood. 2019. 134 (Supplement_1): 577)/LCAR-B38M (Wang et al. Blood. 2019. 134 (Supplement_1): 579), P-BCMA-101 (Costello et al. Blood. 2019. 134 (Supplement_1): 3184), bb21217 (Berdeja et al. Blood. 2019. 134 (Supplement_1): 927), CT103A (Li et al. Blood. 2019; 134(Supplement_1):929), CT053 (Ji et al., Blood. 2019; 134(Supplement_1):4435), MTV273, CART-BCMA, C-CAR088 (Yao et al. Blood. 2019; 134 (Supplement_1):50) or any BCMA-directed CAR T therapy described in, for example, WO 2018/085690; WO 2016/094304; WO 2018/085690; WO 2016/014789; WO 2019/108900; WO/2018/014038; WO 2017/173256; WO 2016/090320, WO 2016/090327, WO 2019/090003; WO 2017/025038; US 2016/0046724; US 2017/0183418; Fu et al., Blood. 2019; 134:3154; Cohen et al. J. Clin. Invest. 2019. 129(6): 2210-2221; Ali et al., Blood 2016; 128(13):1688 1700; Borrello et al., J Clin Invest. 2019; 129(6):2175-2177; Lin et al. Molecular Cancer (2019) 18:154; and Steiner et al., (2020) memo—Magazine of European Medical Oncology 13:43-49).

In some embodiments, the anti-BCMA CAR comprises a $V_H$ region comprising a CDR-H1, a CDR-H2, and a CDR-H3 comprising the amino acid sequence of SEQ ID NOs: 257, 258, and 259, respectively; and a $V_L$ region comprising a CDR-L1, CDR-L2, and CDR-L3 comprising the amino acid sequence of SEQ ID NOs:260, 261, and 262, respectively; and/or a $V_H$ region comprising the sequence set forth in SEQ ID NO:125 and a $V_L$ region comprising the sequence set forth in SEQ ID NO:127; and/or amino acid residues 22-493 of the sequence set forth in SEQ ID NO:265, and/or the sequence encoded by SEQ ID NO:266. In some aspects, the anti-BCMA CAR comprises the mature polypeptide sequence of the sequence set forth in SEQ ID NO:265. In some embodiments, the anti-BCMA CAR comprises a $V_H$ region comprising a CDR-H1, a CDR-H2, and a CDR-H3 comprising the amino acid sequence of SEQ ID NOs: 260, 261, and 262, respectively; and a $V_L$ region comprising a CDR-L1, CDR-L2, and CDR-L3 comprising the amino acid sequence of SEQ ID NOs: 257, 258, and 259, respectively; and/or a $V_H$ region comprising the sequence set forth in SEQ ID NO:125 and a $V_L$ region comprising the sequence set forth in SEQ ID NO:127; and/or amino acid residues 22-493 of the sequence set forth in SEQ ID NO:263, and/or the sequence set forth in SEQ ID NO:264. In some aspects, the anti-BCMA CAR comprises the mature polypeptide sequence of the sequence set forth in SEQ ID NO:263. In some aspects, the anti-BCMA CAR comprises the mature polypeptide sequence of the sequence set forth in SEQ ID NO: 312. In some embodiments, the BCMA-specific CAR is or comprises Idecabtagene vicleucel (Ide-cel, bb2121) (see, e.g., Raje et al. N Engl J Med. 2019. 380:1726-1737; WO 2018/085690; WO 2016/094304; WO 2018/085690 or WO 2016/014789). In some embodiments, the BCMA-specific CAR include those described in WO 2018/085690; WO 2016/094304; WO 2018/085690 or WO 2016/014789, which are hereby incorporated by reference in their entirety.

In some embodiments, the anti-BCMA CAR is a multivalent CAR, such as a dual epitope-binding CAR, for example, a CAR comprising two different single-domain antibodies, e.g., VHH, directed to different epitopes on BCMA. In some aspects, the anti-BCMA CAR binds to one or more epitopes of BCMA selected from among the sequences set forth in SEQ ID NOS:303-309. In some embodiments, the BCMA-specific CAR is or comprises JNJ-4528 (also called LCAR-B38M) (see, e.g., Madduri et al. Blood. 2019. 134 (Supplement_1): 577; Wang et al. Blood. 2019. 134 (Supplement_1): 579; Xu et al. PNAS 2019. 116(19) 9543-9551; Zhao et al., Journal of Hematology & Oncology 11:141 (2018); WO 2018/028647; WO 2017/025038). In some embodiments, the anti-BCMA CAR comprises the amino acid residues beginning at residue 22 to the end of the sequence set forth in any one of SEQ ID NOS: 265-302, and/or the mature polypeptide sequence of the sequence set forth in any one of SEQ ID NOS: 265-302, and/or the CAR encoded by a sequence of nucleotides that encodes the CAR set forth in any one of SEQ ID NOS: 265-302; and/or any described in WO 2018/028647 or WO 2017/025038, which are hereby incorporated by reference in their entirety. In some embodiments, the anti-BCMA CAR comprises the amino acid residues beginning at residue 22 to the end of the sequence set forth in any one of SEQ ID NOS: 265-302.

In some aspects, the BCMA-specific CAR comprises a Centyrin as an extracellular binding domain, instead of a single chain variable fragment (scFv). In some aspects, centyrins are modified fibronectin type III (FN3) domain proteins with high specificity and a large range of binding affinities, but are smaller than an scFv (see, e.g., Goldberg et al., Protein Eng Des Sel. 2016 December; 29(12):563-572). In some embodiments, the BCMA-specific CAR P-BCMA-101 (Costello et al. Blood. 2019. 134 (Supplement_1): 3184; Fu et al., Blood. 2019; 134:3154; WO 2018/014038 and WO 2019/173636). In some embodiments, the BCMA-specific CAR comprises the amino acid residues 22-334 of the sequence set forth in SEQ ID NO: 310, and/or the mature polypeptide sequence of the sequence set forth in SEQ ID NO:310, and/or the CAR encoded by a sequence of nucleotides that encodes the CAR set forth in any one of SEQ ID NO:310 and/or any described in WO 2018/014038 or WO 2019/173636, which are hereby incorporated by reference in their entirety. In some embodiments, the BCMA-specific CAR comprises the amino acid residues 22-334 of the sequence set forth in SEQ ID NO: 310.

E. Exemplary Features of BCMA-Binding Recombinant Receptors

In some aspects, the antibodies or antigen-binding fragments thereof, in the recombinant receptors expressed by the engineered cells, have one or more specified functional features, such as binding properties, including recognizing or binding to particular epitopes, such as to epitopes that are similar to or overlap with those specifically bound by other antibodies such as reference antibodies, or epitopes that are different from those specifically bound by other antibodies such as reference antibodies, the ability to compete for binding with other antibodies such as reference antibodies, and/or particular binding affinities. In other embodiments, the antibodies or antigen-binding fragments thereof, in the recombinant receptors, recognize, such as specifically recognize, or bind, e.g., specifically bind, to epitopes that are different from, or do not overlap with those specifically bound by other antibodies such as reference antibodies. For example, the epitopes specifically bound by the antibodies, in the recombinant receptors, are different from those specifically bound by other antibodies such as reference antibodies. In some embodiments, the antibodies and antigen binding fragments thereof do not directly compete for, or compete to a lower degree, with binding with other antibodies such as reference antibodies.

In some embodiments, the antibodies or antigen-binding fragments thereof specifically recognize or specifically bind to BCMA protein. In any of the embodiments, an antibody or antigen binding fragment, in the recombinant receptors, that specifically recognize BCMA, specifically binds BCMA. In some embodiments provided herein, BCMA protein refers to human BCMA, a mouse BCMA protein, or a non-human primate (e.g., cynomolgus monkey) BCMA protein. In some embodiments of any of the embodiments herein, BCMA protein refers to human BCMA protein. The observation that an antibody or recombinant receptors, binds to BCMA protein or specifically binds to BCMA protein does not necessarily mean that it binds to a BCMA protein of every species. For example, in some embodiments, features of binding to BCMA protein, such as the ability to specifically bind thereto and/or to compete for binding thereto with a reference antibody, and/or to bind with a particular affinity or compete to a particular degree, in some embodiments, refers to the ability with respect to a human BCMA protein and the antibody may not have this feature with respect to a BCMA protein of another species, such as mouse.

In some embodiments, the antibody or antigen-binding fragment binds to a mammalian BCMA protein, including to naturally occurring variants of BCMA, such as certain splice variants or allelic variants.

In some embodiments, the antibodies specifically bind to human BCMA protein, such as to an epitope or region of human BCMA protein, such as the human BCMA protein comprising the amino acid sequence of SEQ ID NO:164 (GenBank No. BAB60895.1), or SEQ ID NO:165 (NCBI No. NP_001183.2) or an allelic variant or splice variant thereof. In one embodiment, the human BCMA protein is encoded by a transcript variant or is an isoform that has the sequence of amino acids forth in SEQ ID NO:163. In some embodiments, the antibodies bind to cynomolgus monkey BCMA protein, such as the cynomolgus monkey BCMA protein set forth in SEQ ID NO:147 (GenBank No. EHH60172.1). In some embodiments, the antibodies bind to human BCMA but do not bind to or bind in a lower level or degree or affinity to cynomolgus monkey BCMA protein, such as the cynomolgus monkey BCMA protein set forth in SEQ ID NO:147 (GenBank No. EHH60172.1). In some embodiments, the antibodies do not bind to or bind in a lower level or degree or affinity to mouse BCMA protein, such as the mouse BCMA protein set forth in SEQ ID NO:179 (NCBI No. NP_035738.1). In some embodiments, the antibodies bind to mouse BCMA protein, such as the mouse BCMA protein set forth in SEQ ID NO:179 (NCBI No. NP_035738.1). In some embodiments, the antibodies bind to mouse BCMA protein, with lower affinity than its binding to a human BCMA protein and/or a cynomolgus monkey BCMA protein. In some embodiments, the antibodies bind to mouse BCMA protein and/or a cynomolgus monkey BCMA protein with lower affinity than its binding to a human BCMA protein. In some embodiments, the antibodies bind to mouse BCMA protein and/or a cynomolgus monkey BCMA protein with similar binding affinity compared to its binding to a human BCMA protein.

In some embodiments, the provided antigen-binding domain or CAR exhibits preferential binding to membrane-bound BCMA as compared to soluble BCMA. In some embodiments, the provided antigen-binding domain or CAR exhibits greater binding affinity for, membrane-bound BCMA compared to soluble BCMA.

In one embodiment, the extent of binding of an anti-BCMA antibody or antigen-binding domain or CAR to an unrelated, non-BCMA protein, such as a non-human BCMA protein or other non-BCMA protein, is less than at or about 10% of the binding of the antibody or antigen-binding domain or CAR to human BCMA protein or human membrane-bound BCMA as measured, e.g., by a radioimmunoassay (RIA). In some embodiments, among the antibodies or antigen-binding domains in the Recombinant receptors, are antibodies or antigen-binding domains or Recombinant receptors in which binding to mouse BCMA protein is less than or at or about 10% of the binding of the antibody to human BCMA protein. In some embodiments, among the antibodies or antigen-binding domains in the Recombinant receptors, are antibodies in which binding to cynomolgus monkey BCMA protein is less than or at or about 10% of the binding of the antibody to human BCMA protein. In some embodiments, among the antibodies or antigen-binding domains in the Recombinant receptors, are antibodies in which binding to cynomolgus monkey BCMA protein and/or a mouse BCMA protein is similar to or about the same as the binding of the antibody to human BCMA protein. In some embodiments, among the antibodies or antigen-binding domains in the Recombinant receptors, are antibodies or antigen-binding domains or Recombinant receptors in which binding to soluble BCMA protein is less than or at or about 10% of the binding of the antibody to membrane-bound BCMA protein.

In some embodiments, the antibody specifically binds to, and/or competes for binding thereto with a reference antibody, and/or binds with a particular affinity or competes to a particular degree, to a BCMA protein, e.g., human BCMA, a mouse BCMA protein, or a non-human primate (e.g., cynomolgus monkey) BCMA protein.

In some embodiments, the antibodies, in the Recombinant receptors, are capable of binding BCMA protein, such as human BCMA protein, with at least a certain affinity, as measured by any of a number of known methods. In some embodiments, the affinity is represented by an equilibrium dissociation constant ($K_D$); in some embodiments, the affinity is represented by $EC_{50}$.

A variety of assays are known for assessing binding affinity and/or determining whether a an antibody or fragment thereof or a recombinant receptor specifically binds to a particular ligand (e.g., an antigen, such as a BCMA protein). It is within the level of a skilled artisan to determine the binding affinity of an antibody or a recombinant receptor, for an antigen, e.g., BCMA, such as human BCMA or cynomolgus BCMA or mouse BCMA, such as by using any of a number of binding assays that are well known in the art. For example, in some embodiments, a BIAcore® instrument can be used to determine the binding kinetics and constants of a complex between two proteins (e.g., an antibody or fragment thereof, and an antigen, such as a BCMA protein), using surface plasmon resonance (SPR) analysis (see, e.g., Scatchard et al., *Ann. N.Y. Acad. Sci.* 51:660, 1949; Wilson, Science 295:2103, 2002; Wolff et al., *Cancer Res.* 53:2560, 1993; and U.S. Pat. Nos. 5,283,173, 5,468,614, or the equivalent).

SPR measures changes in the concentration of molecules at a sensor surface as molecules bind to or dissociate from the surface. The change in the SPR signal is directly proportional to the change in mass concentration close to the surface, thereby allowing measurement of binding kinetics between two molecules. The dissociation constant for the complex can be determined by monitoring changes in the refractive index with respect to time as buffer is passed over the chip. Other suitable assays for measuring the binding of one protein to another include, for example, immunoassays such as enzyme linked immunosorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Other exemplary assays include, but are not limited to, Western blot, ELISA, analytical ultracentrifugation, spectroscopy, flow cytometry, sequencing and other methods for detection of expressed polynucleotides or binding of proteins.

In some embodiments, the antibody or fragment thereof or antigen-binding domain of a CAR, binds, such as specifically binds, to an antigen, e.g., a BCMA protein or an epitope therein, with an affinity or $K_A$ (i.e., an equilibrium association constant of a particular binding interaction with units of 1/M; equal to the ratio of the on-rate [$k_{on}$ or $k_a$] to the off-rate [$k_{off}$ or $k_d$] for this association reaction, assuming bimolecular interaction) equal to or greater than $10^5$ $M^{-1}$. In some embodiments, the antibody or fragment thereof or antigen-binding domain of a CAR exhibits a binding affinity for the peptide epitope with a $K_D$ (i.e., an equilibrium dissociation constant of a particular binding interaction with units of M; equal to the ratio of the off-rate [$k_{off}$ or $k_d$] to the on-rate [$k_{on}$ or $k_a$] for this association reaction, assuming bimolecular interaction) of equal to or less than $10^{-5}$ M. For example, the equilibrium dissociation constant $K_D$ ranges from $10^{-5}$ M to $10^{-13}$ M, such as $10^{-7}$ M to $10^{-11}$ M, $10^{-8}$ M to $10^{-10}$ M, or $10^{-9}$ M to $10^{-10}$ M. The on-rate (association rate constant; $k_{on}$ or $k_a$; units of 1/Ms) and the off-rate (dissociation rate constant; $k_{off}$ or $k_d$; units of 1/s) can be determined using any of the assay methods known in the art, for example, surface plasmon resonance (SPR).

In some embodiments, the binding affinity ($EC_{50}$) and/or the dissociation constant of the antibody (e.g. antigen-binding fragment) or antigen-binding domain of a CAR to about BCMA protein, such as human BCMA protein, is from or from about 0.01 nM to about 500 nM, from or from about 0.01 nM to about 400 nM, from or from about 0.01 nM to about 100 nM, from or from about 0.01 nM to about 50 nM, from or from about 0.01 nM to about 10 nM, from or from about 0.01 nM to about 1 nM, from or from about 0.01 nM to about 0.1 nM, is from or from about 0.1 nM to about 500 nM, from or from about 0.1 nM to about 400 nM, from or from about 0.1 nM to about 100 nM, from or from about 0.1 nM to about 50 nM, from or from about 0.1 nM to about 10 nM, from or from about 0.1 nM to about 1 nM, from or from about 0.5 nM to about 200 nM, from or from about 1 nM to about 500 nM, from or from about 1 nM to about 100 nM, from or from about 1 nM to about 50 nM, from or from about 1 nM to about 10 nM, from or from about 2 nM to about 50 nM, from or from about 10 nM to about 500 nM, from or from about 10 nM to about 100 nM, from or from about 10 nM to about 50 nM, from or from about 50 nM to about 500 nM, from or from about 50 nM to about 100 nM or from or from about 100 nM to about 500 nM. In certain embodiments, the binding affinity ($EC_{50}$) and/or the equilibrium dissociation constant, $K_D$, of the antibody to a BCMA protein, such as human BCMA protein, is at or less than or about 400 nM, 300 nM, 200 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the antibodies bind to a BCMA protein, such as human BCMA protein, with a sub-nanomolar binding affinity, for example, with a binding affinity less than about 1 nM, such as less than about 0.9 nM, about 0.8 nM, about 0.7 nM, about 0.6 nM, about 0.5 nM, about 0.4 nM, about 0.3 nM, about 0.2 nM or about 0.1 nM or less.

In some embodiments, the binding affinity may be classified as high affinity or as low affinity. In some cases, the antibody or fragment thereof or a recombinant receptor or antigen-binding domain of a recombinant receptor, e.g., CAR, that exhibits low to moderate affinity binding exhibits a $K_A$ of up to $10^7$ $M^{-1}$, up to $10^6$ $M^{-1}$, up to $10^5$ $M^{-1}$. In some cases, an antibody or fragment thereof or a recombinant receptor that exhibits high affinity binding to a particular epitope interacts with such epitope with a $K_A$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. In some embodiments, the binding affinity ($EC_{50}$) and/or the equilibrium dissociation constant, $K_D$, of the anti-BCMA antibody or fragment thereof or antigen-binding domain of a recombinant receptor, e.g., CAR, to a BCMA protein, is from or from about 0.01 nM to about 1 μM, 0.1 nM to 1 μM, 1 nM to 1 μM, 1 nM to 500 nM, 1 nM to 100 nM, 1 nM to 50 nM, 1 nM to 10 nM, 10 nM to 500 nM, 10 nM to 100 nM, 10 nM to 50 nM, 50 nM to 500 nM, 50 nM to 100 nM or 100 nM to 500 nM. In certain embodiments, the binding affinity ($EC_{50}$) and/or the dissociation constant of the equilibrium dissociation constant, $K_D$, of the anti-BCMA antibody or fragment thereof or antigen-binding domain of a recombinant receptor, e.g., CAR, to a BCMA protein, is at or about or less than at or about 1 μM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. The degree of affinity of a particular antibody can be compared with the affinity of a known antibody, such as a reference antibody.

In some embodiments, the binding affinity of an anti-BCMA antibody or antigen-binding domain of a recombinant receptor, e.g., CAR, for different antigens, e.g., BCMA proteins from different species can be compared to determine the species cross-reactivity. For example, species cross-reactivity can be classified as high cross reactivity or low cross reactivity. In some embodiments, the equilibrium dissociation constant, $K_D$, for different antigens, e.g., BCMA proteins from different species such as human, cynomolgus monkey or mouse, can be compared to determine species cross-reactivity. In some embodiments, the species cross-reactivity of an anti-BCMA antibody or antigen-binding domain of a CAR can be high, e.g., the anti-BCMA antibody binds to human BCMA and a species variant BCMA to a similar degree, e.g., the ratio of $K_D$ for human BCMA and $K_D$ for the species variant BCMA is or is about 1. In some embodiments, the species cross-reactivity of an anti-BCMA antibody or antigen-binding domain of a CAR can be low, e.g., the anti-BCMA antibody has a high affinity for human BCMA but a low affinity for a species variant BCMA, or vice versa. For example, the ratio of $K_D$ for the species variant BCMA and $K_D$ for the human BCMA is more than 10, 15, 20, 25, 30, 40, 50, 60, 70, 80, 90, 100, 200, 500, 1000, 2000 or more, and the anti-BCMA antibody has low species cross-reactivity. The degree of species cross-reactivity can be compared with the species cross-reactivity of a known antibody, such as a reference antibody.

In some embodiments, the binding affinity of the anti-BCMA antibody or antigen-binding domain of a CAR, for different form or topological type of antigens, e.g., soluble BCMA protein compared to the binding affinity to a membrane-bound BCMA, to determine the preferential binding or relative affinity for a particular form or topological type. For example, in some aspects, the provided anti-BCMA antibodies or antigen-binding domains can exhibit preferential binding to membrane-bound BCMA as compared to soluble BCMA and/or exhibit greater binding affinity for, membrane-bound BCMA compared to soluble BCMA. In some embodiments, the equilibrium dissociation constant, $K_D$, for different form or topological type of BCMA proteins, can be compared to determine preferential binding or relative binding affinity. In some embodiments, the preferential binding or relative affinity to a membrane-bound BCMA compared to soluble BCMA can be high. For example, in some cases, the ratio of $K_D$ for soluble BCMA and the $K_D$ for membrane-bound BCMA is more than 10, 15, 20, 25, 30, 40, 50, 60, 70, 80, 90, 100, 200, 500, 1000, 2000 or more and the antibody or antigen-binding domain preferentially binds or has higher binding affinity for membrane-bound BCMA. In some cases, the ratio of $K_A$ for membrane-bound BCMA and the $K_A$ for soluble BCMA is more than 10, 15, 20, 25, 30, 40, 50, 60, 70, 80, 90, 100, 200, 500, 1000, 2000 or more and the antibody or antigen-binding domain preferentially binds or has higher binding affinity for membrane-bound BCMA. In some cases, the antibody or antigen-binding domain of CAR binds soluble BCMA and membrane-bound BCMA to a similar degree, e.g., the ratio of $K_D$ for soluble BCMA and $K_D$ for membrane-bound BCMA is or is about 1. In some cases, the antibody or antigen-binding domain of CAR binds soluble BCMA and membrane-bound BCMA to a similar degree, e.g., the ratio of $K_A$ for soluble BCMA and $K_A$ for membrane-bound BCMA is or is about 1. The degree of preferential binding or relative affinity for membrane-bound BCMA or soluble BCMA can be compared with that of a known antibody, such as a reference antibody.

In some embodiments, the antibodies or antigen binding fragments thereof, in the Recombinant receptors, e.g., CARs, bind to a similar degree to a human BCMA protein and a non-human BCMA protein or other non-BCMA proteins. For example, in some embodiments, the antibodies or antigen binding fragments thereof or antigen-binding domain of a CAR bind to a human BCMA protein, such as the human BCMA protein comprising the amino acid sequence of SEQ ID NO:164 (GenBank No. BAB60895.1), or SEQ ID NO:165 (NCBI No. NP_001183.2) or an allelic variant or splice variant thereof, with an equilibrium dissociation constant ($K_D$), and to a non-human BCMA, such as a cynomolgus monkey BCMA, such as the cynomolgus monkey BCMA protein set forth in SEQ ID NO:147 (GenBank No. EHH60172.1), with a $K_D$ that is similar, or about the same, or less than 2-fold different, or less than 5-fold different.

In some embodiments, the antibodies or antigen binding fragments thereof, in the Recombinant receptors, e.g., CARs, bind to a similar degree to a soluble BCMA protein and a membrane-bound BCMA protein, with an equilibrium dissociation constant ($K_D$) that is similar, or about the same, or less than 2-fold different, or less than 5-fold different.

For example, in some embodiments, the antibodies, in the Recombinant receptors, e.g., CARs, or antigen binding fragments thereof bind to a human BCMA with a $K_D$ of about or less than at or about 1 μM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less, and binds to a cynomolgus monkey BCMA with a $K_D$ of about or less than at or about 1 μM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the antibodies or antigen binding fragments thereof bind to a mouse BCMA protein with a $K_D$ of about or less than at or about 1 μM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the antibodies or antigen binding fragments thereof, in the Recombinant receptors, e.g., CARs, bind to a human BCMA, a cynomolgus monkey BCMA and a mouse BCMA with high affinity. In some embodiments, the antibodies or antigen binding fragments thereof bind to a human BCMA and cynomolgus monkey BCMA with a high affinity, and to a mouse BCMA with low affinity. In some embodiments, the antibodies or antigen binding fragments thereof bind to a human BCMA and BCMA from other species, or other variants of the BCMA protein, with high affinity.

In some embodiments, the total binding capacity ($R_{max}$), as measured using particular surface plasmon resonance (SPR) conditions, is used to determine the ability or capacity of binding of the antibody or antigen binding fragment thereof, to the antigen, e.g., a BCMA protein, such as a human BCMA protein. For SPR analysis, the "ligand" is the immobilized target molecule on the surface of the sensor, for example, a BCMA protein, and the "analyte" is the tested molecule, e.g., antibody, for binding to the "ligand". For example, the "analyte" can be any of the antibodies, or antigen binding fragments thereof, that binds to a BCMA protein. For a particular ligand and analyte pair in SPR, the $R_{max}$ can be determined assuming a 1:1 binding stoichiometry model, for a particular condition. Binding capacity ($R_{max}$) was determined using the following formula: $R_{max}$ (RU)=(analyte molecular weight)/(ligand molecular weight)×immobilized ligand level (RU). For example, in a particular SPR conditions, the R. of binding between any of the antibody or antigen binding fragment thereof and a BCMA protein, such as a human BCMA or a cynomolgus BCMA, is at least or at least about 50 resonance units (RU), such as about 25 RU, 20 RU, 15 RU, 10 RU, 5 RU or 1 RU.

In some embodiments, the antibodies, such as the human antibodies, in the CAR, specifically bind to a particular epitope or region of BCMA protein, such as generally an extracellular epitope or region. BCMA protein is a type III membrane 184 amino acid protein that contains an extracellular domain, a transmembrane domain, and a cytoplasmic domain. With reference to a human BCMA amino acid sequence set forth in SEQ ID NO:164, the extracellular domain corresponds to amino acids 1-54, amino acids 55-77 correspond to the transmembrane domain, and amino acids 78-184 correspond to the cytoplasmic domain Among the Recombinant receptors, e.g., CARs, are Recombinant receptors, e.g., CARs, that exhibit antigen-dependent activity or signaling, i.e. signaling activity that is measurably absent or at background levels in the absence of the antigen, e.g. BCMA. Thus, in some aspects, Recombinant receptors, e.g., CARs, do not exhibit, or exhibit no more than background or a tolerable or low level of, tonic signaling or antigen-independent activity or signaling in the absence of antigen, e.g. BCMA, being present. In some embodiments, the provided anti-BCMA CAR-expressing cells exhibit biological activity or function, including cytotoxic activity, cytokine production, and ability to proliferate.

In some embodiments, biological activity or functional activity of a chimeric receptor, such as cytotoxic activity, can be measured using any of a number of known methods. The activity can be assessed or determined either in vitro or in vivo. In some embodiments, activity can be assessed once the cells are administered to the subject (e.g., human). Parameters to assess include specific binding of an engineered or natural T cell or other immune cell to antigen, e.g., in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells also can be measured by assaying expression and/or secretion of certain cytokines, such as interleukin-2 (IL-2), interferon-gamma (IFNγ), interleukin-4 (IL-4), TNF-alpha (TNFα), interleukin-6 (IL-6), interleukin-10 (IL-10), interleukin-12 (IL-12), granulocyte-macrophage colony-stimulating factor (GM-CSF), CD107a, and/or TGF-beta (TGFβ). Assays to measure cytokines are well known in the art, and include but are not limited to, ELISA, intracellular cytokine staining, cytometric bead array, RT-PCR, ELISPOT, flow cytometry and bio-assays in which cells responsive to the relevant cytokine are tested for responsiveness (e.g. proliferation) in the presence of a test sample. In some aspects the biological activity is measured by assessing clinical outcome, such as reduction in tumor burden or load.

In some aspects, a reporter cell line can be employed to monitor antigen-independent activity and/or tonic signaling through anti-BCMA CAR-expressing cells. In some embodiments, a T cell line, such as a Jurkat cell line, contains a reporter molecule, such as a fluorescent protein or other detectable molecule, such as a red fluorescent protein, expressed under the control of the endogenous Nur77 transcriptional regulatory elements. In some embodiments, the Nur77 reporter expression is cell intrinsic and dependent upon signaling through a recombinant reporter containing a primary activation signal in a T cell, a signaling domain of a T cell receptor (TCR) component, and/or a signaling domain comprising an immunoreceptor tyrosine-based activation motif (ITAM), such as a CD3 chain. Nur77 expression is generally not affected by other signaling pathways such as cytokine signaling or toll-like receptor (TLR) signaling, which may act in a cell extrinsic manner and may not depend on signaling through the recombinant receptor. Thus, only cells that express the exogenous recombinant receptor, e.g. anti-BCMA CAR, containing the appropriate signaling regions is capable of expressing Nur77 upon stimulation (e.g., binding of the specific antigen). In some cases, Nur77 expression also can show a dose-dependent response to the amount of stimulation (e.g., antigen).

In some embodiments, the provided anti-BCMA CARs exhibit improved expression on the surface of cells, such as compared to an alternative CAR that has an identical amino acid sequence but that is encoded by non-splice site eliminated and/or a codon-optimized nucleotide sequence. In some embodiments, the expression of the recombinant receptor on the surface of the cell can be assessed. Approaches for determining expression of the recombinant receptor on the surface of the cell may include use of chimeric antigen receptor (CAR)-specific antibodies (e.g., Brentjens et al., Sci. Transl. Med. 2013 March; 5(177): 177ra38), Protein L (Zheng et al., J. Transl. Med. 2012 February; 10:29), epitope tags, and monoclonal antibodies that specifically bind to a CAR polypeptide (see international patent application Pub. No. WO2014190273). In some embodiments, the expression of the recombinant receptor on the surface of the cell, e.g., primary T cell, can be assessed, for example, by flow cytometry, using binding molecules that can bind to the recombinant receptor or a portion thereof that can be detected. In some embodiments, the binding molecules used for detecting expression of the recombinant receptor an anti-idiotypic antibody, e.g., an anti-idiotypic agonist antibody specific for a binding domain, e.g., scFv, or a portion thereof. Exemplary anti-idiotypic antibodies are described in PCT/US2020/063492, incorporated herein by reference in its entirety. In some embodiments, the binding molecule is or comprises an isolated or purified antigen, e.g., recombinantly expressed antigen.

F. Multispecific Antibodies

In certain embodiments, the BCMA-binding recombinant receptor, are multispecific. Among the multispecific recombinant receptors include bispecific receptors. Multispecific binding partners, e.g., antibodies, have binding specificities for at least two different sites, which may be in the same or different antigens. In certain embodiments, one of the binding specificities is for BCMA and the other is for another antigen. In some embodiments, additional binding domains bind to and/or recognize a third, or more antigens. In certain embodiments, bispecific antibodies may bind to two different epitopes of BCMA. Bispecific antibodies may also be used to localize cytotoxic agents to cells which express BCMA. Bispecific antibodies can be prepared as full length antibodies or antibody fragments. Among the multispecific antibodies are multispecific single-chain antibodies, e.g., diabodies, triabodies, and tetrabodies, tandem di-scFvs, and tandem tri-scFvs. Also provided are multispecific chimeric receptors, such as multispecific CARs, containing the antibodies (e.g., antigen-binding fragments). Also provided are multispecific cells containing the antibodies or polypeptides including the same, such as cells containing a cell surface protein including the anti-BCMA antibody and an additional cell surface protein, such as an additional chimeric receptor, which binds to a different antigen or a different epitope on BCMA.

Exemplary antigens include B cell specific antigens, other tumor-specific antigens, such as antigens expressed specifically on or associated with a leukemia (e.g., B cell leukemia), lymphoma (e.g., Hodgkin's lymphoma, non-Hodgkin's lymphoma, etc.), or a myeloma, e.g., a multiple myeloma (MM), a plasma cell malignancy (e.g., plasmacytoma). For example, antigens include those expressed specifically on or associated with B cell chronic lymphocytic leukemia (CLL), a diffuse large B-cell lymphoma (DLBCL), acute myeloid leukemia (AML), acute lymphocytic leukemia (ALL), Burkitt lymphoma (e.g., endemic Burkitt lymphoma or sporadic Burkitt lymphoma), mantle cell lymphoma (MCL), non-small cell lung cancer (NSCLC), chronic myeloid (or myelogenous) leukemia (CML), hairy cell leukemia (HCL), small lymphocytic lymphoma (SLL), Marginal zone lymphoma, Hodgkin lymphoma (HL), non-Hodgkin lymphoma (NHL), Anaplastic large cell lymphoma (ALCL), refractory follicular lymphoma, Waldenstrom macroglobulinemia, follicular lymphoma, small non-cleaved cell lymphoma, mucosa-associated lymphatic tissue lymphoma (MALT), marginal zone lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), neuroblastoma, renal cell carcinoma, colon cancer, colorectal cancer, breast cancer, epithelial squamous cell cancer, melanoma, myeloma such as multiple myeloma (e.g., non-secretory multiple myeloma, smoldering multiple myeloma), stomach cancer, esophageal cancer, brain cancer, lung cancer (e.g., small-cell lung cancer), pancreatic cancer, cervical cancer, ovarian cancer, liver cancer (e.g., hepatic carcinoma, hepatoma, etc.), bladder cancer, prostate cancer, testicular cancer, thyroid cancer, uterine cancer, spleen cancer (e.g., splenic lymphoma), adrenal cancer and/or head and neck cancer, and antigens expressed on T cells.

In some embodiments, among the second or additional antigens for multi-targeting strategies includes those in which at least one of the antigens is a universal tumor antigen, or a family member thereof. In some embodiments, the second or additional antigen is an antigen expressed on a tumor. In some embodiments, the BCMA-binding domains, e.g., of a recombinant receptor, target an antigen on the same tumor type as the second or additional antigen. In some embodiments, the second or additional antigen may also be a universal tumor antigen or may be a tumor antigen specific to a tumor type.

Exemplary second or additional antigens include CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PIGF, ED-B fibronectin, an oncogene, an oncogene product, CD66a-d, necrosis antigens, Ii, IL-2, T101, TAC, IL-6, ROR1, TRAIL-R1 (DR4), TRAIL-R2 (DR5), Her2, L1-CAM, mesothelin, CEA, hepatitis B surface antigen, anti-folate receptor, CD24, CD30, CD44, EGFR, EGP-2, EGP-4, EPHa2, ErbB2, ErbB3, ErbB4, erbB dimers, EGFR vIII, FBP, FCRL5, FCRH5, fetal acetylcholine receptor, GD2, GD3, G protein-coupled receptor class C group 5 member D (GPRC5D), HMW-MAA, IL-22R-alpha, IL-13R-alpha2, kdr, kappa light chain, Lewis Y, L1-cell adhesion molecule (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, CD171, G250/CALX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, dual antigen, an antigen associated with a universal tag, a cancer-testes antigen, MUC1, MUC16, NY-ESO-1, MART-1, gp100, oncofetal antigen, VEGF-R2, carcinoembryonic antigen (CEA), prostate specific antigen, PSMA, Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, hTERT, MDM2, CYP1B, WT1, livin, AFP, p53, cyclin (D1), CS-1, BAFF-R, TACI, CD56, TIM-3, CD123, L1-cell adhesion molecule, MAGE-A1, MAGE A3, a cyclin, such as cyclin A1 (CCNA1) and/or a pathogen-specific antigen, biotinylated molecules, molecules expressed by HIV, HCV, HBV and/or other pathogens, and/or in some aspects, neoepitopes or neoantigens thereof. In some embodiments, the antigen is associated with or is a universal tag.

In some aspects, the antigen, e.g., the second or additional antigen, such as the disease-specific antigen and/or related antigen, is expressed on multiple myeloma, such as G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI and/or FcRH5. Other exemplary multiple myeloma antigens include CD56, TIM-3, CD33, CD123, CD44, CD20, CD40, CD74, CD200, EGFR, β2-Microglobulin, HM1.24, IGF-1R, IL-6R, TRAIL-R1, and the activin receptor type IIA (ActRIIA). See Benson and Byrd, J. Clin. Oncol. (2012) 30(16): 2013-15; Tao and Anderson, Bone Marrow Research (2011): 924058; Chu et al., Leukemia (2013) 28(4):917-27; Garfall et al., Discov Med. (2014) 17(91):37-46. In some embodiments, the antigens include those present on lymphoid tumors, myeloma, AIDS-associated lymphoma, and/or post-transplant lymphoproliferations, such as CD38. Antibodies or antigen-binding fragments directed against such antigens are known and include, for example, those described in U.S. Pat. Nos. 8,153,765; 8,603,477, 8,008,450; U.S. Pub. No. US20120189622 or US20100260748; and/or International PCT Publication Nos. WO2006099875, WO2009080829 or WO2012092612 or WO2014210064. In some embodiments, such antibodies or antigen-binding fragments thereof (e.g. scFv) are contained in multispecific antibodies, multispecific chimeric receptors, such as multispecific CARs, and/or multispecific cells.

G. Optimized Anti-BCMA CAR Polynucleotides

In some embodiments, a starting or reference sequence encoding a transgene, such as a BCMA-binding recombinant receptor, e.g., anti-BCMA CAR, is assessed for codon optimization and/or splice site removal.

In some embodiments, the methods are carried out on an anti-BCMA CAR, such as a CAR containing an scFv antigen-binding domain specific to BCMA, a spacer, such as a spacer set forth in SEQ ID NO:174, a costimulatory signaling region, such as a costimulatory signaling domain from 4-1BB and a CD3 zeta signaling region. Exemplary identified splice donor sites and splice acceptor sites, and their corresponding scores, are listed in Tables 7 and 8 below for exemplary anti-BCMA CARs.

TABLE 7

| Predicted Splice Donor Sites | | | | | | |
|---|---|---|---|---|---|---|
| | STARTING SEQUENCE | | | O/SSE SEQUENCE | | |
| Region of Construct | splice donor site | SEQ ID NO | Splice score | optimized splice donor site | SEQ ID NO | Splice score |
| promoter | | | | | | |
| | cgtctag<u>gt</u>aagttt | 206 | 1 | no change | | <0.7 |
| scFv-encoding | | | | | | |
| BCMA-23 | gaccaag<u>gt</u>gaccgt | 207 | N/A | caccaag<u>gt</u>gaccgt | 215 | 0.54 |
| BCMA-26 | tgcactg<u>gt</u>accagc | 208 | 0.55 | no change | | |
| BCMA-52 | taaactg<u>gt</u>accagc | 209 | 0.76 | tgaactg<u>gt</u>atcagc | 216 | <0.7 |

TABLE 7-continued

| Predicted Splice Donor Sites | | | | | | |
|---|---|---|---|---|---|---|
| | STARTING SEQUENCE | | | O/SSE SEQUENCE | | |
| Region of Construct | splice donor site | SEQ ID NO | Splice score | optimized splice donor site | SEQ ID NO | Splice score |
| BCMA-52 | atctcct**g**taagggt | 210 | 0.79 | atctctt**ga**aatggt | 217 | <0.7 |
| BCMA-52 | ggtcaag**gt**actctg | 211 | 0.85 | ggccagg**gc**acactg | 218 | <0.7 |
| BCMA-55 | gaggaca**gt**aagcgg | 212 | 0.66 | gaggaca**gc**aagagg | 219 | <0.5 |
| BCMA-55 | ggtcaag**gt**actctg | 213 | 0.85 | ggccagg**ga**accctg | 220 | <0.5 |
| BCMA-55 | tgcctcc**gt**gtctgc | 214 | <0.50 | tgccagc**gt**tagtgc | 221 | 0.60 |
| Spacer-encoding | | | | | | |
| | aatctaa**gt**acggac | 222 | 0.65 | agtctaa**at**acggac | 189 | <0.7 |
| | tcaactg**gt**acgtgg | 223 | 0.96 | tcaactg**gt**atgtgg | 190 | <0.7 |
| | tcaattg**gt**acgtgg | 254 | 0.97 | tcaactg**gt**atgtgg | 190 | <0.7 |
| | acaatta**gt**aaggca | 224 | 0.43 | accatct**cc**aaggcc | 191 | <0.7 |
| | accacag**gt**gtatac | 225 | 0.42 | gecccag**gt**ttacac | 192 | <0.7 |
| CD3zeta signaling region-encoding | | | | | | |
| | tttccaggtccgccg | 226 | 0.74 | tcagcagatccgccg | 193 | <0.7 |
| Truncated receptor surrogate marker-encoding | | | | | | |
| | ctgctct**gt**gagtta | 227 | 0.56 | ctcctgt**gt**gaactc | 194 | <0.7 |
| | acgcaaa**gt**gtgtaa | 228 | 0.5 | teggaaa**gt**gtgcaa | 195 | <0.7 |
| | caacatg**gt**cagttt | 229 | 0.71 | cagcacg**gc**cagttt | 196 | <0.7 |
| | aacagag**gt**gaaaac | 230 | 0.42 | aaccggg**gc**gagaac | 197 | <0.7 |
| | ctggagg**gt**gagcca | 231 | 0.82 | ctggaag**gc**gagccc | 198 | <0.7 |
| | tcttcat**gt**gagcgg | 252 | 0.84 | tgttcat**gt**gagcgg | 199 | <0.7 |

TABLE 8

| Predicted Splice Acceptor Sites | | | | | | |
|---|---|---|---|---|---|---|
| | STARTING SEQUENCE | | | O/SSE SEQUENCE | | |
| Region of Construct | splice acceptor site | SEQ ID NO | splice score | optimized splice acceptor site | SEQ ID NO | Splice score |
| Promoter | | | | | | |
| | tggctccgcctttttcccg**ag**<br>ggtgggggagaaccgtatat | 232 | 0.50 | no change | | |
| | tgaactgcgtccgccgtct**a**<br>**g**gtaagtttaaagctcaggtc | 233 | 0.71 | no change | | |
| | ttctgttctgcgccgttac**ag**a<br>tccaagctgtgaccggcgc | 234 | 0.89 | no change | | |
| scFv-encoding | | | | | | |
| BCMA-23 | ctactacatgagctggatc**cg**<br>ccaggctccagggaagggg<br>c | 26 | N/A | ctactatatgtcctggatc**ag**acaggcac<br>ctggcaagggcc | 27 | 0.46 |
| BCMA-23 | ggctgattattattgtagc**tc**a<br>tatggaggtagtaggtctt | 25 | N/A | ggcagattactattgttct**ag**ctacggcgg<br>cagcagatcct | 28 | 0.55 |

TABLE 8-continued

| Predicted Splice Acceptor Sites | | | | | | |
|---|---|---|---|---|---|---|
| | STARTING SEQUENCE | | | O/SSE SEQUENCE | | |
| Region of Construct | splice acceptor site | SEQ ID NO | splice score | optimized splice acceptor site | SEQ ID NO | Splice score |
| BCMA-25 | ctatgccatgtcctggttc**ag**gcaggcaccaggcaagggcc | 43 | 0.95 | ctatgccatgtcctggttc**aa**gcaggcaccaggcaagggcc | 48 | <0.7 |
| BCMA-25 | gtccgcctctgtgggcgat**ag**ggtgaccgtgacatgtcgcg | 44 | 0.50 | no change | | |
| BCMA-25 | gtgggctttatccgctcta**ag**gcctacggcggcaccacaga | 45 | 0.55 | no change | | |
| BCMA-25 | gtgacatgtcgcgcctccc**ag**ggcatctctaactacctggc | 46 | 0.67 | no change | | |
| BCMA-25 | tacagcgcctccaccctgcagagcggagtgccctcccggtt | 47 | 0.66 | no change | | |
| BCMA-52 | ctggccatcagtggcctcc**ag**tctgaggatgaggctgatta | 78 | <0.50 | ctggctatttctggactgc**ag**agcgaggacgaggccgacta | 80 | 0.62 |
| BCMA-52 | agatacagcccgtccttcc**aa**ggccacgtcaccatctcagc | 79 | <0.50 | agatacagccctagctttc**ag**ggccacgtgaccatcagcgc | 81 | 0.67 |
| BCMA-55 | cgaggctgattattactgc**ag**ctcaaatacaagaagcagca | 110 | 0.79 | cgaggccgattactactgc**ag**cagcaacacccggtccagca | ill | <0.40 |
| BCMA-55 | gccctcaggggtttctaat**cg**cttctctggctccaagtctg | 109 | <0.50 | gcccagcggcgtgtccaat**ag**attcagcggcagcaagagcg | 112 | 0.40 |
| Spacer-encoding | | | | | | |
| | cgccttgtcctccttgtcc**ag**ctcctcctgttgccggacct | 203 | 0.84 | cgccttgtcctccttgtcc**cg**ctcctcctgttgccggacct | 188 | <0.7 |
| | aagtttctttctgtattcc**ag**gctgaccgtggataaatctc | 239 | 0.97 | cagtttcttcctgtatagt**ag**actcaccgtggataaatcaa | 180 | <0.7 |
| | aagtttctttctgtattcc**ag**gctgaccgtggataaatctc | 239 | 0.97 | aagtttctttctgtattcc**ag**actgaccgtggataaatctc | 187 | |
| | gggcaacgtgttctcttgc**ag**tgtcatgcacgaagccctgc | 240 | 0.55 | gggcaacgtgttcagctgc**ag**cgtgatgcacgaggccctgc | 181 | <0.7 |
| | cagtttcttcctgtatagt**ag**actcaccgtggataaatcaa | 204 | 0.74 | No change | | |
| CD28 TM-encoding | | | | | | |
| | aggggtgctggcctgttac**ag**cctgctggtgacagtcgctt | 141 | 0.4 | cggagtgctggcctgttac**ag**cctgctggttaccgtggcct | 182 | 0.75 |
| 4-1BB/CD3zeta signaling region-encoding | | | | | | |
| | gctgagagtcaagttttccaggtccgccgacgctccagcct | 3 | 0.55 | gctgagagtgaagttcagc**ag**atccgccgacgctccagcct | 183 | <0.7 |
| Truncated Receptor Surrogate Marker-encoding | | | | | | |
| | actcctcctctggatccac**ag**gaactggatattctgaaaac | 249 | 0.74 | acacctccactggatcccc**aa**gagctggatatcctgaaaac | 184 | <0.7 |
| | acagggtttttgctgattc**ag**gcttggcctgaaaacaggac | 250 | 0.73 | accggattcctcctgatcc**aa**gcctggccagagaacagaac | 185 | <0.7 |
| | accggattcctcctgattcaggcctggccagagaacagaac | 205 | 0.82 | accggattcctcctgatcc**aa**gcctggccagagaacagaac | 185 | <0.7 |

TABLE 8-continued

| Predicted Splice Acceptor Sites | | | | | | |
|---|---|---|---|---|---|---|
| | STARTING SEQUENCE | | | O/SSE SEQUENCE | | |
| Region of Construct | splice acceptor site | SEQ ID NO | splice score | optimized splice acceptor site | SEQ ID NO | Splice score |
| | atggtcagttttctcttgc**ag**t cgtcagcctgaacataaca | 251 | 0.89 | acggccagtttagcctggc**tg**tggtgtctc tgaacatcacc | 186 | <0.7 |

In some embodiments, the resulting modified nucleic acid sequence(s) is/are then synthesized and used to transduce cells to test for splicing as indicated by RNA heterogeneity. Exemplary methods are as follows and described in the Examples. Briefly, RNA is harvested from the expressing cells, amplified by reverse transcriptase polymerase chain reaction (RT-PCR) and resolved by agarose gel electrophoresis to determine the heterogeneity of the RNA, compared to the starting sequence. In some cases, improved sequences can be resubmitted to the gene synthesis vendor for further codon optimization and splice site removal, followed by further cryptic splice site evaluation, modification, synthesis and testing, until the RNA on the agarose gel exhibits minimal RNA heterogeneity.

In some embodiments, the provided methods for optimizing a coding nucleic acid sequence encoding a transgene, such as an anti-BCMA CAR provided herein, or a construct provided herein, is to both reduce or eliminate cryptic splice sites (see, e.g., SEQ ID NO: 200 for an exemplary codon optimized and splice site eliminated spacer sequence) and optimize human codon usage (see, e.g., SEQ ID NO: 236 for an exemplary codon optimized and spacer sequence). An exemplary optimization strategy is described in the Examples.

In some embodiments, provided are polynucleotides encoding a chimeric antigen receptor, comprising nucleic acid encoding: (a) an extracellular antigen-binding domain that specifically recognizes BCMA, including any of the antigen-binding domains described below; (b) a spacer of at least 125 amino acids in length; (c) a transmembrane domain; and (d) an intracellular signaling region, wherein following expression of the polynucleotide in a cell, the transcribed RNA, optionally messenger RNA (mRNA), from the polynucleotide, exhibits at least 70%, 75%, 80%, 85%, 90%, or 95% RNA homogeneity. In some embodiments the antigen-binding domain comprises a $V_H$ region and a $V_L$ region comprising the amino acid sequence set forth in SEQ ID NOs:116 and 119, respectively, or a sequence of amino acids having at least 90% identity to SEQ ID NOS:116 and 119, respectively. In some embodiments, the antigen-binding domain comprises a $V_H$ region that is or comprises a CDR-H1, CDR-H2 and CDR-H3 contained within the $V_H$ region amino acid sequence selected from SEQ ID NO: 116 and a $V_L$ region that is or comprises a CDR-L1, CDR-L2 and CDR-L3 contained within the $V_L$ region amino acid sequence selected from SEQ ID NO: 119. In some embodiments, In some embodiments, the antigen-binding domain comprises a $V_H$ region comprising a CDR-H1, CDR-H2, and CDR-H3 comprising the amino acid sequence of SEQ ID NOS:97, 101 and 103, respectively, and a $V_L$ region comprising a CDR-L1, CDR-L2, and CDR-L3 comprising the amino acid sequence of SEQ ID NOS:105, 107 and 108, respectively; or a $V_H$ region comprising a CDR-H1, CDR-H2, and CDR-H3 comprising the amino acid sequence of SEQ ID NOS:96, 100 and 103, respectively, and a $V_L$ region comprising a CDR-L1, CDR-L2, and CDR-L3 comprising the amino acid sequence of SEQ ID NOS:105, 107 and 108, respectively; or a $V_H$ region comprising a CDR-H1, CDR-H2, and CDR-H3 comprising the amino acid sequence of SEQ ID NOS: 95, 99 and 103, respectively, and a $V_L$ region comprising a CDR-L1, CDR-L2, and CDR-L3 comprising the amino acid sequence of SEQ ID NOS:105, 107 and 108, respectively; or a $V_H$ region comprising a CDR-H1, CDR-H2, and CDR-H3 comprising the amino acid sequence of SEQ ID NOS: 94, 98 and 102, respectively, and a $V_L$ region comprising a CDR-L1, CDR-L2, and CDR-L3 comprising the amino acid sequence of SEQ ID NOS: 104, 106 and 108, respectively; or a $V_H$ region that is or comprises the amino acid sequence set forth in SEQ ID NO: 116 and a $V_L$ region that is or comprises the amino acid sequence set forth in SEQ ID NO: 119. In some embodiments, exemplary antigen-binding domain in the chimeric antigen receptor encoded by the polynucleotide include those described in each row of Table 6 herein. In any of such embodiments, the transmembrane domain of the CAR is or comprises a transmembrane domain derived from a CD28; the intracellular signaling region comprises a cytoplasmic signaling domain of a CD3-zeta (CD3ζ) chain or a functional variant or signaling portion thereof and a costimulatory signaling region comprises an intracellular signaling domain of 4-1BB.

In some embodiments, provided are polynucleotides encoding a chimeric antigen receptor, comprising nucleic acid encoding: (a) an extracellular antigen-binding domain that specifically recognizes BCMA, including any of the antigen-binding domains described below; (b) (b) a spacer, wherein the encoding nucleic acid is or comprises, or consists or consists essentially of, the sequence set forth in SEQ ID NO:200 or encodes a sequence of amino acids set forth in SEQ ID NO:174; (c) a transmembrane domain; and (d) an intracellular signaling region. In some embodiments the antigen-binding domain comprises a $V_H$ region and a $V_L$ region comprising the amino acid sequence set forth in SEQ ID NOs:116 and 119, respectively, or a sequence of amino acids having at least 90% identity to SEQ ID NOS:116 and 119, respectively. In some embodiments, the antigen-binding domain comprises a $V_H$ region that is or comprises a CDR-H1, CDR-H2 and CDR-H3 contained within the $V_H$ region amino acid sequence selected from SEQ ID NO: 116 and a $V_L$ region that is or comprises a CDR-L1, CDR-L2 and CDR-L3 contained within the $V_L$ region amino acid sequence selected from SEQ ID NO: 119. In some embodiments, In some embodiments, the antigen-binding domain comprises a $V_H$ region comprising a CDR-H1, CDR-H2, and CDR-H3 comprising the amino acid sequence of SEQ ID NOS:97, 101 and 103, respectively, and a $V_L$ region comprising a CDR-L1, CDR-L2, and CDR-L3 comprising the amino acid sequence of SEQ ID NOS:105, 107 and 108, respectively; or a $V_H$ region comprising a CDR-H1, CDR-H2, and CDR-H3 comprising the amino acid sequence of SEQ ID NOS:96, 100 and 103, respectively, and a $V_L$ region comprising a CDR-L1, CDR-L2, and CDR-L3 comprising the amino acid sequence of SEQ ID NOS:105, 107 and 108, respectively; or a $V_H$ region comprising a CDR-H1, CDR-H2, and CDR-H3 comprising the amino acid sequence of SEQ ID NOS: 95, 99 and 103, respectively, and a $V_L$ region comprising a CDR-L1, CDR-L2, and CDR-L3 comprising the amino acid sequence of SEQ ID NOS:105, 107 and 108, respectively; or a $V_H$ region comprising a CDR-H1, CDR-H2, and CDR-H3 comprising the amino acid sequence of SEQ ID NOS: 94, 98 and 102, respectively, and a $V_L$ region comprising a CDR-L1, CDR-L2, and CDR-L3 comprising the amino acid sequence of SEQ ID NOS: 104, 106 and 108, respectively; or a $V_H$ region that is or comprises the amino acid sequence set forth in SEQ ID NO: 116 and a $V_L$ region that is or comprises the amino acid sequence set forth in SEQ ID NO: 119. In some embodiments, exemplary antigen-binding domain in the chimeric antigen receptor encoded by the polynucleotide include those described in each row of Table 9 herein. In any of such embodiments, the transmembrane domain of the CAR is or comprises a transmembrane domain derived from a CD28; the intracellular signaling region comprises a cytoplasmic signaling domain of a CD3-zeta (CD3ζ) chain or a functional variant or signaling portion thereof and a costimulatory signaling region comprises an intracellular signaling domain of 4-1BB.

Also provided herein are exemplary modified polynucleotides, including polynucleotides that were modified for codon optimization (0) and/or splice site elimination (SSE). Examples of such polynucleotides are set forth in Table 6, wherein exemplary nucleotide (nt) sequences for the components of the exemplary CAR constructs prior to splice site elimination and codon optimization (non-opt), nucleic acid (nt) sequences for the components of the CAR constructs following splice site elimination and optimization (0/SSE), and the corresponding amino acid (aa) sequences encoded by the nucleic acid sequences are provided. The components include the IgG-kappa signaling sequence (ss), the anti-BCMA scFv, spacer region, transmembrane (tm) domain, co-signaling sequence (4-1BB co-sig or CD28 co-sig), CD3-ζ signaling domain (CD3-ζ), T2A ribosomal skip element (T2A) and truncated EGF receptor (EGFRt) sequence. Polynucleotide sequences of exemplary CAR constructs are set forth in SEQ ID NOs: 9-14, encoding the amino acid sequences set forth in SEQ ID NOs: 15-20.

TABLE 9

Exemplary BCMA CAR components (SEQ ID NOs)

| Construct | Sequence | ss | scFv | spacer | TM | 4-1BB co-stim | CD3-ζ |
|---|---|---|---|---|---|---|---|
| BCMA-23-L CAR | non-opt (nt) | 167 | 30 | 175 | 139 | 5 | 144 |
| BCMA-23-L CAR CO/SSE | O/SSE (nt) | 171 | 31 | 200 or 8 | 140 | 6 | 145 |
| both | aa | 166 | 29 | 174 | 138 | 4 | 143 |
| BCMA-25-L CAR | non-opt (nt) | 167 | 50 | 175 | 139 | 5 | 144 |
| BCMA-25-L CAR CO/SSE | O/SSE (nt) | 169 | 51 | 200 or 8 | 140 | 6 | 145 |
| both | Aa | 166 | 49 | 174 | 138 | 4 | 143 |
| BCMA-26-L CAR | non-opt (nt) | 167 | 59 | 175 | 139 | 5 | 144 |
| BCMA-26-L CAR CO/SSE | O/SSE (nt) | 168 | 60 | 200 or 8 | 140 | 6 | 145 |
| both | aa | 166 | 58 | 174 | 138 | 4 | 143 |
| BCMA-52-L CAR | non-opt (nt) | 167 | 82 | 175 | 139 | 5 | 144 |
| BCMA-52-L CAR CO/SSE | O/SSE (nt) | 169 | 84 | 200 or 8 | 140 | 6 | 145 |
| both | Aa | 166 | 83 | 174 | 138 | 4 | 143 |
| BCMA-55-L CAR | non-opt (nt) | 167 | 113 | 175 | 139 | 5 | 144 |
| BCMA-55-L CAR CO/SSE | O/SSE (nt) | 170 | 115 | 200 or 8 | 140 | 6 | 145 |
| both | aa | 166 | 114 | 174 | 138 | 4 | 143 |

| Construct | Sequence | ss | scFv | spacer | TM | CD28 co-stim | CD3-ζ |
|---|---|---|---|---|---|---|---|
| BCMA-55-L-CD28 CAR | non-opt (nt) | 167 | 113 | 175 | 139 | 137 | 144 |
| BCMA-55-L-CD28 CAR CO/SSE | O/SSE (nt) | 170 | 115 | 200 or 8 | 140 | 137 | 145 |
| both | aa | 166 | 114 | 174 | 138 | 136 | 143 |

III. ENGINEERED CELLS AND PROCESSES FOR PRODUCING ENGINEERED CELLS

Also provided are cells such as engineered cells that contain a recombinant receptor (e.g., a chimeric antigen receptor) such as exemplary recombinant receptors that contains an extracellular domain that binds BCMA as described herein. Also provided are populations of such cells, compositions containing such cells and/or enriched for such cells, such as in which cells expressing the BCMA-binding recombinant receptor make up at least 50, 60, 70, 80, 90, 91, 92, 93, 94, 95, 96, 97, 98, 99% or more of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients, and cells and pharmaceutical compositions for use in such methods.

Thus also provided are genetically engineered cells expressing the recombinant receptors containing the antibodies, e.g., cells containing the CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T (TN) cells, effector T cells (TEFF), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some aspects, compositions containing the engineered cells expressing the provided exemplary BCMA-binding recombinant receptor herein was observed to be enriched for immune cell subtypes, e.g., CD4+ or CD8+ T cell subtypes, that were associated with central memory T cell ($T_{CM}$) phenotype, which, in some aspects is associated with increased persistence and durability of the engineered cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more polynucleotides introduced via genetic engineering, and thereby express recombinant or genetically engineered products of such polynucleotides. In some embodiments, the polynucleotides are heterologous, i.e., normally not present in a cell or sample obtained from the cell, such as one obtained from another organism or cell, which for example, is not ordinarily found in the cell being engineered and/or an organism from which such cell is derived. In some embodiments, the polynucleotides are not naturally occurring, such as a polynucleotide not found in nature, including one comprising chimeric combinations of polynucleotides encoding various domains from multiple different cell types. In some embodiments, the cells (e.g., engineered cells) comprise a vector (e.g., a viral vector, expression vector, etc.) as described herein, such as a vector comprising a nucleic acid encoding a recombinant receptor described herein.

In particular examples, immune cells, such as human immune cells are used to express the provided polypeptides encoding chimeric antigen receptors. In some examples, the immune cells are T cells, such as CD4+ and/or CD8+ immune cells, including primary cells, such as primary CD4+ and CD8+ cells.

In particular embodiments, the engineered cells are produced by a process that generates an output composition of enriched T cells from one or more input compositions and/or from a single biological sample. In certain embodiments, the output composition contains cells that express a recombinant receptor, e.g., a CAR, such as an anti-BCMA CAR. In particular embodiments, the cells of the output compositions are suitable for administration to a subject as a therapy, e.g., an autologous cell therapy. In some embodiments, the output composition is a composition of enriched CD4+ and CD8+ T cells.

In some embodiments, the process for generating or producing engineered cells is by a process that includes some or all of the steps of: collecting or obtaining a biological sample; isolating, selecting, or enriching input cells from the biological sample; cryopreserving and storing the input cells; thawing and/or incubating the input cells under stimulating conditions; engineering the stimulated cells to express or contain a recombinant polynucleotide, e.g., a polynucleotide encoding a recombinant receptor such as a CAR; cultivating the engineered cells to a threshold amount, density, or expansion; formulating the cultivated cells in an output composition; and/or cryopreserving and storing the formulated output cells until the cells are released for infusion and/or are suitable to be administered to a subject. In some embodiments, the entire process is performed with a single composition of enriched T cells, e.g., CD4+ and CD8+ T cells. In certain embodiments, the process is performed with two or more input compositions of enriched T cells that are combined prior to and/or during the process to generate or produce a single output composition of enriched T cells. In some embodiments, the enriched T cells are or include engineered T cells, e.g., T cells transduced to express a recombinant receptor.

In particular embodiments, an output composition of engineered cells expressing a recombinant receptor (e.g. anti-BCMA CAR) is produced from an initial and/or input composition of cells. In some embodiments, the input composition is a composition of enriched T cells, enriched CD4+ T cells, and/or enriched CD8+ T cells (herein after also referred to as compositions of enriched T cells, compositions of enriched CD4+ T cells, and compositions of enriched CD8+ T cells, respectively). In some embodiments, a composition enriched in CD4+ T cells contains at least 60%, 65%, 70%, 75%, 80%, 85%, 90%, 95%, 98%, 99%, or 99.9% CD4+ T cells. In particular embodiments, the composition of enriched CD4+ T cells contains 100% CD4+ T cells or contains about 100% CD4+ T cells. In certain embodiments, the composition of enriched T cells includes or contains less than 20%, less than 10%, less than 5%, less than 1%, less than 0.1%, or less than 0.01% CD8+ T cells, and/or contains no CD8+ T cells, and/or is free or substantially free of CD8+ T cells. In some embodiments, the populations of cells consist essentially of CD4+ T cells. In some embodiments, a composition enriched in CD8+ T cells contains at least 75%, 80%, 85%, 90%, 95%, 98%, 99%, or 99.9% CD8+ T cells, or contains or contains about 100% CD8+ T cells. In certain embodiments, the composition of enriched CD8+ T cells includes or contains less than 20%, less than 10%, less than 5%, less than 1%, less than 0.1%, or less than 0.01% CD4+ T cells, and/or contains no CD4+ T cells, and/or is free or substantially free of CD4+ T cells. In some embodiments, the populations of cells consist essentially of CD8+ T cells.

In particular embodiments, an output composition of engineered cells is produced from an initial or input composition of cell that is generated and/or made by combining, mixing, and/or pooling cells including from composition of cells containing enriched T cells, enriched CD4+ T cells, and/or enriched CD8+ T cells. In some embodiments, the input composition of cells is a composition of combined, mixed, and/or pooled CD4+ and CD8+ T cells. In particular embodiments, the input composition contains between 30% and 70%, between 35% and 65%, between 40% and 60%, between 45% and 55%, or about 50% or 50% CD4+ T cells and between 30% and 70%, between 35% and 65%, between 40% and 60%, between 45% and 55%, or about 50% or 50% CD8+ T cells. In certain embodiments, the input composition contains between 45% and 55%, about 50%, or 50% CD4+ T cells and between 45% and 55%, about 50%, or 50% CD8+ T cells.

In certain embodiments, the process for producing engineered cells further can include one or more of: activating and/or stimulating a cells, e.g., cells of an input composition; genetically engineering the activated and/or stimulated cells, e.g., to introduce a polynucleotide encoding a recombinant protein by transduction or transfection; and/or cultivating the engineered cells, e.g., under conditions that promote proliferation and/or expansion. In particular embodiments, the provided methods may be used in connection with harvesting, collecting, and/or formulating output compositions produced after the cells have been incubated, activated, stimulated, engineered, transduced, transfected, and/or cultivated.

In some embodiments, the one or more process steps are carried out, at least in part, in serum free media. In some embodiments, the serum free media is a defined or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors. In some embodiments, the serum free media includes cytokines. In some embodiments, the serum free media includes cytokines or recombinant cytokines. In some embodiments, the serum free media includes recombinant IL-2, IL-15, and/or IL-7. In some embodiments, the serum free media includes glutamine. In some embodiments, the serum free media includes glutamine and recombinant IL-2, IL-15, and IL-7.

In some embodiments, the serum-free media includes a basal media that contains one or more proteins or other additives. In some embodiments, all or a portion of the incubation is performed in basal media. In some embodiments, the basal medium contains a mixture of inorganic salts, sugars, amino acids, and, optionally, vitamins, organic acids and/or buffers or other well-known cell culture nutrients. In addition to nutrients, the medium also helps maintain pH and osmolality. In some aspects, the components of the serum-free media support cell growth, proliferation and/or expansion.

A wide variety of commercially available basal media are well known to those skilled in the art, and include Dulbecco's Modified Eagles Medium (DMEM), Roswell Park Memorial Institute Medium (RPMI), Iscove modified Dulbecco's medium and Hams medium. In some embodiments, the basal medium is Iscove's Modified Dulbecco's Medium, RPMI-1640, or α-MEM. In some embodiments, the basal media is a balanced salt solution (e.g., PBS, DPBS, HBSS, EBSS). In some embodiments, the basal media is selected from Dulbecco's Modified Eagle's Medium (DMEM), Minimal Essential Medium (MEM), Basal Medium Eagle (BME), F-10, F-12, RPMI 1640, Glasgow's Minimal Essential Medium (GMEM), alpha Minimal Essential Medium (alpha MEM), Iscove's Modified Dulbecco's Medium, and M199. In some embodiments, the base media is a complex medium (e.g., RPMI-1640, IMDM). In some embodiments, the base medium is OpTmizer™ CTS™ T-Cell Expansion Basal Medium (Thermo Fisher).

In some embodiments, the basal medium further may comprises a protein or a peptide. In some embodiments, the at least one protein is not of non-mammalian origin. In some embodiments, the at least one protein is human or derived from human. In some embodiments, the at least one protein is recombinant. In some embodiments, the at least one protein includes albumin, transferrin, insulin, fibronectin, aprotinin or fetuin. In some embodiments, the protein comprises one or more of albumin, insulin or transferrin, optionally one or more of a human or recombinant albumin, insulin or transferrin.

In some embodiments, the protein is an albumin or albumin substitute. In some embodiments, the albumin is a human derived albumin. In some embodiments, the albumin is a recombinant albumin. In some embodiments, the albumin is a natural human serum albumin. In some embodiments, the albumin is a recombinant human serum albumin. In some embodiments, the albumin is a recombinant albumin from a non-human source. Albumin substitutes may be any protein or polypeptide source. Examples of such protein or polypeptide samples include but are not limited to bovine pituitary extract, plant hydrolysate (e.g., rice hydrolysate), fetal calf albumin (fetuin), egg albumin, human serum albumin (HSA), or another animal-derived albumins, chick extract, bovine embryo extract, AlbuMAX® I, and AlbuMAX® II. In some embodiments, the protein or peptide comprises a transferrin. In some embodiments, the protein or peptide comprises a fibronectin. In some embodiments, the protein or peptide comprises aprotinin. In some embodiments, the protein comprises fetuin.

In some embodiments, the one or more additional protein is part of a serum replacement supplement that is added to the basal medium. Examples of serum replacement supplements include, for example, Immune Cell Serum Replacement (ThermoFisher, #A2598101) or those described in Smith et al. *Clin Transl Immunology.* 2015 January; 4(1): e31.

In certain embodiments, the basal media is supplemented with additional additives. Additives to cell culture media may include, but is not limited to nutrients, sugars, e.g., glucose, amino acids, vitamins, or additives such as ATP and NADH.

In some embodiments, the basal medium further comprises glutamine, such as L-glutamine. In some aspects, the glutamine is a free form of glutamine, such as L-glutamine. In some embodiments, the concentration of the glutamine, such as L-glutamine, in the basal medium is less than 200 mM, such as less than 150 mM, 100 mM or less, such as 20 mM to 120 mM, or 40 mM to 100 mM, such as or about 80 mM. In some embodiments, the concentration of L-glutamine is about 0.5 mM to about 5 mM (such as 2 mM).

In some embodiments, the basal medium further contains a synthetic amino acid, such as a dipeptide form of L-glutamine, e.g. L-alanyl-L-glutamine. In some embodiments, the concentration of the dipeptide form of L-glutamine (e.g., L-alanyl-L-glutamine) in the basal medium is about 0.5 mM-5 mM. In some embodiments, the concentration of the dipeptide form of L-glutamine (e.g., L-alanyl-L-glutamine) in the basal medium is about 2 mM.

In some embodiments, the provided methods are carried out such that one, more, or all steps in the preparation of cells for clinical use, e.g., in adoptive cell therapy, are carried out without exposing the cells to non-sterile conditions. In some embodiments, the cells are selected, stimulated, transduced, washed, and formulated, all within a closed, sterile system or device. In some embodiments, the one or more of the steps are carried out apart from the closed system or device. In some such embodiments, the cells are transferred apart from the closed system or device under sterile conditions, such as by sterile transfer to a separate closed system.

A. Preparation of Cells for Engineering

In some embodiments, preparation of the engineered cells includes one or more culture and/or preparation steps. The cells for introduction of the recombinant receptor (e.g., CAR) may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some aspects, for production of isolated or secreted polypeptides, in addition to prokaryotes, eukaryotic microbes such as filamentous fungi or yeast are suitable cloning or expression hosts for antibody-encoding vectors, including fungi and yeast strains whose glycosylation pathways have been modified to mimic or approximate those in human cells, resulting in the production of an antibody with a partially or fully human glycosylation pattern. See Gerngross, Nat. Biotech. 22:1409-1414 (2004), and Li et al., Nat. Biotech. 24:210-215 (2006).

Exemplary eukaryotic cells that may be used to express polypeptides, including isolated or secreted polypeptides, include, but are not limited to, COS cells, including COS 7 cells; 293 cells, including 293-6E cells; CHO cells, including CHO-S, DG44. Lec13 CHO cells, and FUT8 CHO cells; PER.C6® cells; and NSO cells. In some embodiments, the antibody heavy chains and/or light chains (e.g., $V_H$ region and/or $V_L$ region) may be expressed in yeast. See, e.g., U.S. Publication No. US 2006/0270045 A1. In some embodiments, a particular eukaryotic host cell is selected based on its ability to make desired post-translational modifications to the heavy chains and/or light chains (e.g., $V_H$ region and/or $V_L$ region). For example, in some embodiments, CHO cells produce polypeptides that have a higher level of sialylation than the same polypeptide produced in 293 cells.

In some embodiments, the preparation methods include steps for freezing, e.g., cryopreserving, the cells, either before or after isolation, selection and/or enrichment and/or incubation for transduction and engineering, and/or after cultivation and/or harvesting of the engineered cells. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. In some embodiments, the cells are frozen, e.g., cryoprotected or cryopreserved, in media and/or solution with a final concentration of or of about 12.5%, 12.0%, 11.5%, 11.0%, 10.5%, 10.0%, 9.5%, 9.0%, 8.5%, 8.0%, 7.5%, 7.0%, 6.5%, 6.0%, 5.5%, or 5.0% DMSO, or between 1% and 15%, between 6% and 12%, between 5% and 10%, or between 6% and 8% DMSO. In particular embodiments, the cells are frozen, e.g., cryoprotected or cryopreserved, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and –5%, between 0.25% and 4%, between 0.5% and 2%, or between 1% and 2% HSA. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to or to about ~80 degrees Celsius at a rate of or of about 1 degree Celsius per minute and stored in the vapor phase of a liquid nitrogen storage tank.

In some embodiments, isolation of the cells or populations includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components. In some embodiments, the methods include density-based cell separation methods, such as the preparation of white blood cells from peripheral blood by lysing the red blood cells and centrifugation through a Percoll or Ficoll gradient.

In some embodiments, at least a portion of the selection step includes incubation of cells with a selection reagent. The incubation with a selection reagent or reagents, e.g., as part of selection methods which may be performed using one or more selection reagents for selection of one or more different cell types based on the expression or presence in or on the cell of one or more specific molecules, such as surface markers, e.g., surface proteins, intracellular markers, or nucleic acid. In some embodiments, any known method using a selection reagent or reagents for separation based on such markers may be used. In some embodiments, the selection reagent or reagents result in a separation that is affinity- or immunoaffinity-based separation. For example, the selection in some aspects includes incubation with a reagent or reagents for separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

In some aspects of such processes, a volume of cells is mixed with an amount of a desired affinity-based selection reagent. The immunoaffinity-based selection can be carried out using any system or method that results in a favorable energetic interaction between the cells being separated and the molecule specifically binding to the marker on the cell, e.g., the antibody or other binding partner on the solid surface, e.g., particle. In some embodiments, methods are carried out using particles such as beads, e.g. magnetic beads, that are coated with a selection agent (e.g. antibody) specific to the marker of the cells. The particles (e.g. beads) can be incubated or mixed with cells in a container, such as a tube or bag, while shaking or mixing, with a constant cell density-to-particle (e.g., bead) ratio to aid in promoting energetically favored interactions. In other cases, the methods include selection of cells in which all or a portion of the selection is carried out in the internal cavity of a centrifugal chamber, for example, under centrifugal rotation. In some embodiments, incubation of cells with selection reagents, such as immunoaffinity-based selection reagents, is performed in a centrifugal chamber. In certain embodiments, the isolation or separation is carried out using a system, device, or apparatus described in International Patent Application, Publication Number WO2009/072003, or US 20110003380 A1. In one example, the system is a system as described in International Publication Number WO2016/073602.

In some embodiments, by conducting such selection steps or portions thereof (e.g., incubation with antibody-coated particles, e.g., magnetic beads) in the cavity of a centrifugal chamber, the user is able to control certain parameters, such as volume of various solutions, addition of solution during processing and timing thereof, which can provide advantages compared to other available methods. For example, the ability to decrease the liquid volume in the cavity during the incubation can increase the concentration of the particles (e.g. bead reagent) used in the selection, and thus the chemical potential of the solution, without affecting the total number of cells in the cavity. This in turn can enhance the pairwise interactions between the cells being processed and the particles used for selection. In some embodiments, carrying out the incubation step in the chamber, e.g., when associated with the systems, circuitry, and control as described herein, permits the user to effect agitation of the solution at desired time(s) during the incubation, which also can improve the interaction.

In some embodiments, at least a portion of the selection step is performed in a centrifugal chamber, which includes incubation of cells with a selection reagent. In some aspects of such processes, a volume of cells is mixed with an amount of a desired affinity-based selection reagent that is far less than is normally employed when performing similar selections in a tube or container for selection of the same number of cells and/or volume of cells according to manufacturer's instructions. In some embodiments, an amount of selection reagent or reagents that is/are no more than 5%, no more than 10%, no more than 15%, no more than 20%, no more than 25%, no more than 50%, no more than 60%, no more than 70% or no more than 80% of the amount of the same selection reagent(s) employed for selection of cells in a tube or container-based incubation for the same number of cells and/or the same volume of cells according to manufacturer's instructions is employed.

In some embodiments, for selection, e.g., immunoaffinity-based selection of the cells, the cells are incubated in the cavity of the chamber in a composition that also contains the selection buffer with a selection reagent, such as a molecule that specifically binds to a surface marker on a cell that it desired to enrich and/or deplete, but not on other cells in the composition, such as an antibody, which optionally is coupled to a scaffold such as a polymer or surface, e.g., bead, e.g., magnetic bead, such as magnetic beads coupled to monoclonal antibodies specific for CD4 and CD8. In some embodiments, as described, the selection reagent is added to cells in the cavity of the chamber in an amount that is substantially less than (e.g. is no more than 5%, 10%, 20%, 30%, 40%, 50%, 60%, 70% or 80% of the amount) as compared to the amount of the selection reagent that is typically used or would be necessary to achieve about the same or similar efficiency of selection of the same number of cells or the same volume of cells when selection is performed in a tube with shaking or rotation. In some embodiments, the incubation is performed with the addition of a selection buffer to the cells and selection reagent to achieve a target volume with incubation of the reagent of, for example, 10 mL to 200 mL, such as at least or about at least 10 mL, 20 mL, 30 mL, 40 mL, 50 mL, 60 mL, 70 mL, 80 mL, 90 mL, 100 mL, 150 mL or 200 mL. In some embodiments, the selection buffer and selection reagent are pre-mixed before addition to the cells. In some embodiments, the selection buffer and selection reagent are separately added to the cells. In some embodiments, the selection incubation is carried out with periodic gentle mixing condition, which can aid in promoting energetically favored interactions and thereby permit the use of less overall selection reagent while achieving a high selection efficiency.

In some embodiments, the total duration of the incubation with the selection reagent is from or from about 5 minutes to 6 hours, such as 30 minutes to 3 hours, for example, at least or about at least 30 minutes, 60 minutes, 120 minutes or 180 minutes.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, such process is carried out within the entirely closed system to which the chamber is integral. In some embodiments, this process (and in some aspects also one or more additional step, such as a previous wash step washing a sample containing the cells, such as an apheresis sample) is carried out in an automated fashion, such that the cells, reagent, and other components are drawn into and pushed out of the chamber at appropriate times and centrifugation effected, so as to complete the wash and binding step in a single closed system using an automated program.

In some embodiments, after the incubation and/or mixing of the cells and selection reagent and/or reagents, the incubated cells are subjected to a separation to select for cells based on the presence or absence of the particular reagent or reagents. In some embodiments, the separation is performed in the same closed system in which the incubation of cells with the selection reagent was performed. In some embodiments, after incubation with the selection reagents, incubated cells, including cells in which the selection reagent has bound are transferred into a system for immunoaffinity-based separation of the cells. In some embodiments, the system for immunoaffinity-based separation is or contains a magnetic separation column.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

In some embodiments, the process steps further include negative and/or positive selection of the incubated cells, such as using a system or apparatus that can perform an affinity-based selection. In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (marker$^{high}$) on the positively or negatively selected cells, respectively.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques.

For example, CD3+, CD28+ T cells can be positively selected using anti-CD3/anti-CD28 conjugated magnetic beads (e.g., DYNABEADS® M-450 CD3/CD28 T Cell Expander, MACSiBeads™, etc.).

In some embodiments, T cells are separated from a PBMC sample by negative selection of markers expressed on non-T cells, such as B cells, monocytes, or other white blood cells, such as CD14. In some aspects, CD4+ and/or CD8+ selection steps are used to separate CD4+ helper and CD8+ cytotoxic T cells from a composition, such as from a PBMC composition such as one obtained via leukapheresis. Such CD4+ and CD8+ populations, in some aspects, can be further sorted into sub-populations by positive or negative selection for markers expressed or expressed to a relatively higher degree on one or more naive, memory, and/or effector T cell subpopulations. In some embodiments, CD4+ and CD8+ cells are mixed at a desired ratio In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35(9):689-701. In some embodiments, combining $T_{CM}$-enriched CD8+ T cells and $CD4^+$ T cells further enhances efficacy.

In embodiments, memory T cells are present in both CD62L+ and CD62L− subsets of CD8+ peripheral blood lymphocytes. PBMC can be enriched for or depleted of CD62L-CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD27, CD28, CD3, and/or CD127; in some aspects, it is based on negative selection for cells expressing or highly expressing CD45RA and/or granzyme B. In some aspects, isolation of a CD8+ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

In some embodiments, central memory CD8+ cells are CD27+, CD28+, CD62L+, CCR7+, CD45RA−, and/or CD45RO+. In some embodiments, central memory CD8+ cells are CD62L+ and CD45RO+. In some embodiments, central memory CD8+ cells are CCR7+ and CD45RO+. In some embodiments, central memory CD8+ cells are CCR7+ and CD45RA−. In some embodiments, central memory CD8+ cells are CD62L+ and CCR7+. In some embodiments, central memory CD8+ cells are CD62L+/CD45RA−, CCR7+/CD45RA−, CD62L+/CCR7+, or CD62L+/CCR7+/CD45RA−, and have intermediate to high expression of CD44. In some embodiments, central memory CD8+ cells are CD27+/CD28+/CD62L+/CD45RA−, CD27+/CD28+/CCR7+/CD45RA−, CD27+/CD28+/CD62L+/CCR7+, or CD27+/CD28+/CD62L+/CCR7+/CD45RA−.

In particular embodiments, a biological sample, e.g., a sample of PBMCs or other white blood cells, are subjected to selection of CD4+ T cells, where both the negative and positive fractions are retained. In certain embodiments, CD8+ T cells are selected from the negative fraction. In some embodiments, a biological sample is subjected to selection of CD8+ T cells, where both the negative and positive fractions are retained. In certain embodiments, CD4+ T cells are selected from the negative fraction.

In a particular example, a sample of PBMCs or other white blood cell sample is subjected to selection of CD4+ cells, where both the negative and positive fractions are retained. The negative fraction then is subjected to negative selection based on expression of CD14 and CD45RA, and positive selection based on a marker characteristic of central memory T cells, such as CD62L or CCR7, where the positive and negative selections are carried out in either order.

In some embodiments, CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, central memory CD4+ cells are CD62L+ and CD45RO+. In some embodiments, central memory CD4+ cells are CD27+, CD28+, CD62L+, CCR7+, CD45RA-, and/or CD45RO+. In some embodiments, central memory CD4+ cells are CD62L+ and CD45RO+. In some embodiments, central memory CD4+ cells are CCR7+ and CD45RO+. In some embodiments, central memory CD4+ cells are CCR7+ and CD45RA−. In some embodiments, central memory CD4+ cells are CD62L+ and CCR7+. In some embodiments, central memory CD4+ cells are CD62L+/CD45RA−, CCR7+/CD45RA−, CD62L+/CCR7+, or CD62L+/CCR7+/CD45RA−, and have intermediate to high expression of CD44. In some embodiments, central memory CD4+ cells are CD27+/CD28+/CD62L+/CD45RA−, CD27+/CD28+/CCR7+/CD45RA−, CD27+/CD28+/CD62L+/CCR7+, or CD27+/CD28+/CD62L+/CCR7+/CD45RA−. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher© Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynabeads® or MACS® beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084, are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subjected to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS®) (Miltenyi Biotec, Auburn, CA). Magnetic Activated Cell Sorting (MACS®) systems are capable of high-purity selection of cells having magnetized particles attached thereto. In certain embodiments, MACS® operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS® system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS® system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy® system (Miltenyi Biotec). The CliniMACS Prodigy® system in some aspects is equipped with a cell processing unity that permits automated washing and fractionation of cells by centrifugation. The CliniMACS Prodigy® system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy® system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) J Immunother. 35(9): 651-660, Terakura et al. (2012) Blood. 1:72-82, and Wang et al. (2012) J Immunother. 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the isolation and/or selection results in one or more input compositions of enriched T cells, e.g., CD3+ T cells, CD4+ T cells, and/or CD8+ T cells. In some embodiments, two or more separate input composition are isolated, selected, enriched, or obtained from a single biological sample. In some embodiments, separate input compositions are isolated, selected, enriched, and/or obtained from separate biological samples collected, taken, and/or obtained from the same subject.

In certain embodiments, the one or more input compositions is or includes a composition of enriched T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD3+ T cells. In particular embodiment, the input composition of enriched T cells consists essentially of CD3+ T cells.

In certain embodiments, the one or more input compositions is or includes a composition of enriched CD4+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD4+ T cells. In certain embodiments, the input composition of CD4+ T cells includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells. In some embodiments, the composition of enriched T cells consists essentially of CD4+ T cells.

In certain embodiments, the one or more compositions is or includes a composition of CD8+ T cells that is or includes at least 60%, at least 65%, at least 70%, at least 75%, at least 80%, at least 85%, at least 90%, at least 95%, at least 98%, at least 99%, at least 99.5%, at least 99.9%, or at or at about 100% CD8+ T cells. In certain embodiments, the composition of CD8+ T cells contains less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free of or substantially free of CD4+ T cells. In some embodiments, the composition of enriched T cells consists essentially of CD8+ T cells.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80 degrees Celsius. at a rate of 1 degrees Celsius per minute and stored in the vapor phase of a liquid nitrogen storage tank.

B. Activation and Stimulation

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

In some embodiments, the provided methods include cultivation, incubation, culture, and/or genetic engineering steps. For example, in some embodiments, provided are methods for incubating and/or engineering the depleted cell populations and culture-initiating compositions. Thus, in some embodiments, the cell populations are incubated in a culture-initiating composition.

The incubation and/or engineering may be carried out in a culture vessel, such as a unit, chamber, well, column, tube, tubing set, valve, vial, culture dish, bag, or other container for culture or cultivating cells.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of stimulating or activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees Celsius, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

In some embodiments, at least a portion of the incubation in the presence of one or more stimulating conditions or a stimulatory agents is carried out in the internal cavity of a centrifugal chamber, for example, under centrifugal rotation, such as described in International Publication Number WO2016/073602. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the stimulating agent is added to cells in the cavity of the chamber in an amount that is substantially less than (e.g. is no more than 5%, 10%, 20%, 30%, 40%, 50%, 60%, 70% or 80% of the amount) as compared to the amount of the stimulating agent that is typically used or would be necessary to achieve about the same or similar efficiency of selection of the same number of cells or the same volume of cells when selection is performed without mixing in a centrifugal chamber, e.g. in a tube or bag with periodic shaking or rotation. In some embodiments, the incubation is performed with the addition of an incubation buffer to the cells and stimulating agent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL or 200 mL. In some embodiments, the incubation buffer and stimulating agent are pre-mixed before addition to the cells. In some embodiments, the incubation buffer and stimulating agent are separately added to the cells. In some embodiments, the stimulating incubation is carried out with periodic gentle mixing condition, which can aid in promoting energetically favored interactions and thereby permit the use of less overall stimulating agent while achieving stimulating and activation of cells.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, the total duration of the incubation, e.g. with the stimulating agent, is between or between about 1 hour and 96 hours, 1 hour and 72 hours, 1 hour and 48 hours, 4 hours and 36 hours, 8 hours and 30 hours or 12 hours and 24 hours, such as at least or about at least 6 hours, 12 hours, 18 hours, 24 hours, 36 hours or 72 hours. In some embodiments, the further incubation is for a time between or about between 1 hour and 48 hours, 4 hours and 36 hours, 8 hours and 30 hours or 12 hours and 24 hours, inclusive.

In particular embodiments, the stimulating conditions include incubating, culturing, and/or cultivating a composition of enriched T cells with and/or in the presence of one or more cytokines. In particular embodiments, the one or more cytokines are recombinant cytokines. In some embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF).

In some embodiments, the stimulation results in activation and/or proliferation of the cells, for example, prior to transduction.

C. Vectors and Methods for Genetic Engineering

Also provided are methods, polynucleotides, compositions, and kits, for expressing the BCMA-binding recombinant receptors (e.g., CARs), and for producing the genetically engineered cells expressing such recombinant receptors. In some embodiments, one or more recombinant receptors (e.g., CARs) or other molecules can be genetically engineered into cells or plurality of cells. The genetic engineering generally involves introduction of a nucleic acid encoding the recombinant or engineered component into the cell, such as by retroviral transduction, transfection, or transformation.

Also provided are polynucleotides encoding the chimeric antigen receptors and/or portions, e.g., chains, thereof. Among the provided polynucleotides are those encoding the anti-BCMA chimeric antigen receptors (e.g., antigen-binding fragment) described herein. Also provided are polynucleotides encoding one or more antibodies and/or portions thereof, e.g., those encoding one or more of the anti-BCMA antibodies (e.g., antigen-binding fragment) described herein and/or other antibodies and/or portions thereof, e.g., antibodies and/or portions thereof that binds other target antigens. The polynucleotides may include those encompassing natural and/or non-naturally occurring nucleotides and bases, e.g., including those with backbone modifications. The terms “nucleic acid molecule”, “nucleic acid” and “polynucleotide” may be used interchangeably, and refer to a polymer of nucleotides. Such polymers of nucleotides may contain natural and/or non-natural nucleotides, and include, but are not limited to, DNA, RNA, and PNA. “Nucleic acid sequence” refers to the linear sequence of nucleotides that comprise the nucleic acid molecule or polynucleotide.

Also provided are polynucleotides that have been optimized for codon usage and/or to eliminate splice sites, such as cryptic splice sites. Also provided are methods of optimizing and producing the coding sequences of chimeric antigen receptors, such as any of the chimeric antigen receptors described herein. Such methods are described in Section II herein.

Also provided are vectors containing the polynucleotides, such as any of the polynucleotides described herein, and host cells containing the vectors, e.g., for producing the antibodies or antigen-binding fragments thereof or cells expressing a recombinant receptor (e.g. CAR) containing such antibodies or fragments. In some embodiments, the vector is a viral vector. In some embodiments, the vector is a retroviral vector, or a lentiviral vector. Also provided are methods for producing the antibodies or antigen-binding fragments thereof or cells expressing a recombinant receptor (e.g. CAR) containing such antibodies or fragments.

In some embodiments, a nucleic acid may encode an amino acid sequence comprising the $V_L$ region and/or an amino acid sequence comprising the $V_H$ region of the antibody (e.g., the light and/or heavy chains of the antibody). The nucleic acid may encode one or more amino acid sequence comprising the $V_L$ region and/or an amino acid sequence comprising the $V_H$ region of the antibody (e.g., the light and/or heavy chains of the antibody). In a further embodiment, one or more vectors (e.g., expression vectors) comprising such polynucleotides are provided. In a further embodiment, a host cell comprising such polynucleotides is provided. In one such embodiment, a host cell comprises (e.g., has been transformed with) a vector comprising a nucleic acid that encodes an amino acid sequence comprising the $V_H$ region of the antibody. In another such embodiment, a host cell comprises (e.g., has been transformed with) (1) a vector comprising a nucleic acid that encodes an amino acid sequence comprising the $V_L$ region of the antibody and an amino acid sequence comprising the $V_H$ region of the antibody, or (2) a first vector comprising a nucleic acid that encodes an amino acid sequence comprising the $V_L$ region of the antibody and a second vector comprising a nucleic acid that encodes an amino acid sequence comprising the $V_H$ region of the antibody. In some embodiments, a host cell comprises (e.g., has been transformed with) one or more vectors comprising one or more nucleic acid that encodes one or more an amino acid sequence comprising one or more antibodies and/or portions thereof, e.g., antigen-binding fragments thereof. In some embodiments, one or more such host cells are provided. In some embodiments, a composition containing one or more such host cells are provided. In some embodiments, the one or more host cells can express different antibodies, or the same antibody. In some embodiments, each of the host cells can express more than one antibody.

Also provided are methods of making the anti-BCMA chimeric antigen receptors. For recombinant production of the chimeric receptors, a nucleic acid sequence encoding a chimeric receptor antibody, e.g., as described herein, may be isolated and inserted into one or more vectors for further cloning and/or expression in a host cell. Such nucleic acid sequences may be readily isolated and sequenced using conventional procedures (e.g., by using oligonucleotide probes that are capable of binding specifically to genes encoding the heavy and light chains of the antibody). In some embodiments, a method of making the anti-BCMA chimeric antigen receptor is provided, wherein the method comprises culturing a host cell comprising a nucleic acid sequence encoding the antibody, as provided above, under conditions suitable for expression of the receptor.

In some cases, the polynucleotide containing nucleic acid sequences encoding the BCMA-binding recombinant receptor, e.g., chimeric antigen receptor (CAR), contains a signal sequence that encodes a signal peptide. In some aspects, the signal sequence may encode a signal peptide derived from a native polypeptide. In other aspects, the signal sequence may encode a heterologous or non-native signal peptide. In some aspects, non-limiting exemplary signal peptide include a signal peptide of the IgG kappa chain set forth in SEQ ID NO: 166, or encoded by the nucleotide sequence set forth in SEQ ID NO: 167 or 168-171; a GMCSFR alpha chain set forth in SEQ ID NO:154 and encoded by the nucleotide sequence set forth in SEQ ID NO:155; a CD8 alpha signal peptide set forth in SEQ ID NO:146; or a CD33 signal peptide set forth in SEQ ID NO:142.

In some embodiments the vector or construct can contain promoter and/or enhancer or regulatory elements to regulate expression of the encoded recombinant receptor. In some examples the promoter and/or enhancer or regulatory elements can be condition-dependent promoters, enhancers, and/or regulatory elements. In some examples these elements drive expression of the transgene. In some examples, the CAR transgene can be operatively linked to a promoter, such as an EF1alpha promoter with an HTLV1 enhancer (SEQ ID NO: 151). In some examples, the CAR transgene is operatively linked to a Woodchuck Hepatitis Virus (WHP) Posttranscriptional Regulatory Element (WPRE; SEQ ID NO: 253), located downstream of the transgene.

In some embodiments, the vector or construct can contain a single promoter that drives the expression of one or more nucleic acid molecules. In some embodiments, such nucleic acid molecules, e.g., transcripts, can be multicistronic (bicistronic or tricistronic, see e.g., U.S. Pat. No. 6,060,273). For example, in some embodiments, transcription units can be engineered as a bicistronic unit containing an IRES (internal ribosome entry site), which allows coexpression of gene products (e.g. encoding a first and second chimeric receptor) by a message from a single promoter. Alternatively, in some cases, a single promoter may direct expression of an RNA that contains, in a single open reading frame (ORF), two or three genes (e.g. encoding a first and second recombinant receptors or a portions of a recombinant receptor) separated from one another by sequences encoding a self-cleavage peptide (e.g., 2A cleavage sequences) or a protease recognition site (e.g., furin). The ORF thus encodes a single polypeptide, which, either during (in the case of T2A) or after translation, is cleaved into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known. Examples of 2A sequences that can be used in the methods and polynucleotides disclosed herein, without limitation, 2A sequences from the foot-and-mouth disease virus (F2A, e.g., SEQ ID NO: 152 or 153), equine rhinitis A virus (E2A, e.g., SEQ ID NO: 148 or 149), *Thosea asigna* virus (T2A, e.g., SEQ ID NO: 241, 242 or 243), and porcine teschovirus-1 (P2A, e.g., SEQ ID NO: 201 or 202) as described in U.S. Patent Publication No. 20070116690. In some embodiments, the one or more different or separate promoters drive the expression of one or more nucleic acid molecules encoding the one or more recombinant receptors or a portion thereof.

Any of the recombinant receptors provided herein, e.g., BCMA-binding recombinant receptors and/or the additional recombinant receptors, can be encoded by polynucleotides containing one or more nucleic acid molecules encoding the receptors, in any combinations or arrangements. For example, one, two, three or more polynucleotides can encode one, two, three or more different receptors or domains. In some embodiments, one vector or construct contains nucleic acid molecules encoding one or more binding recombinant receptors, and a separate vector or construct contains nucleic acid molecules encoding an additional molecule, e.g., an additional recombinant receptor. Each of the nucleic acid molecules can also encode one or more marker(s), such as a surface marker, e.g., truncated EGFR (tEGFR).

Also provided are compositions containing one or more of the nucleic acid molecules, vectors or constructs, such as any described above. In some embodiments, the nucleic acid molecules, vectors, constructs or compositions can be used to engineer cells, such as T cells, to express any of the recombinant receptors, and/or the additional molecules.

In some embodiments, one or more recombinant receptors (e.g., CARs), can be genetically engineered to be expressed in cells or plurality of cells. In some embodiments, a first recombinant receptor and a second molecule, e.g., recombinant receptor, are encoded by the same or separate nucleic acid molecules. In some embodiments, additional molecules are engineered to be expressed in cells or a plurality of cells.

I. Gene Transfer

In some embodiments, methods for producing engineered cells includes the introduction of a polynucleotide encoding a recombinant receptor (e.g. anti-BCMA CAR) into a cell, e.g., such as a stimulated or activated cell. In particular embodiments, the recombinant proteins are recombinant receptors, such as any described in Section I. Introduction of the nucleic acid molecules encoding the recombinant protein, such as recombinant receptor, in the cell may be carried out using any of a number of known vectors. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g., retroviral or lentiviral, transduction, transposons, and electroporation. In some embodiments, the engineering produces one or more engineered compositions of enriched T cells.

In certain embodiments, the one or more compositions of stimulated T cells are or include two separate stimulated compositions of enriched T cells. In particular embodiments, two separate compositions of enriched T cells, e.g., two separate compositions of enriched T cells that have been selected, isolated, and/or enriched from the same biological sample, are separately engineered. In certain embodiments, the two separate compositions include a composition of enriched CD4+ T cells. In particular embodiments, the two separate compositions include a composition of enriched CD8+ T cells. In some embodiments, two separate compositions of enriched CD4+ T cells and enriched CD8+ T cells are genetically engineered separately. In some embodiments, a single composition of enriched T cells is genetically engineered. In certain embodiments, the single composition is a composition of enriched CD4+ T cells. In some embodiments, the single composition is a composition of enriched CD4+ and CD8+ T cells that have been combined from separate compositions prior to the engineering.

In some embodiments, separate compositions of enriched CD4+ and CD8+ T cells are combined into a single composition and are genetically engineered, e.g., transduced or transfected. In certain embodiments, separate engineered compositions of enriched CD4+ and enriched CD8+ T cells are combined into a single composition after the genetic engineering has been performed and/or completed.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications. In certain embodiments, the gene transfer is accomplished by first incubating the cells under stimulating conditions, such as by any of the methods described in Section III-B.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as following administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphoribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions. Exemplary methods include those for transfer of polynucleotides encoding the receptors, including via viral, e.g., retroviral or lentiviral, transduction, transposons, and electroporation.

In some embodiments, recombinant polynucleotides are transferred into cells using recombinant infectious virus particles, such as, e.g., vectors derived from simian virus 40 (SV40), adenoviruses, adeno-associated virus (AAV). In some embodiments, recombinant polynucleotides are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November 29(11): 550-557).

In some embodiments, methods for genetic engineering are carried out by contacting one or more cells of a composition with a nucleic acid molecule encoding the recombinant protein, e.g. recombinant receptor. In some embodiments, the contacting can be effected with centrifugation, such as spinoculation (e.g. centrifugal inoculation). Such methods include any of those as described in International Publication Number WO2016/073602. Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Exemplary kits for use with such systems include, but are not limited to, single-use kits sold by BioSafe SA under product names CS-430.1, CS-490.1, CS-600.1 or CS-900.2.

In some embodiments, the contacting can be effected with centrifugation, such as spinoculation (e.g., centrifugal inoculation). In some embodiments, the composition containing cells, viral particles and reagent can be rotated, generally at relatively low force or speed, such as speed lower than that used to pellet the cells, such as from or from about 600 rpm to 1700 rpm (e.g., at or about or at least 600 rpm, 1000 rpm, or 1500 rpm or 1700 rpm). In some embodiments, the rotation is carried at a force, e.g., a relative centrifugal force, of from or from about 100 g to 3200 g (e.g., at or about or at least at or about 100 g, 200 g, 300 g, 400 g, 500 g, 1000 g, 1500 g, 2000 g, 2500 g, 3000 g or 3200 g), as measured for example at an internal or external wall of the chamber or cavity. The term “relative centrifugal force” or RCF is generally understood to be the effective force imparted on an object or substance (such as a cell, sample, or pellet and/or a point in the chamber or other container being rotated), relative to the earth’s gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured).

In some embodiments, the introducing is carried out by contacting one or more cells of a composition with a nucleic acid molecule encoding the recombinant protein, e.g. recombinant receptor. In some embodiments, the contacting can be effected with centrifugation, such as spinoculation (e.g. centrifugal inoculation). Such methods include any of those as described in International Publication Number WO2016/073602. Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Exemplary kits for use with such systems include, but are not limited to, single-use kits sold by BioSafe SA under product names CS-430.1, CS-490.1, CS-600.1 or CS-900.2.

In some embodiments, the system is included with and/or placed into association with other instrumentation, including instrumentation to operate, automate, control and/or monitor aspects of the transduction step and one or more various other processing steps performed in the system, e.g. one or more processing steps that can be carried out with or in connection with the centrifugal chamber system as described herein or in International Publication Number WO2016/073602. This instrumentation in some embodiments is contained within a cabinet. In some embodiments, the instrumentation includes a cabinet, which includes a housing containing control circuitry, a centrifuge, a cover, motors, pumps, sensors, displays, and a user interface. An exemplary device is described in U.S. Pat. Nos. 6,123,655, 6,733,433 and US 2008/0171951.

In some embodiments, the system comprises a series of containers, e.g., bags, tubing, stopcocks, clamps, connectors, and a centrifuge chamber. In some embodiments, the containers, such as bags, include one or more containers, such as bags, containing the cells to be transduced and the viral vector particles, in the same container or separate containers, such as the same bag or separate bags. In some embodiments, the system further includes one or more containers, such as bags, containing medium, such as diluent and/or wash solution, which is pulled into the chamber and/or other components to dilute, resuspend, and/or wash components and/or compositions during the methods. The containers can be connected at one or more positions in the system, such as at a position corresponding to an input line, diluent line, wash line, waste line and/or output line.

In some embodiments, the chamber is associated with a centrifuge, which is capable of effecting rotation of the chamber, such as around its axis of rotation. Rotation may occur before, during, and/or after the incubation in connection with transduction of the cells and/or in one or more of the other processing steps. Thus, in some embodiments, one or more of the various processing steps is carried out under rotation, e.g., at a particular force. The chamber is typically capable of vertical or generally vertical rotation, such that the chamber sits vertically during centrifugation and the side wall and axis are vertical or generally vertical, with the end wall(s) horizontal or generally horizontal.

In some embodiments, the composition containing cells, the vector, e.g., viral particles, and reagent can be rotated, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm). In some embodiments, the rotation is carried at a force, e.g., a relative centrifugal force, of from or from about 100 g to 3200 g (e.g. at or about or at least at or about 100 g, 200 g, 300 g, 400 g, 500 g, 1000 g, 1500 g, 2000 g, 2500 g, 3000 g or 3200 g), as measured for example at an internal or external wall of the chamber or cavity. The term “relative centrifugal force” or RCF is generally understood to be the effective force imparted on an object or substance (such as a cell, sample, or pellet and/or a point in the chamber or other container being rotated), relative to the earth’s gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured).

In some embodiments, during at least a part of the genetic engineering, e.g. transduction, and/or subsequent to the genetic engineering the cells are transferred to a bioreactor bag assembly for culture of the genetically engineered cells, such as for cultivation or expansion of the cells.

2. Viral Vectors

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November 29(11): 550-557).

In some embodiments, the viral vector or the non-viral DNA contains a nucleic acid that encodes a heterologous recombinant protein. In some embodiments, the heterologous recombinant molecule is or includes a recombinant receptor, e.g., an antigen receptor, SB-transposons, e.g., for gene silencing, capsid-enclosed transposons, homologous double stranded nucleic acid, e.g., for genomic recombination or reporter genes (e.g., fluorescent proteins, such as GFP) or luciferase).

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or human immunodeficiency virus type 1 (HIV-1). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, the viral vector particles contain a genome derived from a retroviral genome based vector, such as derived from a lentiviral genome based vector. In some aspects of the provided viral vectors, the heterologous nucleic acid encoding a recombinant receptor, such as an antigen receptor, such as a CAR, is contained and/or located between the 5' LTR and 3' LTR sequences of the vector genome.

In some embodiments, the viral vector genome is a lentivirus genome, such as an HIV-1 genome or an SIV genome. For example, lentiviral vectors have been generated by multiply attenuating virulence genes, for example, the genes env, vif, vpu and nef can be deleted, making the vector safer for therapeutic purposes. Lentiviral vectors are known. See Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

Non-limiting examples of lentiviral vectors include those derived from a lentivirus, such as Human Immunodeficiency Virus 1 (HIV-1), HIV-2, an Simian Immunodeficiency Virus (SIV), Human T-lymphotropic virus 1 (HTLV-1), HTLV-2 or equine infection anemia virus (E1AV). For example, lentiviral vectors have been generated by multiply attenuating the HIV virulence genes, for example, the genes env, vif, vpr, vpu and nef are deleted, making the vector safer for therapeutic purposes. Lentiviral vectors are known in the art, see Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

In some embodiments, the viral genome vector can contain sequences of the 5' and 3' LTRs of a retrovirus, such as a lentivirus. In some aspects, the viral genome construct may contain sequences from the 5' and 3' LTRs of a lentivirus, and in particular can contain the R and U5 sequences from the 5' LTR of a lentivirus and an inactivated or self-inactivating 3' LTR from a lentivirus. The LTR sequences can be LTR sequences from any lentivirus from any species. For example, they may be LTR sequences from HIV, SIV, FIV or BIV. Typically, the LTR sequences are HIV LTR sequences.

In some embodiments, the nucleic acid of a viral vector, such as an HIV viral vector, lacks additional transcriptional units. The vector genome can contain an inactivated or self-inactivating 3' LTR (Zufferey et al. *J Virol* 72: 9873, 1998; Miyoshi et al., *J Virol* 72:8150, 1998). For example, deletion in the U3 region of the 3' LTR of the nucleic acid used to produce the viral vector RNA can be used to generate self-inactivating (SIN) vectors. This deletion can then be transferred to the 5' LTR of the proviral DNA during reverse transcription. A self-inactivating vector generally has a deletion of the enhancer and promoter sequences from the 3' long terminal repeat (LTR), which is copied over into the 5' LTR during vector integration. In some embodiments enough sequence can be eliminated, including the removal of a TATA box, to abolish the transcriptional activity of the LTR. This can prevent production of full-length vector RNA in transduced cells. In some aspects, the U3 element of the 3' LTR contains a deletion of its enhancer sequence, the TATA box, Sp1, and NF-kappa B sites. As a result of the self-inactivating 3' LTR, the provirus that is generated following entry and reverse transcription contains an inactivated 5' LTR. This can improve safety by reducing the risk of mobilization of the vector genome and the influence of the LTR on nearby cellular promoters. The self-inactivating 3' LTR can be constructed by any method known in the art. In some embodiments, this does not affect vector titers or the in vitro or in vivo properties of the vector.

Optionally, the U3 sequence from the lentiviral 5' LTR can be replaced with a promoter sequence in the viral construct, such as a heterologous promoter sequence. This can increase the titer of virus recovered from the packaging cell line. An enhancer sequence can also be included. Any enhancer/promoter combination that increases expression of the viral RNA genome in the packaging cell line may be used. In one example, the CMV enhancer/promoter sequence is used (U.S. Pat. Nos. 5,385,839 and 5,168,062).

In certain embodiments, the risk of insertional mutagenesis can be minimized by constructing the retroviral vector genome, such as lentiviral vector genome, to be integration defective. A variety of approaches can be pursued to produce a non-integrating vector genome. In some embodiments, a mutation(s) can be engineered into the integrase enzyme component of the pol gene, such that it encodes a protein with an inactive integrase. In some embodiments, the vector genome itself can be modified to prevent integration by, for example, mutating or deleting one or both attachment sites, or making the 3' LTR-proximal polypurine tract (PPT) non-functional through deletion or modification. In some embodiments, non-genetic approaches are available; these include pharmacological agents that inhibit one or more functions of integrase. The approaches are not mutually exclusive; that is, more than one of them can be used at a time. For example, both the integrase and attachment sites can be non-functional, or the integrase and PPT site can be non-functional, or the attachment sites and PPT site can be non-functional, or all of them can be non-functional. Such methods and viral vector genomes are known and available (see Philpott and Thrasher, *Human Gene Therapy* 18:483, 2007; Engelman et al. J Virol 69:2729, 1995; Brown et al *J Virol* 73:9011 (1999); WO 2009/076524; McWilliams et al., *J Virol* 77:11150, 2003; Powell and Levin *J Virol* 70:5288, 1996).

In some embodiments, the vector contains sequences for propagation in a host cell, such as a prokaryotic host cell. In some embodiments, the nucleic acid of the viral vector contains one or more origins of replication for propagation in a prokaryotic cell, such as a bacterial cell. In some embodiments, vectors that include a prokaryotic origin of replication also may contain a gene whose expression confers a detectable or selectable marker such as drug resistance.

The viral vector genome is typically constructed in a plasmid form that can be transfected into a packaging or producer cell line. Any of a variety of known methods can be used to produce retroviral particles whose genome contains an RNA copy of the viral vector genome. In some embodiments, at least two components are involved in making a virus-based gene delivery system: first, packaging plasmids, encompassing the structural proteins as well as the enzymes necessary to generate a viral vector particle, and second, the viral vector itself, i.e., the genetic material to be transferred. Biosafety safeguards can be introduced in the design of one or both of these components.

In some embodiments, the packaging plasmid can contain all retroviral, such as HIV-1, proteins other than envelope proteins (Naldini et al., 1998). In other embodiments, viral vectors can lack additional viral genes, such as those that are associated with virulence, e.g., vpr, vif, vpu and nef, and/or Tat, a primary transactivator of HIV. In some embodiments, lentiviral vectors, such as HIV-based lentiviral vectors, comprise only three genes of the parental virus: gag, pol and rev, which reduces or eliminates the possibility of reconstitution of a wild-type virus through recombination.

In some embodiments, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences, e.g., recombinant nucleic acids, of interest. In some aspects, in order to prevent replication of the genome in the target cell, however, endogenous viral genes required for replication are removed and provided separately in the packaging cell line.

In some embodiments, a packaging cell line is transfected with one or more plasmid vectors containing the components necessary to generate the particles. In some embodiments, a packaging cell line is transfected with a plasmid containing the viral vector genome, including the LTRs, the cis-acting packaging sequence and the sequence of interest, i.e. a nucleic acid encoding an antigen receptor, such as a CAR; and one or more helper plasmids encoding the virus enzymatic and/or structural components, such as Gag, pol and/or rev. In some embodiments, multiple vectors are utilized to separate the various genetic components that generate the retroviral vector particles. In some such embodiments, providing separate vectors to the packaging cell reduces the chance of recombination events that might otherwise generate replication competent viruses. In some embodiments, a single plasmid vector having all of the retroviral components can be used.

In some embodiments, the retroviral vector particle, such as lentiviral vector particle, is pseudotyped to increase the transduction efficiency of host cells. For example, a retroviral vector particle, such as a lentiviral vector particle, in some embodiments is pseudotyped with a VSV-G glycoprotein, which provides a broad cell host range extending the cell types that can be transduced. In some embodiments, a packaging cell line is transfected with a plasmid or polynucleotide encoding a non-native envelope glycoprotein, such as to include xenotropic, polytropic or amphotropic envelopes, such as Sindbis virus envelope, GALV or VSV-G.

In some embodiments, the packaging cell line provides the components, including viral regulatory and structural proteins, that are required in trans for the packaging of the viral genomic RNA into lentiviral vector particles. In some embodiments, the packaging cell line may be any cell line that is capable of expressing lentiviral proteins and producing functional lentiviral vector particles. In some aspects, suitable packaging cell lines include 293 (ATCC CCL X), 293T, HeLA (ATCC CCL 2), D17 (ATCC CCL 183), MDCK (ATCC CCL 34), BHK (ATCC CCL-10) and Cf2Th (ATCC CRL 1430) cells.

In some embodiments, the packaging cell line stably expresses the viral protein(s). For example, in some aspects, a packaging cell line containing the gag, pol, rev and/or other structural genes but without the LTR and packaging components can be constructed. In some embodiments, a packaging cell line can be transiently transfected with nucleic acid molecules encoding one or more viral proteins along with the viral vector genome containing a nucleic acid molecule encoding a heterologous protein, and/or a nucleic acid encoding an envelope glycoprotein.

In some embodiments, the viral vectors and the packaging and/or helper plasmids are introduced via transfection or infection into the packaging cell line. The packaging cell line produces viral vector particles that contain the viral vector genome. Methods for transfection or infection are well known. Non-limiting examples include calcium phosphate, DEAE-dextran and lipofection methods, electroporation and microinjection.

When a recombinant plasmid and the retroviral LTR and packaging sequences are introduced into a special cell line (e.g., by calcium phosphate precipitation for example), the packaging sequences may permit the RNA transcript of the recombinant plasmid to be packaged into viral particles, which then may be secreted into the culture media. The media containing the recombinant retroviruses in some embodiments is then collected, optionally concentrated, and used for gene transfer. For example, in some aspects, after cotransfection of the packaging plasmids and the transfer vector to the packaging cell line, the viral vector particles are recovered from the culture media and titered by standard methods used by those of skill in the art.

In some embodiments, a retroviral vector, such as a lentiviral vector, can be produced in a packaging cell line, such as an exemplary HEK 293T cell line, by introduction of plasmids to allow generation of lentiviral particles. In some embodiments, a packaging cell is transfected and/or contains a polynucleotide encoding gag and pol, and a polynucleotide encoding a recombinant receptor, such as an antigen receptor, for example, a CAR. In some embodiments, the packaging cell line is optionally and/or additionally transfected with and/or contains a polynucleotide encoding a rev protein. In some embodiments, the packaging cell line is optionally and/or additionally transfected with and/or contains a polynucleotide encoding a non-native envelope glycoprotein, such as VSV-G. In some such embodiments, approximately two days after transfection of cells, e.g., HEK 293T cells, the cell supernatant contains recombinant lentiviral vectors, which can be recovered and titered.

Recovered and/or produced retroviral vector particles can be used to transduce target cells using the methods as described. Once in the target cells, the viral RNA is reverse-transcribed, imported into the nucleus and stably integrated into the host genome. One or two days after the integration of the viral RNA, the expression of the recombinant protein, e.g., antigen receptor, such as CAR, can be detected.

In some embodiments, the provided methods involve methods of transducing cells by contacting, e.g., incubating, a cell composition comprising a plurality of cells with a viral particle. In some embodiments, the cells to be transfected or transduced are or comprise primary cells obtained from a subject, such as cells enriched and/or selected from a subject.

In some embodiments, the concentration of cells to be transduced of the composition is from or from about $1.0\times10^5$ cells/mL to $1.0\times10^8$ cells/mL, such as at least or about at least or about $1.0\times10^5$ cells/mL, $5\times10^5$ cells/mL, $1\times10^6$ cells/mL, $5\times10^6$ cells/mL, $1\times10^7$ cells/mL, $5\times10^7$ cells/mL or $1\times10^8$ cells/mL.

In some embodiments, the viral particles are provided at a certain ratio of copies of the viral vector particles or infectious units (IU) thereof, per total number of cells to be transduced (IU/cell). For example, in some embodiments, the viral particles are present during the contacting at or about or at least at or about 0.5, 1, 2, 3, 4, 5, 10, 15, 20, 30, 40, 50, or 60 IU of the viral vector particles per one of the cells.

In some embodiments, the titer of viral vector particles is between or between about $1\times10^6$ IU/mL and $1\times10^8$ IU/mL, such as between or between about $5\times10^6$ IU/mL and $5\times10^7$ IU/mL, such as at least $6\times10^6$ IU/mL, $7\times10^6$ IU/mL, $8\times10^6$ IU/mL, $9\times10^6$ IU/mL, $1\times10^7$ IU/mL, $2\times10^7$ IU/mL, $3\times10^7$ IU/mL, $4\times10^7$ IU/mL, or $5\times10^7$ IU/mL.

In some embodiments, transduction can be achieved at a multiplicity of infection (MOI) of less than 100, such as generally less than 60, 50, 40, 30, 20, 10, 5 or less.

In some embodiments, the method involves contacting or incubating, the cells with the viral particles. In some embodiments, the contacting is for 30 minutes to 72 hours, such as 30 minute to 48 hours, 30 minutes to 24 hours or 1 hour to 24 hours, such as at least or about at least 30 minutes, 1 hour, 2 hours, 6 hours, 12 hours, 24 hours, 36 hours or more.

In some embodiments, contacting is performed in solution. In some embodiments, the cells and viral particles are contacted in a volume of from or from about 0.5 mL to 500 mL, such as from or from about 0.5 mL to 200 mL, 0.5 mL to 100 mL, 0.5 mL to 50 mL, 0.5 mL to 10 mL, 0.5 mL to 5 mL, 5 mL to 500 mL, 5 mL to 200 mL, 5 mL to 100 mL, 5 mL to 50 mL, 5 mL to 10 mL, 10 mL to 500 mL, 10 mL to 200 mL, 10 mL to 100 mL, 10 mL to 50 mL, 50 mL to 500 mL, 50 mL to 200 mL, 50 mL to 100 mL, 100 mL to 500 mL, 100 mL to 200 mL or 200 mL to 500 mL.

In certain embodiments, the input cells are treated, incubated, or contacted with particles that comprise binding molecules that bind to or recognize the recombinant receptor that is encoded by the viral DNA.

In some embodiments, the incubation of the cells with the viral vector particles results in or produces an output composition comprising cells transduced with the viral vector particles.

In some embodiments, recombinant polynucleotides are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant polynucleotides are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the polynucleotides encoding the recombinant products are those described, e.g., in international patent application, Publication No.: WO2014055668, and U.S. Pat. No. 7,446,190.

Among additional polynucleotides, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., Mol. and Cell Biol., 11:6 (1991); and Riddell et al., Human Gene Therapy 3:319-338

(1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

3. Engineered Cells, Vectors and Compositions for Multi-Targeting

Also provided are cells such as engineered cells that can bind to and/or target multiple antigens. In some embodiments, improved selectivity and specificity is achieved through strategies targeting multiple antigens. Such strategies generally involve multiple antigen-binding domains, which typically are present on distinct genetically engineered antigen receptors and specifically bind to distinct antigens. In some embodiments, the cells are engineered with the ability to bind more than one antigen. For example, in some embodiments, the cells are engineered to express multispecific recombinant receptors. In some embodiments, the cells express multiple recombinant receptors, each of which can target one antigen or multiple antigens, e.g., one receptor that targets BCMA, such as any described herein, and another receptor that targets another antigen, e.g., tumor antigen. In some aspects, a plurality of genetically engineered antigen receptors are introduced into the cell, which specifically bind to different antigens, each expressed in or on the disease or condition to be targeted with the cells or tissues or cells thereof. Such features can in some aspects address or reduce the likelihood of off-target effects or increase efficacy. For example, where a single antigen expressed in a disease or condition is also expressed on or in non-diseased or normal cells, such multi-targeting approaches can provide selectivity for desired cell types by requiring binding via multiple antigen receptors in order to activate the cell or induce a particular effector function. In some embodiments, a plurality of cells can be engineered to express one or more different recombinant receptors, each of which can target one antigen or multiple antigens.

Also provided are multispecific cells containing any of the recombinant receptors described herein, such as cells containing an anti-BCMA recombinant receptor and an additional cell surface protein, such as an recombinant chimeric receptor, which binds to a different antigen or a different epitope on BCMA. In some embodiments, provided are compositions of cells that express recombinant receptors, wherein one or more of the multispecific recombinant receptors bind and/or target BCMA. In some embodiments, the multispecific recombinant receptors target one or more different epitopes on BCMA.

In some embodiments, provided are composition of cells, wherein each type of cell expresses one or more recombinant receptors. In some embodiments, the cell comprises (e.g., has been transformed with) one or more vectors comprising one or more nucleic acid that encodes one or more an amino acid sequence comprising one or more antibodies and/or portions thereof, e.g., antigen-binding fragments thereof. In some embodiments, one or more such cells are provided. In some embodiments, a composition containing one or more such cells is provided. In some embodiments, the one or more cells can express different antibodies, or the same antibody. In some embodiments, each of the cells expresses one or more antibodies, such as more than one antibody. In some embodiments, each of the cells expresses a multispecific receptor, e.g., CAR.

In some embodiments, the cells include multi-targeting strategies that target BCMA and a second or additional antigen associated with a particular disease or condition. In some embodiments, the second or additional antigen is targeted by a multispecific receptor and/or a plurality of cells, e.g., one or more cells, each engineered to express one or more recombinant receptors. In some embodiments, a recombinant receptor targeting a second or additional antigen is expressed on the same cell as the BCMA-binding recombinant receptor, or on a different cell.

In some embodiments, among the second or additional antigens for multi-targeting strategies includes those in which at least one of the antigens is a universal tumor antigen, or a family member thereof. In some embodiments, the second or additional antigen is an antigen expressed on a tumor. In some embodiments, the BCMA-binding recombinant receptor target an antigen on the same tumor type as the second or additional antigen. In some embodiments, the second or additional antigen may also be a universal tumor antigen or may be a tumor antigen specific to a tumor type. In some embodiments, the cell further comprises an additional genetically engineered antigen receptor that recognizes a second or additional antigen expressed on a disease or condition to be treated and induces a stimulatory or activating signal.

Exemplary antigens include CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PIGF, ED-B fibronectin, an oncogene, an oncogene product, CD66a-d, necrosis antigens, Ii, IL-2, T101, TAC, IL-6, ROR1, TRAIL-R1 (DR4), TRAIL-R2 (DR5), B cell maturation antigen (BCMA), tEGFR, Her2, L1-CAM, mesothelin, CEA, hepatitis B surface antigen, anti-folate receptor, CD24, CD30, CD44, EGFR, EGP-2, EGP-4, EPHa2, ErbB2, ErbB3, ErbB4, erbB dimers, EGFR vIII, FBP, FCRL5, FCRH5, fetal acetylcholine receptor, GD2, GD3, G protein-coupled receptor class C group 5 member D (GPRC5D), HMW-MAA, IL-22R-alpha, IL-13R-alpha2, kdr, kappa light chain, Lewis Y, L1-cell adhesion molecule (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, dual antigen, an antigen associated with a universal tag, a cancer-testes antigen, MUC1, MUC16, NY-ESO-1, MART-1, gp100, oncofetal antigen, VEGF-R2, carcinoembryonic antigen (CEA), prostate specific antigen, PSMA, Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, hTERT, MDM2, CYP1B, WT1, livin, AFP, p53, cyclin (D1), CS-1, BCMA, BAFF-R, TACI, CD56, TIM-3, CD123, L1-cell adhesion molecule, MAGE-A1, MAGE A3, a cyclin, such as cyclin A1 (CCNA1) and/or a pathogen-specific antigen, biotinylated molecules, molecules expressed by HIV, HCV, HBV and/or other pathogens, and/or in some aspects, neoepitopes or neoantigens thereof. In some embodiments, the antigen is associated with or is a universal tag.

In some embodiments, the plurality of antigens, e.g., the first antigen, e.g., BCMA, and the second or additional antigens, are expressed on the cell, tissue, or disease or condition being targeted, such as on the cancer cell. In some aspects, the cell, tissue, disease or condition is multiple myeloma or a multiple myeloma cell. One or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

In some aspects, the antigen, e.g., the second or additional antigen, such as the disease-specific antigen and/or related antigen, is expressed on multiple myeloma, such as G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI and/or FcRH5. Other exemplary multiple myeloma antigens include CD56, TIM-3, CD33, CD123, CD44, CD20, CD40, CD74, CD200, EGFR, β2-Microglobulin, HM1.24, IGF-1R, IL-6R, TRAIL-R1, and the activin receptor type IIA (ActRIIA). See Benson and Byrd, J. Clin. Oncol. (2012) 30(16): 2013-15; Tao and Anderson, Bone Marrow Research (2011): 924058; Chu et al., Leukemia (2013) 28(4):917-27; Garfall et al., Discov Med. (2014) 17(91):37-46. In some embodiments, the antigens include those present on lymphoid tumors, myeloma, AIDS-associated lymphoma, and/or post-transplant lymphoproliferations, such as CD38. Antibodies or antigen-binding fragments directed against such antigens are known and include, for example, those described in U.S. Pat. Nos. 8,153,765; 8,603,477, 8,008,450; U.S. Pub. No. US20120189622 or US20100260748; and/or International PCT Publication Nos. WO2006099875, WO2009080829 or WO2012092612 or WO2014210064. In some embodiments, such antibodies or antigen-binding fragments thereof (e.g. scFv) are contained in multispecific antibodies, multispecific chimeric receptors, such as multispecific CARs, and/or multispecific cells.

In some embodiments, the cells and methods include multi-targeting strategies, such as expression of two or more genetically engineered receptors on the cell, each recognizing a different antigen and typically each including a different intracellular signaling component. Such multi-targeting strategies are described, for example, in International Patent Application, Publication No.: WO 2014055668 A1 (describing combinations of a stimulatory or activating and costimulatory CARs, e.g., targeting two different antigens present individually on off-target, e.g., normal cells, but present together only on cells of the disease or condition to be treated) and Fedorov et al., Sci. Transl. Medicine, 5(215) (December, 2013) (describing cells expressing a stimulatory or an activating and an inhibitory CAR, such as those in which the stimulatory or activating CAR binds to one antigen expressed on both normal or non-diseased cells and cells of the disease or condition to be treated, and the inhibitory CAR binds to another antigen expressed only on the normal cells or cells which it is not desired to treat).

In some embodiments, a plurality of cells, each engineered to express one or more recombinant receptors, are provided. For example, in some embodiments, one cell is engineered to express a recombinant receptor that binds and/or targets BCMA, and another cell is engineered to express a recombinant receptor that binds and/or targets an additional or second antigen. In some embodiments, the cells can each express a multispecific recombinant receptor, where one or more of the target antigen is BCMA. In some of such embodiments, the plurality of cells can be administered together or separately. In some embodiments, the plurality of cells are administered simultaneously or concurrently with the cells, e.g., administered on the same day, and/or sequentially with or intermittently with, in any order, another engineered cell in the plurality. For example, in some embodiments, an engineered cell expressing a BCMA-binding recombinant receptor, e.g., CAR, is administered simultaneously with or sequentially with, in any order, another engineered cell expressing a recombinant receptor that binds a different target antigen or a different epitope on BCMA. In some embodiments, the plurality of cells can be in the same composition. Exemplary compositions of the cells include compositions described in Section IV below.

D. Cultivation, Expansion and Formulation of Engineered Cells

In some embodiments, the provided methods include one or more steps for cultivating cells, e.g., cultivating cells under conditions that promote proliferation and/or expansion. In some embodiments, cells are cultivated under conditions that promote proliferation and/or expansion subsequent to a step of genetically engineering, e.g., introducing a recombinant polypeptide to the cells by transduction or transfection. In particular embodiments, the cells are cultivated after the cells have been incubated under stimulating conditions and transduced or transfected with a recombinant polynucleotide, e.g., a polynucleotide encoding a recombinant receptor.

In certain embodiments, the one or more compositions of engineered T cells are or include two separate compositions of enriched T cells. In particular embodiments, two separate compositions of enriched T cells, e.g., two separate compositions of enriched T cells selected, isolated, and/or enriched from the same biological sample, are separately cultivated under stimulating conditions. In certain embodiments, the two separate compositions include a composition of enriched CD4+ T cells. In particular embodiments, the two separate compositions include a composition of enriched CD8+ T cells. In some embodiments, two separate compositions of enriched CD4+ T cells and enriched CD8+ T cells are separately cultivated, e.g., under conditions that promote proliferation and/or expansion.

In some embodiments, a single composition of enriched T cells is cultivated. In some embodiments, the single composition is a composition of enriched CD4+ and CD8+ T cells that have been combined from separate compositions prior to the cultivation. In some embodiments, separate compositions of enriched CD4+ and CD8+ T cells are combined into a single composition and are cultivated, e.g., under conditions that promote proliferation and/or expansion. In certain embodiments, separate cultivated compositions of enriched CD4+ and enriched CD8+ T cells are combined into a single composition after the cultivation has been performed and/or completed.

In some embodiments, cultivation is carried out under conditions that promote proliferation and/or expansion. In some embodiments, such conditions may be designed to induce proliferation, expansion, activation, and/or survival of cells in the population. In particular embodiments, the stimulating conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to promote growth, division, and/or expansion of the cells.

In particular embodiments, the cells are cultivated in the presence of one or more cytokines. In particular embodiments, the one or more cytokines are recombinant cytokines. In some embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines, e.g. a recombinant cytokine, is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more recombinant cytokine includes IL-2, IL-7 and/or IL-15. In some embodiments, the cells, e.g., engineered cells, are cultivated in the presence of a cytokine, e.g., a recombinant human cytokine, at a concentration of between 1 IU/mL and 2,000 IU/mL, between 10 IU/mL and 100 IU/mL, between 50 IU/mL and 200 IU/mL, between 100 IU/mL and 500 IU/mL, between 100 IU/mL and 1,000 IU/mL, between 500 IU/mL and 2,000 IU/mL, or between 100 IU/mL and 1,500 IU/mL.

In some embodiments, the cultivation is performed under conditions that generally include a temperature suitable for the growth of primary immune cells, such as human T lymphocytes, for example, at least about 25 degrees Celsius, generally at least about 30 degrees Celsius, and generally at or about 37 degrees Celsius. In some embodiments, the composition of enriched T cells is incubated at a temperature of 25 to 38 degrees Celsius, such as 30 to 37 degrees Celsius, for example at or about 37 degrees Celsius±2 degrees Celsius. In some embodiments, the incubation is carried out for a time period until the culture, e.g. cultivation or expansion, results in a desired or threshold density, number or dose of cells. In some embodiments, the incubation is greater than or greater than about or is for or about for 24 hours, 48 hours, 72 hours, 96 hours, 5 days, 6 days, 7 days, 8 days, 9 days or more.

In particular embodiments, the cultivation is performed in a closed system. In certain embodiments, the cultivation is performed in a closed system under sterile conditions. In particular embodiments, the cultivation is performed in the same closed system as one or more steps of the provided systems. In some embodiments the composition of enriched T cells is removed from a closed system and placed in and/or connected to a bioreactor for the cultivation. Examples of suitable bioreactors for the cultivation include, but are not limited to, GE Xuri™ W25, GE Xuri™ W5, Sartorius BioSTAT® RM 20|50, Finesse SmartRocker™ Bioreactor Systems, and Pall® XRS Bioreactor Systems. In some embodiments, the bioreactor is used to perfuse and/or mix the cells during at least a portion of the cultivation step.

In some embodiments, the mixing is or includes rocking and/or motioning. In some cases, the bioreactor can be subject to motioning or rocking, which, in some aspects, can increase oxygen transfer. Motioning the bioreactor may include, but is not limited to rotating along a horizontal axis, rotating along a vertical axis, a rocking motion along a tilted or inclined horizontal axis of the bioreactor or any combination thereof. In some embodiments, at least a portion of the incubation is carried out with rocking. The rocking speed and rocking angle may be adjusted to achieve a desired agitation. In some embodiments the rock angle is 20°, 19°, 18°, 17°, 16°, 15°, 14°, 13°, 12°, 11°, 10°, 9°, 8°, 7°, 6°, 5°, 4°, 3°, 2° or 1°. In certain embodiments, the rock angle is between 6-16°. In other embodiments, the rock angle is between 7-16°. In other embodiments, the rock angle is between 8-12°. In some embodiments, the rock rate is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 rpm. In some embodiments, the rock rate is between 4 and 12 rpm, such as between 4 and 6 rpm, inclusive.

In some embodiments, the bioreactor maintains the temperature at or near 37° C. and CO2 levels at or near 5% with a steady air flow at, at about, or at least 0.01 L/min, 0.05 L/min, 0.1 L/min, 0.2 L/min, 0.3 L/min, 0.4 L/min, 0.5 L/min, 1.0 L/min, 1.5 L/min, or 2.0 L/min or greater than 2.0 L/min. In certain embodiments, at least a portion of the cultivation is performed with perfusion, such as with a rate of 290 ml/day, 580 ml/day, and/or 1160 ml/day, e.g., depending on the timing in relation to the start of the cultivation and/or density of the cultivated cells. In some embodiments, at least a portion of the cell culture expansion is performed with a rocking motion, such as at an angle of between 5° and 10°, such as 6°, at a constant rocking speed, such as a speed of between 5 and 15 RPM, such as 6 RMP or 10 RPM.

In some embodiments, the provided methods for manufacturing, generating or producing a cell therapy and/or engineered cells may include formulation of cells, such as formulation of genetically engineered cells resulting from the provided processing steps prior to or after the incubating, engineering, and cultivating, and/or one or more other processing steps as described. In some embodiments, one or more of the processing steps, including formulation of cells, can be carried out in a closed system. In some cases, the cells are processed in one or more steps (e.g. carried out in the centrifugal chamber and/or closed system) for manufacturing, generating or producing a cell therapy and/or engineered cells may include formulation of cells, such as formulation of genetically engineered cells resulting from the provided transduction processing steps prior to or after the culturing, e.g. cultivation and expansion, and/or one or more other processing steps as described.

In some embodiments, the dose of cells comprising cells engineered with a recombinant antigen receptor, e.g. CAR or TCR, is provided as a composition or formulation, such as a pharmaceutical composition or formulation. Such compositions can be used in accord with the provided methods, such as in the prevention or treatment of diseases, conditions, and disorders, or in detection, diagnostic, and prognostic methods. In some cases, the cells can be formulated in an amount for dosage administration, such as for a single unit dosage administration or multiple dosage administration.

In some embodiments, cells can be formulated into a container, such as a bag or vial.

In some embodiments, the cells are formulated in a pharmaceutically acceptable buffer, which may, in some aspects, include a pharmaceutically acceptable carrier or excipient. In some embodiments, the processing includes exchange of a medium into a medium or formulation buffer that is pharmaceutically acceptable or desired for administration to a subject. In some embodiments, the processing steps can involve washing the transduced and/or expanded cells to replace the cells in a pharmaceutically acceptable buffer that can include one or more optional pharmaceutically acceptable carriers or excipients. Exemplary of such pharmaceutical forms, including pharmaceutically acceptable carriers or excipients, can be any described below in conjunction with forms acceptable for administering the cells and compositions to a subject. The pharmaceutical composition in some embodiments contains the cells in amounts effective to treat or prevent the disease or condition, such as a therapeutically effective or prophylactically effective amount.

In some embodiments, the formulation buffer contains a cryopreservative. In some embodiments, the cell are formulated with a cryopreservative solution that contains 1.0% to 30% DMSO solution, such as a 5% to 20% DMSO solution or a 5% to 10% DMSO solution. In some embodiments, the cryopreservation solution is or contains, for example, PBS containing 20% DMSO and 8% human serum albumin (HSA), or other suitable cell freezing media. In some embodiments, the cryopreservative solution is or contains, for example, at least or about 7.5% DMSO. In some embodiments, the processing steps can involve washing the transduced and/or expanded cells to replace the cells in a cryopreservative solution. In some embodiments, the cells are frozen, e.g., cryoprotected or cryopreserved, in media and/or solution with a final concentration of or of about 12.5%, 12.0%, 11.5%, 11.0%, 10.5%, 10.0%, 9.5%, 9.0%, 8.5%, 8.0%, 7.5%, 7.0%, 6.5%, 6.0%, 5.5%, or 5.0% DMSO, or between 1% and 15%, between 6% and 12%, between 5% and 10%, or between 6% and 8% DMSO. In particular embodiments, the cells are frozen, e.g., cryoprotected or cryopreserved, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and 5%, between 0.25% and 4%, between 0.5% and 2%, or between 1% and 2% HSA.

In some embodiments, the formulation is carried out using one or more processing step including washing, diluting or concentrating the cells, such as the cultured or expanded cells. In some embodiments, the processing can include dilution or concentration of the cells to a desired concentration or number, such as unit dose form compositions including the number of cells for administration in a given dose or fraction thereof. In some embodiments, the processing steps can include a volume-reduction to thereby increase the concentration of cells as desired. In some embodiments, the processing steps can include a volume-addition to thereby decrease the concentration of cells as desired. In some embodiments, the processing includes adding a volume of a formulation buffer to transduced and/or expanded cells. In some embodiments, the volume of formulation buffer is from or from about 10 mL to 1000 mL, such as at least or about at least or about or 50 mL, 100 mL, 200 mL, 300 mL, 400 mL, 500 mL, 600 mL, 700 mL, 800 mL, 900 mL or 1000 mL.

In some embodiments, such processing steps for formulating a cell composition is carried out in a closed system. Exemplary of such processing steps can be performed using a centrifugal chamber in conjunction with one or more systems or kits associated with a cell processing system, such as a centrifugal chamber produced and sold by Biosafe SA, including those for use with the Sepax® or Sepax 2® cell processing systems. An exemplary system and process is described in International Publication Number WO2016/073602. In some embodiments, the method includes effecting expression from the internal cavity of the centrifugal chamber a formulated composition, which is the resulting composition of cells formulated in a formulation buffer, such as pharmaceutically acceptable buffer, in any of the above embodiments as described. In some embodiments, the expression of the formulated composition is to a container, such as the vials of the biomedical material vessels described herein, that is operably linked as part of a closed system with the centrifugal chamber. In some embodiments, the biomedical material vessels are configured for integration and or operable connection and/or is integrated or operably connected, to a closed system or device that carries out one or more processing steps. In some embodiments, the biomedical material vessel is connected to a system at an output line or output position. In some cases, the closed system is connected to the vial of the biomedical material vessel at the inlet tube. Exemplary close systems for use with the biomedical material vessels described herein include the Sepax® and Sepax® 2 system.

In some embodiments, the closed system, such as associated with a centrifugal chamber or cell processing system, includes a multi-port output kit containing a multi-way tubing manifold associated at each end of a tubing line with a port to which one or a plurality of containers can be connected for expression of the formulated composition. In some aspects, a desired number or plurality of vials, can be sterilely connected to one or more, generally two or more, such as at least 3, 4, 5, 6, 7, 8 or more of the ports of the multi-port output. For example, in some embodiments, one or more containers, e.g., biomedical material vessels, can be attached to the ports, or to fewer than all of the ports. Thus, in some embodiments, the system can effect expression of the output composition into a plurality of vials of the biomedical material vessels.

In some aspects, cells can be expressed to the one or more of the plurality of output containers, e.g., vials, in an amount for dosage administration, such as for a single unit dosage administration or multiple dosage administration. For example, in some embodiments, the vials, may each contain the number of cells for administration in a given dose or fraction thereof. Thus, each vial, in some aspects, may contain a single unit dose for administration or may contain a fraction of a desired dose such that more than one of the plurality of vials, such as two of the vials, or 3 of the vials, together constitute a dose for administration.

Thus, the containers, e.g. bags or vials, generally contain the cells to be administered, e.g., one or more unit doses thereof. The unit dose may be an amount or number of the cells to be administered to the subject or twice the number (or more) of the cells to be administered. It may be the lowest dose or lowest possible dose of the cells that would be administered to the subject.

In some embodiments, each of the containers, e.g. bags or vials, individually comprises a unit dose of the cells. Thus in some embodiments, each of the containers comprises the same or approximately or substantially the same number of cells. In some embodiments, each unit dose contains at least or about at least $1\times10^6$, $2\times10^6$, $5\times10^6$, $1\times10^7$, $5\times10^7$, or $1\times10^8$ engineered cells, total cells, T cells, or PBMCs. In some embodiments, the volume of the formulated cell composition in each container, e.g. bag or vial, is 10 mL to 100 mL, such as at least or about at least 20 mL, 30 mL, 40 mL, 50 mL, 60 mL, 70 mL, 80 mL, 90 mL or 100 mL. In some embodiments, the cells in the container, e.g. bag or vials, can be cryopreserved. In some embodiments, the container, e.g. vials, can be stored in liquid nitrogen until further use.

In some aspects, the engineered cells or cell compositions are assessed at one or more stages or time points during the manufacturing process, including before the engineered cells or cell compositions containing the engineered cells are released for infusion, ready for administration to a subject, and/or administered to a subject. In some embodiments, engineered cells or cell compositions are released for infusion, ready for administration to a subject, and/or administered to a subject after assessing the number, amount or percentage of cells that have been engineered and/or that are expressing the anti-BCMA CAR in accordance with the provided embodiments, e.g., on a portion, fraction, and/or sample of engineered cells or cell compositions. In particular embodiments, the engineered cells or cell compositions are released for infusion, ready for administration to a subject, and/or administered to a subject after the cells are determined to be safe, e.g., sterile and/or free, and/or have desired biological characteristics following the completion of the one or more methods, such as containing less than or more than a required threshold copy number of nucleic acid sequences encoding the anti-BCMA CAR as described herein. In some embodiments, such assessment can be used to determine the number and/or percentage of CAR-expressing cells to determine the appropriate dose of cells for administration. In some aspects, for subjects that have received a prior adoptive cell therapy, such as a prior BCMA-directed recombinant receptor (e.g., CAR) expressing T cell therapy (CAR T cell therapy), the provided methods and uses can also include assessing the engineered cells or cell compositions for the presence, amount and/or level of the prior BCMA-directed recombinant receptor (e.g., CAR). In some aspects, the assessment for the presence, amount and/or level of the prior BCMA-directed recombinant receptor (e.g., CAR) can be used to detect any remaining cells that express the prior recombinant receptor, and if necessary, exclude such cells that still express a prior recombinant receptor or enrich for cells that do not express the prior recombinant receptor. In some aspects, such methods can be used to reduce or prevent administering of cells that still contain the prior recombinant receptor (e.g., CAR).

In some embodiments, the presence and/or amount of the anti-BCMA CAR (and in some cases, the prior recombinant receptor) is assessed by detecting the expression of the recombinant receptor or the presence of nucleic acid sequences encoding the recombinant receptor. In some aspects, the presence of the recombinant receptor can be assessed using any methods that can detect the presence, absence, level and/or amount of a protein or a nucleic acid from a biological sample, for example, using nucleic acid-based methods, such as quantitative PCR (qPCR); or cell-based methods, such as flow cytometry, or other assays, such as an immunoassay, ELISA, or chromatography/mass spectrometry-based assays. The anti-BCMA CAR or cells expressing the anti-BCMA CAR may be detected by flow cytometry-based or quantitative PCR-based methods and extrapolation to total cell numbers using known methods. See, e.g., Brentjens et al., *Sci Transl Med.* 2013 5(177), Park et al, *Molecular Therapy* 15(4):825-833 (2007), Savoldo et al., *JCI* 121(5):1822-1826 (2011), Davila et al., (2013) *PLoS ONE* 8(4):e61338, Davila et al., *Oncoimmunology* 1(9): 1577-1583 (2012), Lamers, *Blood* 2011 117:72-82, Jensen et al., *Biol Blood Marrow Transplant* 2010 September; 16(9): 1245-1256, Brentjens et al., *Blood* 2011 118(18):4817-4828.

Exemplary nucleic acid based methods to assess the presence of recombinant receptor include polymerase chain reaction-based methods, such as quantitative PCR (qPCR), digital PCR (dPCR) or droplet digital PCR (ddPCR). In some aspects, the presence, absence and/or amount of a particular sequence can be detected using a probe or a primer, that can specifically bind, detect, recognize and/or amplify all or a portion of the nucleic acid sequence encoding the recombinant receptor. In some embodiments, the primers or probe used for qPCR or other nucleic acid-based methods are specific for binding, recognizing and/or amplifying nucleic acids encoding the recombinant protein (e.g., the anti-BCMA CAR, and in some cases, the prior recombinant receptor), and/or other components or elements of the plasmid and/or vector, including regulatory elements, e.g., promoters, transcriptional and/or post-transcriptional regulatory elements or response elements, or markers, e.g., surrogate markers. In some aspects, exemplary nucleic acid based methods to assess the presence of recombinant receptor include high-throughput RNA sequencing (RNA-seq) or other high-throughput methods to assess expression of nucleic acids in a sample. In some aspects, exemplary methods for assessing the engineered cells or composition for the presence and/or amount of nucleic acids encoding the anti-BCMA CAR, include those described in WO 2020/033916.

Exemplary cell- or protein-based methods to assess the presence of recombinant receptor (e.g., the anti-BCMA CAR, and in some cases, the prior recombinant receptor), include flow cytometry, an enzyme-linked immunosorbent assay (ELISA), enzyme immunoassay (EIA), radioimmunoassay (RIA), surface plasmon resonance (SPR), Western Blot, Lateral flow assay, immunohistochemistry, protein array or immuno-PCR (iPCR).

In some embodiments, the presence of BCMA-directed recombinant receptor (e.g., the anti-BCMA CAR, and in some cases, the prior recombinant receptor) expressing cells in the engineered cells or cell composition can be detected using reagents such as an isolated or purified antigen, e.g., recombinantly expressed antigen, for example, recombinant BCMA-Fc (soluble human BCMA fused at its C-terminus to an Fc region of IgG). In some embodiments, the presence of anti-BCMA CAR-expressing cells in the engineered cells or cell composition can be detected using reagents that can specifically detect the presence of the anti-BCMA CAR, such as an anti-idiotypic antibody, an anti-idiotypic agonist antibody specific for a binding domain, e.g., scFv, or a portion thereof. Exemplary anti-idiotypic antibodies are described in PCT/US2020/063492, incorporated herein by reference in its entirety. In some embodiments, the binding molecule is or comprises an isolated or purified antigen, e.g., recombinantly expressed antigen. In some cases, for example, for subjects that have received a prior BCMA-directed recombinant receptor expressing cell (e.g., CAR T cell) therapy, the amount or level of BCMA-binding recombinant receptors as assessed using an isolated or purified antigen (e.g., recombinant BCMA-Fc; detecting any recombinant receptor that binds to BCMA, including the prior BCMA-directed recombinant receptor and the anti-BCMA CAR for use in accordance with the provided methods) and the amount or level of the anti-BCMA CAR as detected using particular recombinant receptor-specific reagent, e.g., an anti-idiotypic antibody against the specific anti-BCMA CAR, can be compared. In some cases, the differences between the two amounts can indicate the presence and/or amount of cells expressing the prior recombinant receptor, e.g., a prior BCMA-directed CAR T therapy.

In some embodiments, such cells produced by the method, or a composition comprising such cells, are administered to a subject for treating a disease or condition.

E. Exemplary Process and Features

In some embodiments, engineered cells, such as those that express an anti-BCMA CAR as described, used in accord with the provided methods are produced or generated by a process for selecting, isolating, activating, stimulating, expanding, cultivating, and/or formulating cells. In some embodiments, such methods include any as described.

In some embodiments, at least one separate composition of enriched CD4+ T cells and at least one separate composition of enriched CD8+ T cells are isolated, selected, enriched, or obtained from a single biological sample, e.g., a sample of PBMCs or other white blood cells from the same donor such as a patient or healthy individual. In some embodiments, a separate composition of enriched CD4+ T cells and a separate composition of enriched CD8+ T cells originated, e.g., were initially isolated, selected, and/or enriched, from the same biological sample, such as a single biological sample obtained, collected, and/or taken from a single subject. In some embodiments, a biological sample is first subjected to selection of CD4+ T cells, where both the negative and positive fractions are retained, and the negative fraction is further subjected to selection of CD8+ T cells. In other embodiments, a biological sample is first subjected to selection of CD8+ T cells, where both the negative and positive fractions are retained, and the negative fraction is further subjected to selection of CD4+ T cells. In some embodiments, methods of selection are carried out as described in International PCT publication No. WO2015/164675. In some aspects, a biological sample is first positively selected for CD8+ T cells to generate at least one composition of enriched CD8+ T cells, and the negative fraction is then positively selected for CD4+ T cells to generate at least one composition of enriched CD4+ T cells, such that the at least one composition of enriched CD8+ T cells and the at least one composition of enriched CD4+ T cells are separate compositions from the same biological sample, e.g., from the same donor patient or healthy individual. In some aspects, two or more separate compositions of enriched T cells, e.g., at least one being a composition of enriched CD4+ T cells and at least one being a separate composition of enriched CD8+ T cells from the same donor, are separately frozen, e.g., cryoprotected or cryopreserved in a cryopreservation media.

In some embodiments, cells from a composition of enriched CD4+ T cells and cells from a composition of enriched CD8+ T cells are mixed, combined, and/or pooled to generate an input composition containing CD4+ T cells and CD8+ T cells. In certain embodiments, the compositions of enriched CD4+ T cells and CD8+ T cells are pooled, mixed, and/or combined prior to incubating the cells under stimulating conditions. In certain embodiments, the compositions of enriched CD4+ and CD8+ T cells are pooled, mixed, and/or combined subsequent to isolating, enriching, and/or selecting the CD4+ and CD8+ T cells from a biological sample. In particular embodiments, the compositions of enriched CD4+ and CD8+ T cells are pooled, mixed, and/or combined subsequent to freezing, e.g., cryopreserving, and thawing the compositions of enriched CD4+ and CD8+ T cells.

In particular embodiments, the input composition contains a ratio of between 3:1 and 1:3, between 2:1 and 1:2, between 1.5 and 0.75, between 1.25 and 0.75, or between 1.2 and 0.8 CD4+ T cells to CD8+ T cells. In particular embodiments, the input composition contains a ratio of between 3:1 and 1:3 CD4+ T cells to CD8+ T cells. In particular embodiments, the input composition contains a ratio of between 2:1 and 1:2 CD4+ T cells to CD8+ T cells. In certain embodiments, the input composition contains a ratio of or of about 2:1 CD4+ T cells to CD8+ T cells. In certain embodiments, the input composition contains a ratio of or of about 1:1 CD4+ T cells to CD8+ T cells.

In some aspects, two or more separate compositions of enriched T cells, e.g., at least one being a composition of enriched CD4+ T cells and at least one being a separate composition of enriched CD8+ T cells from the same biological sample, are thawed and mixed, combined, and/or pooled, and the compositions may be optionally washed before or after the mixing, combining, and/or pooling. In some aspects, the mixed, combined, and/or pooled and optionally washed compositions of enriched T cells form an input composition. In some aspects, the input composition (e.g., comprising CD4+ T cells and CD8+ T cells at a ratio of or of about 1:1) is activated and/or stimulated by contacting with a stimulatory reagent (e.g., by incubation with CD3/CD28 conjugated magnetic beads for T cell activation). In some aspects, the activated/stimulated cell composition is engineered, transduced, and/or transfected, e.g., using a viral vector encoding a recombinant protein (e.g. CAR), to express the same recombinant protein in the CD4+ T cells and CD8+ T cells of the cell composition. In some aspects, the method comprises removing the stimulatory reagent, e.g., magnetic beads, from the cell composition. In some aspects, a cell composition containing engineered CD4+ T cells and engineered CD8+ T cells is cultivated, e.g., for expansion of the CD4+ T cell and/or CD8+ T cell populations therein. In certain embodiments, a cell composition from the cultivation is harvested and/or collected and/or formulated, e.g., by washing the cell composition in a formulation buffer. In certain embodiments, a formulated cell composition comprising CD4+ T cells and CD8+ T cells is frozen, e.g., cryoprotected or cryopreserved in a cryopreservation media. In some aspects, engineered CD4+ T cells and CD8+ T cells in the formulation originate from the same donor or biological sample and express the same recombination protein (e.g., CAR), and the formulation is administered to a subject in need thereof such as the same donor.

In some embodiments, engineered cells, such as those that express an anti-BCMA CAR as described, and compositions containing such cells, such as compositions containing CD4+ and CD8+ T cells expressing an anti-BCMA chimeric antigen receptor (CAR), used in accord with the provided methods are produced or generated by an exemplary process that includes separately selecting CD4+ and CD8+ T cells from a sample prior to combining the selected cells at a defined ratio for subsequent processing steps.

In some aspects of an exemplary process, separate compositions of CD4+ and CD8+ cells are selected from isolated PBMCs from a human leukapheresis sample, and the selected cell compositions are cryopreserved. In some embodiments, the human subject is a subject that has multiple myeloma (MM). In some aspects, the selected CD4+ and CD8+ T cell compositions are subsequently thawed and mixed at a ratio of 1:1 of viable CD4+ T cells to viable CD8+ T cells prior to carrying out steps for stimulation, transduction and expansion. In an exemplary embodiment, approximately $300\times10^6$ T cells ($150\times10^6$ CD4+ and $150\times10^6$ CD8+ T cells) from the mixed cell composition, at a density of about $3\times10^6$ cells/mL, are stimulated in the presence of paramagnetic polystyrene-coated beads with attached anti-CD3 and anti-CD28 antibodies at a 1:1 bead to cell ratio in serum-free media. In some embodiments, the media also contain recombinant IL-2, IL-7, and IL-15. The stimulation is carried out by incubation for between 18 to 30 hours.

In some aspects of an exemplary process, following the incubation, approximately $100\times10^6$ viable cells from the stimulated cell composition are washed and resuspended in the exemplary serum free media containing recombinant IL-2, IL-7, and IL-15. In some cases, no transduction adjuvant is added. In some aspects, the cells are transduced with an exemplary lentiviral vector encoding any of the exemplary anti-BCMA CARs described herein (e.g., containing an scFv antigen-binding domain specific for BCMA, a CD28 transmembrane region, a 4-1BB costimulatory signaling region, and a CD3-zeta derived intracellular signaling domain), by spinoculation for 60 minutes followed by incubation for about 18 to 30 hours at about 37° C. In some aspects, the density of the cells post-spinoculation is about $1\times10^6$ cells/mL.

In some embodiments, the transduced cells are then cultivated for expansion by transfer to a bioreactor (e.g., a rocking motion bioreactor) in about 500 mL of the exemplary serum free media containing twice the concentration of IL-2, IL-7, and IL-15 as used during the incubation and transduction steps. In some exemplary processes, the exemplary media does not contain poloxamer.

In some aspects, after a threshold cell density of greater than or about $0.6\times10^6$ cells/mL is achieved, media is added step-wise with shots of fresh media being added periodically, such as between about 2 and about 15 minutes to a volume of 1000 mL and the cells are cultivated under steady rocking conditions (non-perfusion) until a threshold viable cell density of greater than or about $0.6\times10^6$ cells/mL is achieved. In some embodiments, if the viable cell density is greater than $0.8\times10^6$cells/mL, a combination fill/perfusion step is initiated wherein first media is added in a step-wise manner, for example, as indicated above, until a target volume of 1000 mL, then perfusion is initiated, such as described below. In some aspects, media is then replaced by semi-continuous perfusion with continual mixing. In some embodiments, the perfusion rate and/or rocking speed are increased at least one time during the expansion phase as cell density increased. In some embodiments, the perfusion rate is increased at least one time during the expansion phase as cell density increased. In some embodiments, media is added to the culture in a step-wise manner with total volume per day determined by viable cell density (such as with higher rates once certain densities are reached), up to a rate, e.g., resulting in approximately 750 mL or 1500 mL of total fresh media added to the culture per day (with higher rates when higher cell concentrations are reached), with shots of fresh media added throughout the day periodically, such as between about every 0.5 and about every 1.5 or 2 hours. In some embodiments, the cells are harvested one day after an exemplary threshold of expansion of about is $3500\times10^6$ or $5500\times10^6$ is achieved. In some embodiments, the cells are harvested at a time one day after the total number of nucleated cells (TNC) had reached at least or at least approximately $3500\times10^6$ and at a point at which the TNC number had reached at least or at least approximately $5500\times10^6$ total nucleated cells. Following harvest, the anti-CD3 and anti-CD28 antibody conjugated beads are removed from the cell composition by exposure to a magnetic field. The cells are then formulated, aliquoted into freezing bags for administration (e.g. CryoStore™ Freezing Bags) and vials for further analysis, and cryopreserved. In some cases, 30 mL volumes of formulated cell composition is aliquoted per bag. In some instances, cells are cryopreserved at a variable concentration, so long as the target cell number is met for the total output composition.

In some embodiments, engineered cells, such as those that express an anti-BCMA CAR as described, and compositions containing such cells, such as compositions containing CD4+ and CD8+ T cells expressing an anti-BCMA chimeric antigen receptor (CAR), used in accord with the provided methods are produced or generated by another exemplary process. In the exemplary process, primary CD4+ and CD8+ cells are enriched from biological samples containing PBMCs from a human leukapheresis sample, including from subjects having multiple myeloma (MM). In some aspects, the enriched CD4+ and enriched CD8+ cell compositions are separately cryopreserved and subsequently thawed and mixed at a ratio of 1:1 of viable CD4+ T cells to viable CD8+ T cells, prior to carrying out steps for stimulation, transduction and expansion. In some aspects, the enriched CD4+ and enriched CD8+ cell compositions are separately cryopreserved and subsequently thawed and mixed at a ratio of 2:1 of viable CD4+ T cells to viable CD8+ T cells, prior to carrying out steps for stimulation, transduction and expansion.

In some embodiments, approximately $300\times10^6$ T cells (for example, $150\times10^6$ CD4+ and $150\times10^6$ CD8+ T cells) from the mixed cell composition, at a density of about $3\times10^6$ cells/mL, are incubated for between 18 and 30 hours in the presence of paramagnetic polystyrene-coated beads with attached anti-CD3 and anti-CD28 antibodies, at a 1:1 bead to cell ratio in an exemplary serum-free media containing recombinant IL-2, IL-7, and IL-15.

In some aspects, following the incubation, at least approximately $100\times10^6$ and up to approximately $200\times10^6$ viable cells from the incubated cell composition are transduced, in the exemplary serum free media with cytokines, with a lentiviral vector encoding any of the exemplary anti-BCMA CARs described herein (e.g., containing an scFv antigen-binding domain specific for BCMA, a CD28 transmembrane region, a 4-1BB costimulatory signaling region, and a CD3-zeta derived intracellular signaling domain), by spinoculation for 60 minutes followed by incubation for about 18 to 30 hours at about 37° C.

In some embodiments, the transduced cells are then expanded by cultivation in a bioreactor (e.g. a rocking motion bioreactor) in about 500 mL of the exemplary serum free media containing twice the concentration of IL-2, IL-7, and IL-15 as used during the incubation and transduction steps. In some aspects, the media does not contain or is free of poloxamer. In some aspects, after a cell density of greater than at or about $0.6\times10^6$ cells/mL is deemed to be achieved, media is added step-wise with shots of fresh media being added periodically, such as between about 2 and about 15 minutes to a volume of 1000 mL and the cells are cultivated under steady rocking conditions (non-perfusion) until a threshold viable cell density of greater than at or about $0.6\times10^6$ cells/mL is achieved. In some aspects, if the viable cell density is greater than $0.8\times10^6$cells/mL, a combination fill/perfusion step is initiated wherein first media is added in a step-wise manner as indicated above, until a target volume of 1000 mL, then perfusion is initiated. In some embodiments, media is replaced by semi-continuous perfusion with continual mixing. In some aspects, the perfusion rate and/or rocking speed are increased at least one time during the expansion phase as cell density increased. In some embodiments, the perfusion rate is increased at least one time during the expansion phase as cell density increased. In some aspects, media is added to the culture in a step-wise manner with total volume per day determined by viable cell density (e.g., with higher rates once certain densities are reached), up to a rate, e.g., resulting in approximately 750 mL or 1500 mL of total fresh media added to the culture per day (e.g., with higher rates when higher cell concentrations are reached), with shots of fresh media added throughout the day periodically, such as between at or about every 0.5 and at or about every 1.5 or 2 hours. In some embodiments, the cells are harvested at a time one day after the total number of nucleated cells (TNC) reaches at least or at least approximately $1000\times10^6$ and at a point at which the TNC number reaches at least or at least approximately $2400\times10^6$ total nucleated cells, with at least 85% viability. In some aspects, following harvest, the anti-CD3 and anti-CD28 antibody conjugated beads are removed from the cell composition.

In some embodiments, the cells are then formulated and aliquots of the composition transferred into containers, e.g., for downstream storage or use. In some embodiments, formulated compositions or portions thereof are transferred freezing bags appropriate for cryopreservation and storage of cell compositions, e.g., for potential administration to subjects (such as CryoStore™ Freezing Bags) and/or compositions or portions thereof are transferred to vials or other containers, such as for further analysis of the cells. In some aspects, cells are cryopreserved, such as under conditions appropriate for downstream thawing and use for administration. In some cases, 30 mL volumes of formulated cells are used in individual bags. In some instances, cells are cryopreserved at a variable total cell concentration, for example, to permit a consistent number or concentration of CAR+ T cells in each dose in the context of cells for administration. In some embodiments, the target CAR+ CD3+ cell number is at or approximately a desired number (such as at or about $37.5\times10^6$) CAR+CD3+ cells per 30 mL or per bag, which in some embodiments involves varying total cell concentrations among compositions generated from different donors or patients.

In some aspects, for individual leukapheresis samples obtained from a range of multiple myeloma patients, such an exemplary process to generate engineered cell compositions from such samples, can result in a range of duration of the portion of the process from initiation of activation through harvest of between 5 and 8 days, and an average duration among these samples of 5.5 days. In some aspects, the average number of cumulative population doublings over the process for this group of samples can be approximately 5.

In some aspects, the exemplary processes described herein can be used to generate engineered T cell compositions from a number of human multiple myeloma leukapheresis samples. In some aspects, various parameters, including those reflective of cell phenotype, function and cell engineering are assessed. In some embodiments, T cell purity, T cell lineage representation, transduction frequency and functionality are observed to be substantially similar as for compositions generated with these leukapheresis products using a different exemplary process (e.g., described above). In some aspects, a reduced number of population doublings and average duration of days between activation initiation and harvest is observed, with production using the exemplary process described above, compared to a different exemplary process (e.g., described above). In some aspects, similar or increased percentages of central memory-phenotype cells (and similar or decreased percentages of effector memory-phenotype cells) are observed in engineered cell compositions produced by the different exemplary processes described herein.

In some embodiments, the engineered cell compositions are generated using a process that, in some aspects have particular success rates such as high success rates or rates of success greater than a threshold rate, such as those that are able to generate therapeutic cell compositions, such as able to generate such compositions having certain required or desired features, for a large number or percentage of samples, such as for all or a high percentage of samples each derived from a different individual subject or patient, such as a subject or patient to be treated with the therapeutic composition (e.g., in the context of autologous cell therapy). In some aspects, the subjects or patients have a disease or condition such as a cancer such as a blood or hematological cancer such as a multiple myeloma. In some aspects, the samples—from which, for a high percentage thereof, it is possible to generate therapeutic cell compositions—are patient samples including those that are variable for example in terms of cell phenotypes or other parameters of the samples or cells thereof. In some embodiments, the engineered cell compositions that have improved or high degrees of cell health such as compared to cell compositions generated via other processes. In some embodiments, the compositions include a high percentage of cells that are negative of an apoptotic marker. In some embodiments, the engineered cell compositions are generated by a method which generates a composition comprising polyfunctional cells with robust cytokine production. In some embodiments, the engineered cell compositions are generated by a method which generates T cell compositions that are enriched for a memory phenotype, enriched for a central memory phenotype, and/or enriched for cells that are CD27+, CD28+, CCR7+, CD45RA−, CD45RO+, CD62L+, CD3+, granzyme B−, and/or CD127+. In some embodiments, at least 20, 25, 30, 35, 40, 45, 50, 55, 60, 65, 70, 75, or 80% or more of the cells in the composition (or at least 20, 25, 30, 35, 40, 45, 50, 55, 60, 65, 70, 75, or 80% or more of the cells in the composition for at least half or a majority of samples produced using particular methods or, on average, for samples produced using particular methods), of the T cells in the composition, or of the engineered T cells in the composition, are T cells of a central memory phenotype; are CD27+, CD28+; are CCR7+, CD45RA−; and/or are CCR7+, CD45RO+. In some embodiments, at least 50, 55, 60, 65, 70, 75, or 80 or 85 or 90 or 95% or more of the cells in the composition (or at least 50, 55, 60, 65, 70, 75, or 80 or 85 or 90 or 95% or more of the cells in the composition for at least half or a majority of samples produced using particular methods or, on average, for samples produced using particular methods), of the T cells in the composition, or of the engineered T cells in the composition, are T cells of a memory phenotype; are CD45RA−; and/or are CD45RO+.

In certain embodiments, the cells of the composition have a high portion and/or frequency of central memory cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the cells of the composition are of a memory phenotype, are of a central memory phenotype, or are central memory T cells. In certain embodiments, at least or at or about 50%, at least or at or about 55%, at least or at or about 60%, or at least or at or about 65% of the cells of the composition are central memory T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the cells of the composition are of a memory phenotype, are of a central memory phenotype, or are central memory T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the T cells of the composition are of a memory phenotype, are of a central memory phenotype, or are central memory T cells. In certain embodiments, at least or at or about 50%, at least or at or about 55%, at least or at or about 60%, or at least or at or about 65% of the T cells of the composition are of a memory phenotype, are of a central memory phenotype, or are central memory T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the T cells of the composition are of a memory phenotype, are of a central memory phenotype, or are central memory T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD4+ T cells of the composition are central memory CD4+ T cells. In certain embodiments, at least or at or about 50%, at least or at or about 55%, at least or at or about 60%, or at least or at or about 65% of the CD4+ T cells of the composition are central memory CD4+ T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD4+ T cells of the composition are central memory CD4+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD4+ CAR+ T cells of the composition are central memory CD4+ CAR+ T cells. In certain embodiments, at least or at or about 50%, at least or at or about 55%, at least or at or about 60%, or at least or at or about 65% of the CD4+ CAR+ T cells of the composition are central memory CD4+ CAR+ T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD4+ CAR+ T cells of the composition are central memory CD4+ CAR+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD8+ T cells of the composition are central memory CD8+ T cells. In certain embodiments, at least or at or about 50%, at least or at or about 55%, at least or at or about 60%, or at least or at or about 65% of the CD8+ T cells of the composition are central memory CD8+ T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD8+ T cells of the composition are central memory CD8+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD8+ CAR+ T cells of the composition are central memory CD8+ CAR+ T cells. In certain embodiments, at least or at or about 50%, at least or at or about 55%, at least or at or about 60%, or at least or at or about 65% of the CD8+ CAR+ T cells of the composition are central memory CD8+ CAR+ T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD8+ CAR+ T cells of the composition are central memory CD8+ CAR+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of CAR+ T cells (e.g., the CD4+ T cells and CD8+ T cells) of the composition are central memory CD4+ or CD8+ T cells. In certain embodiments, at least or at or about 50%, at least or at or about 55%, at least or at or about 60%, or at least or at or about 65% of the CAR+ T cells (e.g., CD4+ T cells and CD8+ T cells) of the composition are central memory CD4+ or CD8+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the cells in the composition are CD27+, CD28+, CCR7+, CD45RA−, CD45RO+, CD62L+, CD3+, CD95+, granzyme B-, and/or CD127+. In some embodiments, at least or at or about 50%, at least or at or about 55%, at least or at or about 60%, or at least or at or about 65% of the CAR+ T cells in the composition are CD27+, CD28+, CCR7+, CD45RA−, CD45RO+, CD62L+, CD3+, CD95+, granzyme B-, and/or CD127+.

In some embodiments, iterations of the method produce a plurality of the compositions, optionally from human biological samples in which the method is carried out among a plurality of different individual subjects. In some embodiments, the average (i.e., mean) or median percentage of cells of a memory phenotype in the plurality of the compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of cells of a central memory phenotype in the plurality of the compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of cells that are CD27+, CD28+, CCR7+, CD45RA−, CD45RO+, CD62L+, CD3+, CD95+, granzyme B-, and/or CD127+ in the plurality of the compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of cells that are CCR7+/CD45RA- or CCR7+/CD45RO+ in the plurality of the compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of central memory CD4+ T cells in the engineered CD4+ T cells (e.g., CAR+CD4+ T cells) of the plurality of the compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of central memory CD8+ T cells in the engineered CD8+ T cells (e.g., CAR+CD8+ T cells) of the plurality of the compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%. In some embodiments, the average (i.e., mean) or median percentage of central memory T cells (e.g., CD4+ central memory T cells and CD8+ central memory T cells) in the engineered T cells (e.g., CAR+ T cells) of the plurality of the compositions is between at or about 40% and at or about 65%, between at or about 40% and at or about 45%, between at or about 45% and at or about 50%, between at or about 50% and at or about 55%, between at or about 55% and at or about 60%, or between at or about 60% and at or about 65%.

IV. PHARMACEUTICAL COMPOSITIONS

Also provided are compositions including the engineered cells expressing the BCMA-binding recombinant receptor, including pharmaceutical compositions and formulations. Among such compositions are those that include engineered cells, such as a plurality of engineered cells, expressing the provided anti-BCMA recombinant receptors (e.g. CARs). In some aspects, also provided are compositions, e.g., cell compositions for use in the provided methods and uses, e.g., therapeutic methods and uses. In some embodiments, the provided compositions are capable of achieving certain therapeutic outcomes, e.g., response or safety outcomes, when administered to subjects that have a disease or disorder, e.g., multiple myeloma.

Provided are pharmaceutical formulations comprising BCMA-binding recombinant chimeric antigen receptors or engineered cells expressing said receptors, a plurality of engineered cells expressing said receptors and/or additional agents for combination treatment or therapy. The pharmaceutical compositions and formulations generally include one or more optional pharmaceutically acceptable carrier(s) or excipient(s). In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell, additional therapeutic agent, and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being treated with the cells or compositions thereof, preferably those with activities complementary to the cells or compositions thereof, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The pharmaceutical composition in some embodiments contains cells or compositions thereof in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In certain embodiments, in the context of genetically engineered cells containing the recombinant receptor, e.g., CAR, a subject is administered the range of at or about one million to at or about 100 billion cells, such as, e.g., 1 million to at or about 50 billion cells (e.g., at or about 5 million cells, at or about 25 million cells, at or about 50 million cells, at or about 500 million cells, at or about 1 billion cells, at or about 5 billion cells, at or about 20 billion cells, at or about 30 billion cells, at or about 40 billion cells, or a range defined by any two of the foregoing values), such as at or about 10 million to at or about 100 billion cells (e.g., at or about 20 million cells, at or about 30 million cells, at or about 40 million cells, at or about 60 million cells, at or about 70 million cells, at or about 80 million cells, at or about 90 million cells, at or about 10 billion cells, at or about 25 billion cells, at or about 50 billion cells, at or about 75 billion cells, at or about 90 billion cells, or a range defined by any two of the foregoing values), and in some cases at or about 100 million cells to at or about 50 billion cells (e.g., at or about 120 million cells, at or about 150 million cells, at or about 250 million cells, at or about 300 million cells, at or about 350 million cells, at or about 450 million cells, at or about 650 million cells, at or about 800 million cells, at or about 900 million cells, at or about 1.2 billion cells, at or about 3 billion cells, at or about 30 billion cells, at or about 45 billion cells) or any value in between these ranges, and/or such a number of cells per kilogram of body weight of the subject. In some aspects, in the context of genetically engineered cells expressing the recombinant receptor, e.g., CAR, a composition can contain at least the number of cells for administration for a dose of cell therapy, such as about or at least a number of cells described herein for administration, e.g., in Section LA (3).

The may be administered using standard administration techniques, formulations, and/or devices. Provided are formulations and devices, such as syringes and vials, for storage and administration of the compositions. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, intracranial, intrathoracic, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the therapeutic agent in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

Also provided are pharmaceutical compositions for combination therapy. Any of the additional agents for combination therapy described herein, such as agents described in Section I.B, can be prepared and administered as one or more pharmaceutical compositions, with the engineered cells expressing BCMA-binding recombinant receptors described herein. The combination therapy can be administered in one or more pharmaceutical compositions, e.g., where the cells expressing the recombinant receptor are in the same pharmaceutical composition as the additional agent, or in separate pharmaceutical compositions. For example, in some embodiments, the additional agent is an additional engineered cell, e.g., cell engineered to express a different recombinant receptor, and is administered in the same composition or in a separate composition. In some embodiments, each of the pharmaceutical composition is formulated in a suitable formulation according to the particular cells, e.g., engineered cells expressing the recombinant receptor, and/or additional agent, and the particular dosage regimen and/or method of delivery.

V. ARTICLES OF MANUFACTURE OR KITS

Also provided are articles of manufacture or kits containing the provided genetically engineered cells (e.g., expressing the BCMA-binding recombinant receptor), and/or compositions comprising the same and/or an additional therapeutic agent (e.g., recombinant IL-1Ra), for example, for combination therapy. Also provided are articles of manufacture or kits containing the provided recombinant receptors (e.g., CARs), genetically engineered cells, and/or compositions comprising the same. The articles of manufacture may include a container and a label or package insert on or associated with the container. Suitable containers include, for example, bottles, vials, syringes, test tubes, IV solution bags, etc. The containers may be formed from a variety of materials such as glass or plastic. In some embodiments, the container has a sterile access port. Exemplary containers include an intravenous solution bags, vials, including those with stoppers pierceable by a needle for injection. The article of manufacture or kit may further include a package insert indicating that the compositions can be used to treat a particular condition such as a condition described herein (e.g., multiple myeloma). Alternatively, or additionally, the article of manufacture or kit may further include another or the same container comprising a pharmaceutically-acceptable buffer. It may further include other materials such as other buffers, diluents, filters, needles, and/or syringes.

The label or package insert may indicate that the composition is used for treating the BCMA-expressing or BCMA-associated disease, disorder or condition in an individual. The label or a package insert, which is on or associated with the container, may indicate directions for reconstitution and/or use of the formulation. The label or package insert may further indicate that the formulation is useful or intended for subcutaneous, intravenous, or other modes of administration for treating or preventing a BCMA-expressing or BCMA-associated disease, disorder or condition in an individual.

The container in some embodiments holds a composition which is by itself or combined with another composition effective for treating, preventing and/or diagnosing the condition. The article of manufacture or kit may include (a) a first container with a composition contained therein (i.e., first medicament), wherein the composition includes the antibody (e.g., anti-BCMA antibody) or antigen-binding fragment thereof or recombinant receptor (e.g., CAR); and (b) a second container with a composition contained therein (i.e., second medicament), wherein the composition includes an additional agent, e.g., for combination therapy, such as an IL-1Ra (e.g. anakinra), a cytotoxic or other therapeutic agent, and which article or kit further comprises instructions on the label or package insert for treating the subject with the second medicament, in an effective amount.

VI. DEFINITIONS

As used herein, reference to a "corresponding form" of an antibody means that when comparing a property or activity of two antibodies, the property is compared using the same form of the antibody. For example, if it is stated that an antibody has greater activity compared to the activity of the corresponding form of a first antibody, that means that a particular form, such as an scFv of that antibody, has greater activity compared to the scFv form of the first antibody.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The terms "full length antibody," "intact antibody," and "whole antibody" are used herein interchangeably to refer to an antibody having a structure substantially similar to a native antibody structure or having heavy chains that contain an Fc region as defined herein.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-BCMA antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The terms "polypeptide" and "protein" are used interchangeably to refer to a polymer of amino acid residues, and are not limited to a minimum length. Polypeptides, including the antibodies and antibody chains and other peptides, e.g., linkers and BCMA-binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, "percent (%) amino acid sequence identity" and "percent identity" and "sequence identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid. Amino acid substitutions may be introduced into the recombinant receptor of interest and the products screened for a desired activity, e.g., retained/improved antigen binding, or decreased immunogenicity.

Amino acids generally can be grouped according to the following common side-chain properties:

(1) hydrophobic: Norleucine, Met, Ala, Val, Leu, Ile;

(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative amino acid substitutions will involve exchanging a member of one of these classes for another class.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, the singular forms "a," "an," and "the" include plural referents unless the context clearly dictates otherwise. For example, "a" or "an" means "at least one" or "one or more." It is understood that aspects, embodiments, and variations described herein include "comprising," "consisting," and/or "consisting essentially of" aspects, embodiments and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a "composition" refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

VII. EXEMPLARY EMBODIMENTS

Among the provided embodiments are:

1. A method of treating a subject having or suspected of having a disease or disorder associated with B-cell maturation antigen (BCMA) expression, the method comprising administering to the subject a dose of an interleukin-1 receptor antagonist (IL-1Ra) and a cell therapy comprising a dose of engineered T cells comprising a first chimeric antigen receptor (CAR) specific for BCMA, wherein at least one dose of the IL-1Ra is administered prior to the administration of the dose of engineered T cells.

2. A method of treating a subject having or suspected of having a disease or disorder associated with B-cell maturation antigen (BCMA) expression, the method comprising administering a cell therapy comprising a dose of engineered T cells comprising a first chimeric antigen receptor (CAR) specific for BCMA to a subject that has been administered at least one dose of an interleukin-1 receptor antagonist (IL-1Ra).

3. A method of treating a subject having or suspected of having a disease or disorder associated with B-cell maturation antigen (BCMA) expression, the method comprising administering at least one dose of an interleukin-1 receptor antagonist (IL-1Ra) to a subject who is a candidate for a cell therapy comprising a dose of engineered T cells comprising a first chimeric antigen receptor (CAR) specific for BCMA.

4. A method of reducing the severity of, attenuating, and/or preventing the onset of a toxicity in a subject having or suspected of having a disease or disorder associated with B-cell maturation antigen (BCMA) expression to be treated with a cell therapy, the method comprising administering to the subject a dose of an interleukin-1 receptor antagonist (IL-1Ra) and a cell therapy comprising a dose of engineered T cells comprising a first chimeric antigen receptor (CAR) specific for BCMA, wherein at least one dose of the IL-1Ra is administered prior to the administration of the dose of engineered T cells.

5. A method of reducing the severity of, attenuating, and/or preventing the onset of a toxicity in a subject having or suspected of having a disease or disorder associated with B-cell maturation antigen (BCMA) expression to be treated with a cell therapy, the method comprising administering a cell therapy comprising a dose of engineered T cells comprising a first chimeric antigen receptor (CAR) specific for BCMA to a subject that has been administered at least one dose of an interleukin-1 receptor antagonist (IL-1Ra).

6. A method of reducing the severity of, attenuating, and/or preventing the onset of a toxicity in a subject having or suspected of having a disease or disorder associated with B-cell maturation antigen (BCMA) expression to be treated with a cell therapy, the method comprising administering at least one dose of an interleukin-1 receptor antagonist (IL-1Ra) to a subject who is a candidate for a cell therapy comprising a dose of engineered T cells comprising a first chimeric antigen receptor (CAR) specific for BCMA.

7. The method of any of embodiments 1-6, wherein the subject has been administered the at least one dose of the IL-1Ra within at or about 24 hours prior to the dose of engineered T cells.

8. The method of any of embodiments 1-7, wherein the at least one dose of the IL-1Ra comprises at least two dose of the IL-1Ra.

9. A method of treating a subject having or suspected of having a disease or disorder associated with B-cell maturation antigen (BCMA) expression, the method comprising administering to the subject at least two doses of an interleukin-1 receptor antagonist (IL-1Ra) and a cell therapy comprising a dose of engineered T cells comprising a first chimeric antigen receptor (CAR) specific for BCMA, wherein at least one dose of the IL-1Ra is administered within at or about 24 hours prior to the dose of engineered T cells; and at least one dose of the IL-1Ra is administered after the administration of the administration of the dose of engineered T cells.

10. A method of treating a subject having or suspected of having a disease or disorder associated with B-cell maturation antigen (BCMA) expression, the method comprising administering to the subject at least two doses of an interleukin-1 receptor antagonist (IL-1Ra), wherein at least one dose of the IL-1Ra is administered within about or about 24 hours prior to administration of a cell therapy comprising a dose of engineered T cells comprising a first chimeric antigen receptor (CAR) specific for BCMA to the subject; and at least one dose of the IL-1Ra is administered after the administration of the dose of engineered T cells.

11. A method of treating a subject having or suspected of having a disease or disorder associated with B-cell maturation antigen (BCMA) expression, the method comprising administering to the subject a cell therapy comprising a dose of engineered T cells comprising a first chimeric antigen receptor (CAR) specific for BCMA, wherein the subject has been administered at least one dose of an interleukin-1 receptor antagonist (IL-1Ra) within about or about 24 hours prior to administration of the dose of engineered T cells; and the subject is to be administered at least one dose of the IL-1Ra after the administration of the dose of engineered T cells.

12. A method of treating a subject having or suspected of having a disease or disorder associated with B-cell maturation antigen (BCMA) expression, the method comprising:

administering a cell therapy comprising a dose of engineered T cells comprising a first chimeric antigen receptor (CAR) specific for BCMA to a subject that has been administered at least one dose of an interleukin-1 receptor antagonist (IL-1Ra) within at or about 24 hour prior to the administration of the dose of engineered T cells; and administering at least one dose of the IL-1Ra after the administration of the dose of engineered T cells.

13. A method of reducing the severity of, attenuating, and/or preventing the onset of a toxicity in a subject having or suspected of having a disease or disorder associated with B-cell maturation antigen (BCMA) expression to be treated with a cell therapy, the method comprising administering to the subject at least two doses of an interleukin-1 receptor antagonist (IL-1Ra) and a cell therapy comprising a dose of engineered T cells comprising a first chimeric antigen receptor (CAR) specific for BCMA, wherein at least one dose of the IL-1Ra is administered within at or about 24 hours prior to the administration of the dose of engineered T cells; and at least one dose of the IL-1Ra is administered after the administration of the dose of engineered T cells.

14. A method of reducing the severity of, attenuating, and/or preventing the onset of a toxicity in a subject having or suspected of having a disease or disorder associated with B-cell maturation antigen (BCMA) expression to be treated with a cell therapy, the method comprising administering a cell therapy comprising a dose of engineered T cells comprising a first chimeric antigen receptor (CAR) specific for BCMA to a subject that has been administered at least one dose of an interleukin-1 receptor antagonist (IL-1Ra) within at or about 24 hour prior to the administration of the dose of engineered T cells; and administering at least one dose of the IL-1Ra is administered after the administration of the dose of engineered T cells.

15. The method of any of embodiments 1-14, wherein the at least one dose of IL-1Ra administered prior to the administration of the dose of engineered T cells is administered within at or about 21, 18, 15 or 12 hours prior to the administration of the dose of engineered T cells.

16. The method of any of embodiments 1-15, wherein the at least one dose of the IL-Ra administered prior to the administration of the dose of engineered T cells comprises at least two doses of the IL-1Ra administered prior to the administration of the dose of engineered T cells.

17. The method of embodiment 16, wherein one dose of the at least two doses of IL-1Ra is administered prior to the administration of the dose of engineered T cells is administered within at or about 6, 5, 4, 3 or 2 hours prior to administration of the dose of engineered T cells.

18. The method of embodiment 16 or 17, wherein one dose of the at least two doses of IL-1Ra is administered prior to the administration of the dose of engineered T cells is administered within at or about 3 hours prior to the administration of the dose of engineered T cells.

19. The method of any of embodiments 16-18, wherein one dose of the at least two doses of IL-1Ra is administered within at or about 24 hours prior to the administration of the dose of engineered T cells, and one dose of the at least two doses of IL-1Ra is administered within at or about 3 hours prior to the administration of the dose of engineered T cells.

20. The method of any of embodiments 1-8 and 15-19, further comprising administering at least one dose of the IL-1Ra after the administration of the dose of engineered T cells.

21. The method of any of embodiments 9-20, wherein the at least one dose of the IL-1Ra administered after the administration of the dose of engineered T cells comprises at least 2, 3, 4, 5, 6, 7 or 8 doses of the IL-1Ra administered after the administration of the dose of engineered T cells.

22. The method of any of embodiments 9-21, wherein the at least one dose of the IL-1Ra administered after the administration of the dose of engineered T cells comprises 3, 4, 5, 6 or 7 doses of IL-1Ra administered after the administration of the dose of engineered T cells.

23. The method of any of embodiments 9-22, wherein the at least one dose of the IL-1Ra administered after the administration of the dose of engineered T cells comprises 4 doses of engineered T cells.

24. The method of any of embodiments 9-22, wherein the at least one dose of the IL-1Ra administered after the administration of the dose of engineered T cells comprises 5 doses of IL-1Ra administered after the administration of the dose of engineered T cells.

25. The method of any of embodiments 9-24, wherein the at least one dose of the IL-1Ra administered after the administration of the dose of engineered cells is administered daily for consecutive days.

26. The method of any of embodiments 9-25, wherein the at least one dose of IL-1Ra administered after the administration of the dose of engineered T cells is 4 doses, wherein one of the four doses is administered each day for 4 consecutive days after the administration of the dose of engineered T cells.

27. The method of any of embodiments 9-25, wherein the at least one dose of the IL-1Ra administered after the administration of the dose of engineered T cells is 5 doses administered daily for 5 consecutive days after the administration of the dose of engineered T cells.

28. The method of any of embodiments 20-27, wherein a dose of the IL-1Ra is administered every 24 hours (q24 h) on Days 2-5.

29. A method of reducing the severity of, attenuating, and/or preventing the onset of a toxicity in a subject having or suspected of having a disease or disorder associated with B-cell maturation antigen (BCMA) expression to be treated with a cell therapy, the method comprising administering to the subject at least 6 doses of an interleukin-1 receptor antagonist (IL-1Ra) and a cell therapy comprising a dose of engineered T cells comprising a first chimeric antigen receptor (CAR) specific for BCMA, wherein the cell therapy is administered on Day 1 and:

(a) one dose of the IL-1Ra is administered within about or about 24 hours prior to the administration of the dose of engineered T cells, optionally the night before the administration of the dose of the engineered T cells;

(b) one dose of the IL-1Ra is administered within about or about 3 hours prior to the administration of the dose of engineered T cells on Day 1;

(c) four doses of the IL-1Ra are administered after the administration of the dose of engineered T cells, wherein one dose of the four doses is administered each day on Days 2, 3, 4, and 5.

30. The method of any of embodiments 1-29, further comprising administering at least one additional dose of the IL-1Ra after the administration of the dose of engineered T cells if the subject exhibits symptoms or signs of a cytokine release syndrome (CRS).

31. The method of embodiment 30, wherein the at least one additional dose of the IL-1Ra comprises administration of a plurality of doses, optionally wherein the plurality of doses is administered daily for consecutive days, until the symptoms or signs of CRS is resolved.

32. The method of embodiment 31, wherein the plurality of doses is administered twice daily for consecutive days, until the symptoms or signs of CRS is resolved.

33. The method of any of embodiments 20-32, wherein, if the subject exhibits symptoms or signs of a cytokine release syndrome (CRS), a dose of IL-1Ra is administered every 12 hours (q12 h) until the symptoms or signs of CRS resolve.

34. The method of any of embodiments 30-33, wherein the daily administration of the IL-1Ra is administered at or about the same time each day.

35. The method of any of embodiments 1-34, wherein the IL-1Ra is a recombinant IL-1Ra.

36. The method of any of embodiments 1-35, wherein the IL-1Ra comprises the sequence set forth in SEQ ID NO:256 or a sequence having at least 90%, 91%, 92%, 93%, 94%, 95%, 96%, 97%, 98% or 99% or higher sequence identity to SEQ ID NO:256 that retains function as an IL-1R antagonist.

37. The method of any of embodiments 1-36, wherein the IL-1Ra is anakinra.

38. The method of embodiment 37, wherein anakinra is recombinant anakinra.

39. The method of any of embodiments 1-38, wherein each dose of the IL-1Ra is at or about 500 mg, at or about 400 mg, at or about 300 mg, at or about 200 mg, at or about 100 mg or at or about 50 mg, or a range defined by any of the foregoing, optionally wherein each dose of the recombinant IL-1Ra is from at or about 50 mg to at or about 200 mg.

40. The method of any of embodiments 1-39, wherein each dose of the IL-1Ra is at or about 100 mg.

41. The method of any of embodiments 1-40, wherein the IL-1Ra is administered subcutaneously.

42. The method of any of embodiments 1-41, wherein the method reduces the severity of, attenuates, and/or prevents the onset of a toxicity associated with administration of the cell therapy.

43. The method of any of embodiments 4-8 and 13-42, wherein the toxicity is a cytokine release syndrome (CRS).

44. The method of embodiment 43, wherein the CRS is a severe CRS or a grade 3 or higher CRS.

45. The method of any of embodiments 4-8 and 13-42, wherein the toxicity is a neurotoxicity (NT).

46. The method of embodiment 45, wherein the NT is a severe NT or a grade 2 or higher NT or a grade 3 or higher NT.

47. The method of any of embodiments 4-8 and 13-42, wherein the toxicity is a macrophage activation syndrome (MAS) or a hemophagocytic lympho-histiocytosis (HLH).

48. The method of any of embodiments 1-47, wherein at or prior to the administration of the dose of engineered T cells, the subject has been administered one or more prior BCMA-directed therapy selected from among:

a prior dose of engineered T cells comprising a second CAR specific for BCMA;

a prior administration of a BCMA-directed T cell engager (TCE); and a prior administration of a BCMA-directed antibody-drug conjugate (ADC).

49. A method of treating a subject having or suspected of having a disease or disorder associated with B-cell maturation antigen (BCMA) expression, the method comprising administering to the subject a cell therapy comprising a dose of engineered T cells comprising a first chimeric antigen receptor (CAR) specific for BCMA, wherein at or prior to the administration of the dose of engineered T cells, the subject has been administered one or more prior BCMA-directed therapy selected from among:

a prior dose of engineered T cells comprising a second CAR specific for BCMA;

a prior administration of a BCMA-directed T cell engager (TCE); and a prior administration of a BCMA-directed antibody-drug conjugate (ADC).

50. A method of treating a subject having or suspected of having a disease or disorder associated with B-cell maturation antigen (BCMA) expression, the method comprising administering to the subject a cell therapy comprising a dose of engineered T cells comprising a first chimeric antigen receptor (CAR) specific for BCMA, to a subject that has previously received one or more prior BCMA-directed therapy selected from among:

a prior dose of engineered T cells comprising a second CAR specific for BCMA;

a prior administration of a BCMA-directed T cell engager (TCE); and a prior administration of a BCMA-directed antibody-drug conjugate (ADC).

51. The method of any of embodiments 48-50, wherein the subject has relapsed following or has been refractory to the one or more prior BCMA-directed therapy.

52. The method of any of embodiments 48-51, wherein the subject has relapsed following or has been refractory to the one or more prior BCMA-directed therapy within at or about 1 year prior to the administration of the dose of engineered T cells comprising the first CAR.

53. The method of any of embodiments 48-51, wherein the subject has relapsed following or has been refractory to the one or more prior BCMA-directed therapy within at or about 6 months prior to the administration of the dose of engineered T cells comprising the first CAR.

54. The method of any of embodiments 48-51, wherein the subject has relapsed following or has been refractory to the one or more prior BCMA-directed therapy within at or about 3 months prior to the administration of the dose of engineered T cells comprising the first CAR.

55. The method of any of embodiments 48-54, wherein the BCMA-directed TCE is or comprises a bispecific antibody or a bispecific T cell engager (BiTE).

56. The method of any of embodiments 48-55, wherein the BCMA-directed TCE is selected from among one or more of AMG 420/BI 836909, AMG 701, CC-93269, JNJ-64007957, PF-06863135 and REGN5458.

57. The method of any of embodiments 48-56, wherein the BCMA-directed ADC is selected from among one or more of Belantamab mafodotin (GSK2857916), MEDI2228, CC-99712 and AMG 224.

58. The method of any of embodiments 1-57, wherein the first CAR comprises:

(a) an extracellular antigen-binding domain, comprising:

a variable heavy chain ($V_H$) comprising a heavy chain complementarity determining region 1 (CDR-H1), a heavy chain complementarity determining region 2 (CDR-H2) and a heavy chain complementarity determining region 3 (CDR-H3) contained within the sequence set forth in SEQ ID NO: 116 and a variable light chain ($V_L$) comprising a light chain complementarity determining region 1 (CDR-L1), a light chain complementarity determining region 2 (CDR-L2) and a light chain complementarity determining region 3 (CDR-L3) contained within the sequence set forth in SEQ ID NO: 119;

a $V_H$ comprising a CDR-H1, a CDR-H2 and a CDR-H3 sequences set forth in SEQ ID NOS:97, 101 and 103, respectively, and a $V_L$ comprising a CDR-L1, a CDR-L2 and a CDR-L3 sequences set forth in SEQ ID NOS:105, 107 and 108, respectively;

a $V_H$ comprising a CDR-H1, a CDR-H2 and a CDR-H3 sequences set forth in SEQ ID NOS:96, 100 and 103, respectively, and a $V_L$ comprising a CDR-L1, a CDR-L2 and a CDR-L3 sequences set forth in SEQ ID NOS:105, 107 and 108, respectively;

a $V_H$ comprising a CDR-H1, a CDR-H2 and a CDR-H3 sequences set forth in SEQ ID NOS:95, 99 and 103, respectively, and a $V_L$ comprising a CDR-L1, a CDR-L2 and a CDR-L3 sequences set forth in SEQ ID NOS: 105, 107 and 108, respectively;

a $V_H$ comprising a CDR-H1, a CDR-H2 and a CDR-H3 sequences set forth in SEQ ID NOS:94, 98 and 102, respectively, and a $V_L$ comprising a CDR-L1, a CDR-L2 and a CDR-L3 sequences set forth in SEQ ID NOS: 104, 106 and 108, respectively; or a $V_H$ comprising the amino acid sequence of SEQ ID NO: 116 and a $V_L$ comprising the amino acid sequence of SEQ ID NO: 119;

(b) a spacer comprising an IgG4/2 chimeric hinge or a modified IgG4 hinge; an IgG2/4 chimeric $C_H2$ region; and an IgG4 $C_H3$ region, which optionally is about 228 amino acids in length; or a spacer set forth in SEQ ID NO: 174;

(c) a transmembrane domain, optionally a transmembrane domain from a human CD28; and (d) an intracellular signaling region comprising a cytoplasmic signaling domain of a CD3-zeta (CD3ζ) chain and a costimulatory signaling region comprising an intracellular signaling domain of a T cell costimulatory molecule or a signaling portion thereof.

59. The method of embodiment 58, wherein the $V_H$ is or comprises the amino acid sequence of SEQ ID NO: 116; and the $V_L$ is or comprises the amino acid sequence of SEQ ID NO: 119.

60. The method of embodiment 58 or 59, wherein the extracellular antigen-binding domain comprises an scFv.

61. The method of any of embodiments 58-60, wherein the $V_H$ and the $V_L$ are joined by a flexible linker, optionally wherein the flexible linker comprises the amino acid sequence GGGGSGGGGSGGGGS (SEQ ID NO:1).

62. The method of any of embodiments 58-61, wherein the $V_H$ is carboxy-terminal to the $V_L$.

63. The method of any of embodiments 58-62, wherein the extracellular antigen-binding domain comprises the amino acid sequence of SEQ ID NO: 114 or an amino acid sequence having at least 90%, 91%, 92%, 93%, 94%, 95%, 96%, 97%, 98%, or 99% sequence identity to the amino acid sequence of SEQ ID NO: 114.

64. The method of any of embodiments 58-63, wherein the extracellular antigen-binding domain comprises the amino acid sequence of SEQ ID NO: 114.

65. The method of any of embodiments 58-64, wherein a nucleic acid encoding the extracellular antigen-binding domain comprises (a) the sequence of nucleotides of SEQ ID NO:113; (b) a sequence of nucleotides that has at least 90% sequence identity thereto; or (c) a degenerate sequence of (a) or (b).

66. The method of any of embodiments 58-65, wherein the nucleic acid encoding the extracellular antigen-binding domain comprises the sequence of nucleotides of SEQ ID NO:115.

67. The method of any of embodiments 58-66, wherein the transmembrane domain is or comprises a transmembrane domain from human CD28.

68. The method of any of embodiments 58-67, wherein the transmembrane domain is or comprises the sequence set forth in SEQ ID NO:138 or a sequence of amino acids that has at least 90% sequence identity to SEQ ID NO:138.

69. The method of any of embodiments 1-57, wherein the first CAR comprises an extracellular antigen-binding domain comprising:

a variable heavy chain ($V_H$) comprising a heavy chain complementarity determining region 1 (CDR-H1), a heavy chain complementarity determining region 2 (CDR-H2) and a heavy chain complementarity determining region 3 (CDR-H3) contained within the sequence set forth in SEQ ID NO: 125 and a variable light chain ($V_L$) comprising a light chain complementarity determining region 1 (CDR-L1), a light chain complementarity determining region 2 (CDR-L2) and a light chain complementarity determining region 3 (CDR-L3) contained within the sequence set forth in SEQ ID NO: 127; and/or a $V_H$ comprising a CDR-H1, a CDR-H2 and a CDR-H3 sequences set forth in SEQ ID NOS: 260, 261, and 262, respectively, and a $V_L$ comprising a CDR-L1, a CDR-L2 and a CDR-L3 sequences set forth in SEQ ID NOS: 257, 258, and 259, respectively.

70. The method of embodiment 69, wherein the $V_H$ is or comprises the amino acid sequence of SEQ ID NO: 125; and the $V_L$ is or comprises the amino acid sequence of SEQ ID NO: 127.

71. The method of embodiment 69 or embodiment 70, wherein the extracellular antigen-binding domain comprises the amino acid sequence of SEQ ID NO: 128 or an amino acid sequence having at least 90%, 91%, 92%, 93%, 94%, 95%, 96%, 97%, 98%, or 99% sequence identity to the amino acid sequence of SEQ ID NO: 128.

72. The method of any of embodiments 58-71, wherein the cytoplasmic signaling domain is or comprises the sequence set forth in SEQ ID NO:143 or a sequence of amino acids that has at least 90% sequence identity to SEQ ID NO:143.

73. The method of any of embodiments 58-72, wherein the costimulatory signaling region comprises an intracellular signaling domain of CD28, 4-1BB, or ICOS, or a signaling portion thereof.

74. The method of any of embodiments 58-73, wherein the costimulatory signaling region comprises an intracellular signaling domain of 4-1BB, optionally human 4-1BB.

75. The method of any of embodiments 58-74, wherein the costimulatory signaling region is or comprises the sequence set forth in SEQ ID NO:4 or a sequence of amino acids that has at least 90% sequence identity to the sequence set forth in SEQ ID NO: 4.

76. The method of any of embodiments 58-75, wherein the costimulatory signaling region is between the transmembrane domain and the cytoplasmic signaling domain of a CD3-zeta (CD31) chain.

77. The method of any of embodiments 1-76, wherein the first CAR comprises from its N to C terminus in order: the extracellular antigen-binding domain, the spacer, the transmembrane domain and the intracellular signaling region.

78. The method of any of embodiments 1-77, wherein the first CAR comprises (a) an extracellular antigen-binding domain, comprising:

a variable heavy chain ($V_H$) comprising a heavy chain complementarity determining region 1 (CDR-H1), a heavy chain complementarity determining region 2 (CDR-H2) and a heavy chain complementarity determining region 3 (CDR-H3) contained within the sequence set forth in SEQ ID NO: 116 and a variable light chain ($V_L$) comprising a light chain complementarity determining region 1 (CDR-L1), a light chain complementarity determining region 2 (CDR-L2) and a light chain complementarity determining region 3 (CDR-L3) contained within the sequence set forth in SEQ ID NO: 119;

(b) a spacer comprising a modified IgG4 hinge; an IgG2/4 chimeric $C_H2$ region; and an IgG4 $C_H3$ region, that is about 228 amino acids in length;

(c) a transmembrane domain from a human CD28; and (d) an intracellular signaling region comprising a cytoplasmic signaling domain of a CD3-zeta (CD3ζ) chain and a costimulatory signaling region comprising an intracellular signaling domain of a 4-1BB.

79. The method of any of embodiments 1-78, wherein the first CAR comprises (a) an extracellular antigen-binding domain, comprising the sequence set forth in SEQ ID NO: 114 or a sequence of amino acids having at least 90% sequence identity to the amino acid sequence of SEQ ID NO: 114;

(b) a spacer comprising the sequence set forth in SEQ ID NO: 174 or a sequence of amino acids that has at least 90% sequence identity to SEQ ID NO:174;

(c) a transmembrane domain comprising the sequence set forth in SEQ ID NO:138 or a sequence of amino acids that has at least 90% sequence identity to SEQ ID NO:138; and (d) an intracellular signaling region comprising a cytoplasmic signaling comprising the sequence set forth in SEQ ID NO:143 or a sequence of amino acids that has at least 90% sequence identity to SEQ ID NO:143 and a costimulatory signaling region comprising the sequence set forth in SEQ ID NO:4 or a sequence of amino acids that has at least 90% sequence identity to the sequence set forth in SEQ ID NO: 4.

80. The method of any of embodiments 1-79, wherein the first CAR comprises (a) an extracellular antigen-binding domain, comprising the sequence set forth in SEQ ID NO: 114;

(b) a spacer comprising the sequence set forth in SEQ ID NO: 174;

(c) a transmembrane domain comprising the sequence set forth in SEQ ID NO:138; and (d) an intracellular signaling region comprising a cytoplasmic signaling comprising the sequence set forth in SEQ ID NO:143 and a costimulatory signaling region comprising the sequence set forth in SEQ ID NO:4.

81. The method of any of embodiments 1-80, wherein the first CAR comprises the sequence set forth in SEQ ID NO:19.

82. The method of any of embodiments 1-81, wherein the first CAR is encoded by a polynucleotide sequence comprising the sequence set forth in SEQ ID NO: 13 or a sequence that exhibits at least 85%, 86%, 87%, 88%, 89%, 90%, 91%, 92%, 93%, 94%, 95%, 96%, 97%, 98%, or 99% sequence identity thereto.

83. The method of any of embodiments 1-68 and 72-82, wherein the first CAR is encoded by a polynucleotide sequence comprising the sequence set forth in SEQ ID NO: 13.

84. The method of any of embodiments 1-57 and 69-77, wherein the first CAR comprises the sequence set forth in SEQ ID NO:312.

85. The method of any of embodiments 48-84, wherein the first CAR and the second CAR bind to the same epitope of BCMA.

86. The method of any of embodiments 48-84, wherein the first CAR and the second CAR bind to different epitopes of BCMA.

87. The method of any of embodiments 48-86, wherein the first CAR and the second CAR are different.

88. The method of any of embodiments 48-87, wherein the second CAR comprises:

a $V_H$ region comprising a CDR-H1, a CDR-H2, and a CDR-H3 comprising the amino acid sequence of SEQ ID NOs:260, 261, and 262, respectively; and a NIL region comprising a CDR-L1, CDR-L2, and CDR-L3 comprising the amino acid sequence of SEQ ID NOs:257, 258, and 259, respectively;

a $V_H$ region comprising the sequence set forth in SEQ ID NO:125 and a $V_L$ region comprising the sequence set forth in SEQ ID NO:127;

the amino acid residues 22-493 of the sequence set forth in SEQ ID NO:263; and/or the sequence encoded by SEQ ID NO:264.

89. The method of any of embodiments 48-88, wherein the second CAR is a multivalent CAR.

90. The method of any of embodiments 48-89, wherein the second CAR comprises the amino acid residues beginning at residue 22 to the end of the sequence set forth in any one of SEQ ID NOS: 265-302.

91. The method of any of embodiments 48-89, wherein the second CAR comprises a Centyrin-containing CAR.

92. The method of any of embodiments 48-91, wherein the second CAR comprises the amino acid residues 22-334 of the sequence set forth in SEQ ID NO: 310.

93. The method of any of embodiments 48-85, wherein the first CAR and the second CAR are the same.

94. The method of any of embodiments 48-93, wherein the dose of engineered T cells comprising the first CAR is generated from a sample comprising T cells obtained from the same subject that has previously been administered the prior dose of engineered T cells comprising the second CAR.

95. The method of any of embodiments 48-94, wherein the dose of engineered T cells comprising the first CAR is generated from a sample comprising T cells obtained from the subject after the subject has been administered the prior dose of engineered T cells comprising the second CAR.

96. The method of any of embodiments 48-95, wherein prior to administering the dose of engineered T cells comprising the first CAR, the method further comprises assessing, in a test sample obtained from the subject, the presence or amount of (i) cells expressing the second CAR or a (ii) nucleotide sequence present in the construct encoding the second CAR.

97. The method of any of embodiments 94-96, wherein the test sample is obtained from the subject at the same time as obtaining the sample comprising T cells for generating the dose of engineered T cells comprising the first CAR from the same subject.

98. The method of any of embodiments 48-97, wherein prior to the administration of the dose of engineered T cells comprising the first CAR, the method further comprises assessing the presence or amount of (i) cells expressing the second CAR or (ii) a nucleotide sequence present in the construct encoding the second CAR in a composition comprising the dose of engineered T cells comprising the first CAR.

99. The method of any of embodiments 96-98, wherein the assessing the presence or amount of cells expressing the second CAR is carried out by contacting the sample or the composition comprising the dose of engineered T cells with a purified or recombinant BCMA, optionally a BCMA-Fc.

100. The method of any of embodiments 96-98, wherein the assessing the presence or amount of the nucleotide sequence present in a construct encoding the second CAR is carried out by quantitative polymerase chain reaction (qPCR).

101. The method of any of embodiments 58-100, wherein the binding of the extracellular antigen-binding domain and/or the first CAR, or a measure indicative of function or activity of the first CAR following exposure to cells expressing surface BCMA, is not reduced or blocked or is not substantially reduced or blocked in the presence of a soluble or shed form of BCMA.

102. The method of embodiment 101, wherein the concentration or amount of the soluble or shed form of BCMA corresponds to a concentration or amount present in the serum or blood or plasma of the subject or of a multiple myeloma patient, or on average in a multiple myeloma patient population, or at a concentration or amount of the soluble or shed BCMA at which the binding or measure is reduced or blocked, or is substantially reduced or blocked, for cells expressing a reference anti-BCMA recombinant receptor, optionally a reference anti-BCMA CAR, in the same assay.

103. The method of any of embodiments 1-102, wherein the dose of engineered T cells comprising the first CAR comprises between at or about $1\times10^7$ CAR+ T cells and at or about $2\times10^9$ CAR+ T cells.

104. The method of any of embodiments 1-103, wherein the dose of engineered T cells comprising the first CAR comprises between at or about $1\times10^7$ CAR+ T cells and at or about $1\times10^9$ CAR+ T cells.

105. The method of any of embodiments 1-104, wherein the dose of engineered T cells comprising the first CAR comprises between at or about $1\times10^8$ CAR+ T cells and at or about $8\times10^8$ CAR+ T cells.

106. The method of any of embodiments 1-104, wherein the dose of engineered T cells comprises at or about $5\times10^7$ cells or CAR+ T cells.

107. The method of any of embodiments 1-105, wherein the dose of engineered T cells comprising the first CAR comprises at or about $1.5\times10^8$ cells or CAR+ T cells.

108. The method of any of embodiments 1-105, wherein the dose of engineered T cells comprising the first CAR comprises at or about $3\times10^8$ cells or CAR+ T cells.

109. The method of any of embodiments 1-105, wherein the dose of engineered T cells comprising the first CAR comprises at or about $4.5\times10^8$ cells or CAR+ T cells.

110. The method of any of embodiments 1-105, wherein the dose of engineered T cells comprising the first CAR comprises at or about 5.5×108 cells or CAR+ T cells.

111. The method of any of embodiments 1-105, wherein the dose of engineered T cells comprising the first CAR comprises at or about $6\times10^8$ cells or CAR+ T cells.

112. The method of any of embodiments 1-111, wherein the dose of engineered T cells comprising the first CAR comprises a combination of $CD4^+$ T cells and $CD8^+$ T cells.

113. The method of any of embodiments 1-112, wherein the dose of engineered T cells comprising the first CAR comprise a combination of $CD4^+$ CAR+ T cells and $CD8^+$ CAR+ T cells.

114. The method of embodiment 112 or 113, wherein the ratio of $CD4^+$ CAR+ T cells to $CD8^+$ CAR+ T cells and/or of $CD4^+$ T cells to $CD8^+$ T cells is or is approximately 1:1 or is between at or approximately 1:3 and at or approximately 3:1.

115. The method of any of embodiments 1-114, wherein the dose of engineered T cells comprising the first CAR comprises $CD3^+$ CAR+ T cells.

116. The method of any of embodiments 1-115, wherein less than at or about 25%, 20%, 15%, 10%, 9%, 8%, 7%, 6%, 5%, 4%, 3%, 2% or 1% of the CAR+ T cells in the dose of engineered T cells comprising the first CAR express a marker of apoptosis, optionally Annexin V or active Caspase 3.

117. The method of any of embodiments 1-116, wherein prior to the administration of the dose of engineered T cells comprising the first CAR, the subject has been administered a lymphodepleting therapy comprising the administration of fludarabine at or about 20-40 mg/m$^2$ body surface area of the subject, optionally at or about 30 mg/m$^2$, daily, for 2-4 days, and/or cyclophosphamide at or about 200-400 mg/m$^2$ body surface area of the subject, optionally at or about 300 mg/m$^2$, daily, for 2-4 days.

118. The method of embodiment 117, wherein the lymphodepleting therapy comprises the administration of fludarabine at or about 30 mg/m$^2$body surface area of the subject, daily, and cyclophosphamide at or about 300 mg/m$^2$ body surface area of the subject, daily, for 3 days.

119. The method of any of embodiments 1-118, wherein the disease or disorder—associated with BCMA expression is an autoimmune disease or disorder.

120. The method of any of embodiments 1-119, wherein the disease or disorder associated with BCMA expression is a cancer, optionally a BCMA-expressing cancer.

121. The method of embodiment 120, wherein the cancer is a B cell malignancy. 122. The method of embodiment 120 or 121, wherein the cancer is a lymphoma, a leukemia, or a plasma cell malignancy.

123. The method of any of embodiments 120-122, wherein the cancer is a lymphoma and the lymphoma is Burkitt's lymphoma, non-Hodgkin's lymphoma (NHL), Hodgkin's lymphoma, Waldenstrom macroglobulinemia, follicular lymphoma, small non-cleaved cell lymphoma, mucosa-associated lymphatic tissue lymphoma (MALT), marginal zone lymphoma, splenic lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), or mantle cell lymphoma (MCL).

124. The method of any of embodiments 120-122, wherein the cancer is a leukemia and the leukemia is chronic lymphocytic leukemia (CLL), plasma cell leukemia or acute lymphocytic leukemia (ALL).

125. The method of any of embodiments 120-122, wherein the cancer is a plasma cell malignancy and the plasma cell malignancy is multiple myeloma (MM) or plasmacytoma.

126. The method of any of embodiments 120-122 and 125, wherein the cancer is multiple myeloma (MM), optionally a relapsed or refractory multiple myeloma (R/R MM).

127. The method of any of embodiments 1-126, wherein the subject has been administered three or more prior therapies for the disease or disorder, optionally four or more prior therapies, optionally selected from among:

autologous stem cell transplant (ASCT);

an immunomodulatory agent;

a proteasome inhibitor; and an anti-CD38 antibody.

128. The method of embodiment 127, wherein the immunomodulatory agent is selected from among thalidomide, lenalidomide and pomalidomide.

129. The method of embodiment 127 or 128, wherein the proteasome inhibitor is selected from among bortezomib, carfilzomib and ixazomib.

130. The method of any of embodiments 127-129, wherein the anti-CD38 antibody is or comprises daratumumab.

131. The method of any of embodiments 1-130, wherein the subject has been administered between 3 and 15 or between 4 and 15 prior therapies, or about 10 prior therapies.

132. The method of any of embodiments 127-131, wherein the subject has relapsed following or has been refractory to one or more of the 3 or more prior therapies.

133. The method of any of embodiments 127-132, wherein the subject has relapsed following or has been refractory to at least 3 or at least 4 of the 3 or more prior therapies.

134. The method of embodiment 132 or 133, wherein the subject has been refractory to or has not responded to bortezomib, carfilzomib, lenalidomide, pomalidomide and/or an anti-CD38 monoclonal antibody.

135. The method of any of embodiments 1-134, wherein the subject has had prior autologous stem cell transplant.

136. The method of any of embodiments 1-134, wherein the subject has not had prior autologous stem cell transplant.

137. The method of any of embodiments 1-136, wherein the subject does not have an active or a history of plasma cell leukemia (PCL).

138. The method of any of embodiments 1-137, wherein the subject has developed secondary plasma cell leukemia (PCL).

139. The method of any of embodiments 1-138, wherein the subject is an adult subject or is 25 or 35 years of age or older.

140. The method of any of embodiments 1-139, wherein the subject has a time from diagnosis of the disease or disorder of approximately 4 years or between 2 and 15 years or between 2 and 12 years.

141. The method of any of embodiments 1-140, wherein the subject has IMWG high risk cytogenetics.

VIII. EXAMPLES

The following examples are included for illustrative purposes only and are not intended to limit the scope of the invention.

Example 1: Generation of Nucleic Acid Constructs and Chimeric Antigen Receptors (CARs) Binding to BCMA Polynucleotides encoding exemplary chimeric antigen receptors (CARs), each containing a human anti-BCMA scFv antigen-binding domain, were generated. Among the CARs generated were CARs containing scFvs containing $V_H$ and $V_L$ sequences described in WO2016090320, WO2016090327 and WO2019090003. In some cases of the scFv, the $V_H$ was amino-terminal to the $V_L$ and in some cases the $V_L$ was amino-terminal to the $V_H$. Exemplary scFv regions in generated CARs are set forth in Table E1.

TABLE E1

| Sequence identifier (SEQ ID NO) for Exemplary scFvs | | | | | | | | | |
|---|---|---|---|---|---|---|---|---|---|
| Antigen-binding domain | CDR-H1 | CDR-H2 | CDR-H3 | CDR-L1 | CDR-L2 | CDR-L3 | $V_H$ | $V_L$ | scFv |
| BCMA-23 | 34 | 35 | 36 | 22 | 23 | 24 | 32 | 33 | 29 |
| BCMA-25 | 37 | 38 | 39 | 40 | 41 | 42 | 52 | 53 | 49 |
| BCMA-26 | 34 | 35 | 54 | 55 | 56 | 57 | 61 | 62 | 58 |
| BCMA-52 | 66 | 70 | 72 | 74 | 76 | 77 | 85 | 88 | 83 |
| BCMA-55 | 97 | 101 | 103 | 105 | 107 | 108 | 116 | 119 | 114 |

Epitopes recognized, e.g., specifically bound by exemplary anti-BCMA scFv clones, were determined based on full discontinuous epitope mapping by Chemical Linkage of Peptides onto Scaffolds (CLIPS; Pepscan Presto BV, Lelystad, The Netherlands; see, e.g., Timmerman et al., (2007) J. Mol. Recognit. 20: 283-329). BCMA-23 and BCMA-25 scFv were observed to bind to a peptide of SNTPPLTCQR (set forth in SEQ ID NO:160), which could be recognized in a linear form. In some aspects, such antibodies recognize a non-linear or linear epitope including residues of such peptide of SEQ ID NO: 160, and in some aspects recognize a non-linear epitope further including residues of CIPCQLR (set forth in SEQ ID NO:159), SNTPPLTCQR and/or SVTNSVK (set forth in SEQ ID NO:161). The BCMA-26 scFv was observed to recognize an epitope comprising residues present in CSQNEYF (set forth in SEQ ID NO:162) and LLHACIPCQLR (set forth in SEQ ID NO:158). BCMA-52-scFv-mFc was observed to bind to an epitope containing residues of the following discontinuous peptides: QNEYF (SEQ ID NO:91), CIPCQL (SEQ ID NO:92), and CQRYC (SEQ ID NO:93). BCMA-55-scFv was observed to specifically bind to an epitope containing residues present in peptides comprising discontinuous portions of the human BCMA polypeptide sequence, individually comprising the following sequences: MLMAG (SEQ ID NO:122), YFDSLL (SEQ ID NO:123), and QLRCSSNTPPL (SEQ ID NO:124).

The exemplary polynucleotide CAR constructs contained nucleic acids encoding a human IgG-kappa signaling sequence (SEQ ID NO: 167, encoding SEQ ID NO: 166); a human anti-BCMA scFv set forth above; a spacer (such as a spacer containing a modified IgG4-hinge $C_H2$-$C_H3$ (SEQ ID NO:175, encoding SEQ ID NO:174); also referred to as a "long spacer" or LS); a human CD28 transmembrane domain; a human 4-1BB-derived intracellular co-signaling sequence; and a human CD3-zeta derived intracellular signaling domain.

The nucleotide sequences encoding various BCMA CARs were assessed for potential splice sites and modified in a conservative manner, including removal of potential predicted cryptic splice donor and acceptor sites.

cDNA clones encoding such CARs, were linked to a downstream ribosomal skip element (such as T2A-encoding sequence SEQ ID NO: 244 or 245, encoding SEQ ID NO: 243) followed by a truncated receptor-encoding sequence, and cloned into a lentiviral expression vector.

Example 2: Administration of Anti-BCMA CAR-Expressing Cells to Subjects with Relapsed or Refractory Multiple Myeloma (MM)

Chimeric antigen-receptor (CAR)-expressing T cell compositions containing autologous T cells expressing a CAR specific for B-cell maturation antigen (BCMA) were administered to human subjects with relapsed and/or refractory multiple myeloma (MM).

A. Subjects and Treatment

Compositions containing autologous T cells engineered to express an exemplary CAR specific for BCMA, described in Example 1 above, were administered to adult human subjects with relapsed or refractory (R/R) multiple myeloma (MM), who had received 3 or more prior treatments (the 3 or more prior treatments including at least a proteasome inhibitor, an immunomodulatory agent and an anti-CD38 monoclonal antibody, in each case unless the subject was not a candidate to receive such treatment such as by way of it being contraindicated).

The administered T cell compositions had been generated by a process including immunoaffinity-based enrichment of CD4+ and CD8+ cell populations from leukapheresis samples from individual subjects with MM, combining cells of such populations, such as at or at approximately a 1:1 ratio, and subjecting the combined cells to processing steps including for stimulation, cell transduction and expansion, in an exemplary serum-free media, cryopreservation, and generation of cells with a range of CD4+ to CD8+ CAR T cell ratios. The process resulted in a cell composition that was observed to be enriched for a central memory phenotype as compared to the starting samples and to cell compositions generated using a different manufacturing process. The CAR contained a BCMA-55-derived scFv binding domain, a modified IgG-derived $C_H2$-$C_H3$-hinge spacer, a CD28 transmembrane domain, and an intracellular signaling region including, in series, a 4-1BB endodomain and a CD3zeta endodomain, as described in Example 1.

Two to seven days prior to CAR+ T cell infusion, subjects received a lymphodepleting chemotherapy (LDC) with fludarabine (flu, 30 $mg/m^2$/day) and cyclophosphamide (Cy, 300 $mg/m^2$/day) for 3 days, the LDC completed at least 48 hours prior to CAR+ T cell infusion. The cryopreserved cell compositions were thawed at bedside prior to intravenous administration, with the day of infusion being designated day 1. On day 1, subjects were administered a dose of CAR-expressing T cells as follows: a single dose of dose level 1 (DL1) containing $5\times10^7$ total CAR-expressing T cells, or a single dose of dose level 2 (DL2) containing $1.5\times10^8$ total CAR-expressing T cells.

At a particular time point of analysis, 19 adult subjects had been enrolled in an ongoing clinical study involving such therapy. Of these 19 subjects at this particular time point, 13 subjects had been administered the anti-BCMA CAR+ cells, each either at DL1 or DL2. Of these 13 subjects, at this particular time point in the ongoing study, 8 subjects were evaluable for attributes indicative of safety (evaluability based on ≥1 month follow-up) (n=5 DL1; n=3 DL2). One subject had been unable to receive CAR+ T cells, due to sepsis after LDC, leading to death before CAR+ T cell administration. Three subjects (all DL1) were evaluable at this time point for confirmed response (evaluability based on ≥2 month follow-up) according to International Myeloma Working Group (IMWG) uniform response criteria (Kumar et al. (2016) Lancet Oncol 17(8):e328-346).

For these 8 subjects assessed at this time point, median follow-up was 5 weeks (range 4-13 weeks). Median age was 53 years (range 36-66 years) with a median time from diagnosis of 4 years (range 2-12 years). Subjects had received a median of 10 prior regimens (range 4-15 prior regimens) for MM. Of the 8 subjects, 4 (50%) had been refractory (no response or progression within 60 days of last therapy) to bortezomib, carfilzomib, lenalidomide, pomalidomide and an anti-CD38 monoclonal antibody. Seven of the 8 subjects (88%) had received prior autologous stem cell transplant, and 4 of 8 (50%) had IMWG high risk cytogenetics.

At the time of the assessment at the time point in the ongoing study, no dose-limiting toxicities (DLTs) had been observed in the subjects assessed receiving DL1 or DL2. Cytokine release syndrome (CRS), all grade 1 or 2, had been observed in 6 of the 8 (75%) subjects at the time point. Median onset of CRS at the time point among the 8 subjects was 9 days (range 4-10 days) with a median duration of 4.5 days (range 2-19 days). None of the subjects with grade 2 CRS at the time point had required vasopressor support and only 1 subject had received tocilizumab. None of the subjects had exhibited CRS of grade 3 or higher. Three of 8 (38%) subjects had experienced neurologic adverse events (AE). Two of the eight subjects at the time point had exhibited grade 1 events, and 1 had exhibited a grade 3 event (lethargy), which had resolved within 24 hours after receiving steroids. Onset of neurologic AEs was 9, 11 and 12 days, with a duration of 2, 3 and 1 days, respectively, for the 3 subjects experiencing neurological AE. The subject who had experienced grade 3 neurotoxicity (NT) as-of the analysis at this time point had developed secondary plasma cell leukemia (PCL) just prior to receiving LDC.

All 8 subjects at the time point were observed to have had evidence of objective response, including the subject with secondary PCL. Three subjects, all administered DL1, were observed to have achieved confirmed responses (1 partial response, PR; 2 stringent complete response, sCR), whereas the remaining subjects remained unconfirmed (1 complete response, CR; 2 very good partial response, VGPR; 1 PR, 1 minimal response, MR). As of the time point for assessment, no subject had been observed to have progressed.

The results showed that at the assessed dose levels, administration of the anti-BCMA CAR cell therapy exhibited favorable safety profiles, with no DLTs reported at this time point in an ongoing clinical study. The results were consistent with a conclusion that at this time point the incidence of grade 3 or higher NT was low, and no grade 3 or higher CRS had been observed with clinical response.

Example 3: Further Assessment of Response and Safety Outcomes Following Administration of Anti-BCMA CAR-Expressing Cells to Subjects with Relapsed or Refractory Multiple Myeloma (MM)

Response and safety outcomes were assessed in subjects at subsequent points in time in the clinical study described in Example 2, with certain additional subjects receiving different doses of cells.

A. Subjects and Treatment

The analysis at the time points presented in this example is based on assessment of a total of 44 subjects that had been administered the anti-BCMA CAR-expressing cells. The 44 subjects were adult human subjects with relapsed or refractory (R/R) multiple myeloma (MM), who had received and failed 3 or more prior treatments (the 3 or more prior treatments including at least (1) an autologous stem cell transplantation, (2) a proteasome inhibitor and an immunomodulatory agent, either alone or in combination, and (3) an anti-CD38 monoclonal antibody, as a part of a combination therapy or a monotherapy, in each case unless the subject was not a candidate to receive such treatment such as by way of it being contraindicated). Among the subjects treated were subjects that had failed the last line of therapy, and having Eastern Cooperative Oncology Group (ECOG) scores of between 0 and 1. The subjects were not selected based on the level of BCMA expression in a sample from the subject.

On day 1, subjects were administered a dose of CAR+ T cells as follows: a single dose of dose level 1 (DL1) containing $5\times10^7$ total CAR+ T cells, a single dose of dose level 2 (DL2) containing $1.5\times10^8$ total CAR+ T cells, a single dose of dose level 2A (DL2A) containing $3.0\times10^8$ total CAR+ T cells, or a single dose of dose level 3 (DL3) containing $4.5\times10^8$ total CAR+ T cells. On day 15 after administration, a bone marrow examination was performed, and disease was assessed on day 29 after administration.

Subjects were monitored over time for response, including the objective response rate (ORR), complete response (CR), stringent complete response (sCR), partial response (PR), very good partial response (VGPR), minimal residual disease (MRD), progressive disease (PD), stable disease (SD), and minimal response (MR) (e.g., according to International Myeloma Working Group (IMWG) uniform response criteria; Kumar et al. (2016) Lancet Oncol 17(8): e328-346), and development of any adverse events, such as serious adverse events (SAEs). Minimal residual disease (MRD) was assessed in by next-generation sequencing (NGS), in subjects where the predominant clonotype was identified at screen evaluation.

Expansion and long-term persistence of the anti-BCMA $CAR^+$ T cells in the peripheral blood of subjects in the DL1, DL2, and DL3 cohorts was assessed at Days 1, 5, 8, 11, 15, 22, 29, 60, and 90 following administration of the CAR-expressing T cells, by quantitative polymerase chain reaction (qPCR) of genomic DNA preparations from whole blood samples from the subjects, using primers specific for the vector encoding the anti-BCMA CAR (vector copies/μg genomic DNA). Levels of soluble BCMA (sBCMA) in serum samples from subjects were also measured prior to administration of CAR+ T cells and at various time points following administration of CAR+ T cells.

Demographics and baseline characteristics of the total, DL1, DL2, and DL3 cohort subjects at the time point are set forth in Table E2. The subjects generally had highly refractory myeloma, with 77% of the subjects having high-risk cytogenetics. More than 50% of the subjects who received a bridging therapy exhibited disease progression before receiving administration of the anti-BCMA CAR+ T cells. The subjects were also shown to generally have a high tumor burden prior to administration of the CAR+ T cells, as indicated by serum and urine M-protein levels, serum free light chain (FLC) levels, and the presence of plasma cells in the bone marrow and extramedullary plasmacytomas.

TABLE E2

Demographics and Baseline Characteristics of Subjects

| Characteristic | Total (N = 44) | CAR+ T cell dose DL 1 50 × $10^6$ (N = 14) | DL 2 150 × $10^6$ (N = 28) | DL 3 450 × $10^6$ (N = 2) |
|---|---|---|---|---|
| Median (range) age, y | 62 (36-79) | 56 (36-70) | 63 (42-79) | 67 (64-69) |
| Male, n (%) | 25 (57) | 9 (64) | 15 (54) | 1 (50) |
| High-risk cytogenetics, n (%)[a] | 34 (77) | 11 (79) | 22 (79) | 1 (50) |
| ECOG performance status 0 or 1, n (%) | 43 (98) | 14 (100) | 27 (96) | 2 (100) |
| Median (range) time since initial diagnosis, years | 6 (2-17) | 6 (2-15) | 5 (2-17) | 6 (5-7) |
| ISS stage III, n (%) | 11 (25) | 1 (7) | 9 (32) | 1 (50) |
| Measurable serum M-protein spike, n (%) | 24 (55) | 4 (29) | 19 (68) | 1 (50) |
| Measurable urine M-protein spike, n (%) | 23 (55) | 8 (62) | 14 (52) | 1 (50) |
| Measurable by sFLC only, n (%) | 8 (18) | 4 (29) | 3 (11) | 1 (50) |
| Plasma cells in BM before LDC, median (range) % | 40 (0-100) | 50 (3-100) | 35 (0-95) | 31 (12-50) |
| EMP, n (%) | 13 (30) | 5 (36) | 8 (29) | 0 |
| Received bridging chemotherapy, n (%) | 34 (77) | 9 (64) | 23 (82) | 2 (100) |
| Progressed on bridging chemotherapy, n (%) | 19 (56) | 5 (56) | 12 (52) | 2 (100) |

BM, bone marrow; ECOG, Eastern Cooperative Oncology Group; EMP extramedullary plasmacytomas; ISS, International Staging System; sFLC, serum free light chain.
[a]High-risk cytogenetics is based on local testing and includes: del(17p), t(4; 14), t(14; 16), 1q21 amp.

The treatment history of the total, DL1, DL2, and DL3 cohort subjects at the time point are set forth in Table E3.

TABLE E3

Treatment History Characteristics of Subjects

| | Total (n = 44) | CAR+ T cell DL 1 50 × $10^6$ (n = 14) | DL 2 150 × $10^6$ (n = 28) | DL 3 450 × $10^6$ (n = 2) |
|---|---|---|---|---|
| Median (range) of prior regimens | 7 (3-23) | 8 (4-23) | 7 (3-14) | 7 (7-7) |
| Prior autologous SCT, n (%) | | | | |
| 1 | 30 (68) | 10 (71) | 19 (68) | 1 (50) |
| >1 | 12 (27) | 4 (29) | 7 (25) | 1 (50) |
| Cumulative exposure, n (%) | | | | |
| Prior PI, IMiD, and anti-CD38 agent | 44 (100) | 14 (100) | 28 (100) | 2 (100) |
| Prior 2 PIs, 2 IMiDs, and anti-CD38 agent | 38 (86) | 12 (86) | 24 (86) | 2 (100) |

SCT, stem cell transplant; IMiD, immunomodulatory drug; PI, proteasome inhibitor.

B. Safety and Response Outcomes after Treatment

Table E4 sets forth the serious adverse events (SAEs) that occurred in the total, DL1, DL2, and DL3 cohorts.

TABLE E4

Safety Outcome After CAR+ Cell Administration

| | Total (n = 44) | CAR+ T cell dose DL 1 50 × $10^6$ (n = 14) | DL 2 150 × $10^6$ (n = 28) | DL 3 450 × $10^6$ (n = 2) |
|---|---|---|---|---|
| Any SAE, n (%) | 12 (27) | 1 (7) | 9 (32) | 2 (100) |
| AEs of special interest grade ≥3/4, n (%) | | | | |
| Neutropenia | 38 (86) | 11 (79) | 25 (89) | 2 (100) |
| Anemia | 22 (50) | 6 (43) | 15 (54) | 1 (50) |
| Thrombocytopenia | 19 (43) | 4 (29) | 13 (46) | 2 (100) |
| Febrile neutropenia | 8 (18) | 1 (7) | 6 (21) | 1 (50) |
| Infections[a] | 6 (14) | 0 | 4 (14) | 2 (100) |
| CRS | 4 (9) | 1 (7) | 2 (7) | 1 (50) |
| Neurological events[b] | 3 (7) | 0 | 2 (7) | 1 (50) |
| TLS | 1 (2) | 0 | 1 (4) | 0 |
| DLT, n | 1 | 0 | 0 | 1 |

CRS, cytokine release syndrome; DLT, dose limiting toxicity; SAE, serious adverse event; AESI, adverse events of special interest.
[a]Pneumonia, appendicitis, Campylobacter infection, cellulitis, sepsis.
[b]Confusional state, agitation, areflexia, lethargy, depressed state of consciousness.

A DLT of grade 4 CRS occurred in a subject in the DL3 cohort who had a history of chronic kidney disease related to the myeloma, with a neurological event of confusion, as well as a lack of pharyngeal reflex, acute kidney injury, and *Klebsiella pneumonia* sepsis as a nosocomial infection, and deceased on Day 19 following administration of the CAR+ T cells.

Table E5 shows the safety outcome of the total, DL1, DL2, and DL3 cohorts with respect to CRS and neurological events. Neurological events were generally associated with CRS. Grade 1 or 2 CRS occurred in 71% of total subjects, while Grade 3 or higher CRS was observed in only 9% of total subjects. One subject experienced a grade 4 neurological event of areflexia. One subject who had a CRS event required a high-dose vasopressor.

TABLE E5

| Cytokine Release Syndrome and Neurological Events | | | | |
|---|---|---|---|---|
| | | CAR+ T cell dose | | |
| | Total (n = 44) | DL 1 50 × $10^6$ (n = 14) | DL 2 150 × $10^6$ (n = 28) | DL 3 450 × $10^6$ (n = 2) |
| Cytokine release syndrome, n (%) | 35 (80) | 11 (79) | 22 (79) | 2 (100) |
| Median time to onset, days (range) | 3 (1-10) | 7 (3-10) | 3 (1-10) | 1 |
| Median duration, days (range) | 5 (1-19) | 3 (2-16) | 5 (1-19) | 8 |
| Neurological events, n (%) | 11 (25) | 1 (7) | 8 (29) | 2 (100) |
| Median time to onset, days (range) | 3 (1-12) | 11 | 3 (1-12) | 3 (2-3) |
| Median duration, days (range) | 6 (1-58) | 3 | 9 (1-58) | 6 |
| Treatment of CRS and neurological events, n (%) | | | | |
| Tocilizumab | 15 (34) | 3 (21) | 10 (36) | 2 (100) |
| Siltuximab | 3 (7) | 0 | 2 (7) | 1 (50) |
| Anakinra | 2 (5) | 0 | 1 (4) | 1 (50) |
| Steroids | 9 (20) | 1 (7) | 6 (21) | 2 (100) |
| Tocilizumab and Steroids | 8 (18) | 1 (7) | 5 (18) | 2 (100) |
| Admitted to ICU, n (%) | 3 (7) | 0 | 1 (4) | 2 (100) |

CRS, Cytokine Release Syndrome.

With respect to prolonged cytopenias, e.g., as determined based on laboratory assessment, Grade 3 or 4 anemia and thrombocytopenia prior to the start of lymphodepleting chemotherapy occurred in 18% of subjects. Grade 3 or 4 cytopenias lasting longer than 29 days occurred in 28/42 subjects (67%). The cytopenias were resolved to grade ≤2 by month 3 in 17/24 subjects (71%) with 3 months follow-up. The median time to resolution, in which, in some cases, recovery was defined as grade 2 or lower without transfusion within 1 week of laboratory assessment or without growth factor support within 1 week of lab assessment (2 weeks for pegfilgrastim), was 2.1 months for neutropenia, 2.2 months for anemia, and 3.4 months for thrombocytopenia.

Objective response rates (ORR) based on the best overall response, among the total, DL1, DL2, and DL3 cohorts are shown in FIG. 1. In all subjects, an ORR of 82% was observed, with 48% of the subject exhibiting a response better than VGPR. A complete response (CR) rate of 43% was observed in the lowest dose level of $5\times10^7$ total CAR-expressing T cells (DL1). One subject in the DL3 cohort was not evaluable for efficacy due to the lack of post-baseline response evaluation at Day 29. Table E6 sets forth the results of minimal residual disease (MRD) assessment by next-generation sequencing (NGS), in 21 subjects in which MRD evaluation was possible.

TABLE E6

| MRD Assessment by NGS | | |
|---|---|---|
| | Day 29/Month 2 (n = 21) | Month 3 (n = 4) |
| MRD negative (≤$10^{-5}$) subjects, n (%) | 9 (43) | 3 (75) |

Figure 2:
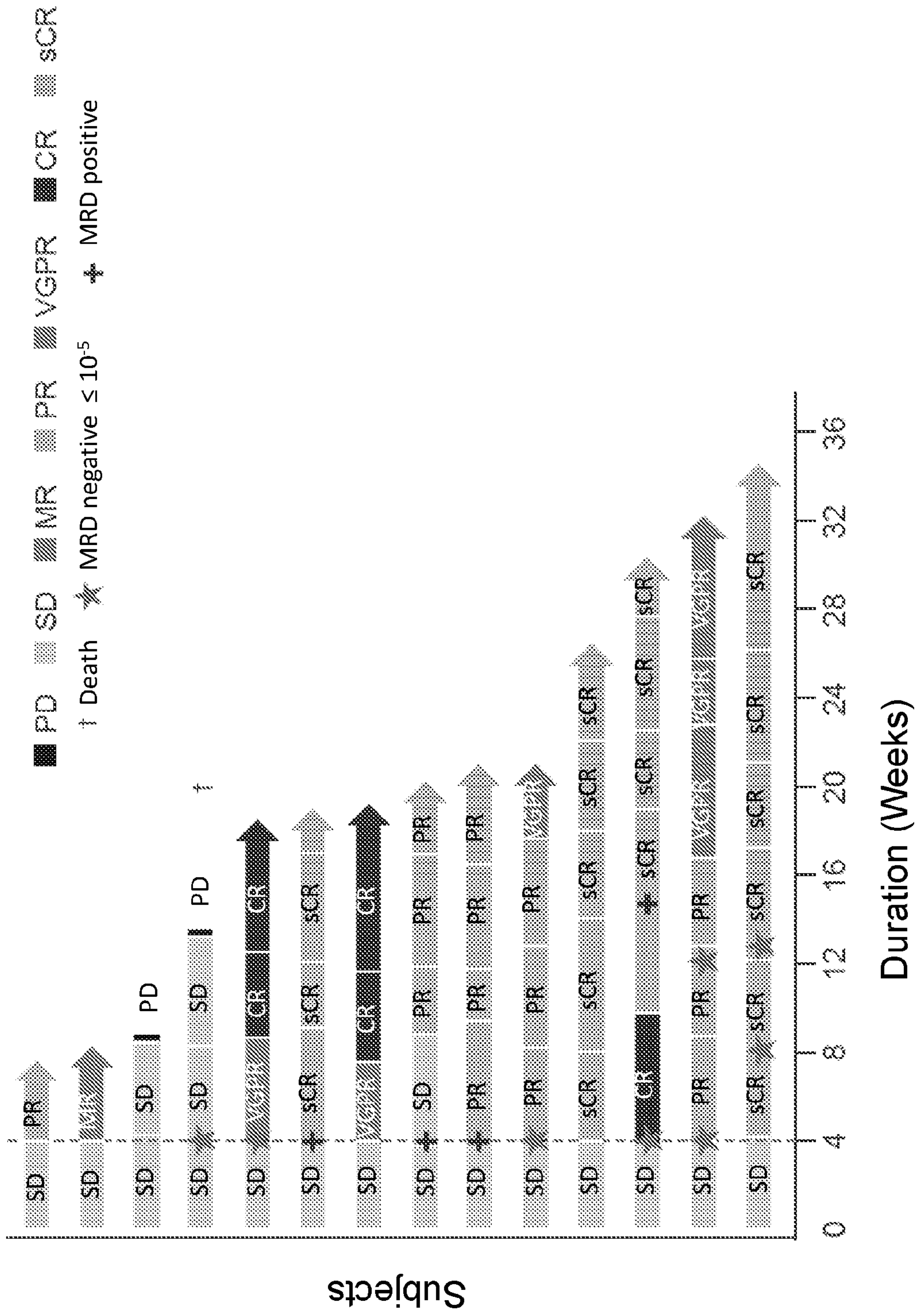
FIG. 2 shows the assessment of response over time, in subjects in the DL1 cohorts at the longest follow-up, after administration of the CAR-expressing T cells (n=14).

The assessment of response over time, in subjects in the DL1 cohorts at the longest follow-up, after administration of the CAR-expressing T cells (n=14) is shown in FIG. 2. In general, response was observed to continue improve over time, with five (5) out of 14 subjects (36%) showing a deepening of response after day 29. Six (6) out of nine (9) subjects evaluated for MRD, were MRD negative (as assessed by NGS) at day 29, with one subject that had an MRD assessment at month 2.

C. Persistence

Figure 3:
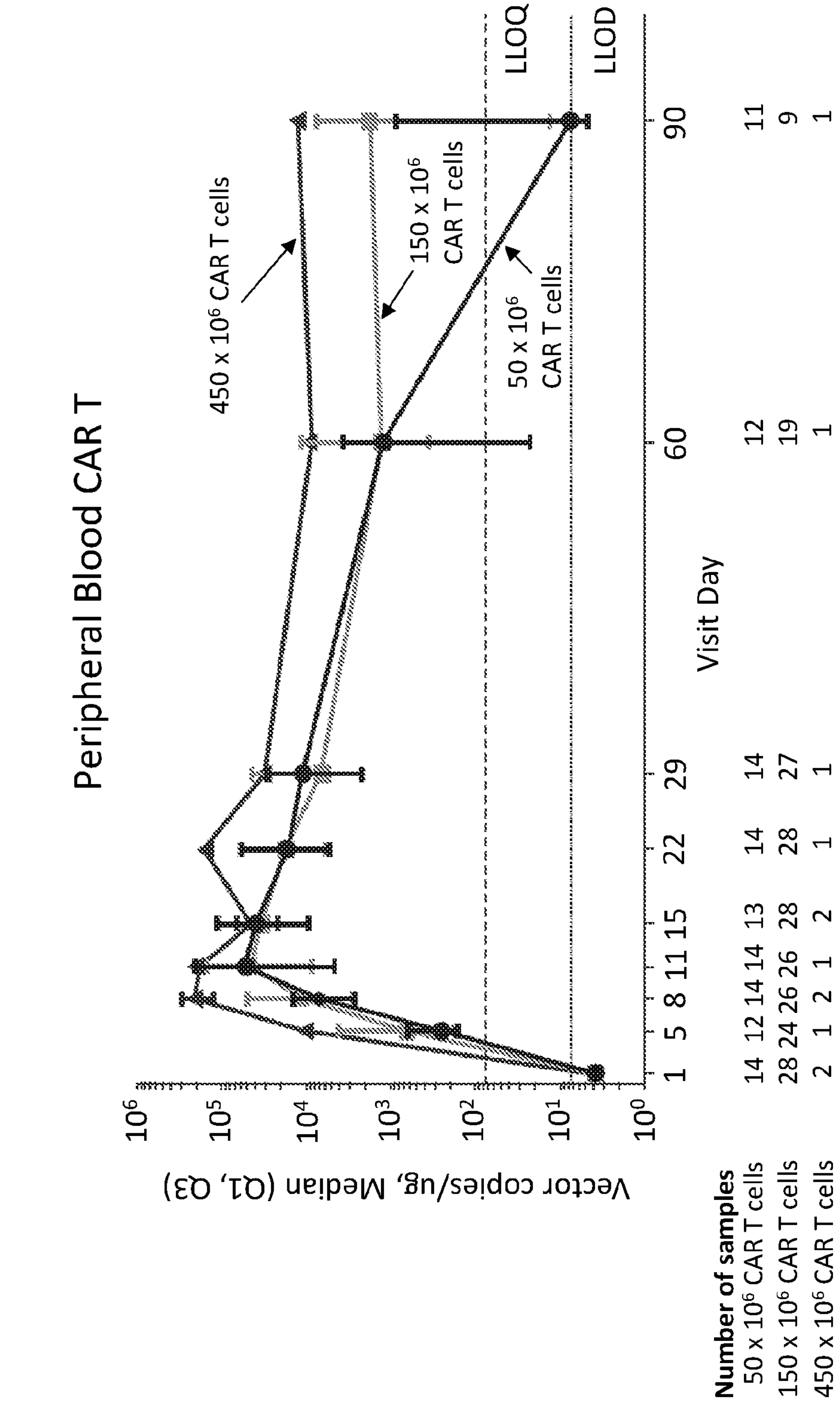
FIG. 3 shows the expansion and long-term persistence of CAR+ T cells in the peripheral blood of subjects in the DL1, DL2, and DL3 cohorts, as measured by quantitative polymerase chain reaction (qPCR) of genomic DNA preparations from whole blood samples to detect vector sequences encoding the CAR (vector copies/μg genomic DNA). LLOQ, lower limit of quantification; LLOD, lower limit of detection.

The expansion and long-term persistence of CARP T cells in the peripheral blood of subjects in the DL1, DL2, and DL3 cohorts are shown in FIG. 3. The results were consistent with a robust expansion of CARP T cells observed at all dose levels (DL1, DL2, and DL3). In general, an increased persistence past month 2 was observed in subjects administered a dose of $150\times10^6$ total CAR-expressing T cells (DL2 and DL3).

D. Soluble BCMA

Figure 4A:
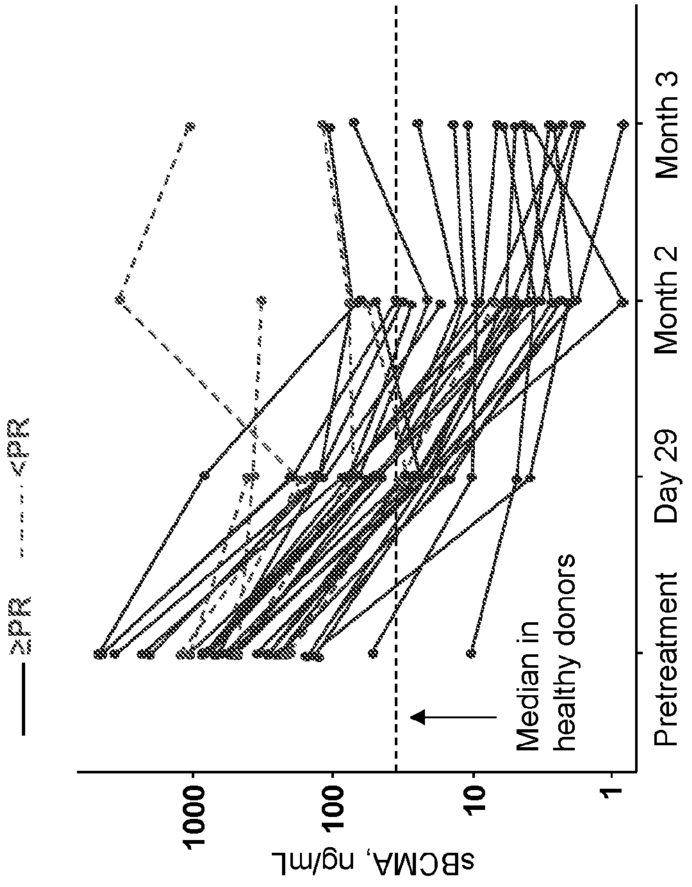
FIG. 4A shows the level of soluble BCMA (sBCMA) (ng/mL) in the serum of subjects prior to CAR+ T cell administration and at various time points after administration (Day 29, Month 2, and Month 3) in subjects with an overall response of PR or better (PR, VGPR, CR or sCR; responders) as compared to subjects with an overall response that is worse than PR (MR or SD; non-responders).
Figure 4B:
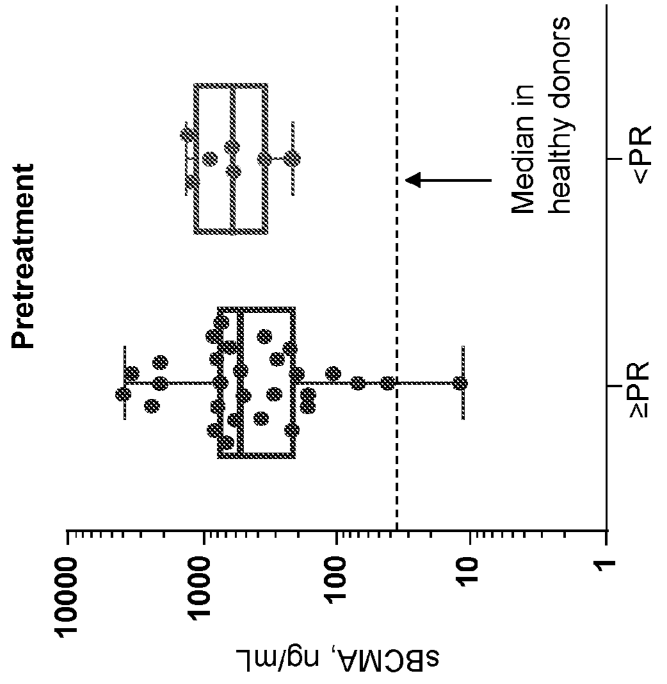
FIG. 4B shows the level of sBCMA prior to CAR+ T cell administration (pre-treatment) in subjects who exhibited an overall response of PR or better (PR, VGPR, CR or sCR; responders) and in subjects who exhibited a response worse than PR (MR or SD; non-responders).

The level of soluble BCMA (sBCMA) (ng/mL) in the serum of the subjects prior to CAR+ T cell administration and at various time points after administration, is shown in FIG. 4A. FIG. 4B shows the level of sBCMA prior to CAR+ T cell administration (pre-treatment) in subjects who exhibited an overall response of PR or better (responders) and in subjects who exhibited a response worse than PR (MR or SD; non-responders). Responses were observed in subjects across broad range of sBCMA levels, and response or the lack of response did not correlate with sBCMA levels. A decline in sBCMA level was observed after anti-BCMA CAR administration, consistent with tumor killing activity by the anti-BCMA CAR+ cells. The results showed a greater decline of sBCMA observed in subjects with an overall response of PR or better (PR, VGPR, CR or sCR; responders) as compared to subjects with an overall response that is worse than PR (MR or SD; non-responders) at day 29 or later. The results were consistent with the observation that the anti-BCMA CAR+ T cells were not inhibited by high pre-treatment levels of sBCMA.

E. Conclusion

The results were consistent with an observation of a high overall response rate (ORR) (82%) in response to administration of anti-BCMA CAR+ cells, which express a fully human antigen-binding domain and is generated by a manufacturing process that results in a population enriched for central memory T cell phenotypes, was high in heavily pre-treated subjects with relapsed/refractory multiple myeloma (R/R MM), 77% of whom had high-risk cytogenetics. A robust expansion of the administered cells were observed at all dose level tested, and approximately 27% of the subject achieved a complete response (CR) or stringent complete response (sCR), with a general observation of deepening response over time. A high rate of CR and sCR of 43% was observed at the lowest dose level administered (50×10[6] CAR+ T cells). The results also were consistent with a manageable toxicity profile, including low rates of grade 3 or higher CRS (9%) and grade 3 or higher neurological events (7%). Grade 1 or 2 CRS was observed in approximately 71% of the subjects, and grade 1 or 2 neurological events was observed in 18% of the subjects. The results also showed that the anti-BCMA CAR+ T cells showed activity in subjects with a high pre-treatment level of soluble BCMA.

Example 4: Further Assessment of Response and Safety Outcomes Following Administration of Anti-BCMA CAR-Expressing Cells to Subjects with Relapsed or Refractory Multiple Myeloma (MM)

Response and safety outcomes were assessed in patients at subsequent points in time in the clinical study described in Examples 2 and 3, with certain additional subjects receiving different doses of cells.

A. Subjects and Treatment

The analysis at the time points presented in this example is based on assessment of a total of 51 subjects that had been administered the anti-BCMA CAR-expressing cells. The 51 subjects were adult human subjects with relapsed or refractory (R/R) multiple myeloma (MM), who have received and failed 3 or more prior treatments (the 3 or more prior treatments including at least (1) an autologous stem cell transplantation, (2) a proteasome inhibitor, (3) an immunomodulatory agent, and/or (4) an anti-CD38 monoclonal antibody, in each case unless the subject was not a candidate to receive such treatment such as by way of it being contraindicated).

On day 1, subjects were administered a dose of CAR+ T cells as follows: a single dose of dose level 2A (DL2A) containing $3.0\times10^8$ total CAR+ T cells, a single dose of dose level 3 (DL3) containing $4.5\times10^8$ total CAR+ T cells or a single dose of dose level 3A (DL3A) containing $6.0\times10^8$ total CAR+ T cells. Subjects were monitored and response was assessed as described in Examples 2 and 3 above.

B. Safety and Response Outcomes after Treatment

At the time of assessment, 51 subjects had received the anti-BCMA CAR-expressing cells at DL2A (n=19), DL3 (n=19) and DL3A (n=13). The median age was 61 (33-77) years; median time from diagnosis was 7.0 (1.7-23.6) years; and subjects had a median of 6 (3-18) prior regimens. Overall, 92% of subjects had 2 prior immunomodulatory agent therapies, 2 proteasome inhibitor therapies, and an anti-CD38 monoclonal antibody therapy, 92% had prior autologous stem cell transplant (ASCT), and 96% of subjects were refractory to the last therapy; 61% of subjects had bridging therapy (77% were refractory). Two subjects had dose-limiting toxicities: grade 3 neurological event (NE) for more than 7 days at DL2A and Grade 4 neutropenia for >28 d at DL3. One subject had unrelated Grade 5 cardiac arrest with steroid-induced myopathy as a contributing factor 53 days post-infusion. Grade 3/4 cytokine release syndrome (CRS) occurred in 2% of subjects (any grade, 92%); median time to onset and resolution were 2 (1-4) days and 3 (1-10) days. Grade 3/4 NEs occurred in 4% of subjects (any grade, 10%). Median time to onset and resolution were 6 (1-6) days and 5 (2-8) day. CRS/NEs were managed with tocilizumab and/or steroids (78%), anakinra (14%), and/or vasopressors (6%). Grade 3 or higher anemia, neutropenia, and thrombocytopenia occurred in 21%, 55%, and 44% of subjects, at Day 29 (median time to resolution to Grade 2 or less of any cytopenia, ≤2.1 mo). Grade 3 or higher infections occurred in 14%. A total of 44 subjects were evaluated for response, as set forth in Table E7. Median PFS was not reached. Robust cellular expansion was observed at all dose levels.

TABLE E7

| Safety Outcome After CAR+ Cell Administration | | | | |
|---|---|---|---|---|
| n (%) | DL2A ($3.0\times10^8$) N = 19 | DL3 ($4.5\times10^8$) N = 18 | DL3A ($6.0\times10^8$) N = 7 | All N = 44 |
| ORR (sCR + CR + VGPR + PR) | 18 (95) | 17 (94) | 5 (71) | 40 (91) |
| sCR + CR | 5 (26) | 9 (50) | 3 (43) | 17 (39) |
| VGPR | 8 (42) | 3 (17) | 0 | 11 (25) |
| PR | 5 (26) | 5 (28) | 2 (29) | 12 (27) |
| Median follow-up, mo | 6.1 | 5.8 | 1.7 | 5.9 |
| CRS Grade ≥ 3[a] | 0 | 1 (5) | 0 | 1 (2) |
| NE Grade ≥ 3[a] | 1 (5) | 1 (5) | 0 | 2 (4) |

[a]n = 19, 19, 13, and 51 for DL2A, DL3, DL3A and total.

C. Conclusion

The results were consistent with an observation of manageable safety profile and high response rate in response to administration of $3.0\times10^8$, $4.5\times10^8$ or $6.0\times10^8$ total anti-BCMA CAR+ T cells, with a 91% objective response rate (ORR) and 39% subjects achieving a complete response (CR) or a stringent CR (sCR). A deepening of the response over time were observed.

Example 5: Prophylactic Administration of an Interleukin-1 Receptor Antagonists (IL-1Ra) with Administration of Anti-BCMA CAR-Expressing Cells to Subjects with Relapsed or Refractory Multiple Myeloma (MM)

An interleukin-1 receptor antagonist (IL-1Ra), Anakinra (AKR), was prophylactically administered to human subjects with relapsed and/or refractory multiple myeloma (MM) administered chimeric antigen-receptor (CAR)-expressing T cell compositions containing autologous T cells expressing a CAR specific for B-cell maturation antigen (BCMA), to assess the effect on the onset, incidence and severity of potential events such as cytokine release syndrome (CRS).

Compositions containing autologous T cells were engineered to express an exemplary CAR specific for BCMA, described in Example 1 above, and were administered to adult human subjects with relapsed or refractory (R/R) multiple myeloma (MM) who had received 3 or more prior treatments.

The administered T cell compositions were generated by a process generally as described in Example 2 above. The CAR contained a BCMA-55-derived scFv binding domain, a modified IgG-derived $C_H2$-$C_H3$-hinge spacer, a CD28 transmembrane domain, and an intracellular signaling region including, in series, a 4-1BB endodomain and a CD3zeta endodomain, with optimized polynucleotides encoding the CAR, as described in Example 1.

Two to seven days prior to CAR+ T cell infusion, subjects received a lymphodepleting chemotherapy (LDC) with fludarabine (flu, 30 mg/m$^2$/day) and cyclophosphamide (Cy, 300 mg/m$^2$/day) for 3 days, the LDC completed at least 48 hours prior to CAR+ T cell infusion. The cell compositions were administered intravenously, with the day of infusion being designated Day 1. On Day 1, subjects are administered a dose of CAR+ T cells as follows: either a single dose of dose level 3 (DL3) containing $4.5\times10^8$ total CAR+ T cells, or a single dose of dose level 3A (DL3A) containing $6.0\times10^8$ total CAR+ T cells. Specifically, in the study described in this example, fourteen patients were administered a single dose containing $6.0\times10^8$ total CAR+ T cells.

Subjects received 2 doses of 100 mg AKR administered subcutaneously (SC) prior to CAR+ T cell infusion: one dose was administered the night before administration of the anti-BCMA CAR-expressing cells, and one dose was administered 3 hours before administration of the anti-BCMA CAR-expressing cells on Day 1 (n=14). Subjects then received four additional doses of AKR following administration of the anti-BCMA CAR-expressing cells: a single dose of 100 mg SC AKR was administered once daily for four consecutive days (a dose on each of Days 2-5; e.g. q24 h). In the case of CRS onset, 100 mg SC AKR was administered twice daily (e.g. q12 h) until CRS resolution. The doses of AKR were administered at approximately the same time every day. In the case of worsening of CRS and/or in case of onset of neurological toxicity, the toxicity management guidelines were followed. All subjects who received conforming anti-BCMA CAR-expressing T cell product and received at least 1 dose of prophylactic AKR were evaluated for safety and tolerability of the anti-BCMA CAR-expressing T cells following prophylactic treatment with Anakinra.

Subjects administered the anti-BCMA CAR-expressing cells but not treated with AKR served as a control group (n=19). In the AKR-treated and non-AKR-treated groups, the median number of prior regimens was 6 and 5, and bridging therapy was used in 57% and 68% of subjects, respectively.

The incidence and onset of cytokine release syndrome (CRS) as graded by Lee (2014) criteria, neurological events (NE), expansion and persistence (e.g., pharmacokinetics) of CAR-expressing cells in the blood of subjects, and the response to the CAR-expressing T cell treatment, including the objective response rate (ORR), rate of complete response (CR) or stringent complete response (sCR), according to the IMWG Uniform Response Criteria were determined. The median follow-up range was 3.0 (1.8-6.2) months for the subjects treated with AKR and 8.8 (5.3-12.2) months for the control subjects. Results are shown in Table E8.

The use of AKR prophylaxis was observed to have no adverse effect on the incidence of NE, infection, macrophage activation syndrome/hemophagocytic lymphohistiocytosis (MAS/HLH), CAR+ T cell expansion, or disease response. In particular, the total frequency of CRS was similar in the two groups of subjects, but with fewer Grade 2 CRS events in the AKR-treated subjects; relative risk (95% CI)=0.54 (0.21, 1.38). No Grade 3 or higher CRS events were seen in either group. The incidence of neurological events (NE), Grade 3 or higher infection, and MAS/HLH were also similar between the groups. Tocilizumab and steroid use was numerically lower in subjects treated with AKR. CAR+ T cell expansion kinetics were similar in the two groups. All subjects were assessed for efficacy at two months, with an overall response rate (ORR) of 100% in AKR-treated subjects and 95% in control subjects.

TABLE E8

Disease characteristics and safety outcomes after CAR+ cell administration

| | AKR Group n = 14 | Non-AKR Group n = 19 |
|---|---|---|
| International staging system, stage I/II/III, % | 43/36/21 | 47/37/16 |
| Measurable serum and/or urine M-protein, n (%) | 13 (93) | 14 (74) |
| LDH > ULN, n (%) | 3 (21) | 0 (0) |
| CRS, G1/G2/G ≥ 3, % | 64/29/0 | 37/53/0 |
| CRS time to onset/duration, median (range), days | 2 (1-11)/ 3 (2-8) | 2 (1-2)/ 3 (1-7) |
| NE, G1/G2/G ≥ 3, % | 7/7/7 | 5/5/0 |
| Infection, G1/G2/G ≥ 3, % | 0/0/14 | 15/11/11 |
| MAS/HLH, G1/G2/G ≥ 3, % | 0/7/0 | 5/0/5 |
| Any T/multiple T any S/T + S, % | 79/29/43/43 | 90/37/63/63 |

CRS: cytokine release syndrome; G: Grade; HLH: hemophagocytic lymphohistiocytosis; LDH: lactate dehydrogenase; MAS: macrophage activation syndrome; NE: neurological event; S: Steroid; T: Tocilizumab; ULN: upper limit of normal.

These results are consistent with a finding that the incidence of Grade 2 or higher CRS may be lowered by Anakinra prophylaxis in combination with administration of anti-BCMA CAR-expressing T cells.

Example 6: Administration of Anti-BCMA CAR-Expressing Cells to Subjects with Relapsed or Refractory Multiple Myeloma (MM) Previously Treated with BCMA-Directed Therapy for MM Chimeric antigen-receptor (CAR)-expressing T cell compositions containing autologous T cells expressing a CAR specific for B-cell maturation antigen (BCMA) are administered to human subjects with relapsed and/or refractory multiple myeloma (MM) that have previously received a prior BCMA-directed therapy.

Compositions containing autologous T cells engineered to express an exemplary CAR specific for BCMA, described in Example 1 above, are administered to adult human subjects with relapsed or refractory (R/R) multiple myeloma (MM), who have received a prior BCMA-directed therapy for the MM, achieved at least a partial response (PR) per IMWG response criteria and subsequently progressed. Prior BCMA-directed therapy can include a BCMA-directed CAR-expressing T cell therapy; a BCMA-directed T-cell engager (TCE), which include antibodies which bind simultaneously to a surface tumor cell antigen and a component of the T-cell receptor (TCR) complex to induce T cell-mediated killing of tumor cells harboring the target surface antigen; and a BCMA-directed antibody-drug conjugate (ADC). For subjects that have received a prior BCMA-directed CAR-expressing T cell therapy, the last administration of the prior CAR T-cell therapy must have been received at least 6 months prior to the beginning of the study. Subjects with prior BCMA-directed anti-myeloma therapy are not required to have received at least 3 prior anti-myeloma treatment regimens and are not required to be refractory to the last anti-myeloma regimen.

The administered T cell compositions are generated by a process generally as described in Example 2 above. In some cases, for subjects that have received a prior BCMA-directed CAR-expressing T cell therapy, the primary T cell populations from the subject, e.g., obtained from leukapheresis samples, are assessed for the presence or expression of the prior BCMA-directed CAR, for example, by flow cytometry staining with recombinant BCMA-Fc (soluble human BCMA fused at its C-terminus to an Fc region of IgG), and/or by quantitative polymerase chain reaction (PCR) with primers or probes specific for sequences present in the construct containing nucleic acid sequences encoding the prior BCMA-directed CAR. The BCMA-binding CAR for the therapy (e.g., new BCMA-binding CAR) contains a BCMA-55-derived scFv binding domain, a modified IgG-derived $C_H2$-$C_H3$-hinge spacer, a CD28 transmembrane domain, and an intracellular signaling region including, in series, a 4-1BB endodomain and a CD3zeta endodomain, with optimized polynucleotides encoding the CAR, as described in Example 1.

In some cases, for subjects that have received a prior BCMA-directed CAR-expressing T cell therapy, the generated cell compositions for administration, e.g., expressing the BCMA-binding CAR described in Example 1, are assessed for presence, amount or number of the prior BCMA-directed CAR and/or the BCMA-binding CAR for the cell therapy (e.g., new BCMA-binding CAR; described in Example 1). In some cases, the presence, amount or number of the prior BCMA-directed CAR-expressing cells and cells expressing the BCMA-binding CAR for the cell therapy (e.g., new BCMA-binding CAR), can be detected by flow cytometry staining with recombinant BCMA-Fc. In some cases, the presence, amount or number of cells expressing the BCMA-binding CAR for the cell therapy (e.g., new BCMA-binding CAR), can be detected by flow cytometry staining with an anti-idiotypic antibody specific for the BCMA-binding CAR for the cell therapy (e.g., new BCMA-binding CAR). In some cases, the presence of the BCMA-binding CAR for the cell therapy (e.g., new BCMA-binding CAR) is also assessed by qPCR with primers or probes specific for sequences present in the construct containing nucleic acid sequences encoding the BCMA-binding CAR for the cell therapy (e.g., new BCMA-binding CAR). Any of such amount or number can be used to determine the presence and/or proportion of the prior BCMA-directed CAR present in the cell composition for administration and/or to determine the dose of cells expressing the BCMA-binding CAR for the cell therapy.

Two to seven days prior to CAR+ T cell infusion, subjects receive a lymphodepleting chemotherapy (LDC) with fludarabine (flu, 30 mg/m$^2$/day) and cyclophosphamide (Cy, 300 mg/m$^2$/day) for 3 days, the LDC completed at least 48 hours prior to CAR+ T cell infusion. The cell compositions are administered intravenously, with the day of infusion being designated Day 1. On Day 1, subjects are administered a dose of CAR+ T cells as follows: a single dose of dose level 1 (DL1) containing $5\times10^7$ total CAR+ T cells; a single dose of dose level 2 (DL2) containing $1.5\times10^8$ total CAR+ T cells; a single dose of dose level 2A (DL2A) containing $3.0\times10^8$ total CAR+ T cells; a single dose of dose level 3 (DL3) containing $4.5\times10^8$ total CAR+ T cells; or a single dose of dose level 3A (DL3A) containing $6.0\times10^8$ total CAR+ T cells.

The response to the CAR-expressing T cell treatment, including the objective response rate (ORR), rate of complete response (CR) or stringent complete response (sCR), according to the IMWG Uniform Response Criteria are determined. The incidence and severity of adverse events (AEs) and the incidence and severity of laboratory abnormalities are also determined.

Example 7: Assessment of T Cell Compositions Generated by Exemplary Manufacturing Processes In an exemplary process, 50 CAR+ T cell compositions containing autologous T cells expressing an anti-BCMA CAR were generated from apheresis collected from 50 separate human subjects (one apheresis from each subject), including 10 healthy donors and 40 multiple myeloma patients. CD4+ and CD8+ T cells were selected from the apheresis samples and separately cryopreserved. The cells were then thawed, and the separate CD4+ T cells and CD8+ T cells were combined at a 1:1 ratio of viable CD4+ to CD8+ cells. The combined CD4+ and CD8+ T cells were stimulated, transduced with a vector encoding a CAR, and expanded, in an exemplary serum-free media, and frozen by cryopreservation, generally as described in Example 2.

In an exemplary alternative process, therapeutic T cell compositions were generated by a process including immunoaffinity-based selection of T cells from leukapheresis samples from 55 individual human cancer subjects. Bulk T cells were subjected to activation and transduction with a viral vector encoding a CAR, expansion and cryopreservation.

The cells in the frozen compositions were thawed and assessed by flow cytometry for viability, expression of an apoptotic marker such as active caspase 3 (CAS), and surface expression of CD3, CD4, CD8, CD27, CD28, CCR7, CD45RA, and CAR. The percentage of CD3+ cells, percentage of CAR+ apoptotic marker negative cells in CD3+ CAR+ cells in the compositions, and the percentage of central memory CD4+ CAR+ cells and central memory CD8+ CAR+ cells in the compositions were determined. Cell phenotypes of the cell compositions generated by the manufacturing process were assessed and in some aspects were compared to those of the cell compositions generated by the alternative process.

Figure 5A:
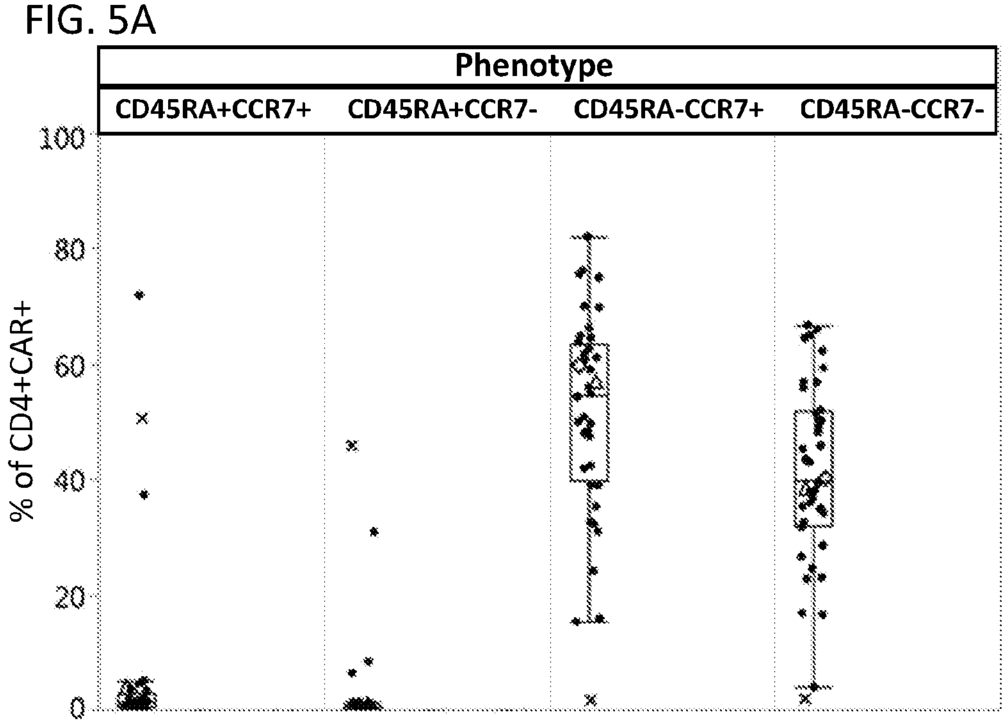
FIGS. 5A-5D depict exemplary phenotypical profiles of 40 engineered CAR+ T cell compositions, each from a multiple myeloma patient. CD45RA×CCR7 expression profiles among the CAR+ T cell compositions are shown for the CD4+ populations (FIG. 5A) and the CD8+ populations (FIG. 5B). CD27×CD28 expression profiles among the CAR+ T cell compositions are shown for the CD4+ populations (FIG. 5C) and the CD8+ populations (FIG. 5D). Each CAR+ T cell composition is shown by a dot (●), a cross (x), a diamond (◇), or a triangle (Δ).
Figure 5B:
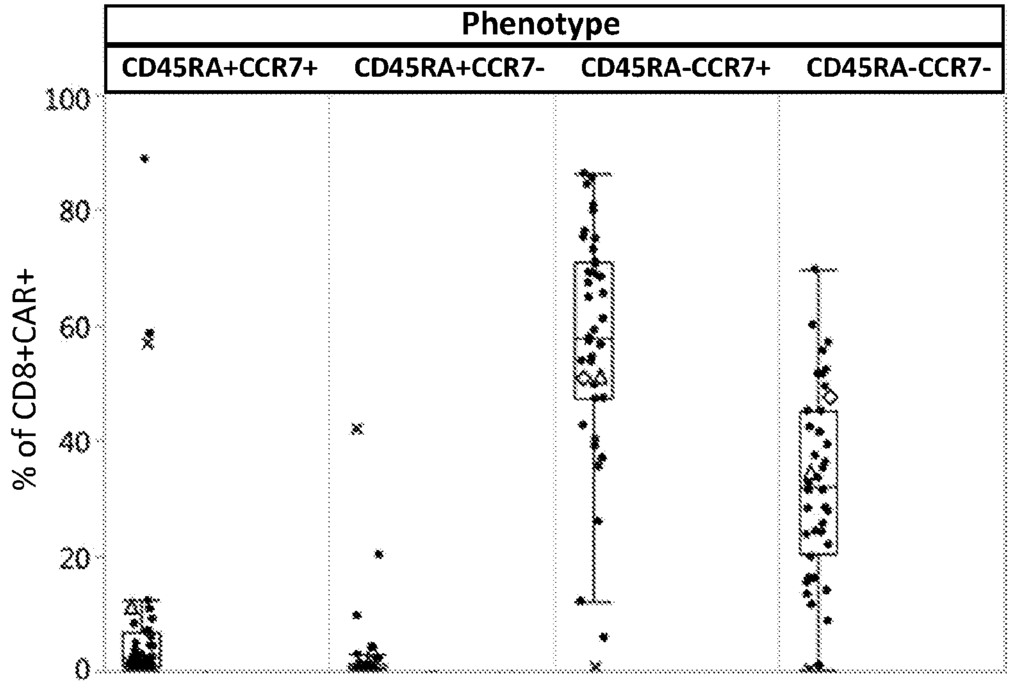
Figure 5C:
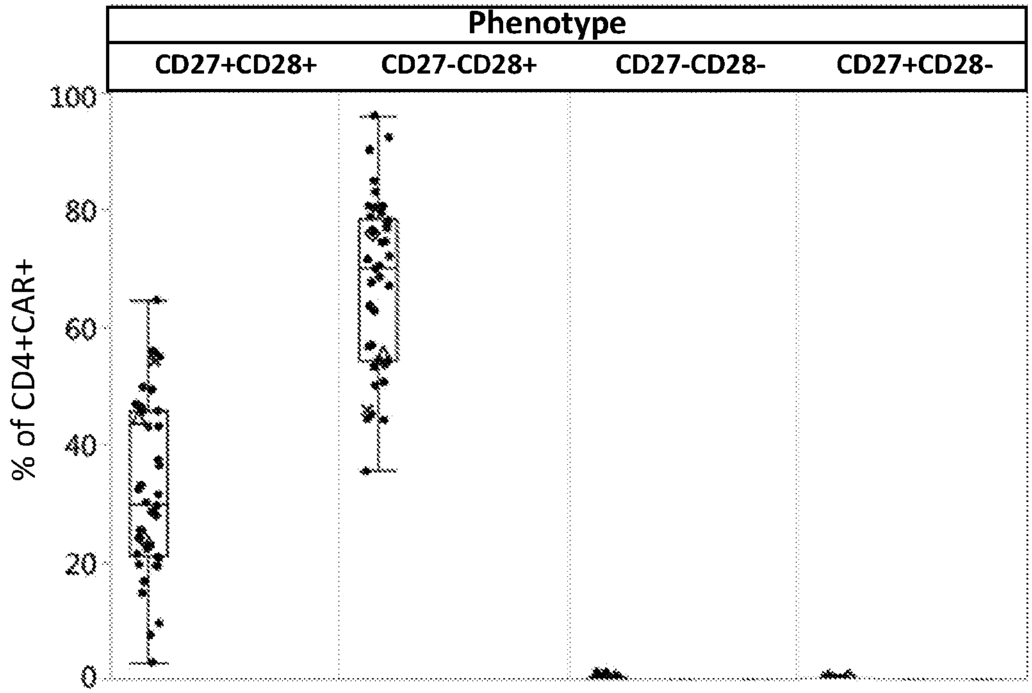
Figure 5D:
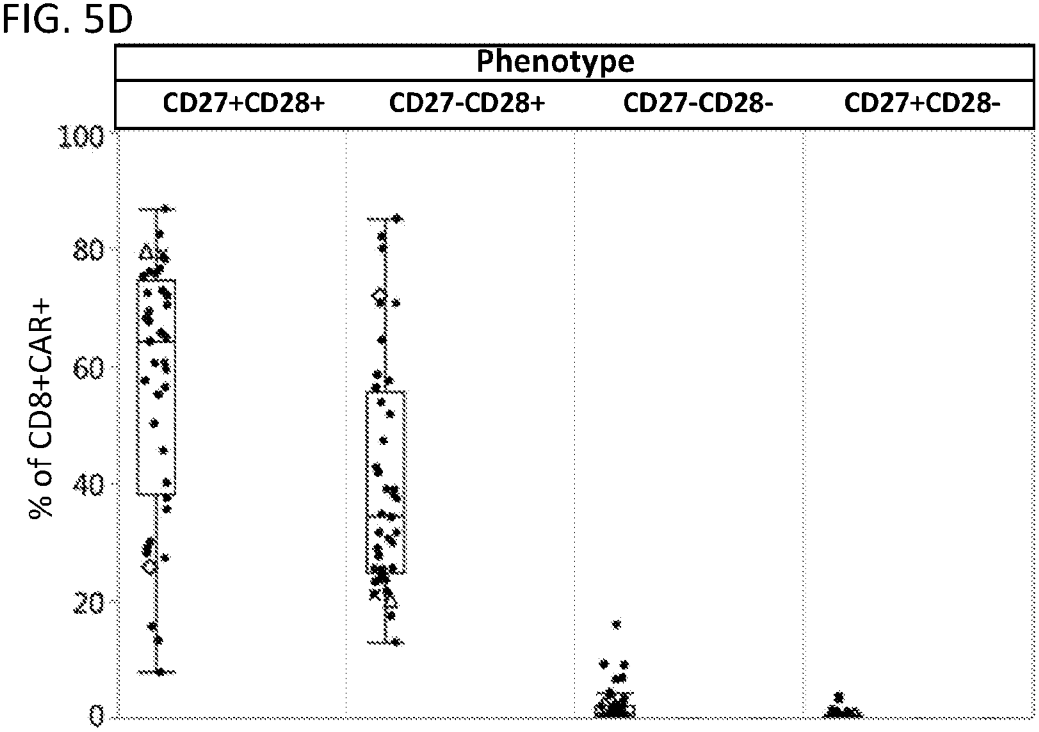

The manufacturing process of this example resulted in engineered cell compositions meeting certain pre-determined features, including threshold numbers of cells expressing the CAR in a cell composition administration to the patients, in 100% of the human biological samples on which it was carried out. FIGS. 5A and 5B show median (horizontal lines), interquartile range (box), and 1.5× interquartile range (whiskers) for percentages of cells of the indicated phenotypes (based on CD45RA and CCR7 surface expression), among CD4+ CAR+ cells (FIG. 5A) and among CD8+ CAR+ cells (FIG. 5B) in the compositions, respectively, for compositions individually generated from the group of samples from the 40 multiple myeloma subjects. FIGS. 5C and 5D show median (horizontal lines), interquartile range (box), and 1.5× interquartile range (whiskers) for percentages of cells of the indicated phenotypes (based on CD27 and CD28 surface expression), among CD4+ CAR+ cells (FIG. 5C) and among CD8+ CAR+ cells (FIG. 5D) in the compositions, respectively, for compositions individually generated from the group of samples from the 40 multiple myeloma subjects. For individual leukapheresis samples obtained from a range of multiple myeloma patients, using this exemplary process to generate engineered cell compositions from such samples, it was observed that the range of duration of the portion of the process from initiation of activation through harvest was between 7 and 10 days, and an average duration among these samples of approximately 7.5 days. It was further determined that the average number of cumulative population doublings over the course of the process among the different samples was approximately 7.5.

In this study, engineered T cell populations in the cell compositions produced by the exemplary process included less than 15% cells expressing an apoptotic marker, and were enriched for a central memory phenotype as compared to the starting samples and to cell compositions generated using the exemplary alternative process.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| SEQ ID NO: | Sequence | Description |
|---|---|---|
| 1 | GGGGSGGGGSGGGGS | $(4GS)_3$ linker (aa) |
| 2 | GGGS | 3GS linker (aa) |
| 3 | gctgagagtcaagttttccaggtccgccgacgctccagcct | 4-1BB/CD3 zeta predicted splice acceptor site |
| 4 | KRGRKKLLYIFKQPFMRPVQTTQEEDGCSCRFPEEEEGGCEL | 4-1BB-derived intracellular co-signaling sequence (aa) |
| 5 | aagcgggggagaaagaaactgctgtatattttcaaacagccctttatgaga<br>cctgtgcagactacccaggaggaagacggatgcagctgtaggtttcccgag<br>gaagaggaaggaggctgtgagctg | 4-1BB-derived intracellular co-signaling sequence (nt) |
| 6 | aagcggggcagaaagaagctgctctacatcttcaagcagcccttcatgcgg<br>cccgtgcagaccacacaagaggaagatggctgctcctgcagattccccgag<br>gaagaagaaggcggctgcgagctg | 4-1BB-derived intracellular co-signaling sequence (nt) |
| 7 | GGGGS | 4GS linker (aa) |
| 8 | gaatctaagtacggaccgccttgtcctccttgtcccgctcctcctgttgcc<br>ggaccttccgtgttcctgtttcctccaaagcctaaggacaccctgatgatc<br>agcaggacccctgaagtgacctgcgtggtggtggatgtgtcccaagaggat<br>cccgaggtgcagttcaactggtatgtggacggcgtggaagtgcacaacgcc<br>aagaccaagcctagagaggaacagttccagagcacctacagagtggtgtcc<br>gtgctgacagtgctgcaccaggattggctgaacggcaaagagtacaagtgc<br>aaggtgtccaacaagggcctgcctagcagcatcgagaaaaccatctccaag<br>gccaagggccagccaagagagccccaggtttacacactgcctccaagccaa<br>gaggaaatgaccaagaatcaggtgtccctgacatgcctggtcaagggcttc<br>tacccctccgatatcgccgtggaatgggagagcaatggccagcctgagaac<br>aactacaagaccacacctcctgtgctggacagcgacggcagtttcttcctg<br>tatagtagactcaccgtggataaatcaagatggcaagagggcaacgtgttc<br>agctgcagcgtgatgcacgaggccctgcacaaccactacacccagaaaagc<br>ctgagcctgtctctgggcaag | Alternative CO/SSE spacer (nt) |
| 9 | gaggtgcagctggtggagtccggaggaggcctggtgaagccaggaggctcc<br>ctgaggctgtcttgcgcagccagcggcttcacctttagcgactactatatg<br>tcctggatcagacaggcacctggcaagggcctggagtgggtgagctacatc<br>agctcctctggctccacaatctactatgccgactctgtgaagggccggttt<br>accatcagcagagataacgccaagaattccctgtatctgcagatgaacagc<br>ctgagggccgaggacacagccgtgtactattgcgccaaggtggacggcgat<br>tacaccgaggattattggggccagggcacactggtgaccgtgagctccggc<br>ggcggcggctctggaggaggaggcagcggcggaggaggctcccagtctgcc<br>ctgacacagccagccagcgtgtccggctctcccggacagtccatcacaatc<br>tcttgtaccggctctagctccgacgtgggcaagtacaacctggtgtcctgg<br>tatcagcagcccccctggcaaggcccctaagctgatcatctacgatgtgaac<br>aagaggccatctggcgtgagcaatcgcttcagcggctccaagtctggcaat<br>accgccacactgaccatcagcggcctgcagggcgacgatgaggcagattac<br>tattgttctagctacggcggcagcagatcctacgtgttcggcacaggcacc<br>aaggtgaccgtgctggaatctaagtacggaccgccttgtcctccttgtccc<br>gctcctcctgttgccggaccttccgtgttcctgtttcctccaaagcctaag<br>gacaccctgatgatcagcaggacccctgaagtgacctgcgtggtggtggat<br>gtgtcccaagaggatcccgaggtgcagttcaactggtatgtggacggcgtg<br>gaagtgcacaacgccaagaccaagcctagagaggaacagttccagagcacc<br>tacagagtggtgtccgtgctgacagtgctgcaccaggattggctgaacggc<br>aaagagtacaagtgcaaggtgtccaacaagggcctgcctagcagcatcgag<br>aaaaccatctccaaggccaagggccagccaagagagccccaggtttacaca<br>ctgcctccaagccaagaggaaatgaccaagaatcaggtgtccctgacatgc<br>ctggtcaagggcttctacccctccgatatcgccgtggaatgggagagcaat<br>ggccagcctgagaacaactacaagaccacacctcctgtgctggacagcgac<br>ggcagtttcttcctgtatagtagactcaccgtggataaatcaagatggcaa<br>gagggcaacgtgttcagctgcagcgtgatgcacgaggccctgcacaaccac<br>tacacccagaaaagcctgagcctgtctctgggcaagatgttctgggtgctc<br>gtggtcgttggcggagtgctggcctgttacagcctgctggttaccgtggcc<br>ttcatcatcttttgggtcaagcggggcagaaagaagctgctctacatcttc | anti-BMCA CAR |

| SEQ ID NO: | Sequence | Description |
|---|---|---|
| | aagcagcccttcatgcggcccgtgcagaccacacaagaggaagatggctgc<br>tcctgcagattccccgaggaagaagaaggcggctgcgagctgagagtgaag<br>ttcagcagatccgccgacgctccagcctatcagcagggccaaaaccagctg<br>tacaacgagctgaacctggggagaagagaagagtacgacgtgctggataag<br>cggagaggcagagatcctgaaatgggcggcaagcccagacggaagaatcct<br>caagagggcctgtataatgagctgcagaaagacaagatggccgaggcctac<br>agcgagatcggaatgaagggcgagcgcagaagaggcaagggacacgatgga<br>ctgtaccagggcctgagcaccgccaccaaggatacctatgacgcactgcac<br>atgcaggccctgccacctaga | |
| 10 | gaggtgcagctggtgcagagcggaggaggcctggtgcagcctggcaggtcc<br>ctgcgcctgtcttgcaccgccagcggcttcacatttggcgactatgccatg<br>tcctggttcaagcaggcaccaggcaagggcctggagtgggtgggctttatc<br>cgctctaaggcctacggcggcaccacagagtatgccgccagcgtgaagggc<br>cggttcaccatcagccgggacgactctaagagcatcgcctacctgcagatg<br>aactctctgaagaccgaggacacagccgtgtactattgcgcagcatggagc<br>gccccaaccgattattggggccagggcaccctggtgacagtgagctccggc<br>ggcggcggctctggaggaggaggaagcggaggaggaggatccgacatccag<br>atgacacagtcccctgcctttctgtccgcctctgtgggcgatagggtgacc<br>gtgacatgtcgcgcctcccagggcatctctaactacctggcctggtatcag<br>cagaagcccggcaatgcccctcggctgctgatctacagcgcctccaccctg<br>cagagcggagtgccctcccggttcagaggaaccggctatggcacagagttt<br>tctctgaccatcgacagcctgcagccagaggatttcgccacatactattgt<br>cagcagtcttacaccagccggcagacatttggccccggcacaagactggat<br>atcaaggagtctaaatacggaccgccttgtcctccttgtcccgctcctcct<br>gttgccggaccttccgtgttcctgtttcctccaaagcctaaggacaccctg<br>atgatcagcaggacccctgaagtgacctgcgtggtggtggatgtgtcccaa<br>gaggatcccgaggtgcagttcaactggtatgtggacggcgtggaagtgcac<br>aacgccaagaccaagcctagagaggaacagttccagagcacctacagagtg<br>gtgtccgtgctgacagtgctgcaccaggattggctgaacggcaaagagtac<br>aagtgcaaggtgtccaacaagggcctgcctagcagcatcgagaaaaccatc<br>tccaaggccaagggccagccaagagagccccaggtttacacactgcctcca<br>agccaagaggaaatgaccaagaatcaggtgtccctgacatgcctggtcaag<br>ggcttctacccctccgatatcgccgtggaatgggagagcaatggccagcct<br>gagaacaactacaagaccacacctcctgtgctggacagcgacggcagtttc<br>ttcctgtatagtagactcaccgtggataaatcaagatggcaagagggcaac<br>gtgttcagctgcagcgtgatgcacgaggccctgcacaaccactacacccag<br>aaaagcctgagcctgtctctgggcaagatgttctgggtgctcgtggtcgtt<br>ggcggagtgctggcctgttacagcctgctggttaccgtggccttcatcatc<br>ttttgggtcaagcggggcagaaagaagctgctctacatcttcaagcagccc<br>ttcatgcggcccgtgcagaccacacaagaggaagatggctgctcctgcaga<br>ttccccgaggaagaagaaggcggctgcgagctgagagtgaagttcagcaga<br>tccgccgacgctccagcctatcagcagggccaaaaccagctgtacaacgag<br>ctgaacctggggagaagagaagagtacgacgtgctggataagcggagaggc<br>agagatcctgaaatgggcggcaagcccagacggaagaatcctcaagagggc<br>ctgtataatgagctgcagaaagacaagatggccgaggcctacagcgagatc<br>ggaatgaagggcgagcgcagaagaggcaagggacacgatggactgtaccag<br>ggcctgagcaccgccaccaaggatacctatgacgcactgcacatgcaggcc<br>ctgccacctaga | anti-BMCA CAR |
| 11 | gaggtgcagctggtggagtccggaggaggcctggtgaagccaggaggctct<br>ctgaggctgagctgcgcagcctccggcttcaccttttctgactactatatg<br>agctggatcaggcaggcaccaggcaagggcctggagtgggtgtcttacatc<br>agctcctctggcagcacaatctctatgccgactccgtgaagggcaggttc<br>accatctctcgcgataacgccaagaatagcctgtatctgcagatgaactcc<br>ctgcgggccgaggatacagccgtgtactattgcgccaaggtggacggcccc<br>ccttcctttgatatctggggccagggcacaatggtgaccgtgagctccgga<br>ggaggaggatccggcggaggaggctctggcggcggcggctctagctatgtg<br>ctgacccagccaccatccgtgtctgtggcacctggacagacagcaaggatc<br>acctgtggagcaaacaatatcggcagcaagtccgtgcactggtaccagcag<br>aagcctggccaggccccaatgctggtggtgtatgacgatgacgatcggccc<br>agcggcatccctgagagattttctggcagcaactccggcaataccgccaca<br>ctgaccatctctggagtggaggcaggcgacgaggcagattacttctgtcac<br>ctgtgggaccggagcagagatcactacgtgttcggcacaggcaccaagctg<br>accgtgctggaatctaagtacggaccgccttgtcctccttgtcccgctcct<br>cctgttgccggaccttccgtgttcctgtttcctccaaagcctaaggacacc<br>ctgatgatcagcaggacccctgaagtgacctgcgtggtggtggatgtgtcc<br>caagaggatcccgaggtgcagttcaactggtatgtggacggcgtggaagtg<br>cacaacgccaagaccaagcctagagaggaacagttccagagcacctacaga<br>gtggtgtccgtgctgacagtgctgcaccaggattggctgaacggcaaagag<br>tacaagtgcaaggtgtccaacaagggcctgcctagcagcatcgagaaaacc<br>atctccaaggccaagggccagccaagagagccccaggtttacacactgcct<br>ccaagccaagaggaaatgaccaagaatcaggtgtccctgacatgcctggtc<br>aagggcttctacccctccgatatcgccgtggaatgggagagcaatggccag<br>cctgagaacaactacaagaccacacctcctgtgctggacagcgacggcagt | anti-BMCA CAR |

-continued

| SEQ ID NO: | Sequence | Description |
|---|---|---|
| | ttcttcctgtatagtagactcaccgtggataaatcaagatggcaagagggc<br>aacgtgttcagctgcagcgtgatgcacgaggccctgcacaaccactacacc<br>cagaaaagcctgagcctgtctctgggcaagatgttctgggtgctcgtggtc<br>gttggcggagtgctggcctgttacagcctgctggttaccgtggccttcatc<br>atcttttgggtcaagcggggcagaaagaagctgctctacatcttcaagcag<br>cccttcatgcggcccgtgcagaccacacaagaggaagatggctgctcctgc<br>agattccccgaggaagaagaaggcggctgcgagctgagagtgaagttcagc<br>agatccgccgacgctccagcctatcagcagggccaaaaccagctgtacaac<br>gagctgaacctggggagaagagaagagtacgacgtgctggataagcggaga<br>ggcagagatcctgaaatgggcggcaagcccagacggaagaatcctcaagag<br>ggcctgtataatgagctgcagaaagacaagatggccgaggcctacagcgag<br>atcggaatgaagggcgagcgcagaagaggcaagggacacgatggactgtac<br>cagggcctgagcaccgccaccaaggatacctatgacgcactgcacatgcag<br>gccctgccacctaga | |
| 12 | agctatgagctgacacagcctccaagcgcctctggcacacctggacagcga<br>gtgacaatgagctgtagcggcaccagcagcaacatcggcagccacagcgtg<br>aactggtatcagcagctgcctggcacagcccctaaactgctgatctacacc<br>aacaaccagcggcctagcggcgtgcccgatagattttctggcagcaagagc<br>ggcacaagcgccagcctggctatttctggactgcagagcgaggacgaggcc<br>gactattattgtgccgcctgggacggctctctgaacggccttgtttttggc<br>ggaggcaccaagctgacagtgctgggatctagaggtggcggaggatctggc<br>ggcggaggaagcggaggcggcggatctcttgaaatggctgaagtgcagctg<br>gtgcagtctggcgccgaagtgaagaagcctggcgagagcctgaagatcagc<br>tgcaaaggcagcggctacagcttcaccagctactggatcggctgggtccga<br>cagatgcctggcaaaggccttgagtggatgggcatcatctaccccggcgac<br>agcgacaccagatacagccctagctttcagggccacgtgaccatcagcgcc<br>gacaagtctatcagcaccgcctacctgcagtggtccagcctgaaggcctct<br>gacaccgccatgtactactgcgccagatactctggcagcttcgacaattgg<br>ggccagggcacactggtcaccgtgtccagcgagtctaaatacggaccgcct<br>tgtcctccttgtcccgctcctcctgttgccggaccttccgtgttcctgttt<br>cctccaaagcctaaggacaccctgatgatcagcaggacccctgaagtgacc<br>tgcgtggtggtggatgtgtcccaagaggatcccgaggtgcagttcaactgg<br>tatgtggacggcgtggaagtgcacaacgccaagaccaagcctagagaggaa<br>cagttccagagcacctacagagtggtgtccgtgctgacagtgctgcaccag<br>gattggctgaacggcaaagagtacaagtgcaaggtgtccaacaagggcctg<br>cctagcagcatcgagaaaaccatctccaaggccaagggccagccaagagag<br>ccccaggtttacacactgcctccaagccaagaggaaatgaccaagaatcag<br>gtgtccctgacatgcctggtcaagggcttctacccctccgatatcgccgtg<br>gaatgggagagcaatggccagcctgagaacaactacaagaccacacctcct<br>gtgctggacagcgacggcagtttcttcctgtatagtagactcaccgtggat<br>aaatcaagatggcaagagggcaacgtgttcagctgcagcgtgatgcacgag<br>gccctgcacaaccactacacccagaaaagcctgagcctgtctctgggcaag<br>atgttctgggtgctcgtggtcgttggcggagtgctggcctgttacagcctg<br>ctggttaccgtggccttcatcatcttttgggtcaagcggggcagaaagaag<br>ctgctctacatcttcaagcagcccttcatgcggcccgtgcagaccacacaa<br>gaggaagatggctgctcctgcagattccccgaggaagaagaaggcggctgc<br>gagctgagagtgaagttcagcagatccgccgacgctccagcctatcagcag<br>ggccaaaaccagctgtacaacgagctgaacctggggagaagagaagagtac<br>gacgtgctggataagcggagaggcagagatcctgaaatgggcggcaagccc<br>agacggaagaatcctcaagagggcctgtataatgagctgcagaaagacaag<br>atggccgaggcctacagcgagatcggaatgaagggcgagcgcagaagaggc<br>aagggacacgatggactgtaccagggcctgagcaccgccaccaaggatacc<br>tatgacgcactgcacatgcaggccctgccacctaga | anti-BMCA CAR |
| 13 | cagtctgccctgacacagcctgccagcgttagtgctagtcccggacagtct<br>atcgccatcagctgtaccggcaccagctctgacgttggctggtatcagcag<br>caccctggcaaggcccctaagctgatgatctacgaggacagcaagaggccc<br>agcggcgtgtccaatagattcagcggcagcaagagcggcaacaccgccagc<br>ctgacaattagcggactgcaggccgaggacgaggccgattactactgcagc<br>agcaacacccggtccagcacactggtttttggcggaggcaccaagctgaca<br>gtgctgggatctagaggtggcggaggatctggcggcggaggaagcggaggc<br>ggcggatctcttgaaatggctgaagtgcagctggtgcagtctggcgccgag<br>atgaagaaacctggcgcctctctgaagctgagctgcaaggccagcggctac<br>accttcatcgactactacgtgtactggatgcggcaggcccctggacaggga<br>ctcgaatctatgggctggatcaaccccaatagcggcggcaccaattacgcc<br>cagaaattccagggcagagtgaccatgaccagagacaccagcatcagcacc<br>gcctacatggaactgagccggctgagatccgacgacaccgccatgtactac<br>tgcgccagatctcagcgcgacggctacatggattattggggccagggaacc<br>ctggtcaccgtgtccagcgagtctaaatacggaccgccttgtcctccttgt<br>cccgctcctcctgttgccggaccttccgtgttcctgtttcctccaaagcct<br>aaggacaccctgatgatcagcaggacccctgaagtgacctgcgtggtggtg<br>gatgtgtcccaagaggatcccgaggtgcagttcaactggtatgtggacggc<br>gtggaagtgcacaacgccaagaccaagcctagagaggaacagttccagagc<br>acctacagagtggtgtccgtgctgacagtgctgcaccaggattggctgaac | anti-BMCA CAR |

-continued

| SEQ ID NO: | Sequence | Description |
|---|---|---|
| | ggcaaagagtacaagtgcaaggtgtccaacaagggcctgcctagcagcatc<br>gagaaaaccatctccaaggccaagggccagccaagagagccccaggtttac<br>acactgcctccaagccaagaggaaatgaccaagaatcaggtgtccctgaca<br>tgcctggtcaagggcttctacccctccgatatcgccgtggaatgggagagc<br>aatggccagcctgagaacaactacaagaccacacctcctgtgctggacagc<br>gacggcagtttcttcctgtatagtagactcaccgtggataaatcaagatgg<br>caagagggcaacgtgttcagctgcagcgtgatgcacgaggccctgcacaac<br>cactacacccagaaaagcctgagcctgtctctgggcaagatgttctgggtg<br>ctcgtggtcgttggcggagtgctggcctgttacagcctgctggttaccgtg<br>gccttcatcatcttttgggtcaagcggggcagaaagaagctgctctacatc<br>ttcaagcagcccttcatgcggcccgtgcagaccacacaagaggaagatggc<br>tgctcctgcagattccccgaggaagaagaaggcggctgcgagctgagagtg<br>aagttcagcagatccgccgacgctccagcctatcagcagggccaaaaccag<br>ctgtacaacgagctgaacctggggagaagagaagagtacgacgtgctggat<br>aagcggagaggcagagatcctgaaatgggcggcaagcccagacggaagaat<br>cctcaagagggcctgtataatgagctgcagaaagacaagatggccgaggcc<br>tacagcgagatcggaatgaagggcgagcgcagaagaggcaagggacacgat<br>ggactgtaccagggcctgagcaccgccaccaaggatacctatgacgcactg<br>cacatgcaggccctgccacctaga | |
| 14 | cagtctgccctgacacagcctgccagcgttagtgctagtcccggacagtct<br>atcgccatcagctgtaccggcaccagctctgacgttggctggtatcagcag<br>caccctggcaaggcccctaagctgatgatctacgaggacagcaagaggccc<br>agcggcgtgtccaatagattcagcggcagcaagagcggcaacaccgccagc<br>ctgacaattagcggactgcaggccgaggacgaggccgattactactgcagc<br>agcaacacccggtccagcacactggtttttggcggaggcaccaagctgaca<br>gtgctgggatctagaggtggcggaggatctggcggcggaggaagcggaggc<br>ggcggatctcttgaaatggctgaagtgcagctggtgcagtctggcgccgag<br>atgaagaaacctggcgcctctctgaagctgagctgcaaggccagcggctac<br>accttcatcgactactacgtgtactggatgcggcaggcccctggacaggga<br>ctcgaatctatgggctggatcaaccccaatagcggcggcaccaattacgcc<br>cagaaattccagggcagagtgaccatgaccagagacaccagcatcagcacc<br>gcctacatggaactgagccggctgagatccgacgacaccgccatgtactac<br>tgcgccagatctcagcgcgacggctacatggattattggggccagggaacc<br>ctggtcaccgtgtccagcgagtctaaatacggaccgccttgtcctccttgt<br>cccgctcctcctgttgccggaccttccgtgttcctgtttcctccaaagcct<br>aaggacaccctgatgatcagcaggacccctgaagtgacctgcgtggtggtg<br>gatgtgtcccaagaggatcccgaggtgcagttcaactggtatgtggacggc<br>gtggaagtgcacaacgccaagaccaagcctagagaggaacagttccagagc<br>acctacagagtggtgtccgtgctgacagtgctgcaccaggattggctgaac<br>ggcaaagagtacaagtgcaaggtgtccaacaagggcctgcctagcagcatc<br>gagaaaaccatctccaaggccaagggccagccaagagagccccaggtttac<br>acactgcctccaagccaagaggaaatgaccaagaatcaggtgtccctgaca<br>tgcctggtcaagggcttctacccctccgatatcgccgtggaatgggagagc<br>aatggccagcctgagaacaactacaagaccacacctcctgtgctggacagc<br>gacggcagtttcttcctgtatagtagactcaccgtggataaatcaagatgg<br>caagagggcaacgtgttcagctgcagcgtgatgcacgaggccctgcacaac<br>cactacacccagaaaagcctgagcctgtctctgggcaagatgttctgggtg<br>ctcgtggtcgttggcggagtgctggcctgttacagcctgctggttaccgtg<br>gccttcatcatcttttgggtcaggagtaagaggagcaggctcctgcacagt<br>gactacatgaacatgactccccgccgccccgggcccacccgcaagcattac<br>cagccctatgccccaccacgcgacttcgcagcctatcgctccagagtgaag<br>ttcagcagatccgccgacgctccagcctatcagcagggccaaaaccagctg<br>tacaacgagctgaacctggggagaagagaagagtacgacgtgctggataag<br>cggagaggcagagatcctgaaatgggcggcaagcccagacggaagaatcct<br>caagagggcctgtataatgagctgcagaaagacaagatggccgaggcctac<br>agcgagatcggaatgaagggcgagcgcagaagaggcaagggacacgatgga<br>ctgtaccagggcctgagcaccgccaccaaggatacctatgacgcactgcac<br>atgcaggccctgccacctaga | anti-BMCA CAR |
| 15 | EVQLVESGGGLVKPGGSLRLSCAASGFTFSDYYMSWIRQAPGKGLEWVSYI<br>SSSGSTIYYADSVKGRFTISRDNAKNSLYLQMNSLRAEDTAVYYCAKVDGD<br>YTEDYWGQGTLVTVSSGGGGSGGGGSGGGGSQSALTQPASVSGSPGQSITI<br>SCTGSSSDVGKYNLVSWYQQPPGKAPKLIIYDVNKRPSGVSNRFSGSKSGN<br>TATLTISGLQGDDEADYYCSSYGGSRSYVFGTGTKVTVLESKYGPPCPPCP<br>APPVAGPSVFLFPPKPKDTLMISRTPEVTCVVVDVSQEDPEVQFNWYVDGV<br>EVHNAKTKPREEQFQSTYRVVSVLTVLHQDWLNGKEYKCKVSNKGLPSSIE<br>KTISKAKGQPREPQVYTLPPSQEEMTKNQVSLTCLVKGFYPSDIAVEWESN<br>GQPENNYKTTPPVLDSDGSFFLYSRLTVDKSRWQEGNVFSCSVMHEALHNH<br>YTQKSLSLSLGKMFWVLVVVGGVLACYSLLVTVAF11FWVKRGRKKLLYIF<br>KQPFMRPVQTTQEEDGCSCRFPEEEEGGCELRVKFSRSADAPAYQQGQNQL<br>YNELNLGRREEYDVLDKRRGRDPEMGGKPRRKNPQEGLYNELQKDKMAEAY<br>SEIGMKGERRRGKGHDGLYQGLSTATKDTYDALHMQALPPR | anti-BMCA CAR |

-continued

| SEQ ID NO: | Sequence | Description |
|---|---|---|
| 16 | EVQLVQSGGGLVQPGRSLRLSCTASGFTFGDYAMSWFKQAPGKGLEWVGFI<br>RSKAYGGTTEYAASVKGRFTISRDDSKSIAYLQMNSLKTEDTAVYYCAAWS<br>APTDYWGQGTLVTVSSGGGGSGGGGSGGGGSDIQMTQSPAFLSASVGDRVT<br>VTCRASQGISNYLAWYQQKPGNAPRLLIYSASTLQSGVPSRFRGTGYGTEF<br>SLTIDSLQPEDFATYYCQQSYTSRQTFGPGTRLDIKESKYGPPCPPCPAPP<br>VAGPSVFLFPPKPKDTLMISRTPEVTCVVVDVSQEDPEVQFNWYVDGVEVH<br>NAKTKPREEQFQSTYRVVSVLTVLHQDWLNGKEYKCKVSNKGLPSSIEKTI<br>SKAKGQPREPQVYTLPPSQEEMTKNQVSLTCLVKGFYPSDIAVEWESNGQP<br>ENNYKTTPPVLDSDGSFFLYSRLTVDKSRWQEGNVFSCSVMHEALHNHYTQ<br>KSLSLSLGKMFWVLVVVGGVLACYSLLVTVAFIIFWVKRGRKKLLYIFKQP<br>FMRPVQTTQEEDGCSCRFPEEEEGGCELRVKFSRSADAPAYQQGQNQLYNE<br>LNLGRREEYDVLDKRRGRDPEMGGKPRRKNPQEGLYNELQKDKMAEAYSEI<br>GMKGERRRGKGHDGLYQGLSTATKDTYDALHMQALPPR | anti-BMCA CAR |
| 17 | EVQLVESGGGLVKPGGSLRLSCAASGFTFSDYYMSWIRQAPGKGLEWVSYI<br>SSSGSTIYYADSVKGRFTISRDNAKNSLYLQMNSLRAEDTAVYYCAKVDGP<br>PSFDIWGQGTMVTVSSGGGGSGGGGSGGGGSSYVLTQPPSVSVAPGQTARI<br>TCGANNIGSKSVHWYQQKPGQAPMLVVYDDDDRPSGIPERFSGSNSGNTAT<br>LTISGVEAGDEADYFCHLWDRSRDHYVFGTGTKLTVLESKYGPPCPPCPAP<br>PVAGPSVFLFPPKPKDTLMISRTPEVTCVVVDVSQEDPEVQFNWYVDGVEV<br>HNAKTKPREEQFQSTYRVVSVLTVLHQDWLNGKEYKCKVSNKGLPSSIEKT<br>ISKAKGQPREPQVYTLPPSQEEMTKNQVSLTCLVKGFYPSDIAVEWESNGQ<br>PENNYKTTPPVLDSDGSFFLYSRLTVDKSRWQEGNVFSCSVMHEALHNHYT<br>QKSLSLSLGKMFWVLVVVGGVLACYSLLVTVAF11FWVKRGRKKLLYIFKQ<br>PFMRPVQTTQEEDGCSCRFPEEEEGGCELRVKFSRSADAPAYQQGQNQLYN<br>ELNLGRREEYDVLDKRRGRDPEMGGKPRRKNPQEGLYNELQKDKMAEAYSE<br>IGMKGERRRGKGHDGLYQGLSTATKDTYDALHMQALPPR | anti-BMCA CAR |
| 18 | SYELTQPPSASGTPGQRVTMSCSGTSSNIGSHSVNWYQQLPGTAPKLLIYT<br>NNQRPSGVPDRFSGSKSGTSASLAISGLQSEDEADYYCAAWDGSLNGLVFG<br>GGTKLTVLGSRGGGGSGGGGSGGGGSLEMAEVQLVQSGAEVKKPGESLKIS<br>CKGSGYSFTSYWIGWVRQMPGKGLEWMGIIYPGDSDTRYSPSFQGHVTISA<br>DKSISTAYLQWSSLKASDTAMYYCARYSGSFDNWGQGTLVTVSSESKYGPP<br>CPPCPAPPVAGPSVFLFPPKPKDTLMISRTPEVTCVVVDVSQEDPEVQFNW<br>YVDGVEVHNAKTKPREEQFQSTYRVVSVLTVLHQDWLNGKEYKCKVSNKGL<br>PSSIEKTISKAKGQPREPQVYTLPPSQEEMTKNQVSLTCLVKGFYPSDIAV<br>EWESNGQPENNYKTTPPVLDSDGSFFLYSRLTVDKSRWQEGNVFSCSVMHE<br>ALHNHYTQKSLSLSLGKMFWVLVVVGGVLACYSLLVTVAFIIFWVKRGRKK<br>LLYIFKQPFMRPVQTTQEEDGCSCRFPEEEEGGCELRVKFSRSADAPAYQQ<br>GQNQLYNELNLGRREEYDVLDKRRGRDPEMGGKPRRKNPQEGLYNELQKDK<br>MAEAYSEIGMKGERRRGKGHDGLYQGLSTATKDTYDALHMQALPPR | anti-BMCA CAR |
| 19 | QSALTQPASVSASPGQSIAISCTGTSSDVGWYQQHPGKAPKLMIYEDSKRP<br>SGVSNRFSGSKSGNTASLTISGLQAEDEADYYCSSNTRSSTLVFGGGTKLT<br>VLGSRGGGGSGGGGSGGGGSLEMAEVQLVQSGAEMKKPGASLKLSCKASGY<br>TFIDYYVYWMRQAPGQGLESMGWINPNSGGTNYAQKFQGRVTMTRDTSIST<br>AYMELSRLRSDDTAMYYCARSQRDGYMDYWGQGTLVTVSSESKYGPPCPPC<br>PAPPVAGPSVFLFPPKPKDTLMISRTPEVTCVVVDVSQEDPEVQFNWYVDG<br>VEVHNAKTKPREEQFQSTYRVVSVLTVLHQDWLNGKEYKCKVSNKGLPSSI<br>EKTISKAKGQPREPQVYTLPPSQEEMTKNQVSLTCLVKGFYPSDIAVEWES<br>NGQPENNYKTTPPVLDSDGSFFLYSRLTVDKSRWQEGNVFSCSVMHEALHN<br>HYTQKSLSLSLGKMFWVLVVVGGVLACYSLLVTVAFIIFWVKRGRKKLLYI<br>FKQPFMRPVQTTQEEDGCSCRFPEEEEGGCELRVKFSRSADAPAYQQGQNQ<br>LYNELNLGRREEYDVLDKRRGRDPEMGGKPRRKNPQEGLYNELQKDKMAEA<br>YSEIGMKGERRRGKGHDGLYQGLSTATKDTYDALHMQALPPR | anti-BMCA CAR |
| 20 | QSALTQPASVSASPGQSIAISCTGTSSDVGWYQQHPGKAPKLMIYEDSKRP<br>SGVSNRFSGSKSGNTASLTISGLQAEDEADYYCSSNTRSSTLVFGGGTKLT<br>VLGSRGGGGSGGGGSGGGGSLEMAEVQLVQSGAEMKKPGASLKLSCKASGY<br>TFIDYYVYWMRQAPGQGLESMGWINPNSGGTNYAQKFQGRVTMTRDTS1ST<br>AYMELSRLRSDDTAMYYCARSQRDGYMDYWGQGTLVTVSSESKYGPPCPPC<br>PAPPVAGPSVFLFPPKPKDTLMISRTPEVTCVVVDVSQEDPEVQFNWYVDG<br>VEVHNAKTKPREEQFQSTYRVVSVLTVLHQDWLNGKEYKCKVSNKGLPSSI<br>EKTISKAKGQPREPQVYTLPPSQEEMTKNQVSLTCLVKGFYPSDIAVEWES<br>NGQPENNYKTTPPVLDSDGSFFLYSRLTVDKSRWQEGNVFSCSVMHEALHN<br>HYTQKSLSLSLGKMFWVLVVVGGVLACYSLLVTVAFIIFWVRSKRSRLLHS<br>DYMNMTPRRPGPTRKHYQPYAPPRDFAAYRSRVKFSRSADAPAYQQGQNQL<br>YNELNLGRREEYDVLDKRRGRDPEMGGKPRRKNPQEGLYNELQKDKMAEAY<br>SEIGMKGERRRGKGHDGLYQGLSTATKDTYDALHMQALPPR | anti-BMCA CAR |
| 21 | YFDSL | BCMA epitope |
| 22 | TGSSSDVGKYNLVS | BCMA-23 CDR-L1 (aa) |

-continued

| SEQ ID NO: | Sequence | Description |
|---|---|---|
| 23 | DVNKRPS | BCMA-23 CDR-L2 (aa) |
| 24 | SSYGGSRSYV | BCMA-23 CDR-L3 (aa) |
| 25 | ggctgattattattgtagctcatatggaggtagtaggtctt | BCMA-23 predicted splice acceptor site |
| 26 | ctactacatgagctggatccgccaggctccagggaaggggc | BCMA-23 predicted splice acceptor site |
| 27 | ctactatatgtcctggatcagacaggcacctggcaagggcc | BCMA-23 predicted splice acceptor site (O/SSE) |
| 28 | ggcagattactattgttctagctacggcggcagcagatcct | BCMA-23 predicted splice acceptor site (O/SSE) |
| 29 | EVQLVESGGGLVKPGGSLRLSCAASGFTFSDYYMSWIRQAPGKGLEWVSYI SSSGSTIYYADSVKGRFTISRDNAKNSLYLQMNSLRAEDTAVYYCAKVDGD YTEDYWGQGTLVTVSSGGGGSGGGGSGGGGSQSALTQPASVSGSPGQSITI SCTGSSSDVGKYNLVSWYQQPPGKAPKLIIYDVNKRPSGVSNRFSGSKSGN TATLTISGLQGDDEADYYCSSYGGSRSYVFGTGTKVTVL | BCMA-23 scFv (aa) |
| 30 | GAAGTGCAGCTGGTGGAGTCTGGGGGAGGCTTGGTCAAGCCTGGAGGGTCC CTGAGACTCTCCTGTGCAGCCTCTGGATTCACCTTCAGTGACTACTACATG AGCTGGATCCGCCAGGCTCCAGGGAAGGGGCTGGAGTGGGTTTCATACATT AGTAGTAGTGGTAGTACCATATACTACGCAGACTCTGTGAAGGGCCGATTC ACCATCTCCAGGGACAACGCCAAGAACTCACTGTATCTGCAAATGAACAGC CTGAGAGCCGAGGACACGGCCGTGTATTACTGTGCGAAAGTAGACGGAGAC TACACAGAGGACTACTGGGGCCAGGGAACCCTGGTCACCGTCTCCTCAGGT GGAGGCGGTTCAGGCGGAGGTGGCTCTGGCGGTGGCGGATCGCAGTCTGCC CTGACTCAGCCTGCCTCCGTGTCTGGGTCTCCTGGACAGTCGATCACTATC TCCTGCACTGGAAGCAGCAGTGATGTTGGCAAATATAATCTTGTCTCCTGG TACCAACAGCCCCCAGGCAAAGCCCCCAAGCTCATAATTTATGACGTCAAT AAGCGGCCCTCAGGGGTTTCTAATCGCTTCTCTGGCTCCAAGTCTGGCAAC ACGGCCACCCTGACAATCTCTGGGCTCCAGGGTGACGACGAGGCTGATTAT TATTGTAGCTCATATGGAGGTAGTAGGTCTTATGTCTTCGGAACTGGGACC AAGGTGACCGTCCTA | BCMA-23 scFv (nt) |
| 31 | gaggtgcagctggtggagtccggaggaggcctggtgaagccaggaggctcc ctgaggctgtcttgcgcagccagcggcttcacctttagcgactactatatg tcctggatcagacaggcacctggcaagggcctggagtgggtgagctacatc agctcctctggctccacaatctactatgccgactctgtgaagggccggttt accatcagcagagataacgccaagaattccctgtatctgcagatgaacagc ctgagggccgaggacacagccgtgtactattgcgccaaggtggacggcgat tacaccgaggattattggggccagggcacactggtgaccgtgagctccggc ggcggcggctctggaggaggaggcagcggcggaggaggctcccagtctgcc ctgacacagccagccagcgtgtccggctctcccggacagtccatcacaatc tcttgtaccggctctagctccgacgtgggcaagtacaacctggtgtcctgg tatcagcagccccctggcaaggcccctaagctgatcatctacgatgtgaac aagaggccatctggcgtgagcaatcgcttcagcggctccaagtctggcaat accgccacactgaccatcagcggcctgcagggcgacgatgaggcagattac tattgttctagctacggcggcagcagatcctacgtgttcggcacaggcacc aaggtgaccgtgctg | BCMA-23 scFv (nt) |
| 32 | EVQLVESGGGLVKPGGSLRLSCAASGFTFSDYYMSWIRQAPGKGLEWVSYI SSSGSTIYYADSVKGRFTISRDNAKNSLYLQMNSLRAEDTAVYYCAKVDGD YTEDYWGQGTLVTVSS | BCMA-23 $V_H$ Chain (aa) |
| 33 | QSALTQPASVSGSPGQSITISCTGSSSDVGKYNLVSWYQQPPGKAPKLIIY DVNKRPSGVSNRFSGSKSGNTATLTISGLQGDDEADYYCSSYGGSRSYVFG TGTKVTVL | BCMA-23 $V_L$ Chain (aa) |
| 34 | DYYMS | BCMA-23,-26 CDR-H1 (aa) Kabat numbering |
| 35 | YISSSGSTIYYADSVKG | BCMA-23,-26 CDR-H2 (aa) Kabat numbering |
| 36 | VDGDYTEDY | BCMA-23 CDR-H3 (aa) |
| 37 | DYAMS | BCMA-25 CDR-H1 (aa) Kabat numbering |

-continued

| SEQ ID NO: | Sequence | Description |
|---|---|---|
| 38 | FIRSKAYGGTTEYAASVKG | BCMA-25 CDR-H2 (aa) Kabat numbering |
| 39 | WSAPTDY | BCMA-25 CDR-H3 (aa) |
| 40 | RASQGISNYLA | BCMA-25 CDR-L1 (aa) |
| 41 | SASTLQS | BCMA-25 CDR-L2 (aa) |
| 42 | QQSYTSRQT | BCMA-25 CDR-L3 (aa) |
| 43 | ctatgccatgtcctggttcaggcaggcaccaggcaagggcc | BCMA-25 predicted splice acceptor site |
| 44 | gtccgcctctgtgggcgatagggtgaccgtgacatgtcgcg | BCMA-25 predicted splice acceptor site |
| 45 | gtgggctttatccgctctaaggcctacggcggcaccacaga | BCMA-25 predicted splice acceptor site |
| 46 | gtgacatgtcgcgcctcccagggcatctctaactacctggc | BCMA-25 predicted splice acceptor site |
| 47 | tacagcgcctccaccctgcagagcggagtgccctcccggtt | BCMA-25 predicted splice acceptor site |
| 48 | ctatgccatgtcctggttcaagcaggcaccaggcaagggcc | BCMA-25 predicted splice acceptor site (O/SSE) |
| 49 | EVQLVQSGGGLVQPGRSLRLSCTASGFTFGDYAMSWFRQAPGKGLEWVGFI<br>RSKAYGGTTEYAASVKGRFTISRDDSKSIAYLQMNSLKTEDTAVYYCAAWS<br>APTDYWGQGTLVTVSSGGGGSGGGGSGGGGSDIOMTQSPAFLSASVGDRVT<br>VTCRASQGISNYLAWYQQKPGNAPRLLIYSASTLQSGVPSRFRGTGYGTEE<br>SLTIDSLQPEDFATYYCQQSYTSRQTFGPGTRLDIK | BCMA-25 scFv sequence (aa) |
| 50 | gaggtgcagctggtgcagagcggaggaggcctggtgcagcctggcaggtcc<br>ctgcgcctgtcttgcaccgccagcggcttcacatttggcgactatgccatg<br>tcctggttcaggcaggcaccaggcaagggcctggagtgggtgggctttatc<br>cgctctaaggcctacggcggcaccacagagtatgccgccagcgtgaagggc<br>cggttcaccatcagccgggacgactctaagagcatcgcctacctgcagatg<br>aactctctgaagaccgaggacacagccgtgtactattgcgcagcatggagc<br>gccccaaccgattattggggccagggcaccctggtgacagtgagctccggc<br>ggcggcggctctggaggaggaggaagcggaggaggaggatccgacatccag<br>atgacacagtcccctgcctttctgtccgcctctgtgggcgatagggtgacc<br>gtgacatgtcgcgcctcccagggcatctctaactacctggcctggtatcag<br>cagaagcccggcaatgcccctcggctgctgatctacagcgcctccaccctg<br>cagagcggagtgccctcccggttcagaggaaccggctatggcacagagttt<br>tctctgaccatcgacagcctgcagccagaggatttcgccacatactattgt<br>cagcagtcttacaccagccggcagacatttggccccggcacaagactggat<br>atcaag | BCMA-25 scFV(nt) |
| 51 | gaggtgcagctggtgcagagcggaggaggcctggtgcagcctggcaggtcc<br>ctgcgcctgtcttgcaccgccagcggcttcacatttggcgactatgccatg<br>tcctggttcaagcaggcaccaggcaagggcctggagtgggtgggctttatc<br>cgctctaaggcctacggcggcaccacagagtatgccgccagcgtgaagggc<br>cggttcaccatcagccgggacgactctaagagcatcgcctacctgcagatg<br>aactctctgaagaccgaggacacagccgtgtactattgcgcagcatggagc<br>gccccaaccgattattggggccagggcaccctggtgacagtgagctccggc<br>ggcggcggctctggaggaggaggaagcggaggaggaggatccgacatccag<br>atgacacagtcccctgcctttctgtccgcctctgtgggcgatagggtgacc<br>gtgacatgtcgcgcctcccagggcatctctaactacctggcctggtatcag<br>cagaagcccggcaatgcccctcggctgctgatctacagcgcctccaccctg<br>cagagcggagtgccctcccggttcagaggaaccggctatggcacagagttt<br>tctctgaccatcgacagcctgcagccagaggatttcgccacatactattgt<br>cagcagtcttacaccagccggcagacatttggccccggcacaagactggat<br>atcaag | BCMA-25 scFV(nt) (O/SSE) |
| 52 | EVQLVQSGGGLVQPGRSLRLSCTASGFTFGDYAMSWFRQAPGKGLEWVGFI<br>RSKAYGGTTEYAASVKGRFTISRDDSKSIAYLQMNSLKTEDTAVYYCAAWS<br>APTDYWGQGTLVTVSS | BCMA-25 VH chain (aa) |
| 53 | DIQMTQSPAFLSASVGDRVTVTCRASQGISNYLAWYQQKPGNAPRLLIYSA<br>STLQSGVPSRFRGTGYGTEFSLTIDSLQPEDFATYYCQQSYTSRQTFGPGT<br>RLDIK | BCMA-25 VL chain (aa) |

-continued

| SEQ ID NO: | Sequence | Description |
|---|---|---|
| 54 | VDGPPSFDI | BCMA-26 CDR-H3 (aa) |
| 55 | GANNIGSKSVH | BCMA-26 CDR-L1 (aa) |
| 56 | DDDDRPS | BCMA-26 CDR-L2 (aa) |
| 57 | HLWDRSRDHYV | BCMA-26 CDR-L3 (aa) |
| 58 | EVQLVESGGGLVKPGGSLRLSCAASGFTFSDYYMSWIRQAPGKGLEWVSYI SSSGSTIYYADSVKGRFTISRDNAKNSLYLQMNSLRAEDTAVYYCAKVDGP PSFDIWGQGTMVTVSSGGGGSGGGGSGGGGSSYVLTQPPSVSVAPGQTARI TCGANNIGSKSVHWYQQKPGQAPMLVVYDDDDRPSGIPERFSGSNSGNTAT LTISGVEAGDEADYFCHLWDRSRDHYVFGTGTKLTVL | BCMA-26 scFv sequence (aa) |
| 59 | gaggtgcagctggtggagtccggaggaggcctggtgaagccaggaggctct ctgaggctgagctgcgcagcctccggcttcaccttttctgactactatatg agctggatcaggcaggcaccaggcaagggcctggagtgggtgtcttacatc agctcctctggcagcacaatctactatgccgactccgtgaagggcaggttc accatctctcgcgataacgccaagaatagcctgtatctgcagatgaactcc ctgcgggccgaggatacagccgtgtactattgcgccaaggtggacggcccc ccttcctttgatatctggggccagggcacaatggtgaccgtgagctccgga ggaggaggatccggcggaggaggctctggcggcggcggctctagctatgtg ctgacccagccaccatccgtgtctgtggcacctggacagacagcaaggatc acctgtggagcaaacaatatcggcagcaagtccgtgcactggtaccagcag aagcctggccaggccccaatgctggtggtgtatgacgatgacgatcggccc agcggcatccctgagagattttctggcagcaactccggcaataccgccaca ctgaccatctctggagtggaggcaggcgacgaggcagattacttctgtcac ctgtgggaccggagcagagatcactacgtgttcggcacaggcaccaagctg accgtgctg | BCMA-26 scFV(nt) |
| 60 | gaggtgcagctggtggagtccggaggaggcctggtgaagccaggaggctct ctgaggctgagctgcgcagcctccggcttcaccttttctgactactatatg agctggatcaggcaggcaccaggcaagggcctggagtgggtgtcttacatc agctcctctggcagcacaatctactatgccgactccgtgaagggcaggttc accatctctcgcgataacgccaagaatagcctgtatctgcagatgaactcc ctgcgggccgaggatacagccgtgtactattgcgccaaggtggacggcccc ccttcctttgatatctggggccagggcacaatggtgaccgtgagctccgga ggaggaggatccggcggaggaggctctggcggcggcggctctagctatgtg ctgacccagccaccatccgtgtctgtggcacctggacagacagcaaggatc acctgtggagcaaacaatatcggcagcaagtccgtgcactggtaccagcag aagcctggccaggccccaatgctggtggtgtatgacgatgacgatcggccc agcggcatccctgagagattttctggcagcaactccggcaataccgccaca ctgaccatctctggagtggaggcaggcgacgaggcagattacttctgtcac ctgtgggaccggagcagagatcactacgtgttcggcacaggcaccaagctg accgtgctg | BCMA-26 scFV(nt) (O/SSE) |
| 61 | EVQLVESGGGLVKPGGSLRLSCAASGFTFSDYYMSWIRQAPGKGLEWVSYI SSSGSTIYYADSVKGRFTISRDNAKNSLYLQMNSLRAEDTAVYYCAKVDGP PSFDIWGQGTMVTVSS | BCMA-26 Vh Chain (aa) |
| 62 | SYVLTQPPSVSVAPGQTARITCGANNIGSKSVHWYQQKPGQAPMLVVYDDD DRPSGIPERFSGSNSGNTATLTISGVEAGDEADYFCHLWDRSRDHYVFGTG TKLTVL | BCMA-26 VL chain (aa) |
| 63 | GYSFTSYW | BCMA-52 CDR-H1 (aa) |
| 64 | GYSFTSYWIG | BCMA-52 CDR-H1 (aa) - AbM numbering |
| 65 | GYSFTSY | BCMA-52 CDR-H1 (aa) - Chothia numbering |
| 66 | SYWIG | BCMA-52 CDR-H1 (aa) - Kabat numbering |
| 67 | IYPGDSDT | BCMA-52 CDR-H2 (aa) |
| 68 | IIYPGDSDTR | BCMA-52 CDR-H2 (aa) - AbM numbering |
| 69 | YPGDSD | BCMA-52 CDR-H2 (aa) - Chothia numbering |

-continued

| SEQ ID NO: | Sequence | Description |
|---|---|---|
| 70 | IIYPGDSDTRYSPSFQG | BCMA-52 CDR-H2 (aa) - Kabat numbering |
| 71 | ARYSGSFDN | BCMA-52 CDR-H3 (aa) |
| 72 | YSGSFDN | BCMA-52 CDR-H3 (aa) - Kabat, Chothia, and AbM numbering |
| 73 | SSNIGSHS | BCMA-52 CDR-L1 (aa) |
| 74 | SGTSSNIGSHSVN | BCMA-52 CDR-L1 (aa) - Kabat, Chothia, and AbM numbering |
| 75 | TNN | BCMA-52 CDR-L2 (aa) |
| 76 | TNNQRPS | BCMA-52 CDR-L2 (aa) - Kabat, Chothia, and AbM numbering |
| 77 | AAWDGSLNGLV | BCMA-52 CDR-L3 (aa) - Kabat, Chothia, and AbM numbering |
| 78 | ctggccatcagtggcctccagtctgaggatgaggctgatta | BCMA-52 predicted splice acceptor site |
| 79 | agatacagcccgtccttccaaggccacgtcaccatctcagc | BCMA-52 predicted splice acceptor site |
| 80 | ctggctatttctggactgcagagcgaggacgaggccgacta | BCMA-52 predicted splice acceptor site (O/SSE) |
| 81 | agatacagccctagctttcagggccacgtgaccatcagcgc | BCMA-52 predicted splice acceptor site (O/SSE) |
| 82 | tcctatgagctgactcagccaccctcagcgtctgggacccccgggcagagg gtcaccatgtcttgttctggaaccagctccaacatcggaagtcactctgta aactggtaccagcagctcccaggaacggcccccaaactcctcatctatact aataatcagcggccctcaggggtccctgaccgattctctggctccaagtct ggcacctcagcctccctggccatcagtggcctccagtctgaggatgaggct gattattactgtgcagcatgggatggcagcctgaatggtctggtattcggc ggagggaccaagctgaccgtcctaggttctagaggtggtggtggtagcggc ggcggcggctctggtggtggtggatccctcgagatggccgaggtgcagctg gtgcagtctggagcagaggtgaaaaagcccggggagtctctgaagatctcc tgtaagggttctggatacagctttaccagctactggatcggctgggtgcgc cagatgcccgggaaaggcctggagtggatggggatcatctatcctggtgac tctgataccagatacagcccgtccttccaaggccacgtcaccatctcagct gacaagtccatcagcactgcctacctgcagtggagcagcctgaaggcctcg gacaccgccatgtattactgtgcgcgctactctggttctttcgataactgg ggtcaaggtactctggtgaccgtctcctca | BCMA-52 scFv |
| 83 | SYELTQPPSASGTPGQRVTMSCSGTSSNIGSHSVNWYQQLPGTAPKLLIYT NNQRPSGVPDRFSGSKSGTSASLAISGLQSEDEADYYCAAWDGSLNGLVFG GGTKLTVLGSRGGGGSGGGGSGGGGSLEMAEVQLVQSGAEVKKPGESLKIS CKGSGYSFTSYWIGWVRQMPGKGLEWMGIIYPGDSDTRYSPSFQGHVTISA DKSISTAYLQWSSLKASDTAMYYCARYSGSFDNWGQGTLVTVSS | BCMA-52 scFv (aa) |
| 84 | agctatgagctgacacagcctccaagcgcctctggcacacctggacagcga gtgacaatgagctgtagcggcaccagcagcaacatcggcagccacagcgtg aactggtatcagcagctgcctggcacagcccctaaactgctgatctacacc aacaaccagcggcctagcggcgtgcccgatagattttctggcagcaagagc ggcacaagcgccagcctggctatttctggactgcagagcgaggacgaggcc gactattattgtgccgcctgggacggctctctgaacggccttgtttttggc ggaggcaccaagctgacagtgctgggatctagaggtggcggaggatctggc ggcggaggaagcggaggcggcggatctcttgaaatggctgaagtgcagctg gtgcagtctggcgccgaagtgaagaagcctggcgagagcctgaagatcagc tgcaaaggcagcggctacagcttcaccagctactggatcggctgggtccga cagatgcctggcaaaggccttgagtggatgggcatcatctaccccggcgac agcgacaccagatacagccctagctttcagggccacgtgaccatcagcgcc gacaagtctatcagcaccgcctacctgcagtggtccagcctgaaggcctct | BCMA-52 scFv (nt) (O/SSE) |

-continued

| SEQ ID NO: | Sequence | Description |
|---|---|---|
| | gacaccgccatgtactactgcgccagatactctggcagcttcgacaattgg ggccagggcacactggtcaccgtgtccagc | |
| 85 | EVQLVQSGAEVKKPGESLKISCKGSGYSFTSYWIGWVRQMPGKGLEWMGII YPGDSDTRYSPSFQGHVTISADKSISTAYLQWSSLKASDTAMYYCARYSGS FDNWGQGTLVTVSS | BCMA-52 VH chain (aa) |
| 86 | gaggtgcagctggtgcagtctggagcagaggtgaaaaagcccggggagtct ctgaagatctcctgtaagggttctggatacagctttaccagctactggatc ggctgggtgcgccagatgcccgggaaaggcctggagtggatggggatcatc tatcctggtgactctgataccagatacagcccgtccttccaaggccacgtc accatctcagctgacaagtccatcagcactgcctacctgcagtggagcagc ctgaaggcctcggacaccgccatgtattactgtgcgcgctactctggttct ttcgataactggggtcaaggtactctggtgaccgtctcctcagc | BCMA-52 VH chain (nt) |
| 87 | gaagtgcagctggtgcagtctggcgccgaagtgaagaagcctggcgagagc ctgaagatcagctgcaaaggcagcggctacagcttcaccagctactggatc ggctgggtccgacagatgcctggcaaaggccttgagtggatgggcatcatc taccccggcgacagcgacaccagatacagccctagctttcagggccacgtg accatcagcgccgacaagtctatcagcaccgcctacctgcagtggtccagc ctgaaggcctctgacaccgccatgtactactgcgccagatactctggcagc ttcgacaattggggccagggcacactggtcaccgtgtccagc | BCMA-52 VH chain (nt) (O/SSE) |
| 88 | SYELTQPPSASGTPGQRVTMSCSGTSSNIGSHSVNWYQQLPGTAPKLLIYT NNQRPSGVPDRFSGSKSGTSASLAISGLQSEDEADYYCAAWDGSLNGLVFG GGTKLTVLG | BCMA-52 VL chain (aa) |
| 89 | tcctatgagctgactcagccaccctcagcgtctgggacccccgggcagagg gtcaccatgtcttgttctggaaccagctccaacatcggaagtcactctgta aactggtaccagcagctcccaggaacggcccccaaactcctcatctatact aataatcagcggccctcaggggtccctgaccgattctctggctccaagtct ggcacctcagcctccctggccatcagtggcctccagtctgaggatgaggct gattattactgtgcagcatgggatggcagcctgaatggtctggtattcggc ggagggaccaagctgaccgtcctaggt | BCMA-52 VL chain (nt) |
| 90 | agctatgagctgacacagcctccaagcgcctctggcacacctggacagcga gtgacaatgagctgtagcggcaccagcagcaacatcggcagccacagcgtg aactggtatcagcagctgcctggcacagcccctaaactgctgatctacacc aacaaccagcggcctagcggcgtgcccgatagattttctggcagcaagagc ggcacaagcgccagcctggctatttctggactgcagagcgaggacgaggcc gactattattgtgccgcctgggacggctctctgaacggccttgtttttggc ggaggcaccaagctgacagtgctggga | BCMA-52 VL chain (nt) (O/SSE) |
| 91 | QNEYF | BCMA-52-scFV-mFc BCMA binding epitope 1 |
| 92 | CIPCQL | BCMA-52-scFV-mFc BCMA binding epitope 2 |
| 93 | CQRYC | BCMA-52-scFV-mFc BCMA binding epitope 3 |
| 94 | GYTFIDYY | BCMA-55 CDR-H1 (aa) |
| 95 | GYTFIDYYVY | BCMA-55 CDR-H1 (aa) - AbM numbering |
| 96 | GYTFIDY | BCMA-55 CDR-H1 (aa) - Chothia numbering |
| 97 | DYYVY | BCMA-55 CDR-H1 (aa) - Kabat numbering |
| 98 | INPNSGGT | BCMA-55 CDR-H2 (aa) |
| 99 | WINPNSGGTN | BCMA-55 CDR-H2 (aa) - AbM numbering |
| 100 | NPNSGG | BCMA-55 CDR-H2 (aa) - Chothia numbering |
| 101 | WINPNSGGTNYAQKFQG | BCMA-55 CDR-H2 (aa) - Kabat numbering |
| 102 | ARSQRDGYMDY | BCMA-55 CDR-H3 (aa) |

-continued

| SEQ ID NO: | Sequence | Description |
|---|---|---|
| 103 | SQRDGYMDY | BCMA-55 CDR-H3 (aa) - Kabat, Chothia, and AbM numbering |
| 104 | ISCTGTSSD | BCMA-55 CDR-L1 (aa) |
| 105 | TGTSSDVG | BCMA-55 CDR-L1 (aa) - Kabat, Chothia, and AbM numbering |
| 106 | EDS | BCMA-55 CDR-L2 (aa) |
| 107 | EDSKRPS | BCMA-55 CDR-L2 (aa) - Kabat, Chothia, and AbM numbering |
| 108 | SSNTRSSTLV | BCMA-55 CDR-L3 (aa) - Kabat, Chothia, and AbM numbering |
| 109 | gccctcaggggtttctaatcgcttctctggctccaagtctg | BCMA-55 predicted splice acceptor site |
| 110 | cgaggctgattattactgcagctcaaatacaagaagcagca | BCMA-55 predicted splice acceptor site |
| ill | cgaggccgattactactgcagcagcaacacccggtccagca | BCMA-55 predicted splice acceptor site (O/SSE) |
| 112 | gcccagcggcgtgtccaatagattcagcggcagcaagagcg | BCMA-55 predicted splice acceptor site (O/SSE) |
| 113 | caatctgccctgactcagcctgcctccgtgtctgcgtctcctggacagtcg<br>atcgccatctcctgcactggaaccagcagtgacgttggttggtatcaacag<br>cacccaggcaaagcccccaaactcatgatttatgaggacagtaagcggccc<br>tcaggggtttctaatcgcttctctggctccaagtctggcaacacggcctcc<br>ctgaccatctctgggctccaggctgaggacgaggctgattattactgcagc<br>tcaaatacaagaagcagcactttggtgttcggcggagggaccaagctgacc<br>gtcctaggttctagaggtggtggtggtagcggcggcggcggctctggtggt<br>ggtggatccctcgagatggccgaagtgcagctggtgcagtctggggctgag<br>atgaagaagcctggggcctcactgaagctctcctgcaaggcttctggatac<br>accttcatcgactactatgtatactggatgcgacaggcccctggacaaggg<br>cttgagtccatgggatggatcaaccctaacagtggtggcacaaactatgca<br>cagaagtttcagggcagggtcaccatgaccagggacacgtccatcagcaca<br>gcctacatggagctgagcaggctgagatctgacgacaccgccatgtattac<br>tgtgcgcgctcccagcgtgacggttacatggattactggggtcaaggtact<br>ctggtgaccgtctcctca | BCMA-55 scFv |
| 114 | QSALTQPASVSASPGQSIAISCTGTSSDVGWYQQHPGKAPKLMIYEDSKRP<br>SGVSNRFSGSKSGNTASLTISGLQAEDEADYYCSSNTRSSTLVFGGGTKLT<br>VLGSRGGGGSGGGGSGGGGSLEMAEVQLVQSGAEMKKPGASLKLSCKASGY<br>TFIDYYVYWMRQAPGQGLESMGWINPNSGGTNYAQKFQGRVTMTRDTSIST<br>AYMELSRLRSDDTAMYYCARSQRDGYMDYWGQGTLVTVSS | BCMA-55 scFv (aa) |
| 115 | cagtctgccctgacacagcctgccagcgttagtgctagtcccggacagtct<br>atcgccatcagctgtaccggcaccagctctgacgttggctggtatcagcag<br>caccctggcaaggcccctaagctgatgatctacgaggacagcaagaggccc<br>agcggcgtgtccaatagattcagcggcagcaagagcggcaacaccgccagc<br>ctgacaattagcggactgcaggccgaggacgaggccgattactactgcagc<br>agcaacacccggtccagcacactggtttttggcggaggcaccaagctgaca<br>gtgctgggatctagaggtggcggaggatctggcggcggaggaagcggaggc<br>ggcggatctcttgaaatggctgaagtgcagctggtgcagtctggcgccgag<br>atgaagaaacctggcgcctctctgaagctgagctgcaaggccagcggctac<br>accttcatcgactactacgtgtactggatgcggcaggcccctggacaggga<br>ctcgaatctatgggctggatcaaccccaatagcggcggcaccaattacgcc<br>cagaaattccagggcagagtgaccatgaccagagacaccagcatcagcacc<br>gcctacatggaactgagccggctgagatccgacgacaccgccatgtactac<br>tgcgccagatctcagcgcgacggctacatggattattggggccagggaacc<br>ctggtcaccgtgtccagc | BCMA-55 scFv (nt) (O/SSE) |
| 116 | EVQLVQSGAEMKKPGASLKLSCKASGYTFIDYYVYWMRQAPGQGLESMGWI<br>NPNSGGTNYAQKFQGRVTMTRDTSISTAYMELSRLRSDDTAMYYCARSQRD<br>GYMDYWGQGTLVTVSS | BCMA-55 VH chain (aa) |

-continued

| SEQ ID NO: | Sequence | Description |
|---|---|---|
| 117 | gaagtgcagctggtgcagtctggggctgagatgaagaagcctggggcctca ctgaagctctcctgcaaggcttctggatacaccttcatcgactactatgta tactggatgcgacaggcccctggacaagggcttgagtccatgggatggatc aaccctaacagtggtggcacaaactatgcacagaagtttcagggcagggtc accatgaccagggacacgtccatcagcacagcctacatggagctgagcagg ctgagatctgacgacaccgccatgtattactgtgcgcgctcccagcgtgac ggttacatggattactggggtcaaggtactctggtgaccgtctcctca | BCMA-55 VH chain (nt) |
| 118 | gaagtgcagctggtgcagtctggcgccgagatgaagaaacctggcgcctct ctgaagctgagctgcaaggccagcggctacaccttcatcgactactacgtg tactggatgcggcaggcccctggacagggactcgaatctatgggctggatc aaccccaatagcggcggcaccaattacgcccagaaattccagggcagagtg accatgaccagagacaccagcatcagcaccgcctacatggaactgagccgg ctgagatccgacgacaccgccatgtactactgcgccagatctcagcgcgac ggctacatggattattggggccagggaaccctggtcaccgtgtccagc | BCMA-55 VH chain (nt) (O/SSE) |
| 119 | QSALTQPASVSASPGQSIAISCTGTSSDVGWYQOHPGKAPKLMIYEDSKRP SGVSNRFSGSKSGNTASLTISGLQAEDEADYYCSSNTRSSTLVFGGGTKLT VLG | BCMA-55 VL chain (aa) |
| 120 | caatctgccctgactcagcctgcctccgtgtctgcgtctcctggacagtcg atcgccatctcctgcactggaaccagcagtgacgttggttggtatcaacag cacccaggcaaagcccccaaactcatgatttatgaggacagtaagcggccc tcaggggtttctaatcgcttctctggctccaagtctggcaacacggcctcc ctgaccatctctgggctccaggctgaggacgaggctgattattactgcagc tcaaatacaagaagcagcactttggtgttcggcggagggaccaagctgacc gtccta | BCMA-55 VL chain (nt) |
| 121 | cagtctgccctgacacagcctgccagcgttagtgctagtcccggacagtct atcgccatcagctgtaccggcaccagctctgacgttggctggtatcagcag caccctggcaaggcccctaagctgatgatctacgaggacagcaagaggccc agcggcgtgtccaatagattcagcggcagcaagagcggcaacaccgccagc ctgacaattagcggactgcaggccgaggacgaggccgattactactgcagc agcaacacccggtccagcacactggtttttggcggaggcaccaagctgaca gtgctg | BCMA-55 VL chain (nt) (O/SSE) |
| 122 | MLMAG | BCMA-55-scFV-mFc BCMA binding epitope 1 |
| 123 | YFDSLL | BCMA-55-scFV-mFc BCMA binding epitope 2 |
| 124 | QLRCSSNTPPL | BCMA-55-scFV-mFc BCMA binding epitope 3 |
| 125 | QIQLVQSGPELKKPGETVKISCKASGYTFTDYSINWVKRAPGKGLKWMGWI NTETREPAYAYDFRGRFAFSLETSASTAYLQINNLKYEDTATYFCALDYSY AMDYWGQGTSVTVSS | BCMA-C1 $V_H$ Chain (aa) |
| 126 | QIQLVQSGPELKKPGETVKISCKASGYTFTDYSINWVKRAPGKGLKWMGWI NTETREPAYAYDFRGRFAFSLETSASTAYLQINNLKYEDTATYFCALDYSY AMDYWGQGTSVTVSSGGGGSGGGGSGGGGSDIVLTQSPPSLAMSLGKRATI SCRASESVTILGSHLIHWYQQKPGQPPTLLIQLASNVQTGVPARFSGSGSR TDFTLTIDPVEEDDVAVYYCLQSRTIPRTFGGGTKLEIK | BCMA-C1 VH-VL scFv (aa) |
| 127 | DIVLTQSPPSLAMSLGKRATISCRASESVTILGSHLIHWYQQKPGQPPTLL IQLASNVQTGVPARFSGSGSRTDFTLTIDPVEEDDVAVYYCLQSRTIPRTF GGGTKLEIK | BCMA-C1 VL Chain (aa) |
| 128 | DIVLTQSPPSLAMSLGKRATISCRASESVTILGSHLIHWYQQKPGQPPTLL IQLASNVQTGVPARFSGSGSRTDFTLTIDPVEEDDVAVYYCLQSRTIPRTF GGGTKLEIKGGGGSGGGGSGGGGSQIQLVQSGPELKKPGETVKISCKASGY TFTDYSINWVKRAPGKGLKWMGWINTETREPAYAYDFRGRFAFSLETSAST AYLQINNLKYEDTATYFCALDYSYAMDYWGQGTSVTVSS | BCMA-C1 VL-VH scFv (aa) |
| 129 | QIQLVQSGPDLKKPGETVKLSCKASGYTFTNFGMNWVKQAPGKGFKWMAWI NTYTGESYFADDFKGRFAFSVETSATTAYLQINNLKTEDTATYFCARGEIY YGYDGGFAYWGQGTLVTVSAGGGGSGGGGSGGGGSDVVMTQSHRFMSTSVG DRVSITCRASQDVNTAVSWYQQKPGQSPKLLIFSASYRYTGVPDRFTGSGS GADFTLTISSVQAEDLAVYYCQQHYSTPWTFGGGTKLDIK | BCMA-C2 VH-VL scFv (aa) |
| 130 | DVVMTQSHRFMSTSVGDRVSITCRASQDVNTAVSWYQQKPGQSPKLLIFSA SYRYTGVPDRFTGSGSGADFTLTISSVQAEDLAVYYCQQHYSTPWTFGGGT KLDIKGGGGSGGGGSGGGGSQIQLVQSGPDLKKPGETVKLSCKASGYTFTN | BCMA-C2 VL-VH scFv (aa) |

| SEQ ID NO: | Sequence | Description |
|---|---|---|
| | FGMNWVKQAPGKGFKWMAWINTYTGESYFADDFKGRFAFSVETSATTAYLQ INNLKTEDTATYFCARGEIYYGYDGGFAYWGQGTLVTVSA | |
| 131 | QIQLVQSGPDLKKPGETVKLSCKASGYTFTNFGMNWVKQAPGKGFKWMAWI NTYTGESYFADDFKGRFAFSVETSATTAYLQINNLKTEDTATYFCARGEIY YGYDGGFAYWGQGTLVTVSA | BCMA-C2 $V_H$ Chain (aa) |
| 132 | DVVMTQSHRFMSTSVGDRVSITCRASQDVNTAVSWYQQKPGQSPKLLIFSA SYRYTGVPDRFTGSGSGADFTLTISSVQAEDLAVYYCQQHYSTPWTFGGGT KLDIK | BCMA-C2 $V_L$ Chain (aa) |
| 133 | QNEYFDSLL | BMCA epitope |
| 134 | IEVMYPPPYLDNEKSNGTIIHVKGKHLCPSPLFPGPSKP | CD28 ectodomain spacer (aa) |
| 135 | attgaagttatgtatcctcctccttacctagacaatgagaagagcaatgga accattatccatgtgaaagggaaacacctttgtccaagtcccctatttccc ggaccttctaagccc | CD28 ectodomain spacer (nt) |
| 136 | RSKRSRLLHSDYMNMTPRRPGPTRKHYQPYAPPRDFAAYRS | CD28 endo (aa) |
| 137 | aggagtaagaggagcaggctcctgcacagtgactacatgaacatgactccc cgccgccccgggcccacccgcaagcattaccagccctatgccccaccacgc gacttcgcagcctatcgctcc | CD28 endo (nt) |
| 138 | MFWVLVVVGGVLACYSLLVTVAF11FWV | CD28 transmembrane domain (aa) |
| 139 | atgttttgggtgctggtcgtggtcggaggggtgctggcctgttacagcctg ctggtgacagtcgctttcatcatcttctgggtg | CD28 transmembrane domain (nt) |
| 140 | atgttctgggtgctcgtggtcgttggcggagtgctggcctgttacagcctg ctggttaccgtggccttcatcatcttttgggtc | CD28 transmembrane domain (nt) |
| 141 | aggggtgctggcctgttacagcctgctggtgacagtcgctt | CD28TM predicted splice acceptor site |
| 142 | MPLLLLLPLLWAGALA | CD33 signal peptide |
| 143 | RVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYD ALHMQALPPR | CD3-zeta derived intracellular signaling domain (aa) |
| 144 | agagtcaagttttccaggtccgccgacgctccagcctaccagcaggggcag aaccagctgtacaacgagctgaacctgggcagaagggaagagtacgacgtc ctggataagcggagaggccgggaccctgagatgggcggcaagcctcggcgg aagaacccccaggaaggcctgtataacgaactgcagaaagacaagatggcc gaggcctacagcgagatcggcatgaagggcgagcggaggcggggcaagggc cacgacggcctgtatcagggcctgtccaccgccaccaaggatacctacgac gccctgcacatgcaggccctgcccccaagg | CD3-zeta derived intracellular signaling domain (nt) |
| 145 | agagtgaagttcagcagatccgccgacgctccagcctatcagcagggccaa aaccagctgtacaacgagctgaacctggggagaagagaagagtacgacgtg ctggataagcggagaggcagagatcctgaaatgggcggcaagcccagacgg aagaatcctcaagagggcctgtataatgagctgcagaaagacaagatggcc gaggcctacagcgagatcggaatgaagggcgagcgcagaagaggcaaggga cacgatggactgtaccagggcctgagcaccgccaccaaggatacctatgac gcactgcacatgcaggccctgccacctaga | CD3-zeta derived intracellular signaling domain (nt) |
| 146 | MALPVTALLLPLALLLHA | CD8 alpha signal peptide |
| 147 | MLQMARQCSQNEYFDSLLHDCKPCQLRCSSTPPLTCQRYCNASMTNSVKGM NAILWTCLGLSLIISLAVFVLTFLLRKMSSEPLKDEFKNTGSGLLGMANID LEKGRTGDEIVLPRGLEYTVEECTCEDCIKNKPKVDSDHCFPLPAMEEGAT ILVTTKTNDYCNSLSAALSVTEIEKSISAR | Cynomolgus BCMA; GenBank No. EHH60172.1 |
| 148 | QCTNYALLKLAGDVESNPGP | E2A peptide (aa) |
| 149 | GSGQCTNYALLKLAGDVESNPGP | E2A peptide (aa) |
| 150 | ctttttcgcaacgggtttgc | EF1a/HTLV promoter forward primer |

-continued

| SEQ ID NO: | Sequence | Description |
|---|---|---|
| 151 | ggatctgcgatcgctccggtgcccgtcagtgggcagagcgcacatcgccca cagtccccgagaagttggggggaggggtcggcaattgaaccggtgcctaga gaaggtggcgcggggtaaactgggaaagtgatgtcgtgtactggctccgcc tttttcccgagggtgggggagaaccgtatataagtgcagtagtcgccgtga acgttctttttcgcaacgggtttgccgccagaacacagctgaagcttcgag gggctcgcatctctccttcacgcgcccgccgccctacctgaggccgccatc cacgccggttgagtcgcgttctgccgcctcccgcctgtggtgcctcctgaa ctgcgtccgccgtctaggtaagtttaaagctcaggtcgagaccgggccttt gtccggcgctcccttggagcctacctagactcagccggctctccacgcttt gcctgaccctgcttgctcaactctacgtctttgtttcgttttctgttctgc gccgttacagatccaagctgtgaccggcgcctac | EF1 alpha promoter with HTLV1 enhancer |
| 152 | VKQTLNFDLLKLAGDVESNPGP | F2A peptide (aa) |
| 153 | GSGVKQTLNFDLLKLAGDVESNPGP | F2A peptide (aa) |
| 154 | MLLLVTSLLLCELPHPAFLLIP | GMCSFR alpha chain signal peptide |
| 155 | atgcttctcctggtgacaagccttctgctctgtgagttaccacacccagca ttcctcctgatccca | GMCSFR alpha chain signal sequence |
| 156 | ESKYGPPCPPCPAPEFLGGPSVFLFPPKPKDTLMISRTPEVTCVVVDVSQE DPEVQFNWYVDGVEVHNAKTKPREEQFNSTYRVVSVLTVLHQDWLNGKEYK CKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGNV FSCSVMHEALHNHYTQKSLSLSLGK | Hinge-$C_H2$-$C_H3$ spacer (aa) |
| 157 | ESKYGPPCPPCPGQPREPQVYTLPPSQEEMTKNQVSLTCLVKGFYPSDIAV EWESNGQPENNYKTTPPVLDSDGSFFLYSRLTVDKSRWQEGNVFSCSVMHE ALHNHYTQKSLSLSLGK | Hinge-$C_H3$ spacer (aa) |
| 158 | LLHACIPCQLR | human BCMA epitope (residues 17-27) |
| 159 | CIPCQLR | human BCMA epitope (residues 21-27) |
| 160 | SNTPPLTCQR | human BCMA epitope (residues 30-39) |
| 161 | SVINSVK | human BCMA epitope (residues 44-50) |
| 162 | CSQNEYF | human BCMA epitope (residues 8-15) |
| 163 | MLQMAGQCSQNEYFDSLLHACIPCQLRCSSNTPPLTCQRYCNARSGLLGMA NIDLEKSRTGDEIILPRGLEYTVEECTCEDCIKSKPKVDSDHCFPLPAMEE GATILVTTKTNDYCKSLPAALSATEIEKSISAR | Human BCMA Variant; GenBank No. ABN42510.1 |
| 164 | MLQMAGQCSQNEYFDSLLHACIPCQLRCSSNTPPLTCQRYCNASVTNSVKG TNAILWTCLGLSLIISLAVFVLMFLLRKISSEPLKDEFKNTGSGLLGMANI DLEKSRIGDEIILPRGLEYTVEECTCEDCIKSKPKVDSDHCFPLPAMEEGA TILVTTKTNDYCKSLPAALSATEIEKSISAR | Human BCMA; GenBank No. BAB60895.1 |
| 165 | MLQMAGQCSQNEYFDSLLHACIPCQLRCSSNTPPLTCQRYCNASVTNSVKG TNAILWTCLGLSLIISLAVFVLMFLLRKINSEPLKDEFKNTGSGLLGMANI DLEKSRIGDEIILPRGLEYTVEECTCEDCIKSKPKVDSDHCFPLPAMEEGA TILVTTKTNDYCKSLPAALSATEIEKSISAR | Human BCMA; NCBI No. NP_001183.2 |
| 166 | MVLQTQVFISLLLWISGAYG | human IgG-kappa signal peptide (aa) |
| 167 | atggtgctgcagacccaggtgttcatcagcctgctgctgtggatctccgga gcatacgga | human IgG-kappa signal sequence (nt) |
| 168 | atggtgctgcagacacaggtgttcatcagcctgctgctgtggatctccgga gcatacgga | human IgG-kappa signal sequence (nt) |
| 169 | atggtgctgcagacccaggtgttcatcagcctgctgctgtggatctctggc gcctacggc | human IgG-kappa signal sequence (nt) |

-continued

| SEQ ID NO: | Sequence | Description |
|---|---|---|
| 170 | atggtgctgcagacccaggtgttcatcagcctgctgctgtggatctctggc gcctatgga | human IgG-kappa signal sequence (nt) |
| 171 | atggtgctgcagacacaggtgttcatctccctgctgctgtggatctctgga gcatacgga | human IgG-kappa signal sequence (nt) |
| 172 | ASTKGPSVFPLAPCSRSTSESTAALGCLVKDYFPEPVTVSWNSGALTSGVH TFPAVLQSSGLYSLSSVVTVPSSNFGTQTYTCNVDHKPSNTKVDKTVERKC CVECPPCPAPPVAGPSVFLFPPKPKDTLMISRTPEVTCVVVDVSHEDPEVQ FNWYVDGVEVHNAKTKPREEQFNSTFRVVSVLTVVHQDWLNGKEYKCKVSN KGLPAPIEKTISKTKGQPREPQVYTLPPSREEMTKNQVSLTCLVKGFYPSD ISVEWESNGQPENNYKTTPPMLDSDGSFFLYSKLTVDKSRWQQGNVFSCSV MHEALHNHYTQKSLSLSPGK | Human IgG2 Fc (Uniprot P01859) |
| 173 | ASTKGPSVFPLAPCSRSTSESTAALGCLVKDYFPEPVTVSWNSGALTSGVH TFPAVLQSSGLYSLSSVVTVPSSSLGTKTYTCNVDHKPSNTKVDKRVESKY GPPCPSCPAPEFLGGPSVFLFPPKPKDTLMISRTPEVTCVVVDVSQEDPEV QFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPS DIAVEWESNGQPENNYKTTPPVLDSDGSFFLYSRLTVDKSRWQEGNVFSCS VMHEALHNHYTQKSLSLSLGK | Human IgG4 Fc (Uniprot P01861) |
| 174 | ESKYGPPCPPCPAPPVAGPSVFLFPPKPKDTLMISRTPEVTCVVVDVSQED PEVQFNWYVDGVEVHNAKTKPREEQFQSTYRVVSVLTVLHQDWLNGKEYKC KVSNKGLPSSIEKTISKAKGQPREPQVYTLPPSQEEMTKNQVSLTCLVKGF YPSDIAVEWESNGQPENNYKTTPPVLDSDGSFFLYSRLTVDKSRWQEGNVF SCSVMHEALHNHYTQKSLSLSLGK | IgG4/IgG2 hinge-IgG2/IgG4 $C_H2$-IgG4 $C_H3$ spacer (aa) |
| 175 | gaatctaagtacggaccgccctgccctccctgccctgctcctcctgtggct ggaccaagcgtgttcctgtttccacctaagcctaaagataccctgatgatt tcccgcacacctgaagtgacttgcgtggtcgtggacgtgagccaggaggat ccagaagtgcagttcaactggtacgtggacggcgtggaagtccacaatgct aagactaaaccccgagaggaacagtttcagtcaacttaccgggtcgtgagc gtgctgaccgtcctgcatcaggattggctgaacgggaaggagtataagtgc aaagtgtctaataagggactgcctagctccatcgagaaaacaattagtaag gcaaaagggcagcctcgagaaccacaggtgtataccctgcccccctagccag gaggaaatgaccaagaaccaggtgtccctgacatgtctggtcaaaggcttc tatccaagtgacatcgccgtggagtgggaatcaaatgggcagcccgagaac aattacaagaccacaccacccgtgctggactctgatggaagtttctttctg tattccaggctgaccgtggataaatctcgctggcaggagggcaacgtgttc tcttgcagtgtcatgcacgaagccctgcacaatcattatacacagaagtca ctgagcctgtccctgggcaaa | IgG4/IgG2 hinge-IgG2/IgG4 $C_H2$-IgG4 $C_H3$ spacer (nt) |
| 176 | GSTSGSGKPGSGEGSTKG | Linker (aa) |
| 177 | tttatttagtctccagaaaaaggggggaatgaaagaccccacctgtaggtt tggcaagctaggatcaaggttaggaacagagagacagcagaatatgggcca aacaggatatctgtggtaagcagttcctgccccggctcagggccaagaaca gttggaacagcagaatatgggccaaacaggatatctgtggtaagcagttcc tgccccggctcagggccaagaacagatggtccccagatgcggtcccgccct cagcagtttctagagaaccatcagatgtttccagggtgccccaaggacctg aaatgaccctgtgccttatttgaactaaccaatcagttcgcttctcgcttc tgttcgcgcgcttctgctccccgagctcaataaaagagccca | MND promoter |
| 178 | ggatctgcgatcgctccggtgcccgtcagtgggcagagcgcacatcgccca cagtccccgagaagttggggggaggggtcggcaattgaaccggtgcctaga gaaggtggcgcggggtaaactgggaaagtgatgtcgtgtactggctccgcc tttttcccgagggtgggggagaaccgtatataagtgcagtagtcgccgtga acgttctttttcgcaacgggtttgccgccagaacacagctgaagcttcgag gggctcgcatctctccttcacgcgcccgccgccctacctgaggccgccatc cacgccggttgagtcgcgttctgccgcctcccgcctgtggtgcctcctgaa ctgcgtccgccgtctaggtaagtttaaagctcaggtcgagaccgggccttt gtccggcgctcccttggagcctacctagactcagccggctctccacgcttt gcctgaccctgcttgctcaactctacgtctttgtttcgttttctgttctgc gccgttacagatccaagctgtgaccggcgcctacggctagcgcc | modified EF1 alpha promoter |
| 179 | MAQQCFHSEYFDSLLHACKPCHLRCSNPPATCQPYCDPSVTSSVKGTYTVL WIFLGLTLVLSLALFTISFLLRKMNPEALKDEPQSPGQLDGSAQLDKADTE LTRIRAGDDRIFPRSLEYTVEECTCEDCVKSKPKGDSDHFFPLPAMEEGAT ILVTTKTGDYGKSSVPTALQSVMGMEKPTHTR | Mouse BCMA; NCBI No. NP_035738.1 |
| 180 | cagtttcttcctgtatagtagactcaccgtggataaatcaa | Optimized splice acceptor site |

-continued

| SEQ ID NO: | Sequence | Description |
|---|---|---|
| 181 | gggcaacgtgttcagctgcagcgtgatgcacgaggccctgc | Optimized splice acceptor site |
| 182 | cggagtgctggcctgttacagcctgctggttaccgtggcct | Optimized splice acceptor site |
| 183 | gctgagagtgaagttcagcagatccgccgacgctccagcct | Optimized splice acceptor site |
| 184 | acacctccactggatccccaagagctggatatcctgaaaac | Optimized splice acceptor site |
| 185 | accggattcctcctgatccaagcctggccagagaacagaac | Optimized splice acceptor site |
| 186 | acggccagtttagcctggctgtggtgtctctgaacatcacc | Optimized splice acceptor site |
| 187 | aagtttctttctgtattccagactgaccgtggataaatctc | Optimized splice acceptor site |
| 188 | cgccttgtcctccttgtcccgctcctcctgttgccggacct | optimized splice acceptor site |
| 189 | agtctaaatacggac | Optimized splice donor site |
| 190 | tcaactggtatgtgg | Optimized splice donor site |
| 191 | accatctccaaggcc | Optimized splice donor site |
| 192 | gccccaggtttacac | Optimized splice donor site |
| 193 | tcagcagatccgccg | Optimized splice donor site |
| 194 | ctcctgtgtgaactc | Optimized splice donor site |
| 195 | tcggaaagtgtgcaa | Optimized splice donor site |
| 196 | cagcacggccagttt | Optimized splice donor site |
| 197 | aaccggggcgagaac | Optimized splice donor site |
| 198 | ctggaaggcgagccc | Optimized splice donor site |
| 199 | tgttcatgtgagcgg | Optimized splice donor site |
| 200 | gagtctaaatacggaccgccttgtcctccttgtcccgctcctcctgttgcc ggaccttccgtgttcctgtttcctccaaagcctaaggacaccctgatgatc agcaggacccctgaagtgacctgcgtggtggtggatgtgtcccaagaggat cccgaggtgcagttcaactggtatgtggacggcgtggaagtgcacaacgcc aagaccaagcctagagaggaacagttccagagcacctacagagtggtgtcc gtgctgacagtgctgcaccaggattggctgaacggcaaagagtacaagtgc aaggtgtccaacaagggcctgcctagcagcatcgagaaaaccatctccaag gccaagggccagccaagagagccccaggtttacacactgcctccaagccaa gaggaaatgaccaagaatcaggtgtccctgacatgcctggtcaagggcttc taccccctccgatatcgccgtggaatgggagagcaatggccagcctgagaac aactacaagaccacacctcctgtgctggacagcgacggcagtttcttcctg tatagtagactcaccgtggataaatcaagatggcaagagggcaacgtgttc agctgcagcgtgatgcacgaggccctgcacaaccactacacccagaaaagc ctgagcctgtctctgggcaag | optimized SSE IgG4/IgG2 hinge-IgG2/IgG4 $C_H2$-IgG4 Ch3 spacer (nt) |
| 201 | ATNFSLLKQAGDVEENPGP | P2A peptide (aa) |
| 202 | GSGATNFSLLKQAGDVEENPGP | P2A peptide (aa) |

-continued

| SEQ ID NO: | Sequence | Description |
|---|---|---|
| 203 | cgccttgtcctccttgtccagctcctcctgttgccggacct | predicted splice acceptor site |
| 204 | cagtttcttcctgtatagtagactcaccgtggataaatcaa | predicted splice acceptor site |
| 205 | accggattcctcctgattcaggcctggccagagaacagaac | predicted splice acceptor site |
| 206 | cgtctaggtaagttt | Predicted splice donor site |
| 207 | gaccaaggtgaccgt | Predicted splice donor site |
| 208 | tgcactggtaccagc | Predicted splice donor site |
| 209 | taaactggtaccagc | Predicted splice donor site |
| 210 | atctcctgtaagggt | Predicted splice donor site |
| 211 | ggtcaaggtactctg | Predicted splice donor site |
| 212 | gaggacagtaagcgg | Predicted splice donor site |
| 213 | ggtcaaggtactctg | Predicted splice donor site |
| 214 | tgcctccgtgtctgc | Predicted splice donor site |
| 215 | caccaaggtgaccgt | Predicted splice donor site |
| 216 | tgaactggtatcagc | Predicted splice donor site |
| 217 | atctcttgaaatggt | Predicted splice donor site |
| 218 | ggccagggcacactg | Predicted splice donor site |
| 219 | gaggacagcaagagg | Predicted splice donor site |
| 220 | ggccagggaaccctg | Predicted splice donor site |
| 221 | tgccagcgttagtgc | Predicted splice donor site |
| 222 | aatctaagtacggac | Predicted splice donor site |
| 223 | tcaactggtacgtgg | Predicted splice donor site |
| 224 | acaattagtaaggca | Predicted splice donor site |
| 225 | accacaggtgtatac | Predicted splice donor site |
| 226 | tttccaggtccgccg | Predicted splice donor site |
| 227 | ctgctctgtgagtta | Predicted splice donor site |

-continued

| SEQ ID NO: | Sequence | Description |
|---|---|---|
| 228 | acgcaaagtgtgtaa | Predicted splice donor site |
| 229 | caacatggtcagttt | Predicted splice donor site |
| 230 | aacagaggtgaaaac | Predicted splice donor site |
| 231 | ctggagggtgagcca | Predicted splice donor site |
| 232 | tggctccgcctttttcccgagggtgggggagaaccgtatat | promoter predicted splice acceptor site |
| 233 | tgaactgcgtccgccgtctaggtaagtttaaagctcaggtc | promoter predicted splice acceptor site |
| 234 | ttctgttctgcgccgttacagatccaagctgtgaccggcgc | promoter predicted splice acceptor site |
| 235 | gatatcgaattcctgcagcc | Reverse primer 5′ of WPRE |
| 236 | GAGTCTAAATACGGACCGCCTTGTCCTCCTTGTCCAGCTCCTCCTGTTGCC GGACCTTCCGTGTTCCTGTTTCCTCCAAAGCCTAAGGACACCCTGATGATC AGCAGGACCCCTGAAGTGACCTGCGTGGTGGTGGATGTGTCCCAAGAGGAT CCCGAGGTGCAGTTCAATTGGTACGTGGACGGCGTGGAAGTGCACAACGCC AAGACCAAGCCTAGAGAGGAACAGTTCCAGAGCACCTACAGAGTGGTGTCC GTGCTGACAGTGCTGCACCAGGATTGGCTGAACGGCAAAGAGTACAAGTGC AAGGTGTCCAACAAGGGCCTGCCTAGCAGCATCGAGAAAACCATCTCCAAG GCCAAGGGCCAGCCAAGAGAGCCCCAGGTTTACACACTGCCTCCAAGCCAA GAGGAAATGACCAAGAATCAGGTGTCCCTGACATGCCTGGTCAAGGGCTTC TACCCCTCCGATATCGCCGTGGAATGGGAGAGCAATGGCCAGCCTGAGAAC AACTACAAGACCACACCTCCTGTGCTGGACAGCGACGGCAGTTTCTTCCTG TATAGTAGACTCACCGTGGATAAATCAAGATGGCAAGAGGGCAACGTGTTC AGCTGCAGCGTGATGCACGAGGCCCTGCACAACCACTACACCCAGAAAAGC CTGAGCCTGTCTCTGGGCAAA | Spacer-codon optimized (nt) |
| 237 | ESKYGPPCPPCP | Spacer (IgG4hinge) (aa) |
| 238 | gaatctaagtacggaccgccctgccccccttgccct | Spacer (IgG4hinge) (nt) |
| 239 | aagtttctttctgtattccaggctgaccgtggataaatctc | spacer predicted splice acceptor site |
| 240 | gggcaacgtgttctcttgcagtgtcatgcacgaagccctgc | spacer predicted splice acceptor site |
| 241 | EGRGSLLTCGDVEENPGP | T2A peptide (aa) |
| 242 | GSGEGRGSLLTCGDVEENPGP | T2A peptide (aa) |
| 243 | LEGGGEGRGSLLTCGDVEENPGPR | T2A peptide (aa) |
| 244 | ctcgagggcggcggagagggcagaggaagtcttctaacatgcggtgacgtg gaggagaatcccggccctagg | T2A peptide (nt) |
| 245 | cttgaaggtggtggcgaaggcagaggcagcctgcttacatgcggagatgtg gaagagaaccccggacctaga | T2A peptide (nt) |
| 246 | MLLLVTSLLLCELPHPAFLLIPRKVCNGIGIGEFKDSLSINATNIKHFKNC TSISGDLHILPVAFRGDSFTHTPPLDPQELDILKTVKEITGFLLIQAWPEN RTDLHAFENLEIIRGRTKQHGQFSLAVVSLNITSLGLRSLKEISDGDVIIS GNKNLCYANTINWKKLFGTSGQKTKIISNRGENSCKATGQVCHALCSPEGC WGPEPRDCVSCRNVSRGRECVDKCNLLEGEPREFVENSECIQCHPECLPQA MNITCTGRGPDNCIQCAHYIDGPHCVKTCPAGVMGENNTLVWKYADAGHVC HLCHPNCTYGCTGPGLEGCPTNGPKIPSIATGMVGALLLLLVVALGIGLFM | truncated EGFR (tEGFR) sequence (aa) |
| 247 | atgcttctcctggtgacaagccttctgctctgtgagttaccacacccagca ttcctcctgatcccacgcaaagtgtgtaacggaataggtattggtgaattt aaagactcactctccataaatgctacgaatattaaacacttcaaaaactgc acctccatcagtggcgatctccacatcctgccggtggcatttaggggtgac tccttcacacatactcctcctctggatccacaggaactggatattctgaaa | truncated EGFR (tEGFR) sequence (nt) |

-continued

| SEQ ID NO: | Sequence | Description |
|---|---|---|
| | accgtaaaggaaatcacagggtttttgctgattcaggcttggcctgaaaac aggacggacctccatgcctttgagaacctagaaatcatacgcggcaggacc aagcaacatggtcagttttctcttgcagtcgtcagcctgaacataacatcc ttgggattacgctccctcaaggagataagtgatggagatgtgataatttca ggaaacaaaaatttgtgctatgcaaatacaataaactggaaaaaactgttt gggacctccggtcagaaaaccaaaattataagcaacagaggtgaaaacagc tgcaaggccacaggccaggtctgccatgccttgtgctcccccgagggctgc tggggcccggagcccagggactgcgtctcttgccggaatgtcagccgaggc agggaatgcgtggacaagtgcaaccttctggagggtgagccaagggagttt gtggagaactctgagtgcatacagtgccacccagagtgcctgcctcaggcc atgaacatcacctgcacaggacggggaccagacaactgtatccagtgtgcc cactacattgacggccccactgcgtcaagacctgcccggcaggagtcatg ggagaaaacaacaccctggtctggaagtacgcagacgccggccatgtgtgc cacctgtgccatccaaactgcacctacggatgcactgggccaggtcttgaa ggctgtccaacgaatgggcctaagatcccgtccatcgccactgggatggtg ggggccctcctcttgctgctggtggtggccctggggatcggcctcttcatg tga | |
| 248 | atgctgctcctcgtgacaagcctgctcctgtgtgaactccctcatccagct tttctgctcattcctcggaaagtgtgcaacggcatcggcatcggagagttc aaggacagcctgagcatcaatgccaccaacatcaagcacttcaagaattgc accagcatcagcggcgacctgcacattctgcctgtggcctttagaggcgac agcttcacccacacacctccactggatccccaagagctggatatcctgaaa accgtgaaagagattaccggattcctcctgatccaagcctggccagagaac agaaccgatctgcacgccttcgagaacctcgagatcatcagaggccggacc aaacagcacggccagtttagcctggctgtggtgtctctgaacatcaccagt ctgggcctgagaagcctgaaagaaatctccgacggcgacgtgatcatctcc ggaaacaagaacctgtgctacgccaacaccatcaactggaagaagctgttc ggcacctccggccagaaaacaaagatcatctctaaccggggcgagaacagc tgcaaggccaccggacaagtttgtcacgccctgtgtagccctgaaggctgt tggggacccgaacctagagactgtgtgtcctgccggaatgtgtcccggggc agagaatgtgtggataagtgcaacctgctggaaggcgagccccgcgagttt gtggaaaacagcgagtgcatccagtgtcaccccgagtgtctgccccaggcc atgaacattacatgcaccggcagaggccccgacaactgtattcagtgcgcc cactacatcgacggccctcactgcgtgaaaacatgtccagctggcgtgatg ggagagaacaacaccctcgtgtggaagtatgccgacgccggacatgtgtgc cacctgtgtcaccctaattgcacctacggctgtaccggacctggcctggaa ggatgccctacaaacggccctaagatccccagcattgccaccggaatggtt ggagccctgctgcttctgttggtggtggccctcggaatcggcctgttcatg tga | truncated EGFR (tEGFR) sequence (nt) (O/SSE) |
| 249 | actcctcctctggatccacaggaactggatattctgaaaac | truncated marker predicted splice acceptor site |
| 250 | acagggtttttgctgattcaggcttggcctgaaaacaggac | truncated marker predicted splice acceptor site |
| 251 | atggtcagttttctcttgcagtcgtcagcctgaacataaca | truncated marker predicted splice acceptor site |
| 252 | tcttcatgtgagcgg | truncated marker predicted splice donor site |
| 253 | aatcaacctctggattacaaaatttgtgaaagattgactggtattcttaac tatgttgctccttttacgctatgtggatacgctgctttaatgcctttgtat catgctattgcttcccgtatggctttcattttctcctccttgtataaatcc tggttgctgtctctttatgaggagttgtggcccgttgtcaggcaacgtggc gtggtgtgcactgtgtttgctgacgcaacccccactggttggggcattgcc accacctgtcagctcctttccgggactttcgctttccccctccctattgcc acggcggaactcatcgccgcctgccttgcccgctgctggacaggggctcgg ctgttgggcactgacaattccgtggtgttgtcggggaaatcatcgtccttt ccttggctgctcgcctgtgttgccacctggattctgcgcgggacgtccttc tgctacgtcccttcggccctcaatccagcggaccttccttcccgcggcctg ctgccggctctgcggcctcttccgcgtcttcgccttcgccctcagacgagt cggatctccctttgggccgcctccccgc | Woodchuck Hepatitis Virus (WHP) Posttranscriptional Regulatory Element (WPRE) |
| 254 | tcaattggtacgtgg | predicted splice site |
| 255 | SRGGGGSGGGGSGGGGSLEMA | Linker (aa) |

-continued

| SEQ ID NO: | Sequence | Description |
|---|---|---|
| 256 | MRPSGRKSSKMQAFRIWDVNQKTFYLRNNQLVAGYLQGPNVNLEEKIDVVP<br>IEPHALFLGIHGGKMCLSCVKSGDETRLQLEAVNITDLSENRKQDKRFAFI<br>RSDSGPTTSFESAACPGWFLCTAMEADQPVSLTNMPDEGVMVTKFYFQEDE | Anakinra |
| 257 | RASESVTILGSHLIH | CDR-L1 (Kabat) (aa) |
| 258 | LASNVQT | CDR-L2 (Kabat) (aa) |
| 259 | LQSRTIPRT | CDR-L3 (Kabat) (aa) |
| 260 | DYSIN | CDR-H1 (Kabat) (aa) |
| 261 | WINTETREPAYAYDFRG | CDR-H2 (Kabat) (aa) |
| 262 | DYSYAMDY | CDR-H3 (Kabat) (aa) |
| 263 | MALPVTALLLPLALLLHAARPDIVLTQSPPSLAMSLGKRATISCRASESVT<br>ILGSHLIHWYQQKPGQPPTLLIQLASNVQTGVPARFSGSGSRIDFTLTIDP<br>VEEDDVAVYYCLQSRTIPRTFGGGTKLEIKGSTSGSGKPGSGEGSTKGQIQ<br>LVQSGPELKKPGETVKISCKASGYTFTDYSINWVKRAPGKGLKWMGWINTE<br>TREPAYAYDFRGRFAFSLETSASTAYLQINNLKYEDTATYFCALDYSYAMD<br>YWGQGTSVTVSSAAATTTPAPRPPTPAPTIASQPLSLRPEACRPAAGGAVH<br>TRGLDFACDIYIWAPLAGTCGVLLLSLVITLYCKRGRKKLLYIFKQPFMRP<br>VQTTQEEDGCSCRFPEEEEGGCELRVKFSRSADAPAYQQGQNQLYNELNLG<br>RREEYDVLDKRRGRDPEMGGKPRRKNPQEGLYNELQKDKMAEAYSEIGMKG<br>ERRRGKGHDGLYQGLSTATKDTYDALHMQALPPR | Anti-BCMA CAR (aa) |
| 264 | ATGGCACTCCCCGTCACCGCCCTTCTCTTGCCCCTCGCCCTGCTGCTGCAT<br>GCTGCCAGGCCCGACATTGTGCTCACTCAGTCACCTCCCAGCCTGGCCATG<br>AGCCTGGGAAAAAGGGCCACCATCTCCTGTAGAGCCAGTGAGTCCGTCACA<br>ATCTTGGGGAGCCATCTTATTCACTGGTATCAGCAGAAGCCCGGGCAGCCT<br>CCAACCCTTCTTATTCAGCTCGCGTCAAACGTCCAGACGGGTGTACCTGCC<br>AGATTTTCTGGTAGCGGGTCCCGCACTGATTTTACACTGACCATAGATCCA<br>GTGGAAGAAGACGATGTGGCCGTGTATTATTGTCTGCAGAGCAGAACGATT<br>CCTCGCACATTTGGTGGGGGTACTAAGCTGGAGATTAAGGGAAGCACGTCC<br>GGCTCAGGGAAGCCGGGCTCCGGCGAGGGAAGCACGAAGGGGCAAATTCAG<br>CTGGTCCAGAGCGGACCTGAGCTGAAAAAACCCGGCGAGACTGTTAAGATC<br>AGTTGTAAAGCATCTGGCTATACCTTCACCGACTACAGCATAAATTGGGTG<br>AAACGGGCCCCTGGAAAGGGCCTCAAATGGATGGGTTGGATCAATACCGAA<br>ACTAGGGAGCCTGCTTATGCATATGACTTCCGCGGAGATTCGCCTTTTCA<br>CTCGAGACATCTGCCTCTACTGCTTACCTCCAAATAAACAACCTCAAGTAT<br>GAAGATACAGCCACTTACTTTTGCGCCCTCGACTATAGTTACGCCATGGAC<br>TACTGGGGACAGGGAACCTCCGTTACCGTCAGTTCCGCGGCCGCAACCACA<br>ACACCTGCTCCAAGGCCCCCCACACCCGCTCCAACTATAGCCAGCCAACCA<br>TTGAGCCTCAGACCTGAAGCTTGCAGGCCCGCAGCAGGAGGCGCCGTCCAT<br>ACGCGAGGCCTGGACTTCGCGTGTGATATTTATATTTGGGCCCCTTTGGCC<br>GGAACATGTGGGGTGTTGCTTCTCTCCCTTGTGATCACTCTGTATTGTAAG<br>CGCGGGAGAAAGAAGCTCCTGTACATCTTCAAGCAGCCTTTTATGCGACCT<br>GTGCAAACCACTCAGGAAGAAGATGGGTGTTCATGCCGCTTCCCCGAGGAG<br>GAAGAAGGAGGGTGTGAACTGAGGGTGAAATTTTCTAGAAGCGCCGATGCT<br>CCCGCATATCAGCAGGGTCAGAATCAGCTCTACAATGAATTGAATCTCGGC<br>AGGCGAGAAGAGTACGATGTTCTGGACAAGAGACGGGGCAGGGATCCCGAG<br>ATGGGGGGAAAGCCCCGGAGAAAAAATCCTCAGGAGGGGTTGTACAATGAG<br>CTGCAGAAGGACAAGATGGCTGAAGCCTATAGCGAGATCGGAATGAAAGGC<br>GAAAGACGCAGAGGCAAGGGGCATGACGGTCTGTACCAGGGTCTCTCTACA<br>GCCACCAAGGACACTTATGATGCGTTGCATATGCAAGCCTTGCCACCCCGC<br>TAATGA | Anti-BCMA CAR (nt) |
| 265 | MALPVTALLLPLALLLHAARPQVQLVESGGGLVQPGGSLRLSCEASGFTLD<br>YYAIGWFRQAPGKEREGVICISRSDGSTYYADSVKGRFTISRDNAKKTVYL<br>QMISLKPEDTAAYYCAAGADCSGYLRDYEFRGQGTQVTVSSGGGGSQVQLV<br>ESGGGLVQPGGSLRLSCEASGFTLDYYAIGWFRQAPGKEREGVICISRSDG<br>STYYADSVKGRFTISRDNAKKTVYLQMISLKPEDTAAYYCAAGADCSGYLR<br>DYEFRGQGTQVTVSSTSTTTPAPRPPTPAPTIASQPLSLRPEACRPAAGGA<br>VHTRGLDFACDIYIWAPLAGTCGVLLLSLVITLYCKRGRKKLLYIFKQPFM<br>RPVQTTQEEDGCSCRFPEEEEGGCELRVKFSRSADAPAYQQGQNQLYNELN<br>LGRREEYDVLDKRRGRDPEMGGKPRRKNPQEGLYNELQKDKMAEAYSEIGM<br>KGERRRGKGHDGLYQGLSTATKDTYDALHMQALPPR | Multivalent anti-BCMA CAR (aa) |
| 266 | MALPVTALLLPLALLLHAARPQVQLVESGGGLVQPGGSLRLSCEASGFTLD<br>YYAIGWFRQAPGKEREGVICISRSDGSTYYADSVKGRFTISRDNAKKTVYL<br>QMISLKPEDTAAYYCAAGADCSGYLRDYEFRGQGTQVTVSSGGGGSQVQLV<br>ESGGGLVQPGGSLRLSCEASGFTLDYYAIGWFRQAPGKEREGVICISRSDG<br>STYYADSVKGRFTISRDNAKKTVYLQMISLKPEDTAAYYCAAGADCSGYLR | Multivalent anti-BCMA CAR (aa) |

| SEQ ID NO: | Sequence | Description |
|---|---|---|
| | DYEFRGQGTQVTVSSGGGGSQVQLVESGGGLVQPGGSLRLSCEASGFTLDY<br>YAIGWFRQAPGKEREGVICISRSDGSTYYADSVKGRFTISRDNAKKTVYLQ<br>MISLKPEDTAAYYCAAGADCSGYLRDYEFRGQGTQVTVSSTSTTTPAPRPP<br>TPAPTIASQPLSLRPEACRPAAGGAVHTRGLDFACDIYIWAPLAGTCGVLL<br>LSLVITLYCKRGRKKLLYIFKQPFMRPVQTTQEEDGCSCRFPEEEEGGCEL<br>RVKFSRSADAPAYQQGQNQLYNELNLGRREEYDVLDKRRGRDPEMGGKPRR<br>KNPQEGLYNELQKDKMAEAYSEIGMKGERRRGKGHDGLYQGLSTATKDTYD<br>ALHMQALPPR | |
| 267 | MALPVTALLLPLALLLHAARPQVKLEESGGGLVQAGRSLRLSCAASEHTFS<br>SHVMGWFRQAPGKERESVAVIGWRD1STSYADSVKGRFTISRDNAKKTLYL<br>QMNSLKPEDTAVYYCAARRIDAADFDSWGQGTQVTVSSGGGGSEVQLVESG<br>GGLVQAGGSLRLSCAASGRTFTMGWFRQAPGKEREFVAAISLSPTLAYYAE<br>SVKGRFTISRDNAKNTVVLQMNSLKPEDTALYYCAADRKSVMSIRPDYWGQ<br>GTQVTVSSTSTTTPAPRPPTPAPTIASQPLSLRPEACRPAAGGAVHTRGLD<br>FACDIYIWAPLAGTCGVLLLSLVITLYCKRGRKKLLYIFKQPFMRPVQTTQ<br>EEDGCSCRFPEEEEGGCELRVKFSRSADAPAYQQGQNQLYNELNLGRREEY<br>DVLDKRRGRDPEMGGKPRRKNPQEGLYNELQKDKMAEAYSEIGMKGERRRG<br>KGHDGLYQGLSTATKDTYDALHMQALPPR | Multivalent anti-BCMA CAR (aa) |
| 268 | MALPVTALLLPLALLLHAARPQVKLEESGGGLVQAGRSLRLSCAASEHTFS<br>SHVMGWFRQAPGKERESVAVIGWRDISTSYADSVKGRFTISRDNAKKTLYL<br>QMNSLKPEDTAVYYCAARRIDAADFDSWGQGTQVTVSSGGGGSGGGGSGGG<br>GSEVQLVESGGGLVQAGGSLRLSCAASGRTFTMGWFRQAPGKEREFVAAIS<br>LSPTLAYYAESVKGRFTISRDNAKNTVVLQMNSLKPEDTALYYCAADRKSV<br>MSIRPDYWGQGTQVTVSSTSTTTPAPRPPTPAPTIASQPLSLRPEACRPAA<br>GGAVHTRGLDFACDIYIWAPLAGTCGVLLLSLVITLYCKRGRKKLLYIFKQ<br>PFMRPVQTTQEEDGCSCRFPEEEEGGCELRVKFSRSADAPAYQQGQNQLYN<br>ELNLGRREEYDVLDKRRGRDPEMGGKPRRKNPQEGLYNELQKDKMAEAYSE<br>IGMKGERRRGKGHDGLYQGLSTATKDTYDALHMQALPPR | Multivalent anti-BCMA CAR (aa) |
| 269 | MALPVTALLLPLALLLHAARPQVKLEESGGGLVQAGRSLRLSCAASEHTFS<br>SHVMGWFRQAPGKERESVAVIGWRDISTSYADSVKGRFTISRDNAKKTLYL<br>QMNSLKPEDTAVYYCAARRIDAADFDSWGQGTQVTVSSGGGGSGGGGSGGG<br>GSGGGGSGGGGSEVQLVESGGGLVQAGGSLRLSCAASGRTFTMGWFRQAPG<br>KEREFVAAISLSPTLAYYAESVKGRFTISRDNAKNTVVLQMNSLKPEDTAL<br>YYCAADRKSVMSIRPDYWGQGTQVTVSSTSTTTPAPRPPTPAPTIASQPLS<br>LRPEACRPAAGGAVHTRGLDFACDIYIWAPLAGTCGVLLLSLVITLYCKRG<br>RKKLLYIFKQPFMRPVQTTQEEDGCSCRFPEEEEGGCELRVKFSRSADAPA<br>YQQGQNQLYNELNLGRREEYDVLDKRRGRDPEMGGKPRRKNPQEGLYNELQ<br>KDKMAEAYSEIGMKGERRRGKGHDGLYQGLSTATKDTYDALHMQALPPR | Multivalent anti-BCMA CAR (aa) |
| 270 | MALPVTALLLPLALLLHAARPEVQLVESGGGLVQAGGSLRLSCAASGRTFT<br>MGWFRQAPGKEREFVAA1SLSPTLAYYAESVKGRFTISRDNAKNTVVLQMN<br>SLKPEDTALYYCAADRKSVMSIRPDYWGQGTQVTVSSGGGGSGGGGSQVKL<br>EESGGGLVQAGRSLRLSCAASEHTFSSHVMGWFRQAPGKERESVAVIGWRD<br>ISTSYADSVKGRFTISRDNAKKTLYLQMNSLKPEDTAVYYCAARRIDAADF<br>DSWGQGTQVTVSSTSTTTPAPRPPTPAPTIASQPLSLRPEACRPAAGGAVH<br>TRGLDFACDIYIWAPLAGTCGVLLLSLVITLYCKRGRKKLLYIFKQPFMRP<br>VQTTQEEDGCSCRFPEEEEGGCELRVKFSRSADAPAYQQGQNQLYNELNLG<br>RREEYDVLDKRRGRDPEMGGKPRRKNPQEGLYNELQKDKMAEAYSEIGMKG<br>ERRRGKGHDGLYQGLSTATKDTYDALHMQALPPR | Multivalent anti-BCMA CAR (aa) |
| 271 | MALPVTALLLPLALLLHAARPEVQLVESGGGLVQAGGSLRLSCAASGRTFT<br>MGWFRQAPGKEREFVAA1SLSPTLAYYAESVKGRFTISRDNAKNTVVLQMN<br>SLKPEDTALYYCAADRKSVMSIRPDYWGQGTQVTVSSGGGGSGGGGSGGGG<br>SQVKLEESGGGLVQAGRSLRLSCAASEHTFSSHVMGWFRQAPGKERESVAV<br>IGWRDISTSYADSVKGRFTISRDNAKKTLYLQMNSLKPEDTAVYYCAARRI<br>DAADFDSWGQGTQVTVSSTSTTTPAPRPPTPAPTIASQPLSLRPEACRPAA<br>GGAVHTRGLDFACDIYIWAPLAGTCGVLLLSLVITLYCKRGRKKLLYIFKQ<br>PFMRPVQTTQEEDGCSCRFPEEEEGGCELRVKFSRSADAPAYQQGQNQLYN<br>ELNLGRREEYDVLDKRRGRDPEMGGKPRRKNPQEGLYNELQKDKMAEAYSE<br>IGMKGERRRGKGHDGLYQGLSTATKDTYDALHMQALPPR | Multivalent anti-BCMA CAR (aa) |
| 272 | MALPVTALLLPLALLLHAARPEVQLVESGGGLVQAGGSLRLSCAASGRTFT<br>MGWFRQAPGKEREFVAA1SLSPTLAYYAESVKGRFTISRDNAKNTVVLQMN<br>SLKPEDTALYYCAADRKSVMSIRPDYWGQGTQVTVSSGGGGSGGGGSGGGG<br>SGGGGSQVKLEESGGGLVQAGRSLRLSCAASEHTFSSHVMGWFRQAPGKER<br>ESVAVIGWRDISTSYADSVKGRFTISRDNAKKTLYLQMNSLKPEDTAVYYC<br>AARRIDAADFDSWGQGTQVTVSSTSTTTPAPRPPTPAPTIASQPLSLRPEA<br>CRPAAGGAVHTRGLDFACDIYIWAPLAGTCGVLLLSLVITLYCKRGRKKLL<br>YIFKQPFMRPVQTTQEEDGCSCRFPEEEEGGCELRVKFSRSADAPAYQQGQ<br>NQLYNELNLGRREEYDVLDKRRGRDPEMGGKPRRKNPQEGLYNELQKDKMA<br>EAYSEIGMKGERRRGKGHDGLYQGLSTATKDTYDALHMQALPPR | Multivalent anti-BCMA CAR (aa) |

-continued

| SEQ ID NO: | Sequence | Description |
|---|---|---|
| 273 | MALPVTALLLPLALLLHAARPQVKLEESGGGLVQAGRSLRLSCAASEHTFS SHVMGWFRQAPGKERESVAVIGWRDISTSYADSVKGRFTISRDNAKKTLYL QMNSLKPEDTAVYYCAARRIDAADFDSWGQGTQVTVSSGGGGSAVQLVESG GGLVQAGDSLRLTCTASGRAFSTYFMAWFRQAPGKEREFVAGIAWSGGSTA YADSVKGRFTISRDNAKNTVYLQMNSLKSEDTAVYYCASRGIEVEEFGAWG QGTQVTVSSTSTTTPAPRPPTPAPTIASQPLSLRPEACRPAAGGAVHTRGL DFACDIYIWAPLAGTCGVLLLSLVITLYCKRGRKKLLYIFKQPFMRPVQTT QEEDGCSCRFPEEEEGGCELRVKFSRSADAPAYQQGQNQLYNELNLGRREE YDVLDKRRGRDPEMGGKPRRKNPQEGLYNELQKDKMAEAYSEIGMKGERRR GKGHDGLYQGLSTATKDTYDALHMQALPPR | Multivalent anti-BCMA CAR (aa) |
| 274 | MALPVTALLLPLALLLHAARPQVKLEESGGGLVQAGRSLRLSCAASEHTFS SHVMGWFRQAPGKERESVAVIGWRDISTSYADSVKGRFTISRDNAKKTLYL QMNSLKPEDTAVYYCAARRIDAADFDSWGQGTQVTVSSGGGGSGGGGSGGG GSAVQLVESGGGLVQAGDSLRLTCTASGRAFSTYFMAWFRQAPGKEREFVA GIAWSGGSTAYADSVKGRFTISRDNAKNTVYLQMNSLKSEDTAVYYCASRG IEVEEFGAWGQGTQVTVSSTSTTTPAPRPPTPAPTIASQPLSLRPEACRPA AGGAVHIRGLDFACDIYIWAPLAGTCGVLLLSLVITLYCKRGRKKLLYIFK QPFMRPVQTTQEEDGCSCRFPEEEEGGCELRVKFSRSADAPAYQQGQNQLY NELNLGRREEYDVLDKRRGRDPEMGGKPRRKNPQEGLYNELQKDKMAEAYS EIGMKGERRRGKGHDGLYQGLSTATKDTYDALHMQALPPR | Multivalent anti-BCMA CAR (aa) |
| 275 | MALPVTALLLPLALLLHAARPQVKLEESGGGLVQAGRSLRLSCAASEHTFS SHVMGWFRQAPGKERESVAVIGWRDISTSYADSVKGRFTISRDNAKKTLYL QMNSLKPEDTAVYYCAARRIDAADFDSWGQGTQVTVSSGGGGSGGGGSGGG GSGGGGSGGGGSAVQLVESGGGLVQAGDSLRLTCTASGRAFSTYFMAWFRQ APGKEREFVAGIAWSGGSTAYADSVKGRFTISRDNAKNTVYLQMNSLKSED TAVYYCASRGIEVEEFGAWGQGTQVTVSSTSTTTPAPRPPTPAPTIASQPL SLRPEACRPAAGGAVHTRGLDFACDIYIWAPLAGTCGVLLLSLVITLYCKR GRKKLLYIFKQPFMRPVQTTQEEDGCSCRFPEEEEGGCELRVKFSRSADAP AYQQGQNQLYNELNLGRREEYDVLDKRRGRDPEMGGKPRRKNPQEGLYNEL QKDKMAEAYSEIGMKGERRRGKGHDGLYQGLSTATKDTYDALHMQALPPR | Multivalent anti-BCMA CAR (aa) |
| 276 | MALPVTALLLPLALLLHAARPAVQLVESGGGLVQAGDSLRLTCTASGRAFS TYFMAWFRQAPGKEREFVAGIAWSGGSTAYADSVKGRFTISRDNAKNTVYL QMNSLKSEDTAVYYCASRGIEVEEFGAWGQGTQVTVSSGGGGSGGGGSQVK LEESGGGLVQAGRSLRLSCAASEHTFSSHVMGWFRQAPGKERESVAVIGWR DISTSYADSVKGRFTISRDNAKKTLYLQMNSLKPEDTAVYYCAARRIDAAD FDSWGQGTQVTVSSTSTTTPAPRPPTPAPTIASQPLSLRPEACRPAAGGAV HTRGLDFACDIYIWAPLAGTCGVLLLSLVITLYCKRGRKKLLYIFKQPFMR PVQTTQEEDGCSCRFPEEEEGGCELRVKFSRSADAPAYQQGQNQLYNELNL GRREEYDVLDKRRGRDPEMGGKPRRKNPQEGLYNELQKDKMAEAYSEIGMK GERRRGKGHDGLYQGLSTATKDTYDALHMQALPPR | Multivalent anti-BCMA CAR (aa) |
| 277 | MALPVTALLLPLALLLHAARPAVQLVESGGGLVQAGDSLRLTCTASGRAFS TYFMAWFRQAPGKEREFVAGIAWSGGSTAYADSVKGRFTISRDNAKNTVYL QMNSLKSEDTAVYYCASRGIEVEEFGAWGQGTQVTVSSGGGGSGGGGSGGG GSQVKLEESGGGLVQAGRSLRLSCAASEHTFSSHVMGWFRQAPGKERESVA VIGWRDISTSYADSVKGRFTISRDNAKKTLYLQMNSLKPEDTAVYYCAARR IDAADFDSWGQGTQVTVSSTSTTTPAPRPPTPAPTIASQPLSLRPEACRPA AGGAVHTRGLDFACDIYIWAPLAGTCGVLLLSLVITLYCKRGRKKLLYIFK QPFMRPVQTTQEEDGCSCRFPEEEEGGCELRVKFSRSADAPAYQQGQNQLY NELNLGRREEYDVLDKRRGRDPEMGGKPRRKNPQEGLYNELQKDKMAEAYS EIGMKGERRRGKGHDGLYQGLSTATKDTYDALHMQALPPR | Multivalent anti-BCMA CAR (aa) |
| 278 | MALPVTALLLPLALLLHAARPAVQLVESGGGLVQAGDSLRLTCTASGRAFS TYFMAWFRQAPGKEREFVAGIAWSGGSTAYADSVKGRFTISRDNAKNTVYL QMNSLKSEDTAVYYCASRGIEVEEFGAWGQGTQVTVSSGGGGSGGGGSGGG GSGGGGSQVKLEESGGGLVQAGRSLRLSCAASEHTFSSHVMGWFRQAPGKE RESVAVIGWRD1STSYADSVKGRFTISRDNAKKTLYLQMNSLKPEDTAVYY CAARRIDAADFDSWGQGTQVTVSSTSTTTPAPRPPTPAPTIASQPLSLRPE ACRPAAGGAVHTRGLDFACDIYIWAPLAGTCGVLLLSLVITLYCKRGRKKL LYIFKQPFMRPVQTTQEEDGCSCRFPEEEEGGCELRVKFSRSADAPAYQQG QNQLYNELNLGRREEYDVLDKRRGRDPEMGGKPRRKNPQEGLYNELQKDKM AEAYSEIGMKGERRRGKGHDGLYQGLSTATKDTYDALHMQALPPR | Multivalent anti-BCMA CAR (aa) |
| 279 | MALPVTALLLPLALLLHAARPEVQLVESGGGMVQAGDSLRLSCVQSTYTVN SDVMGWFRQAPGKEREFVGAIMWNDGITYLQDSVKGRFTIFRDNAKNTVYL QMNSLKLEDTAVYYCAASKGRYSEYEYWGQGTQVTVSSGGGGSQVKLEESG GRLVQPRGSLRLSCAGSGRTFSTYGMAWFRQAPGKEREFVASKASMNYSGR TYYADSVKGRFTIARDNAKNMVFLQMNNLKPEDTAVYYCAAGTGCSTYGCF DAQIIDYWGKGTLVTVSSTSTTTPAPRPPTPAPTIASQPLSLRPEACRPAA GGAVHTRGLDFACDIYIWAPLAGTCGVLLLSLVITLYCKRGRKKLLYIFKQ PFMRPVQTTQEEDGCSCRFPEEEEGGCELRVKFSRSADAPAYQQGQNQLYN | Multivalent anti-BCMA CAR (aa) |

| SEQ ID NO: | Sequence | Description |
|---|---|---|
| | ELNLGRREEYDVLDKRRGRDPEMGGKPRRKNPQEGLYNELQKDKMAEAYSE IGMKGERRRGKGHDGLYQGLSTATKDTYDALHMQALPPR | |
| 280 | MALPVTALLLPLALLLHAARPEVQLVESGGGMVQAGDSLRLSCVQSTYTVN SDVMGWFRQAPGKEREFVGAIMWNDGITYLQDSVKGRFTIFRDNAKNTVYL QMNSLKLEDTAVYYCAASKGRYSEYEYWGQGTQVTVSSGGGGSGGGGSGGG GSQVKLEESGGRLVQPRGSLRLSCAGSGRTFSTYGMAWFRQAPGKEREFVA SKASMNYSGRTYYADSVKGRFTIARDNAKNMVFLQMNNLKPEDTAVYYCAA GTGCSTYGCFDAQIIDYWGKGTLVTVSSTSTTTPAPRPPTPAPTIASQPLS LRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADAPA YQQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR | Multivalent anti-BCMA CAR (aa) |
| 281 | MALPVTALLLPLALLLHAARPEVQLVESGGGMVOAGDSLRLSCVQSTYTVN SDVMGWFRQAPGKEREFVGAIMWNDGITYLQDSVKGRFTIFRDNAKNTVYL QMNSLKLEDTAVYYCAASKGRYSEYEYWGQGTQVTVSSGGGGSGGGGSGGG GSGGGGSGGGGSQVKLEESGGRLVQPRGSLRLSCAGSGRTFSTYGMAWFRQ APGKEREFVASKASMNYSGRTYYADSVKGRFTIARDNAKNMVFLQMNNLKP EDTAVYYCAAGTGCSTYGCFDAQIIDYWGKGTLVTVSSTSTTTPAPRPPTP APTIASQPLSLRPEACRPAAGGAVHTRGLDFACDIYIWAPLAGTCGVLLLS LVITLYCKRGRKKLLYIFKQPFMRPVQTTQEEDGCSCRFPEEEEGGCELRV KFSRSADAPAYQQGQNQLYNELNLGRREEYDVLDKRRGRDPEMGGKPRRKN PQEGLYNELQKDKMAEAYSEIGMKGERRRGKGHDGLYQGLSTATKDTYDAL HMQALPPR | Multivalent anti-BCMA CAR (aa) |
| 282 | MALPVTALLLPLALLLHAARPEVQLVESGGGMVQAGDSLRLSCVQSTYTVN SDVMGWFRQAPGKEREFVGAIMWNDGITYLQDSVKGRFTIFRDNAKNTVYL QMNSLKLEDTAVYYCAASKGRYSEYEYWGQGTQVTVSSGGGGSGGGGSQVK LEESGGRLVQPRGSLRLSCAGSGRTFSTYGMAWFRQAPGKEREFVASKASM NYSGRTYYADSVKGRFTIARDNAKNMVFLQMNNLKPEDTAVYYCAAGTGCS TYGCFDAQIIDYWGKGTLVTVSSTSTTTPAPRPPTPAPTIASQPLSLRPEA CRPAAGGAVHTRGLDFACDIYIWAPLAGTCGVLLLSLVITLYCKRGRKKLL YIFKQPFMRPVQTTQEEDGCSCRFPEEEEGGCELRVKFSRSADAPAYQQGQ NQLYNELNLGRREEYDVLDKRRGRDPEMGGKPRRKNPQEGLYNELQKDKMA EAYSEIGMKGERRRGKGHDGLYQGLSTATKDTYDALHMQALPPR | Multivalent anti-BCMA CAR (aa) |
| 283 | MALPVTALLLPLALLLHAARPEVQLVESGGGMVQAGDSLRLSCVQSTYTVN SDVMGWFRQAPGKEREFVGAIMWNDGITYLQDSVKGRFTIFRDNAKNTVYL QMNSLKLEDTAVYYCAASKGRYSEYEYWGQGTQVTVSSGGGGSGGGGSGGG GSQVKLEESGGRLVQPRGSLRLSCAGSGRTFSTYGMAWFRQAPGKEREFVA SKASMNYSGRTYYADSVKGRFTIARDNAKNMVFLQMNNLKPEDTAVYYCAA GTGCSTYGCFDAQIIDYWGKGTLVTVSSTSTTTPAPRPPTPAPTIASQPLS LRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADAPA YQQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR | Multivalent anti-BCMA CAR (aa) |
| 284 | MALPVTALLLPLALLLHAARPEVQLVESGGGMVQAGDSLRLSCVQSTYTVN SDVMGWFRQAPGKEREFVGAIMWNDGITYLQDSVKGRFTIFRDNAKNTVYL QMNSLKLEDTAVYYCAASKGRYSEYEYWGQGTQVTVSSGGGGSGGGGSGGG GSGGGGSQVKLEESGGRLVQPRGSLRLSCAGSGRTFSTYGMAWFRQAPGKE REFVASKASMNYSGRTYYADSVKGRFTIARDNAKNMVFLQMNNLKPEDTAV YYCAAGTGCSTYGCFDAQIIDYWGKGTLVTVSSTSTTTPAPRPPTPAPTIA SQPLSLRPEACRPAAGGAVHTRGLDFACDIYIWAPLAGTCGVLLLSLVITL YCKRGRKKLLYIFKQPFMRPVQTTQEEDGCSCRFPEEEEGGCELRVKFSRS ADAPAYQQGQNQLYNELNLGRREEYDVLDKRRGRDPEMGGKPRRKNPQEGL YNELQKDKMAEAYSEIGMKGERRRGKGHDGLYQGLSTATKDTYDALHMQAL PPR | Multivalent anti-BCMA CAR (aa) |
| 285 | MALPVTALLLPLALLLHAARPQVKLEESGGRLVQPRGSLRLSCAGSGRTFS TYGMAWFRQAPGKEREFVASKASMNYSGRTYYADSVKGRFTIARDNAKNMV FLQMNNLKPEDTAVYYCAAGTGCSTYGCFDAQIIDYWGKGTLVTVSSGGGG SQVKLEESGGGLVQAGGSLRLSCAASGGTLSKNTVAWVRQAPGKERGFVTS ITCDGRTTYYANSVNGRFPINRNNAENLVVLQMNSLKPDDTALYYCAAYRK SIMSIQPDYWGQGTQVTVSSTSTTTPAPRPPTPAPTIASQPLSLRPEACRP AAGGAVHTRGLDFACDIYIWAPLAGTCGVLLLSLVITLYCKRGRKKLLYIF KQPFMRPVQTTQEEDGCSCRFPEEEEGGCELRVKFSRSADAPAYQQGQNQL YNELNLGRREEYDVLDKRRGRDPEMGGKPRRKNPQEGLYNELQKDKMAEAY SEIGMKGERRRGKGHDGLYQGLSTATKDTYDALHMQALPPR | Multivalent anti-BCMA CAR (aa) |
| 286 | MALPVTALLLPLALLLHAARPQVKLEESGGRLVQPRGSLRLSCAGSGRTFS TYGMAWFRQAPGKEREFVASKASMNYSGRTYYADSVKGRFTIARDNAKNMV FLQMNNLKPEDTAVYYCAAGTGCSTYGCFDAQIIDYWGKGTLVTVSSGGGG SGGGGSGGGGSQVKLEESGGGLVQAGGSLRLSCAASGGTLSKNTVAWVRQA | Multivalent anti-BCMA CAR (aa) |

| SEQ ID NO: | Sequence | Description |
|---|---|---|
| | PGKERGFVTSITCDGRTTYYANSVNGRFPINRNNAENLVVLQMNSLKPDDT ALYYCAAYRKSIMSIQPDYWGQGTQVTVSSTSTTTPAPRPPTPAPTIASQP LSLRPEACRPAAGGAVHTRGLDFACDIYIWAPLAGTCGVLLLSLVITLYCK RGRKKLLYIFKQPFMRPVQTTQEEDGCSCRFPEEEEGGCELRVKFSRSADA PAYQQGQNQLYNELNLGRREEYDVLDKRRGRDPEMGGKPRRKNPQEGLYNE LQKDKMAEAYSEIGMKGERRRGKGHDGLYQGLSTATKDTYDALHMQALPPR | |
| 287 | MALPVTALLLPLALLLHAARPQVKLEESGGRLVQPRGSLRLSCAGSGRTFS TYGMAWFRQAPGKEREFVASKASMNYSGRTYYADSVKGRETIARDNAKNMV FLQMNNLKPEDTAVYYCAAGTGCSTYGCFDAQIIDYWGKGTLVTVSSGGGG SGGGGSGGGGSGGGGSGGGGSQVKLEESGGGLVQAGGSLRLSCAASGGTLS KNTVAWVRQAPGKERGFVTSITCDGRTTYYANSVNGRFPINRNNAENLVVL QMNSLKPDDTALYYCAAYRKSIMSIQPDYWGQGTQVTVSSTSTTTPAPRPP TPAPTIASQPLSLRPEACRPAAGGAVHTRGLDFACDIYIWAPLAGTCGVLL LSLVITLYCKRGRKKLLYIFKQPFMRPVQTTQEEDGCSCRFPEEEEGGCEL RVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYD ALHMQALPPR | Multivalent anti-BCMA CAR (aa) |
| 288 | MALPVTALLLPLALLLHAARPQVKLEESGGRLVQPRGSLRLSCAGSGRTFS TYGMAWFRQAPGKEREFVASKASMNYSGRTYYADSVKGRETIARDNAKNMV FLQMNNLKPEDTAVYYCAAGTGCSTYGCFDAQIIDYWGKGTLVTVSSGGGG SGGGGSQVKLEESGGGLVQAGGSLRLSCAASGGTLSKNTVAWVRQAPGKER GFVTSITCDGRTTYYANSVNGRFPINRNNAENLVVLQMNSLKPDDTALYYC AAYRKSIMSIQPDYWGQGTQVTVSSTSTTTPAPRPPTPAPTIASQPLSLRP EACRPAAGGAVHTRGLDFACDIYIWAPLAGTCGVLLLSLVITLYCKRGRKK LLYIFKQPFMRPVQTTQEEDGCSCRFPEEEEGGCELRVKFSRSADAPAYQQ GQNQLYNELNLGRREEYDVLDKRRGRDPEMGGKPRRKNPQEGLYNELQKDK MAEAYSEIGMKGERRRGKGHDGLYQGLSTATKDTYDALHMQALPPR | Multivalent anti-BCMA CAR (aa) |
| 289 | MALPVTALLLPLALLLHAARPQVKLEESGGRLVQPRGSLRLSCAGSGRTFS TYGMAWFRQAPGKEREFVASKASMNYSGRTYYADSVKGRFTIARDNAKNMV FLQMNNLKPEDTAVYYCAAGTGCSTYGCFDAQIIDYWGKGTLVTVSSGGGG SGGGGSGGGGSQVKLEESGGGLVQAGGSLRLSCAASGGTLSKNTVAWVRQA PGKERGFVTSITCDGRTTYYANSVNGRFPINRNNAENLVVLQMNSLKPDDT ALYYCAAYRKSIMSIQPDYWGQGTQVTVSSTSTTTPAPRPPTPAPTIASQP LSLRPEACRPAAGGAVHTRGLDFACDIYIWAPLAGTCGVLLLSLVITLYCK RGRKKLLYIFKQPFMRPVQTTQEEDGCSCRFPEEEEGGCELRVKFSRSADA PAYQQGQNQLYNELNLGRREEYDVLDKRRGRDPEMGGKPRRKNPQEGLYNE LQKDKMAEAYSEIGMKGERRRGKGHDGLYQGLSTATKDTYDALHMQALPPR | Multivalent anti-BCMA CAR (aa) |
| 290 | MALPVTALLLPLALLLHAARPQVKLEESGGRLVQPRGSLRLSCAGSGRTFS TYGMAWFRQAPGKEREFVASKASMNYSGRTYYADSVKGRFTIARDNAKNMV FLQMNNLKPEDTAVYYCAAGTGCSTYGCFDAQIIDYWGKGTLVTVSSGGGG SGGGGSGGGGSGGGGSQVKLEESGGGLVQAGGSLRLSCAASGGTLSKNTVA WVRQAPGKERGFVTSITCDGRTTYYANSVNGRFPINRNNAENLVVLQMNSL KPDDTALYYCAAYRKSIMSIQPDYWGQGTQVTVSSTSTTTPAPRPPTPAPT IASQPLSLRPEACRPAAGGAVHTRGLDFACDIYIWAPLAGTCGVLLLSLVI TLYCKRGRKKLLYIFKQPFMRPVQTTQEEDGCSCRFPEEEEGGCELRVKFS RSADAPAYQQGQNQLYNELNLGRREEYDVLDKRRGRDPEMGGKPRRKNPQE GLYNELQKDKMAEAYSEIGMKGERRRGKGHDGLYQGLSTATKDTYDALHMQ ALPPR | Multivalent anti-BCMA CAR (aa) |
| 291 | MALPVTALLLPLALLLHAARPQVKLEESGGGLVQAGGSLRLSCAASGGTLS KNTVAWVRQAPGKERGFVTSITCDGRTTYYANSVNGRFPINRNNAENLVVL QMNSLKPDDTALYYCAAYRKSIMSIQPDYWGQGTQVTVSSGGGGSQVQLVE SGGGLVQAGGSLRLSCAASGGTLSKNTVAWFRQAPGKERGFVASITWDGRT TYYADSVKGRFTISRDNAKNTVYLQMNSLKPEDTAVYVCADLGKWPAGPAD YWGQGTQVTVSSTSTTTPAPRPPTPAPTIASQPLSLRPEACRPAAGGAVHT RGLDFACDIYIWAPLAGTCGVLLLSLVITLYCKRGRKKLLYIFKQPFMRPV QTTQEEDGCSCRFPEEEEGGCELRVKFSRSADAPAYQQGQNQLYNELNLGR REEYDVLDKRRGRDPEMGGKPRRKNPQEGLYNELQKDKMAEAYSEIGMKGE RRRGKGHDGLYQGLSTATKDTYDALHMQALPPR | Multivalent anti-BCMA CAR (aa) |
| 292 | MALPVTALLLPLALLLHAARPQVKLEESGGGLVQAGGSLRLSCAASGGTLS KNTVAWVRQAPGKERGFVTSITCDGRTTYYANSVNGRFPINRNNAENLVVL QMNSLKPDDTALYYCAAYRKSIMSIQPDYWGQGTQVTVSSGGGGSGGGGSG GGGSQVQLVESGGGLVQAGGSLRLSCAASGGTLSKNTVAWFRQAPGKERGF VASITWDGRTTYYADSVKGRFTISRDNAKNTVYLQMNSLKPEDTAVYVCAD LGKWPAGPADYWGQGTQVTVSSTSTTTPAPRPPTPAPTIASQPLSLRPEAC RPAAGGAVHTRGLDFACDIYIWAPLAGTCGVLLLSLVITLYCKRGRKKLLY IFKQPFMRPVQTTQEEDGCSCRFPEEEEGGCELRVKFSRSADAPAYQQGQN QLYNELNLGRREEYDVLDKRRGRDPEMGGKPRRKNPQEGLYNELQKDKMAE AYSEIGMKGERRRGKGHDGLYQGLSTATKDTYDALHMQALPPR | Multivalent anti-BCMA CAR (aa) |

-continued

| SEQ ID NO: | Sequence | Description |
|---|---|---|
| 293 | MALPVTALLLPLALLLHAARPQVKLEESGGGLVQAGGSLRLSCAASGGTLSKNTVAWVRQAPGKERGFVTSITCDGRTTYYANSVNGRFPINRNNAENLVVLQMNSLKPDDTALYYCAAYRKSIMSIQPDYWGQGTQVTVSSGGGGSGGGGSGGGGSGGGGSGGGGSQVQLVESGGGLVQAGGSLRLSCAASGGTLSKNTVAWFRQAPGKERGFVASITWDGRTTYYADSVKGRFTISRDNAKNTVYLQMNSLKPEDTAVYVCADLGKWPAGPADYWGQGTQVTVSSTSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | Multivalent anti-BCMA CAR (aa) |
| 294 | MALPVTALLLPLALLLHAARPQVKLEESGGGLVQAGGSLRLSCAASGGTLSKNTVAWVRQAPGKERGFVTSITCDGRTTYYANSVNGRFPINRNNAENLVVLQMNSLKPDDTALYYCAAYRKSIMSIQPDYWGQGTOVTVSSGGGGSGGGGSQVQLVESGGGLVQAGGSLRLSCAASGGTLSKNTVAWFRQAPGKERGFVAS1TWDGRTTYYADSVKGRFTISRDNAKNTVYLQMNSLKPEDTAVYVCADLGKWPAGPADYWGQGTQVTVSSTSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | Multivalent anti-BCMA CAR (aa) |
| 295 | MALPVTALLLPLALLLHAARPQVKLEESGGGLVQAGGSLRLSCAASGGTLSKNTVAWVRQAPGKERGFVTSITCDGRTTYYANSVNGRFPINRNNAENLVVLQMNSLKPDDTALYYCAAYRKSIMSIQPDYWGQGTQVTVSSGGGGSGGGGSGGGGSQVQLVESGGGLVQAGGSLRLSCAASGGTLSKNTVAWFRQAPGKERGFVASITWDGRTTYYADSVKGRFTISRDNAKNTVYLQMNSLKPEDTAVYVCADLGKWPAGPADYWGQGTQVTVSSTSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | Multivalent anti-BCMA CAR (aa) |
| 296 | MALPVTALLLPLALLLHAARPQVKLEESGGGLVQAGGSLRLSCAASGGTLSKNTVAWVRQAPGKERGFVTSITCDGRTTYYANSVNGRFPINRNNAENLVVLQMNSLKPDDTALYYCAAYRKSIMSIQPDYWGQGTQVTVSSGGGGSGGGGSGGGGSGGGGSQVQLVESGGGLVQAGGSLRLSCAASGGTLSKNTVAWFRQAPGKERGFVASITWDGRTTYYADSVKGRFTISRDNAKNTVYLQMNSLKPEDTAVYVCADLGKWPAGPADYWGQGTQVTVSSTSTTTPAPRPPTPAPTIASQPLSLRPEACRPAAGGAVHIRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | Multivalent anti-BCMA CAR (aa) |
| 297 | MALPVTALLLPLALLLHAARPQVQLVESGGGLVQAGGSLRLSCAASGGTLSKNTVAWFRQAPGKERGEVASITWDGRTTYYADSVKGRFTISRDNAKNTVYLQMNSLKPEDTAVYVCADLGKWPAGPADYWGQGTQVTVSSGGGGSDVQLVESGGGLVQAGGSLRLSCAASGGTLSKNTVAWVRQAPGKERGFVTSITCDGRTTYYANSVKGRFPISRDNAENTVYLQMNSLKPEDTAGYVCADLGKWPAGSADYWGQGTHVTVSSTSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | Multivalent anti-BCMA CAR (aa) |
| 298 | MALPVTALLLPLALLLHAARPQVQLVESGGGLVQAGGSLRLSCAASGGTLSKNTVAWFRQAPGKERGEVASITWDGRTTYYADSVKGRFTISRDNAKNTVYLQMNSLKPEDTAVYVCADLGKWPAGPADYWGQGTQVTVSSGGGGSGGGGSGGGSDVQLVESGGGLVQAGGSLRLSCAASGGTLSKNTVAWVRQAPGKERGFVTSITCDGRTTYYANSVKGRFPISRDNAENTVYLQMNSLKPEDTAGYVCADLGKWPAGSADYWGQGTHVTVSSTSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | Multivalent anti-BCMA CAR (aa) |
| 299 | MALPVTALLLPLALLLHAARPQVQLVESGGGLVQAGGSLRLSCAASGGTLSKNTVAWFRQAPGKERGFVASITWDGRTTYYADSVKGRFTISRDNAKNTVYLQMNSLKPEDTAVYVCADLGKWPAGPADYWGQGTQVTVSSGGGGSGGGGSGGGGSGGGGSGGGGSDVQLVESGGGLVQAGGSLRLSCAASGGTLSKNTVAWVRQAPGKERGFVTSITCDGRTTYYANSVKGRFPISRDNAENTVYLQMNSLKPEDTAGYVCADLGKWPAGSADYWGQGTHVTVSSTSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSAD | Multivalent anti-BCMA CAR (aa) |

| SEQ ID NO: | Sequence | Description |
|---|---|---|
| | APAYQQGQNQLYNELNLGRREEYDVLDKRRGRDPEMGGKPRRKNPQEGLYN ELQKDKMAEAYSEIGMKGERRRGKGHDGLYQGLSTATKDTYDALHMQALPP R | |
| 300 | MALPVTALLLPLALLLHAARPQVQLVESGGGLVQAGGSLRLSCAASGGTLS KNTVAWFRQAPGKERGFVASITWDGRTTYYADSVKGRFTISRDNAKNTVYL QMNSLKPEDTAVYVCADLGKWPAGPADYWGQGTQVTVSSGGGGSGGGGSDV QLVESGGGLVQAGGSLRLSCAASGGTLSKNTVAWVRQAPGKERGFVTSITC DGRTTYYANSVKGRFPISRDNAENTVYLQMNSLKPEDTAGYVCADLGKWPA GSADYWGQGTHVTVSSTSTTTPAPRPPTPAPTIASQPLSLRPEACRPAAGG AVHTRGLDFACDIYIWAPLAGTCGVLLLSLVITLYCKRGRKKLLYIFKQPF MRPVQTTQEEDGCSCRFPEEEEGGCELRVKFSRSADAPAYQQGQNQLYNEL NLGRREEYDVLDKRRGRDPEMGGKPRRKNPQEGLYNELQKDKMAEAYSEIG MKGERRRGKGHDGLYQGLSTATKDTYDALHMQALPPR | Multivalent anti-BCMA CAR (aa) |
| 301 | MALPVTALLLPLALLLHAARPQVQLVESGGGLVQAGGSLRLSCAASGGTLS KNTVAWFRQAPGKERGFVASITWDGRTTYYADSVKGRFTISRDNAKNTVYL QMNSLKPEDTAVYVCADLGKWPAGPADYWGQGTQVTVSSGGGGSGGGGSGG GGSDVQLVESGGGLVQAGGSLRLSCAASGGTLSKNTVAWVRQAPGKERGFV TSITCDGRTTYYANSVKGRFPISRDNAENTVYLQMNSLKPEDTAGYVCADL GKWPAGSADYWGQGTHVTVSSTSTTTPAPRPPTPAPTIASQPLSLRPEACR PAAGGAVHTRGLDFACDIYIWAPLAGTCGVLLLSLVITLYCKRGRKKLLYI FKQPFMRPVQTTQEEDGCSCRFPEEEEGGCELRVKFSRSADAPAYQQGQNQ LYNELNLGRREEYDVLDKRRGRDPEMGGKPRRKNPQEGLYNELQKDKMAEA YSEIGMKGERRRGKGHDGLYQGLSTATKDTYDALHMQALPPR | Multivalent anti-BCMA CAR (aa) |
| 302 | MALPVTALLLPLALLLHAARPQVQLVESGGGLVQAGGSLRLSCAASGGTLS KNTVAWFRQAPGKERGFVASITWDGRTTYYADSVKGRFTISRDNAKNTVYL QMNSLKPEDTAVYVCADLGKWPAGPADYWGQGTQVTVSSGGGGSGGGGSGG GGSGGGGSDVQLVESGGGLVQAGGSLRLSCAASGGTLSKNTVAWVRQAPGK ERGFVTSITCDGRTTYYANSVKGRFPISRDNAENTVYLQMNSLKPEDTAGY VCADLGKWPAGSADYWGQGTHVTVSSTSTTTPAPRPPTPAPTIASQPLSLR PEACRPAAGGAVHTRGLDFACDIYIWAPLAGTCGVLLLSLVITLYCKRGRK KLLYIFKQPFMRPVQTTQEEDGCSCRFPEEEEGGCELRVKFSRSADAPAYQ QGQNQLYNELNLGRREEYDVLDKRRGRDPEMGGKPRRKNPQEGLYNELQKD KMAEAYSEIGMKGERRRGKGHDGLYQGLSTATKDTYDALHMQALPPR | Multivalent anti-BCMA CAR (aa) |
| 303 | MLQMAGQCSQ | BCMA epitope |
| 304 | CSQNEYFDSLLHAC | BCMA epitope |
| 305 | NEYFDSLLHACIP | BCMA epitope |
| 306 | ACIPCQLRCSS | BCMA epitope |
| 307 | CQLRCSSNTPPLTCQRYCN | BCMA epitope |
| 308 | LTCQRYCNAS | BCMA epitope |
| 309 | ASVTNSVKGTNA | BCMA epitope |
| 310 | MALPVTALLLPLALLLHAARPMLPAPKNLWSRITEDSARLSVVTAPDAAFD SFPIRYIETLIWGEAIWLDVPGSERSYDLTGLKPGTEYAVVITGVKGGRFS SPLVASFTTTTTPAPRPPTPAPTIASQPLSLRPEACRPAAGGAVHTRGLDF ACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYD VLDKRRGRDPEMGGKPRRKNPQEGLYNELQKDKMAEAYSEIGMKGERRRGK GHDGLYQGLSTATKDTYDALHMQALPPR | Anti-BCMA Centyrin CAR (aa) |
| 311 | MALPVTALLLPLALLLHAARP | Signal sequence |
| 312 | DIVLTQSPPSLAMSLGKRATISCRASESVTILGSHLIHWYQQKPGQPPTLL IQLASNVQTGVPARFSGSGSRTDFTLTIDPVEEDDVAVYYCLQSRTIPRTF GGGTKLEIKGSTSGSGKPGSGEGSTKGQIQLVQSGPELKKPGETVKISCKA SGYTFTDYSINWVKRAPGKGLKWMGWINTETREPAYAYDFRGRFAFSLETS ASTAYLQINNLKYEDTATYFCALDYSYAMDYWGQGTSVTVSSAAATTTPAP RPPTPAPTIASQPLSLRPEACRPAAGGAVHTRGLDFACDIYIWAPLAGTCG VLLLSLVITLYCKRGRKKLLYIFKQPFMRPVQTTQEEDGCSCRFPEEEEGG CELRVKFSRSADAPAYQQGQNQLYNELNLGRREEYDVLDKRRGRDPEMGGK PRRKNPQEGLYNELQKDKMAEAYSEIGMKGERRRGKGHDGLYQGLSTATKD TYDALHMQALPPR | Anti-BCMA CAR (aa) |

The invention claimed is:

1. A method of reducing the severity of, attenuating, and/or preventing the onset of a toxicity in a subject in response to a cell therapy, wherein the cell therapy is for treating the subject having or suspected of having a disease or disorder associated with B-cell maturation antigen (BCMA) expression, the method comprising administering to the subject at least two doses of an interleukin-1 receptor antagonist (IL-1Ra) and the cell therapy comprising a dose of engineered T cells comprising a chimeric antigen receptor (CAR) specific for BCMA, wherein the cell therapy is administered on Day 1 and wherein:
 - at least one dose of the at least two doses of IL-1Ra is administered within about or about 24 hours prior to the administration of the dose of engineered T cells; and
 - at least one dose of the at least two doses of IL-1Ra is administered after the administration of the dose of engineered T cells.

2. The method of claim 1, wherein at least two doses of the IL-1Ra are administered prior to the administration of the dose of engineered T cells.

3. The method of claim 1, wherein a dose of IL-1Ra is administered every 24 hours (q24h) on Days 2-5.

4. A method of reducing the severity of, attenuating, and/or preventing the onset of a toxicity in a subject having or suspected of having a disease or disorder associated with B-cell maturation antigen (BCMA) expression to be treated with a cell therapy, the method comprising administering to the subject at least 6 doses of an interleukin-1 receptor antagonist (IL-1Ra) and a cell therapy comprising a dose of engineered T cells comprising a chimeric antigen receptor (CAR) specific for BCMA, wherein the cell therapy is administered on Day 1, and wherein:
 - (a) one dose of the at least 6 doses of IL-1Ra is administered within about or about 24 hours prior to the administration of the dose of engineered T cells;
 - (b) one dose of the at least 6 doses of IL-1Ra is administered within about or about 3 hours prior to the administration of the dose of engineered T cells on Day 1; and
 - (c) four doses of the at least 6 doses of IL-1Ra are administered after the administration of the dose of engineered T cells, wherein one dose of the four doses is administered each day on Days 2, 3, 4, and 5.

5. The method of claim 1, further comprising administering at least one additional dose of the IL-1Ra if the subject exhibits symptoms or signs of a cytokine release syndrome (CRS) after the administration of the dose of engineered T cells.

6. The method of claim 4, further comprising: after (c) if the subject exhibits symptoms or signs of a cytokine release syndrome (CRS) after the administration of the dose of engineered T cells, administering a dose of IL-1Ra every 12 hours (q12h) until the symptoms or signs of CRS resolve.

7. The method of claim 1, wherein the IL-1Ra is a recombinant IL-1Ra.

8. The method of claim 1, wherein the IL-1Ra comprises the sequence set forth in SEQ ID NO:256 or a sequence having at least 90% sequence identity to SEQ ID NO:256 that retains function as an IL-1Ra.

9. The method of claim 1, wherein the IL-1Ra is anakinra.

10. The method of claim 1, wherein each dose of the IL-1Ra is from about 50 mg to about 200 mg.

11. The method of claim 1, wherein each dose of the IL-1Ra is at or about 100 mg.

12. The method of claim 1, wherein the toxicity is a cytokine release syndrome (CRS).

13. The method of claim 1, wherein the toxicity is a neurotoxicity (NT).

14. The method of claim 1, wherein the CAR comprises an extracellular antigen-binding domain comprising
 - a variable heavy chain ($V_H$) comprising a heavy chain complementarity determining region 1 (CDR-H1), a heavy chain complementarity determining region 2 (CDR-H2) and a heavy chain complementarity determining region 3 (CDR-H3) contained within the sequence set forth in SEQ ID NO: 116 and a variable light chain ($V_L$) comprising a light chain complementarity determining region 1 (CDR-L1), a light chain complementarity determining region 2 (CDR-L2) and a light chain complementarity determining region 3 (CDR-L3) contained within the sequence set forth in SEQ ID NO: 119.

15. The method of claim 14, wherein the extracellular antigen-binding domain comprises the amino acid sequence of SEQ ID NO: 114 or an amino acid sequence having at least 90% sequence identity to the amino acid sequence of SEQ ID NO: 114.

16. The method of claim 1, wherein the CAR comprises:
 - (a) a spacer comprising an IgG4/2 chimeric hinge or a modified IgG4 hinge; an IgG2/4 chimeric $C_H2$ region; and an IgG4 $C_H3$ region;
 - (b) a transmembrane domain; and
 - (c) an intracellular signaling region comprising a cytoplasmic signaling domain of a CD3-zeta (CD3ζ) chain and a costimulatory signaling region comprising an intracellular signaling domain of a T cell costimulatory molecule or a signaling portion thereof.

17. The method of claim 16, wherein the spacer is a spacer set forth in SEQ ID NO: 174.

18. The method of claim 1, wherein the CAR comprises an extracellular antigen-binding domain comprising:
 - a variable heavy chain ($V_H$) comprising a heavy chain complementarity determining region 1 (CDR-H1), a heavy chain complementarity determining region 2 (CDR-H2) and a heavy chain complementarity determining region 3 (CDR-H3) contained within the sequence set forth in SEQ ID NO: 125 and a variable light chain ($V_L$) comprising a light chain complementarity determining region 1 (CDR-L1), a light chain complementarity determining region 2 (CDR-L2) and a light chain complementarity determining region 3 (CDR-L3) contained within the sequence set forth in SEQ ID NO: 127; or a $V_H$ comprising a CDR-H1, a CDR-H2 and a CDR-H3 set forth in SEQ ID NOS: 260, 261, and 262, respectively, and a $V_L$ comprising a CDR-L1, a CDR-L2 and a CDR-L3 set forth in SEQ ID NOS: 257, 258, and 259, respectively.

19. The method of claim 18, wherein the extracellular antigen-binding domain comprises the amino acid sequence of SEQ ID NO: 128 or an amino acid sequence having at least 90% sequence identity to the amino acid sequence of SEQ ID NO: 128.

20. The method of claim 1, wherein the CAR comprises (a) a spacer comprising a CD8 hinge region;

(b) a transmembrane domain; and (c) an intracellular signaling region comprising a cytoplasmic signaling domain of a CD3-zeta (CD3ζ) chain and a costimulatory signaling region comprising an intracellular signaling domain of a T cell costimulatory molecule or a signaling portion thereof.

21. The method of claim 1, wherein the first-CAR comprises the sequence set forth in SEQ ID NO:19 or SEQ ID NO:312.

22. The method of claim 1, wherein the dose of engineered T cells comprising the CAR comprises between at or about $1\times10^7$ CAR+ T cells and at or about $1\times10^9$ CAR+ T cells.

23. The method of claim 1, wherein the dose of engineered T cells comprising the CAR comprises a combination of $CD4^+$ T cells and $CD8^+$ T cells.

24. The method of claim 1, wherein the disease or disorder associated with BCMA expression is an autoimmune disease or disorder.

25. The method of claim 1, wherein the disease or disorder is a BCMA-expressing cancer.

26. The method of claim 25, wherein the BCMA-expressing cancer is multiple myeloma (MM).

27. The method of claim 26, wherein the subject has relapsed following or has been refractory to one or more prior therapies.

28. The method of claim 1, wherein the subject is human.

29. The method of claim 25, wherein the BCMA-expressing cancer is a relapsed or refractory multiple myeloma (r/r MM).

30. The method of claim 1, wherein the CAR comprises an extracellular antigen-binding domain comprising a $V_H$ comprising a CDR-H1, a CDR-H2 and a CDR-H3 set forth in SEQ ID NOS: 97, 101 and 103, respectively, and a $V_L$ comprising a CDR-L1, a CDR-L2 and a CDR-L3 set forth in SEQ ID NOS: 105, 107 and 108, respectively.

* * * * *